United States Patent
Zhang et al.

(10) Patent No.: US 8,614,092 B2
(45) Date of Patent: *Dec. 24, 2013

(54) NUCLEOTIDE-SPECIFIC RECOGNITION SEQUENCES FOR DESIGNER TAL EFFECTORS

(71) Applicants: The Broad Institute Inc., Cambridge, MA (US); Massachusetts Institute of Technology, Cambridge, MA (US)

(72) Inventors: Feng Zhang, Cambridge, MA (US); Le Cong, Cambridge, MA (US)

(73) Assignees: The Broad Institute Inc., Cambridge, MA (US); Massachusetts Institute of Technology, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/732,266

(22) Filed: Dec. 31, 2012

(65) Prior Publication Data

US 2013/0137160 A1    May 30, 2013

Related U.S. Application Data

(60) Division of application No. 13/604,945, filed on Sep. 6, 2012, now Pat. No. 8,450,107, which is a continuation-in-part of application No. 13/554,922, filed on Jul. 20, 2012.

(60) Provisional application No. 61/565,171, filed on Nov. 30, 2011.

(51) Int. Cl.
    *C12N 15/85* (2006.01)
    *C12N 15/00* (2006.01)

(52) U.S. Cl.
    USPC .................. 435/325; 435/69.7; 435/69.1

(58) Field of Classification Search
    None
    See application file for complete search history.

(56) References Cited

U.S. PATENT DOCUMENTS

| 6,528,620 B1 | 3/2003 | Ayer et al. |
| 2011/0145940 A1 | 6/2011 | Voytas et al. |
| 2011/0239315 A1 | 9/2011 | Bonas et al. |
| 2011/0301073 A1 | 12/2011 | Gregory et al. |
| 2012/0064620 A1 | 3/2012 | Bonas et al. |
| 2012/0110685 A1 | 5/2012 | Bonas et al. |
| 2012/0122205 A1 | 5/2012 | Bonas et al. |
| 2012/0270273 A1 | 10/2012 | Zhang et al. |

FOREIGN PATENT DOCUMENTS

WO    WO 2010/079430    7/2010

OTHER PUBLICATIONS

Jens Boch, et al., Breaking the Code of DNA Binding Specificity of TAL-Type III Effectors, www.sciencexpress.org/ Oct. 29, 2009, p. 1-8, 10.1126/science.1178811.
Tomas Cermak, et al., Efficient Design and Assembly of Custom TALEN and Other TAL Effector-Based Constructs for DNA Targeting, Nucleic Acids Research (2011) vol. 39, No. 12, p. 1-11.
Magdy M. Mahfouz, et al., Targeted Transcriptional Repression Using a Chimeric TALE-SRDX Repressor Protein, Plant Mol. Biol. (2012) vol. 78, p. 311-321.
Jeffrey C. Miller, et al., A TALE Nuclease Architecture for Efficient Genome Editing, Nature Biotechonology (2011) vol. 29, No. 2, p. 143-148.
Robert Morbitzer, et al., Assembly of Custom TALE-Type DNA Binding Domains by Modular Cloning, Nucleic Acids Research (2011) vol. 39, No. 13, p. 5790-5799.
Matthew J. Moscou, et al., A Simple Cipher Governs DNA Recognition by TAL Effectors, Science (2009) vol. 326, No. 11, p. 1501.
Daniel F. Voytas, et al., DNA Binding Made Easy, Science (2009) vol. 326, p. 1491-1492.
Feng Zhang, et al., Efficient Construction of Sequence-Specific TAL Effectors for Modulating Mammalian Transcription, Nature Biotechnology (2011) vol. 29, No. 2, p. 149-153.

*Primary Examiner* — Michele K Joike
(74) *Attorney, Agent, or Firm* — Vedder Price P.C.; Thomas J. Kowalski; Smitha B. Uthaman

(57) ABSTRACT

The invention relates to methods of altering expression of a genomic locus of interest or specifically targeting a genomic locus of interest in an animal cell, which may involve contacting the genomic locus with a non-naturally occurring or engineered composition that includes a deoxyribonucleic acid (DNA) binding polypeptide having a N-terminal capping region, a DNA binding domain comprising at least five or more Transcription activator-like effector (TALE) monomers and at least one or more half-monomers specifically ordered to target the genomic locus of interest, and a C-terminal capping region, wherein the polypeptide includes at least one or more effector domains, and wherein the polypeptide is encoded by and translated from a codon optimized nucleic acid molecule so that the polypeptide preferentially binds to the DNA of the genomic locus.

20 Claims, 62 Drawing Sheets

FIG. 2A

TALE repressor screening constructs amino acid sequences

SOX2 TALE repressor (KRAB 1-97)
MSRTRLPSPPAPSPAFSADSFSDLLRQFDPSLFNTSLFDSLPPFGAHHTEAATG
EWDEVQSGLRAADAPPPTMRVAVTAARPPRAKPAPRRRAAQPSDASPAAQV
DLRTLGYSQQQQEKIKPKVRSTVAQHHEALVGHGFTHAHIVALSQHPAALGT
VAVKYQDMIAALPEATHEAIVGVGKQWSGARALEALLTVAGELRGPPLQLD
TGQLLKIAKRGGVTAVEAVHAWRNALTGAPLNLTPEQVVAIASNGGGKQAL
ETVQRLLPVLCQAHGLTPEQVVAIASNGGGKQALETVQRLLPVLCQAHGLTP
EQVVAIASNIGGKQALETVQRLLPVLCQAHGLTPEQVVAIASNGGGKQALET
VQRLLPVLCQAHGLTPEQVVAIASNGGGKQALETVQRLLPVLCQAHGLTPEQ
VVAIASHDGGKQALETVQRLLPVLCQAHGLTPEQVVAIASHDGGKQALETV
QRLLPVLCQAHGLTPEQVVAIASHDGGKQALETVQRLLPVLCQAHGLTPEQV
VAIASNGGGKQALETVQRLLPVLCQAHGLTPEQVVAIASNNGGKQALETVQ
RLLPVLCQAHGLTPEQVVAIASNIGGKQALETVQRLLPVLCQAHGLTPEQVV
AIASHDGGKQALETVQRLLPVLCQAHGLTPEQVVAIASNIGGRPALESIVAQL
SRPDPALAALTNDHLVALACLGGRPALDAVKKGLPHAPALIKRTNRRIPERTS
HRVADHAQVVRVLGFFQCHSHPAQAFDDAMTQFGMSRHGLLQLFRRVGVT
ELEARSGTLPPASQRWDRILQASGMKRAKPSPTSTQTPDQASLHAFADSLER
DLDAPSPMHEGDQTRASASPKKKRKVEASMDAKSLTAWSRTLVTFKDVFVD
FTREEWKLLDTAQQIVYRNVMLENYKNLVSLGYQLTKPDVILRLEKGEEPW
LVEREIHQETHPDSETAFEIKSSV

SOX2 TALE repressor (KRAB 1-75)
MSRTRLPSPPAPSPAFSADSFSDLLRQFDPSLFNTSLFDSLPPFGAHHTEAATG
EWDEVQSGLRAADAPPPTMRVAVTAARPPRAKPAPRRRAAQPSDASPAAQV
DLRTLGYSQQQQEKIKPKVRSTVAQHHEALVGHGFTHAHIVALSQHPAALGT
VAVKYQDMIAALPEATHEAIVGVGKQWSGARALEALLTVAGELRGPPLQLD
TGQLLKIAKRGGVTAVEAVHAWRNALTGAPLNLTPEQVVAIASNGGGKQAL
ETVQRLLPVLCQAHGLTPEQVVAIASNGGGKQALETVQRLLPVLCQAHGLTP
EQVVAIASNIGGKQALETVQRLLPVLCQAHGLTPEQVVAIASNGGGKQALET
VQRLLPVLCQAHGLTPEQVVAIASNGGGKQALETVQRLLPVLCQAHGLTPEQ
VVAIASHDGGKQALETVQRLLPVLCQAHGLTPEQVVAIASHDGGKQALETV
QRLLPVLCQAHGLTPEQVVAIASHDGGKQALETVQRLLPVLCQAHGLTPEQV
VAIASNGGGKQALETVQRLLPVLCQAHGLTPEQVVAIASNNGGKQALETVQ
RLLPVLCQAHGLTPEQVVAIASNIGGKQALETVQRLLPVLCQAHGLTPEQVV
AIASHDGGKQALETVQRLLPVLCQAHGLTPEQVVAIASNIGGRPALESIVAQL
SRPDPALAALTNDHLVALACLGGRPALDAVKKGLPHAPALIKRTNRRIPERTS
HRVADHAQVVRVLGFFQCHSHPAQAFDDAMTQFGMSRHGLLQLFRRVGVT
ELEARSGTLPPASQRWDRILQASGMKRAKPSPTSTQTPDQASLHAFADSLER
DLDAPSPMHEGDQTRASASPKKKRKVEASMDAKSLTAWSRTLVTFKDVFVD
FTREEWKLLDTAQQIVYRNVMLENYKNLVSLGYQLTKPDVILRLEKGEEPW
LV

FIG. 2B

SOX2 TALE repressor (KRAB 11-75)
MSRTRLPSPPAPSPAFSADSFSDLLRQFDPSLFNTSLFDSLPPFGAHHTEAATG
EWDEVQSGLRAADAPPPTMRVAVTAARPPRAKPAPRRRAAQPSDASPAAQV
DLRTLGYSQQQQEKIKPKVRSTVAQHHEALVGHGFTHAHIVALSQHPAALGT
VAVKYQDMIAALPEATHEAIVGVGKQWSGARALEALLTVAGELRGPPLQLD
TGQLLKIAKRGGVTAVEAVHAWRNALTGAPLNLTPEQVVAIASNGGGKQAL
ETVQRLLPVLCQAHGLTPEQVVAIASNGGGKQALETVQRLLPVLCQAHGLTP
EQVVAIASNIGGKQALETVQRLLPVLCQAHGLTPEQVVAIASNGGGKQALET
VQRLLPVLCQAHGLTPEQVVAIASNGGGKQALETVQRLLPVLCQAHGLTPEQ
VVAIASHDGGKQALETVQRLLPVLCQAHGLTPEQVVAIASHDGGKQALETV
QRLLPVLCQAHGLTPEQVVAIASHDGGKQALETVQRLLPVLCQAHGLTPEQV
VAIASNGGGKQALETVQRLLPVLCQAHGLTPEQVVAIASNNGGKQALETVQ
RLLPVLCQAHGLTPEQVVAIASNIGGKQALETVQRLLPVLCQAHGLTPEQVV
AIASHDGGKQALETVQRLLPVLCQAHGLTPEQVVAIASNIGGRPALESIVAQL
SRPDPALAALTNDHLVALACLGGRPALDAVKKGLPHAPALIKRTNRRIPERTS
HRVADHAQVVRVLGFFQCHSHPAQAFDDAMTQFGMSRHGLLQLFRRVGVT
ELEARSGTLPPASQRWDRILQASGMKRAKPSPTSTQTPDQASLHAFADSLER
DLDAPSPMHEGDQTRASASPKKKRKVEASRTLVTFKDVFVDFTREEWKLLD
TAQQIVYRNVMLENYKNLVSLGYQLTKPDVILRLEKGEEPWLV

SOX2 TALE repressor (mSin Interaction Domain, SID)
MSRTRLPSPPAPSPAFSADSFSDLLRQFDPSLFNTSLFDSLPPFGAHHTEAATG
EWDEVQSGLRAADAPPPTMRVAVTAARPPRAKPAPRRRAAQPSDASPAAQV
DLRTLGYSQQQQEKIKPKVRSTVAQHHEALVGHGFTHAHIVALSQHPAALGT
VAVKYQDMIAALPEATHEAIVGVGKQWSGARALEALLTVAGELRGPPLQLD
TGQLLKIAKRGGVTAVEAVHAWRNALTGAPLNLTPEQVVAIASNGGGKQAL
ETVQRLLPVLCQAHGLTPEQVVAIASNGGGKQALETVQRLLPVLCQAHGLTP
EQVVAIASNIGGKQALETVQRLLPVLCQAHGLTPEQVVAIASNGGGKQALET
VQRLLPVLCQAHGLTPEQVVAIASNGGGKQALETVQRLLPVLCQAHGLTPEQ
VVAIASHDGGKQALETVQRLLPVLCQAHGLTPEQVVAIASHDGGKQALETV
QRLLPVLCQAHGLTPEQVVAIASHDGGKQALETVQRLLPVLCQAHGLTPEQV
VAIASNGGGKQALETVQRLLPVLCQAHGLTPEQVVAIASNNGGKQALETVQ
RLLPVLCQAHGLTPEQVVAIASNIGGKQALETVQRLLPVLCQAHGLTPEQVV
AIASHDGGKQALETVQRLLPVLCQAHGLTPEQVVAIASNIGGRPALESIVAQL
SRPDPALAALTNDHLVALACLGGRPALDAVKKGLPHAPALIKRTNRRIPERTS
HRVADHAQVVRVLGFFQCHSHPAQAFDDAMTQFGMSRHGLLQLFRRVGVT
ELEARSGTLPPASQRWDRILQASGMKRAKPSPTSTQTPDQASLHAFADSLER
DLDAPSPMHEGDQTRASASPKKKRKVEASMNIQMLLEAADYLERREREAEH
GYASMLP

FIG. 6A

CACNA1C TALE amino acid sequences

CACNA1C Site 1 NN activator (TALE1-NN)
MSRTRLPSPPAPSPAFSADSFSDLLRQFDPSLFNTSLFDSLPPFGAHHTEAATG
EWDEVQSGLRAADAPPPTMRVAVTAARPPRAKPAPRRRAAQPSDASPAAQV
DLRTLGYSQQQQEKIKPKVRSTVAQHHEALVGHGFTHAHIVALSQHPAALGT
VAVKYQDMIAALPEATHEAIVGVGKQWSGARALEALLTVAGELRGPPLQLD
TGQLLKIAKRGGVTAVEAVHAWRNALTGAPLNLTPEQVVAIASHDGGKQAL
ETVQRLLPVLCQAHGLTPEQVVAIASNNGGKQALETVQRLLPVLCQAHGLTP
EQVVAIASNNGGKQALETVQRLLPVLCQAHGLTPEQVVAIASHDGGKQALE
TVQRLLPVLCQAHGLTPEQVVAIASHDGGKQALETVQRLLPVLCQAHGLTPE
QVVAIASHDGGKQALETVQRLLPVLCQAHGLTPEQVVAIASHDGGKQALET
VQRLLPVLCQAHGLTPEQVVAIASNGGGKQALETVQRLLPVLCQAHGLTPEQ
VVAIASNNGGKQALETVQRLLPVLCQAHGLTPEQVVAIASHDGGKQALETV
QRLLPVLCQAHGLTPEQVVAIASHDGGKQALETVQRLLPVLCQAHGLTPEQV
VAIASNNGGKQALETVQRLLPVLCQAHGLTPEQVVAIASNNGGKQALETVQ
RLLPVLCQAHGLTPEQVVAIASHDGGKQALETVQRLLPVLCQAHGLTPEQVV
AIASHDGGKQALETVQRLLPVLCQAHGLTPEQVVAIASHDGGKQALETVQRL
LPVLCQAHGLTPEQVVAIASNIGGRPALESIVAQLSRPDPALAALTNDHLVAL
ACLGGRPALDAVKKGLPHAPALIKRTNRRIPERTSHRVADHAQVVRVLGFFQ
CHSHPAQAFDDAMTQFGMSRHGLLQLFRRVGVTELEARSGTLPPASQRWDR
ILQASGMKRAKPSPTSTQTPDQASLHAFADSLERDLDAPSPMHEGDQTRASA
SPKKKRKVEASGSGRADALDDFDLDMLGSDALDDFDLDMLGSDALDDFDL
DMLGSDALDDFDLDMLIN

FIG. 6B

CACNA1C Site 1 NK activator (TALE1-NK)
MSRTRLPSPPAPSPAFSADSFSDLLRQFDPSLFNTSLFDSLPPFGAHHTEAATG
EWDEVQSGLRAADAPPPTMRVAVTAARPPRAKPAPRRRAAQPSDASPAAQV
DLRTLGYSQQQQEKIKPKVRSTVAQHHEALVGHGFTHAHIVALSQHPAALGT
VAVKYQDMIAALPEATHEAIVGVGKQWSGARALEALLTVAGELRGPPLQLD
TGQLLKIAKRGGVTAVEAVHAWRNALTGAPLNLTPEQVVAIASHDGGKQAL
ETVQRLLPVLCQAHGLTPEQVVAIASNKGGKQALETVQRLLPVLCQAHGLTP
EQVVAIASNKGGKQALETVQRLLPVLCQAHGLTPEQVVAIASHDGGKQALE
TVQRLLPVLCQAHGLTPEQVVAIASHDGGKQALETVQRLLPVLCQAHGLTPE
QVVAIASHDGGKQALETVQRLLPVLCQAHGLTPEQVVAIASHDGGKQALET
VQRLLPVLCQAHGLTPEQVVAIASNGGGKQALETVQRLLPVLCQAHGLTPEQ
VVAIASNKGGKQALETVQRLLPVLCQAHGLTPEQVVAIASHDGGKQALETV
QRLLPVLCQAHGLTPEQVVAIASHDGGKQALETVQRLLPVLCQAHGLTPEQV
VAIASNKGGKQALETVQRLLPVLCQAHGLTPEQVVAIASNKGGKQALETVQ
RLLPVLCQAHGLTPEQVVAIASHDGGKQALETVQRLLPVLCQAHGLTPEQVV
AIASHDGGKQALETVQRLLPVLCQAHGLTPEQVVAIASHDGGKQALETVQRL
LPVLCQAHGLTPEQVVAIASNIGGRPALESIVAQLSRPDPALAALTNDHLVAL
ACLGGRPALDAVKKGLPHAPALIKRTNRRIPERTSHRVADHAQVVRVLGFFQ
CHSHPAQAFDDAMTQFGMSRHGLLQLFRRVGVTELEARSGTLPPASQRWDR
ILQASGMKRAKPSPTSTQTPDQASLHAFADSLERDLDAPSPMHEGDQTRASA
SPKKKRKVEASGSGRADALDDFDLDMLGSDALDDFDLDMLGSDALDDFDL
DMLGSDALDDFDLDMLIN

CACNA1C Site 1 NH activator (TALE1-NH)
MSRTRLPSPPAPSPAFSADSFSDLLRQFDPSLFNTSLFDSLPPFGAHHTEAATG
EWDEVQSGLRAADAPPPTMRVAVTAARPPRAKPAPRRRAAQPSDASPAAQV
DLRTLGYSQQQQEKIKPKVRSTVAQHHEALVGHGFTHAHIVALSQHPAALGT
VAVKYQDMIAALPEATHEAIVGVGKQWSGARALEALLTVAGELRGPPLQLD
TGQLLKIAKRGGVTAVEAVHAWRNALTGAPLNLTPEQVVAIASHDGGKQAL
ETVQRLLPVLCQAHGLTPEQVVAIASNHGGKQALETVQRLLPVLCQAHGLTP
EQVVAIASNHGGKQALETVQRLLPVLCQAHGLTPEQVVAIASHDGGKQALE
TVQRLLPVLCQAHGLTPEQVVAIASHDGGKQALETVQRLLPVLCQAHGLTPE
QVVAIASHDGGKQALETVQRLLPVLCQAHGLTPEQVVAIASHDGGKQALET
VQRLLPVLCQAHGLTPEQVVAIASNGGGKQALETVQRLLPVLCQAHGLTPEQ
VVAIASNHGGKQALETVQRLLPVLCQAHGLTPEQVVAIASHDGGKQALETV
QRLLPVLCQAHGLTPEQVVAIASHDGGKQALETVQRLLPVLCQAHGLTPEQV
VAIASNHGGKQALETVQRLLPVLCQAHGLTPEQVVAIASNHGGKQALETVQ
RLLPVLCQAHGLTPEQVVAIASHDGGKQALETVQRLLPVLCQAHGLTPEQVV
AIASHDGGKQALETVQRLLPVLCQAHGLTPEQVVAIASHDGGKQALETVQRL
LPVLCQAHGLTPEQVVAIASNIGGRPALESIVAQLSRPDPALAALTNDHLVAL
ACLGGRPALDAVKKGLPHAPALIKRTNRRIPERTSHRVADHAQVVRVLGFFQ
CHSHPAQAFDDAMTQFGMSRHGLLQLFRRVGVTELEARSGTLPPASQRWDR
ILQASGMKRAKPSPTSTQTPDQASLHAFADSLERDLDAPSPMHEGDQTRASA
SPKKKRKVEASGSGRADALDDFDLDMLGSDALDDFDLDMLGSDALDDFDL
DMLGSDALDDFDLDMLIN

FIG. 6C

CACNA1C Site 1 HN activator (TALE1-HN)
MSRTRLPSPPAPSPAFSADSFSDLLRQFDPSLFNTSLFDSLPPFGAHHTEAATG
EWDEVQSGLRAADAPPPTMRVAVTAARPPRAKPAPRRRAAQPSDASPAAQV
DLRTLGYSQQQQEKIKPKVRSTVAQHHEALVGHGFTHAHIVALSQHPAALGT
VAVKYQDMIAALPEATHEAIVGVGKQWSGARALEALLTVAGELRGPPLQLD
TGQLLKIAKRGGVTAVEAVHAWRNALTGAPLNLTPEQVVAIASHDGGKQAL
ETVQRLLPVLCQAHGLTPEQVVAIASHNGGKQALETVQRLLPVLCQAHGLTP
EQVVAIASHNGGKQALETVQRLLPVLCQAHGLTPEQVVAIASHDGGKQALE
TVQRLLPVLCQAHGLTPEQVVAIASHDGGKQALETVQRLLPVLCQAHGLTPE
QVVAIASHDGGKQALETVQRLLPVLCQAHGLTPEQVVAIASHDGGKQALET
VQRLLPVLCQAHGLTPEQVVAIASNGGGKQALETVQRLLPVLCQAHGLTPEQ
VVAIASHNGGKQALETVQRLLPVLCQAHGLTPEQVVAIASHDGGKQALETV
QRLLPVLCQAHGLTPEQVVAIASHDGGKQALETVQRLLPVLCQAHGLTPEQV
VAIASHNGGKQALETVQRLLPVLCQAHGLTPEQVVAIASHNGGKQALETVQ
RLLPVLCQAHGLTPEQVVAIASHDGGKQALETVQRLLPVLCQAHGLTPEQVV
AIASHDGGKQALETVQRLLPVLCQAHGLTPEQVVAIASHDGGKQALETVQRL
LPVLCQAHGLTPEQVVAIASNIGGRPALESIVAQLSRPDPALAALTNDHLVAL
ACLGGRPALDAVKKGLPHAPALIKRTNRRIPERTSHRVADHAQVVRVLGFFQ
CHSHPAQAFDDAMTQFGMSRHGLLQLFRRVGVTELEARSGTLPPASQRWDR
ILQASGMKRAKPSPTSTQTPDQASLHAFADSLERDLDAPSPMHEGDQTRASA
SPKKKRKVEASGSGRADALDDFDLDMLGSDALDDFDLDMLGSDALDDFDL
DMLGSDALDDFDLDMLIN

CACNA1C Site 2 NN activator (TALE2-NN)
MSRTRLPSPPAPSPAFSADSFSDLLRQFDPSLFNTSLFDSLPPFGAHHTEAATG
EWDEVQSGLRAADAPPPTMRVAVTAARPPRAKPAPRRRAAQPSDASPAAQV
DLRTLGYSQQQQEKIKPKVRSTVAQHHEALVGHGFTHAHIVALSQHPAALGT
VAVKYQDMIAALPEATHEAIVGVGKQWSGARALEALLTVAGELRGPPLQLD
TGQLLKIAKRGGVTAVEAVHAWRNALTGAPLNLTPEQVVAIASNNGGKQAL
ETVQRLLPVLCQAHGLTPEQVVAIASNNGGKQALETVQRLLPVLCQAHGLTP
EQVVAIASNGGGKQALETVQRLLPVLCQAHGLTPEQVVAIASNIGGKQALET
VQRLLPVLCQAHGLTPEQVVAIASNNGGKQALETVQRLLPVLCQAHGLTPEQ
VVAIASNIGGKQALETVQRLLPVLCQAHGLTPEQVVAIASHDGGKQALETVQ
RLLPVLCQAHGLTPEQVVAIASHDGGKQALETVQRLLPVLCQAHGLTPEQVV
AIASNGGGKQALETVQRLLPVLCQAHGLTPEQVVAIASNGGGKQALETVQRL
LPVLCQAHGLTPEQVVAIASNIGGKQALETVQRLLPVLCQAHGLTPEQVVAI
ASNNGGKQALETVQRLLPVLCQAHGLTPEQVVAIASNNGGKQALETVQRLL
PVLCQAHGLTPEQVVAIASNNGGKQALETVQRLLPVLCQAHGLTPEQVVAIA
SHDGGKQALETVQRLLPVLCQAHGLTPEQVVAIASNGGGKQALETVQRLLP
VLCQAHGLTPEQVVAIASNIGGRPALESIVAQLSRPDPALAALTNDHLVALAC
LGGRPALDAVKKGLPHAPALIKRTNRRIPERTSHRVADHAQVVRVLGFFQCH
SHPAQAFDDAMTQFGMSRHGLLQLFRRVGVTELEARSGTLPPASQRWDRIL
QASGMKRAKPSPTSTQTPDQASLHAFADSLERDLDAPSPMHEGDQTRASASP
KKKRKVEASGSGRADALDDFDLDMLGSDALDDFDLDMLGSDALDDFDLDM
LGSDALDDFDLDMLIN

FIG. 6D

CACNA1C Site 2 NK activator (TALE2-NK)

MSRTRLPSPPAPSPAFSADSFSDLLRQFDPSLFNTSLFDSLPPFGAHHTEAATG
EWDEVQSGLRAADAPPPTMRVAVTAARPPRAKPAPRRRAAQPSDASPAAQV
DLRTLGYSQQQQEKIKPKVRSTVAQHHEALVGHGFTHAHIVALSQHPAALGT
VAVKYQDMIAALPEATHEAIVGVGKQWSGARALEALLTVAGELRGPPLQLD
TGQLLKIAKRGGVTAVEAVHAWRNALTGAPLNLTPEQVVAIASNKGGKQAL
ETVQRLLPVLCQAHGLTPEQVVAIASNKGGKQALETVQRLLPVLCQAHGLTP
EQVVAIASNGGGKQALETVQRLLPVLCQAHGLTPEQVVAIASNIGGKQALET
VQRLLPVLCQAHGLTPEQVVAIASNKGGKQALETVQRLLPVLCQAHGLTPEQ
VVAIASNIGGKQALETVQRLLPVLCQAHGLTPEQVVAIASHDGGKQALETVQ
RLLPVLCQAHGLTPEQVVAIASHDGGKQALETVQRLLPVLCQAHGLTPEQVV
AIASNGGGKQALETVQRLLPVLCQAHGLTPEQVVAIASNGGGKQALETVQRL
LPVLCQAHGLTPEQVVAIASNIGGKQALETVQRLLPVLCQAHGLTPEQVVAI
ASNKGGKQALETVQRLLPVLCQAHGLTPEQVVAIASNKGGKQALETVQRLL
PVLCQAHGLTPEQVVAIASNKGGKQALETVQRLLPVLCQAHGLTPEQVVAIA
SHDGGKQALETVQRLLPVLCQAHGLTPEQVVAIASNGGGKQALETVQRLLP
VLCQAHGLTPEQVVAIASNIGGRPALESIVAQLSRPDPALAALTNDHLVALAC
LGGRPALDAVKKGLPHAPALIKRTNRRIPERTSHRVADHAQVVRVLGFFQCH
SHPAQAFDDAMTQFGMSRHGLLQLFRRVGVTELEARSGTLPPASQRWDRIL
QASGMKRAKPSPTSTQTPDQASLHAFADSLERDLDAPSPMHEGDQTRASASP
KKKRKVEASGSGRADALDDFDLDMLGSDALDDFDLDMLGSDALDDFDLDM
LGSDALDDFDLDMLIN

CACNA1C Site 2 NH activator (TALE2-NH)
MSRTRLPSPPAPSPAFSADSFSDLLRQFDPSLFNTSLFDSLPPFGAHHTEAATG
EWDEVQSGLRAADAPPPTMRVAVTAARPPRAKPAPRRRAAQPSDASPAAQV
DLRTLGYSQQQQEKIKPKVRSTVAQHHEALVGHGFTHAHIVALSQHPAALGT
VAVKYQDMIAALPEATHEAIVGVGKQWSGARALEALLTVAGELRGPPLQLD
TGQLLKIAKRGGVTAVEAVHAWRNALTGAPLNLTPEQVVAIASNHGGKQAL
ETVQRLLPVLCQAHGLTPEQVVAIASNHGGKQALETVQRLLPVLCQAHGLTP
EQVVAIASNGGGKQALETVQRLLPVLCQAHGLTPEQVVAIASNIGGKQALET
VQRLLPVLCQAHGLTPEQVVAIASNHGGKQALETVQRLLPVLCQAHGLTPEQ
VVAIASNIGGKQALETVQRLLPVLCQAHGLTPEQVVAIASHDGGKQALETVQ
RLLPVLCQAHGLTPEQVVAIASHDGGKQALETVQRLLPVLCQAHGLTPEQVV
AIASNGGGKQALETVQRLLPVLCQAHGLTPEQVVAIASNGGGKQALETVQRL
LPVLCQAHGLTPEQVVAIASNIGGKQALETVQRLLPVLCQAHGLTPEQVVAI
ASNHGGKQALETVQRLLPVLCQAHGLTPEQVVAIASNHGGKQALETVQRLL
PVLCQAHGLTPEQVVAIASNHGGKQALETVQRLLPVLCQAHGLTPEQVVAIA
SHDGGKQALETVQRLLPVLCQAHGLTPEQVVAIASNGGGKQALETVQRLLP
VLCQAHGLTPEQVVAIASNIGGRPALESIVAQLSRPDPALAALTNDHLVALAC
LGGRPALDAVKKGLPHAPALIKRTNRRIPERTSHRVADHAQVVRVLGFFQCH
SHPAQAFDDAMTQFGMSRHGLLQLFRRVGVTELEARSGTLPPASQRWDRIL
QASGMKRAKPSPTSTQTPDQASLHAFADSLERDLDAPSPMHEGDQTRASASP
KKKRKVEASGSGRADALDDFDLDMLGSDALDDFDLDMLGSDALDDFDLDM
LGSDALDDFDLDMLIN

FIG. 6E

CACNA1C Site 2 HN activator (TALE2-HN)
MSRTRLPSPPAPSPAFSADSFSDLLRQFDPSLFNTSLFDSLPPFGAHHTEAATG
EWDEVQSGLRAADAPPPTMRVAVTAARPPRAKPAPRRRAAQPSDASPAAQV
DLRTLGYSQQQQEKIKPKVRSTVAQHHEALVGHGFTHAHIVALSQHPAALGT
VAVKYQDMIAALPEATHEAIVGVGKQWSGARALEALLTVAGELRGPPLQLD
TGQLLKIAKRGGVTAVEAVHAWRNALTGAPLNLTPEQVVAIASHNGGKQAL
ETVQRLLPVLCQAHGLTPEQVVAIASHNGGKQALETVQRLLPVLCQAHGLTP
EQVVAIASNGGGKQALETVQRLLPVLCQAHGLTPEQVVAIASNIGGKQALET
VQRLLPVLCQAHGLTPEQVVAIASHNGGKQALETVQRLLPVLCQAHGLTPEQ
VVAIASNIGGKQALETVQRLLPVLCQAHGLTPEQVVAIASHDGGKQALETVQ
RLLPVLCQAHGLTPEQVVAIASHDGGKQALETVQRLLPVLCQAHGLTPEQVV
AIASNGGGKQALETVQRLLPVLCQAHGLTPEQVVAIASNGGGKQALETVQRL
LPVLCQAHGLTPEQVVAIASNIGGKQALETVQRLLPVLCQAHGLTPEQVVAI
ASHNGGKQALETVQRLLPVLCQAHGLTPEQVVAIASHNGGKQALETVQRLL
PVLCQAHGLTPEQVVAIASHNGGKQALETVQRLLPVLCQAHGLTPEQVVAIA
SHDGGKQALETVQRLLPVLCQAHGLTPEQVVAIASNGGGKQALETVQRLLP
VLCQAHGLTPEQVVAIASNIGGRPALESIVAQLSRPDPALAALTNDHLVALAC
LGGRPALDAVKKGLPHAPALIKRTNRRIPERTSHRVADHAQVVRVLGFFQCH
SHPAQAFDDAMTQFGMSRHGLLQLFRRVGVTELEARSGTLPPASQRWDRIL
QASGMKRAKPSPTSTQTPDQASLHAFADSLERDLDAPSPMHEGDQTRASASP
KKKRKVEASGSGRADALDDFDLDMLGSDALDDFDLDMLGSDALDDFDLDM
LGSDALDDFDLDMLIN

CACNA1C Site 1 NN repressor (TALE1-NN)
MSRTRLPSPPAPSPAFSADSFSDLLRQFDPSLFNTSLFDSLPPFGAHHTEAATG
EWDEVQSGLRAADAPPPTMRVAVTAARPPRAKPAPRRRAAQPSDASPAAQV
DLRTLGYSQQQQEKIKPKVRSTVAQHHEALVGHGFTHAHIVALSQHPAALGT
VAVKYQDMIAALPEATHEAIVGVGKQWSGARALEALLTVAGELRGPPLQLD
TGQLLKIAKRGGVTAVEAVHAWRNALTGAPLNLTPEQVVAIASHDGGKQAL
ETVQRLLPVLCQAHGLTPEQVVAIASNNGGKQALETVQRLLPVLCQAHGLTP
EQVVAIASNNGGKQALETVQRLLPVLCQAHGLTPEQVVAIASHDGGKQALE
TVQRLLPVLCQAHGLTPEQVVAIASHDGGKQALETVQRLLPVLCQAHGLTPE
QVVAIASHDGGKQALETVQRLLPVLCQAHGLTPEQVVAIASHDGGKQALET
VQRLLPVLCQAHGLTPEQVVAIASNGGGKQALETVQRLLPVLCQAHGLTPEQ
VVAIASNNGGKQALETVQRLLPVLCQAHGLTPEQVVAIASHDGGKQALETV
QRLLPVLCQAHGLTPEQVVAIASHDGGKQALETVQRLLPVLCQAHGLTPEQV
VAIASNNGGKQALETVQRLLPVLCQAHGLTPEQVVAIASNNGGKQALETVQ
RLLPVLCQAHGLTPEQVVAIASHDGGKQALETVQRLLPVLCQAHGLTPEQVV
AIASHDGGKQALETVQRLLPVLCQAHGLTPEQVVAIASHDGGKQALETVQRL
LPVLCQAHGLTPEQVVAIASNIGGRPALESIVAQLSRPDPALAALTNDHLVAL
ACLGGRPALDAVKKGLPHAPALIKRTNRRIPERTSHRVADHAQVVRVLGFFQ
CHSHPAQAFDDAMTQFGMSRHGLLQLFRRVGVTELEARSGTLPPASQRWDR
ILQASGMKRAKPSPTSTQTPDQASLHAFADSLERDLDAPSPMHEGDQTRASA
SPKKKRKVEASMNIQMLLEAADYLERREREAEHGYASMLP

FIG. 6F

CACNA1C Site 1 NK repressor (TALE1-NK)
MSRTRLPSPPAPSPAFSADSFSDLLRQFDPSLFNTSLFDSLPPFGAHHTEAATG
EWDEVQSGLRAADAPPPTMRVAVTAARPPRAKPAPRRRAAQPSDASPAAQV
DLRTLGYSQQQQEKIKPKVRSTVAQHHEALVGHGFTHAHIVALSQHPAALGT
VAVKYQDMIAALPEATHEAIVGVGKQWSGARALEALLTVAGELRGPPLQLD
TGQLLKIAKRGGVTAVEAVHAWRNALTGAPLNLTPEQVVAIASHDGGKQAL
ETVQRLLPVLCQAHGLTPEQVVAIASNKGGKQALETVQRLLPVLCQAHGLTP
EQVVAIASNKGGKQALETVQRLLPVLCQAHGLTPEQVVAIASHDGGKQALE
TVQRLLPVLCQAHGLTPEQVVAIASHDGGKQALETVQRLLPVLCQAHGLTPE
QVVAIASHDGGKQALETVQRLLPVLCQAHGLTPEQVVAIASHDGGKQALET
VQRLLPVLCQAHGLTPEQVVAIASNGGGKQALETVQRLLPVLCQAHGLTPEQ
VVAIASNKGGKQALETVQRLLPVLCQAHGLTPEQVVAIASHDGGKQALETV
QRLLPVLCQAHGLTPEQVVAIASHDGGKQALETVQRLLPVLCQAHGLTPEQV
VAIASNKGGKQALETVQRLLPVLCQAHGLTPEQVVAIASNKGGKQALETVQ
RLLPVLCQAHGLTPEQVVAIASHDGGKQALETVQRLLPVLCQAHGLTPEQVV
AIASHDGGKQALETVQRLLPVLCQAHGLTPEQVVAIASHDGGKQALETVQRL
LPVLCQAHGLTPEQVVAIASNIGGRPALESIVAQLSRPDPALAALTNDHLVAL
ACLGGRPALDAVKKGLPHAPALIKRTNRRIPERTSHRVADHAQVVRVLGFFQ
CHSHPAQAFDDAMTQFGMSRHGLLQLFRRVGVTELEARSGTLPPASQRWDR
ILQASGMKRAKPSPTSTQTPDQASLHAFADSLERDLDAPSPMHEGDQTRASA
SPKKKRKVEASMNIQMLLEAADYLERREREAEHGYASMLP

CACNA1C Site 1 NH repressor (TALE1-NH)
MSRTRLPSPPAPSPAFSADSFSDLLRQFDPSLFNTSLFDSLPPFGAHHTEAATG
EWDEVQSGLRAADAPPPTMRVAVTAARPPRAKPAPRRRAAQPSDASPAAQV
DLRTLGYSQQQQEKIKPKVRSTVAQHHEALVGHGFTHAHIVALSQHPAALGT
VAVKYQDMIAALPEATHEAIVGVGKQWSGARALEALLTVAGELRGPPLQLD
TGQLLKIAKRGGVTAVEAVHAWRNALTGAPLNLTPEQVVAIASHDGGKQAL
ETVQRLLPVLCQAHGLTPEQVVAIASNHGGKQALETVQRLLPVLCQAHGLTP
EQVVAIASNHGGKQALETVQRLLPVLCQAHGLTPEQVVAIASHDGGKQALE
TVQRLLPVLCQAHGLTPEQVVAIASHDGGKQALETVQRLLPVLCQAHGLTPE
QVVAIASHDGGKQALETVQRLLPVLCQAHGLTPEQVVAIASHDGGKQALET
VQRLLPVLCQAHGLTPEQVVAIASNGGGKQALETVQRLLPVLCQAHGLTPEQ
VVAIASNHGGKQALETVQRLLPVLCQAHGLTPEQVVAIASHDGGKQALETV
QRLLPVLCQAHGLTPEQVVAIASHDGGKQALETVQRLLPVLCQAHGLTPEQV
VAIASNHGGKQALETVQRLLPVLCQAHGLTPEQVVAIASNHGGKQALETVQ
RLLPVLCQAHGLTPEQVVAIASHDGGKQALETVQRLLPVLCQAHGLTPEQVV
AIASHDGGKQALETVQRLLPVLCQAHGLTPEQVVAIASHDGGKQALETVQRL
LPVLCQAHGLTPEQVVAIASNIGGRPALESIVAQLSRPDPALAALTNDHLVAL
ACLGGRPALDAVKKGLPHAPALIKRTNRRIPERTSHRVADHAQVVRVLGFFQ
CHSHPAQAFDDAMTQFGMSRHGLLQLFRRVGVTELEARSGTLPPASQRWDR
ILQASGMKRAKPSPTSTQTPDQASLHAFADSLERDLDAPSPMHEGDQTRASA
SPKKKRKVEASMNIQMLLEAADYLERREREAEHGYASMLP FIG. 8
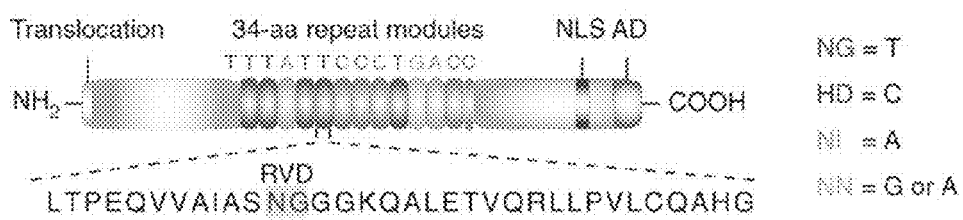
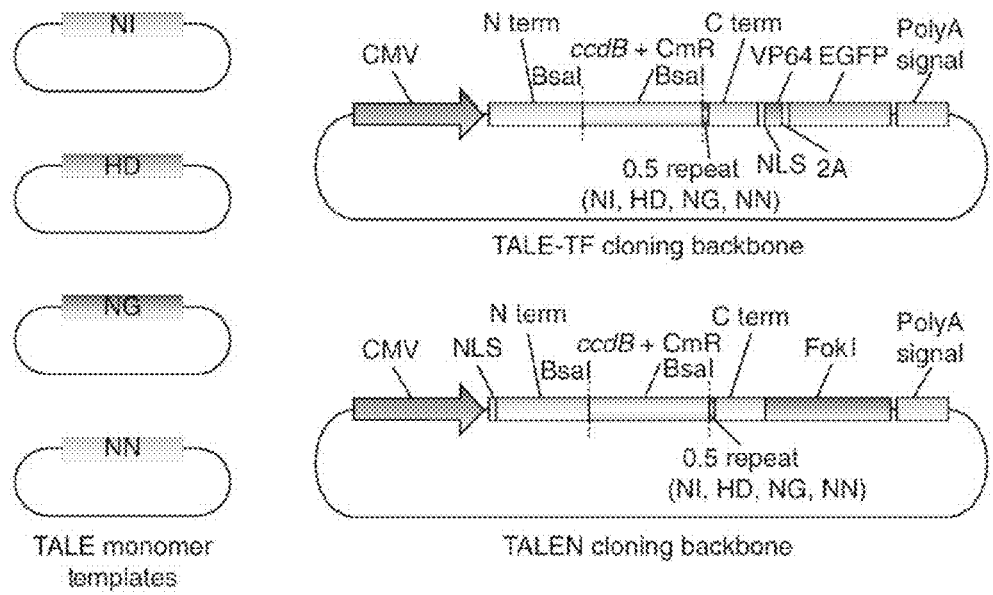
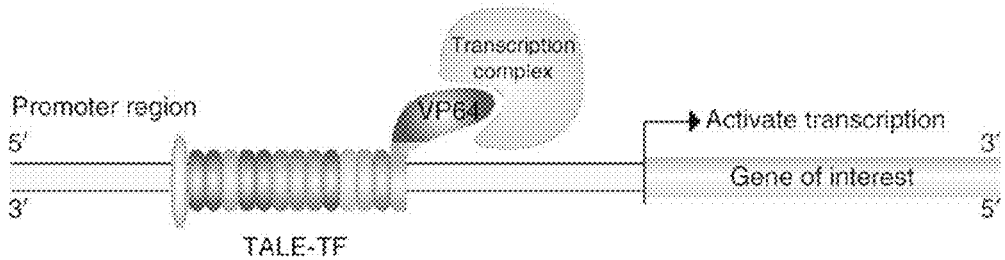
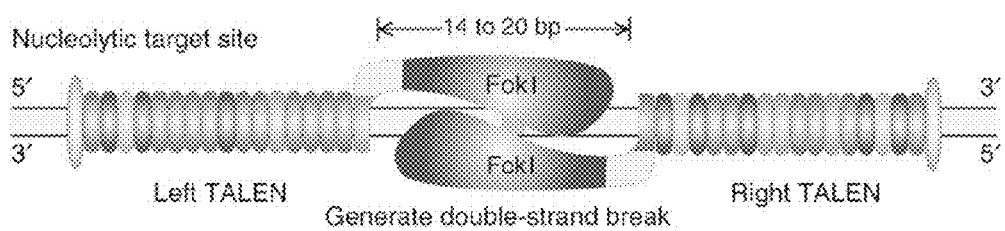

FIG. 9

|  | Species | Genomic loci | References |
|---|---|---|---|
| TALE-TF | Arabidopsis thaliana | egl3 | 5 |
|  |  | knat1 |  |
|  | Homo sapiens | KLF4 | 3 |
|  |  | SOX2 |  |
|  |  | NTF3 | 4 |
|  |  | PUMA | 8 |
|  |  | IFNA1 |  |
|  |  | IFNB1 |  |
| TALEN | Saccharomyces cerevisiae | ura3 | 9 |
|  |  | lys2 |  |
|  |  | ade2 |  |
|  | H. sapiens | CCR5 | 4 |
|  |  | NTF3 |  |
|  |  | PPP1R12C (AAVS1) | 13 |
|  |  | OCT4 (POU5F1) |  |
|  |  | PITX3 |  |
|  | Caenorhabditis elegans | ben-1 | 11 |
|  | Danio rerio | hey2 | 58, 59 |
|  |  | gria3a |  |
|  |  | trikb |  |
|  | Rattus norvegicus | Igm | 60 |

FIG. 10

| Day | Duration | Steps | Task |
|---|---|---|---|
| 0 | 3 h | 1–4 | Generate monomer library plate using PCR |
|   | 3 h | 5–9 | Purify and normalize concentration of each monomer using gel |
| 1 | 4 h | 10–15 | First Golden Gate cut-ligation to generate circularized hexamer |
|   | 1 h | 16–17 | Exonuclease treatment to remove non-hexamers |
|   | 1 h | 18–19 | Amplify hexamers using PCR |
|   | 1 h | 20–25 | Gel purify amplified hexamers and normalize concentration |
|   | Overnight | 26–28 | Second Golden Gate cut-ligation to generate final TALE construct |
| 2 | 2 h | 29–30 | Transform Golden Gate cut-ligation product |
| 3 | 2 h | 31–35 | Colony PCR to identify successful TALE clones, and seed cultures |
| 4 | 2 h | 36–38 | Plasmid preparation and send samples for sequencing verification |
| 5 | 1 h | 39 | Seed cell lines to test TALE function |
|   | 3 h | 40–45 | Quantify DNA and transfect cell line with successful clones |
| 6–8 | Varies | 46A or 46B | Test transcription modulation using qRT-PCR or nuclease activity using Surveyor assay |

TALE construction: Days 0–4
Functional testing: Days 5–8

FIG. 11A

All plasmids are available at the website of AddGene under TALE_Toolbox.

TALE Monomer templates: NI, NG, NN, and HD monomers
For each plasmid, only the monomer sequence is shown. The variable diresidue is highlighted in yellow. All plasmids are kan$^R$.

> pNI_v2
CTCACCCCAGAGCAGGTCGTGGCAATTGCGAGCAACATCGGGGGAAAGCAGGCACTCGAAACCGTCCAGAGGTTGCTGCCTGTGCTGTGCCAAGC
GCACGGA

> pNG_v2
CTCACCCCAGAGCAGGTCGTGGCAATTGCGAGCAACGGAGGGGGAAAGCAGGCACTCGAAACCGTCCAGAGGTTGCTGCCTGTGCTGTGCCAAGC
GCACGGA

> pNN_v2
CTCACCCCAGAGCAGGTCGTGGCAATTGCGAGCAACAACGGGGGAAAGCAGGCACTCGAAACCGTCCAGAGGTTGCTGCCTGTGCTGTGCCAAGC
GCACGGA

> pHD_v2
CTCACCCCAGAGCAGGTCGTGGCAATTGCGAGCCATGACGGGGGAAAGCAGGCACTCGAAACCGTCCAGAGGTTGCTGCCTGTGCTGTGCCAAGC
GCACGGA

FIG. 11B

TALE-TF Backbone plasmids: NI, NG, NN, and HD 0.5 repeats
For each plasmid, only the coding region is shown. *BsaI* type IIs enzyme sites are colored in blue. NLS is colored in red. VP64 is colored in purple. 2A-GFP is colored in green. For the 0.5 repeat, the variable diresidue is highlighted in yellow. All plasmids are amp$^R$.

> pTALE-TF_v2 (NI)
ATGTCGCGGACCCGGCTCCCTTCCCCACCCGCACCCAGCCCAGCGTTTTCGGCCGACTCGTTCTCAGACCTGCTTAGGCAGTTCGACCCCTCACTGTT
TAACACATCGTTGTTCGACTCCCTTCCTCCGTTTGGGGCGCACCATACGGAGGCGGCCACCGGGGAGTGGGATGAGGTGCAGTCGGGATTGAGAG
CTGCGGATGCACCACCCCCAACCATGCGGGTGGCCGTCACCGCTGCCCGACCGCCGAGGGCGAAGCCCGCACCAAGGCGGAGGGCAGCGCAACCGT
CCGACGCAAGCCCCGCAGCGCAAGTAGATTTGAGAACTTTGGGATATTCACAGCAGCAGCAGGAAAAGATCAAGCCCAAAGTGAGGTCGACAGTC
GCGCAGCATCACGAAGCGCTGGTGGGTCATGGGTTTACACATGCCCACATCGTAGCCTTGTCGCAGCACCCTGCAGCCCTTGGCACGGTCGCCGTC
AAGTACCAGGACATGATTGCGGCGTTGCCGGAAGCCACACATGAGGCGATCGTCGGTGTGGGGAAACAGTGGAGCGGAGCCCGAGCGCTTGAGG
CCCTGTTGACGGTCGCGGGAGAGCTGAGAGGGCCTCCCCTTCAGCTGGACACGGGCCAGTTGCTGAAGATCGCGAAGCGGGGAGGAGTCACGGCG
GTCGAGGCGGTGCACGCGTGGCGCAATGCGCTCACGGGAGCACCCCTCAACCTGACAgagaccGCGGCCGCATTAGGCACCCCAGGCTTTACACTTTA
TGCTTCCGGCTCGTATAATGTGTGGATTTTGAGTTAGGATCCGTCGAGATTTTCAGGAGCTAAGGAAGCTAAAATGGAGAAAAAAATCACTGGA
TATACCACCGTTGATATATCCCAATGGCATCGTAAAGAACATTTTGAGGCATTTCAGTCAGTTGCTCAATGTACCTATAACCAGACCGTTCAGCT
GGATATTACGGCCTTTTTAAAGACCGTAAAGAAAAATAAGCACAAGTTTTATCCGGCCTTTATTCACATTCTTGCCCGCCTGATGAATGCTCATC
CGGAATTCCGTATGGCAATGAAAGACGGTGAGCTGGTGATATGGGATAGTGTTCACCCTTGTTACACCGTTTTCCATGAGCAAACTGAAACGTTT
TCATCGCTCTGGAGTGAATACCACGACGATTTCCGGCAGTTTCTACACATATATTCGCAAGATGTGGCGTGTTACGGTGAAAACCTGGCCTATTT
CCCTAAAAGGGTTTATTGAGAATATGTTTTTCGTCTCAGCCAATCCCTGGGTGAGTTTCACCAGTTTTGATTTAAACGTGGCCAATATGGACAACT
TCTTCGCCCCCGTTTTCACCATGGGCAAATATTATACGCAAGGCGACAAGGTGCTGATGCCGCTGGCGATTCAGGTTCATCATGCCGTTTGTGATG
GCTTCCATGTCGGCAGAATGCTTAATGAATTACAACAGTACTGCGATGAGTGGCAGGGCGGGGCGTAAAGATCTGGATCCGGCTTACTAAAAGC
CAGATAACAGTATGCGTATTTGCGCGCTGATTTTTGCGGTATAAGAATATATACTGATATGTATACCCGAAGTATGTCAAAAAGAGGGTATGCTA
TGAAGCAGCGTATTACAGTGACAGTTGACAGCGACAGCTATCAGTTGCTCAAGGCATATATGATGTCAATATCTCCGGTCTGGTAAGCACAACCA
TGCAGAATGAAGCCCGTCGTCTGCGTGCCGAACGCTGGAAAGCGGAAAATCAGGAAGGGATGGCTGAGGTCGCCCGGTTTATTGAAATGAACGG
CTCTTTTGCTGACGAGAACAGGGGCTGGTGAAATGCAGTTTAAGGTTTACACCTATAAAAGAGAGAGCCGTTATCGTCTGTTTGTGGATGTACA
GAGTGATATTATTGACACGCCCGGGCGACGGATGGTGATCCCCTGGCCAGTGCACGTCTGCTGTCAGATAAAGTCTCCCGTGAACTTTACCCGGT
GGTGCATATCGGGGATGAAAGCTGGCGCATGATGACCACCGATATGGCCAGTGTGCCGGTCTCCGTTATCGGGGAAGAAGTGGCTGATCTCAGCC
ACCGCGAAAATGACATCAAAAACGCCATTAACCTGATGTTCTGGGGAATATAAATGTCAGGCTCCCTTATACACAGCCAGTCTGCAGGTCGACggt
ctcGACTCACGCCTGAGCAGGTAGTGGCTATTGCATCCAATATCGGGGGCAGACCCGCACTGGAGTCAATCGTGGCCCAGCTTTCGAGGCCGGACC
CCGCGCTGGCCGCACTCACTAATGATCATCTTGTAGCGCTGGCCTGCCTCGGCGGACGACCCGCCTTGGATGCGGTGAAGAAGGGGCTCCCGCACG
CGCCTGCATTGATTAAGCGGACCAACAGAAGGATTCCCGAGAGGACATCACATCGAGTGGCAGATCACGCGCAAGTGGTCCGCGTGCTCGGATTC
TTCCAGTGTCACTCCCACCCCGCACAAGCGTTCGATGACGCCATGACTCAATTTGGTATGTCGAGACACGGACTGCTGCAGCTCTTTCGTAGAGTC
GGTGTCACAGAACTCGAGGCCCGCTCGGGCACACTGCCTCCCGCCTCCCAGCGGTGGGACAGGATTCTCCAAGCGAGCGGTATGAAACGCGCGAAG
CCTTCACCTACGTCAACTCAGACACCTGACCAGGCGAGCCTTCATGCGTTCGCAGACTCGCTGGAGAGGGATTTGGACGCGCCCTCGCCCATGCAT
GAAGGGGACCAAACTCGCGCGTCAGCTAGCCCCAAGAAGAAGAGAAAGGTGGAGGCCAGCGGTTCCGGACGGGCTGACGCATTGGACGATTTTG
ATCTGGATATGCTGGGAAGTGACGCCCTCGATGATTTTGACCTTGACATGCTTGGTTCGGATGCCCTTGATGACTTTGACCTCGACATGCTCGGC
AGTGACGCCCTTGATGATTTCGACCTGGACATGCTGATTAACTCTAGAGGCAGTGGAGAGGGCAGAGGAAGTCTGCTAACATGCGGTGACGTCG
AGGAGAATCCTGGCCCAGTGAGCAAGGGCGAGGAGCTGTTCACCGGGGTGGTGCCCATCCTGGTCGAGCTGGACGGCGACGTAAACGGCCACAAG
TTCAGCGTGTCCGGCGAGGGCGAGGGCGATGCCACCTACGGCAAGCTGACCCTGAAGTTCATCTGCACCACCGGCAAGCTGCCCGTGCCCTGGCCC
ACCCTCGTGACCACCCTGACCTACGGCGTGCAGTGCTTCAGCCGCTACCCCGACCACATGAAGCAGCACGACTTCTTCAAGTCCGCCATGCCCGAAG
GCTACGTCCAGGAGCGCACCATCTTCTTCAAGGACGACGGCAACTACAAGACCCGCGCCGAGGTGAAGTTCGAGGGCGACACCCTGGTGAACCGC
ATCGAGCTGAAGGGCATCGACTTCAAGGAGGACGGCAACATCCTGGGGCACAAGCTGGAGTACAACTACAACAGCCACAACGTCTATATCATGGC
CGACAAGCAGAAGAACGGCATCAAGGTGAACTTCAAGATCCGCCACAACATCGAGGACGGCAGCGTGCAGCTCGCCGACCACTACCAGCAGAACA
CCCCCATCGGCGACGGCCCCGTGCTGCTGCCCGACAACCACTACCTGAGCACCCAGTCCGCCCTGAGCAAAGACCCCAACGAGAAGCGCGATCACAT
GGTCCTGCTGGAGTTCGTGACCGCCGCCGGGATCACTCTCGGCATGGACGAGCTGTACAAGTAA

FIG. 11C

```
> pTALE-TF_v2 (NG)
ATGTCGCGGACCCGGCTCCCTTCCCCACCCGCACCCAGCCCAGCGTTTTCGGCCGACTCGTTCTCAGACCTGCTTAGGCAGTTCGACCCCTCACTGTT
TAACACATCGTTGTTCGACTCCCTTCCTCCGTTTGGGGCGCACCATACGGAGGCGGCCACCGGGGAGTGGGATGAGGTGCAGTCGGGATTGAGAG
CTGCGGATGCACCACCCCCAACCATGCGGGTGGCCGTCACCGCTGCCCGACCGCCGAGGGCGAAGCCCGCACCAAGGCGGAGGGCAGCGCAACCGT
CCGACGCAAGCCCCGCAGCGCAAGTAGATTTGAGAACTTTGGGATATTCACAGCAGCAGCAGGAAAAGATCAAGCCCAAAGTGAGGTCGACAGTC
GCGCAGCATCACGAAGCGCTGGTGGGTCATGGGTTTACACATGCCCACATCGTAGCCTTGTCGCAGCACCCTGCAGCCCTTGGCACGGTCGCCGTC
AAGTACCAGGACATGATTGCGGCGTTGCCGGAAGCCACACATGAGGCGATCGTCGGTGTGGGGAAACAGTGGAGCGGAGCCCGAGCGCTTGAGG
CCCTGTTGACGGTCGCGGGAGAGCTGAGAGGGCCTCCCCTTCAGCTGGACACGGGCCAGTTGCTGAAGATCGCGAAGCGGGGAGGAGTCACGGCG
GTCGAGGCGGTGCACGCGTGGCGCAATGCGCTCACGGGAGCACCCCTCAACCTGACAgagaccGCGGCCGCATTAGGCACCCAGGCTTTACACTTTA
TGCTTCCGGCTCGTATAATGTGTGGATTTTGAGTTAGGATCCGTCGAGATTTTCAGGAGCTAAGGAAGCTAAAATGGAGAAAAAAATCACTGGA
TATACCACCGTTGATATATCCCAATGGCATCGTAAAGAACATTTTGAGGCATTTCAGTCAGTTGCTCAATGTACCTATAACCAGACCGTTCAGCT
GGATATTACGGCCTTTTTAAAGACCGTAAAGAAAAATAAGCACAAGTTTTATCCGGCCTTTATTCACATTCTTGCCCGCCTGATGAATGCTCATC
CGGAATTCCGTATGGCAATGAAAGACGGTGAGCTGGTGATATGGGATAGTGTTCACCCGTTGTTACACCGTTTTCCATGAGCAAACTGAAACGTTT
TCATCGCTCTGGAGTGAATACCACGACGATTTCCGGCAGTTTCTACACATATATTCGCAAGATGTGGCGTGTTACGGTGAAAACCTGGCCTATTT
CCCTAAAGGGTTTATTGAGAATATGTTTTTCGTCTCAGCCAATCCCTGGGTGAGTTTCACCAGTTTTGATTTAAACGTGGCCAATATGGACAACT
TCTTCGCCCCCGTTTTCACCATGGGCAAATATTATACGCAAGGCGACAAGGTGCTGATGCCGCTGGCGATTCAGGTTCATCATGCCGTTTGTGATG
GCTTCCATGTCGGCAGAATGCTTAATGAATTACAACAGTACTGCGATGAGTGGCAGGGCGGGGCGTAAAGATCTGGATCCGGCTTACTAAAAGC
CAGATAACAGTATGCGTATTTGCGCGCTGATTTTTGCGGTATAAGAATATATACTGATATGTATACCCGAAGTATGTCAAAAAGAGGTATGCTA
TGAAGCAGCGTATTACAGTGACAGTTGACAGCGACAGCTATCAGTTGCTCAAGGCATATATGATGTCAATATCTCCGGTCTGGTAAGCACAACCA
TGCAGAATGAAGCCCGTCGTCTGCGTGCCGAACGCTGGAAAGCGGAAAATCAGGAAGGGATGGCTGAGGTCGCCCGGTTTATTGAAATGAACGG
CTCTTTTGCTGACGAGAACAGGGGCTGGTGAAATGCAGTTTAAGGTTTACACCTATAAAGAGAGAGCCGTTATCGTCTGTTTGTGGATGTACA
GAGTGATATTATTGACACGCCCGGGCGACGGATGGTGATCCCCTGGCCAGTGCACGTCTGCTGTCAGATAAAGTCTCCCGTGAACTTTACCCGGT
GGTGCATATCGGGGATGAAAGCTGGCGCATGATGACCACCGATATGGCCAGTGTGCCGGTCTCCGTTATCGGGGAAGAAGTGGCTGATCTCAGCC
ACCGCGAAAATGACATCAAAAACGCCATTAACCTGATGTTCTGGGGAATATAAATGTCAGGCTCCCTTATACACAGCCAGTCTGCAGGTCGACggt
ctcGACTCACGCCTGAGCAGGTAGTGGCTATTGCATCCAATGGCGGGGGCAGACCCGCACTGGAGTCAATCGTGGCCCAGCTTTCGAGGCCGGACC
CCGCGCTGGCCGCACTCACTAATGATCATCTTGTAGCGCTGGCCTGCCTCGGCGGACGACCCGCCTTGGATGCGGTGAAGAAGGGGCTCCCGCACG
CGCCTGCATTGATTAAGCGGACCAACAGAAGGATTCCCGAGAGGACATCACATCGAGTGGCAGATCACGCGCAAGTGGTCCGCGTGCTCGGATTC
TTCCAGTGTCACTCCCACCCCGCACAAGCGTTCGATGACGCCATGACTCAATTTGGTATGTCGAGACACGGACTGCTGCAGCTCTTTCGTAGAGTC
GGTGTCACAGAACTCGAGGCCCGCTCGGGCACACTGCCTCCCGCCTCCCAGCGGTGGGACAGGATTCTCCAAGCGAGCGGTATGAAACGCGCGAAG
CCTTCACCTACGTCAACTCAGACACCTGACCAGGCGAGCCTTCATGCGTTCGCAGACTCGCTGGAGAGGGATTTGGACGCGCCCTCGCCCATGCAT
GAAGGGGACCAAACTCGCGCGTCAGCTAGCCCCAAGAAGAAGAGAAAGGTGGAGGCCAGCGGTTCCGGACGGGCTGACGCATTGGACGATTTTG
ATCTGGATATGCTGGGAAGTGACGCCCTCGATGATTTTGACCTTGACATGCTTGGTTCGGATGCCCTTGATGACTTTGACCTCGACATGCTCGGC
AGTGACGCCCTTGATGATTTCGACCTGGACATGCTGATTAACTCTAGAGGCAGTGGAGAGGGCAGAGGAAGTCTGCTAACATGCGGTGACGTCG
AGGAGAATCCTGGCCCAGTGAGCAAGGGCGAGGAGCTGTTCACCGGGGTGGTGCCCATCCTGGTCGAGCTGGACGGCGACGTAAACGGCCACAAG
TTCAGCGTGTCCGGCGAGGGCGAGGGCGATGCCACCTACGGCAAGCTGACCCTGAAGTTCATCTGCACCACCGGCAAGCTGCCCGTGCCCTGGCCC
ACCCTCGTGACCACCCTGACCTACGGCGTGCAGTGCTTCAGCCGCTACCCCGACCACATGAAGCAGCACGACTTCTTCAAGTCCGCCATGCCCGAAG
GCTACGTCCAGGAGCGCACCATCTTCTTCAAGGACGACGGCAACTACAAGACCCGCGCCGAGGTGAAGTTCGAGGGCGACACCCTGGTGAACCGC
ATCGAGCTGAAGGGCATCGACTTCAAGGAGGACGGCAACATCCTGGGGCACAAGCTGGAGTACAACTACAACAGCCACAACGTCTATATCATGGC
CGACAAGCAGAAGAACGGCATCAAGGTGAACTTCAAGATCCGCCACAACATCGAGGACGGCAGCGTGCAGCTCGCCGACCACTACCAGCAGAACA
CCCCCATCGGCGACGGCCCCGTGCTGCTGCCCGACAACCACTACCTGAGCACCCAGTCCGCCCTGAGCAAAGACCCCAACGAGAAGCGCGATCACAT
GGTCCTGCTGGAGTTCGTGACCGCCGCCGGGATCACTCTCGGCATGGACGAGCTGTACAAGTAA
```

FIG. 11D

> pTALE-TF_v2 (NN)
ATGTCGCGGACCCGGCTCCCTTCCCCACCCGCACCCAGCCCAGCGTTTTCGGCCGACTCGTTCTCAGACCTGCTTAGGCAGTTCGACCCCTCACTGTT
TAACACATCGTTGTTCGACTCCCTTCCTCCGTTTGGGGCGCACCATACGGAGGCGGCCACCGGGGAGTGGGATGAGGTGCAGTCGGGATTGAGAG
CTGCGGATGCACCACCCCCAACCATGCGGGTGGCCGTCACCGCTGCCCGACCGCCGAGGGCGAAGCCCGCACCAAGGCGGAGGGCAGCGCAACCGT
CCGACGCAAGCCCGCAGCGCAAGTAGATTTGAGAACTTTGGGATATTCACAGCAGCAGCAGGAAAAGATCAAGCCCAAAGTGAGGTCGACAGTC
GCGCAGCATCACGAAGCGCTGGTGGGTCATGGGTTTACACATGCCCACATCGTAGCCTTGTCGCAGCACCCTGCAGCCCTTGGCACGGTCGCCGTC
AAGTACCAGGACATGATTGCGGCGTTGCCGGAAGCCACACATGAGGCGATCGTCGGTGTGGGGAAACAGTGGAGCGGAGCCCGAGCGCTTGAGG
CCCTGTTGACGGTCGCGGGAGAGCTGAGAGGGCCTCCCCTTCAGCTGGACACGGGCCAGTTGCTGAAGATCGCGAAGCGGGGAGGAGTCACGGCG
GTCGAGGCGGTGCACGCGTGGCGCAATGCGCTCACGGGAGCACCCCTCAACCTGACAgagaccGCGGCCGCATTAGGCACCCCAGGCTTTACACTTTA
TGCTTCCGGCTCGTATAATGTGTGGATTTTGAGTTAGGATCCGTCGAGATTTTCAGGAGCTAAGGAAGCTAAAATGGAGAAAAAAATCACTGGA
TATACCACCGTTGATATATCCCAATGGCATCGTAAAGAACATTTTGAGGCATTTCAGTCAGTTGCTCAATGTACCTATAACCAGACCGTTCAGCT
GGATATTACGGCCTTTTTAAAGACCGTAAAGAAAAATAAGCACAAGTTTTATCCGGCCTTTATTCACATTCTTGCCCGCCTGATGAATGCTCATC
CGGAATTCCGTATGGCAATGAAAGACGGTGAGCTGGTGATATGGGATAGTGTTCACCCTTGTTACACCGTTTTCCATGAGCAAACTGAAACGTTT
TCATCGCTCTGGAGTGAATACCACGACGATTTCCGGCAGTTTCTACACATATATTCGCAAGATGTGGCGTGTTACGGTGAAAACCTGGCCTATTT
CCCTAAAGGGTTTATTGAGAATATGTTTTTCGTCTCAGCCAATCCCTGGGTGAGTTTCACCAGTTTTGATTTAAACGTGGCCAATATGGACAACT
TCTTCGCCCCCGTTTTCACCATGGGCAAATATTATACGCAAGGCGACAAGGTGCTGATGCCGCTGGCGATTCAGGTTCATCATGCCGTTTGTGATG
GCTTCCATGTCGGCAGAATGCTTAATGAATTACAACAGTACTGCGATGAGTGGCAGGGCGGGGCGTAAAGATCTGGATCCGGCTTACTAAAAGC
CAGATAACAGTATGCGTATTTGCGCGCTGATTTTTGCGGTATAAGAATATATACTGATATGTATACCCGAAGTATGTCAAAAAGAGGTATGCTA
TGAAGCAGCGTATTACAGTGACAGTTGACAGCGACAGCTATCAGTTGCTCAAGGCATATATGATGTCAATATCTCCGGTCTGGTAAGCACAACCA
TGCAGAATGAAGCCCGTCGTCTGCGTGCCGAACGCTGGAAAGCGGAAAATCAGGAAGGGATGGCTGAGGTCGCCCGGTTTATTGAAATGAACGG
CTCTTTTGCTGACGAGAACAGGGGCTGGTGAAATGCAGTTTAAGGTTTACACCTATAAAAGAGAGAGCCGTTATCGTCTGTTTGTGGATGTACA
GAGTGATATTATTGACACGCCCGGGCGACGGATGGTGATCCCCTGGCCAGTGCACGTCTGCTGTCAGATAAAGTCTCCCGTGAACTTTACCCGGT
GGTGCATATCGGGGATGAAAGCTGGCGCATGATGACCACCGATATGGCCAGTGTGCCGGTCTCCGTTATCGGGAAGAAGTGGCTGATCTCAGCC
ACCGCGAAAATGACATCAAAAACGCCATTAACCTGATGTTCTGGGGAATATAAATGTCAGGCTCCCTTATACACAGCCAGTCTGCAGGTCGACggt
cttcGACTCACGCCTGAGCAGGTAGTGGCTATTGCATCCAATAACGGGGGCAGACCCGCACTGGAGTCAATCGTGGCCCAGCTTTCGAGGCCGGACC
CCGCGCTGGCCGCACTCACTAATGATCATCTTGTAGCGCTGGCCTGCCTCGGCGGACGACCCGCCTTGGATGCGGTGAAGAAGGGGCTCCCGCACG
CGCCTGCATTGATTAAGCGGACCAACAGAAGGATTCCCGAGAGGACATCACATCGAGTGGCAGATCACGCGCAAGTGGTCCGCGTGCTCGGATTC
TTCCAGTGTCACTCCCACCCCGCACAAGCGTTCGATGACGCCATGACTCAATTTGGTATGTCGAGCACGGACTGCTGCAGCTCTTTCGTAGAGTC
GGTGTCACAGAACTCGAGGCCCGCTCGGGCACACTGCCTCCCGCCTCCCAGCGGTGGGACAGGATTCTCCAAGCGAGCGGTATGAAACGCGCGAAG
CCTTCACCTACGTCAACTCAGACACCTGACCAGGCGAGCCTTCATGCGTTCGCAGACTCGCTGGAGAGGGATTTGGACGCGCCCTCGCCCATGCAT
GAAGGGGACCAAACTCGCGCGTCAGCTAGCCCCAAGAAGAAGAGAAAGGTGGAGGCCAGCGGTTCCGGACGGGCTGACGCATTGGACGATTTTG
ATCTGGATATGCTGGGAAGTGACGCCCTCGATGATTTTGACCTTGACATGCTTGGTTCGGATGCCCTTGATGACTTTGACCTCGACATGCTCGGC
AGTGACGCCCTTGATGATTTCGACCTGGACATGCTGATTAACTCTAGAGGCAGTGGAGAGGGCAGAGGAAGTCTGCTAACATGCGGTGACGTCG
AGGAGAATCCTGGCCCAGTGAGCAAGGGCGAGGAGCTGTTCACCGGGGTGGTGCCCATCCTGGTCGAGCTGGACGGCGACGTAAACGGCCACAAG
TTCAGCGTGTCCGGCGAGGGCGAGGGCGATGCCACCTACGGCAAGCTGACCCTGAAGTTCATCTGCACCACCGGCAAGCTGCCCGTGCCCTGGCCC
ACCCTCGTGACCACCCTGACCTACGGCGTGCAGTGCTTCAGCCGCTACCCCGACCACATGAAGCAGCACGACTTCTTCAAGTCCGCCATGCCCGAAG
GCTACGTCCAGGAGCGCACCATCTTCTTCAAGGACGACGGCAACTACAAGACCCGCGCCGAGGTGAAGTTCGAGGGCGACACCCTGGTGAACCGC
ATCGAGCTGAAGGGCATCGACTTCAAGGAGGACGGCAACATCCTGGGGCACAAGCTGGAGTACAACTACAACAGCCACAACGTCTATATCATGGC
CGACAAGCAGAAGAACGGCATCAAGGTGAACTTCAAGATCCGCCACAACATCGAGGACGGCAGCGTGCAGCTCGCCGACCACTACCAGCAGAACA
CCCCCATCGGCGACGGCCCCGTGCTGCTGCCCGACAACCACTACCTGAGCACCCAGTCCGCCCTGAGCAAAGACCCCAACGAGAAGCGCGATCACAT
GGTCCTGCTGGAGTTCGTGACCGCCGCCGGGATCACTCTCGGCATGGACGAGCTGTACAAGTAA

FIG. 11E

```
> pTALE-TF_v2 (HD)
ATGTCGCGGACCCGGCTCCCTTCCCCACCCGCACCCAGCCCAGCGTTTTCGGCCGACTCGTTCTCAGACCTGCTTAGGCAGTTCGACCCCTCACTGTT
TAACACATCGTTGTTCGACTCCCTTCCTCCGTTTGGGGCGCACCATACGGAGGCGGCCACCGGGGAGTGGGATGAGGTGCAGTCGGGATTGAGAG
CTGCGGATGCACCACCCCAACCATGCGGGTGGCCGTCACCGCTGCCCGACCGCCGAGGGCGAAGCCCGCACCAAGGCGGAGGGCAGCGCAACCGT
CCGACGCAAGCCCGCAGCGCAAGTAGATTTGAGAACTTTGGGATATTCACAGCAGCAGCAGGAAAAGATCAAGCCCAAAGTGAGGTCGACAGTC
GCGCAGCATCACGAAGCGCTGGTGGGTCATGGGTTTACACATGCCCACATCGTAGCCTTGTCGCAGCACCCTGCAGCCCTTGGCACGGTCGCCGTC
AAGTACCAGGACATGATTGCGGCGTTGCCGGAAGCCACACATGAGGCGATCGTCGGTGTGGGGAAACAGTGGAGCGGAGCCCGAGCGCTTGAGG
CCCTGTTGACGGTCGCGGGAGAGCTGAGAGGGCCTCCCCTTCAGCTGGACACGGGCCAGTTGCTGAAGATCGCGAAGCGGGGAGGAGTCACGGCG
GTCGAGGCGGTGCACGCGTGGCGCAATGCGCTCACGGGAGCACCCCTCAACCTGACAgagaccGCGGCCGCATTAGGCACCCCAGGCTTTACACTTTA
TGCTTCCGGCTCGTATAATGTGTGGATTTTGAGTTAGGATCCGTCGAGATTTTCAGGAGCTAAGGAAGCTAAAATGGAGAAAAAAATCACTGGA
TATACCACCGTTGATATATCCCAATGGCATCGTAAAGAACATTTTGAGGCATTTCAGTCAGTTGCTCAATGTACCTATAACCAGACCGTTCAGCT
GGATATTACGGCCTTTTTAAAGACCGTAAAGAAAAATAAGCACAAGTTTTATCCGGCCTTTATTCACATTCTTGCCCGCCTGATGAATGCTCATC
CGGAATTCCGTATGGCAATGAAAGACGGTGAGCTGGTGATATGGGATAGTGTTCACCCTTGTTACACCGTTTTCCATGAGCAAACTGAAACGTTT
TCATCGCTCTGGAGTGAATACCACGACGATTTCCGGCAGTTTCTACACATATATTCGCAAGATGTGGCGTGTTACGGTGAAAACCTGGCCTATTT
CCCTAAAGGGTTTATTGAGAATATGTTTTTCGTCTCAGCCAATCCCTGGGTGAGTTTCACCAGTTTTGATTTAAACGTGGCCAATATGGACAACT
TCTTCGCCCCCGTTTTCACCATGGGCAAATATTATACGCAAGGCGACAAGGTGCTGATGCCGCTGGCGATTCAGGTTCATCATGCCGTTTGTGATG
GCTTCCATGTCGGCAGAATGCTTAATGAATTACAACAGTACTGCGATGAGTGGCAGGGCGGGGCGTAAAGATCTGGATCCGGCTTACTAAAAGC
CAGATAACAGTATGCGTATTTGCGCGCTGATTTTTGCGGTATAAGAATATATACTGATATGTATACCCGAAGTATGTCAAAAAGAGGTATGCTA
TGAAGCAGCGTATTACAGTGACAGTTGACAGCGACAGCTATCAGTTGCTCAAGGCATATATGATGTCAATATCTCCGGTCTGGTAAGCACAACCA
TGCAGAATGAAGCCCGTCGTCTGCGTGCCGAACGCTGGAAAGCGGAAAATCAGGAAGGGATGGCTGAGGTCGCCCGGTTTATTGAAATGAACGG
CTCTTTTGCTGACGAGAACAGGGGCTGGTGAAATGCAGTTTAAGGTTTACACCTATAAAAGAGAGAGCCGTTATCGTCTGTTTGTGGATGTACA
GAGTGATATTATTGACACGCCCGGGCGACGGATGGTGATCCCCCTGGCCAGTGCACGTCTGCTGTCAGATAAAGTCTCCCGTGAACTTTACCCGGT
GGTGCATATCGGGGATGAAAGCTGGCGCATGATGACCACCGATATGGCCAGTGTGCCGGTCTCCGTTATCGGGGAAGAAGTGGCTGATCTCAGCC
ACCGCGAAAATGACATCAAAAACGCCATTAACCTGATGTTCTGGGGAATATAAATGTCAGGCTCCCTTATACACAGCCAGTCTGCAGGTCGACggt
ctcGACTCACGCCTGAGCAGGTAGTGGCTATTGCATCCCATGACGGGGGCAGACCCGCACTGGAGTCAATCGTGGCCCAGCTTTCGAGGCCGGACCC
CGCGCTGGCCGCACTCACTAATGATCATCTTGTAGCGCTGGCCTGCCTCGGCGGACGACCCGCCTTGGATGCGGTGAAGAAGGGGCTCCCGCACGC
GCCTGCATTGATTAAGCGGACCAACAGAAGGATTCCCGAGAGGACATCACATCGAGTGGCAGATCACGCGCAAGTGGTCCGCGTGCTCGGATTCT
TCCAGTGTCACTCCCACCCCGCACAAGCGTTCGATGACGCCATGACTCAATTTGGTATGTCGAGACACGGACTGCTGCAGCTCTTTCGTAGAGTCG
GTGTCACAGAACTCGAGGCCCGCTCGGGCACACTGCCTCCCGCCTCCCAGCCGGTGGGACAGGATTCTCCAAGCGAGCGGTATGAAACGCGCGAAGC
CTTCACCTACGTCAACTCAGACACCTGACCAGGCGAGCCTTCATGCGTTCGCAGACTCGCTGGAGAGGGATTTGGACGCGCCCTCGCCCATGCATG
AAGGGGACCAAACTCGCGCGTCAGCTAGCCCCAAGAAGAAGAGAAAGGTGGAGGCCAGCGGTTCCGGACGGGCTGACGCATTGGACGATTTTGA
TCTGGATATGCTGGGAAGTGACGCCCTCGATGATTTTGACCTTGACATGCTTGGTTCGGATGCCCTTGATGACTTTGACCTCGACATGCTCGGCA
GTGACGCCCTTGATGATTTCGACCTGGACATGCTGATTAACTCTAGAGGCAGTGGAGAGGGCAGAGGAAGTCTGCTAACATGCGGTGACGTCGA
GGAGAATCCTGGCCCAGTGAGCAAGGGCGAGGAGCTGTTCACCGGGGTGGTGCCCATCCTGGTCGAGCTGGACGGCGACGTAAACGGCCACAAGT
TCAGCGTGTCCGGCGAGGGCGAGGGCGATGCCACCTACGGCAAGCTGACCCTGAAGTTCATCTGCACCACCGGCAAGCTGCCCGTGCCCTGGCCCA
CCCTCGTGACCACCCTGACCTACGGCGTGCAGTGCTTCAGCCGCTACCCCGACCACATGAAGCAGCACGACTTCTTCAAGTCCGCCATGCCCGAAGG
CTACGTCCAGGAGCGCACCATCTTCTTCAAGGACGACGGCAACTACAAGACCCGCGCCGAGGTGAAGTTCGAGGGCGACACCCTGGTGAACCGCA
TCGAGCTGAAGGGCATCGACTTCAAGGAGGACGGCAACATCCTGGGGCACAAGCTGGAGTACAACTACAACAGCCACAACGTCTATATCATGGCC
GACAAGCAGAAGAACGGCATCAAGGTGAACTTCAAGATCCGCCACAACATCGAGGACGGCAGCGTGCAGCTCGCCGACCACTACCAGCAGAACAC
CCCCATCGGCGACGGCCCCGTGCTGCTGCCCGACAACCACTACCTGAGCACCCAGTCCGCCCTGAGCAAAGACCCCAACGAGAAGCGCGATCACATG
GTCCTGCTGGAGTTCGTGACCGCCGCCGGGATCACTCTCGGCATGGACGAGCTGTACAAGTAA
```

FIG. 11F

TALEN Backbone plasmids: NI, NG, NN, and HD 0.5 repeat
For each plasmid, only the coding region is shown. *Bsa*I type IIs enzyme sites are colored in blue. NLS is colored in red. *Fok*I is colored in orange. For the 0.5 repeat, the variable diresidue is highlighted in yellow. All plasmids are amp^R.

```
> pTALEN_v2 (NI)
ATGGACTATAAGGACCACGACGGAGACTACAAGGATCATGATATTGATTACAAAGACGATGACGATAAGATGGCCCCAAAGAAGAAGC
GGAAGGTCGGTATCCACGGAGTCCCAGCAGCCGTAGATTTGAGAACTTTGGGATATTCACAGCAGCAGCAGGAAAAGATCAAGCCCAA
AGTGAGGTCGACAGTCGCGCAGCATCACGAAGCGCTGGTGGGTCATGGGTTTACACATGCCCACATCGTAGCCTTGTCGCAGCACCCTGC
AGCCCTTGGCACGGTCGCCGTCAAGTACCAGGACATGATTGCGGCGTTGCCGGAAGCCACACATGAGGCGATCGTCGGTGTGGGGAAAC
AGTGGAGCGGAGCCCGAGCGCTTGAGGCCCTGTTGACGGTCGCGGGAGAGCTGAGAGGGCCTCCCCTTCAGCTGGACACGGGCCAGTTG
CTGAAGATCGCGAAGCGGGGAGGAGTCACGGCGGTCGAGGCGGTGCACGCGTGGCGCAATGCGCTCACGGGAGCACCCCTCAACCTGAC
AgagaccGCGGCCGCATTAGGCACCCCAGGCTTTACACTTTATGCTTCCGGCTCGTATAATGTGTGGATTTTGAGTTAGGATCCGTCGAGA
TTTTCAGGAGCTAAGGAAGCTAAAATGGAGAAAAAAATCACTGGATATACCACCGTTGATATATCCCAATGGCATCGTAAAGAACATT
TTGAGGCATTTCAGTCAGTTGCTCAATGTACCTATAACCAGACCGTTCAGCTGGATATTACGGCCTTTTTAAAGACCGTAAAGAAAAAT
AAGCACAAGTTTTATCCGGCCTTTATTCACATTCTTGCCCGCCTGATGAATGCTCATCCGGAATTCCGTATGGCAATGAAAGACGGTGA
GCTGGTGATATGGGATAGTGTTCACCCTTGTTACACCGTTTTCCATGAGCAAACTGAAACGTTTTCATCGCTCTGGAGTGAATACCACG
ACGATTTCCGGCAGTTTCTACACATATATTCGCAAGATGTGGCGTGTTACGGTGAAAACCTGGCCTATTTCCCTAAAGGGTTTATTGAG
AATATGTTTTCGTCTCAGCCAATCCCTGGGTGAGTTTCACCAGTTTTGATTTAAACGTGGCCAATATGGACAACTTCTTCGCCCCCGTT
TTCACCATGGGCAAATATTATACGCAAGGCGACAAGGTGCTGATGCCGCTGGCGATTCAGGTTCATCATGCCGTTTGTGATGGCTTCCA
TGTCGGCAGAATGCTTAATGAATTACAACAGTACTGCGATGAGTGGCAGGGCGGGGCGTAAAGATCTGGATCCGGCTTACTAAAAGCC
AGATAACAGTATGCGTATTTGCGCGCTGATTTTTGCGGTATAAGAATATATACTGATATGTATACCCGAAGTATGTCAAAAAGAGGTA
TGCTATGAAGCAGCGTATTACAGTGACAGTTGACAGCGACAGCTATCAGTTGCTCAAGGCATATATGATGTCAATATCTCCGGTCTGGT
AAGCACAACCATGCAGAATGAAGCCCGTCGTCTGCGTGCCGAACGCTGGAAAGCGGAAAATCAGGAAGGGATGGCTGAGGTCGCCCGGT
TTATTGAAATGAACGGCTCTTTTGCTGACGAGAACAGGGGCTGGTGAAATGCAGTTTAAGGTTTACACCTATAAAAGAGAGAGCCGTT
ATCGTCTGTTTGTGGATGTACAGAGTGATATTATTGACACGCCCGGCGACGGATGGTGATCCCCCTGGCCAGTGCACGTCTGCTGTCA
GATAAAGTCTCCCGTGAACTTTACCCGGTGGTGCATATCGGGGATGAAAGCTGGCGCATGATGACCACCGATATGGCCAGTGTGCCGGT
CTCCGTTATCGGGGAAGAAGTGGCTGATCTCAGCCACCGCGAAAATGACATCAAAAACGCCATTAACCTGATGTTCTGGGGAATATAAA
TGTCAGGCTCCCTTATACACAGCCAGTCTGCAGGTCGACggtctcGACTCACGCCTGAGCAGGTAGTGGCTATTGCATCCAACATCGGGGG
CAGACCCGCACTGGAGTCAATCGTGGCCCAGCTTTCGAGGCCGGACCCCGCGCTGGCCGCACTCACTAATGATCATCTTGTAGCGCTGGC
CTGCCTCGGCGGACGACCCGCCTTGGATGCGGTGAAGAAGGGGCTCCCGCACGCGCCTGCATTGATTAAGCGGACCAACAGAAGGATTC
CCGAGAGGACATCACATCGAGTGGCAGGTTCCCAACTCGTGAAGAGTGAACTTGAGGAGAAAAAGTCGGAGCTGCGGCACAAATTGAA
ATACGTACCGCATGAATACATCGAACTTATCGAAATTGCTAGGAACTCGACTCAAGACAGAATCCTTGAGATGAAGGTAATGGAGTTC
TTTATGAAGGTTTATGGATACCGAGGGAAGCATCTCGGTGGATCACGAAAACCCGACGGAGCAATCTATACGGTGGGGAGCCCGATTG
ATTACGGAGTGATCGTCGACACGAAAGCCTACAGCGGTGGGTACAATCTTCCCATCGGGCAGGCAGATGAGATGCAACGTTATGTCGAA
GAAAATCAGACCAGGAACAAACACATCAATCCAAATGAGTGGTGGAAAGTGTATCCTTCATCAGTGACCGAGTTTAAGTTTTTGTTTG
TCTCTGGGCATTTCAAAGGCAACTATAAGGCCCAGCTCACACGGTTGAATCACATTACGAACTGCAATGGTGCGGTTTTGTCCGTAGAG
GAACTGCTCATTGGTGGAGAAATGATCAAAGCGGGAACTCTGACACTGGAAGAAGTCAGACGCAAGTTTAACAATGGCGAGATCAATT
TCCGCTCATAA
```

FIG. 11G

> pTALEN_v2 (NG)
ATGGACTATAAGGACCACGACGGAGACTACAAGGATCATGATATTGATTACAAAGACGATGACGATAAGATGGCCCCAAAGAAGAAGC
GGAAGGTCGGTATCCACGGAGTCCCAGCAGCCGTAGATTTGAGAACTTTGGGATATTCACAGCAGCAGCAGGAAAAGATCAAGCCCAA
AGTGAGGTCGACAGTCGCGCAGCATCACGAAGCGCTGGTGGGTCATGGGTTTACACATGCCCACATCGTAGCCTTGTCGCAGCACCCTGC
AGCCCTTGGCACGGTCGCCGTCAAGTACCAGGACATGATTGCGGCGTTGCCGGAAGCCACACATGAGGCGATCGTCGGTGTGGGGAAAC
AGTGGAGCGGAGCCCGAGCGCTTGAGGCCCTGTTGACGGTCGCGGGAGAGCTGAGAGGGCCTCCCCTTCAGCTGGACACGGGCCAGTTG
CTGAAGATCGCGAAGCGGGGAGGAGTCACGGCGGTCGAGGCGGTGCACGCGTGGCGCAATGCGCTCACGGGAGCACCCCTCAACCTGAC
AgagaccGCGGCCGCATTAGGCACCCCAGGCTTTACACTTTATGCTTCCGGCTCGTATAATGTGTGGATTTTGAGTTAGGATCCGTCGAGA
TTTTCAGGAGCTAAGGAAGCTAAAATGGAGAAAAAAATCACTGGATATACCACCGTTGATATATCCCAATGGCATCGTAAAGAACATT
TTGAGGCATTTCAGTCAGTTGCTCAATGTACCTATAACCAGACCGTTCAGCTGGATATTACGGCCTTTTTAAAGACCGTAAAGAAAAAT
AAGCACAAGTTTTATCCGGCCTTTATTCACATTCTTGCCCGCCTGATGAATGCTCATCCGGAATTCCGTATGGCAATGAAAGACGGTGA
GCTGGTGATATGGGATAGTGTTCACCCTTGTTACACCGTTTTCCATGAGCAAACTGAAACGTTTTCATCGCTCTGGAGTGAATACCACG
ACGATTTCCGGCAGTTTCTACACATATATTCGCAAGATGTGGCGTGTTACGGTGAAAACCTGGCCTATTTCCCTAAAGGGTTTATTGAG
AATATGTTTTTCGTCTCAGCCAATCCCTGGGTGAGTTTCACCAGTTTTGATTTAAACGTGGCCAATATGGACAACTTCTTCGCCCCCGTT
TTCACCATGGGCAAATATTATACGCAAGGCGACAAGGTGCTGATGCCGCTGGCGATTCAGGTTCATCATGCCGTTTGTGATGGCTTCCA
TGTCGGCAGAATGCTTAATGAATTACAACAGTACTGCGATGAGTGGCAGGGCGGGGCGTAAAGATCTGGATCCGGCTTACTAAAAGCC
AGATAACAGTATGCGTATTTGCGCGCTGATTTTGCGGTATAAGAATATATACTGATATGTATACCCGAAGTATGTCAAAAAGAGGTA
TGCTATGAAGCAGCGTATTACAGTGACAGTTGACAGCGACAGCTATCAGTTGCTCAAGGCATATATGATGTCAATATCTCCGGTCTGGT
AAGCACAACCATGCAGAATGAAGCCCGTCGTCTGCGTGCCGAACGCTGGAAAGCGGAAAATCAGGAAGGGATGGCTGAGGTCGCCCGGT
TTATTGAAATGAACGGCTCTTTTGCTGACGAGAACAGGGGCTGGTGAAATGCAGTTTAAGGTTTACACCTATAAAAGAGAGAGCCGTT
ATCGTCTGTTTGTGGATGTACAGAGTGATATTATTGACACGCCCGGCGACGGATGGTGATCCCCTGGCCAGTGCACGTCTGCTGTCA
GATAAAGTCTCCCGTGAACTTTACCCGGTGGTGCATATCGGGGATGAAAGCTGGCGCATGATGACCACCGATATGGCCAGTGTGCCGGT
CTCCGTTATCGGGGAAGAAGTGGCTGATCTCAGCCACCGCGAAAATGACATCAAAAACGCCATTAACCTGATGTTCTGGGGAATATAAA
TGTCAGGCTCCCTTATACACAGCCAGTCTGCAGGTCGACggtctcGACTCACGCCTGAGCAGGTAGTGGCTATTGCATCCAACGGAGGGG
CAGACCCGCACTGGAGTCAATCGTGGCCCAGCTTTCGAGGCCGGACCCCGCGCTGGCCGCACTCACTAATGATCATCTTGTAGCGCTGGC
CTGCCTCGGCGGACGACCCGCCTTGGATGCGGTGAAGAAGGGGCTCCCGCACGCGCCTGCATTGATTAAGCGGACCAACAGAAGGATTC
CCGAGAGGACATCACATCGAGTGGCAGGTTCCCAACTCGTGAAGAGTGAACTTGAGGAGAAAAAGTCGGAGCTGCGGCACAAATTGAA
ATACGTACCGCATGAATACATCGAACTTATCGAAATTGCTAGGAACTCGACTCAAGACAGAATCCTTGAGATGAAGGTAATGGAGTTC
TTTATGAAGGTTTATGGATACCGAGGGAAGCATCTCGGTGGATCACGAAAACCCGACGGAGCAATCTATACGGTGGGGAGCCCGATTG
ATTACGGAGTGATCGTCGACACGAAAGCCTACAGCGGTGGGTACAATCTTCCCATCGGGCAGGCAGATGAGATGCAACGTTATGTCGAA
GAAAATCAGACCAGGAACAAACACATCAATCCAAATGAGTGGTGGAAAGTGTATCCTTCATCAGTGACCGAGTTTAAGTTTTTGTTTG
TCTCTGGGCATTTCAAAGGCAACTATAAGGCCCAGCTCACACGGTTGAATCACATTACGAACTGCAATGGTGCGGTTTTGTCCGTAGAG
GAACTGCTCATTGGTGGAGAAATGATCAAAGCGGGAACTCTGACACTGGAAGAAGTCAGACGCAAGTTTAACAATGGCGAGATCAATT
TCCGCTCATAA

FIG. 11H

> pTALEN_v2 (NN)
ATGGACTATAAGGACCACGACGGAGACTACAAGGATCATGATATTGATTACAAAGACGATGACGATAAGATGGCCCCAAAGAAGAAGC
GGAAGGTCGGTATCCACGGAGTCCCAGCAGCCGTAGATTTGAGAACTTTGGGATATTCACAGCAGCAGCAGGAAAAGATCAAGCCCAA
AGTGAGGTCGACAGTCGCGCAGCATCACGAAGCGCTGGTGGGTCATGGGTTTACACATGCCCACATCGTAGCCTTGTCGCAGCACCCTGC
AGCCCTTGGCACGGTCGCCGTCAAGTACCAGGACATGATTGCGGCGTTGCCGGAAGCCACACATGAGGCGATCGTCGGTGTGGGGAAAC
AGTGGAGCGGAGCCCGAGCGCTTGAGGCCCTGTTGACGGTCGCGGGAGAGCTGAGAGGGCCTCCCCTTCAGCTGGACACGGGCCAGTTG
CTGAAGATCGCGAAGCGGGGAGGAGTCACGGCGGTCGAGGCGGTGCACGCGTGGCGCAATGCGCTCACGGGAGCACCCCTCAACCTGAC
AgagaccGCGGCCGCATTAGGCACCCCAGGCTTTACACTTTATGCTTCCGGCTCGTATAATGTGTGGATTTTGAGTTAGGATCCGTCGAGA
TTTTCAGGAGCTAAGGAAGCTAAAATGGAGAAAAAAATCACTGGATATACCACCGTTGATATATCCCAATGGCATCGTAAAGAACATT
TTGAGGCATTTCAGTCAGTTGCTCAATGTACCTATAACCAGACCGTTCAGCTGGATATTACGGCCTTTTTAAAGACCGTAAAGAAAAAT
AAGCACAAGTTTTATCCGGCCTTTATTCACATTCTTGCCCGCCTGATGAATGCTCATCCGGAATTCCGTATGGCAATGAAAGACGGTGA
GCTGGTGATATGGGATAGTGTTCACCCTTGTTACACCGTTTTCCATGAGCAAACTGAAACGTTTTCATCGCTCTGGAGTGAATACCACG
ACGATTTCCGGCAGTTTCTACACATATATTCGCAAGATGTGGCGTGTTACGGTGAAACCTGGCCTATTTCCCTAAAGGGTTTATTGAG
AATATGTTTTCGTCTCAGCCAATCCCTGGGTGAGTTTCACCAGTTTTGATTTAAACGTGGCCAATATGGACAACTTCTTCGCCCCCGTT
TTCACCATGGGCAAATATTATACGCAAGGCGACAAGGTGCTGATGCCGCTGGCGATTCAGGTTCATCATGCCGTTTGTGATGGCTTCCA
TGTCGGCAGAATGCTTAATGAATTACAACAGTACTGCGATGAGTGGCAGGGCGGGGCGTAAAGATCTGGATCCGGCTTACTAAAAGCC
AGATAACAGTATGCGTATTTGCGCGCTGATTTTTGCGGTATAAGAATATATACTGATATGTATACCCGAAGTATGTCAAAAAGAGGTA
TGCTATGAAGCAGCGTATTACAGTGACAGTTGACAGCGACAGCTATCAGTTGCTCAAGGCATATATGATGTCAATATCTCCGGTCTGGT
AAGCACAACCATGCAGAATGAAGCCCGTCGTCTGCGTGCCGAACGCTGGAAAGCGGAAAATCAGGAAGGGATGGCTGAGGTCGCCCGGT
TTATTGAAATGAACGGCTCTTTTGCTGACGAGAACAGGGGCTGGTGAAATGCAGTTTAAGGTTTACACCTATAAAGAGAGAGCCGTT
ATCGTCTGTTTGTGGATGTACAGAGTGATATTATTGACACGCCCGGGCGACGGATGGTGATCCCCTGGCCAGTGCACGTCTGCTGTCA
GATAAAGTCTCCCGTGAACTTTACCCGGTGGTGCATATCGGGGATGAAAGCTGGCGCATGATGACCACCGATATGGCCAGTGTGCCGGT
CTCCGTTATCGGGGAAGAAGTGGCTGATCTCAGCCACCGCGAAAATGACATCAAAAACGCCATTAACCTGATGTTCTGGGGAATATAAA
TGTCAGGCTCCCTTATACACAGCCAGTCTGCAGGTCGACggtctcGACTCACGCCTGAGCAGGTAGTGGCTATTGCATCCAACAACGGGGG
CAGACCCGCACTGGAGTCAATCGTGGCCCAGCTTTCGAGGCCGGACCCCGCGCTGGCCGCACTCACTAATGATCATCTTGTAGCGCTGGC
CTGCCTCGGCGGACGACCCGCCTTGGATGCGGTGAAGAAGGGGCTCCCGCACGCGCCTGCATTGATTAAGCGGACCAACAGAAGGATTC
CCGAGAGGACATCACATCGAGTGGCAGGTTCCCAACTCGTGAAGAGTGAACTTGAGGAGAAAAAGTCGGAGCTGCGGCACAAATTGAA
ATACGTACCGCATGAATACATCGAACTTATCGAAATTGCTAGGAACTCGACTCAAGACAGAATCCTTGAGATGAAGGTAATGGAGTTC
TTTATGAAGGTTTATGGATACCGAGGGAAGCATCTCGGTGGATCACGAAAACCCGACGGAGCAATCTATACGGTGGGGAGCCCGATTG
ATTACGGAGTGATCGTCGACACGAAAGCCTACAGCGGTGGGTACAATCTTCCCATCGGGCAGGCAGATGAGATGCAACGTTATGTCGAA
GAAAATCAGACCAGGAACAAACACATCAATCCAAATGAGTGGTGGAAAGTGTATCCTTCATCAGTGACCGAGTTTAAGTTTTGTTTG
TCTCTGGGCATTTCAAAGGCAACTATAAGGCCCAGCTCACACGGTTGAATCACATTACGAACTGCAATGGTGCGGTTTTGTCCGTAGAG
GAACTGCTCATTGGTGGAGAAATGATCAAAGCGGGAACTCTGACACTGGAAGAAGTCAGACGCAAGTTTAACAATGGCGAGATCAATT
TCCGCTCATAA

FIG. 11I

```
> pTALEN_v2 (HD)
ATGGACTATAAGGACCACGACGGAGACTACAAGGATCATGATATTGATTACAAAGACGATGACGATAAGATGGCCCCAAAGAAGAAGC
GGAAGGTCGGTATCCACGGAGTCCCAGCAGCCGTAGATTTGAGAACTTTGGGATATTCACAGCAGCAGGAAAAGATCAAGCCCAA
AGTGAGGTCGACAGTCGCGCAGCATCACGAAGCGCTGGTGGGTCATGGGTTTACACATGCCCACATCGTAGCCTTGTCGCAGCACCCTGC
AGCCCTTGGCACGGTCGCCGTCAAGTACCAGGACATGATTGCGGCGTTGCCGGAAGCCACACATGAGGCGATCGTCGGTGTGGGGAAAC
AGTGGAGCGGAGCCCGAGCGCTTGAGGCCCTGTTGACGGTCGCGGGAGAGCTGAGAGGGCCTCCCCTTCAGCTGGACACGGGCCAGTTG
CTGAAGATCGCGAAGCGGGGAGGAGTCACGGCGGTCGAGGCGGTGCACGCGTGGCGCAATGCGCTCACGGGAGCACCCCTCAACCTGAC
AgagaccGCGGCCGCATTAGGCACCCCAGGCTTTACACTTTATGCTTCCGGCTCGTATAATGTGTGGATTTTGAGTTAGGATCCGTCGAGA
TTTTCAGGAGCTAAGGAAGCTAAAATGGAGAAAAAAATCACTGGATATACCACCGTTGATATATCCCAATGGCATCGTAAAGAACATT
TTGAGGCATTTCAGTCAGTTGCTCAATGTACCTATAACCAGACCGTTCAGCTGGATATTACGGCCTTTTTAAAGACCGTAAAGAAAAAT
AAGCACAAGTTTTATCCGGCCTTTATTCACATTCTTGCCCGCCTGATGAATGCTCATCCGGAATTCCGTATGGCAATGAAAGACGGTGA
GCTGGTGATATGGGATAGTGTTCACCCTTGTTACACCGTTTTCCATGAGCAAACTGAAACGTTTTCATCGCTCTGGAGTGAATACCACG
ACGATTTCCGGCAGTTTCTACACATATATTCGCAAGATGTGGCGTGTTACGGTGAAAACCTGGCCTATTTCCCTAAAGGGTTTATTGAG
AATATGTTTTCGTCTCAGCCAATCCCTGGGTGAGTTTCACCAGTTTTGATTTAAACGTGGCCAATATGGACAACTTCTTCGCCCCCGTT
TTCACCATGGGCAAATATTATACGCAAGGCGACAAGGTGCTGATGCCGCTGGCGATTCAGGTTCATCATGCCGTTTGTGATGGCTTCCA
TGTCGGCAGAATGCTTAATGAATTACAACAGTACTGCGATGAGTGGCAGGGCGGGCGTAAAGATCTGGATCCGGCTTACTAAAAGCC
AGATAACAGTATGCGTATTTGCGCGCTGATTTTTGCGGTATAAGAATATATACTGATATGTATACCCGAAGTATGTCAAAAAGAGGTA
TGCTATGAAGCAGCGTATTACAGTGACAGTTGACAGCGACAGCTATCAGTTGCTCAAGGCATATATGATGTCAATATCTCCGGTCTGGT
AAGCACAACCATGCAGAATGAAGCCCGTCGTCTGCGTGCCGAACGCTGGAAAGCGGAAAATCAGGAAGGGATGGCTGAGGTCGCCCGGT
TTATTGAAATGAACGGCTCTTTTGCTGACGAGAACAGGGGCTGGTGAAATGCAGTTTAAGGTTTACACCTATAAAAGAGAGAGCCGTT
ATCGTCTGTTTGTGGATGTACAGAGTGATATTATTGACACGCCCGGGCGACGGATGGTGATCCCCCTGGCCAGTGCACGTCTGCTGTCA
GATAAAGTCTCCCGTGAACTTTACCCGGTGGTGCATATCGGGGATGAAAGCTGGCGCATGATGACCACCGATATGGCCAGTGTGCCGGT
CTCCGTTATCGGGGAAGAAGTGGCTGATCTCAGCCACCGCGAAAATGACATCAAAAACGCCATTAACCTGATGTTCTGGGGAATATAAA
TGTCAGGCTCCCTTATACACAGCCAGTCTGCAGGTCGACggtctcGACTCACGCCTGAGCAGGTAGTGGCTATTGCATCCCATGACGGGGG
CAGACCCGCACTGGAGTCAATCGTGGCCCAGCTTTCGAGGCCGGACCCCGCGCTGGCCGCACTCACTAATGATCATCTTGTAGCGCTGGC
CTGCCTCGGCGGACGACCCGCCTTGGATGCGGTGAAGAAGGGGCTCCCGCACGCGCCTGCATTGATTAAGCGGACCAACAGAAGGATTC
CCGAGAGGACATCACATCGAGTGGCAGGTTCCCAACTCGTGAAGAGTGAACTTGAGGAGAAAAAGTCGGAGCTGCGGCACAAATTGAA
ATACGTACCGCATGAATACATCGAACTTATCGAAATTGCTAGGAACTCGACTCAAGACAGAATCCTTGAGATGAAGGTAATGGAGTTC
TTTATGAAGGTTTATGGATACCGAGGGAAGCATCTCGGTGGATCACGAAAACCCGACGGAGCAATCTATACGGTGGGGAGCCCGATTG
ATTACGGAGTGATCGTCGACACGAAAGCCTACAGCGGTGGGTACAATCTTCCCATCGGGCAGGCAGATGAGATGCAACGTTATGTCGAA
GAAAATCAGACCAGGAACAAACACATCAATCCAAATGAGTGGTGGAAAGTGTATCCTTCATCAGTGACCGAGTTTAAGTTTTTGTTTG
TCTCTGGGCATTTCAAAGGCAACTATAAGGCCCAGCTCACACGGTTGAATCACATTACGAACTGCAATGGTGCGGTTTTGTCCGTAGAG
GAACTGCTCATTGGTGGAGAAATGATCAAAGCGGGAACTCTGACACTGGAAGAAGTCAGACGCAAGTTTAACAATGGCGAGATCAATT
TCCGCTCATAA
```

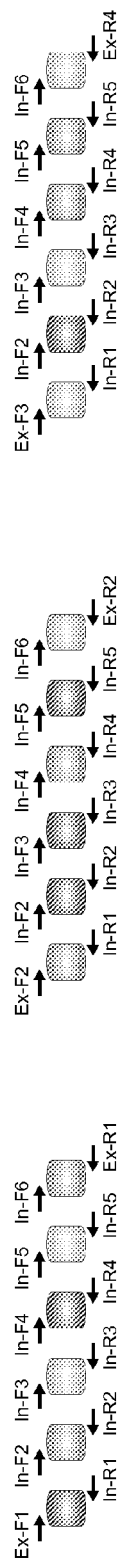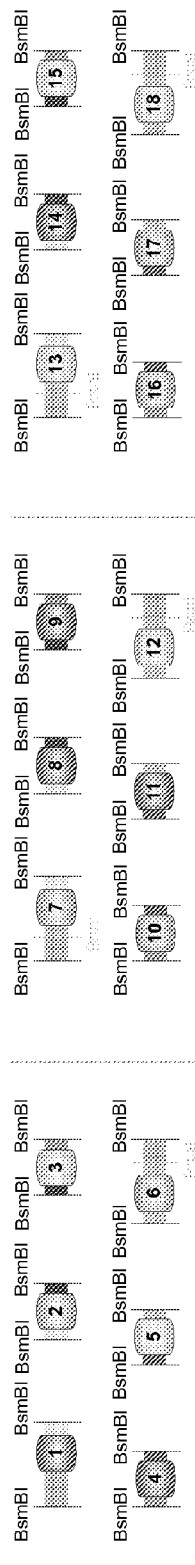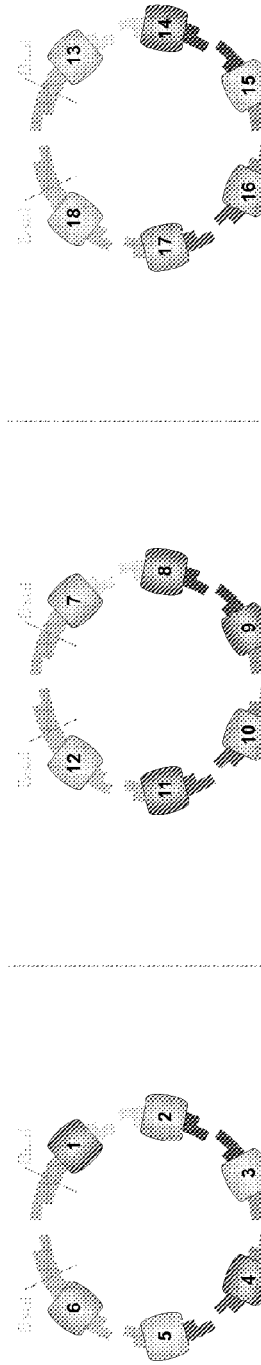
FIG. 12A

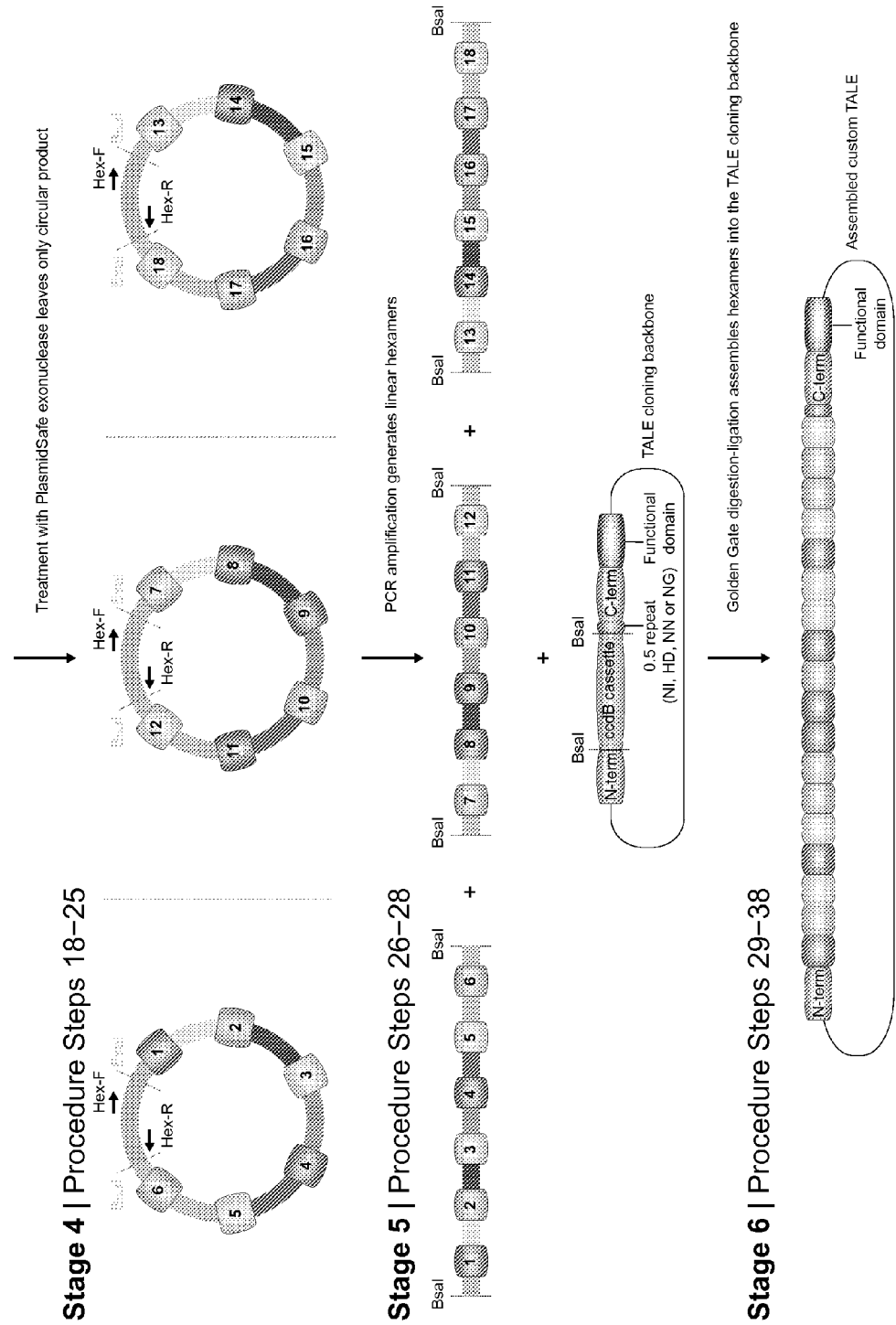

FIG. 15

| Name | Sequence | Purpose |
|---|---|---|
| Ex-F1 | 5'-TGCGTCcgtctcCGAACCTTAAACCGGCCAACATACCggtctcCTGACCCCAGAGCAGGTCGTG-3' | Monomer amplification (primers Ex-F1 through In-R5) |
| Ex-F2 | 5'-TGCGTCcgtctcCGAACCTTAAACCGGCCAACATACCggtctcGACTTACACCCGAACAAGTCGTGGCAATTGCCAGC-3' | |
| Ex-F3 | 5'-TGCGTCcgtctcCGAACCTTAAACCGGCCAACATACCggtctcGCGGGCCTCACCCCAGAGCAGGTCG-3' | |
| Ex-F4 | 5'-TGCGTCcgtctcCGAACCTTAAACCGGCCAACATACCggtctcGTGGGCTCACCCCAGAGCAGGTCG-3' | |
| Ex-R1 | 5'-GCTGACcgtctcCGTTCAGTCTGTCTTTCCCCTTTCCggtctcTAAGTCCGTGCGCTTGGCAC-3' | |
| Ex-R2 | 5'-GCTGACcgtctcCGTTCAGTCTGTCTTTCCCCTTTCCggtctcAGCCGTGCGCTTGGCACAG-3' | |
| Ex-R3 | 5'-GCTGACcgtctcCGTTCAGTCTGTCTTTCCCCTTTCCggtctcTCCCATGGGCCTGACATAACACAGGCAGCAACCTCTG-3' | |
| Ex-R4 | 5'-GCTGACcgtctcCGTTCAGTCTGTCTTTCCCCTTTCCggtctcTGAGTCCGTGCGCTTGGCAC-3' | |
| In-F2 | 5'-CTTGTTATGGCGAGTTGCCcgtctcGTATGCCAGAGCAGGTCGTGGC-3' | |
| In-F3 | 5'-CCAAAGATTCAACCGTCCTGcgtctcGAACCCCAGAGCAGGTCGTG-3' | |
| In-F4 | 5'-TATTCATGCTTGGACGGACTcgtctcGGTTGACCCCAGAGCAGGTCGTG-3' | |
| In-F5 | 5'-GTCCTAGTGAGGAATACCGGcgtctcGCCTGACCCCAGAGCAGGTCGTG-3' | |
| In-F6 | 5'-TTCCTTGATACCGTAGCTCGcgtctcGGACACCAGAGCAGGTCGTGGC-3' | |
| In-R1 | 5'-TCTTATCGGTGCTTCGTTCTcgtctcCCGTAAGTCCGTGCGCTTGGCAC-3' | |
| In-R2 | 5'-CGTTCTTTCCGGTCGTTAGcgtctcTGGTTAGTCCGTGCGCTTGGCAC-3' | |
| In-R3 | 5'-TGAGCCTTATGATTTCCGTcgtctcTCAACCCGTGCGCTTGGCACAG-3' | |
| In-R4 | 5'-AGTCTGTCTTTCCCCTTTCCcgtctcTCAGGCCGTGCGCTTGGCACAG-3' | |
| In-R5 | 5'-CCGAAGAATCGCAGATCCTAcgtctcTTGTCAGTCCGTGCGCTTGGCAC-3' | |
| Hex-F | 5'-CTTAAACCGGCCAACATACC-3' | Hexamer amplification |
| Hex-R | 5'-AGTCTGTCTTTCCCCTTCC-3' | |
| TALE-Seq-F1 (aka colony PCR forward) | 5'-CCAGTTGCTGAAGATCGCGAAGC-3' | Sequencing forward primer used to check monomers 1-6; also used as colony PCR forward primer |
| TALE-Seq-F2 | 5'-ACTTACACCCGAACAAGTCG-3' | Sequencing forward primer used to check monomers 7-12 |
| TALE-Seq-R1 (aka colony PCR reverse) | 5'-TGCCACTCGATGTGATGCCTC-3' | Sequencing primer used to check monomers 13-18 for TALEs with less than 18 full monomer repeats, and used to check monomers 19-24 for TALEs with more than 18 monomers (use TALE-Seq-R2 to check monomers 13-18 in this case); also used as colony PCR reverse primer |
| TALE-Seq-R2 | 5'-CCCATGGGCCTGACATAA-3' | Sequencing reverse primer used to check monomers 13-18 in TALEs with more than 18 full monomer repeats |

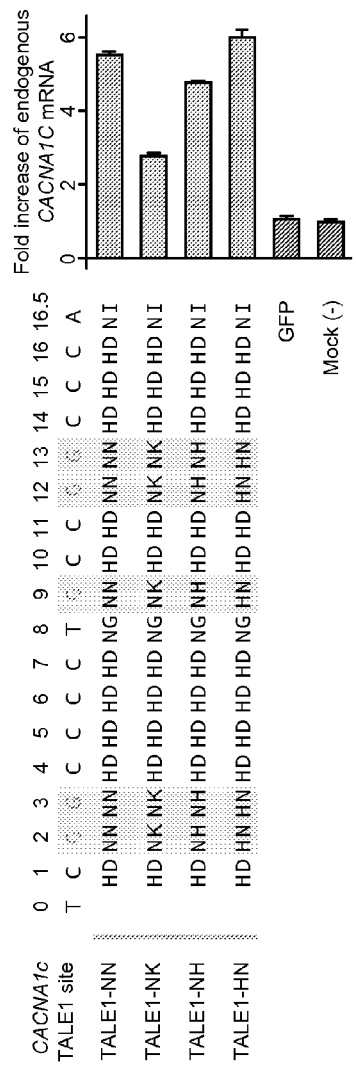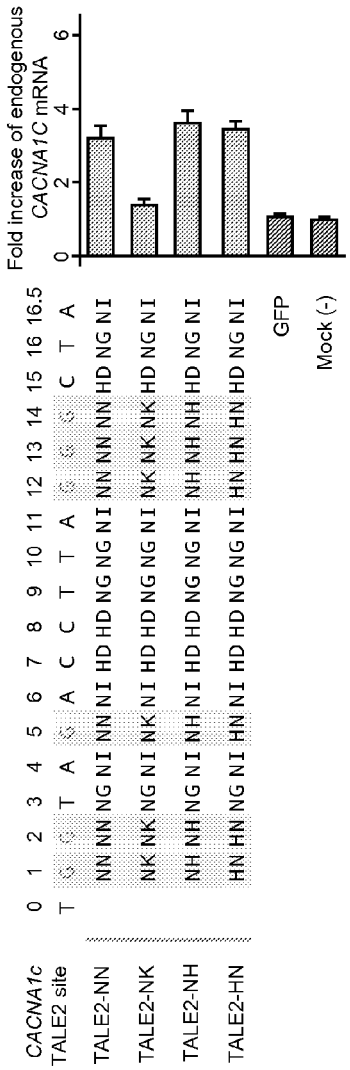

Fig. 24A

| SEQ ID NO.s | Monomers (RVD removed) | Frequency |
|---|---|---|
| 110 | LTPDQVVAIASGGKQALETVQRLLPVLCQDHG | 754 |
| 111 | LTPEQVVAIASGGKQALETVQRLLPVLCQAHG | 278 |
| 112 | LTPDQVVAIASGGKQALETVQRLLPVLCQAHG | 254 |
| 113 | LTPAQVVAIASGGKQALETVQRLLPVLCQAHG | 147 |
| 114 | LTPAQVVAIASGGKQALETVQRLLPVLCQDHG | 143 |
| 115 | LTPDQVVAIASGGKQALETVQRLLPVLCEQHG | 107 |
| 116 | LTPDQVVAIANGGKQALETVQRLLPVLCQDHG | 72 |
| 117 | LTLDQVVAIASGGKQALETVQRLLPVLCQDHG | 47 |
| 118 | LTPQQVVAIASGGKQALETVQRLLPVLCQAHG | 47 |
| 119 | LTPDQVVAIANGGKQALETVQRLLPVLCQAHG | 40 |
| 120 | LTPNQVVAIASGGKQALETVQRLLPVLCQDHG | 35 |
| 121 | LTLDQVVAIASGGKQALETVQRLLPVLCQAHG | 27 |
| 122 | LTPAQVVAIANGGKQALETVQRLLPVLCQDHG | 20 |
| 123 | LTPEQVVAIASGGKQALETVQALLPVLCQAHG | 19 |
| 124 | LTLDQVVAIASGSKQALETVQRLLPVLCQDHG | 19 |
| 125 | LTQDQVVAIASGGKQALETVQRLLPVLCQDHG | 18 |
| 126 | LSPDQVVAIASGGKQALETVQRLLPVLCQDHG | 13 |
| 127 | LTPDQVVAIANGGKQALETLQRLLPVLCQDHG | 13 |
| 128 | LTPDQVVAIASGGKQALETLQRLLPVLCQDHG | 11 |
| 129 | LTPDQVVAIASGGKQALETVQRLLPVLRQAHG | 11 |
| 130 | LTPDQVVAIASGGNQALETVQRLLPVLCQAHG | 11 |
| 131 | LTPDQVVAIASGGKQALATVQRLLPVLCQAHG | 10 |
| 132 | LTPAQVVAIANGGKQALETVQRLLPVLCQAHG | 9 |
| 133 | LTLAQVVAIASGGKQALETVQRLLPVLCQAHG | 9 |
| 134 | LTPEQVVAIACGGKQALETVQRLLPVLCQAHG | 9 |
| 135 | LTPAQVVAIASGGKQALETVQQLLPVLCEQHG | 9 |
| 136 | LTPQQVVAIASGGRPALETVQRLLPVLCQAHG | 9 |
| 137 | LTPDQVVAIASGSKQALETVQRLLPVLCQDHG | 8 |
| 138 | LTPNQVVAIASGGKQALETVQRLLPVLCQAHG | 8 |
| 139 | LTPDQVVAIASGGKQALGTVQRLLPVLCQDHG | 8 |
| 140 | LTLAQVVAIASGGKQALETVQRLLPVLCQDHG | 8 |
| 141 | LTPAQAVAIASGGKQALETVQRLLPVLCQDHG | 7 |
| 142 | LTPAQVVAIASGGNQALETVQRLLPVLCQDHG | 7 |
| 143 | LTPDQVVAIASGGKQALETLQRLLPVLCQAHG | 7 |
| 144 | LTPDQVVAIANGGKQALETLQRLLPVLCQAHG | 7 |
| 145 | LTPDQVVTIASGGKQALETVQRLLPVLCQDHG | 7 |
| 146 | LTPAQVVAIANGGKQALETVRRLLPVLCQDHG | 7 |
| 147 | LTPDQVVAIASGGNQALETVQRLLPVLCQDHG | 6 |
| 148 | LTPDQVVAIASGGKQALETVQRLLPVLCQTHG | 6 |
| 149 | LPPDQVVAIASGGKQALETVQRLLPVLCQDHG | 6 |

Fig. 24B

| SEQ ID NO.s | Monomers (RVD removed) | Frequency |
|---|---|---|
| 150 | LTSDQVVAIASGGKQALETVQRLLPVLCQDHG | 6 |
| 151 | LTPAQVVAIASGGKQALETVQRLLPVLCEQHG | 6 |
| 152 | LIPAQVVAIASGGKQALETVQRLLPVLCQDHG | 5 |
| 153 | LTPAQVVAIASGGKQALETMQRLLPVLCQAHG | 5 |
| 154 | LTRDQVVAIASGGKQALETVQRLLPVLCQDHG | 5 |
| 155 | LTPDQVVATASGGKQALETVQRLLPVLCQDHG | 5 |
| 156 | LIPDQVVAIANGGKQALETVQRLLPVLCQAHG | 5 |
| 157 | LTPDQVVAIASGGKQALETVQRLLPVLCQNHG | 5 |
| 158 | LTLDQVVAIASGGKKALETVQRLLPVLCQDHG | 4 |
| 159 | LTPDQLVAIANGGKQALETVQRLLPVLCQDHG | 4 |
| 160 | LTPDQVVAIASGGKQALETVQRLLPVLCQGHG | 4 |
| 161 | LTPDQVVAIASGGKQALETVQRLLPVLCQEHG | 4 |
| 162 | LTLDKVVAIASGGKQALETVQRLLPVLCQDHG | 4 |
| 163 | LTPAQVVAIASGSKQALETVQRLLPVLCQAHG | 4 |
| 164 | LTPDKVVAIASGGKQALETVQRLLPVLCQAHG | 4 |
| 165 | LTQDQVVAIASGGKQALETVQRLLPVLYQDHG | 4 |
| 166 | LTPAQVVAIVSGGKQALETVQRLLPVLCQAHG | 4 |
| 167 | LTPDKVVAIANGGKQALETVQRLLPVLCQDHG | 4 |
| 168 | LTQDQVVAIASGGKQALETVQRLLPVLCQAHG | 4 |
| 169 | LTPDQVMAIANGGKQALETVQRLLPVLCQDHG | 4 |
| 170 | LTTDQVVAIASGGKQALETVQRLLPVLCQAHG | 4 |
| 171 | LTPDQVVAIASGSKQALETVQRLLPVLCQAHG | 3 |
| 172 | LTPDQVVAIANGGKQALETVQRLLLVLCQAHG | 3 |
| 173 | LTQEQVVAIASGGKQALETVQRLLPVLCQAHG | 3 |
| 174 | LTPDQVVTIANGGKQALETVQRLLPVLCQAHG | 3 |
| 175 | LSPAQVVAIASGGKQALETVQRLLPVLCHDHG | 3 |
| 176 | LTPDQVVAIASGGKQALEMVQRLLPVLCQAHG | 3 |
| 177 | LIPDQVVAIASGGKQALETVQRLLPVLCQDHG | 3 |
| 178 | LTPVQVVAIASGGKQALETVQRLLPVLCQDHG | 3 |
| 179 | LTPDQVVAIASGGKQALKTVQRLLPVLCQDHG | 3 |
| 180 | LTPDQVVAIASGGKQALETMQRLLPVLCQAHG | 3 |
| 181 | LTPAQVVAIASGGKQALETVQRLFPVLCQDHG | 3 |
| 182 | LTPAQVVAIASGGKQALETVQQLLPVLCQAHG | 3 |
| 183 | LTPAQVVALSGGKQALETVQRLLPVLCQDHG | 3 |
| 184 | LTPDQVVAIASGGRPALETVQRLLPVLCEQHG | 3 |
| 185 | LTPDQVVAIASGGKQALATVQRLLPVLCQDHG | 3 |
| 186 | LTQVQVVAIASGGKQALETVQRLLPVLCQAHG | 3 |
| 187 | LTPDQVVAIARGGKQALETVQRLLPVLCQAHG | 3 |
| 188 | LPPDQVVAIASGGKQALETVQRLLPVLCQAHG | 3 |
| 189 | LTLDQVVAIASGSKQALETVQRLLPVLCQAHG | 3 |

Fig. 24C

| SEQ ID NO.s | Monomers (RVD removed) | Frequency |
|---|---|---|
| 190 | LSPDQVVAIANGGKQALETLQRLLPVLCQTHA | 3 |
| 191 | LNPDQVVAIASGGKQALETVQRLLPVLCQDHG | 3 |
| 192 | LTPDQVMAIASGGKQALETVQRLLPVLCQDHG | 3 |
| 193 | LTPAQVVAIASGGKQALETVRRLLPVLCQAHG | 3 |
| 194 | LTPDQVVAIASGGKQTLETVQRLLPVLCQDHG | 3 |
| 195 | LTPDQVMTIASGGKQALETVQRLLPVLCQDHG | 3 |
| 196 | LTPAQVVTIASGGKQALETVQRLLPVLCQDHG | 3 |
| 197 | LTPAQVVAIASGGKQALETVQRLLPVLCRAHG | 3 |
| 198 | LSPDQVVAIASGGKQALETVQRLLPVLCQAHG | 3 |
| 199 | LTPDQVVGIASGGKQALETVQRLLPVLCQDHG | 2 |
| 200 | LTPDQVVAIASGGKQALETVQRLLPVLCQANG | 2 |
| 201 | LTPAQVVAIASGGKQALETVQRLLPVLCQTHG | 2 |
| 202 | LTPDQVVAIASGGKQALEMVQRLLPVLCQDHG | 2 |
| 203 | LTPDQVVAIASGGKQALETMQRLLPVLCQDHG | 2 |
| 204 | LTPDQVVAIANGGKQALATVQRLLPVLCQDHG | 2 |
| 205 | LTPDQVVTIASGGKQALETVQRLLPVLCQAHG | 2 |
| 206 | LTPDQVVAIASGGKQALETVQRLLTVLCQDHG | 2 |
| 207 | MTPDQVVAIASGGKQALETVQRLLPVLCQDHG | 2 |
| 208 | LAPDQVVAVASGGKQALETVQRLLPVLCQDHG | 2 |
| 209 | LTPAQVVAIASGGKQALKTVQQLLPVLCEQHG | 2 |
| 210 | LTPDQVVAIARGGKQALETVQRLLPVLCQDHG | 2 |
| 211 | LTPDQVVAIASGGKQALETVQQLLPVLCQAHG | 2 |
| 212 | LTPDQVLAIASGGKQALETLQRLLPVLCQDHG | 2 |
| 213 | LTPEQVVAIARGGKQALETVQRLLPVLCQAHG | 2 |
| 214 | LTPAQVVAIASGGKQALETMQRLLPVLCRAHG | 2 |
| 215 | LTPDQVVAIANGGKQALEMVQRLLPVLCQDHG | 2 |
| 216 | LTTDQVVTIASGGKQALETVQRLLPVLCQDHG | 2 |
| 217 | LTPTQVMAIANGGKQALETVQRLLPVLCQDHG | 2 |
| 218 | LTPQQVVAIASGGKQALETVQALLPVLCQAHG | 2 |
| 219 | LTPDQVVAIASGGKQALETVQRLLPMLCQDHG | 2 |
| 220 | LTSAQVVAIANGGKQALETVQRLLPVLCQDHG | 2 |
| 221 | LTPDQVVAIASGGKQALETVQQLLPVLCQDHG | 2 |
| 222 | LTPDQVVAIANGGKQALATVQRLLPVLCQAHG | 2 |
| 223 | LTPAQVVAIASGGKQALETVQRLLPMLCQAHG | 2 |
| 224 | LTLDQVVAIASGGKQALETVQRLLPVLCQARG | 2 |
| 225 | LTPAQVVAIASGGKQALETLQRLLPVLCQDHG | 2 |
| 226 | LTPDQVVAIANGGKQALETVQRLLPVLCQNHG | 2 |
| 227 | LTPDQVVTIASGGKQALEMVQRLLPVLCQDHG | 2 |
| 228 | LTPDQVVAIASGGKQALERVQRLLPVLCEQHG | 1 |
| 229 | LTPEQVVAICGGKQALETVQALLPVLRQAHG | 1 |

Fig. 24D

| SEQ ID NO.s | Monomers (RVD removed) | Frequency |
|---|---|---|
| 230 | LTPDQVVAIASGGKQALETVQRLLPVLCRDHG | 1 |
| 231 | LTPEQVVAIASGGKQALETVQRLLPMLCQAHG | 1 |
| 232 | LTPEQVVAIACGGKQALETVQRLLPVLRHAHG | 1 |
| 233 | LTPDQVVAIASGGKQALETVQRLLPVLCQHHG | 1 |
| 234 | LIPDQVVAIASGGKQALETVQRLLPVLCQHHG | 1 |
| 235 | LTRAQVVAIASGGKQALETVQRLLPVLCEQHG | 1 |
| 236 | LTPDQVVAIANGGKQAVGTVQRLLPVLCQAHG | 1 |
| 237 | LTLDQVVAIASGGKQALETVQRLLPVLCEQHG | 1 |
| 238 | LTPAQVVAIASGGKQALETVQRLLPMLCQDHG | 1 |
| 239 | LTPDQVVAIASGSKQALETMQRLLPVLCQDHG | 1 |
| 240 | LTPDQVVAIASGGKQALETVQRLLPVLCKQHG | 1 |
| 241 | LTLDQVVAIASGGKQALETVQRLLPVLCQTHG | 1 |
| 242 | LTPDQVVAIASGGKQALEAVQRLLPVLCQDHG | 1 |
| 243 | LTPAQVVTIASGGKQALETVQRLLPVLCEQHG | 1 |
| 244 | LTPAQVMAIASGGKQALETVQRLLPVLCQDHG | 1 |
| 245 | LTREQVVAIASGGKQALETVQRLLPVLRQAHG | 1 |
| 246 | LTLAQVVAIANGGKQALETVQRLLPVLCQAHG | 1 |
| 247 | LTLEQVVAIASGGKQALETVQRLLPVLCQAHG | 1 |
| 248 | LTPQQVVAIASGGKQALETVQRLLPVLCEQHG | 1 |
| 249 | LSPDQVVAIANGGKQALETVQRLLPVLCQDHG | 1 |
| 250 | LTPDQVVAIANGGKQALETVQRLLPVLCQHHG | 1 |
| 251 | LTPEQVVAIASGGKQALETVQALLPVLRQAHG | 1 |
| 252 | LSQDQVVAIASGGKQALETVQRLLPVLCQDHG | 1 |
| 253 | LPPEQVVAIASGGKQALETVQRLLPVLCQAHG | 1 |
| 254 | LTPDQVVAIASGGKQALEAVQRLLPVLCQAHG | 1 |
| 255 | LTPDQVVAIANGGKQALETVQRLLPVLCQEHG | 1 |
| 256 | LTLDQVAAIASGGKQALETVQRLLPVLCQAHG | 1 |
| 257 | LTPDQVVAIASGGKQALETVQRVLPVLCQDHG | 1 |
| 258 | LIPAQVVAIASGGKQALETVQRLLPVLCQAHG | 1 |
| 259 | LTPAQVVAIASGGKQALETVQRLLPVLRQAHG | 1 |
| 260 | LTPAQVVAIASGSKQALETVQRLLPVLCQTHG | 1 |
| 261 | LTPQQVVAIASGGKQALETVQRLLPVLCQDHG | 1 |
| 262 | LTPDQVVAIANGGKQAVETVQRLLPVLCQAHG | 1 |
| 263 | LSPDQVVTIASGGKQALETLQRLLPVLCQDHG | 1 |
| 264 | LTPVQVVAIASGGKQALETVQRLLPVLCQAHG | 1 |
| 265 | LTLDQVVAIASGSKQALETVQRLLPVLCQTHG | 1 |
| 266 | LTPAQVVAIACGGKQALETVRRLLPVLCQAHG | 1 |
| 267 | LTPAQVVAIASGSKQALETVQRLFPVLCQAHG | 1 |
| 268 | LPPAQVVAIASGGKQALETVQRLLPVLCQAHG | 1 |
| 269 | LTPDQVVAIASGGKQALETVQRLLPVLFQEHG | 1 |

Fig. 24E

| SEQ ID NO.s | Monomers (RVD removed) | Frequency |
|---|---|---|
| 270 | LTPAKVVAIASGGKQALETVQRLLPVLCQDHG | 1 |
| 271 | LTPVQVVAIASGGKQALATVQRLLPVLCQDHG | 1 |
| 272 | LTPDQVVAIASGGKQALETVQRLLPGLCQDHG | 1 |
| 273 | LTLAQVVAIANGGKQALETVQRLLPVLCQDHG | 1 |
| 274 | LTPAQVVAIASGGKQALETVQRLLTVLCQDHG | 1 |
| 275 | LPPAQVVAIASGGKQALETVQRLLPVLCQDHG | 1 |
| 276 | LTPAQAVAIASGGKQALETVQRLLPVLCQAHG | 1 |
| 277 | LTPAQVVAIVSGGKQALETVQRLLPVLCQTHG | 1 |
| 278 | LTPDQVVAVAGGGKQALETVQRLLPVLCQDHG | 1 |
| 279 | LTPDQVVAIASGGKQALGTVQRLLPVLCQAHG | 1 |
| 280 | LPPAQVVAIASGGKQALETVQRLLPVLCEAHG | 1 |
| 281 | LTTDQVVAIASGGKQALETVQRLLPVLCQDHG | 1 |
| 282 | LTPDQVVAIANGGKQALETVQRLVPVLCQDHG | 1 |
| 283 | LTPDQVVAIASGGKQALETVQRLLPVLCQTHA | 1 |
| 284 | LTLAQVVAIASGGKQALETVQRLLPVLCQTHG | 1 |
| 285 | LTPNQLVAIANGGKQALETVQRLLPVLCQDHG | 1 |
| 286 | LSPAQVVAIASGSKQALETVQRLLPVLCQDHG | 1 |
| 287 | LTPDQVVAIASGGKQALETVQRVLPVLCQAHG | 1 |
| 288 | LTPDQVMAIANGGKQALETVQRLLPVLCQAHG | 1 |
| 289 | LTPEQVVAIASGGRQALETVQRLLPVLCQAHG | 1 |
| 290 | LTPAQVVAIASGGKQALETVQWLLPVLCQAHG | 1 |
| 291 | LTPDKVVAIASGGKQALETVQRLLPVLCQDHG | 1 |
| 292 | LTPAQVMAIANGGKQALETVQRLLPVLCQDHG | 1 |
| 293 | LTQDQVVAIASGGKQALETVQRLLPVLCQANG | 1 |
| 294 | LTPAQVVAIASGGKPALETVQRLLPVLCEQHG | 1 |
| 295 | LTPDQVVAIASSGKQALETMQRLLPVLCQDHG | 1 |
| 296 | LTPDQVVAIASGSKQALETVQRLLPVLRQDHG | 1 |
| 297 | LTPYQVVAIASGSKQALETVQRLLPVLCQDHG | 1 |
| 298 | LTPYQVVAIASGGKQALETVQRLLPVLCQAHG | 1 |
| 299 | LTLDQVVAIASGGKQALETVQRLLPVLCQEHG | 1 |
| 300 | LTLEQVVAIASGGKQALETVQRLLLVLCQAHG | 1 |
| 301 | LTPDQVVAIASGGKQALETVRRLLQVLCQDHG | 1 |
| 302 | LTPDQVVAIASGGKQALETVQRLLPVLRQDHG | 1 |
| 303 | LTPDQVVSIANGGKQALETVQRLLPVLCQAHG | 1 |
| 304 | LTPDQVVAIANGGKQALETVQRLLPVLCQTHG | 1 |
| 305 | LTPDQVVAIASGGKQALETVKRLLPVLCQAHG | 1 |
| 306 | LTTDQVVAIANGGKQALETVQRLLPVLCQDHG | 1 |
| 307 | LIPQQVVAIASGGKQALETVQRLLPVLCQDHG | 1 |
| 308 | LTLTQVVAIASGGKQALETVQRLLPVLCQAHG | 1 |
| 309 | LTPTQVVAIASGGKQALETVQRLLPVLCQDHG | 1 |

Fig. 24F

| SEQ ID NO.s | Monomers (RVD removed) | Frequency |
|---|---|---|
| 310 | LTPTQVMAIANGGKQALETVQRLLPVLCQAHG | 1 |
| 311 | LTPDQVVAVASGGKQALETVQRLLPVLCQAHG | 1 |
| 312 | LTPAQVVAIASGSKQALETVQRLLPVLCQDHG | 1 |
| 313 | LTPGQVVAIASGGKRALETVQRLLPVLCQDHG | 1 |
| 314 | LTPDQVVVIASGGKQALETVQRLLPVLCQAHG | 1 |
| 315 | LPPDQVVAIASGSKQALETVQRLLPVLCQDHG | 1 |
| 316 | LTPDQVVTIANGSKQALETVQRLLPVLCQAHG | 1 |
| 317 | LTPAQVVAIASGGKQALETVQRLLQVLCQDHG | 1 |
| 318 | LTPDHVVAIASGGKQALETVQRLLPVLCQDHG | 1 |
| 319 | LTPDQVVAIASGGKQALETVQRLLQVLCQDHG | 1 |
| 320 | LTPDQVVAIASGGRQALETVQRLLPVLCEQHG | 1 |
| 321 | LHPGQVVAIASGGKQALETVQRLLPVLCQAHG | 1 |
| 322 | LTLDQVVSIASGGKQALETVQRLLPVLCQDHG | 1 |
| 323 | LTPDQVVAIASGGKQALETVQRLLPALCQDHG | 1 |
| 324 | LTPDQVVAIASGGKPALETVQRLLPVLCEQHG | 1 |
| 325 | LTPAQVVAIASGGKQALKTVQRLLPVLCQAHG | 1 |
| 326 | LTPDQVVAIASGGKRALETVQRLLPVLCQAHG | 1 |
| 327 | LNPDQVVAIASGGKQALETVQRLLPVLCQAHG | 1 |
| 328 | LTPDQVVAIASGGKQALETVKRLLPVLCQDHG | 1 |
| 329 | LTLDQVVAIANGGKQALETVQRLLPVLCQAHG | 1 |
| 330 | LTPAQVVAIASGGKQALETVQRLLPVLCRDHG | 1 |
| 331 | LTPAQVLAIASGGKQALETVQRLLTVLCQDHG | 1 |
| 332 | LTPAQVVAIASGGKQALETMQRLLPVLCQDHG | 1 |
| 333 | LTPDQVVAIASGGKQALETVQRLLPGLCQAHG | 1 |
| 334 | LTREQVVAIASGGKQALETVQALLPVLRQAHG | 1 |
| 335 | LTPAQVVAIASGGKQALETVQRLLPVLCQVHG | 1 |
| 336 | LTPNQVVAIASGGKQALETVQRLLLVLCQDHG | 1 |
| 337 | LTPDQVMAIASGGKQALETVQRLLPVLCQAHG | 1 |
| 338 | LTREQVVAIASGGKQALETVQRLLPVLCQDHG | 1 |
| 339 | LSTAQVVAIASGGKQALEGIGEQLLKLRTAPYG | 1 |
| 340 | LSTAQVVAVASGGKPALEAVRAQLLALRAAPYG | 1 |

FIG. 28
a
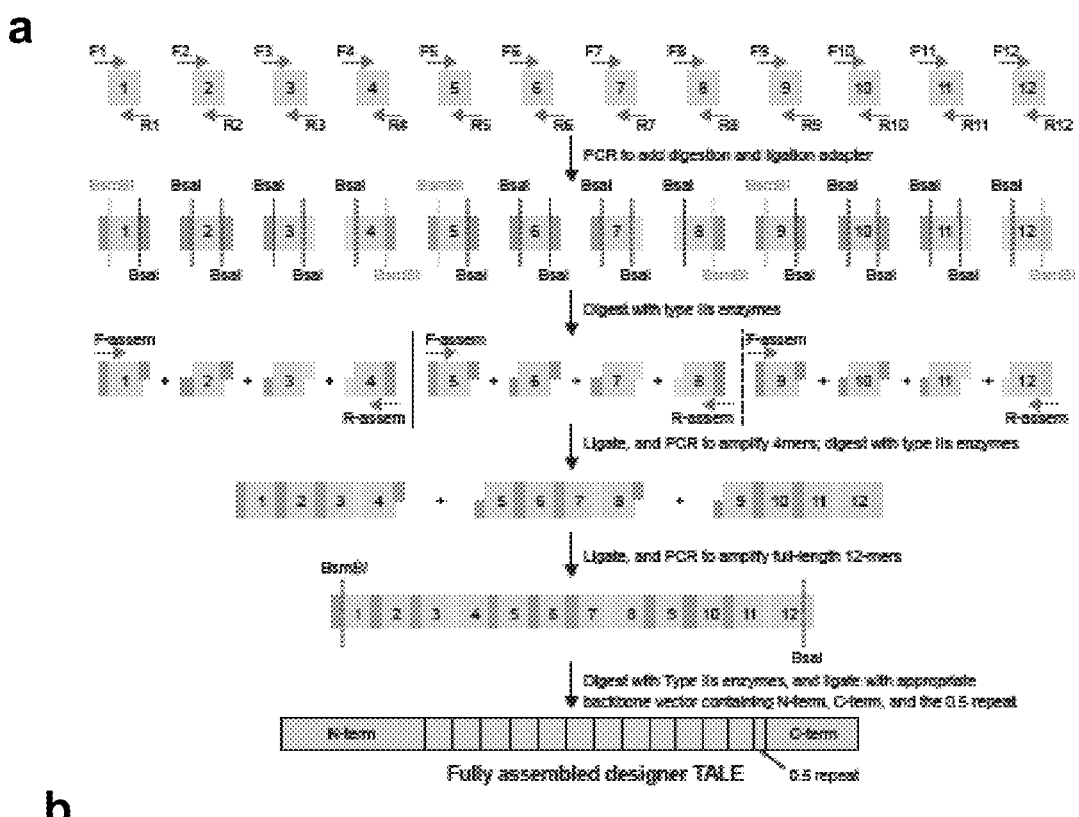
b
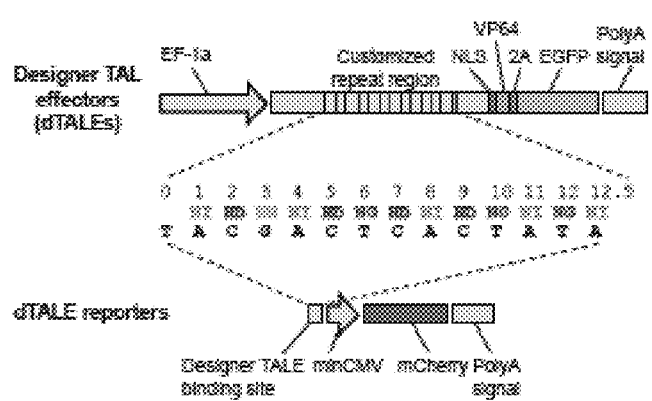
c
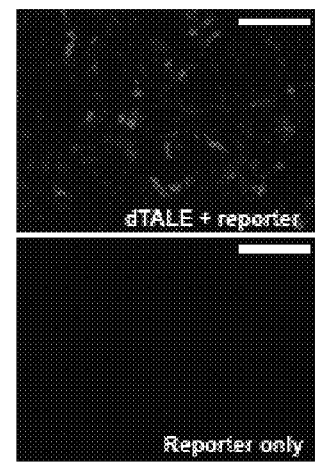

FIG. 29
a
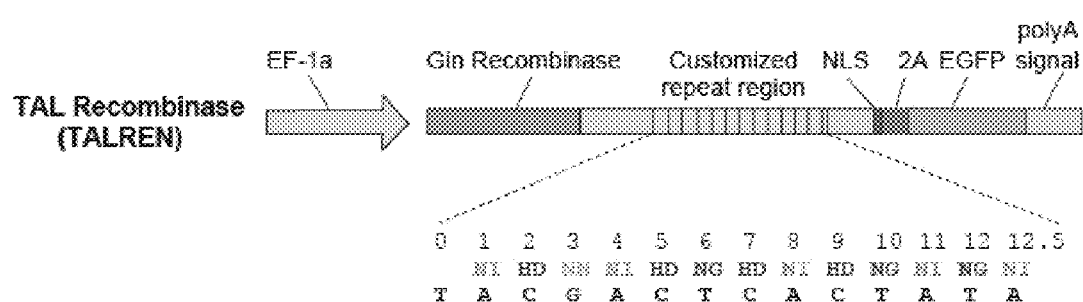
b
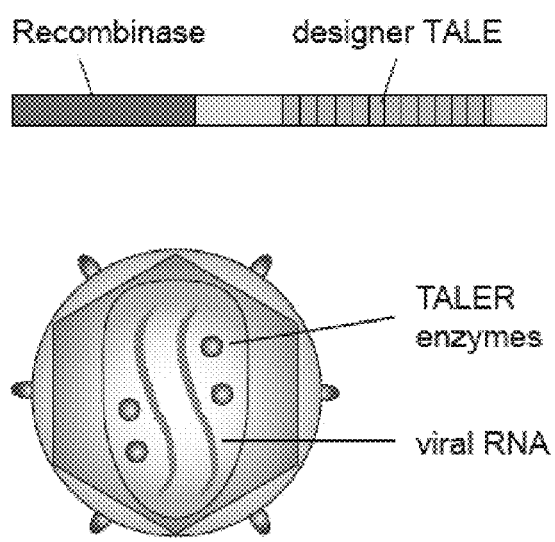

NUCLEOTIDE-SPECIFIC RECOGNITION SEQUENCES FOR DESIGNER TAL EFFECTORS

INCORPORATION BY REFERENCE

This application is a divisional of U.S. application Ser. No. 13/604,945, filed Sep. 6, 2012, which is a continuation-in-part of U.S. application serial No. 13/554,922, filed Jul. 20, 2012, which claims priority from U.S. provisional application No. 61/565,171, filed on Nov. 30, 2011.

The foregoing applications, and a10 documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any document in this application is not an admission that such document is available as prior art to the present invention.

FEDERAL FUNDING

This invention was made with government support under Grant No. 7R01NS073124-03 awarded by the National Institutes of Health. The federal government may have certain rights in this invention.

SEQUENCE LISTING

The instant application contains a Sequence Listing which has been submitted in ASCII format via EFS-Web and is hereby incorporated by reference in its entirety. Said ASCII copy, created on Sep. 5, 2012, is named 44790126.txt and is 465,621 bytes in size.

FIELD OF THE INVENTION

The present invention broadly relates to gene editing, in particular to non-naturally occurring or engineered compositions which may comprise polypeptides that bind specific nucleic acid sequences to manipulate expression of a genomic locus or gene, particularly a mammalian genomic locus or a gene in a cell or tissue; nucleic acids encoding the same; methods of generating, preparing or constructing said polypeptides and the nucleic acids encoding the same; methods encompassing application of said polypeptides and nucleic acids; host cells, vectors and kits which may comprise said polypeptides and nucleic acids encoding them and uses thereof.

BACKGROUND

Gene expression is the process by which an organism's genetic code is converted into a functional gene product and is common to all forms of life. Nearly all physiological processes depend on the regulation of gene expression and the ability to manipulate (e.g. alter, repress or activate) specific genes is a powerful tool in the life sciences. Manipulation of a cellular genome in a sequence-specific manner would have wide applications in many areas, including research, diagnostics and therapeutics. However, site-specific genome manipulation requires efficient and precise genome targeting. Thus, there is great need for improved compositions and methods that facilitate the targeting of specific genomic sites with efficiency and precision.

SUMMARY OF THE INVENTION

The present invention provides for methods of targeted manipulation of a gene or genomic locus. The manipulation may occur by means of either altering gene expression, particularly by repression or activation or by means of site-specific gene-editing particularly by the generation of site specific double-strand breaks followed by non-homologous repair or homology directed repair. In some embodiments, the methods of the invention use deoxyribonucleic acid (DNA)-binding polypeptides or proteins which may comprise one or more Transcription activator-like effector (TALE) monomers and half-monomers attached to additional sequences which include functional protein domains, to function as proteins that include but are not limited to engineered transcription factors (TALE-TFs) such as repressors and activators, engineered nucleases (TALENs), recombinases (TALERs or TALRENs, both terms are used interchangeably throughout the application), transposases, integrases, methylases, demethylases and invertases. With regards to TALEs, mention is also made of U.S. patent application Ser. Nos. 13/016,297, 13/019,526, 13/362,660, 13/218,050, 12/965,590, 13/068,735 and PCT application PCT/IB2010/000154, the disclosures of which are incorporated by reference herein in their entirety. In a preferred embodiment the gene or genomic locus is present in an animal or non-plant cell.

The present invention provides for a method of repressing expression of a genomic locus of interest in an animal cell, which may comprise contacting the genomic locus with a non-naturally occurring or engineered composition which may comprise a DNA binding polypeptide which may comprise: a N-terminal capping region, a DNA binding domain which may comprise at least five or more TALE monomers and at least one or more half-monomers specifically ordered to target the genomic locus of interest, and a C-terminal capping region, wherein these three parts of the polypeptide are arranged in a predetermined N-terminus to C-terminus orientation, wherein the polypeptide includes at least one or more repressor domains, and wherein the polypeptide is encoded by and translated from a codon optimized nucleic acid molecule so that the polypeptide preferentially binds to DNA of the genomic locus. In a preferred embodiment the animal is a mammal.

The present invention provides for a method of selectively targeting a genomic locus of interest in an animal cell, which may comprise contacting the genomic locus with a non-naturally occurring or engineered composition which may comprise a DNA binding polypeptide which may comprise: a N-terminal capping region, a DNA binding domain which may comprise at least five or more TALE monomers and at least one or more half-monomers specifically ordered to target the genomic locus of interest, and a C-terminal capping region, wherein these three parts of the polypeptide are arranged in a predetermined N-terminus to C-terminus orientation, wherein the polypeptide includes at least one or more effector domains, wherein the polypeptide is encoded by and translated from a codon optimized nucleic acid molecule so that the polypeptide preferentially binds to DNA of the genomic locus, wherein the DNA binding domain may comprise $(X_{1-11}\text{-}X_{12}X_{13}\text{-}X_{14\text{-}33 \text{ or } 34 \text{ or } 35})_z$, wherein $X_{1-11}$ is a chain of 11 contiguous amino acids, wherein $X_{12}X_{13}$ is a repeat variable diresidue (RVD), wherein $X_{14\text{-}33 \text{ or } 34 \text{ or } 35}$ is a chain of 21, 22 or 23 contiguous amino acids, wherein z is at least 5 to 40, more preferably at least 10 to 26 and wherein at least one RVD is selected from the group consisting of (a) HH, KH, NH, NK, NQ, RH, RN, SS for recognition of guanine (G); (b) SI for recognition of adenine (A); (c) HG, KG, RG for recognition of thymine (T); (d) RD, SD for recognition of cytosine (C); (e) NV, HN for recognition of A or G and (f) H*, HA, KA, N*, NA, NC, NS, RA, S*for recognition of A or T or G or C, wherein (*) means that the amino acid at $X_{13}$ is absent. In a preferred embodiment the animal is a mammal.

The present invention provides for a method of selectively targeting a genomic locus of interest in an animal cell, which may comprise contacting the genomic locus with a non-naturally occurring or engineered composition which may comprise a DNA binding polypeptide which may comprise: a N-terminal capping region, a DNA binding domain which may comprise at least five or more TALE monomers and at least one or more half-monomers specifically ordered to target the genomic locus of interest, and a C-terminal capping region, wherein these three parts of the polypeptide are arranged in a predetermined N-terminus to C-terminus orientation, wherein the polypeptide includes at least one or more effector domains, wherein the polypeptide is encoded by and translated from a codon optimized nucleic acid molecule so that the polypeptide preferentially binds to DNA of the genomic locus, wherein the DNA binding domain may comprise $(X_{1-11}\text{-}X_{12}X_{13}\text{-}X_{14\text{-}33 \text{ or } 34 \text{ or } 35})_z$, wherein $X_{1-11}$ is a chain of 11 contiguous amino acids, wherein $X_{12}X_{13}$ is a repeat variable diresidue (RVD), wherein $X_{14\text{-}33 \text{ or } 34 \text{ or } 35}$ is a chain of 21, 22 or 23 contiguous amino acids, wherein z is at least 5 to 40, more preferably at least 10 to 26, and wherein at least one of the following is present [LTLD] (SEQ ID NO: 1) or [LTLA] (SEQ ID NO: 2) or [LTQV] (SEQ ID NO: 3) at $X_{1-5}$, or [EQHG] (SEQ ID NO: 4) or [RDHG] (SEQ ID NO: 5) at positions $X_{30\text{-}33}$ or $X_{31\text{-}34}$ or $X_{32\text{-}35}$. In a preferred embodiment the animal is a mammal.

The present invention provides for a method of altering expression of a genomic locus of interest, preferably in an animal or non-plant cell, which may comprise contacting the genomic locus with a non-naturally occurring or engineered composition which may comprise a DNA binding polypeptide which may comprise a N-terminal capping region, a DNA binding domain which may comprise at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more regulatory or functional protein domains. In an advantageous embodiment of the invention the polypeptide is encoded by and expressed from a codon optimized nucleic acid molecule so that the polypeptide preferentially binds to DNA of the genomic locus. In a preferred embodiment the animal is a mammal.

The present invention provides for a method of repressing expression of a genomic locus of interest, preferably in a mammalian cell, which may comprise contacting the genomic locus with a non-naturally occurring or engineered composition which may comprise a DNA binding polypeptide which may comprise a N-terminal capping region, a DNA binding domain which may comprise at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more repressor domains. In an advantageous embodiment of the invention the polypeptide is encoded by and expressed from a codon optimized nucleic acid molecule so that the polypeptide preferentially binds to the DNA of the genomic locus.

The present invention provides for a method of repressing expression of a gene in a cell or cell line (preferably of mammalian origin), which may comprise contacting specific nucleic acids associated with the gene with a non-naturally occurring or engineered composition which may comprise a DNA binding polypeptide which may comprise a N-terminal capping region, a DNA binding domain which may comprise at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more repressor domains. In an advantageous embodiment of the invention the polypeptide is encoded by and expressed from a codon optimized nucleic acid molecule so that the polypeptide preferentially binds to DNA of the genomic locus.

The present invention also provides for a method of activating expression of a genomic locus of interest, preferably in a mammalian cell, which may comprise contacting the genomic locus with a non-naturally occurring or engineered composition which may comprise a DNA binding polypeptide which may comprise a N-terminal capping region, a DNA binding domain which may comprise at least one or more TALE monomers or half-monomers specifically ordered to target the genomic locus of interest and a C-terminal capping region, wherein these three parts are arranged in a predetermined N-terminus to C-terminus orientation and wherein the polypeptide includes at least one or more activator domains. In an advantageous embodiment of the invention the polypeptide is encoded by and expressed from a codon optimized nucleic acid molecule so that the polypeptide preferentially binds to the DNA of the genomic locus.

The present invention also provides for a method of activating expression of a gene in a cell or cell line (preferably of mammalian origin), which may comprise contacting specific nucleic acids associated with the gene with a non-naturally occurring or engineered composition which may comprise a DNA binding polypeptide which may comprise a N-terminal capping region, a DNA binding domain which may comprise at least one or more TALE monomers or half-monomers specifically ordered to target the genomic locus of interest and a C-terminal capping region, wherein these three parts are arranged in a predetermined N-terminus to C-terminus orientation and wherein the polypeptide includes at least one or more activator domains. In an advantageous embodiment of the invention the polypeptide is encoded by and expressed from a codon optimized nucleic acid molecule so that the polypeptide preferentially binds to DNA of the genomic locus.

The present invention provides for a method of altering expression of a genomic locus of interest, preferably in a mammalian cell, which may comprise contacting the genomic locus with a non-naturally occurring or engineered composition which may comprise a DNA binding polypeptide which may comprise a N-terminal capping region, a DNA binding domain which may comprise at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more recombinase domains. In an advantageous embodiment of the invention the polypeptide is encoded by and expressed from a codon optimized nucleic acid molecule so that the polypeptide preferentially binds to the DNA of the genomic locus. In a further advantageous embodiment, the polypeptide is delivered into the mammalian cell by a viral delivery system. In yet another embodiment, the viral delivery system is a lentiviral delivery system.

The present invention provides for a method of altering expression of a gene in a cell or cell line (preferably of mammalian origin), which may comprise contacting specific nucleic acids associated with the gene with a non-naturally occurring or engineered composition which may comprise a DNA binding polypeptide which may comprise a N-terminal capping region, a DNA binding domain which may comprise at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more recombinase domains. In an advantageous embodiment of the invention the polypeptide is encoded by and expressed from a codon optimized nucleic acid molecule so that the polypeptide preferentially binds to DNA of the genomic locus. In a further advantageous embodiment, the polypeptide is delivered into the cell or cell line by a viral delivery system. In yet another embodiment, the viral delivery system is a lentiviral delivery system.

The present invention also provides for a non-naturally occurring or engineered composition for preferentially binding to DNA of a genomic locus or of a gene in a cell or cell line, preferably of an animal or non-plant origin, wherein the composition may comprise a DNA binding polypeptide which may comprise: a N-terminal capping region, a DNA binding domain which may comprise at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more regulatory or functional protein domains. In an advantageous embodiment of the invention the polypeptide is encoded by and expressed from a codon optimized nucleic acid molecule so that the polypeptide preferentially binds to DNA of the genomic locus or gene.

The present invention also provides for a non-naturally occurring or engineered composition for preferentially binding to DNA of a genomic locus or of a gene in a cell or cell line, preferably of mammalian origin, wherein the composition may comprise a DNA binding polypeptide which may comprise: a N-terminal capping region, a DNA binding domain which may comprise at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more repressor domains. In an advantageous embodiment of the invention the polypeptide is encoded by and expressed from a codon optimized nucleic acid molecule so that the polypeptide preferentially binds to DNA of the genomic locus or gene.

The present invention also provides for a non-naturally occurring or engineered composition for preferentially binding to DNA of a genomic locus or of a gene in a cell or cell line, preferably of mammalian origin, wherein the composition may comprise a DNA binding polypeptide which may comprise: a N-terminal capping region, a DNA binding domain which may comprise at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more activator domains. In an advantageous embodiment of the invention the polypeptide is encoded by and expressed from a codon optimized nucleic acid molecule so that the polypeptide preferentially binds to DNA of the genomic locus or gene.

The present invention also provides for a non-naturally occurring or engineered composition for preferentially binding to DNA of a genomic locus or of a gene in a cell or cell line, preferably of mammalian origin, wherein the composition may comprise a DNA binding polypeptide which may comprise: a N-terminal capping region, a DNA binding domain which may comprise at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more recombinase domains. In an advantageous embodiment of the invention the polypeptide is encoded by and expressed from a codon optimized nucleic acid molecule so that the polypeptide preferentially binds to DNA of the genomic locus or gene.

The present invention also provides for a method of modifying the sequence of a mammalian genomic locus of interest, which may comprise contacting the genomic locus with a non-naturally occurring or engineered composition which may comprise a DNA binding polypeptide which may comprise a N-terminal capping region, a DNA binding domain which may comprise at least one or more TALE monomers or half-monomers specifically ordered to target the genomic locus of interest and a C-terminal capping region, wherein these three parts are arranged in a predetermined N-terminus to C-terminus orientation and wherein the DNA binding domain is attached to a catalytic domain of a restriction endonuclease. In an advantageous embodiment of the invention the polypeptide is encoded by and expressed from a codon optimized nucleic acid molecule so that the polypeptide preferentially binds to mammalian DNA. In an advantageous embodiment of the invention the sequence is modified by the introduction of a site-specific double strand break in the sequence which facilitates genome editing through non-homologous repair or homology directed repair. In an advantageous embodiment, an exogenous nucleic acid or DNA is introduced into the genomic locus. In an additional advantageous embodiment, integration into the genome occurs through non-homology dependent targeted integration. In certain preferred embodiments, the exogenous polynucleotide may comprise a recombinase recognition site (e.g. loxP, FLP or a Gin site) for recognition by a cognate recombinase (e.g. Cre, FRT or Gin invertase/recombinase, respectively). In certain embodiments, the exogenous sequence is integrated into the genome of an animal.

The present invention also provides for a method of modifying the sequence of a gene in a cell or cell line (preferably of mammalian origin), which may comprise contacting specific nucleic acids associated with the gene with a non-naturally occurring or engineered composition which may comprise a DNA binding polypeptide which may comprise a N-terminal capping region, a DNA binding domain which may comprise at least one or more TALE monomers or half-monomers specifically ordered to target the genomic locus of interest and a C-terminal capping region, wherein these three parts are arranged in a predetermined N-terminus to C-terminus orientation and wherein the DNA binding domain is attached to a catalytic domain of a restriction endonuclease. In an advantageous embodiment of the invention the polypeptide is encoded by and expressed from a codon optimized nucleic acid molecule so that the polypeptide preferentially binds to mammalian DNA. In an advantageous embodiment of the invention the sequence is modified by the introduction of a site-specific double strand break in the sequence which facilitates genome editing through non-homologous repair or homology directed repair. In an advantageous embodiment, an exogenous nucleic acid or DNA is introduced into the gene present in the cell or cell line. In an advantageous embodiment, an exogenous nucleic acid or DNA is introduced into the genomic locus. In an additional advantageous embodiment, integration into the genome occurs through non-homology dependent targeted integration. In certain preferred embodiments, the exogenous polynucleotide may comprise a recombinase recognition site (e.g. loxP, FLP or a Gin site) for recognition by a cognate recombinase (e.g. Cre, FRT or Gin invertase/recombinase, respectively). In certain embodiments, the exogenous sequence is integrated into the genome of an animal.

The present invention also provides for a method of construction and generation of the DNA binding polypeptides described herein which may comprise a N-terminal capping region, a DNA binding domain which may comprise at least one or more TALE monomers or half-monomers specifically ordered to target the genomic locus of interest and a C-terminal capping region. In an advantageous embodiment of the invention the polypeptide is encoded by and expressed from a codon optimized nucleic acid molecule so that the polypeptide preferentially binds to mammalian DNA. In a further advantageous embodiment, the construction of the DNA binding domain in the polypeptide uses hierarchical ligation assembly (as described in Example 2).

The present invention also provides for a method of selectively recognizing a specific nucleic acid sequence with a DNA binding polypeptide, wherein the polypeptide is constructed to include at least one or more TALE monomers and half monomers ordered or arranged in a particular orientation dictated by the sequence of the specific nucleic acid linked to additional TALE protein sequences, for efficiently recognizing the specific nucleic acid sequence.

The present invention also provides for pharmaceutical compositions which may comprise the DNA binding polypeptide or the nucleic acids encoding them. In a preferred embodiment the composition may comprise one or more pharmaceutically acceptable excipients.

In addition, advantageous embodiments of the invention include host cells, cell lines and transgenic organisms (e.g., plants, fungi, animals) which may comprise these DNA-binding polypeptides/nucleic acids and/or modified by these polypeptides (e.g., genomic modification that is passed into the next generation). Further preferred embodiments include cells and cell lines which include but are not limited to plant cells, insect cells, bacterial cells, yeast cells, viral cells, human cells, primate cells, rat cells, mouse cells, zebrafish cells, madin-darby canine cells, hamster cells, xenopus cells and stem cells. An advantageous embodiment of the invention is the cell and cell lines being of mammalian origin. In a preferred embodiment, the DNA binding polypeptide further may comprise a reporter or selection marker. In advantageous embodiments the selection marker may be a fluorescent marker, while in other aspects, the reporter is an enzyme.

Further advantageous embodiments of the invention include host cells which may comprise these polypeptides/ nucleic acids and/or modified by these polypeptides (e.g., genomic modification that is passed into the next generation). The host cell may be stably transformed or transiently transfected or a combination thereof with one or more of these protein expression vectors. In other embodiments, the one or more protein expression vectors express one or more fusion proteins in the host cell. In another embodiment, the host cell may further comprise an exogenous polynucleotide donor sequence. Any prokaryotic or eukaryotic host cells may be employed, including, but not limited to, bacterial, plant, fish, yeast, algae, insect, worm or mammalian cells. In some embodiments, the host cell is a plant cell. In other aspects, the host cell is part of a plant tissue such as the vegetative parts of the plant, storage organs, fruit, flower and/or seed tissues. In further embodiments, the host cell is an algae cell. In other embodiments, the host cell is a fibroblast. In any of the embodiments, described herein, the host cell may comprise a stem cell, for example an embryonic stem cell. The stem cell may be a mammalian stem cell, for example, a hematopoietic stem cell, a mesenchymal stem cell, an embryonic stem cell, a neuronal stem cell, a muscle stem cell, a liver stem cell, a skin stem cell, an induced pluripotent stem cell and/or combinations thereof. In certain embodiments, the stem cell is a human induced pluripotent stem cell (hiPSC) or a human embryonic stem cell (hESC). In any of the embodiments, described herein, the host cell may comprise an embryo cell, for example one or more mouse, rat, rabbit or other mammal cell embryos. In some aspects, stem cells or embryo cells are used in the development of transgenic animals, including, for example, animals with TALE-mediated genomic modifications that are integrated into the germline such that the mutations are heritable. In further aspects, these transgenic animals are used for research purposes, i.e., mice, rats, rabbits; while in other aspects, the transgenic animals are livestock animals, i.e., cows, chickens, pigs, sheep, etc. In still further aspects, the transgenic animals are those used for therapeutic purposes, i.e. goats, cows, chickens, pigs; and in other aspects, the transgenic animals are companion animals, i.e. cats, dogs, horses, birds or fish.

The present invention also provides a method for identifying suitable or novel target sequences or binding sites for engineered or designed DNA binding proteins. In some advantageous embodiments, the target site identified has an increased number of guanine nucleotides ("G") as compared to a natural or wild-type TALE target sequence. In other embodiments, the target does not require flanking thymidine nucleotides ("T"), as typical in naturally occurring TALE proteins. In some embodiments, the repeat-variable diresidues (RVDs) (the 2 hypervariable amino acids at position 12 and 13 in the TALE monomer the combination of which dictate nucleotide specificity) selected for use in the engineered DNA-binding polypeptides of the invention are one or more of NH (asparagine-histidine), RN (arginine-asparagine) or KH (lysine-histidine) RVDs for the recognition of G nucleotides in the target sequence. Hence, additionally provided in this invention are novel (non-naturally occurring) RVDs, differing from those found in nature, which are capable of recognizing nucleotide bases. Non-limiting examples of atypical or non-naturally occurring RVDs (amino acid sequences at positions 12 and 13 of the TALE monomer) include RVDs as shown in FIGS. 4A and 4B. In another advantageous embodiment, selection of RVDs may be made on the basis of their measured activity, specificity or affinity for a particular nucleotide (as described in Example 3).

Another advantageous embodiment of the invention is that in any of the compositions or methods described herein, the regulatory or functional domain may be selected from the group consisting of a transcriptional repressor, a transcriptional activator, a nuclease domain, a DNA methyl transferase, a protein acetyltransferase, a protein deacetylase, a protein methyltransferase, a protein deaminase, a protein kinase, and a protein phosphatase. In some aspects, the functional domain is an epigenetic regulator. In plants, such a TALE fusion may be removed by out-crossing using standard techniques.

A further advantageous embodiment of the invention is that in any of the compositions or methods described herein, the DNA-binding polypeptide may be encoded by a nucleic acid operably linked to a promoter, wherein the methods of altering gene expression comprise the step of first administering the nucleic acid encoding the polypeptide to a cell. In preferred embodiments the promoter may be constitutive, inducible or tissue-specific. The polypeptide of the invention may be expressed from an expression vector which include but are not limited a retroviral expression vector, an adenoviral expression vector, a lentiviral vector, a DNA plasmid expression vector and an AAV expression vector.

The present invention also provides DNA binding polypeptides with effector domains that may be constructed to specifically target nucleic acids associated with genes that encode for proteins which include but are not limited to transcription factors, proteins that may be involved with the transport of neurotransmitters, neurotransmitter synthases, synaptic proteins, plasticity proteins, presynaptic active zone proteins, post synaptic density proteins, neurotransmitter receptors, epigenetic modifiers, neural fate specification factors, axon guidance molecules, ion channels, CpG binding proteins, proteins involved in ubiquitination, hormones, homeobox proteins, growth factors, oncogenes, and proto-oncogenes.

Nucleic acids associated with a gene may be upstream of, or adjacent to, a transcription initiation site of the gene. Alternatively, the target site may be adjacent to an RNA polymerase pause site downstream of a transcription initiation site of the endogenous cellular gene. In still further embodiments, certain DNA binding proteins, e.g., TALENs bind to a site within the coding sequence of a gene or in a non-coding sequence within or adjacent to the gene; such as for example, a leader sequence, trailer sequence or intron, or within a non-transcribed region, either upstream or downstream of the coding region. Hence in preferred embodiments, polypeptides of the invention may be constructed to function as nucleases, activators or repressors to alter the expression of any of the genes which encode proteins that include but are not limited to those listed in the previous paragraph.

The present invention also provides compositions and methods for in vivo genomic manipulation. In certain embodiments, mRNAs encoding DNA binding proteins which may comprise one or more functional or regulatory protein domains may be injected into germ line cells or embryos for introducing specific double strand breaks as required.

In yet a further advantageous embodiment, provided herein are kits which may comprise the DNA binding proteins of the invention and the nucleic acid molecules encoding them. These kits may comprise plasmids, expression vectors and host cells of the invention and may be used to facilitate genomic manipulation by the user. In some instances, the kits are used for diagnostic purposes.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to them in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings, in which:

FIG. 2A-B provides amino acid sequences (SEQ ID NOS 29-32, respectively, in order of appearance) of exemplary TALE repressors.

FIG. 3 discloses SEQ ID NOS 56-59, respectively, in order of appearance.

FIG. 5 shows the G/A base specificity of CACNA1C dTALEs containing one of four different RVDs.

FIG. 6A-F provides amino acid sequences (SEQ ID NOS 38-48, respectively, in order of appearance) of exemplary CACNA1C TALE activators and repressors.

FIG. 7 discloses SEQ ID NO: 63.

FIG. 8 shows in (a) Natural structure of TALEs derived from *Xanthomonas* sp. Each DNA-binding module consists of 34 amino acids, where the RVDs in the 12th and 13th amino acid positions of each repeat specify the DNA base being targeted according to the cipher NG=T, HD=C, NI=A, and NN=G or A. The DNA-binding modules are flanked by nonrepetitive N and C termini, which carry the translocation, nuclear localization (NLS) and transcription activation (AD) domains. A cryptic signal within the N terminus specifies a thymine as the first base of the target site. FIG. 8(a) discloses SEQ ID NOS 64-65, respectively, in order of appearance. (b)

Figure 1:
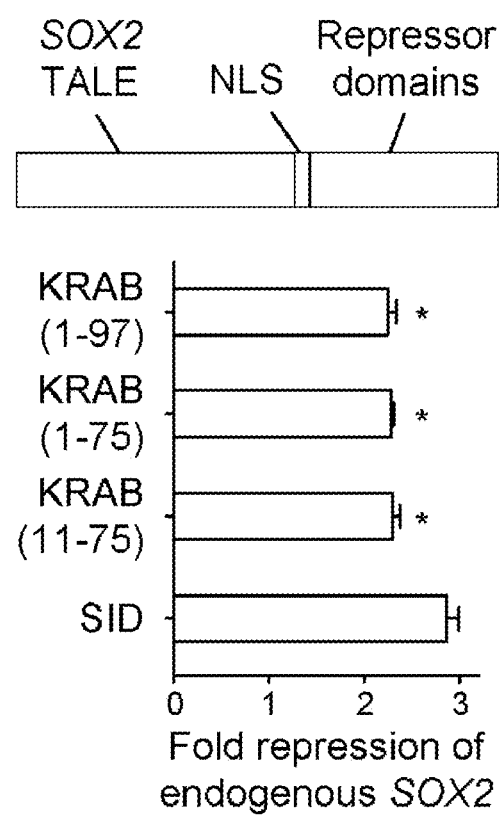
FIG. 1 is a schematic of an exemplary dTALE-repressor architecture.

The TALE toolbox allows rapid and inexpensive construction of custom TALE-TFs and TALENs. The kit consists of 12 plasmids in total: four monomer plasmids to be used as templates for PCR amplification, four TALE-TF and four TALEN cloning backbones corresponding to four different bases targeted by the 0.5 repeat. CMV, cytomegalovirus promoter; N term, nonrepetitive N terminus from the Hax3 TALE; C term, nonrepetitive C terminus from the Hax3 TALE; BsaI, type IIs restriction sites used for the insertion of custom TALE DNA-binding domains; ccdB+CmR, negative selection cassette containing the ccdB negative selection gene and chloramphenicol resistance gene; NLS, nuclear localization signal; VP64, synthetic transcriptional activator derived from VP16 protein of herpes simplex virus; 2A, 2A self-cleavage linker; EGFP, enhanced green fluorescent protein; polyA signal, polyadenylation signal; FokI, catalytic domain from the FokI endonuclease. (c) TALEs may be used to generate custom TALE-TFs and modulate the transcription of endogenous genes from the genome. The TALE DNA-binding domain is fused to the synthetic VP64 transcriptional activator, which recruits RNA polymerase and other factors needed to initiate transcription. (d) TALENs may be used to generate site-specific double-strand breaks to facilitate genome editing through nonhomologous repair or homology directed repair. Two TALENs target a pair of binding sites flanking a 16-bp spacer. The left and right TALENs recognize the top and bottom strands of the target sites, respectively. Each TALE DNA-binding domain is fused to the catalytic domain of FokI endonuclease; when FokI dimerizes, it cuts the DNA in the region between the left and right TALEN-binding sites.

FIG. 9 shows a list of applications of custom TALEs on endogenous genome targets.

FIG. 10 shows the timeline for the construction of TALE-TFs and TALENs. Steps for the construction and functional testing of TALE-TFs and TALENs are outlined. TALEs may be constructed and sequence verified in 5 d following a series of ligation and amplification steps. During the construction phase, samples may be stored at −20° C. at the end of each step and continued at a later date. After TALE construction, functional validation via qRT-PCR (for TALE-TFs) and Surveyor nuclease assay (for TALENs) may be completed in 2-3 d.

FIG. 11A-I shows a listing of sequences (SEQ ID NOS 66-77, respectively, in order of appearance) that are codon optimized for expression in human cells.

FIG. 12A-B shows a schematic of the construction process for a custom TALE containing an 18-mer tandem repeat DNA-binding domain. Stage 1: specific primers are used to amplify each monomer and add the appropriate ligation adaptors (Procedure Steps 1-9). Stage 2: hexameric tandem repeats (1-6, 7-12 and 13-18) are assembled first using Golden gate digestion-ligation. The 5' ends of monomers 1, 7 and 13 and the 3' ends of monomers 6, 12 and 18 are designed so that each tandem hexamer assembles into an intact circle (Procedure Steps 10-15). Stage 3: the Golden Gate reaction is treated with an exonuclease to remove all linear DNA, leaving only the properly assembled tandem hexamer (Procedure Steps 16 and 17). Stage 4: each tandem hexamer is amplified individually using PCR and purified (Procedure Steps 18-25). Stage 5: tandem hexamers corresponding to 1-6, 7-12 and 13-18 are ligated into the appropriate TALE-TF or TALEN cloning backbone using Golden Gate cut-ligation (Procedure Steps 26-28). Stage 6: the assembled TALE-TF or TALEN is transformed into competent cells, and successful clones are isolated and sequence verified (Procedure Steps 29-38).

Figure 13:
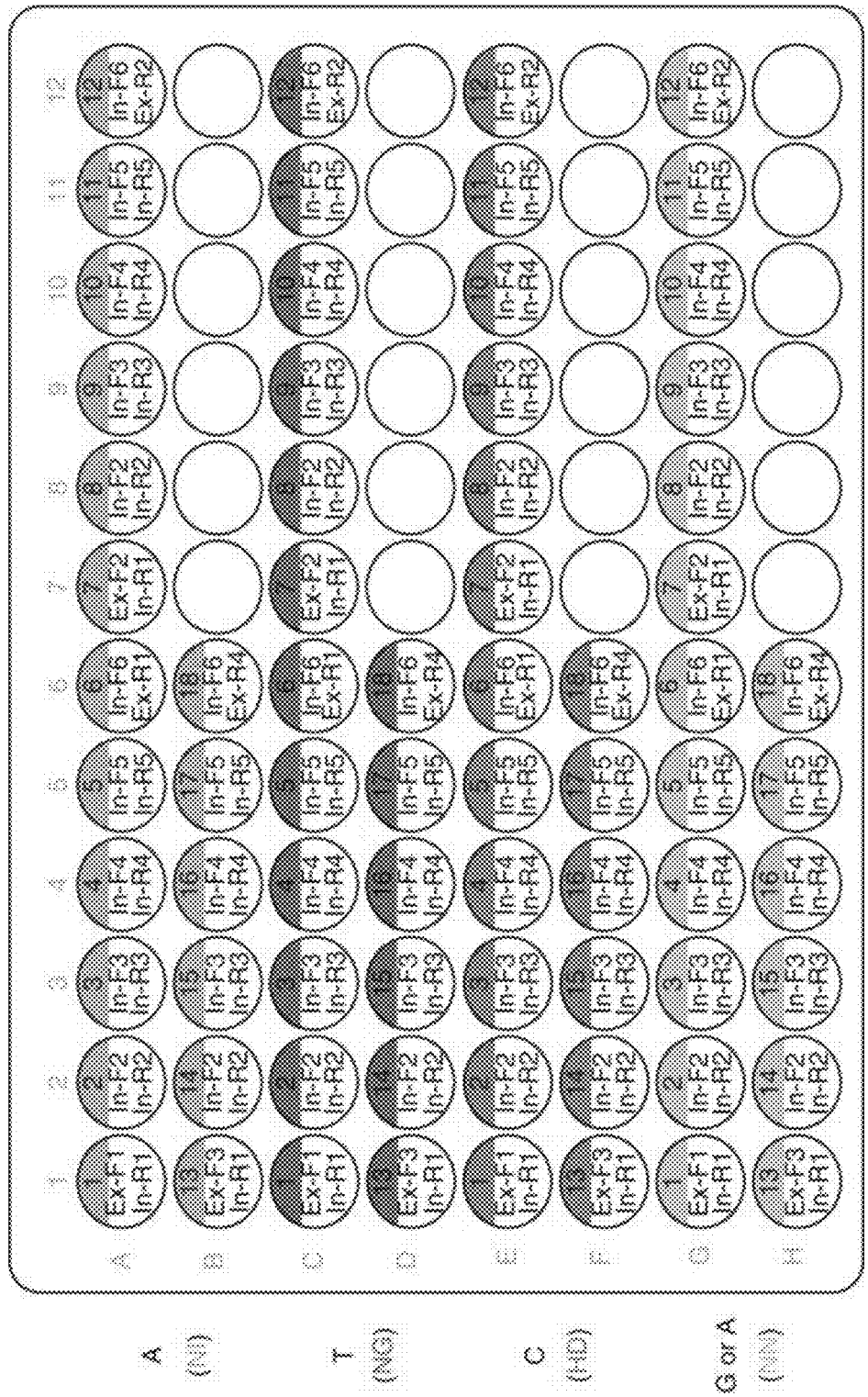

FIG. 13 shows a PCR plate setup used to generate a plate of monomers for constructing custom 18-mer TALE DNA-binding domains. One 96-well plate may be used to carry out 72 reactions (18 for each monomer template). The position of each monomer and the primers used for the position is indicated in the well. Color coding in the well indicates the monomer used as the PCR template. Typically, two to four plates of 100-μl PCRs are pooled together and purified to generate a monomer library of sufficient quantity for production of many TALEs. During TALE construction, the corresponding monomer for each DNA base in the 18-bp target sequence may be easily picked from the plate.

Figure 14:
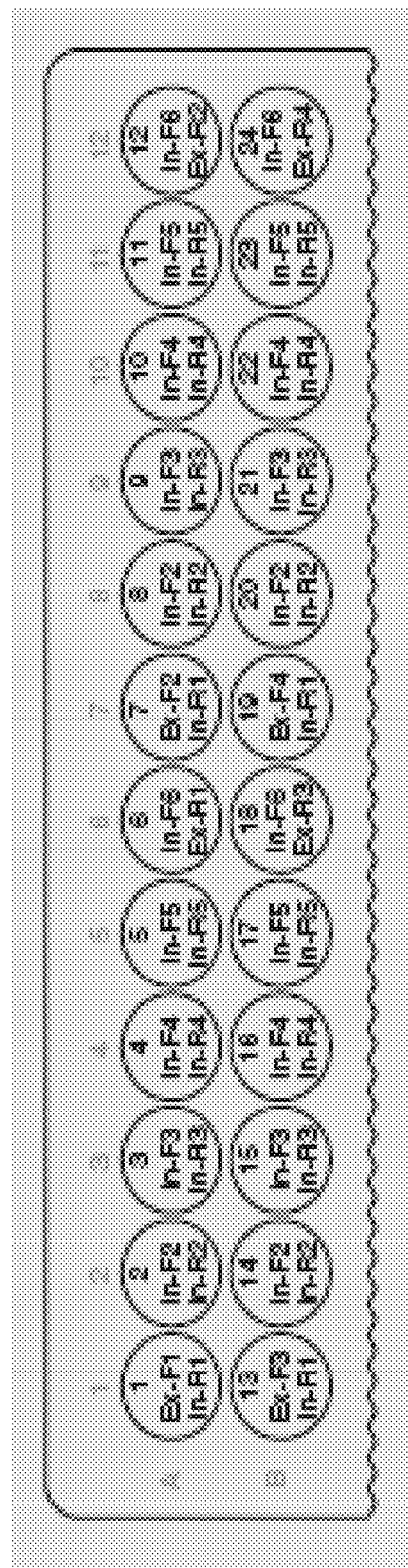

FIG. 14 shows a protocol to build TALEs that target DNA sequences of different lengths.

FIG. 15 shows a listing of primer sequences (SEQ ID NOS 78-101, respectively, in order of appearance) for TALE construction.

Figure 16:
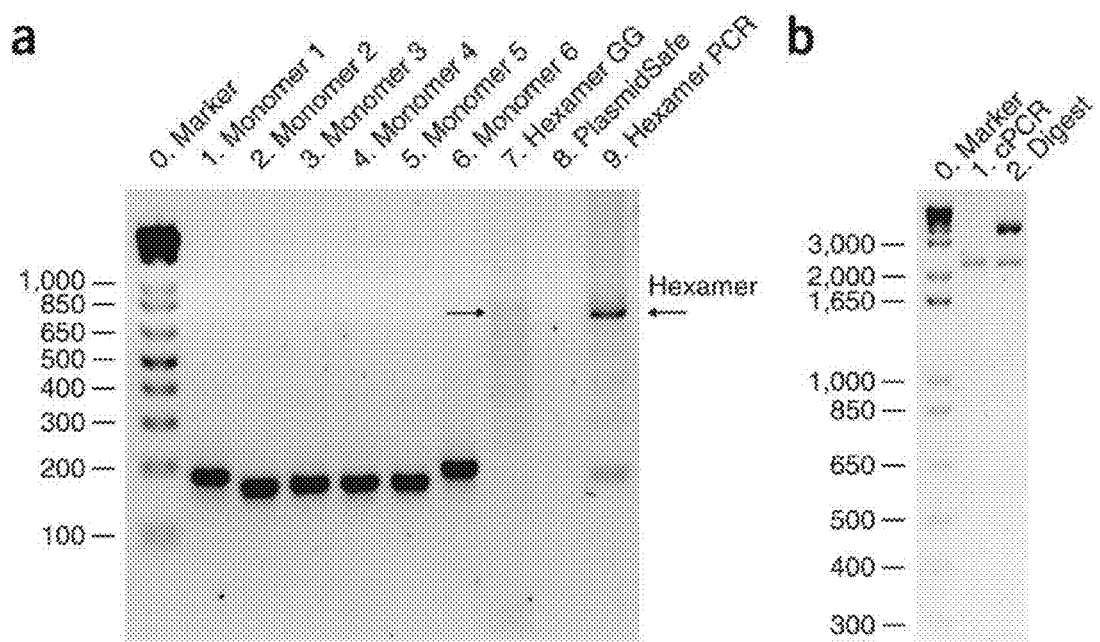

FIG. 16 shows gel results from the TALE construction process explained in Example 1 (a) Lanes 1-6: products from the monomer PCR (Stage 1 in FIG. 12) after purification and gel normalization (Procedure Steps 8 and 9). The molar concentrations of samples shown on this gel were normalized so that equal moles of monomers are mixed for downstream steps. Monomers 1 and 6 are slightly longer than monomers 2-5 because of the addition of sequences used for circularization. Lane 7: result of the hexamer Golden Gate cut-ligation (Procedure Step 15). A series of bands with size ~700 bp and lower may be seen. Successful hexamer Golden Gate assembly should show a band ~700 bp (as indicated by arrow). Lane 8: hexamer assembly after PlasmidSafe exonuclease treatment (Procedure Step 17). Typically, the amount of circular DNA remaining is difficult to visualize by gel. Lane 9: result of hexamer amplification (Procedure Step 20). A band of ~700 bp should be clearly visible. The hexamer gel band should be gel purified to remove shorter DNA fragments. (b) Properly assembled TALE-TFs and TALENs may be verified using bacterial colony PCR (2,175-bp band, lane 1; Procedure Step 35) and restriction digestion with AfeI (2,118-bp band for correctly assembled 18-mer in either backbone; other bands for TALE-TF are 165, 3,435, 3,544 bp; other bands for TALEN are 165, 2,803, 3,236 bp; the digest shown is for TALE-TF backbone vector, lane 2, see Procedure Step 35).

Figure 17:
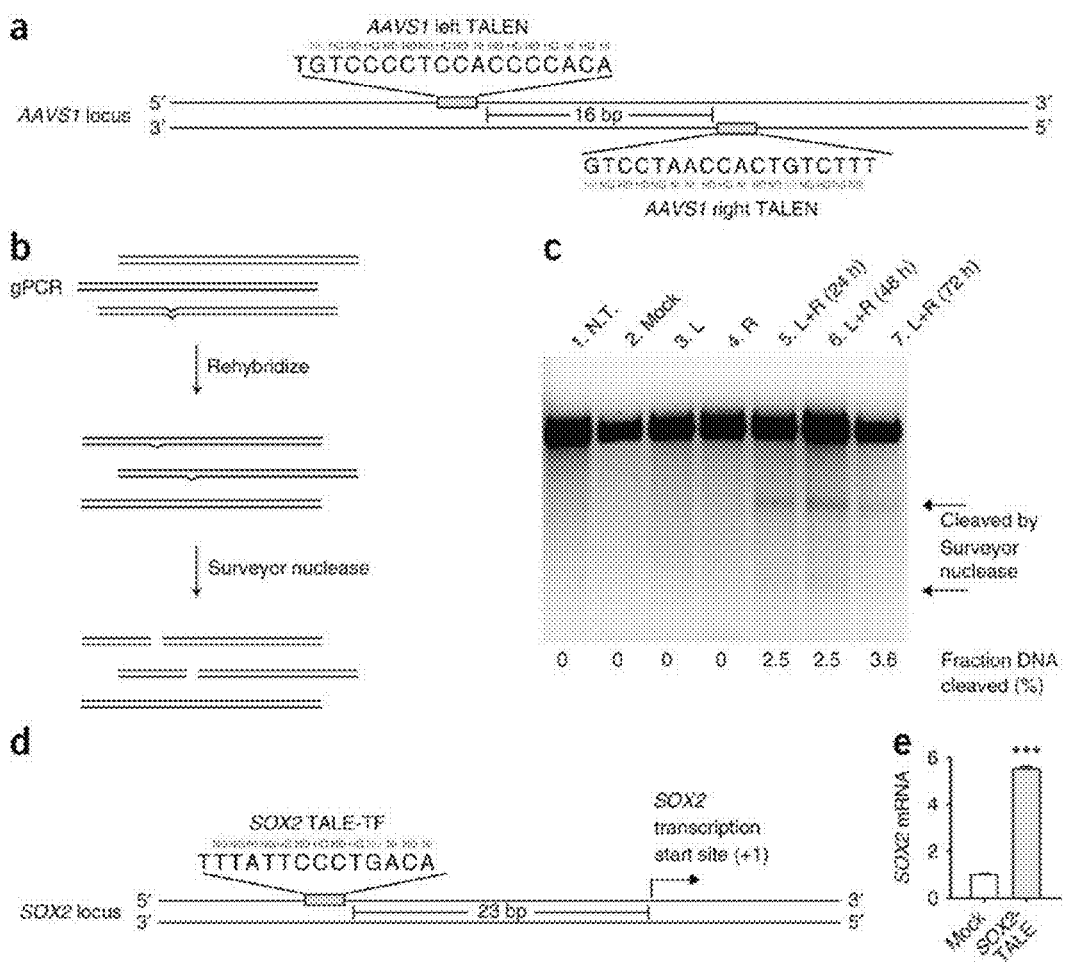

FIG. 17 shows TALE-TF and TALEN activity in 293FT cells. (a) This schematic shows a pair of TALENs designed to target the AAVS1 locus in the human genome. The TALENs target a pair of binding sites flanking a 16-bp spacer. The left and right TALENs recognize the top and bottom strands of the target sites, respectively, and each recognition site begins with a T. The nucleotide sequences (SEQ ID NOS 102-103, respectively, in order of appearance) of the target sites are shown, with the corresponding TALEN RVD specifying the DNA base being targeted shown above. Each TALE DNA-binding domain is fused to the catalytic domain of FokI endonuclease; when FokI dimerizes, it cuts the DNA in the region between the left and right TALEN-binding sites. (b) Schematic of the Surveyor nuclease assay used to determine TALEN cleavage efficiency. First, genomic PCR (gPCR) is used to amplify the TALEN target region from a heterogeneous population of TALEN-modified and TALEN-unmodified cells, and the gPCR products are reannealed slowly to generate heteroduplexes. The reannealed heteroduplexes are cleaved by Surveyor nuclease, whereas homoduplexes are left intact. TALEN cleavage efficiency is calculated based on the fraction of cleaved DNA. (c) Gel showing the Surveyor nuclease result from the AAVS1 TALEN pair. Lanes 1-4: controls from un-transfected (NT) cells and cells transfected with a plasmid carrying GFP (Mock), AAVS1 left TALEN only (L), and AAVS1 right TALEN only (R). Lanes 5-7: cells transfected with AAVS1 left and right TALENs (L+R) for 24, 48 and 72 h. The two lower bands indicated by the arrows are Surveyor-cleaved DNA products. (d) This schematic shows a TALE-TF designed to target the SOX2 locus in the human genome. The SOX2 TALE-TF recognizes the sense strand of the SOX2 proximal promoter, and the recognition site begins with T. The nucleotide sequence (SEQ ID NO: 104) of the target site is shown, with the corresponding TALEN repeat variable diresidue (RVD) specifying each DNA base being targeted shown above. The TALE DNA-binding domain is fused to the synthetic VP64 transcriptional activator, which recruits RNA polymerase and other factors needed to initiate transcription. (e) 293FT cells transfected with the SOX2 TALE-TF exhibited a five-fold increase in the amount of SOX2 mRNA compared with mock-transfected cells. Error bars indicate s.e.m.; n=3. *** indicates P<0.005. Panel e was modified with permission from ref 3.

Figure 18A:
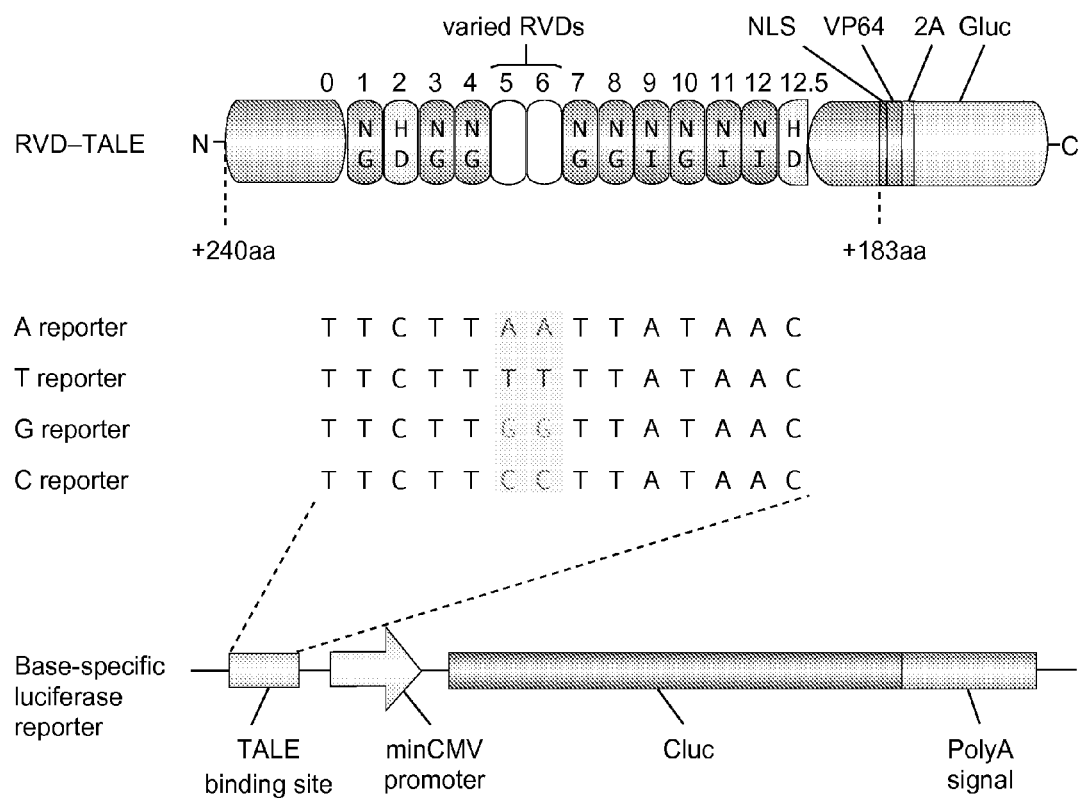
Figure 18B:
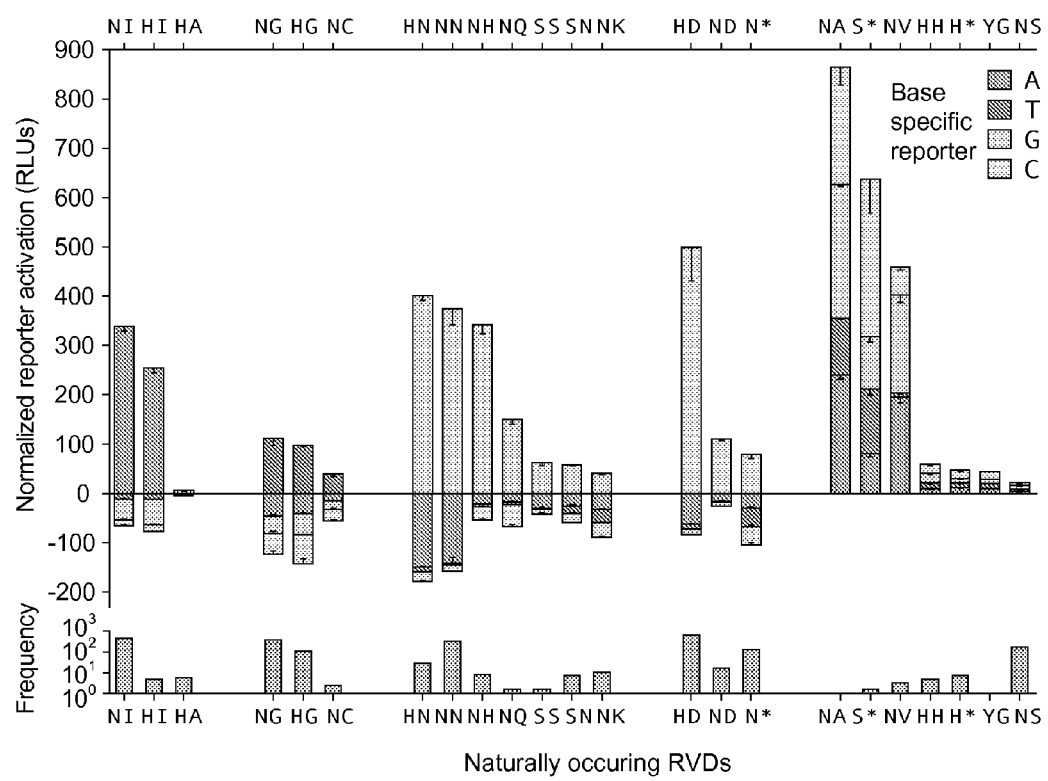

FIG. 18A-B shows a schematic for the identification of an optimal guanine-specific repeat variable diresidue (RVD). (a) Design of the TALE RVD screening system. Each RVD screening TALE (RVD-TALE) contains 12.5 repeats with RVDs 5 and 6 substituted with the 23 naturally occurring RVDs, and is fused to a *Gaussia* luciferase gene via a 2A peptide linker. The truncations used for the TALE is marked at the N- and C-termini with numbers of amino acids retained (top). Four different base-specific reporters with A, T, G, and C substituted in the 6th and 7th nucleotides of the binding site are used to determine the base-specificity of each RVD (middle). Each reporter is constructed by placing the TALE binding site upstream of a minimal CMV promoter driving *Cypridina* luciferase (bottom). FIG. 18(*a*) discloses SEQ ID NOS 56-59, respectively, in order of appearance. (b) Base-preference of each natural RVD (top) is determined by measuring the levels of relative luminescence unit (RLU) for each base-specific reporter after background subtraction and normalization based on TALE protein expression level (top). RVDs were clustered according to their base-preference after performing one-way analysis of variance (ANOVA) tests on each RVD. For RVDs with a single statistically significant reporter activity (p<0.05, one-way ANOVA), the reporter activity of the preferred base was plotted above the x axis, whereas the reporter activities for the non-preferred bases are shown below the x-axis as negative. RVDs were clustered and ranked without a single preferred base according to their total activity level. The abundance of each RVD in natural TALE sequences, as determined using all available *Xanthomonas* TALE sequences in GenBank, is plotted on a log scale (bottom). All bases in the TALE binding site are color-coded (green for A, red for T, orange for G, and blue for C). NLS, nuclear localization signal; VP64, VP64 viral activation domain; 2A, 2A peptide linker; Gluc, *Gaussia* luciferase gene; minCMV, minimal CMV promoter; Cluc, *Cypridina* luciferase gene; polyA signal, poly-adenylation signal. All results are collected from three independent experiments in HEK 293FT cells. Error bars indicate s.e.m.; n=3.

FIG. 19A-D shows the characterization of guanine-specific repeat-variable diresidues (RVDs). (a) specificity and activity of different Guanine-targeting RVDs. Schematic showing the selection of two TALE binding sites within the CACNA1C locus of the human genome. The TALE RVDs are shown above the binding site sequences and yellow rectangles indicate positions of G-targeting RVDs (left). Four different TALEs using NN, NK, NH, and HN as the putative G-targeting RVD were synthesized for each target site. The specificity for each putative G-targeting RVD is assessed using luciferase reporter assay, by measuring the levels of reporter activation of the wild-type TALE binding site and mutant binding sites, with either 2, 4, or all guanines substituted by adenine. The mutated guanines and adenines are highlighted with orange and green, respectively. FIG. 19(*a*) discloses SEQ ID NOS 63, 105-106, 60, 62, 107-108 and 61, respectively, in order of appearance. (b) Endogenous transcriptional modulation using TALEs containing putative G-specific RVDs. TALEs using NN, NK, NH, and HN as the G-targeting RVD were synthesized to target two distinct 18 bp target sites in the human CACNA1C locus. Changes in mRNA are measured using qRT-PCR as described previously. VP64, VP64 transcription activation domain. All results are collected from three independent experiments in HEK 293FT cells. Error bars indicate s.e.m.; n=3. FIG. 19(*b*) discloses SEQ ID NOS 63 and 62, respectively, in order of appearance.

Figure 20:

FIG. 20 shows the computational analysis of TALE RVD Specificity. Extensive free energy perturbation (FEP) calculations were performed for the relative binding affinities between the TALE and its bound DNA. Images show the three-dimensional configuration and results of the free energy calculation for NN:G (a) and NH:G (b) interactions from one repeat in the TALE-DNA complex. The second amino acid of the guanine-recognizing RVD (i.e., asparagine for RVD NN and histidine for RVD NH) and the guanine base of the bound double-stranded DNA are presented in space filling model and labeled. The free energy calculation results are listed below their corresponding structures.

Figure 21:
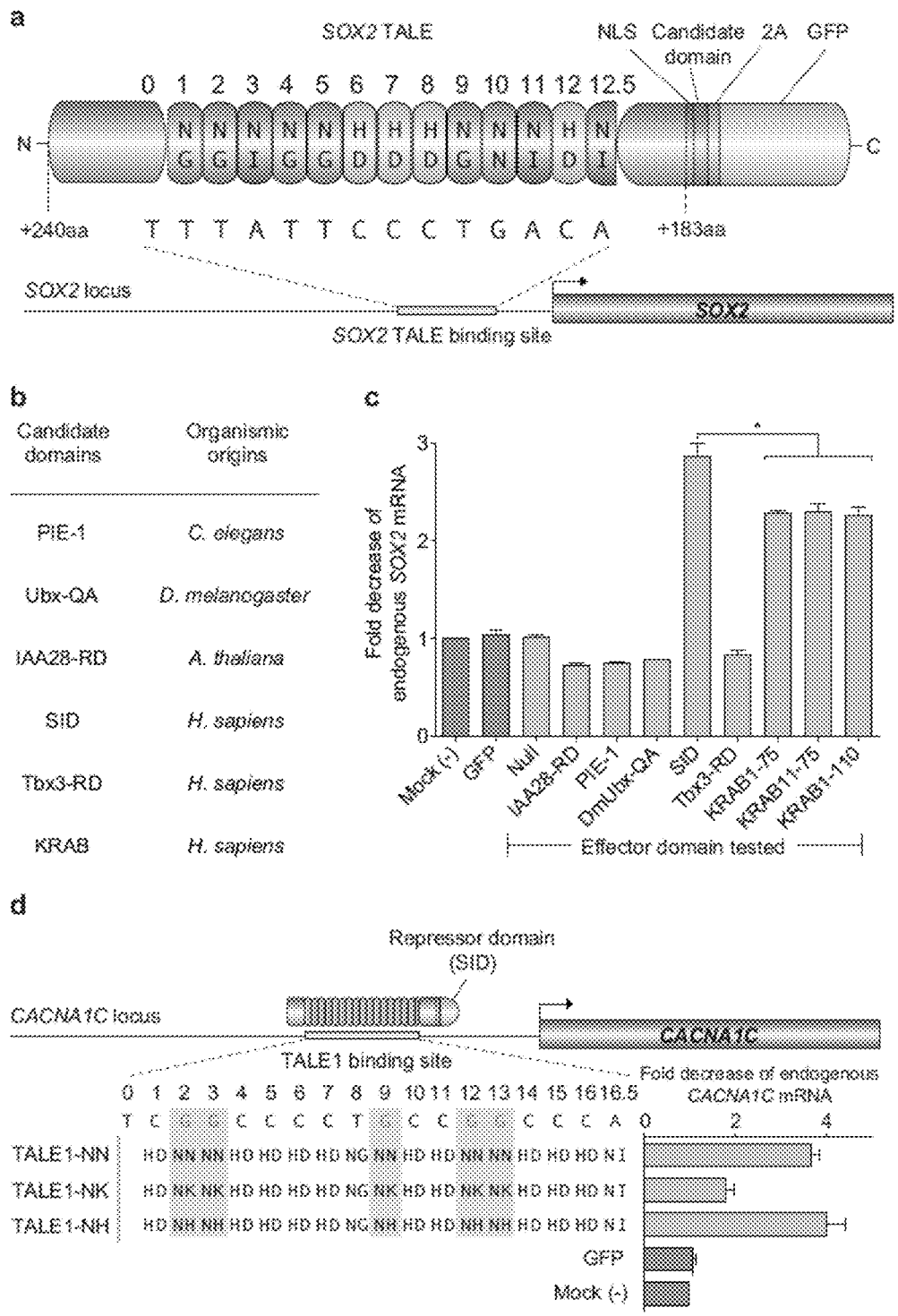

FIG. 21 shows the development of a TALE transcriptional repressor architecture. (a) Design of SOX2 TALE for TALE repressor screening. A TALE targeting a 14 bp sequence (SEQ ID NO: 104) within the SOX2 locus of the human genome was synthesized. (b) List of all repressors screened and their host origin (left). Eight different candidate repressor domains were fused to the C-term of the SOX2 TALE. (c) The fold decrease of endogenous SOX2 mRNA is measured using qRTPCR by dividing the SOX2 mRNA levels in mock transfected cells by SOX2 mRNA levels in cells transfected with each candidate TALE repressor. (d) Transcriptional repression of endogenous CACNA1C. TALEs using NN, NK, and NH as the G-targeting RVD were constructed to target a 18 bp target site (SEQ ID NO: 63) within the human CACNA1C locus (site 1 in FIG. 19). Each TALE is fused to the SID repression domain. NLS, nuclear localization signal; KRAB, Krüppel-associated box; SID, mSin interaction domain. All results are collected from three independent experiments in HEK 293FT cells. Error bars indicate s.e.m.; n=3. * p<0.05, Student's t test.

Figure 22:
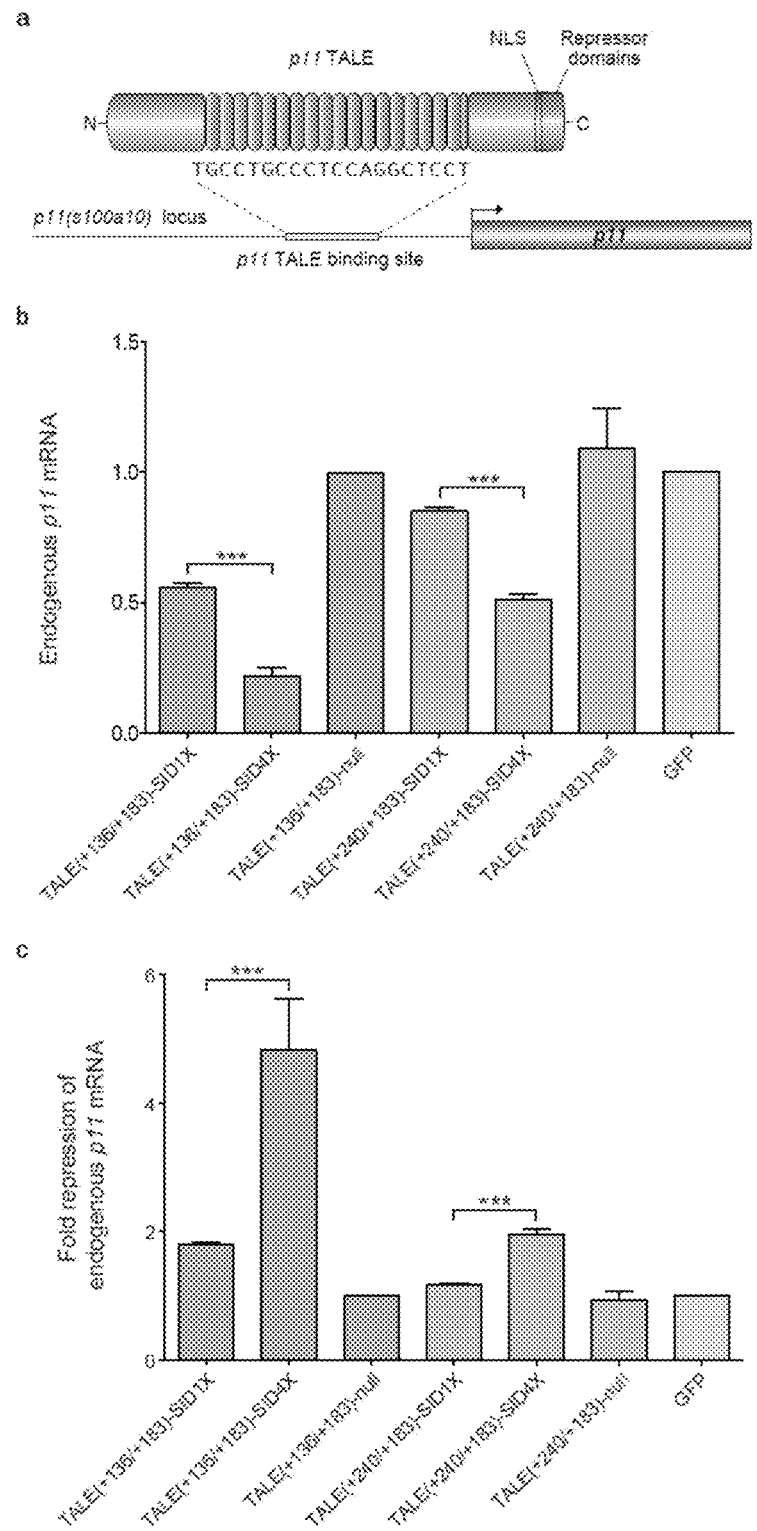

FIG. 22 shows the optimization of TALE transcriptional repressor architecture using SID and SID4X. (a) Design of p11 TALE for testing of TALE repressor architecture. A TALE targeting a 20 bp sequence (SEQ ID NO: 109) (p11 TALE binding site) within the p11 (s100a10) locus of the mouse (*Mus musculus*) genome was synthesized. (b) Transcriptional repression of endogenous mouse p11 mRNA. TALEs targeting the mouse p11 locus harboring two different truncations of the wild type TALE architecture were fused to different repressor domains as indicated on the x-axis. The value in the bracket indicate the number of amino acids at the N- and C-termini of the TALE DNA binding domain flanking the DNA binding repeats, followed by the repressor domain used in the construct. The endogenous p11 mRNA levels were measured using qRT-PCR and normalized to the level in the negative control cells transfected with a GFP-encoding construct. (c) Fold of transcriptional repression of endogenous mouse p11. The fold decrease of endogenous p11 mRNA is measured using qRT-PCR through dividing the p11 mRNA levels in cells transfected with a negative control GFP construct by p11 mRNA levels in cells transfected with each candidate TALE repressors. The labeling of the constructs along the x-axis is the same as previous panel. NLS, nuclear localization signal; SID, mSin interaction domain; SID4X, an optimized four-time tandem repeats of SID domain linked by short peptide linkers. All results are collected from three independent experiments in Neuro2A cells. Error bars indicate s.e.m.; n=3. ***p<0.001, Student's t test.

Figure 23:
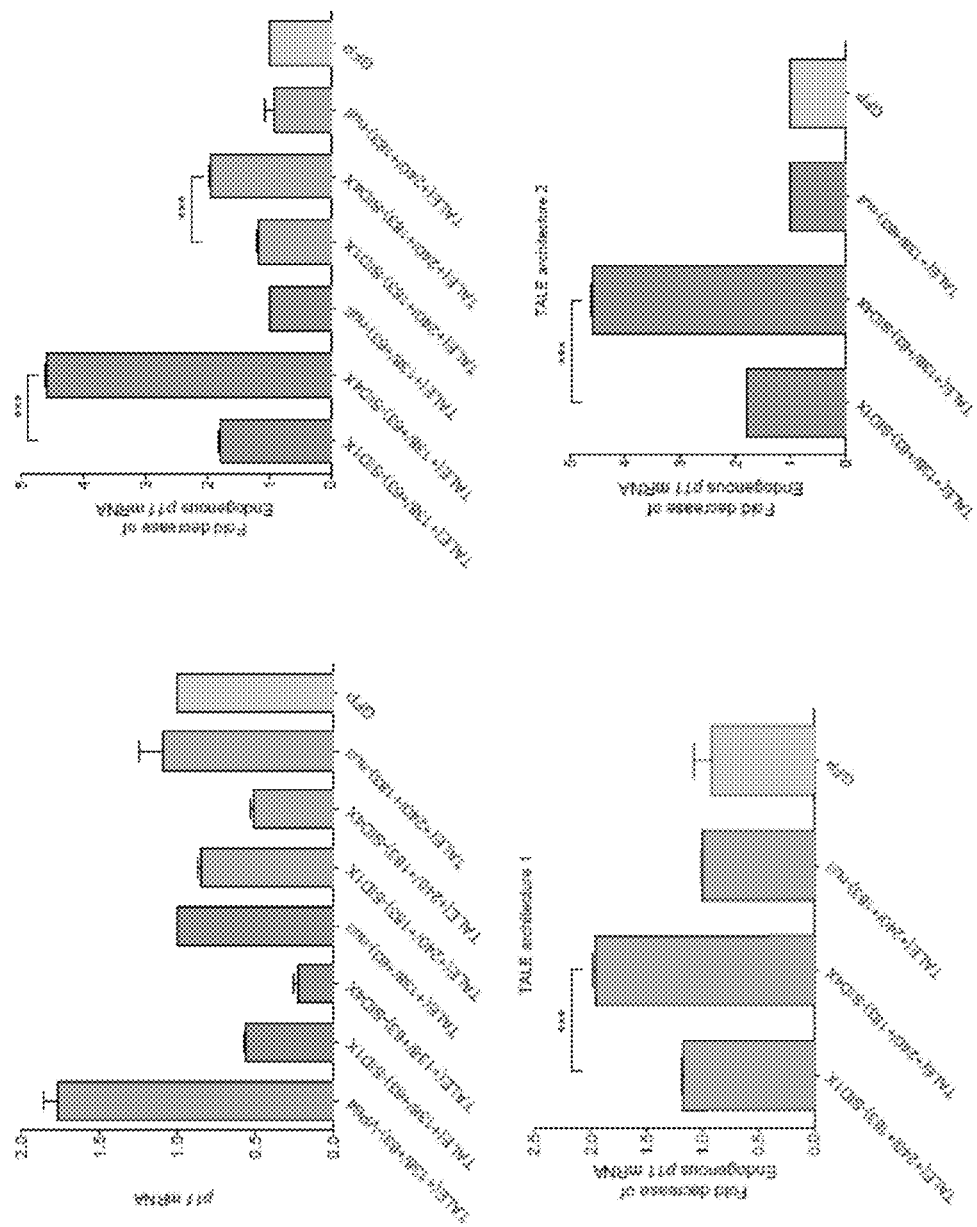

FIG. 23 shows a comparison of two different types of TALE architecture.

FIG. 24A-F shows a table listing monomer sequences (SEQ ID NOS 110-340, respectively, in order of appearance) (excluding the RVDs at positions 12 and 13) and the frequency with which monomers having a particular sequence occur.

Figure 25:
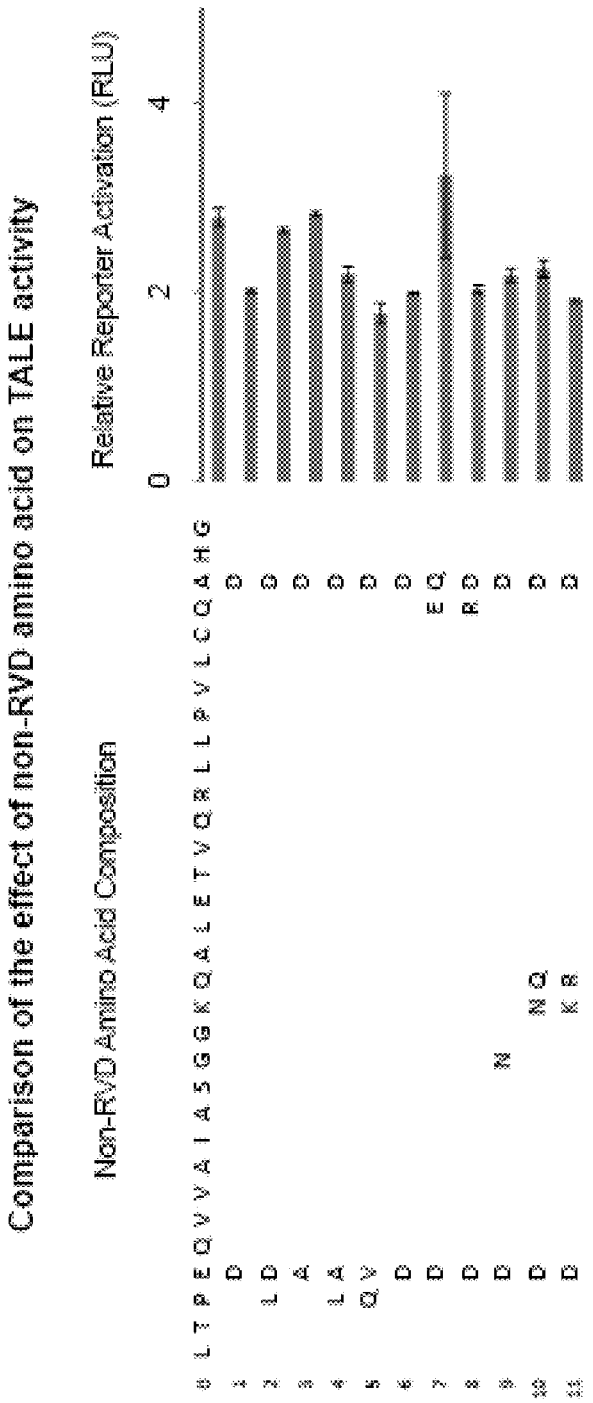

FIG. 25 shows the comparison of the effect of non-RVD amino acid on TALE activity. FIG. 25 discloses SEQ ID NOS 111, 110, 117, 114, 140, 341, 110, 115, 230, 342, 147 and 343, respectively, in order of appearance.

Figure 26:
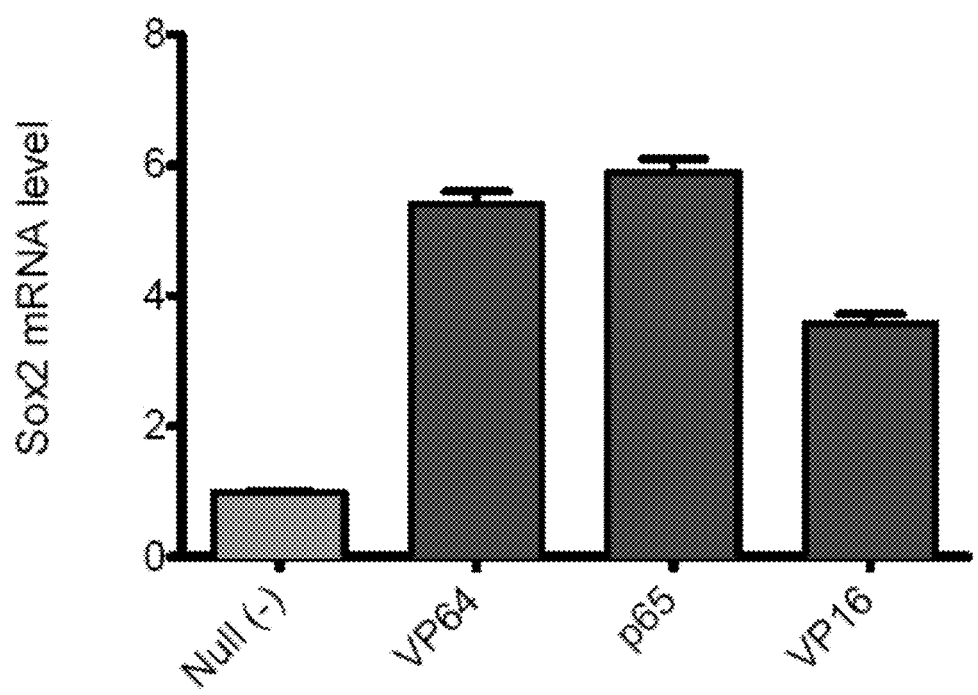

FIG. 26 shows an activator screen comparing levels of activation between VP64, p65 and VP16.

Figure 27:
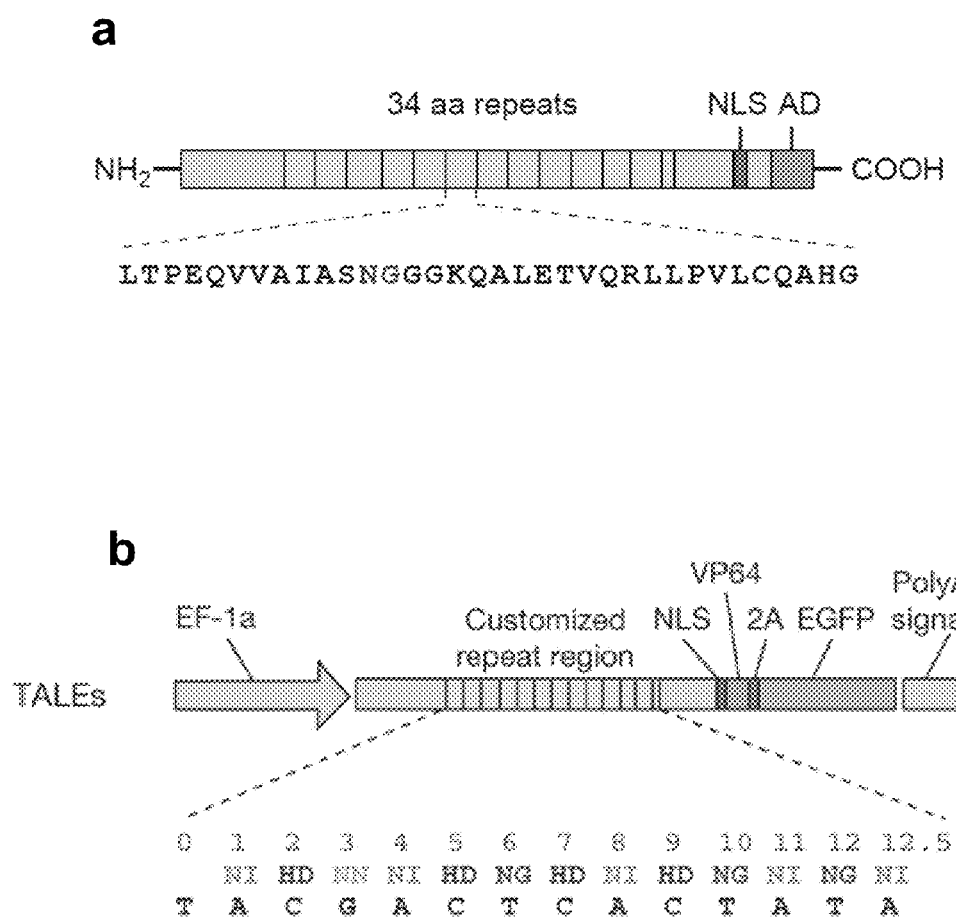

FIG. 27 shows (a) a customized TALE recognizing a designed sequence (SEQ ID NO: 65) wherein the grey portions indicate the TALE N-term (NH2) and C-term (COOH), the blue portions indicate the DNA binding domain sonsisting og the 34 amino acid repeats which bear the RVDs for DNA base recognition and where amino acid positions 12 and 13 specify the DNA-binding code; (b) a TALE recombinase (TALER) in which a TALE targeting the designated sequence is fused to the recombinase. FIG. 27(b) discloses SEQ ID NO: 391.

FIG. 28 shows the construction of designer TALEs and functional testing in mammalian cells. (a) Designer TALEs may be constructed using hierarchical ligation methods (Zhang et al., Nat. Biotech 2011). (b) Design of a reporter system for testing the activityof designer TALEs in mammalian cells. A TALE is fused to a transcriptional activator (VP64) and the reporter construct has the TALE binding site positioned before a minimal CMV promoter. (c) Co-transfection of the designer TALE and its corresponding reporter led to mCherry expression, whereas transfection of the reporter alone did not lead to mCherry expression. FIG. 28(b) discloses SEQ ID NO: 391.

FIG. 29 shows a TALER and the TALER delivery system. (a) A TALER wherein the orange portion indicates a truncated version of Gin recombinase retaining only the catalytic domain, the grey portions indicate the TALE N-term (NH2) and C-term (COOH), the purple portion indicates the nuclear localization signal (NLS) and the deeper grey portion indicates the 2A peptide linker (FIG. 29(a) discloses SEQ ID NO: 391) (b) Schematic representation of a Recombinase-TALE fusion construct and a schematic of the delivery system. The recombinase provides the catalytic function while the designer TALE domain provides the DNA targeting specificity. Rather than delivering the TALER genes, a lentivirus is engineered to package the TALER enzymes. The viral RNA encodes the genetic sequence that TALER inserts into the target genome.

Figure 30:
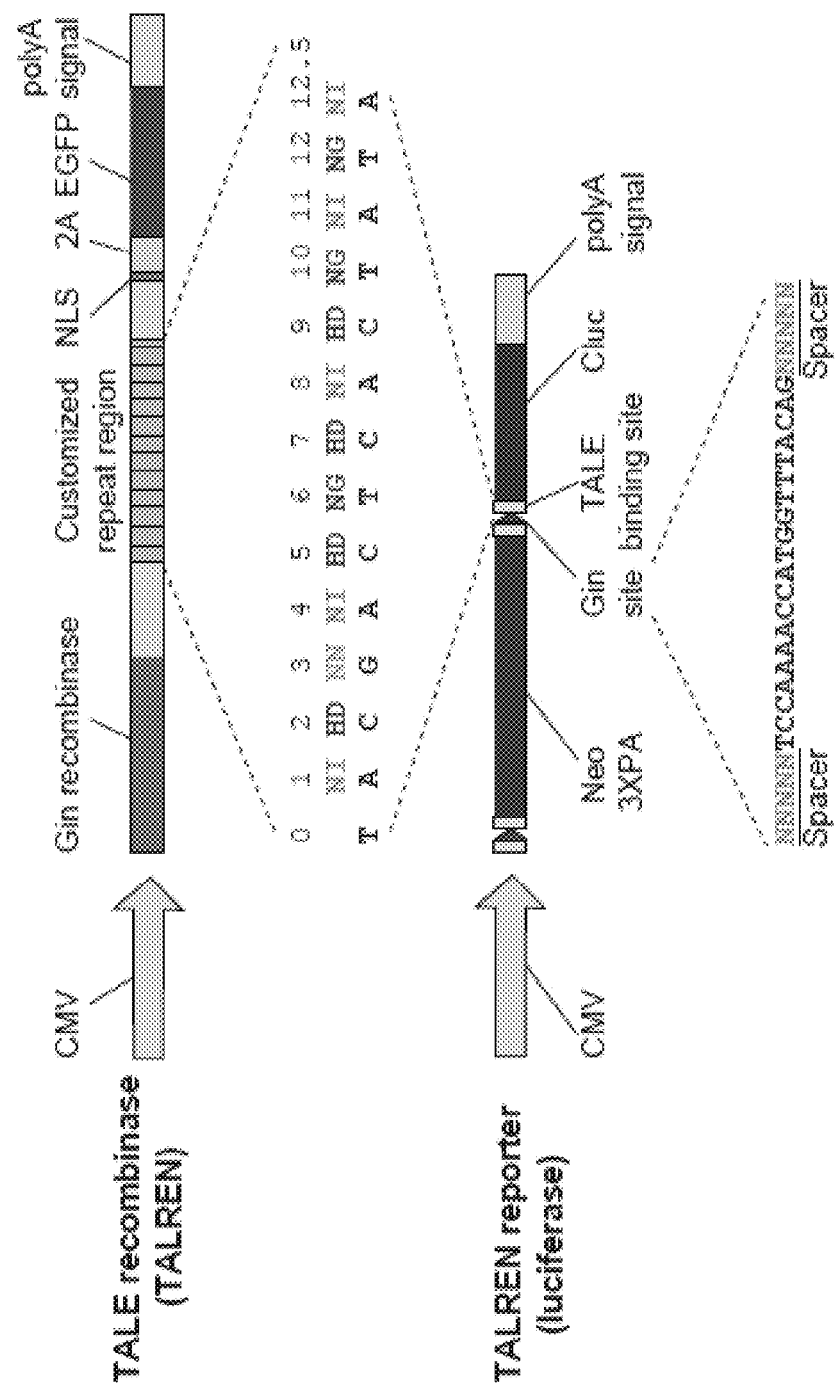

FIG. 30 shows a TALER testing system in which the CMV segment indicates the CMV promoter, the Neo-3×PA segment indicates a neomycin cassette with triple (3×) polyadenylation signal and the Gin Site indicates the core sequences of Gin-DNA interactions. FIG. 30 discloses SEQ ID NOS 391 and 392, respectively, in order of appearance.

Figure 31:
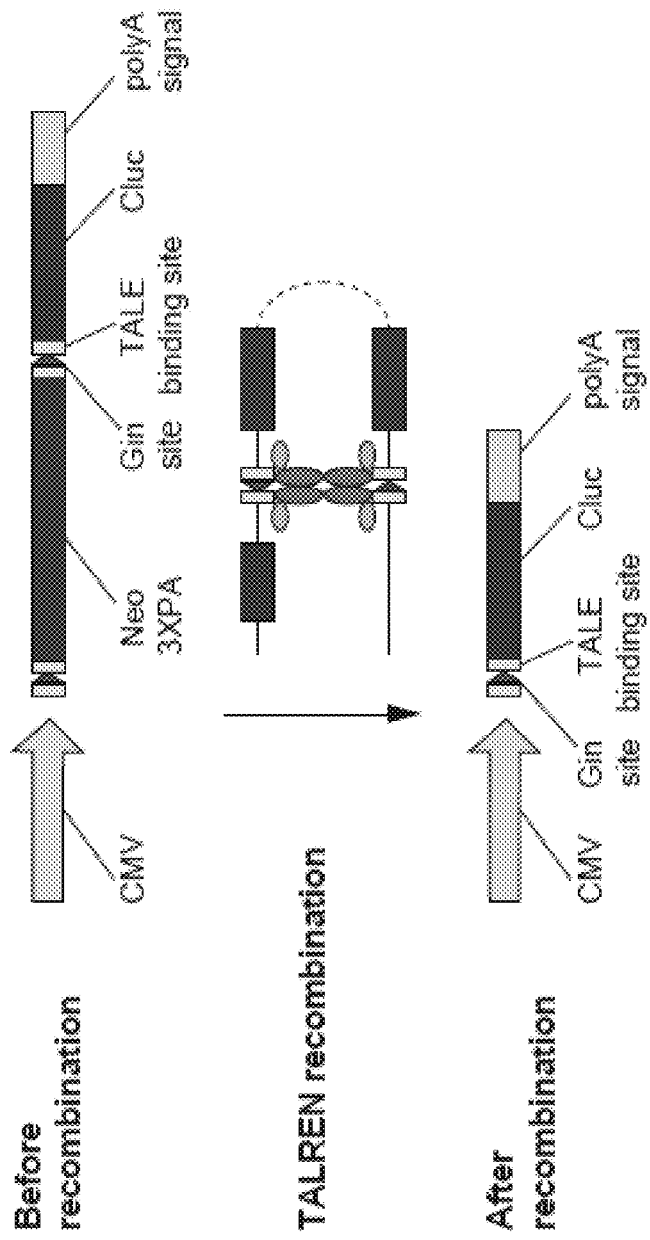

FIG. 31 shows the mechanism of the TALER reporter system. After the TALER successfully carries out the recombination reaction, the 3×PA cassette is removed, allowing expression of the Cluc reporter gene. (Cluc: *Cypridina* luciferase reporter gene).

Figure 32:
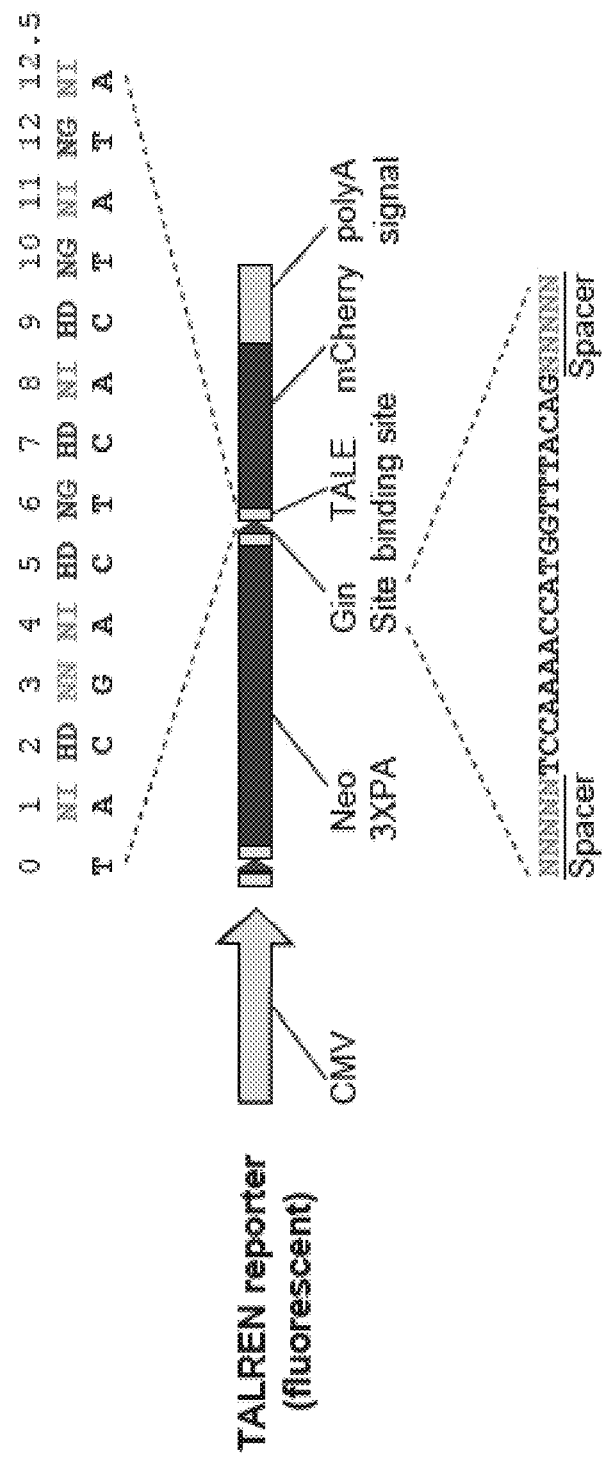

FIG. 32 shows the TALER red fluorescent report system. FIG. 32 discloses SEQ ID NOS 391 and 392, respectively, in order of appearance.

Figure 33:
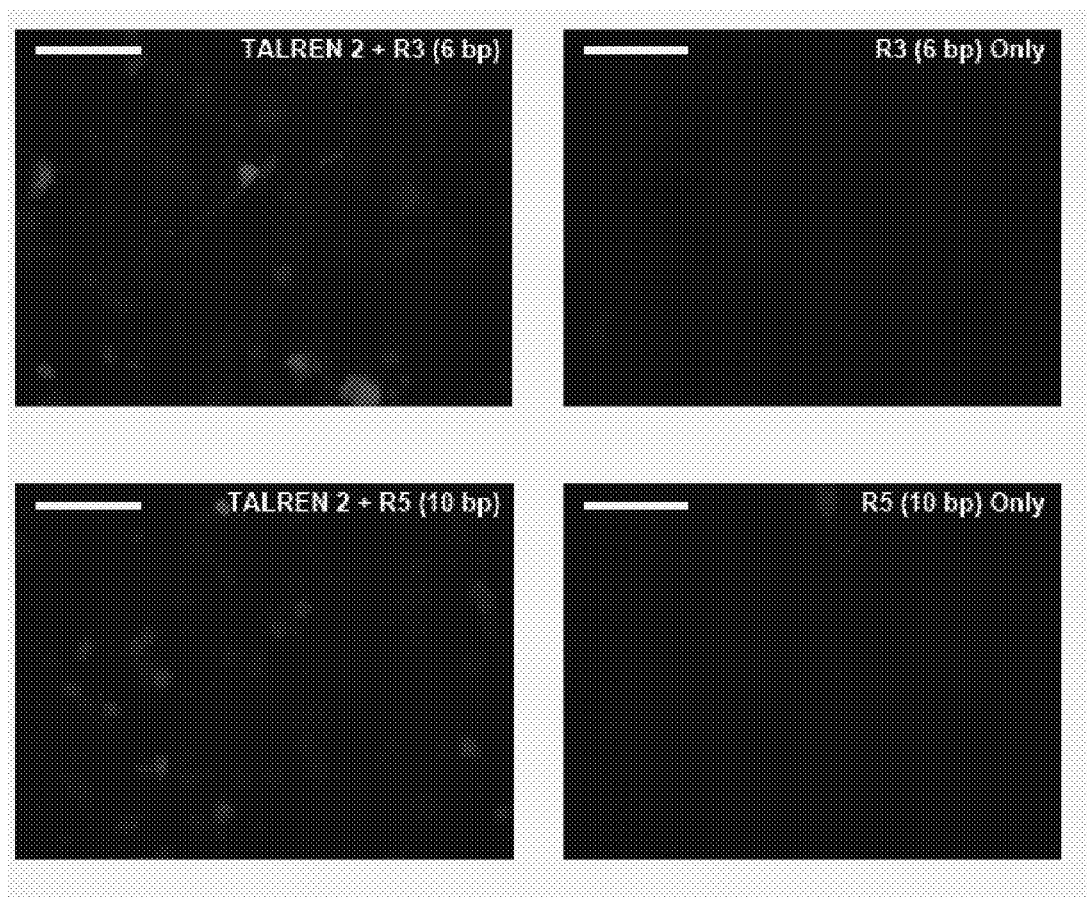

FIG. 33 shows fluorescent images of TALER testing using a red fluorescent (mCherry) reporter. R3 and R5 are reporters with different spacer lengths as specified in the brackets.

Figure 34:
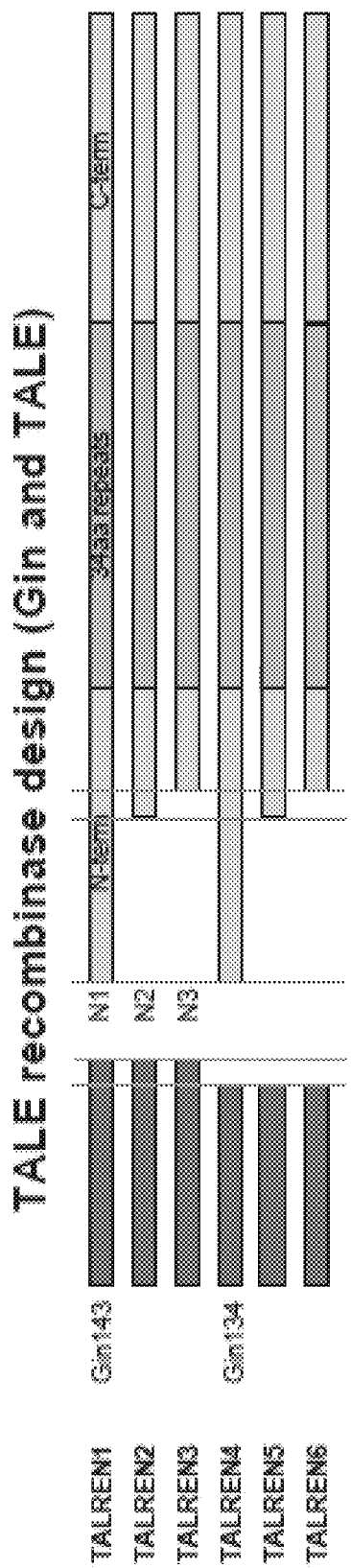

FIG. 34 shows three different truncations used in TALER design.

Figure 35:
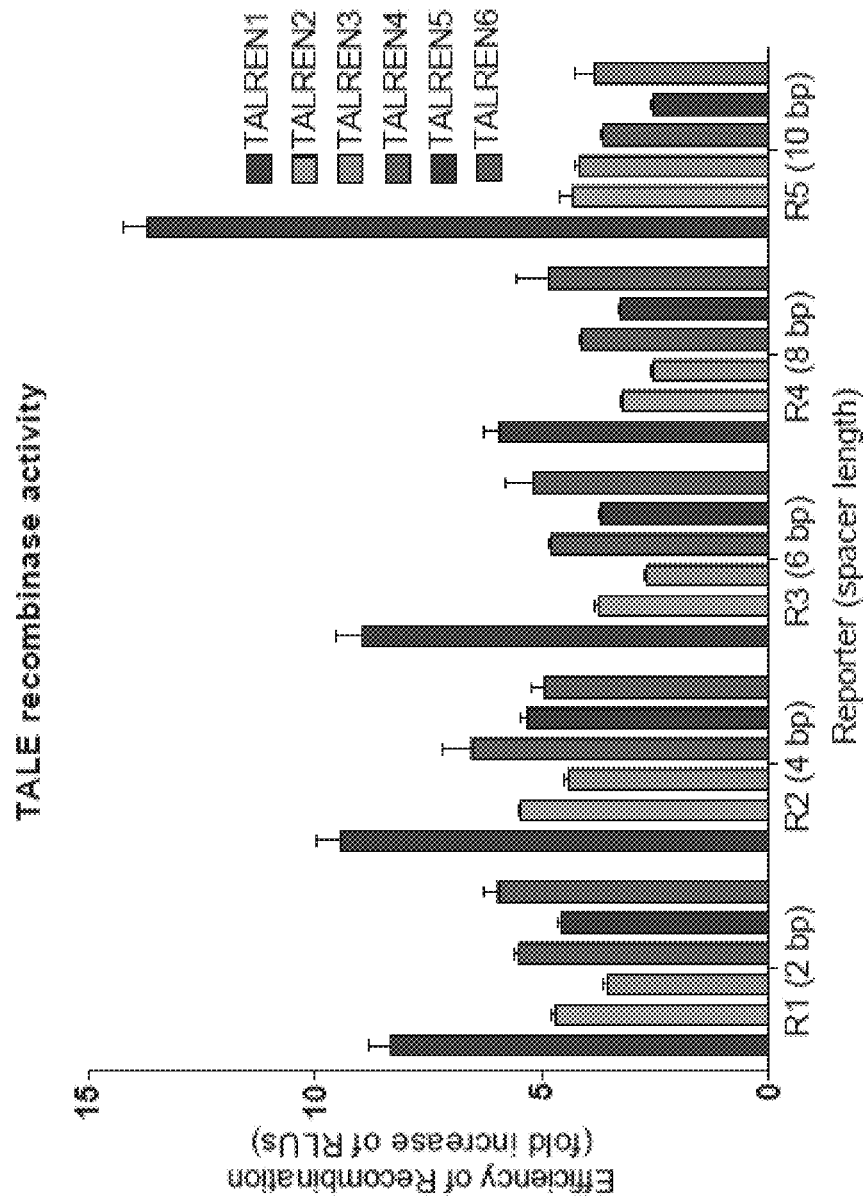

FIG. 35 shows a graphical representation of the testing of the TALER system in terms of TALER activity.

Figure 36:
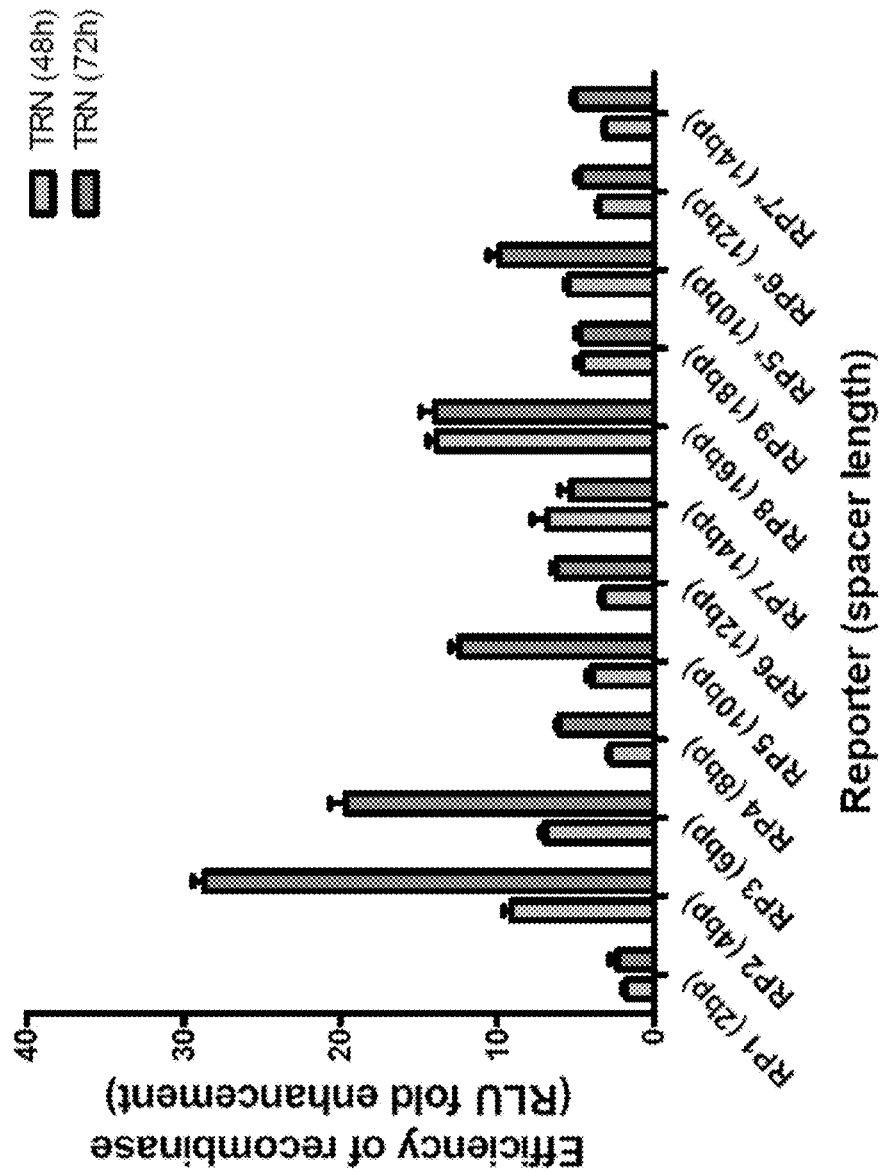

FIG. 36 shows a graphical representation of TALER tests depicting data at different time points (48h and 72h) using TALREN 1.

Figure 37:
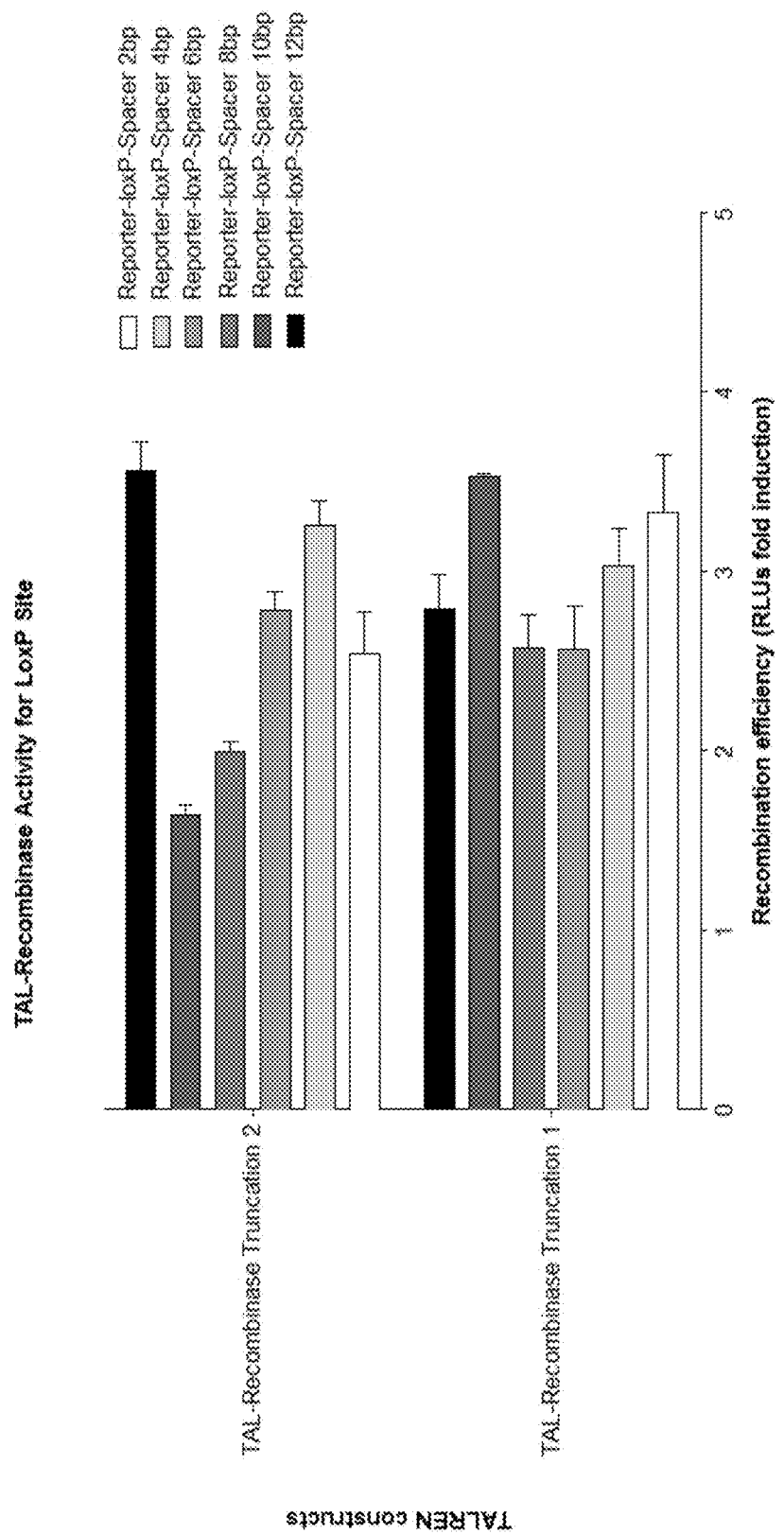

FIG. 37 shows a graphical representation of the testing of the TALER system utilizing a novel core site. The data depicts TAL-recombinase activity for the LoxP site.

DETAILED DESCRIPTION

Provided herein are non-naturally occurring or engineered or isolated compositions which may comprise non-naturally occurring or engineered or isolated or recombinant polypeptides that bind specific nucleic acid sequences to manipulate a mammalian genomic locus. Manipulation may encompass (a) changes in the level of gene expression: gene expression may be repressed or activated or, (b) the genome may be altered: this may be done by homologous recombination after nuclease cleavage (e.g., by using the cell's own repair mechanism) whereby small insertions and deletions may be introduced into a specific genomic location to inactivate a gene, activate it or give it a new function. Also provided herein are the nucleic acids that encode these polypeptides, wherein the nucleic acid molecules are codon optimized to ensure that the poypeptides bind specifically to mammalian DNA.

The present invention provides for a method of altering expression of a mammalian genomic locus of interest, which may comprise contacting the genomic locus with a non-naturally occurring or engineered composition which may comprise a DNA binding polypeptide which may comprise a N-terminal capping region, a DNA binding domain which may comprise at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more regulatory or functional protein domains. In an advantageous embodiment of the invention the polypeptide is encoded by and expressed from a codon optimized nucleic acid molecule so that the polypeptide preferentially binds to mammalian DNA.

The term "nucleic acid" or "nucleic acid molecule" or "nucleic acid sequence" or "polynucleotide" refer to deoxyribonucleic or ribonucleic oligonucleotides in either single- or double-stranded form. The term encompasses oligonucleotides containing known analogues of natural nucleotides. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. Hence the term encompasses both ribonucleic acid (RNA) and DNA, including cDNA, genomic DNA, synthetic (e.g., chemically synthesized) DNA, and DNA (or RNA) containing nucleic acid analogs. An advantageous embodiment of the invention is the nucleic acid being DNA.

As used herein the term "wild type" is a term of the art understood by skilled persons and means the typical form of an organism, strain, gene or characteristic as it occurs in nature as distinguished from mutant or variant forms. Thus, in the present context, the wild type TALEs refer to naturally occurring TALEs.

As used herein the term "variant" should be taken to mean the exhibition of qualities that have a pattern that deviates from what occurs in nature. As used with particular regards to TALE monomers or half monomers, variant TALE monomers are those that may be derived from natural or wild type TALE monomers and that have altered amino acids at positions usually highly conserved in nature and in particular have a combination of amino acids as RVDs that do not occur in nature and which may recognize a nucleotide with a higher activity, specificity and affinity than a naturally occurring RVD. For example, the RVD NI has an accepted specificity for adenine in nature, however Applicants have shown that the RVD RI, which is not a naturally occurring RVD, may have a greater specificity for adenine than NI. Generally, variants may include deletions, insertions and substitutions at the amino acid level and transversions, transitions and inversions at the nucleic acid level among other things, at one or more locations. Variants also include truncations. Variants include homologous and functional derivatives of parent molecules. Variants include sequences that are complementary to sequences that are capable of hybridizing to the nucleotide sequences presented herein.

As used herein, the term "designer TAL Effectors" (dTALEs) refers to isolated or non-naturally occurring TALE polypeptides that may be constructed or engineered de novo or via the translation of isolated or non-naturally occurring nucleic acids that encode TALE polypeptides. In advantageous embodiments, the DNA binding domain of the dTALE or the polypeptides of the invention may have at least 5 of more TALE monomers and at least one or more half-monomers specifically ordered or arranged to target a genomic locus of interest. The construction and generation of dTALEs or polypeptides of the invention may involve any of the methods described herein (e.g., see Example 2).

The terms "isolated" or "purified" or "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. With respect to a polypeptide the terms means that the polypeptide is separated to some extent from the cellular components with which it is normally found in nature (e.g., other polypeptides, lipids, carbohydrates, and nucleic acids). A purified polypeptide may yield a single major band on a non-reducing polyacrylamide gel. A purified polypeptide may be at least about 75% pure (e.g., at least 80%, 85%, 90%, 95%, 97%, 98%, 99%, or 100% pure). Purified polypeptides may be obtained by, for example, extraction from a natural source, de novo by chemical synthesis, or by recombinant production in a host cell or transgenic plant, and may be purified using, for example, affinity chromatography, immunoprecipitation, size exclusion chromatography, and ion exchange chromatography. The extent of purification may be measured using any appropriate method, including, without limitation, column chromatography, polyacrylamide gel electrophoresis, or high-performance liquid chromatography. With respect to nucleic acids for example, a DNA molecule may be deemed to be isolated when one of the nucleic acid sequences normally found immediately flanking that DNA molecule in a naturally occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences, as well as DNA that is incorporated into a vector, an autonomously replicating plasmid, a virus (e.g., a pararetrovirus, a retrovirus, lentivirus, adenovirus, or herpes virus), or the genomic DNA of a prokaryote or eukaryote. In addition, an isolated nucleic acid may include a recombinant nucleic acid such as a DNA molecule that is part of a hybrid or fusion nucleic acid.

Hence in preferred embodiments of the present invention, the dTALEs or polypeptides of the invention are isolated. As used herein, an "isolated" polypeptide is substantially free of cellular material. The language "substantially free of cellular material" includes preparations of dTALE polypeptide in which the polypeptide is separated from cellular components of the cells in which it is produced. For example, an isolated dTALE polypeptide may have less than 30% (by dry weight) of non-dTALE polypeptide, less than about 20% of non-dTALE polypeptide, less than about 10% of non-dTALE polypeptide, or less than about 5% non-dTALE polypeptide.

dTALE polypeptides may be produced by recombinant DNA techniques, as opposed to chemical synthesis. For example, a nucleic acid molecule encoding the protein is cloned into an expression vector, the expression vector is introduced into a host cell and the dTALE polypeptide is expressed in the host cell. The dTALE polypeptide may then be isolated from the cells by an appropriate purification scheme using standard protein purification techniques. As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein or polypeptide") encoded by a recombinant polynucleotide. "Recombinant means" or "recombination" encompasses the ligation of nucleic acids having various coding regions or domains or promoter sequences from different sources into an expression cassette or vector for expression of, e.g., inducible or constitutive expression of polypeptide coding sequences in the vectors of invention.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context.

As used herein, the term "domain" or "protein domain" refers to a part of a protein sequence that may exist and function independently of the rest of the protein chain.

The present invention provides for a DNA binding polypeptide. In an advantageous embodiment of the invention, provided herein are designer transcription activator receptors (dTALEs), which is a term used to describe isolated, non-naturally occurring, recombinant or engineered DNA binding proteins that comprise Transcription activator-like receptor (TALE) monomers or variant TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALEs contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" may be used to refer to the highly conserved repetitive polypeptide sequences within the TALE nucleic acid binding domain and the term "repeat variable di-residues" or "RVD" may be used to refer to the highly variable amino acids at positions 12 and 13 of the polypeptide monomers. A general representation of a TALE monomer which is comprised within the DNA binding domain is $X_{1-11}$-$(X_{12}X_{13})$-$X_{14-33\ or\ 34\ or\ 35}$, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA binding domain may comprise several repeats of TALE monomers and this may be represented as $(X_{1-11}$-$(X_{12}X_{13})$—$X_{14-33\ or\ 34\ or\ 35})_z$, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), monomers with an RVD of NG preferentially bind to thymine (T), monomers with an RVD of HD preferentially bind to cytosine (C) and monomers with an RVD of NN preferentially bind to both adenine (A) and guanine (G). In yet another embodiment of the invention, monomers with an RVD of IG preferentially bind to T. Thus, the number and order of the polypeptide monomer repeats in the nucleic acid binding domain of a TALE determines its nucleic acid target specificity. In still further embodiments of the invention, monomers with an RVD of NS recognize all four base pairs and may bind to A, T, G or C. The structure and function of TALEs is further described in, for example, Moscou et al., *Science* 326:1501 (2009); Boch et al., *Science* 326:1509-1512 (2009); and Zhang et al., *Nature Biotechnology* 29:149-153 (2011), each of which is incorporated by reference in its entirety.

dTALEs or the polypeptides of the invention are isolated, non-naturally occurring, recombinant or engineered nucleic acid-binding proteins that have nucleic acid or DNA binding regions containing polypeptide monomer repeats that are designed to target specific nucleic acid sequences. Previously described dTALEs, such as those in Zhang et al., *Nature Biotechnology* 29:149-153 (2011), used polypeptide monomers having an RVD of NN to target guanine However, such dTALEs had incomplete target specificity because such monomers are able to bind both adenine and guanine with comparable affinity. Furthermore, the small number of RVD sequences with known binding specificity made it difficult, if not impossible, to design dTALEs that recognized a repertoire of degenerative nucleotide sequences with high efficiency.

As described herein, polypeptide monomers having an RVD of HN or NH preferentially bind to guanine and thereby allow the generation of dTALEs with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of dTALEs with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of dTALEs with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine as do monomers having the RVD HN. Monomers having an RVD of NC preferentially bind to adenine, guanine and cytosine, and monomers having an RVD of S (or S*), bind to adenine, guanine, cytosine and thymine with comparable affinity. In more preferred embodiments of the invention, monomers having RVDs of H*, HA, KA, N*, NA, NC, NS, RA, and S* bind to adenine, guanine, cytosine and thymine with comparable affinity. Such polypeptide monomers allow for the generation of degenerative dTALEs able to bind to a repertoire of related, but not identical, target nucleic acid sequences.

Provided herein are dTALE polypeptides having a nucleic acid binding domain containing polypeptide monomers arranged in a predetermined N-terminus to C-terminus order such that each polypeptide monomer binds to a nucleotide of a predetermined target nucleic acid sequence and where at least one of the polypeptide monomers has an RVD of HN or NH and preferentially binds to guanine, an RVD of NV and preferentially binds to adenine and guanine, an RVD of NC and preferentially binds to adenine, guanine and cytosine or an RVD of S and binds to adenine, guanine, cytosine and thymine.

In some embodiments, each polypeptide monomer of the nucleic acid binding domain that binds to adenine has an RVD of NI, NN, NV, NC or S. In certain embodiments, each polypeptide monomer of the nucleic acid binding domain that binds to guanine has an RVD of HN, NH, NN, NV, NC or S. In certain embodiments, each polypeptide monomer of the nucleic acid binding domain that binds to cytosine has an RVD of HD, NC or S. In some embodiments, each polypeptide monomer that binds to thymine has an RVD of NG or S.

In some embodiments, each polypeptide monomer of the nucleic acid binding domain that binds to adenine has an RVD of NI. In certain embodiments, each polypeptide monomer of the nucleic acid binding domain that binds to guanine has an RVD of HN or NH. In certain embodiments, each polypeptide monomer of the nucleic acid binding domain that binds to cytosine has an RVD of HD. In some embodiments, each polypeptide monomer that binds to thymine has an RVD of NG.

Figure 4A:
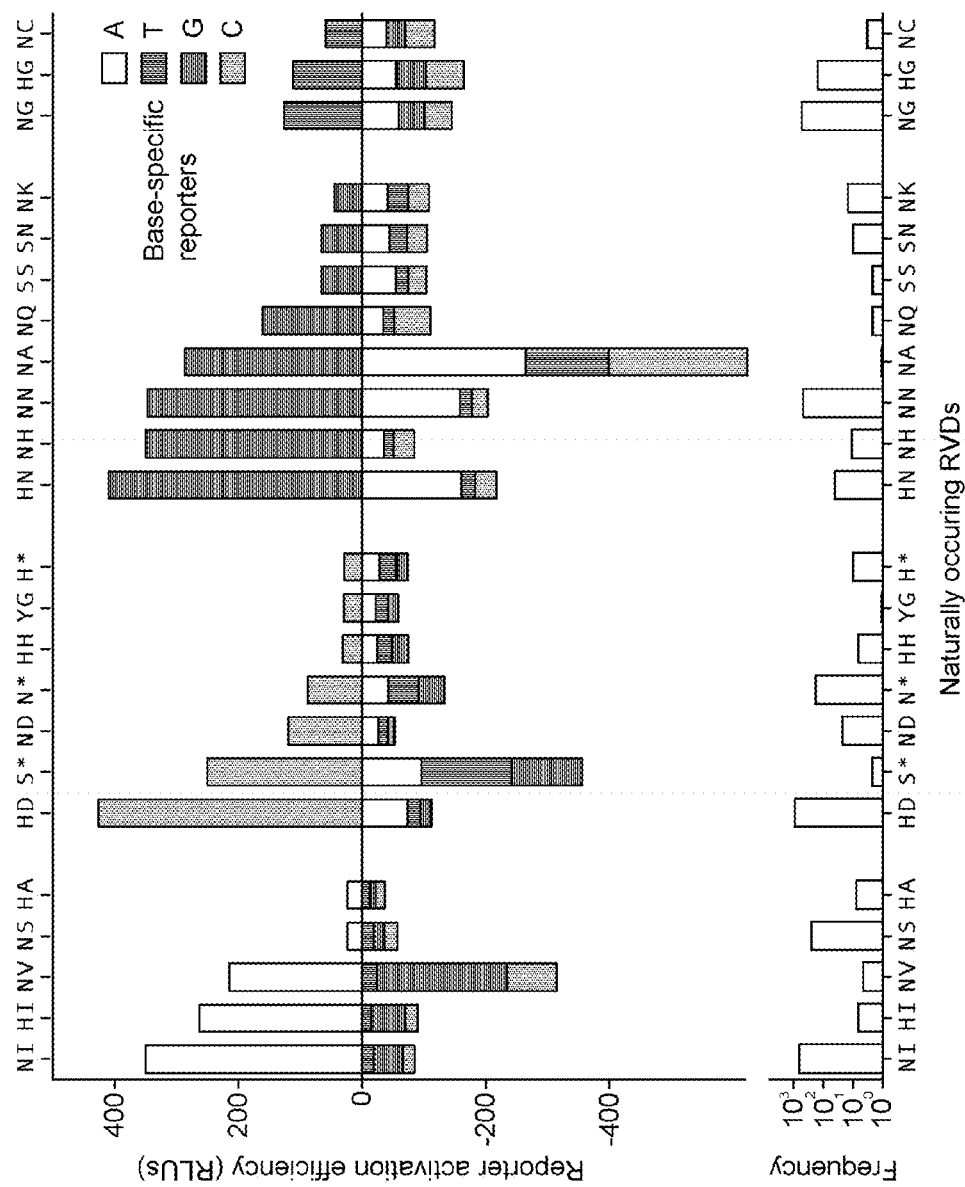
FIG. 4A shows the base-preference of various RVDs as determined using a RVD screening system described herein.
Figure 4B:
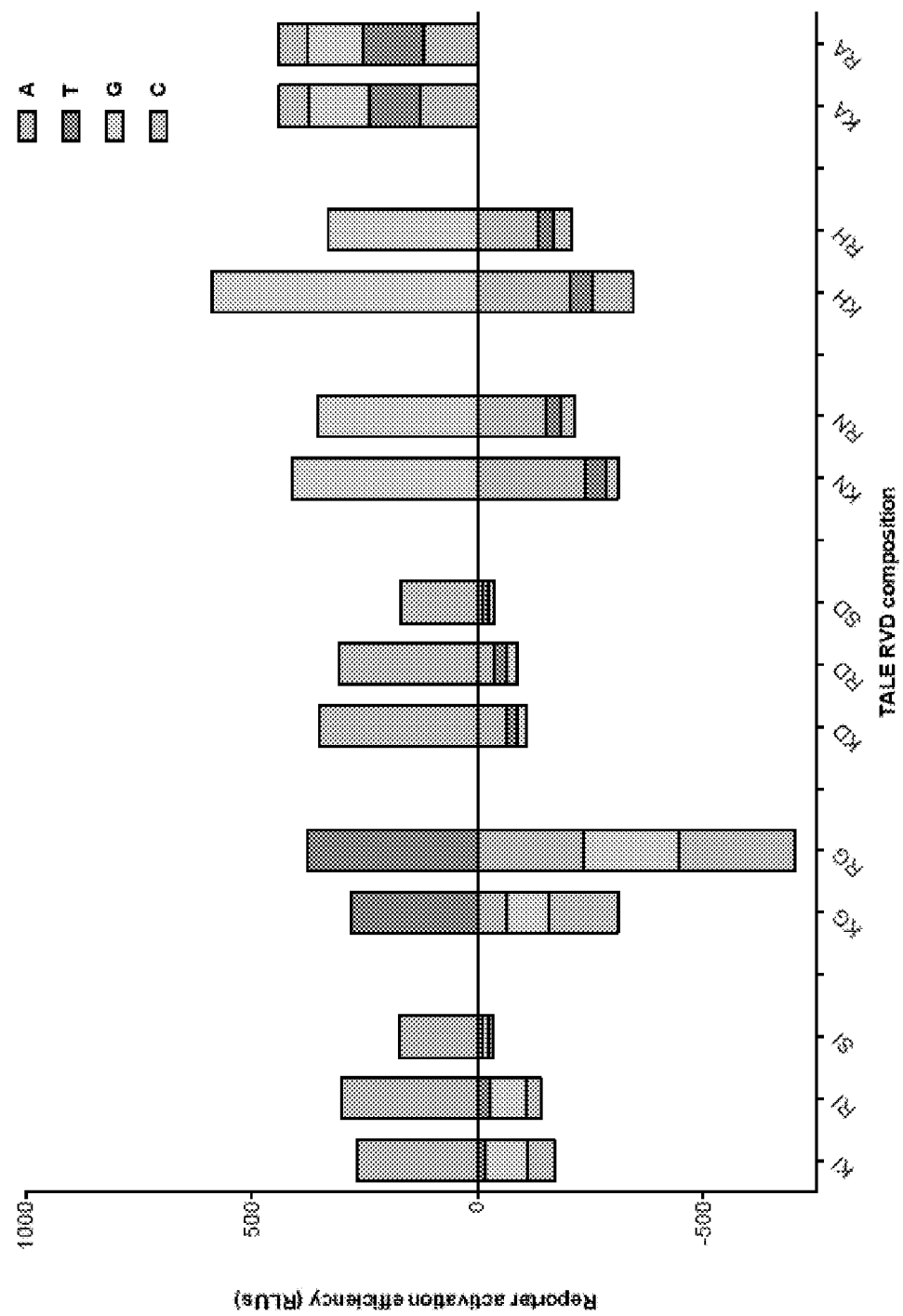
FIG. 4B shows the base-preference of additional RVDs as determined using a RVD screening system described herein.

In even more advantageous embodiments of the invention the RVDs that have a specificity for adenine are NI, RI, KI, HI, and SI. In more preferred embodiments of the invention, the RVDs that have a specificity for adenine are HN, SI and RI, most preferably the RVD for adenine specificity is SI. In even more preferred embodiments of the invention the RVDs that have a specificity for thymine are NG, HG, RG and KG. In further advantageous embodiments of the invention, the RVDs that have a specificity for thymine are KG, HG and RG, most preferably the RVD for thymine specificity is KG or RG. In even more preferred embodiments of the invention the RVDs that have a specificity for cytosine are HD, ND, KD, RD, HH, YG and SD. In a further advantageous embodiment of the invention, the RVDs that have a specificity for cytosine are SD and RD. Refer to FIG. 4B for representative RVDs and the nucleotides they target to be incorporated into the most preferred embodiments of the invention. In a further advantageous embodiment the variant TALE monomers may comprise any of the RVDs that exhibit specificity for a nucleotide as depicted in FIG. 4A. All such TALE monomers allow for the generation of degenerative dTALEs able to bind to a repertoire of related, but not identical, target nucleic acid sequences. In other embodiments of the invention, the RVD SH may have a specificity for G, the RVD IS may have a specificity for A and the RVD IG may have a specificity for T. In still further embodiments of the invention, the RVD NT may bind to G and A. In yet further embodiments of the invention, the RVD NP may bind to A, T and C. In more advantageous embodiments of the invention, at least one selected RVD may be NI, HD, NG, NN, KN, RN, NH, NQ, SS, SN, NK, KH, RH, HH, KI, HI, RI, SI, KG, HG, RG, SD, ND, KD, RD, YG, HN, NV, NS, HA, S*, N*, KA, H*, RA, NA or NC.

The predetermined N-terminal to C-terminal order of the one or more polypeptide monomers of the nucleic acid or DNA binding domain determines the corresponding predetermined target nucleic acid sequence to which the dTALE or polypeptides of the invention may bind. As used herein the monomers and at least one or more half monomers are "specifically ordered or arranged to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8). Therefore, it follows that the length of the nucleic acid or DNA being targeted is equal to the number of full monomers plus two.

For example, nucleic acid binding domains may be engineered to contain 5, 6, 7, 8, 9, 10, 11, 12, 13, 14, 15, 16, 17, 18, 19, 20, 21, 22, 23, 24, 25, or more polypeptide monomers arranged in a N-terminal to C-terminal direction to bind to a predetermined 5, 6, 7, 8, 9, 10, 11, 12, 13, 14, 15, 16, 17, 18, 19, 20, 21, 22, 23, 24, 25 nucleotide length nucleic acid sequence. In more advantageous embodiments of the invention, nucleic acid binding domains may be engineered to contain 5, 6, 7, 8, 9, 10, 11, 12, 13, 14, 15, 16, 17, 18, 19, 20, 21, 22, 23, 24, 25, 26 or more full length polypeptide monomers that are specifically ordered or arranged to target nucleic acid sequences of length 7, 8, 9, 10, 11, 12, 13, 14, 15, 16, 17, 18, 19, 20, 21, 22, 23, 24, 25, 26, 27 and 28 nucleotides, respectively. In certain embodiments the polypeptide monomers are contiguous. In some embodiments, half-monomers may be used in the place of one or more monomers, particularly if they are present at the C-terminus of the dTALE.

Polypeptide monomers are generally 33, 34 or 35 amino acids in length. With the exception of the RVD, the amino acid sequences of polypeptide monomers are highly conserved or as described herein, the amino acids in a polypeptide monomer, with the exception of the RVD, exhibit patterns that effect TALE activity, the identification of which may be used in preferred embodiments of the invention. Representative combinations of amino acids in the monomer sequence, excluding the RVD, are shown by the Applicants to have an effect on TALE activity (FIG. 25). In more preferred embodiments of the invention, when the DNA binding domain may comprise (X1-11-X12X13-X14-33 or 34 or 35)z, wherein X1-11 is a chain of 11 contiguous amino acids, wherein X12X13 is a repeat variable diresidue (RVD), wherein X14-33 or 34 or 35 is a chain of 21, 22 or 23 contiguous amino acids, wherein z is at least 5 to 26, then the preferred combinations of amino acids are [LTLD] (SEQ ID NO: 1) or [LTLA] (SEQ ID NO: 2) or [LTQV] (SEQ ID NO: 3) at X1-4, or [EQHG] (SEQ ID NO: 4) or [RDHG] (SEQ ID NO: 5) at positions X30-33 or X31-34 or X32-35. Furthermore, other amino acid combinations of interest in the monomers are [LTPD] (SEQ ID NO: 6) at X1-4 and [NQALE] (SEQ ID NO: 7) at X16-20 and [DHG] at X32-34 when the monomer is 34 amino acids in length. When the monomer is 33 or 35 amino acids long, then the corresponding shift occurs in the positions of the contiguous amino acids [NQALE] (SEQ ID NO: 7) and [DHG]; preferably, embodiments of the invention may have [NQALE] (SEQ ID NO: 7) at X15-19 or X17-21 and [DHG] at X31-33 or X33-35.

In still further embodiments of the invention, amino acid combinations of interest in the monomers, are [LTPD] (SEQ ID NO: 6) at X1-4 and [KRALE] (SEQ ID NO: 8) at X16-20 and [AHG] at X32-34 or [LTPE] (SEQ ID NO: 9) at X1-4 and [KRALE] (SEQ ID NO: 8) at X16-20 and [DHG] at X32-34 when the monomer is 34 amino acids in length. When the monomer is 33 or 35 amino acids long, then the corresponding shift occurs in the positions of the contiguous amino acids [KRALE] (SEQ ID NO: 8), [AHG] and [DHG]. In preferred embodiments, the positions of the contiguous amino acids may be ([LTPD] (SEQ ID NO: 6) at X1-4 and [KRALE] (SEQ ID NO: 8) at X15-19 and [AHG] at X31-33) or ([LTPE] (SEQ ID NO: 9) at X1-4 and [KRALE] (SEQ ID NO: 8) at X15-19 and [DHG] at X31-33) or ([LTPD] (SEQ ID NO: 6) at X1-4 and [KRALE] (SEQ ID NO: 8) at X17-21 and [AHG] at X33-35) or ([LTPE] (SEQ ID NO: 9) at X1-4 and [KRALE] (SEQ ID NO: 8) at X17-21 and [DHG] at X33-35). In still further embodiments of the invention, contiguous amino acids [NGKQALE] (SEQ ID NO: 10) are present at positions X14-20 or X13-19 or X15-21. These representative positions put forward various embodiments of the invention and provide guidance to identify additional amino acids of interest or combinations of amino acids of interest in all the TALE monomers described herein (FIGS. 24A-F and 25).

Provided below are exemplary amino acid sequences (SEQ ID NOS 11-23, respectively, in order of appearance) of conserved portions of polypeptide monomers. The position of the RVD in each sequence is represented by XX or by X* (wherein (*) indicates that the RVD is a single amino acid and residue 13 (X13) is absent).

```
L T P A Q V V A I A S X X G G K Q A L E T V Q R L L P V L C Q D H G

L T P A Q V V A I A S X * G G K Q A L E T V Q R L L P V L C Q D H G

L T P D Q V V A I A N X X G G K Q A L A T V Q R L L P V L C Q D H G

L T P D Q V V A I A N X X G G K Q A L E T L Q R L L P V L C Q D H G

L T P D Q V V A I A N X X G G K Q A L E T V Q R L L P V L C Q D H G

L T P D Q V V A I A S X X G G K Q A L A T V Q R L L P V L C Q D H G

L T P D Q V V A I A S X X G G K Q A L E T V Q R L L P V L C Q D H G

L T P D Q V V A I A S X X G G K Q A L E T V Q R V L P V L C Q D H G

L T P E Q V V A I A S X X G G K Q A L E T V Q R L L P V L C Q A H G

L T P Y Q V V A I A S X X G S K Q A L E T V Q R L L P V L C Q D H G

L T R E Q V V A I A S X X G G K Q A L E T V Q R L L P V L C Q D H G

L S T A Q V V A I A S X X G G K Q A L E G I G E Q L L K L R T A P Y G

L S T A Q V V A V A S X X G G K P A L E A V R A Q L L A L R A A P Y G
```

A further listing of TALE monomers excluding the RVDs which may be denoted in a sequence (X1-11-X14-34 or X1-11-X14-35), wherein X is any amino acid and the subscript is the amino acid position is provided in FIG. 24A-F. The frequency with which each monomer occurs is also indicated.

As described in Zhang et al., Nature Biotechnology 29:149-153 (2011), dTALE binding efficiency may be increased by including amino acid sequences from the "capping regions" that are directly N-terminal or C-terminal of the DNA binding region of naturally occurring TALEs into dTALEs at positions N-terminal or C-terminal of the dTALE DNA binding region. Thus, in certain embodiments, the dTALEs described herein further comprise an N-terminal capping region and/or a C-terminal capping region.

An exemplary amino acid sequence of a N-terminal capping region is:

```
                                                    (SEQ ID NO: 24)
M D P I R S R T P S P A R E L L S G P Q P D G V Q P T A D R G V S P

P A G G P L D G L P A R R T M S R T R L P S P P A P S P A F S A D S

F S D L L R Q F D P S L F N T S L F D S L P P F G A H H T E A A T G

E W D E V Q S G L R A A D A P P P T M R V A V T A A R P P R A K P A

P R R R A A Q P S D A S P A A Q V D L R T L G Y S Q Q Q Q E K I K P

K V R S T V A Q H H E A L V G H G F T H A H I V A L S Q H P A A L G

T V A V K Y Q D M I A A L P E A T H E A I V G V G K Q W S G A R A L

E A L L T V A G E L R G P P L Q L D T G Q L L K I A K R G G V T A V

E A V H A W R N A L T G A P L N
```

An exemplary amino acid sequence of a C-terminal capping region is:

```
                                                    (SEQ ID NO: 25)
R P A L E S I V A Q L S R P D P A L A A L T N D H L V A L A C L G

G R P A L D A V K K G L P H A P A L I K R T N R R I P E R T S H R

V A D H A Q V V R V L G F F Q C H S H P A Q A F D D A M T Q F G M

S R H G L L Q L F R R V G V T E L E A R S G T L P P A S Q R W D R

I L Q A S G M K R A K P S P T S T Q T P D Q A S L H A F A D S L E

R D L D A P S P M H E G D Q T R A S
```

As used herein the predetermined "N-terminus" to "C terminus" orientation of the N-terminal capping region, the DNA binding domain which may comprise the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the dTALEs described herein.

In certain embodiments, the dTALEs described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the dTALEs described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the dTALEs described herein do not need to have identical sequences to the capping region sequences provided herein. Thus, in some embodiments, the capping region of the dTALEs described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% dentical or share identity to the capping region amino acid sequences provided herein.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

% homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity.

However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affine gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore first requires the production of an optimal alignment, taking into consideration gap penalties. A suitable computer program for carrying out such an alignment is the GCG Wisconsin Bestfit package (Devereux et al., 1984 *Nuc. Acids Research* 12 p387). Examples of other software than may perform sequence comparisons include, but are not limited to, the BLAST package (see Ausubel et al., 1999 *Short Protocols in Molecular Biology*, 4$^{th}$ Ed.—Chapter 18), FASTA (Altschul et al., 1990 *J. Mol. Biol.* 403-410) and the GENEWORKS suite of comparison tools. Both BLAST and FASTA are available for offline and online searching (see Ausubel et al., 1999, *Short Protocols in Molecular Biology, pages 7-58 to 7-60*). However, for some applications, it is preferred to use the GCG Bestfit program. A new tool, called BLAST 2 Sequences is also available for comparing protein and nucleotide sequences (see *FEMS Microbiol Lett.* 1999 174(2): 247-50; *FEMS Microbiol Lett.* 1999 177(1): 187-8 and the website of the National Center for Biotechnology information at the website of the National Institutes for Health).

Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244). Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" *Comput. Appl. Biosci.* 9: 745-756) (Taylor W. R. (1986) "The classification of amino acid conservation" *J. Theor. Biol.* 119; 205-218). Conservative substitutions may be made, for example according to the table below which describes a generally accepted Venn diagram grouping of amino acids.

| Set | | | | | | | | | | Sub-set | | | | |
|---|---|---|---|---|---|---|---|---|---|---|---|---|---|---|
| Hydro-phobic | F | W | Y | H | K | M | I | L | V | A G | C Aromatic Aliphatic | F | W H Y I L V | |
| Polar | W | Y | H | K | R | E | D | C | S | T N | Q Charged Positively charged Negatively charged | H K H K E | K R E D R D | |
| Small | V | C | A | G | S | P | T | N | D | | Tiny | A | G S | |

Embodiments of the invention include sequences which may comprise homologous substitution (substitution and replacement are both used herein to mean the interchange of an existing amino acid residue, with an alternative residue) that may occur i.e., like-for-like substitution such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as 0), pyriylalanine, thienylalanine, naphthylalanine and phenylglycine.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

Additional sequences for the conserved portions of polypeptide monomers and for N-terminal and C-terminal capping regions are included in the sequences with the following gene accession numbers: AAW59491.1, AAQ79773.2, YP_450163.1, YP_001912778.1, ZP_02242672.1, AAW59493.1, AAY54170.1, ZP_02245314.1, ZP_02243372.1, AAT46123.1, AAW59492.1, YP_451030.1, YP_001915105.1, ZP_02242534.1, AAW77510.1, ACD11364.1, ZP_02245056.1, ZP_02245055.1, ZP_02242539.1, ZP_02241531.1, ZP_02243779.1, AAN01357.1, ZP_02245177.1, ZP_02243366.1, ZP_02241530.1, AAS58130.3, ZP_02242537.1, YP_200918.1, YP_200770.1, YP_451187.1, YP_451156.1, AAS58127.2, YP_451027.1, YP_451025.1, AAA92974.1, YP_001913755.1, ABB70183.1, YP_451893.1, YP_450167.1, ABY60855.1, YP_200767.1, ZP_02245186.1, ZP_02242931.1, ZP_02242535.1, AAY54169.1, YP_450165.1, YP_001913452.1, AAS58129.3, ACM44927.1, ZP_02244836.1, AAT46125.1, YP_450161.1, ZP_02242546.1, AAT46122.1, YP_451897.1, AAF98343.1, YP_001913484.1, AAY54166.1, YP_001915093.1, YP_001913457.1, ZP_02242538.1, YP_200766.1, YP_453043.1, YP_001915089.1, YP_001912981.1, ZP_02242929.1, YP_001911730.1, YP_201654.1, YP_199877.1, ABB70129.1, YP_451696.1, YP_199876.1, AAS75145.1, AAT46124.1, YP_200914.1, YP_001915101.1, ZP_02242540.1, AAG02079.2, YP_451895.1, YP_451189.1, YP_200915.1, AAS46027.1, YP_001913759.1, YP_001912987.1, AAS58128.2, AAS46026.1, YP_201653.1, YP_202894.1, YP_001913480.1, ZP_02242666.1, YP_001912775.1, ZP_02242662.1, AAS46025.1, AAC43587.1, BAA37119.1, NP_644725.1, ABO77779.1, BAA37120.1, ACZ62652.1, BAF46271.1, ACZ62653.1, NP_644793.1, ABO77780.1, ZP_02243740.1, ZP_02242930.1, AAB69865.1, AAY54168.1, ZP_02245191.1, YP_001915097.1, ZP_02241539.1, YP_451158.1, BAA37121.1, YP_001913182.1, YP_200903.1, ZP_02242528.1, ZP_06705357.1, ZP_06706392.1, ADI48328.1, ZP_06731493.1, ADI48327.1, ABO77782.1, ZP_06731656.1, NP_942641.1, AAY43360.1, ZP_06730254.1, ACN39605.1, YP_451894.1, YP_201652.1, YP_001965982.1, BAF46269.1, NP_644708.1, ACN82432.1, ABO77781.1, P14727.2, BAF46272.1, AAY43359.1, BAF46270.1, NP_644743.1, ABG37631.1, AABO0675.1, YP_199878.1, ZP_02242536.1, CAA48680.1, ADM80412.1, AAA27592.1, ABG37632.1, ABP97430.1, ZP_06733167.1, AAY43358.1, 2KQ5_A, BAD42396.1, ABO27075.1, YP_002253357.1, YP_002252977.1, ABO27074.1, ABO27067.1, ABO27072.1, ABO27068.1, YP_003750492.1, ABO27073.1, NP_519936.1, ABO27071.1, ABO27070.1, and ABO27069.1, each of which is hereby incorporated by reference.

In some embodiments, the dTALEs described herein also include a nuclear localization signal and/or cellular uptake signal. Such signals are known in the art and may target a dTALE to the nucleus and/or intracellular compartment of a cell. Such cellular uptake signals include, but are not limited to, the minimal Tat protein transduction domain which spans residues 47-57 of the human immunodeficiency virus Tat protein: YGRKKRRQRRR (SEQ ID NO: 26).

In some embodiments, the dTALEs described herein include a nucleic acid or DNA binding domain that is a non-TALE nucleic acid or a non-TALE DNA binding domain. As used herein the term "non-TALE DNA binding domain" refers to a DNA binding domain that has a nucleic acid sequence corresponding to a nucleic acid sequence which is not substantially homologous to a nucleic acid that encodes for a TALE protein or fragment thereof, e.g., a nucleic acid sequence which is different from a nucleic acid that encodes for a TALE protein and which is derived from the same or a different organism. In other embodiments of the invention, the dTALEs described herein include a nucleic acid or DNA binding domain that is linked to a non-TALE polypeptide. A "non-TALE polypeptide" refers to a polypeptide having an amino acid sequence corresponding to a protein which is not substantially homologous to a TALE protein or fragment thereof, e.g., a protein which is different from a TALE protein and which is derived from the same or a different organism. In this context, the term "linked" is intended include any manner by which the nucleic acid binding domain and the non-TALE polypeptide could be connected to each other, including, for example, through peptide bonds by being part of the same polypeptide chain or through other covalent interactions, such as a chemical linker. The non-TALE polypeptide may be linked, for example to the N-terminus and/or C-terminus of the nucleic acid binding domain, may be linked to a C-terminal or N-terminal cap region, or may be connected to the nucleic acid binding domain indirectly.

In still further advantageous embodiments of the invention, the dTALEs or polypeptides of the invention comprise chimeric DNA binding domains. Chimeric DNA binding domains may be generated by fusing a full TALE (including the N- and C-terminal capping regions) with another TALE or non-TALE DNA binding domain such as zinc finger (ZF), helix-loop-helix, or catalytically-inactivated DNA endonucleases (e.g., EcoRI, meganucleases, etc), or parts of TALE may be fused to other DNA binding domains. The chimeric domain may have novel DNA binding specificity that combines the specificity of both domains.

In advantageous embodiments described herein, the dTALEs or polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the dTALEs described herein, the activity mediated by the effector domain is a biological activity. For example, in some embodiments the effector domain is a transcriptional inhibitor (i.e., a repressor domain), such as an mSin interaction domain (SID) or a Krüppel-associated box (KRAB) or fragments of the KRAB domain (further described in Example 3). In some embodiments the effector domain is an enhancer of transcription (i.e. an activation domain), such as the VP16, VP64 or p65 activation domain.

As used herein, VP16 is a herpesvirus protein. It is a very strong transcriptional activator that specifically activates viral immediate early gene expression. VP16 contains two functional domains. The amino-terminal portion of the protein, in association with host cellular proteins, binds to specific sequences upstream of the immediate early gene core promoters. The transcriptional activation domain resides in the carboxyl-terminal 78 amino acids. Embodiments of the invention use this activation domain as it may strongly activate transcription in various systems when attached to the DNA-binding domain of a heterologous protein. The VP16 activation domain is rich in acidic residues and has been regarded as a classic acidic activation domain (AAD). As used herein, VP64 activation doamin is a tetrameric repeat of VP16's minimal activation domain. As used herein, p65 is one of two proteins that the NF-kappa B transcription factor complex is composed of The other protein is p50. The p65 activation domain is a part of the p65 subunit is a potent transcriptional activator even in the absence of p50.

In certain embodiments, the effector domain is a mammalian protein or biologically active fragment thereof. Such effector domains are referred to as "mammalian effector domains."

In certain embodiments, the activity of the effector domain is a non-biological activity. Examples of non-biological activities include fluorescence, luminescence, maltose binding protein ("MBP"), glutathione S transferase (GST), hexahistidine (SEQ ID NO: 27), c-myc, and the FLAG epitope activity, for facilitating detection, purification, monitoring expression, and/or monitoring cellular and subcellular localization. In such embodiments, the dTALE polypeptide may also be used as a diagnostic reagent, for example, to detect mutations in gene sequences, to purify restriction fragments from a solution, or to visualize DNA fragments of a gel.

In other embodiments of the invention, one or more effector domains may be fused to the nucleic acid binding domain of polypeptides of the invention such that it is at the N-terminus, C-terminus, or internal to the polypeptide, so long as it is not located within the dTALE nucleic acid binding domain. The positioning of an effector domain for activity (e.g., enhanced or optimal activity) may be engineered according to structural position requirements and methods well known in the art. In certain host cells (e.g., mammalian host cells), expression and/or secretion of dTALEs may be increased through use of heterologous signal sequences.

In some other preferred embodiments of the invention, the biological activities of effector domains include but are not limited to transposase, integrase, recombinase, resolvase, invertase, protease, DNA methyltransferase, DNA demethylase, histone acetylase, histone deacetylase, nuclease, transcriptional repressor, transcriptional activator, a nuclear-localization signal, a transcription-protein recruiting protein, cellular uptake activity, nucleic acid binding, or antibody presentation activity.

As used herein, the term "recombinase" refers to enzymatic proteins that are involved in genetic recombination. DNA recombinase are frequently utilized to manipulate the structure of geneomes to control gene expression. Recombinases generally target sites that are specific to each recombinase and catalyze DNA exchange between the target sites in a particular direction. The types of resulting DNA alterations may include but are not limited to excision/insertions, inversions, translcations and cassette excahgne. Enzymes categorized as recombinases may include but are not limited to Gin recombinase, Cre recombinase, Hin recombinase, RecA/RAD51, Tre reccombinase and FLP recombinase.

As described above, the dTALEs described herein are able to specifically bind to cytosine containing target nucleic acid sequences. In mammals, genomic DNA methylation of CpG di-nucleotides is an important epigenetic regulator of transcription and epigenetic structure. The dTALEs described herein are therefore useful for the regulation of mammalian DNA methylation. Such dTALEs may contain an effector domain that has DNA methyltransferase activity, such as a DNMT1, DNMT3a or DNMT3b domain, or a biologically active fragment thereof. Hence it is a preferred embodiment of the invention wherein the polypeptide has a DNA methyltransferase domain.

In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

As described in Zhang et al., *Nature Biotechnology* 29:149-153 (2011), a dTALE having a nucleic acid binding domain and an effector domain may be used to target the effector domain's activity to a genomic position having a predetermined nucleic acid sequence recognized by the nucleic acid binding domain. In some embodiments of the invention described herein, dTALE polypeptides are designed and used for targeting gene regulatory activity, such as transcriptional or translational modifier activity, to a regulatory, coding, and/or intergenic region, such as enhancer and/or repressor activity, that may affect transcription upstream and downstream of coding regions, and may be used to enhance or repress gene expression. For example, dTALE polypeptide may comprise effector domains having DNA-binding domains from transcription factors, effector domains from transcription factors (activators, repressors, co-activators, co-repressors), silencers, nuclear hormone receptors, and/or chromatin associated proteins and their modifiers (e.g., methylases, kinases, phosphatases, acetylases and deacetylases). In a further embodiment, useful domains for regulating gene expression may also be obtained from the gene products of oncogenes. In yet further advantageous embodiments of the invention, effector domains having integrase or transposase activity may be used to promote integration of exogenous nucleic acid sequence into specific nucleic acid sequence regions, eliminate (knock-out) specific endogenous nucleic acid sequence, and/or modify epigenetic signals and consequent gene regulation, such as by promoting DNA methyltransferase, DNA demethylase, histone acetylase and histone deacetylase activity. In other embodiments, effector domains having nuclease activity may be used to alter genome structure by nicking or digesting target sequences to which the polypeptides of the invention specifically bind, and may allow introduction of exogenous genes at those sites. In still further embodiments, effector domains having invertase activity may be used to alter genome structure by swapping the orientation of a DNA fragment.

In particularly advantageous embodiments, the dTALEs or polypeptides of the invention may be used to target transcriptional activity. As used herein, the term "transcription factor" refers to a protein or polypeptide that binds specific DNA sequences associated with a genomic locus or gene of interest to control transcription. Transcription factors may promote (as an activator) or block (as a repressor) the recruitment of RNA polymerase to a gene of interest. Transcription factors may perform their function alone or as a part of a larger protein complex. Mechanisms of gene regulation used by transcription factors include but are not limited to a) stabilization or destabilization of RNA polymerase binding, b) acetylation or deacetylation of histone proteins and c) recruitment of co-activator or co-repressor proteins. Furthermore, transcription factors play roles in biological activities that include but are not limited to basal transcription, enhancement of transcription, development, response to intercellular signaling, response to environmental cues, cell-cycle control and pathogenesis. With regards to information on transcriptional factors, mention is made of Latchman and DS (1997) *Int. J. Biochem. Cell Biol.* 29 (12): 1305-12; Lee T I, Young R A (2000) *Annu. Rev. Genet.* 34: 77-137 and Mitchell P J, Tjian R (1989) *Science* 245 (4916): 371-8, herein incorporated by reference in their entirety.

In some embodiments, effector domains having resolvase activity may alter the genomic structure by changing the linking state of the DNA, e.g., by releasing concatemers. In some embodiments, effector domains having deaminase activity may be used to remove amino group(s) from a molecule. For example, dTALE having a transcription activator effector domain may increase a gene's expression, and a dTALE having an effector domain with epigenetic modification activity may alter the epigenetic status of a locus to render it either more or less heterochromatic. In some embodiments of the polypeptides described herein, the effector domain may have a nucleic acid binding activity distinct from the activity mediated by the nucleic acid binding domain of the polypeptide.

In other advantageous embodiments of the polypeptides of the invention, the effector domain may comprise a peptide or polypeptide sequence responsive to a ligand, such as a hormone receptor ligand binding domain and may be used to act as a "gene switch" and be regulated by inducers, such as small molecule or protein ligands, specific for the ligand binding domain. In still further embodiments of the invention, the effector domain may comprise sequences or domains of polypeptides that mediate direct or indirect protein-protein interactions, such as, for example, a leucine zipper domain, a STAT protein N-terminal domain, and/or an FK506 binding protein. Specific examples of nucleic acid and protein sequences useful as effector domains are well known in the art. With regards to effector domains, mention is made of PCT publication WO 1999/045132, the contents of which are incorporated by reference herein in their entirety.

In additional advantageous embodiments of the invention one or more effector domains comprise an N-terminal domain 5' or a C-terminal domain 3', or a fragment or polypeptide sequence thereof that is at least 50%, at least 55%, at least 60%, at least 65%, at least 70%, at least 75%, at least 80%, at least 85%, at least 90%, at least 95%, at least 99%, or more identical to the amino acid sequence of the N-terminal domain and/or C-terminal domain from a wild type TALE. In a preferred embodiment of the invention, the N-terminal capping region or fragment thereof is 95% identical to a wild type N-terminal capping region. In another preferred embodiment, the C-terminal capping region or fragment thereof is 95% identical to a wild type C-terminal capping region. In such embodiments, the N-terminal and/or C-terminal domains or a fragment or polypeptide sequence thereof may be selected to enhance the biological activity of another effector domain, such as, for example, to enhance transcriptional activation of a transcriptional activation effector domain.

The polypeptides of the invention which may comprise an effector domain may be produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which may subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a nuclear localization signal, effector domain, etc.). With regards to these molecular techniques, mention is made of U.S. Pat. No. 7,674,892, the contents of which are incorporated by reference herein in their entirety.

The present invention provides for a method of repressing expression of a mammalian genomic locus of interest, which may comprise contacting the genomic locus with a non-naturally occurring or engineered composition which may comprise a DNA binding polypeptide which may comprise a N-terminal capping region, a DNA binding domain which may comprise at least one or more TALE monomers or half-monomers and a C-terminal capping region, wherein these three parts of the polypeptide are arranged in a predetermined N-terminus to C-terminus orientation and wherein the polypeptide includes at least one or more repressor domains. In an advantageous embodiment of the invention the polypeptide is encoded by and expressed from a codon optimized nucleic acid molecule so that the polypeptide preferentially binds to mammalian DNA.

For example, in some advantageous embodiments of the invention, the effector domain is a transcriptional inhibitor (i.e., a repressor domain), such as an mSin interaction domain (SID), SID4X or a Krüppel-associated box (KRAB). As used herein the SID domain is an interaction domain which is present in several transcriptional repressor proteins and may function with additional repressor domains and corepressors. As used herein, SID4X is a tandem repeat of four SID domains linker together by short peptide linkers. As used herein, the KRAB domain is a domain that is usually found in the N-terminal of several zinc finger protein based transcription factors. The KRAB domain may consist of 75 amino acids which repression may be accomplished by a module of about 45 amino acids. Hence, preferred embodiments of the invention may use KRAB domains or fragments thereof as repressor domains.

The present invention also provides for a method of activating expression of a mammalian genomic locus of interest, which may comprise contacting the genomic locus with a non-naturally occurring or engineered composition which may comprise a DNA binding polypeptide which may comprise a N-terminal capping region, a DNA binding domain which may comprise at least one or more TALE monomers or half-monomers and a C-terminal capping region, wherein these three parts are arranged in a predetermined N-terminus to C-terminus orientation and wherein the polypeptide includes at least one or more activator domains. In an advantageous embodiment of the invention the polypeptide is encoded by and expressed from a codon optimized nucleic acid molecule so that the polypeptide preferentially binds to mammalian DNA.

In some embodiments the effector domain is an enhancer of transcription (i.e., an activation domain), such as the VP64 or p65 or VP16 activation domains. A graphical comparison of the effect these different activation domains have on Sox2 mRNA level is provided in FIG. 26.

Provided herein are nucleic acid molecules encoding the dTALE polypeptides described herein. As used herein, the term "encoding" is open. Thus, a nucleic acid molecule encoding a dTALE polypeptide may also encode other polypeptides and may include additional non-coding nucleic acid sequences (e.g., promoters, enhancers). As used herein and as mentioned previously, the term "nucleic acid molecule" is intended to include DNA molecules (i.e., cDNA or genomic DNA) and RNA molecules (i.e., mRNA) and analogs of the DNA or RNA generated using nucleotide analogs in any number of forms and/or conformations.

In certain embodiments, the dTALE-encoding nucleic acid described herein is isolated. As described previously, an "isolated" nucleic acid is free of sequences which naturally flank the nucleic acid (i.e., sequences located at the 5' and 3' ends of the nucleic acid) in the nucleic acid (e.g., genomic DNA) of the organism from which the nucleic acid is derived and is substantially free of cellular material of the organism from which the nucleic acid is derived.

In certain embodiments the dTALE-encoding nucleic acid is part of a vector. As used herein, the term "vector" refers to a nucleic acid molecule capable of transporting another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In certain embodiments, the dTALE nucleic acid molecule described herein is an expression vector. As used herein, "expression vectors" are vectors capable of directing the expression of dTALE polypeptide. Such expression vectors include one or more regulatory sequences operably linked to a sequence that encodes a dTALE polypeptide, thereby allowing dTALE polypeptide to be expressed in a host cell. Within a recombinant expression vector, "operably linked" means that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" includes promoters, enhancers and other expression control elements (e.g., polyadenylation signals). Regulatory sequences include constitutive regulatory signals, inducible regulatory signals and tissue-specific regulatory signals.

In addition, advantageous embodiments of the invention include host cells, cell lines and transgenic organisms (e.g., plants, fungi, animals) which may comprise these DNA-binding polypeptides/nucleic acids and/or modified by these polypeptides (e.g., genomic modification that is passed into the next generation). Further preferred embodiments include cells and cell lines which include but are not limited to plant cells, insect cells, bacterial cells, yeast cells, viral cells, human cells, primate cells, rat cells, mouse cells, zebrafish cells, madin-darby canine cells, hamster cells, xenopus cells and stem cells. Advantageous embodiments of the invention are the cell and cell lines being of animal origin, most preferably of mammalian origin. In a preferred embodiment, the DNA binding polypeptide further may comprise a reporter or selection marker. In advantageous embodiments the selection marker may be a fluorescent marker, while in other aspects, the reporter is an enzyme.

Further advantageous embodiments of the invention include host cells which may comprise these polypeptides/nucleic acids and/or modified by these polypeptides (e.g., genomic modification that is passed into the next generation). The host cell may be stably transformed or transiently transfected or a combination thereof with one or more of these protein expression vectors. In other embodiments, the one or more protein expression vectors express one or fusion proteins in the host cell. In another embodiment, the host cell may further comprise an exogenous polynucleotide donor sequence.

As described previously and as used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes one or more expression control sequences, and an "expression control sequence" is a DNA sequence that controls and regulates the transcription and/or translation of another DNA sequence. Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.). By way of example, some vectors used in recombinant DNA techniques allow entities, such as a segment of DNA (such as a heterologous DNA segment, such as a heterologous cDNA segment), to be transferred into a target cell. The present invention comprehends recombinant vectors that may include viral vectors, bacterial vectors, protozoan vectors, DNA vectors, or recombinants thereof. With regards to recombination and cloning methods, mention is made of U.S. patent application Ser. No. 10/815,730, the contents of which are herein incorporated by reference in their entirety.

A vector may have one or more restriction endonuclease recognition sites (whether type I, II or IIs) at which the sequences may be cut in a determinable fashion without loss of an essential biological function of the vector, and into which a nucleic acid fragment may be spliced or inserted in order to bring about its replication and cloning. Vectors may also comprise one or more recombination sites that permit exchange of nucleic acid sequences between two nucleic acid molecules. Vectors may further provide primer sites, e.g., for PCR, transcriptional and/or translational initiation and/or regulation sites, recombinational signals, replicons, selectable markers, etc. A vector may further contain one or more selectable markers suitable for use in the identification of cells transformed with the vector.

As mentioned previously, vectors capable of directing the expression of genes and/or nucleic acid sequence to which they are operatively linked, in an appropriate host cell (e.g., a prokaryotic cell, eukaryotic cell, or mammalian cell), are referred to herein as "expression vectors." If translation of the desired nucleic acid sequence is required, such as for example, the mRNA encoding a dTALE polypeptide, the vector also typically may comprise sequences required for proper translation of the nucleotide sequence. The term "expression" as used herein with regards to expression vectors, refers to the biosynthesis of a nucleic acid sequence product, i.e., to the transcription and/or translation of a nucleotide sequence, for example, a nucleic acid sequence encoding a dTALE polypeptide in a cell. Expression also refers to biosynthesis of a microRNA or RNAi molecule, which refers to expression and transcription of an RNAi agent such as siRNA, shRNA, and antisense DNA, that do not require translation to polypeptide sequences.

In general, expression vectors of utility in the methods of generating and compositions which may comprise polypeptides of the invention described herein are often in the form of "plasmids," which refer to circular double-stranded DNA loops which, in their vector form, are not bound to a chromosome. In some embodiments of the aspects described herein, all components of a given dTALE polypeptide may be encoded in a single vector. For example, in some embodiments, a vector may be constructed that contains or may comprise all components necessary for a functional dTALE polypeptide as described herein. In some embodiments, individual components (e.g., one or more monomer units and one or more effector domains) may be separately encoded in different vectors and introduced into one or more cells separately. Moreover, any vector described herein may itself comprise predetermined dTALE polypeptide encoding component sequences, such as an effector domain and/or dTALE monomer unit, at any location or combination of locations, such as 5' to, 3' to, or both 5' and 3' to the exogenous nucleic acid molecule which may comprise one or more component dTALE encoding sequences to be cloned in. Such expression vectors are termed herein as which may comprise "backbone sequences."

Several embodiments of the invention relate to vectors that include but are not limited to plasmids, episomes, bacteriophages, or viral vectors, and such vectors may integrate into a host cell's genome or replicate autonomously in the particular cellular system used. In some embodiments of the compositions and methods described herein, the vector used is an episomal vector, i.e., a nucleic acid capable of extra-chromosomal replication and may include sequences from bacteria, viruses or phages. Other embodiments of the invention relate to vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids. In some embodiments, a vector may be a plasmid, bacteriophage, bacterial artificial chromosome (BAC) or yeast artificial chromosome (YAC). A vector may be a single- or double-stranded DNA, RNA, or phage vector.

Viral vectors include, but are not limited to, retroviral vectors, such as lentiviral vectors or gammaretroviral vectors, adenoviral vectors, and baculoviral vectors. For example, a lentiviral vector may be used in the form of lentiviral particles. Other forms of expression vectors known by those skilled in the art which serve equivalent functions may also be used. Expression vectors may be used for stable or transient expression of the polypeptide encoded by the nucleic acid sequence being expressed. A vector may be a self-replicating extrachromosomal vector or a vector which integrates into a host genome. One type of vector is a genomic integrated vector, or "integrated vector", which may become integrated into the chromosomal DNA or RNA of a host cell, cellular system, or non-cellular system. In some embodiments, the nucleic acid sequence encoding the dTALE polypeptides or component sequences, such as an effector domain sequence and/or dTALE monomer unit sequence, described herein, integrates into the chromosomal DNA or RNA of a host cell, cellular system, or non-cellular system along with components of the vector sequence.

The recombinant expression vectors used herein comprise a dTALE nucleic acid in a form suitable for expression of the nucleic acid in a host cell, which indicates that the recombinant expression vector(s) include one or more regulatory sequences, selected on the basis of the host cell(s) to be used for expression, which is operatively linked to the nucleic acid sequence to be expressed.

As used herein, the term "regulatory sequence" is intended to include promoters, enhancers and other expression control elements (e.g., 5' and 3' untranslated regions (UTRs) and polyadenylation signals). With regards to regulatory sequences, mention is made of U.S. patent application Ser. No. 10/491,026, the contents of which are incorporated by reference herein in their entirety.

The terms "promoter", "promoter element" or "promoter sequence" are equivalents and as used herein, refer to a DNA sequence which when operatively linked to a nucleotide sequence of interest is capable of controlling the transcription of the nucleotide sequence of interest into mRNA. Promoters may be constitutive, inducible or regulatable. The term "tissue-specific" as it applies to a promoter refers to a promoter that is capable of directing selective expression of a nucleotide sequence of interest to a specific type of tissue in the relative absence of expression of the same nucleotide sequence of interest in a different type of tissue. Tissue specificity of a promoter may be evaluated by methods known in the art. The term "cell-type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell-type specific" when applied to a promoter also means a promoter capable of promoting selective expression of a nucleotide sequence of interest in a region within a single tissue. Cell-type specificity of a promoter may be assessed using methods well known in the art., e.g., GUS activity staining or immunohistochemical staining. The term "minimal promoter" as used herein refers to the minimal nucleic acid sequence which may comprise a promoter element while also maintaining a functional promoter. A minimal promoter may comprise an inducible, constitutive or tissue-specific promoter. With regards to promoters, mention is made of PCT publication WO 2011/028929 and U.S. application Ser. No. 12/511,940, the contents of which are incorporated by reference herein in their entirety.

In advantageous embodiments of the invention, the expression vectors described herein may be introduced into host cells to thereby produce proteins or peptides, including fusion proteins or peptides, encoded by nucleic acids as described herein (e.g., dTALE polypeptides, variant forms of dTALE polypeptides, dTALE fusion proteins, etc.).

In some embodiments, the recombinant expression vectors which may comprise a nucleic acid encoding a dTALE polypeptide described herein further comprise a 5 'UTR sequence and/or a 3' UTR sequence, thereby providing the nucleic acid sequence transcribed from the expression vector additional stability and translational efficiency.

Certain embodiments of the invention may relate to the use of prokaryotic vectors and variants and derivatives thereof. Other embodiments of the invention may relate to the use of eukaryotic expression vectors. With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety.

In some embodiments of the aspects described herein, a dTALE polypeptide is expressed using a yeast expression vector. Examples of vectors for expression in yeast *S. cerivisae* include, but are not limited to, pYepSec1 (Baldari, et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.).

In other embodiments of the invention, a dTALE polypeptide is expressed in insect cells using, for example, baculovirus expression vectors. Baculovirus vectors available for expression of proteins in cultured insect cells (e.g., Sf 9 cells) include, but are not limited to, the pAc series (Smith et al. (1983) *Mol. Cell. Biol.* 3:2156-2165) and the pVL series (Lucklow and Summers (1989) *Virology* 170:31-39).

In some embodiments of the aspects described herein, a dTALE polypeptide is expressed in mammalian cells using a mammalian expression vector. Non-limiting examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. With regards to viral regulatory elements, mention is made of U.S. patent application Ser. No. 13/248,967, the contents of which are incorporated by reference herein in their entirety.

In some such embodiments, the mammalian expression vector is capable of directing expression of the nucleic acid encoding the dTALE polypeptide in a particular cell type (e.g., tissue-specific regulatory elements are used to express the nucleic acid). Tissue-specific regulatory elements are known in the art and in this regard, mention is made of U.S. Pat. No. 7,776,321, the contents of which are incorporated by reference herein in their entirety.

The vectors which may comprise nucleic acid sequences encoding the dTALE polypeptides described herein may be "introduced" into cells as polynucleotides, preferably DNA, by techniques well known in the art for introducing DNA and RNA into cells. The term "transduction" refers to any method whereby a nucleic acid sequence is introduced into a cell, e.g., by transfection, lipofection, electroporation (methods whereby an instrument is used to create micro-sized holes transiently in the plasma membrane of cells under an electric discharge, see, e.g., Banerjee et al., *Med. Chem.* 42:4292-99

(1999); Godbey et al., *Gene Ther.* 6:1380-88 (1999); Kichler et al., *Gene Ther.* 5:855-60 (1998); Birchaa et al., *J. Pharm.* 183:195-207 (1999)), biolistics, passive uptake, lipid:nucleic acid complexes, viral vector transduction, injection, contacting with naked DNA, gene gun (whereby the nucleic acid is coupled to a nanoparticle of an inert solid (commonly gold) which is then "shot" directly into the target cell's nucleus), calcium phosphate, DEAE dextran, lipofectin, lipofectamine, DIMRIE C™, Superfect™, and Effectin™ (Qiagen™), Unifectin™, Maxifectin™, DOTMA, DOGS™ (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecylammonium bromide), DHDEAB (N,N-di-n-hexadecyl-N, N-dihydroxyethyl ammonium bromide), HDEAB (N-n-hexadecyl-N,N-dihydroxyethylammonium bromide), polybrene, poly(ethylenimine) (PEI), sono-poration (transfection via the application of sonic forces to cells), optical transfection (methods whereby a tiny (~1 μm diameter) hole is transiently generated in the plasma membrane of a cell using a highly focused laser), magnetofection (refers to a transfection method, that uses magnetic force to deliver exogenous nucleic acids coupled to magnetic nanoparticles into target cells), impalefection (carried out by impaling cells by elongated nanostructures, such as carbon nanofibers or silicon nanowires which were coupled to exogenous nucleic acids), and the like. In this regard, mention is made of U.S. patent application Ser. No. 13/088,009, the contents of which are incorporated by reference herein in their entirety.

The nucleic acid sequences encoding the dTALE polypeptides or the vectors which may comprise the nucleic acid sequences encoding the dTALE polypeptides described herein may be introduced into a cell using any method known to one of skill in the art. The term "transformation" as used herein refers to the introduction of genetic material (e.g., a vector which may comprise a nucleic acid sequence encoding a dTALE polypeptide) into a cell, tissue or organism. Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA), which detects the presence of a polypeptide encoded by one or more of the transgenes. For example, a nucleic acid sequence encoding a dTALE polypeptide may further comprise a constitutive promoter operably linked to a second output product, such as a reporter protein. Expression of that reporter protein indicates that a cell has been transformed or transfected with the nucleic acid sequence encoding a dTALE polypeptide. Alternatively, or in combination, transient transformation may be detected by detecting the activity of the dTALE polypeptide. The term "transient transformant" refers to a cell which has transiently incorporated one or more transgenes.

In contrast, the term "stable transformation" or "stably transformed" refers to the introduction and integration of one or more transgenes into the genome of a cell or cellular system, preferably resulting in chromosomal integration and stable heritability through meiosis. Stable transformation of a cell may be detected by Southern blot hybridization of genomic DNA of the cell with nucleic acid sequences, which are capable of binding to one or more of the transgenes. Alternatively, stable transformation of a cell may also be detected by the polymerase chain reaction of genomic DNA of the cell to amplify transgene sequences. The term "stable transformant" refers to a cell, which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene. Transformation also includes introduction of genetic material into plant cells in the form of plant viral vectors involving epichromosomal replication and gene expression, which may exhibit variable properties with respect to meiotic stability. Transformed cells, tissues, or plants are understood to encompass not only the end product of a transformation process, but also transgenic progeny thereof.

For stable transfection of mammalian cells, it is known that, depending upon the expression vector and transfection technique used, only a small fraction of cells may integrate the foreign DNA into their genome. In order to identify and select these integrants, a gene that encodes a selectable biomarker (e.g., resistance to antibiotics) is generally introduced into the host cells along with the gene of interest. Selectable markers include those which confer resistance to drugs, such as G418, hygromycin and methotrexate. Nucleic acid encoding a selectable biomarker may be introduced into a host cell on the same vector as that encoding dTALE or may be introduced on a separate vector. Cells stably transfected with the introduced nucleic acid may be identified by drug selection (e.g., cells that have incorporated the selectable biomarker gene survive, while the other cells die). With regards to transformation, mention is made to U.S. Pat. No. 6,620,986, the contents of which are incorporated by reference herein in their entirety.

A host cell, such as a prokaryotic or eukaryotic host cell in culture, may be used to produce (i.e., express) a dTALE polypeptide as described herein, or may be the cell in which the dTALE polypeptide is expressed to mediate its effect on a target gene sequence. A "host cell" as used herein may be any cell, including non-plant, moneran, fungal, prokaryotic or eukaryotic cell. As defined herein, a "cell" or "cellular system" is the basic structural and functional unit of all known independently living organisms. It is the smallest unit of life that is classified as a living thing, and is often called the building block of life. Some organisms, such as most bacteria, are unicellular (consist of a single cell). Other organisms, such as humans, are multicellular. A "natural cell," as defined herein, refers to any prokaryotic or eukaryotic cell found naturally. A "prokaryotic cell" may comprise a cell envelope and a cytoplasmic region that contains the cell genome (DNA) and ribosomes and various sorts of inclusions. In other embodiments, the cell or cellular system is an artificial or synthetic cell. As defined herein, an "artificial cell" or a "synthetic cell" is a minimal cell formed from artificial parts that may do many things a natural cell may do, such as transcribe and translate proteins and generate ATP.

For example, a dTALE polypeptide may be expressed in bacterial cells, such as *E. coli*; insect cells, such as SF9 or SF-21 cells from *Spodoptera frugiperda* or S2 cells from *Drosophila melanogaster*; plant cells, such as a tobacco plant cell; yeast or fungal cells, such as a cell from *Pichia pastoris, Rhizopus, Aspergillus*, or *S. cerevisiae*; animal cells, such as nematode, insect, plant, bird, reptile, or mammalian cells (such as, for example, cells from a mouse, rat, rabbit, hamster, gerbil, dog, cat, goat, pig, cow, horse, whale, monkey, or human, e.g., 293FT cells, Fao hepatoma cells, primary hepatocytes, Chinese hamster ovary cells (CHO), or COS cells). The cells may be primary cells, immortalized cells, stem cells, or transformed cells. Other suitable host cells are known to those skilled in the art. With regards to host cells, mention is made of U.S. patent application Ser. No. 13/088,009, the contents of which are incorporated by reference herein in their entirety.

In some embodiments of the aspects described herein, a primary somatic cell is used as the host cell for expression of a dTALE polypeptide and/or is the cell type in which the dTALE polypeptide is expressed to mediate its effect on a target gene sequence via its nucleic acid binding domain. Essentially any primary somatic cell type may be used as a host cell for expressing a dTALE polypeptide. Some non-limiting examples of primary cells include, but are not limited to, fibroblast, epithelial, endothelial, neuronal, adipose, cardiac, skeletal muscle, immune cells, hepatic, splenic, lung, circulating blood cells, gastrointestinal, renal, bone marrow, and pancreatic cells. The cell may be a primary cell isolated from any somatic tissue including, but not limited to, brain, liver, lung, gut, stomach, intestine, fat, muscle, uterus, skin, spleen, endocrine organ, bone, etc. The term "somatic cell" as used herein, further encompasses primary cells grown in culture, provided that the somatic cells are not immortalized. With regards to these cells, mention is made of U.S. patent application Ser. No. 13/147,713, the contents of which are incorporated by reference herein in their entirety.

Where the cell is maintained under in vitro conditions, conventional tissue culture conditions and methods may be used, and are known to those of skill in the art. Isolation and culture methods for various cells are well within the abilities of one skilled in the art.

Further, the parental cell may be from any mammalian species, with non-limiting examples including a murine, bovine, simian, porcine, equine, ovine, or human cell. In some embodiments, the cell is a human cell. In an alternate embodiment, the cell is from a non-human organism such as a non-human mammal.

The dTALE polypeptides described herein may be used to repress or activate transcription of known pluripotency factors, such as SOX2 in 293FT cells. Other factors include but are not limited to KLF4, c-Myc, and Oct-4. Accordingly, in some embodiments of the aspects described herein, cells of a cell line are used as the host cell for expression of a dTALE polypeptide and/or are the cell type in which the dTALE polypeptide is expressed to mediate its effect on a target gene sequence via its nucleic acid binding domain. In some such embodiments, the host cell is a mammalian cell line. In some such embodiments, the mammalian cell line is a human cell line.

Examples of human cell lines useful with the compositions and methods provided herein include, but are not limited to, 293T (embryonic kidney), BT-549 (breast), DMS114 (small cell lung), DU145 (prostate), HT-1080 (fibrosarcoma), HEK 293 (embryonic kidney), HeLa (cervical carcinoma), HepG2 (hepatocellular carcinoma), HL-60(TB) (leukemia), HS 578T (breast), HT-29 (colon adenocarcinoma), Jurkat (T lymphocyte), M14 (melanoma), MCF7 (mammary), MDA-MB-453 (mammary epithelial), PERC6® (E1-transformed embryonal retina), RXF 393 (renal), SF-268 (CNS), SF-295 (CNS), THP-1 (monocyte-derived macrophages), TK-10 (renal), U293 (kidney), UACC-257 (melanoma), and XF 498 (CNS). In this regard, mention is made of U.S. Pat. No. 8,183,038, the contents of which are incorporated by reference herein in their entirety.

Examples of non-human primate cell lines useful with the compositions and methods provided herein include, but are not limited to, monkey kidney (CV1-76) cells, African green monkey kidney (VERO-76) cells, green monkey fibroblast (Cos-1) cells, and monkey kidney (CV1) cells transformed by SV40 (Cos-7). Additional mammalian cell lines are known to those of ordinary skill in the art and are catalogued at the American Type Culture Collection catalog (ATCC®, Mamassas, Va.). With regard to non-human primate cell lines, mention is made of U.S. Pat. No. 5,168,050, the contents of which are incorporated by reference herein in their entirety.

Examples of rodent cell lines useful with the compositions and methods provided herein include, but are not limited to, mouse Sertoli (TM4) cells, mouse mammary tumor (MMT) cells, rat hepatoma (HTC) cells, mouse myeloma (NS0) cells, murine hybridoma (Sp2/0) cells, mouse thymoma (EL4) cells, Chinese Hamster Ovary (CHO) cells and CHO cell derivatives, murine embryonic (NIH/3T3, 3T3 L1) cells, rat myocardial (H9c2) cells, mouse myoblast (C2C12) cells, and mouse kidney (miMCD-3) cells. Aspects of rodent cell lines are further described in PCT publication WO/2011/11990, the contents of which are incorporated by reference herein in their entirety.

In other advantageous embodiments of the invention, a stem cell is used as the host cell for expression of the polypeptides of the invention and/or is the cell type in which the dTALE polypeptide is expressed to mediate its effect on a target gene sequence via its nucleic acid binding domain. As used herein, stem cells refer to undifferentiated cells defined by their ability at the single cell level to both self-renew and differentiate to produce progeny cells, including self-renewing progenitors, non-renewing progenitors, and terminally differentiated cells. Stem cells, depending on their level of differentiation, are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts. (mention is made of U.S. Pat. Nos. 5,750,376, 5,851,832, 5,753,506, 5,589,376, 5,824,489, 5,654,183, 5,693,482, 5,672,499, and 5,849,553, all herein incorporated in their entireties by reference). Stem cells that may be used in the compositions and methods which may comprise dTALE polypeptides and nucleic acid sequences encoding dTALE polypeptides described herein may be naturally occurring stem cells or "induced" stem cells generated using the compositions, kits, and methods described herein, or by any method or composition known to one of skill in the art.

Stem cells may be obtained from any mammalian species, e.g., human, primate, equine, bovine, porcine, canine, feline, rodent, e.g., mice, rats, hamsters, etc. Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages, but all within a particular tissue, organ, or physiological system (for example, hematopoietic stem cells (HSC) may produce progeny that include HSC (self-renewal), blood cell restricted oligopotent progenitors and the cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

DNA binding polypeptides of the invention may be used in conjunction with stem cells that include but are not limited to embryonic cells of various types, exemplified by human embryonic stem (hES) cells, described by Thomson et al. (1998) Science 282:1145; embryonic stem cells from other primates, such as Rhesus stem cells (Thomson et al. (1995) Proc. Natl. Acad. Sci. USA 92:7844); marmoset stem cells (Thomson et al. (1996) Biol. Reprod. 55:254); and human embryonic germ (hEG) cells (Shambloft et al., *Proc. Natl. Acad. Sci. USA* 95:13726, 1998). Also of interest are lineage-committed stem cells, such as hematopoietic or pancreatic stem cells. In some embodiments, the host cell transfected with the expression vector which may comprise a sequence encoding a dTALE polypeptide is a multipotent stem cell or progenitor cell. Examples of multipotent cells useful in methods provided herein include, but are not limited to, murine embryonic stem (ES-D3) cells, human umbilical vein endothelial (HuVEC) cells, human umbilical artery smooth muscle (HuASMC) cells, human differentiated stem (HKB-11) cells, and human mesenchymal stem (hMSC) cells. An additional stem cell type of interest for use with the compositions and methods described herein are cancer stem cells. With regards to stem cells, mention is made of PCT publication WO/2011/119901, the contents of which are incorporated by reference herein in their entirety.

Cells derived from embryonic sources may include embryonic stem cells or stem cell lines obtained from a stem cell bank or other recognized depository institution. Other means of producing stem cell lines include the method of Chung et al. (2006) which may comprise taking a blastomere cell from an early stage embryo prior to formation of the blastocyst (at around the 8-cell stage). The technique corresponds to the pre-implantation genetic diagnosis technique routinely practiced in assisted reproduction clinics. The single blastomere cell is then co-cultured with established ES-cell lines and then separated from them to form fully competent ES cell lines.

Cells may also be derived from human umbilical cord blood cells (HUCBC), which are recognized as a rich source of hematopoietic and mesenchymal stem cells (Broxmeyer et al., 1992 Proc. Natl. Acad. Sci. USA 89:4109-4113). Cord blood cells are used as a source of transplantable stem and progenitor cells and as a source of marrow repopulating cells for the treatment of malignant diseases (e.g., acute lymphoid leukemia, acute myeloid leukemia, chronic myeloid leukemia, myelodysplastic syndrome, and neuroblastoma) and non-malignant diseases such as Fanconi's anemia and aplastic anemia (Kohli-Kumar et al., 1993 Br. *J. Haematol.* 85:419-422; Wagner et al., 1992 *Blood* 79; 1874-1881; Lu et al., 1996 *Crit. Rev. Oncol. Hematol.* 22:61-78; Lu et al., 1995 *Cell Transplantation* 4:493-503). One advantage of HUCBC for use with the methods and compositions described herein is the immature immunity of these cells, which is very similar to fetal cells, and thus significantly reduces the risk for rejection by the host (Taylor & Bryson, 1985 *J. Immunol.* 134: 1493-1497). With regards to cord blood cells, mention is made of U.S. application Ser. No. 10/777,425, the contents of which are incorporated by reference herein in their entirety.

In other embodiments of the aspects described herein, cancer stem cells are used as the host cells for expression of a dTALE polypeptide described herein, in order to, for example, differentiate or alter the phenotype of a cancer stem cell to a non-tumorigenic state by activating one or more target gene sequences. Examples of tumors from which samples containing cancer stem cells may be isolated from or enriched, for use with the compositions and methods described herein, include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, mesothelioma, Ewing's tumor, lymphangioendotheliosarcoma, synovioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, astrocytic tumors (e.g., diffuse, infiltrating gliomas, anaplastic astrocytoma, glioblastoma, gliosarcoma, pilocytic astrocytoma, pleomorphic xanthoastrocytoma), oligodendroglial tumors and mixed gliomas (e.g., oligodendroglioma, anaplastic oligodendroglioma, oligoastrocytoma, anaplastic oligoastrocytoma), ependymal tumors (e.g., ependymoma, anaplastic ependymoma, myxopapillary ependymoma, subependymoma), choroid plexus tumors, neuroepithelial tumors of uncertain origin (astroblastoma, chordoid glioma, gliomatosis cerebri), neuronal and mixed-neuronal-glial tumors (e.g., ganglioglioma and gangliocytoma, desmoplastic infantile astrocytoma and ganglioglioma, dysembryoplastic neuroepithelial tumor, central neurocytoma, cerebellar liponeurocytoma, paraganglioglioma), pineal parenchymal tumors, embryonal tumors (medulloepithelioma, ependymoblastoma, medulloblastoma, primitive neuroectodemmal tumor, atypical teratoid/rhabdoid tumor), peripheral neuroblastic tumors, tumors of cranial and peripheral nerves (e.g., schwannoma, neurinofibroma, perineurioma, malignant peripheral nerve sheath tumor), meningeal tumors (e.g., meningeomas, mesenchymal, non-meningothelial tumors, haemangiopericytomas, melanocytic lesions), germ cell tumors, tumors of the sellar region (e.g., craniopharyngioma, granular cell tumor of the neurohypophysis), hemangioblastoma, melanoma, and retinoblastoma. Additionally, the stem cell isolation methods of the invention are applicable to isolating stem cells from tissues other than characterized tumors (e.g., from tissues of diseases such as the so called "stem cell pathologies"). With regards to tumor and cancer stem cells, mention is made of U.S. application Ser. No. 10/195,117, the contents of which are incorporated by reference herein in their entirety.

In other aspects, methods for producing dTALE protein using host cells are further provided. In some embodiments of these methods, the method includes culturing the host cell (into which a recombinant expression vector encoding a dTALE polypeptide has been introduced) in a suitable medium until dTALE polypeptide is produced. In some such embodiments, the method further may comprise isolating the dTALE polypeptide produced from the medium or the host cell.

The term "heterologous" or "exogenous" when used with reference to a nucleic acid, indicates that the nucleic acid is in a cell or a virus where it is not normally found in nature; or, may comprise two or more subsequences that are not found in the same relationship to each other as are normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature; e.g., a human gene operably linked to a promoter sequence inserted into an adenovirus-based vector of the invention. As an example, a heterologous nucleic acid of interest may encode an immunogenic gene product, wherein the adenovirus is administered therapeutically or prophylactically as a carrier or drug-vaccine composition. Heterologous sequences may comprise various combinations of promoters and sequences, examples of which are described in detail herein.

The present invention also provides for pharmaceutical compositions which may comprise the DNA binding polypeptides of the invention or the nucleic acids encoding them. In a preferred embodiment the composition may comprise one or more pharmaceutically acceptable excipients. Pharmaceutically acceptable carrier or excipients, are known to those of skill in the art. See, for example, *Remington's Pharmaceutical Sciences*, 17th ed., 1985; and PCT publication WO 00/42219, the contents of which are incorporated by reference herein in their entirety.

As used herein, the terms "drug composition", "drug", "vaccinal composition", "vaccine", "vaccine composition", "therapeutic composition" and "therapeutic-immunologic composition" cover any composition that induces protection against an antigen or pathogen. In some embodiments, the protection may be due to an inhibition or prevention of infection by a pathogen. In other embodiments, the protection may be induced by an immune response against the antigen(s) of interest, or which efficaciously protects against the antigen; for instance, after administration or injection into the subject, elicits a protective immune response against the targeted antigen or immunogen, or provides efficacious protection against the antigen or immunogen expressed from the inventive adenovirus vectors of the invention. The term "pharmaceutical composition" means any composition that is delivered to a subject. In some embodiments, the composition may be delivered to inhibit or prevent infection by a pathogen.

The terms "immunogenic composition" and "immunological composition" and "immunogenic or immunological composition" cover any composition that confers in a subject a therapeutic effect and/or elicits in a subject an immune response against the antigen, immunogen, or pathogen of interest; for instance, after administration into a subject, elicits an immune response against the targeted immunogen or antigen of interest.

An "immunological response" to a composition, vaccine, antigen, immunogen, pathogen or ligand is the development in the host of a cellular and/or antibody-mediated immune response to the composition, vaccine, antigen, immunogen, pathogen or ligand of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host displays both a rapid (e.g., within <24 hrs.) therapeutic effect and a long-term protective immunological response such that resistance to new infection is enhanced and/or the clinical severity of the disease reduced. Such protection is demonstrated by either a reduction or lack of symptoms normally displayed by an infected host, a quicker recovery time and/or a lowered viral titer in the infected host.

A "therapeutically effective amount" or an "immunologically effective amount" is an amount or concentration of the recombinant vector encoding the gene of interest, that, when administered to a subject, produces a therapeutic response or an immune response to the gene product of interest.

Hence, particularly advantageous embodiments of the invention relate to the administration of a therapeutically effective amount of the polypeptide or polypeptides of the invention to target tissues and cells in an animal in need thereof. In preferred embodiments, the animal is a mammal. Formulations suitable for parenteral administration, such as, for example, by intravenous, intramuscular, intradermal, and subcutaneous routes, include aqueous and non-aqueous, isotonic sterile injection solutions, which may contain antioxidants, buffers, bacteriostats, and solutes that render the formulation isotonic with the blood of the intended recipient, and aqueous and non-aqueous sterile suspensions that may include suspending agents, solubilizers, thickening agents, stabilizers, and preservatives. In the practice of this invention, compositions may be administered, for example, by intravenous infusion, orally, topically, intraperitoneally, intravesically or intrathecally. The formulations of compounds may be presented in unit-dose or multi-dose sealed containers, such as ampules and vials. Injection solutions and suspensions may be prepared from sterile powders, granules, and tablets of the kind previously described.

The dTALES or polypeptides of the invention may also be supplied as components of diagnostic kits. In one embodiment they allow for the rapid identification of genomic markers of interest. In a further embodiment, these proteins may be purified from cells and used in diagnostic kits or for diagnostic reagents for uses such as analyzing the allele type of a gene of interest, measuring mRNA expression levels, etc. The polypeptides of the invention may be attached to silicon chips or beads for multichannel or microfluidic analyses. In yet a further aspect, the polypeptides of the invention may be utilized in kits used to facilitate genomic manipulation by the user and so may provide a polypeptide with an effector domain, for example, a TALEN that cleaves a desired target or a safe harbor locus within a genome. The TALEN may be provided either as nucleic acid (e.g., DNA or RNA) or may be provided as protein. In some instances, the protein may be formulated to increase stability, or may be provided in a dried form. In some instances, the kits are used for diagnostic purposes. In some embodiments of the invention, the TALE-fusion included in the kit is a transcriptional regulator. In other embodiments, the TALE-fusion may comprise a reporter. In yet another embodiment, the kit may comprise any additional component which aids in the construction and delivery of the DNA binding polypeptides of the invention.

The dTALE-expressing nucleic acid molecules described herein may be constructed, for example, using the methods described in Zhang et al., *Nature Biotechnology* 29:149-153 (2011) (Further described in Example 2). These nucleic acids encode for the polypeptides of the invention that are characterized by all the embodiments described herein.

EXAMPLES

Example 1

Targeting the SOX2 Gene Promoter with SID and KRAB Repression Domains

TALEs targeting the promoter of the human SOX2 gene with the mSin interaction domain (SID) or the Krüppel-associated box (KRAB) repression domain were engineered. TALEs were constructed using a Golden-Gate-like cut-ligation strategy. Different truncations of the KRAB domain and SID were codon optimized for mammalian expression and synthesized with flanking NheI and XbaI restriction sites. All repressor domains were cloned into the TALE backbone by replacing the VP64 activation domain using NheI and XbaI restriction sites and verified by sequencing. FIG. 1 depicts a schematic of an exemplary TALE-repressor architecture, while the amino acid sequences of the TALE repressors are provided in FIG. 2. When TALE repressors were introduced into HEK 293FT cells using liposomal transfection, the SID domain repressed the endogenous SOX2 locus 26% more effectively than the KRAB domain (FIG. 1).

Figure 3:
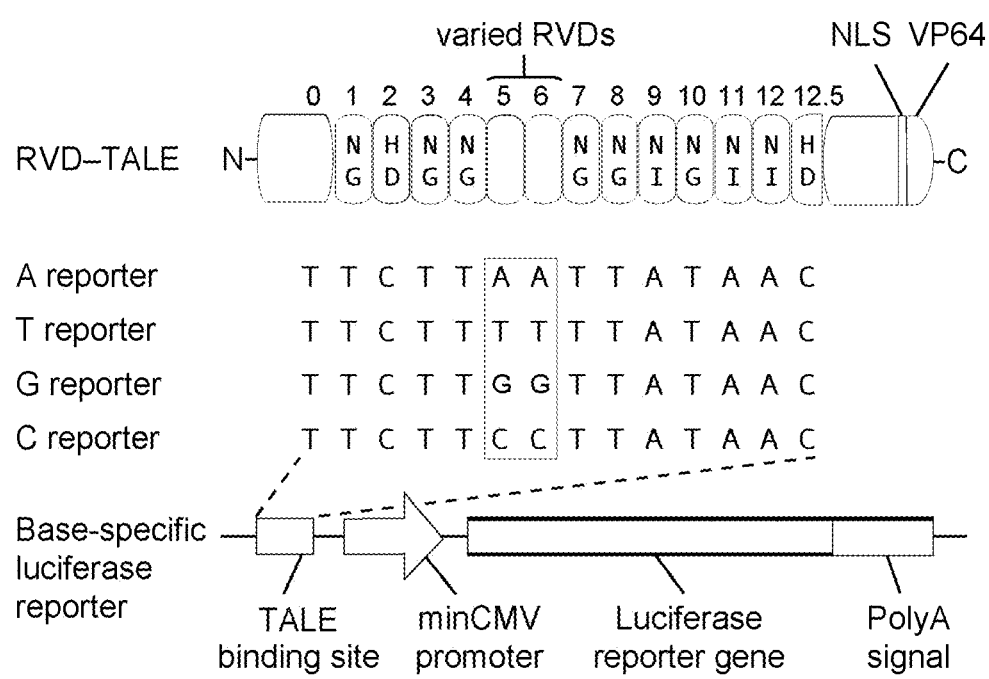
FIG. 3 shows the design of a dTALE repeat variable diresidue ("RVD") screening system.

To identify an RVD specific for G residues, 23 RVDs were evaluated for residue binding (FIGS. 3 and 4). To directly compare the DNA binding specificity and activity of the RVDs, a set of 23 12.5-repeat TALEs were designed where RVDs 5 and 6 were systematically substituted with the 23 test RVDs (RVD-TALEs; FIG. 3). Each RVD-TALE was used to assess the base-preference and activity strength of its corresponding RVD, which was measured by comparing each RVD-TALE's transcriptional activation of four base-specific luciferase reporter plasmids with A, G, T, and C substituted in the 5th and 6th positions of the TALE binding site (A-, G-, T-, or C-reporters; FIG. 3). Luciferase reporter assays were performed by co-transfecting HEK 293FT cells with TALE expression and luciferase reporter plasmids, as well as a control *Gaussia* luciferase plasmid (pCMV-Gluc, New England BioLabs). HEK 293FT cells were seeded into 24-well plates the day prior to transfection at densities of $2\times10^5$ cells/well. Approximately 24h after initial seeding, cells were transfected using Lipofectamine-2000 (Invitrogen) following the manufacturer's protocol. For each well of the 24-well plates 700 ng of dTALE and 50 ng of each reporter plasmids were used to transfect HEK 293FT cells.

The 23 RVD-TALEs exhibited a wide range of DNA base preferences and biological activities in the reporter assay. In particular, NH— and HN-TALEs activated the G-reporter preferentially and at levels similar to the NN-TALE. The NH-TALE also exhibited significantly higher specificity for the G-reporter than the NN-TALE (ratio of G- to A-reporter activations: 16.4 for NH-TALE and 3.5 for NN-TALE; FIG. 4). Additionally, the RVD NA exhibited similar levels of reporter activation for all four bases.

Figure 5A:
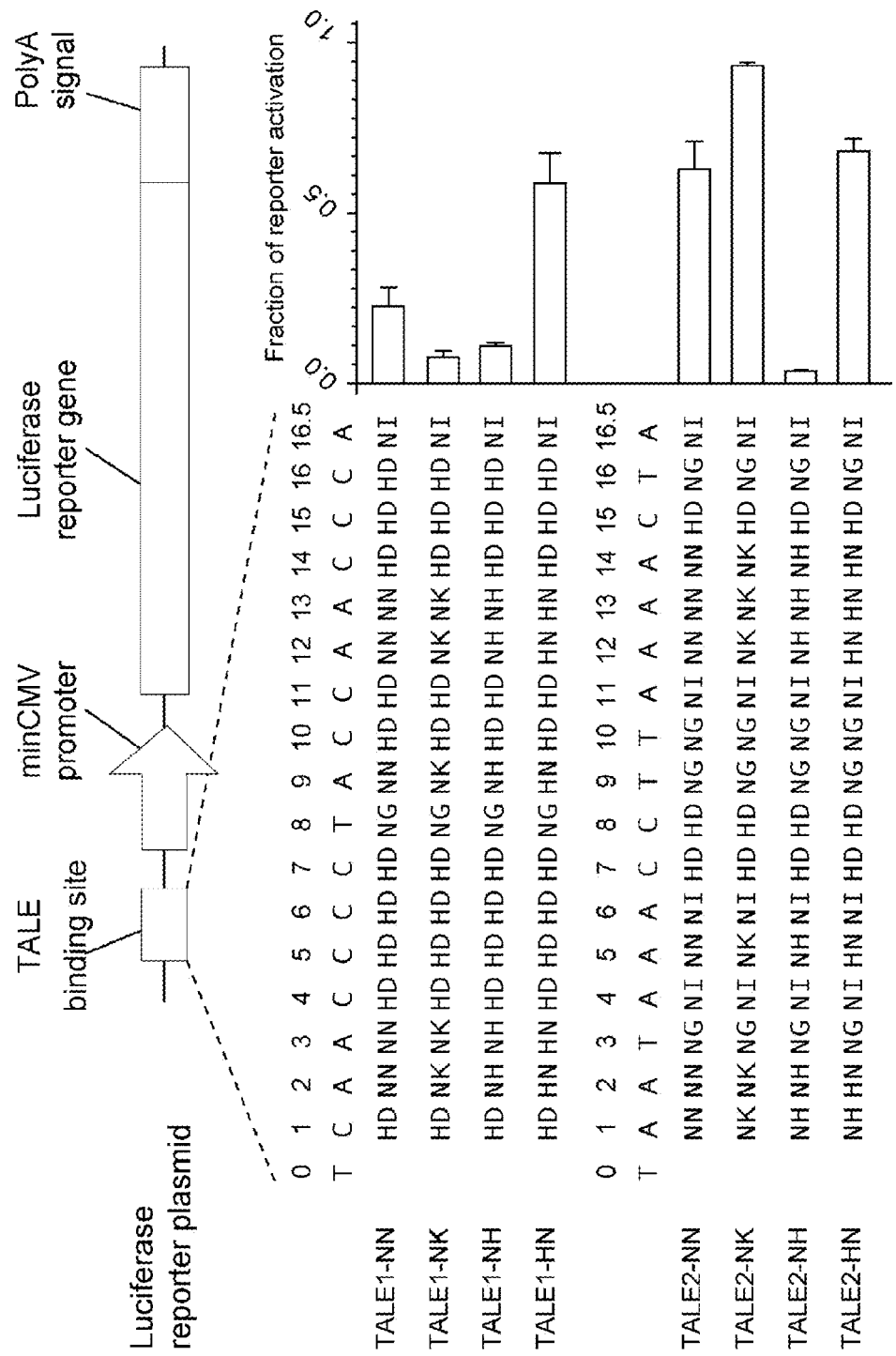
FIG. 5A discloses SEQ ID NOS 60 and 61, respectively, in order of appearance.
Figure 5B:
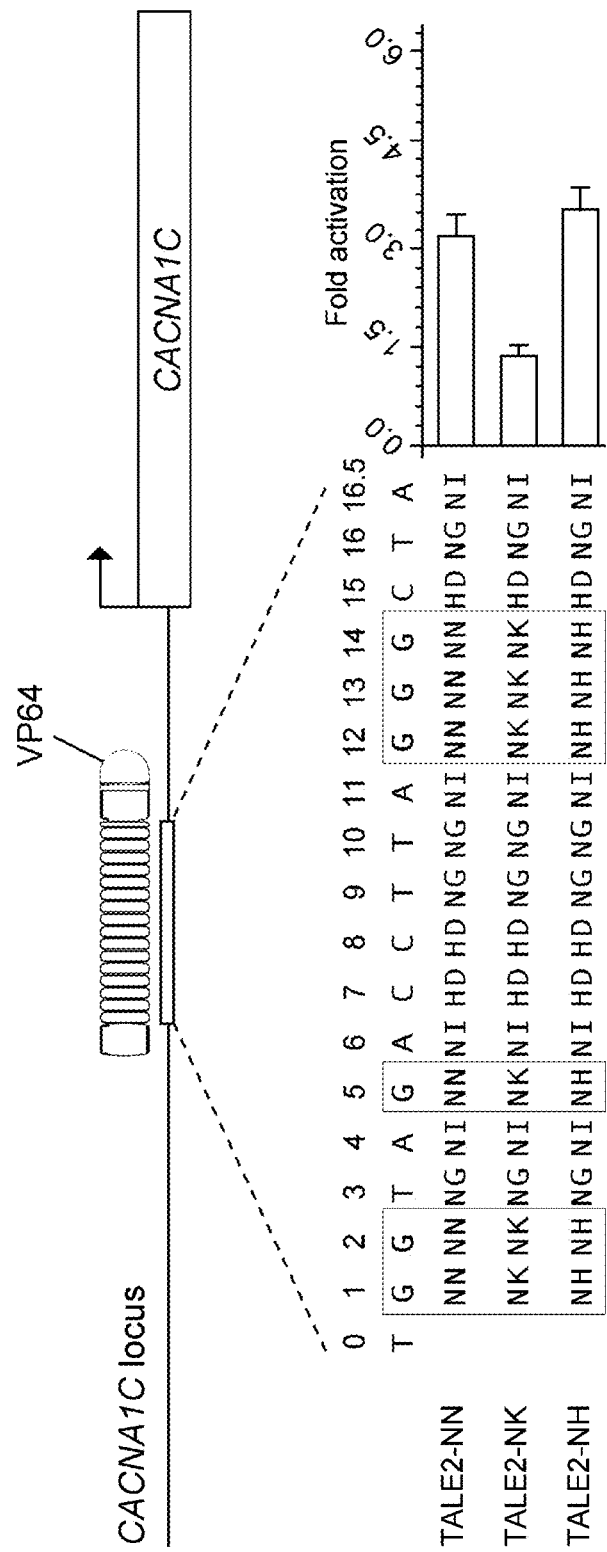
FIG. 5B discloses SEQ ID NO: 62.

To further investigate NH and HN as G-specific RVDs, the specificity and activity strength of NN, NK, NH, and HN were compared. Two 18 bp targets within the CACNA1C locus in the human genome were selected and four TALEs for each target, using NN, NK, NH, or HN as the G-targeting RVD, were constructed (FIGS. 5A-B). Amino acid sequences of exemplary CACNA1C TALES are provided in FIG. 6A-F. A luciferase assay was designed to further characterize the G-specificity of each RVD. For each CACNA 1C target site, two luciferase reporters were constructed, one with the original genomic target sequence, and the other with all of the Gs in the target sequences replaced with As (G-to-A reporter), and compared the activity of each TALE on the wild type and G-to-A reporter (FIG. 5A). Luciferase reporter plasmids were designed and synthesized by cloning the TALE binding site upstream of the minimal CMV promoter driving the expression of a *Cypridina* luciferase gene.

Dual luciferase reporter assays were carried out with the BioLux *Gaussia* luciferase flex assay kit and BioLux *Cypridina* luciferase assay kit (New England Biolabs) following the manufacturer's recommended protocol. Briefly, media from each well of transfected cells were collected 48 hours after transfection. For each sample, 20 µL of the media were added into a 96-well assay plate, mixed with each one of the dual luciferase assay mixes. After brief incubation, as indicated in the manufacturer's protocol, luminescence levels of each sample were measured using the Varioskan flash multimode reader (Thermo Scientific). The fold induction of the luciferase reporters was calculated according to the fold change of luminescence level in the *Cypridina* luciferase assay, normalized to the corresponding luminescence level in the *Gaussia* luciferase assay to control for sample differences.

The TALE with NH as the G-targeting RVD exhibited the highest levels of G-specificity across the CACNA1C targets (less than 10% activation of the G-to-A reporter; FIG. 5A), whereas the TALE with HN as the G-targeting RVD was able to activate the G-to-A luciferase reporters with at least 60% activity.

Figure 7:
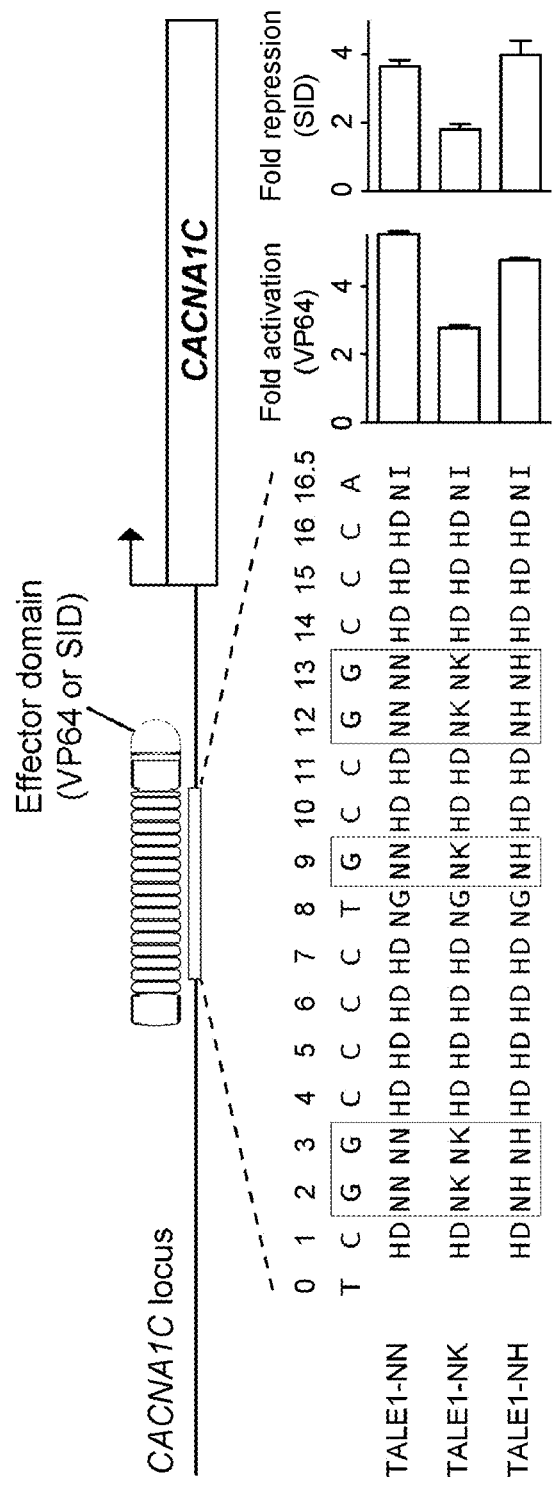
FIG. 7 shows the relative level of endogenous transcriptional activation or repression by TALE1-NN, TALE1-NK and TALE1-NH.

Using qRT-PCR, the levels of transcriptional modulation by TALEs carrying different G-targeting RVDs were compared (NN, NK, and NH; FIG. 5B and FIG. 7). HEK 293FT cells were seeded into 24-well plates. 1 µg of TALE plasmid was transfected using Lipofectamine 2000 (Invitrogen) according to manufacturer's protocol. Transfected cells were cultured at 37° C. for 72 hours before RNA extraction. At least 100,000 cells were harvested and subsequently processed for total RNA extraction using the RNAeasy Plus Mini Kit (Qiagen). cDNA was generated using the High Capacity RNA-to-cDNA Master Mix (Applied Biosystems) according to the manufacturer's recommended protocol. After cDNA synthesis, cDNA from each samples were added to the qRT-PCR assay with the TaqMan Advanced PCR Master Mix (Applied Biosystems) using a StepOne Plus qRT-PCR machine.

The fold activation in the transcriptional levels of SOX2 and CACNA1C mRNA were detected using standard TaqMan Gene Expression Assays with probes having the best coverage (Applied Biosystems; SOX2; Hs01053049_1; CACNA1C; Hs00167681_1). For both CACNA1C targets, TALEs carrying the VP64 activation domain and using NH as the G-targeting RVD were able to achieve similar levels of transcriptional activation as TALEs using NN (~5 and ~3 folds of activation for targets 1 and 2) and twice as much as TALEs using NK (FIG. 5B and FIG. 7). TALEs targeting the SID repression domain to the first CACNA1C target (FIG. 7) showed that the TALE repressor using NH as the G-targeting RVD was able to achieve the same level of transcriptional repression as the NN-containing TALE repressor (~4 fold repression), while the TALE repressor using NK was significantly less active (~2 fold repression).

Example 2

A Transcription Activator—Like Effector Toolbox for Genome Editing

Customized TALEs may be used for a wide variety of genome engineering applications, including transcriptional modulation and genome editing. Here, Applicants describe a toolbox for rapid construction of custom TALE transcription factors (TALE-TFs) and nucleases (TALENs) using a hierarchical ligation procedure. This toolbox facilitates affordable and rapid construction of custom TALE-TFs and TALENs within 1 week and may be easily scaled up to construct TALEs for multiple targets in parallel. Applicants also provide details for testing the activity in mammalian cells of custom TALE-TFs and TALENs using quantitative reverse-transcription PCR and Surveyor nuclease, respectively. The TALE toolbox enables a broad range of biological applications.

Systematic reverse-engineering of the functional architecture of the mammalian genome requires the ability to perform precise perturbations on gene sequences and transcription levels. Tools capable of facilitating targeted genome editing and transcription modulation are essential for elucidating the genetic and epigenetic basis of diverse biological functions and diseases. The recent discovery of the TALE code (1, 2) has enabled the generation of custom TALE DNA-binding domains with programmable specificity (3, 4, 5, 6, 7, 8, 9, 10, 11, 12). When coupled to effector domains, customized TALEs provide a promising platform for achieving a wide variety of targeted genome manipulations (3, 4, 5, 8, 11, 13, 14). Here Applicants describe an improved protocol for rapid construction of customized TALEs and methods to apply these TALEs to achieve endogenous transcriptional activation (3, 4, 5, 8) and site-specific genome editing (4, 7, 9, 11, 12, 13, 14, 15). Investigators should be able to use this protocol to construct TALEs for targets of their choice in less than 1 week.

TALEs are natural bacterial effector proteins used by *Xanthomonas* sp. to modulate gene transcription in host plants to facilitate bacterial colonization (16, 17). The central region of the protein contains tandem repeats of 34-aa sequences (termed monomers) that are required for DNA recognition and binding (18, 19, 20, 21) (FIG. 8). Naturally occurring TALEs were found to have a variable number of monomers, ranging from 1.5 to 33.5 (ref. 16). Although the sequence of each monomer is highly conserved, they differ primarily in two positions termed the repeat variable diresidues (RVDs, 12th and 13th positions). Recent reports have found that the identity of these two residues determines the nucleotide-binding specificity of each TALE repeat and that a simple cipher specifies the target base of each RVD (NI=A, HD=C, NG=T, NN=G or A) (1, 2). Thus, each monomer targets one nucleotide and the linear sequence of monomers in a TALE specifies the target DNA sequence in the 5' to 3' orientation. The natural TALE-binding sites within plant genomes always begin with a thymine (1, 2), which is presumably specified by a cryptic signal within the nonrepetitive N terminus of TALEs. The tandem repeat DNA-binding domain always ends with a half-length repeat (0.5 repeat, FIG. 8). Therefore, the length of the DNA sequence being targeted is equal to the number of full repeat monomers plus two.

Comparison with Other Genome Manipulation Methods: For targeted gene insertion and knockout, there are several techniques that were used widely in the past, such as homologous gene targeting (22, 23, 24), transposases (25, 26), site-specific recombinases (27), meganucleases (28) and integrating viral vectors (29, 30). However, most of these tools target a preferred DNA sequence and cannot be easily engineered to function at noncanonical DNA target sites. The most promising, programmable DNA-binding domain has been the artificial zinc-finger (ZF) technology, which enables arrays of ZF modules to be assembled into a tandem array and target new DNA-binding sites in the genome. Each finger module in a ZF array targets three DNA bases (31, 32). In comparison, TALE DNA-binding monomers target single nucleotides and are much more modular than ZF modules. For instance, when two independent ZF modules are assembled into a new array, the resulting target site cannot be easily predicted based on the known binding sites for the individual finger modules. Most of the intellectual property surrounding the ZF technology platform is proprietary and expensive (>$10,000 per target site). A public effort for ZF technology development also exists through the Zinc Finger Consortium, but the publicly available ZF modules may only target a subset of the 64 possible trinucleotide combinations (33, 34, 35). TALEs theoretically may target any sequence and have already been used in many organisms with impressive success (FIG. 9). Although TALEs seem superior in many ways, ZFs have a longer track record in DNA-targeting applications (32), including their use in human clinical trials (36). Despite their relatively recent development, early results with TALEs were promising and it seems that they may be applied in the same way as ZFs for many DNA-targeting applications (e.g., transcriptional modulator (3, 4, 5, 8), nuclease (4, 7, 9, 11, 12, 13, 14, 15), recombinase (37, 38, 39), transposase (40, 41).

Constructing Customized TALE-TFs and TALENs: Because of the repetitive nature of TALEs, construction of the DNA-binding monomers may be difficult. Previously, a hierarchical ligation strategy was used to overcome the difficulty of assembling the monomers into ordered multimer arrays, taking advantage of degeneracy in the codons surrounding the monomer junction and Type IIs restriction enzymes (3, 6, 7, 8, 9, 10). In the present protocol, Applicants use the same basic strategy used (3) to construct TALE-TFs to modulate transcription of endogenous human genes. Applicants have further improved the TALE assembly system with a few optimizations, including maximizing the dissimilarity of ligation adaptors to minimize misligations and combining separate digest and ligation steps into single Golden Gate (42, 43, 44) reactions. Briefly, each nucleotide-specific monomer sequence is amplified with ligation adaptors that uniquely specify the monomer position within the TALE tandem repeats. Once this monomer library is produced, it may conveniently be reused for the assembly of many TALEs. For each TALE desired, the appropriate monomers are first ligated into hexamers, which are then amplified via PCR. Then, a second Golden Gate digestion-ligation with the appropriate TALE cloning backbone (FIG. 8) yields a fully assembled, sequence-specific TALE. The backbone contains a ccdB negative selection cassette flanked by the TALE N and C termini, which is replaced by the tandem repeat DNA-binding domain when the TALE has been successfully constructed. ccdB selects against cells transformed with an empty backbone, thereby yielding clones with tandem repeats inserted (7).

Assemblies of monomeric DNA-binding domains may be inserted into the appropriate TALE-TF or TALEN cloning backbones to construct customized TALE-TFs and TALENs. TALE-TFs are constructed by replacing the natural activation domain within the TALE C terminus with the synthetic transcription activation domain VP64 (ref. 3; FIG. 8). By targeting a binding site upstream of the transcription start site, TALE-TFs recruit the transcription complex in a site-specific manner and initiate gene transcription. TALENs are constructed by fusing a C-terminal truncation (+63 aa) of the TALE DNA-binding domain (4) with the nonspecific FokI endonuclease catalytic domain (FIG. 8). The +63-aa C-terminal truncation has also been shown to function as the minimal C terminus sufficient for transcriptional modulation (3). TALENs form dimers through binding to two target sequences separated by ~17 bases. Between the pair of binding sites, the FokI catalytic domains dimerize and function as molecular scissors by introducing double-strand breaks (DSBs; FIG. 8). Normally, DSBs are repaired by the nonhomologous end joining (45) pathway (NHEJ), resulting in small deletions and functional gene knockout. Alternatively, TALEN-mediated DSBs may stimulate homologous recombination, enabling site-specific insertion of an exogenous donor DNA template (4, 13).

Applicants also present a short procedure for verifying correct TALE assembly by using colony PCR to verify the correct insert length followed by DNA sequencing. With this cloning procedure, high efficiency (correct length) and high accuracy (correct sequence) is routinely achieved. The cloning procedure is modular in several ways: TALEs to target DNA sequences of different lengths are constructed, and the protocol is the same for producing either TALE-TFs or TALENs. The backbone vectors may be modified with different promoters to achieve cell type-specific expression.

The present protocol includes functional assays for evaluating TALE-TF and TALEN activity in human cells. This step is important because some variability in TALE activity on the endogenous genome has been observed, possibly because of epigenetic repression and/or inaccessible chromatin at certain loci. For TALE-TFs, Applicants performed quantitative reverse-transcription PCR (qRT-PCR) to quantify changes in gene expression. For TALENs, Applicants used the Surveyor mutation detection assay (i.e., the base-mismatch cleaving endonuclease Cel2) to quantify NHEJ. These assays are standard and were described elsewhere (46, 47). Functional characterization is integral to TALE production and is presented in this Application with the assembly procedure. Other functional assays, such as plasmid-based reporter constructs (3, 7), restriction sites destroyed by NHEJ (48) or other enzymes that detect DNA mismatch (49), may also be used to validate TALE activity.

Applicants' protocol (FIG. 2) begins with the generation of a monomer library, which takes 1d and may be reused for building many TALEs. Using the monomer library, several TALEs may be constructed in a single day with an additional 2 d for transformation and sequence verification. To assess TALE function on the endogenous genome, ~3d are taken to go from mammalian cell transfection to qRT-PCR or Surveyor results.

Comparison with Other TALE Assembly Procedures: A number of TALE assembly procedures have described the use of Golden Gate cloning to construct customized TALE DNA-binding domains (3, 6, 7, 8, 9, 10). These methods rely on the use of a large collection of plasmids (typically over 50 plasmids) encoding repeat monomers and intermediate cloning vectors. Applicants' PCR-based approach requires substantially less initial plasmid preparation, as the monomer library may be amplified on one 96-well PCR plate, and it facilitates more rapid construction of custom TALEs. Plasmid-based amplification has a much lower mutation/error rate but, the combination of a high-fidelity polymerase and the short length of the monomer template (~100 nt) results in accurate assembly. For building similar-length TALEs to those presented in this protocol, the plasmid-based approaches also require an additional transformation and colony selection that extends the time needed to build TALEs. Thus, these alternative assembly protocols require a greater time investment both up-front (for monomer library preparation) and on a recurring basis (for each new TALE). For laboratories seeking to produce TALEs quickly, Applicants' protocol requires only a few hours to prepare a complete monomer library and less than 1d to proceed from monomers to the final transformation into bacteria.

Targeting Limitations: There are a few key limitations with the TALE technology. Although the RVD cipher is known, it is still not well understood as to why different TALEs designed according to the same cipher act on their target sites in the native genome with different levels of activity. It is possible that there are yet-unknown sequence dependencies for efficient binding or site-specific constraints (e.g., chromatin states) that are responsible for differences in functional activity. Therefore, at least two or three TALE-TFs or TALEN pairs for each target locus are to be constructed. In addition, it is possible that engineered TALEs may have off-target effects—i.e., binding unintended genomic loci—which may be difficult to detect without additional functional assays at these loci. Given the relatively early state of TALE technology development, these issues remain to be addressed in a conclusive manner.

TALE-TF Target Site Selection: The programmable nature of TALEs allows for a virtually arbitrary selection of target DNA-binding sites. As previously reported, the N terminus of the TALE requires that the target site begin with a thymine nucleotide. For TALE-TFs, Applicants have successfully targeted 14- to 20-bp sequences within 200 bp of the transcription start site (FIG. 8). It may be advantageous to select a longer sequence to reduce off-target activation, as it is known from reporter activation assays that TALEs interact less efficiently with targets containing more than one mismatching base. In the present assembly protocol, ligation of 18 monomers into a backbone containing a nucleotide-specific final 0.5 monomer is described; combined with the initial thymine requirement, this yields a total sequence specificity of 20 nt. Specifically, the TALE-TF-binding site takes the form 5'-TN'9-3'. When selecting TALE-TF-targeting sites for modulating endogenous gene transcription, it is recommended that multiple target sites within the proximal promoter region be targeted (targeting either the sense or antisense strand), as epigenetic and local chromatin dynamics might impede TALE binding. Larger TALEs might be beneficial for TALE-TFs targeting genes with less unique regions upstream of their transcription start site.

TALEN Target Site Selection: Because TALENs function as dimers, a pair of TALENs, referred to as the left and right TALENs, need to be designed to target a given site in the genome. The left and right TALENs target sequences on opposite strands of DNA (FIG. 8). As with TALE-TF, Applicants designed each TALEN to target a 20-bp sequence. TALENs are engineered as a fusion of the TALE DNA-binding domain and a monomeric FokI catalytic domain. To facilitate FokI dimerization, the left and right TALEN target sites are chosen with a spacing of approximately 14-20 bases. Therefore, for a pair of TALENs, each targeting 20-bp sequences, the complete target site should have the form $5'-TN^{19}N^{14-20}N^{19}A-3'$, where the left TALEN targets $5'-TN^{19}-3'$ and the right TALEN targets the antisense strand of $5'-N^{19}A-3'$ (N=A, G, T or C). TALENs should have fewer off-target effects because of the dimerization requirement for the FokI nuclease, although no significant off-target effects are observed in limited sequencing verifications (13). Because DSB formation only occurs if the spacer between the left and right TALEN-binding sites (FIG. 8) is approximately 14-20 bases, nuclease activity is restricted to genomic sites with both the specific sequences of the left TALEN and the right TALEN with this small range of spacing distances between those sites. These constraints should greatly reduce potential off-target effects.

TALE Monomer Design: To ensure that all synthesized TALEs are transcribed at a similar level, all of the monomers are optimized to share identical DNA sequences except in the variable diresidues, and they are codon-optimized for expression in human cells (FIG. 11). This should minimize any difference in translation due to codon availability.

Construction Strategy: Synthesis of monomeric TALE DNA-binding domains in a precise order is challenging because of their highly repetitive nature. Applicants previously took advantage of codon redundancy at the junctions between neighboring monomers and devised a hierarchical ligation strategy to construct ordered assemblies of multiple monomers. In this protocol, Applicants describe a similar strategy, but with several important improvements that make the procedure easier, more flexible and more reliable (FIG. 12).

Previously (3), the digestion and ligation steps were carried out separately with an intervening DNA purification step. This improved protocol adopts the powerful Golden Gate cloning technique (42, 43, 44) requiring less hands-on time and resulting in a more efficient reaction. The Golden Gate procedure involves combining the restriction enzyme and ligase together in a single reaction with a mutually compatible buffer. The reaction is cycled between optimal temperatures for digestion and ligation. Golden Gate digestion-ligation capitalizes on Type IIs restriction enzymes, for which the recognition sequence is spatially separated from where the cut is made. During a Golden Gate reaction, the correctly ligated products no longer contain restriction enzyme recognition sites and cannot be further digested. In this manner, Golden Gate drives the reaction toward the correct ligation product, as the number of cycles of digestion and ligation increases.

For the hierarchical ligation steps, Applicants optimized previous cloning strategy for faster TALE production. The improved design takes advantage of a circularization step that allows only properly assembled hexameric intermediates to be preserved (FIG. 12). Correctly ligated hexamers consist of six monomers ligated together in a closed circle, and incomplete ligation products are left as linear DNA. After this ligation step, an exonuclease degrades all noncircular DNA, leaving intact only the complete circular hexamers. Without circularization and exonuclease treatment, the correct ligation product would need to be gel purified before proceeding. The combination of Golden Gate digestion-ligation and circularization reduces the overall hands-on time required for TALE assembly.

Primer Design for Monomer Library Preparation. Each monomer in the tandem repeat must have its position uniquely specified. The monomer primers are designed to add ligation adaptors that enforce this positioning. The Applicants' protocol uses a hierarchical ligation strategy: For the 18-mer tandem repeat, monomers are first ligated into hexamers. Then, three hexamers are ligated together to form the 18-mer. By breaking down the assembly into two steps, unique ligation junctions for each monomer in the 18-mer are not needed. Instead, the same set of ligation junctions internal to each hexamer are reused in all three hexamers (first ligation step), whereas unique (external) ligation junctions are used to flank each hexamer (second ligation step). As shown in FIG. 13, the internal primers used to amplify the monomers within each hexamer are the same, but the external primers differ between the hexamers. By reusing the same internal primers between different hexamers, the protocol herein minimizes the number of primers necessary for monomer amplification.

Controls. As a negative control for Golden Gate assembly, it is recommended that a separate reaction with only the TALE-TF or TALEN backbone be performed. Transformation of this negative control should result in few or no colonies because of the omission of the tandem repeats and resulting religation of the toxic ccdB insert. After completing the TALE cloning, colony PCR or restriction digests to screen for correct length clones are used. For the final verification of proper assembly, the entire length of the tandem repeats is sequenced. Owing to limits in Sanger sequencing read length, other TALE assembly protocols have difficulty sequencing the entire tandem repeat region (7, 9, 10). The similarity of the monomers within the region makes primer annealing to specific monomers impossible. This problem is overcome by slightly modifying the codon usage at the 5' end of monomer 7 to create a unique annealing site, so that a TALE with an 18-mer DNA-binding array may be verified through a combination of three staggered sequencing reads. Specifically, during the monomer amplification, the codons for the first five amino acids in monomer 7 are mutated via PCR to use different but synonymous codons, creating a unique priming site without changing the encoded TALE protein. This modification allows each hexamer in the 18-mer to be sequenced with a separate sequencing read and requires only a standard read length of ~700 bp for complete sequence verification. For TALEs containing more than 18 full monomer repeats, a third unique priming site is introduced for sequencing at the 3' end of the 18th monomer using a similar approach. For the construction of TALEs containing up to 24 full monomers with the entire tandem repeat region easily sequenced.

Building TALEs that target DNA sequences of different lengths: In the main protocol, hierarchical ligation strategy is presented for the construction of TALEs that contain 18 full monomer repeats; however the general approach may be adapted to construct TALEs of any length. The TALEs containing 18 full repeat monomers bind to 20-bp DNA sequences, where the first and last bases are specified by the N-terminus and the 0.5 repeat, respectively (FIG. 8). This length was chosen because, empirically 20-bp sequences tend to be unique within the human genome. Nevertheless, for different species (e.g., with larger or more repetitive genomes) or for repetitive regions within the human genome, it may be advantageous to construct longer or shorter TALEs. For certain genomic loci, it might also be difficult to identify TALEN target sites that satisfy the spacing constraints when the binding sites for both left and right TALENs are restricted to 20-bp sequences. The main protocol is modified for the construction of TALEs containing up to 24 full monomer repeats by changing the order in which particular primers are used during the preparation of the monomer library plate (as described in Procedure steps 1-9). All other steps remain essentially the same. A plate of the monomer amplification primers (similar to FIG. 13) may be prepared for building TALEs with 24 full monomer repeats, which bind to 26-bp DNA sequences, as illustrated below. In this case, a fourth circular hexamer, corresponding to monomers 19 through 24, is also built and treated identically as the other three circular hexamers (1-6, 7-12 and 13-18) (FIG. 14). For building shorter TALEs, only a single change to monomer amplification is needed: the final monomer should be amplified with the Ex-R4 reverse primer. For example, to build TALEs with 17 monomers instead of 18, the monomer templates (NI, NG, NN, HD) should be amplified with the forward/reverse primer combination IN-F5/Ex-R4. During Gel purification (Step 20 in Procedure) the desired PCR amplicon is a pentamer containing monomers 13-17 and it runs faster than the hexamers (1-6, 7-12). After purification, it is ensured that the pentameric and hexameric intermediates are used at an equimolar ratio in the final Golden Gate digestion-ligation.

Design of Functional Validation Assays. For TALE-TFs, qRT-PCR quantitatively measures the increase in transcription driven by the TALE-TF. For TALENs, the Surveyor assay provides a functional validation of TALEN cutting and quantifies the cutting efficiency of a particular pair of TALENs. These assays should be performed in the same cell type as intended for the TALE application, as TALE efficacy may vary between cell types, presumably because of differences in chromatin state or epigenetic modifications.

For qRT-PCR, commercially available probes are used to measure increased transcription of the TALE-TF-targeted gene. For most genes in the human or mouse genomes, specific probes may be purchased (e.g., TaqMan gene expression probes from Applied Biosystems). There are a wide variety of qRT-PCR protocols, and although one of them is described here others may be substituted. For example, a more economical option is to design custom, transcript-specific primers (e.g., with NCBI Primer-BLAST) and use a standard fluorescent dye to detect amplified double-stranded DNA (e.g., SYBR Green).

For Surveyor, the recommendations given by the assay manufacturer are followed when designing specific primers for genomic PCR. Design primers are typically designed that are ~30 nt long and with melting temperatures of ~65° C. The primers should flank the TALEN target site and generate an amplicon of approximately 300-800 bp with the TALEN target site near the middle. During the design, it is checked that the primers are specific over the intended genome using NCBI Primer-BLAST (see NCBI primer-blast website). Before using the primers for Surveyor, the primers and specific PCR cycling parameters should be tested to ensure that amplification results in a single clean band. In difficult cases in which a single-band product cannot be achieved, it is acceptable to gel-extract the correct-length band before proceeding with heteroduplex reannealing and Surveyor nuclease digestion.

Reagents

TALE construction: TALE monomer template plasmids (Addgene): pNI_v2, pNG_v2, pNN_v2, pHD_v2

TALE transcriptional activator (TALE-TF) plasmids (Addgene): pTALE-TF_v2 (NI), pTALE-TF_v2 (NG), pTALE-TF_v2 (NN), pTALE-TF_v2 (HD)

TALE nuclease (TALEN) backbone plasmids (Addgene): pTALEN_v2 (NI), pTALEN_v2 (NG), pTALEN_v2 (NN), pTALEN_v2 (HD). These plasmids may be obtained individually or bundled together as a single kit from the Zhang Lab plasmid collection at Addgene (see add-gene website). See FIG. 11 for plasmid sequences.

PCR primers for TALE construction (FIG. 15, Integrated DNA Technologies, custom DNA oligonucleotides)

Herculase II fusion polymerase (Agilent Technologies, cat. no. 600679)

Critical: Standard Taq polymerase, which lacks 3'-5' exonuclease proofreading activity, has lower fidelity and may lead to errors in the final assembled TALE. Herculase II is a high-fidelity polymerase (equivalent fidelity to Pfu) that produces high yields of PCR product with minimal optimization. Other high-fidelity polymerases may be substituted.

Herculase II reaction buffer (5×; Agilent Technologies, included with polymerase)

Taq-B polymerase (Enzymatics, cat. no. P725L)

Taq-B buffer (10×; Enzymatics, included with polymerase)

dNTP solution mix (25 mM (each); Enzymatics, cat. no. $N_2O_5L$)

MinElute gel extraction kit (Qiagen, cat. no. 28606)

Critical: MinElute columns should be stored at 4° C. until use.

QIAprep spin miniprep kit (Qiagen, cat. no. 27106)

QIAquick 96 PCR purification (Qiagen, cat. no. 28181)

UltraPure DNaseRNase-free distilled water (Invitrogen, cat. no. 10977-023)

UltraPure TBE buffer (10×; Invitrogen, cat. no. 15581-028)

SeaKem LE agarose (Lonza, cat. no. 50004)

SYBR Safe DNA stain (10,000×; Invitrogen, cat. no. S33102)

Low-DNA mass ladder (Invitrogen, cat. no. 10068-013)

1-kb Plus DNA ladder (Invitrogen, cat. no. 10787-018)

TrackIt CyanOrange loading buffer (Invitrogen, cat. no. 10482-028)

Restriction enzymes: BsmBI (Esp3I) (Fermentas/ThermoScientific, cat. no. ER0451), BsaI-HF (New England Biolabs, cat. no. R3535L), AfeI (New England Biolabs, cat. no. R0652S)

Fermentas Tango Buffer and 10×NEBuffer 4 (included with enzymes)

Bovine serum albumin (100×; New England Biolabs, included with BsaI-HF)

DL-dithiothreitol (DTT; Fermentas/ThermoScientific, cat. no. R0862)

T7 DNA ligase (3,000 U μl–1; Enzymatics, cat. no. L602L)

Critical: Do not substitute the more commonly used T4 ligase. T7 ligase has 1,000-fold higher activity on the sticky ends than on the blunt ends and higher overall activity than commercially available concentrated T4 ligases.

Adenosine 5'-triphosphate (10 mM; New England Biolabs, cat. no. P0756S)

PlasmidSafe ATP-dependent DNase (Epicentre, cat. no. E3101K)

One Shot Stb13 chemically competent *Escherichia coli* (*E. coli*) (Invitrogen, cat. no. C7373-03)

SOC medium (New England Biolabs, cat. no. B9020S)

LB medium (Sigma, cat. no. L3022)

LB agar medium (Sigma, cat. no. L2897)

Ampicillin, sterile filtered (100 mg ml–1; Sigma, cat. no. A5354)

TALEN and TALE-TF functional validation in mammalian cells

HEK293FT cells (Invitrogen, cat. no. R700-07)

Dulbecco's minimum Eagle's medium (DMEM, 1×, high glucose; Invitrogen, cat. no. 10313-039)

Dulbecco's phosphate-buffered saline (DPBS, 1×; Invitrogen, cat. no. 14190-250)

Fetal bovine serum, qualified and heat inactivated (Invitrogen, cat. no. 10438-034)

Opti-MEM I reduced-serum medium (FBS; Invitrogen, cat. no. 11058-021)

GlutaMAX-I (100×; Invitrogen, cat. no. 35050079)

Penicillin-streptomycin (100×; Invitrogen, cat. no. 15140-163)

Trypsin, 0.05% (wt/vol) (1×) with EDTA·4Na (Invitrogen, cat. no. 25300-062)

Lipofectamine 2000 transfection reagent (Invitrogen, cat. no. 11668027)

QuickExtract DNA extraction solution (Epicentre, cat. no. QE09050)

Herculase II fusion polymerase

Critical: As Surveyor assay is sensitive to single-base mismatches, it is important to use only a high-fidelity polymerase. Other high-fidelity polymerases may be substituted; refer to the Surveyor manual for PCR buffer compatibility details.

Herculase II reaction buffer (5×)

Surveyor mutation detection kit for standard gel electrophoresis (Transgenomic, cat. no. 706025)

Critical: The Surveyor assay includes the Ce12 base-mismatch nuclease. Alternatives include the Cell, T7, mung bean and S1 nucleases (50, 51). Of these, Cell has been applied extensively for mutation detection (52, 53, 54) and established protocols are available for its purification (52, 54).

Primers for Surveyor assay of TALEN cutting efficiency (Integrated DNA Technologies, custom DNA oligonucleotides; see Experimental design for further information on primer design)

RNeasy mini kit (Qiagen, cat. no. 74104)

QIAshredder (Qiagen, cat. no. 79654)

RNAse ZAP (Applied Biosystems, cat. no. AM9780)

iScript cDNA synthesis kit (Bio-Rad, cat. no. 170-8890)

TaqMan universal master mix (Applied Biosystems, cat. no. 4364341)

TaqMan gene expression assay probes for the TALE-TF-targeted gene (Applied Biosystems, Refer to website of appliedbiosystems/genomic-products/gene-expression).

Equipment 96-well thermocycler with programmable temperature stepping functionality (Applied Biosystems Veriti, cat. no. 4375786)

Critical: Programmable temperature stepping is needed for the TALEN (Surveyor) functional assay. Other steps only require a PCR-capable thermocycler.

qPCR system (96 well; StepOnePlus real-time PCR system, Applied Biosystems, cat. no. 4376600)

Optical plates (96 well; MicroAmp, Applied Biosystems, cat. no. N801-0560)
PCR plates (96 well; Axygen, cat. no. PCR-96-FS-C)
Strip PCR tubes (8 well; Applied Biosystems, cat. no. N801-0580)
QIAvac 96 vacuum manifold (Qiagen, cat. no. 19504)
Gel electrophoresis system (PowerPac basic power supply, Bio-Rad, cat. no. 164-5050, and Sub-Cell GT System gel tray, Bio-Rad, cat. no. 170-4401)
Digital gel imaging system (GelDoc EZ, Bio-Rad, cat. no. 170-8270, and blue sample tray, Bio-Rad, cat. no. 170-8273)
Blue light transilluminator and orange filter goggles (Safe-Imager 2.0, Invitrogen, cat. no. G6600)
Sterile 20-μl pipette tips for colony picking
Gel quantification software (Bio-Rad, ImageLab, included with GelDoc EZ, or open-source ImageJ from the National Institutes of Health, available at the NIH website)
TALE reference sequence generator (Zhang Lab, visit the website for tale effectors under tools)
Petri dishes (60 mm×15 mm; BD Biosciences, cat. no. 351007)
Incubator for bacteria plates (Quincy Lab, cat. no. 12-140E)
Shaking incubator for bacteria suspension culture (Infors HT Ecotron)
Cell culture-treated polystyrene plates (6 well; Corning, cat. no. 3506)
UV spectrophotometer (NanoDrop 2000c, Thermo Scientific)
Kimwipes (Kimberly-Clark).
Reagent Setup
Tris-borate EDTA (TBE) electrophoresis solution
Dilute TBE buffer in distilled water to 1× working solution for casting agarose gels and for use as a buffer for gel electrophoresis. Buffer may be stored at room temperature (18-22° C.) for at least 1 year.
BSA, 10×
Dilute 100×BSA (supplied with BsaI-HF) to 10× concentration and store it at −20° C. for at least 1 year in 20-μl aliquots.
ATP, 10 mM
Divide 10 mM ATP into 50-μl aliquots and store at −20° C. for up to 1 year; avoid repeated freeze-thaw cycles.
DTT, 10 mM
Prepare 10 mM DTT solution in distilled water and store in 20-μl aliquots at −70° C. for up to 2 years; for each reaction, use a new aliquot, as DTT is easily oxidized.
D10 culture medium
For culture of HEK293FT cells, prepare D10 culture medium by supplementing DMEM with 1× GlutaMAX and 10% (vol/vol) FBS. As indicated in the protocol, this medium may also be supplemented with 1× penicillin-streptomycin. D10 medium may be made in advance and stored at 4° C. for up to 1 month.
Procedure
Steps 1-9: Amplification and normalization of monomer library with ligation adaptors for 18-mer TALE DNA-binding domain construction (Timing: 6 h)
1. Prepare diluted forward and reverse monomer primer mixes. In a 96-well PCR plate, prepare primer mixes for amplifying a TALE monomer library (FIG. 12, stage 1). Mix forward and reverse primers for each of the 18 positions according to the first two rows (A and B) of FIG. 13 and achieve a final concentration of 10 μM for each primer. If multichannel pipettes are used, arrange the oligonucleotide primers in the order indicated in FIG. 13 to allow for easy pipetting. Typically, prepare 50-μl mixes for each primer pair (40 μl of ddH2O, 5 μl of 100 μM forward primer, 5 μl of 100 μM reverse primer).

2. Set up two 96-well monomer library plates according to the organization shown in FIG. 13; each plate contains a total of 72 PCRs (18 positions for each monomer×4 types of monomers). Although it is acceptable to have smaller-volume PCRs, the monomer set is typically made in larger quantities, as one monomer library plate may be used repeatedly for the construction of many TALEs. Each PCR should be made up as follows to a total volume of 200 μl, and then split between the two 96-well plates so that each well contains a 100-μl PCR:

| Component | Amount (μl) | Final concentration |
|---|---|---|
| Monomer template plasmid (5 ng μl$^{-1}$) | 2 | 50 pg μl$^{-1}$ |
| dNTP, 100 mM (25 mM each) | 2 | 1 mM |
| Herculase II PCR buffer, 5× | 40 | 1× |
| Primer mix, 20 μM (10 μM forward primer and 10 μM reverse primers from Step 1) | 4 | 200 nM |
| Herculase II Fusion polymerase | 2 | |
| Distilled water | 150 | |
| Total | 200 (for 2 reactions) | |

Perform PCR on the reactions from Step 2 using the following cycling conditions:

| Cycle number | Denature | Anneal | Extend |
|---|---|---|---|
| 1 | 95° C., 2 min | | |
| 2-31 | 95° C., 20 s | 60° C., 20 s | 72° C., 10 s |
| 32 | | | 72° C., 3 min |

4. After the reaction has completed, use gel electrophoresis to verify that monomer amplification was successful. Cast a 2% (wt/vol) agarose gel in 1×TBE electrophoresis buffer with 1×SYBR Safe dye. The gel should have enough lanes to run out 2 μl of each PCR product from Step 3. Run the gel at 15 V cm−1 for 20 min. It is not necessary to check all 72 reactions at this step; it is sufficient to check all 18 reactions for one type of monomer template. Successful amplification should show an ~100-bp product. Monomers positioned at the ends of each hexamer (monomers 1, 6, 7, 12, 13 and 18) should be slightly longer than the other monomers because of the length difference of the longer external primers.

5. Pool both of the 100-μl PCR plates into a single deep-well plate. Purify the combined reactions using the QIAquick 96 PCR purification kit according to the manufacturer's directions. Elute the DNA from each well using 100 μl of Buffer EB (included with the kit), prewarmed to 55° C. Alternatively, PCR products may also be purified using individual columns found in standard PCR cleanup kits.

Critical step: Before eluting the DNA, let the 96-well column plate air-dry, preferably at 37° C., for 30 min on a clean Kimwipe so that all residual ethanol has enough time to evaporate.

6. Normalization of monomer concentration. Cast a 2% (wt/vol) agarose gel. The gel should have enough lanes to run out 2 μl of each purified PCR product from Step 5. Include in one lane 10 μl of the quantitative DNA ladder. Run the gel at 20 V cm−1 for 20 min.

7. Image the gel using a quantitative gel imaging system. Monomers 1, 6, 7, 12, 13 and 18 are ~170 bp in size, whereas the other monomers are ~150 bp in size (FIG. 16, lanes 1-6). Make sure the exposure is short enough so that none of the bands are saturated.

8. Quantify the integrated intensity of each PCR product band using ImageJ or other gel quantification software. Use the quantitative ladder with known DNA mass (5, 10, 20, 40, 100 ng) to generate a linear fit and quantify the concentration of each purified PCR product.

9. Adjust the plate of purified PCR products by adding Buffer EB so that each monomer has the same molar concentration. As monomers 1, 6, 7, 12, 13 and 18 are longer than the other monomers, it is necessary to adjust them to a slightly higher concentration. For example, monomers 1, 6, 7, 12, 13 and 18 are adjusted to 18 ng μl−1 and the other monomers to 15 ng μl−1.

Critical step: For subsequent digestion and ligation reactions, it is important that all monomers are at equimolar concentrations.

Pause point: Amplified monomers may be stored at −20° C. for several months and may be reused for assembling additional TALEs.

Steps 10-28: Construction of custom 20-bp-targeting TALEs (Timing: 1.5 d (5 h hands-on time)).

10. Select target sequence(s). Typical TALE recognition sequences are identified in the 5' to 3' direction and begin with a 5' thymine. The procedure below describes the construction of TALEs that bind a 20-bp target sequence (5'-$T_0N_1N_2N_3N_4N_5N_6N_7N_8N_9N_{10}N_{11}N_{12}N_{13}N_{14}N_{15}N_{16}N_{17}N_{18}N_{19}$-3', where N=A, G, T or C), where the first base (typically a thymine) and the last base are specified by sequences within the TALE backbone vector. The middle 18 bp are specified by the RVDs within the middle tandem repeat of 18 monomers according to the cipher NI=A, HD=C, NG=T and NN=G or A. For targeting shorter or longer sequences, see Box 1.

11. Divide target sequences into hexamers. Divide N1-N18 into subsequences of length 6 ($N_1N_2N_3N_4N_5N_6$, $N_7N_8N_9N_{10}N_{11}N_{12}$ and $N_{13}N_{14}N_{15}N_{16}N_{17}N_{18}$). For example, a TALE targeting 5'-TGAAGCACTTACTTTA-GAAA-3' (SEQ ID NO: 28) may be divided into hexamers as (T) GAAGCA CTTACT TTAGAA (A) (SEQ ID NO: 28), where the initial thymine and final adenine (in parentheses) are encoded by the appropriate backbone. In this example, the three hexamers are: hexamer 1=NN-NI-NI-NN-HD-NI, hexamer 2=HD-NG-NG-NI-HD-NG and hexamer 3=NG-NG-NI-NN-NI-NI. Because of the adenine in the final position, one of the NI backbones is used: pTALE-TF_v2(NI) or pTALEN_v2(NI).

12. Assembling hexamers using Golden Gate digestion-ligation (FIG. 12, stage 2). Prepare one reaction tube for each hexamer. Using the monomer plate schematic (FIG. 13), pipette 1 μl of each normalized monomer into the corresponding hexamer reaction tube. Repeat this for all hexamers. For example, for the target from Step 10, set up tube 1 (1 μl from each of G1, A2, A3, G4, E5 and A6), tube 2 (1 μl from each of E7, C8, C9, A10, E11 and C12) and tube 3 (1 μl from each of D1, D2, B3, H4, B5 and B6). To construct a TALE with 18 full repeats, three separate hexamer tubes are used.

Critical step: Pay close attention when pipetting the monomers; it is very easy to accidentally pipette from the wrong well during this step.

13. To perform a simultaneous digestion-ligation (Golden Gate) reaction to assemble each hexamer (FIG. 12, stage 2), add the following reagents to each hexamer tube:

| Component | Amount (μl) | Final concentration |
|---|---|---|
| Esp3I (BsmBI), 10 U μl−1 | 0.75 | 0.375 U μl−1 |
| Tango buffer, 10× | 1 | 1× |
| DTT, 10 mM | 1 | 1 mM |
| T7 ligase, 3,000 U μl−1 | 0.25 | 75 U μl−1 |
| ATP, 10 mM | 1 | 1 mM |
| | 4 | |
| Six monomers | 6 × 1 | |
| Total | 10 | |

Critical step: DTT is easily oxidized in air. It should be freshly made or thawed from aliquots stored at −70° C. and used immediately.

14. Place each hexamer tube in a thermocycler to carry out the Golden Gate reactions using the following cycling conditions for ~3 h:

| Cycle number | Digest | Ligate |
|---|---|---|
| 1-15 Hold at 4° C. | 37° C., 5 min | 20° C., 5 min |

Pause point: This reaction may be left to run overnight.

15. Run out the ligation product on a gel to check for ~700-bp bands corresponding to the hexamer products (FIG. 16, lane 7). Cast a 2% (wt/vol) agarose gel in 1×TBE electrophoresis buffer with 2×SYBR Safe dye. The additional dye helps to visualize faint bands. The gel should have enough lanes to run out each Golden Gate reaction from Step 14; load 3 μl of each ligation product in separate lanes. Include 1 μg of the 1-kb Plus DNA ladder in one lane. Run the gel at 15 V cm−1 until there is separation of the 650-bp ladder band from neighboring bands.

16. Exonuclease treatment to degrade noncircular ligation products (FIG. 12, stage 3). During the Golden Gate reaction, only fully ligated hexamers should be able to circularize. PlasmidSafe exonuclease selectively degrades noncircular (incomplete) ligation products. Add the following reagents to each hexamer reaction tube:

| Component | Amount (μl) | Final concentration |
|---|---|---|
| PlasmidSafe DNAse, 10 U μl−1 | 1 | 0.66 U μl−1 |
| PlasmidSafe reaction buffer, 10× | 1 | 1× |
| ATP, 10 mM | 1 | 1 mM |
| | 3 | |
| Golden Gate reaction from Step 14 | 7 | |
| Total | 10 | |

17. Incubate each hexamer reaction tube with PlasmidSafe at 37° C. for 30 min; follow by inactivation at 70° C. for 30 min.

Pause point: After completion, the reaction may be frozen and continued later. The circular DNA should be stable for at least 1 week.

18. Hexamer PCR (FIG. 12, stage 4). Amplify each PlasmidSafe-treated hexamer in a 50-μl PCR using high-fidelity Herculase II polymerase and the hexamer forward and reverse primers (Hex-F and Hex-R; FIG. 15). Add the following reagents to each PCR:

| Component | Amount (μl) | Final concentration |
| --- | --- | --- |
| dNTP, 100 mM (25 mM each) | 0.5 | 1 mM |
| Herculase II reaction buffer, 5× | 10 | 1× |
| Hex-F and Hex-R primers, 10 μM each | 1 | 200 nM |
| Herculase II Fusion DNA polymerase | 0.5 | 1× |
| Distilled water | 37 | |
| | 49 | |
| PlasmidSafe-treated hexamer from Step 17 | 1 | |
| Total | 50 | |

19. Perform PCR on the reactions in Step 18 using the following cycling conditions:

| Cycle number | Denature | Anneal | Extend |
| --- | --- | --- | --- |
| 1 | 95° C., 2 min | | |
| 2-36 | 95° C., 20 s | 60° C., 20 s | 72° C., 30 s |
| 37 | | | 72° C., 3 min |

20. Gel purification of amplified hexamers. Because of the highly repetitive template, it is necessary to purify the amplified hexamer product from the other amplicons. Cast a 2% (wt/vol) agarose gel in 1×TBE electrophoresis buffer with 1×SYBR Safe dye. The gel should have enough lanes to run out each PCR product from Step 19, and the comb size should be big enough to load 40-50 μl of PCR product. Include 1 μg of the 1-kb Plus DNA ladder in one lane. Run the gel at 15 V cm−1 until there is separation of the 650-bp ladder band from neighboring bands. Use a clean razor blade to excise each hexamer band, which should be nearly aligned with the 650-bp band from the ladder (FIG. 16, lane 9).

Caution: Wear appropriate personal protective equipment, including a face mask, to minimize risks associated with prolonged light or mutagenic DNA dye exposure.

Critical step: Avoid any cross-contamination by ethanol sterilization of work surfaces, razor blades, etc. during the gel extraction and between each individual band excision.

21. Purify the hexamer gel bands from Step 20 using the MinElute gel extraction kit according to the manufacturer's directions. Elute the DNA from each reaction using 20 μl of Buffer EB prewarmed to 55° C.

22. Gel normalization of purified hexamer concentrations. Cast a 2% (wt/vol) agarose gel in 1×TBE electrophoresis buffer with 1×SYBR Safe dye. The gel should have enough lanes to run out 2 μl of each purified hexamer from Step 21. Include 10 μl of the quantitative DNA ladder in one lane. Run the gel at 15 V cm−1 until all lanes of the quantitative ladder are clearly separated. Each hexamer lane should contain only a single (purified) band.

23. Image the gel using a quantitative gel imaging system. Each lane should have only the ~700-bp hexamer product. Make sure the exposure is short enough so that none of the bands are saturated.

24. Quantify the integrated intensity of each hexamer band using ImageJ or other gel quantification software. Use the quantitative ladder with known DNA mass (5, 10, 20, 40, 100 ng) to generate a linear fit and quantify the concentration of each purified hexamer.

25. Adjust the concentration of each hexamer to 20 ng μl−1 by adding Buffer EB.

26. Golden Gate assembly of hexamers into TALE backbone (FIG. 12, stage 5). Combine the hexamers and the appropriate TALE backbone vector (transcription factor or nuclease) in a Golden Gate digestion-ligation. For example, a TALE backbone with NI as the 0.5 repeat for the target sequence in Step 10 is used as N19=A. For this ligation, a 1:1 molar ratio of insert to vector works well. Set up one reaction tube for each TALE. In addition, prepare a negative control ligation by including the TALE backbone vector without any hexamers.

| Component | TALE (μl) | Negative control (μl) | Final concentration |
| --- | --- | --- | --- |
| TALE backbone vector (100 ng μl−1) | 1 | 1 | 10 ng μl−1 |
| BsaI-HF (20 U μl−1) | 0.75 | 0.75 | 1.5 U μl−1 |
| NEBuffer 4, 10× | 1 | 1 | 1× |
| BSA, 10× | 1 | 1 | 1× |
| ATP, 10 mM | 1 | 1 | 1 mM |
| T7 ligase (3,000 U μl−1) | 0.25 | 0.25 | 75 U μl−1 |
| | | 5 | |
| Three purified hexamers (20 ng μl−1) | 3 (1 each) | | 2 ng μl−1 each |
| Distilled water | 2 | 5 | |
| Total | 10 | 10 | |

Critical step: As a negative control, set up a separate reaction substituting an equal volume of water in place of the purified hexamers (i.e., including only the TALEN or TALE-TF backbone).

27. Place the tubes from Step 26 in a thermocycler to carry out the Golden Gate reactions using the following cycling conditions for ~4 h:

| Cycle number | Digest | Ligate | Inactivate |
| --- | --- | --- | --- |
| 1-20 | 37° C., 5 min | 20° C., 5 min | |
| 21 | | | 80° C., 20 min |

Pause point: Ligation products may be frozen at ~−20° C. and stored for at least 1 month for transformation into bacteria at a later time.

28. Although it is not necessary, it is possible to run out the ligation product on a gel to check for ~1.8-kbp band corresponding to the properly assembled 18-mer tandem repeat. To check the ligation product, cast a 2% (wt/vol) agarose gel in 1×TBE electrophoresis buffer with 2×SYBR Safe dye. The additional dye helps to visualize faint bands. Load 5 μl of the ligation product from Step 27. Include 1 μg of the 1-kb Plus DNA ladder in one lane. Run the gel at 15 V cm−1 until there is clear separation of the 1,650- and 2,000-bp ladder bands. Alternatively, proceed directly to transformation (Step 29) without running a gel; transformation is very sensitive and, even when a clear band cannot be visualized on the gel, there is often enough plasmid for transformation of high-competency cells.

Steps 29-38: Verifying the correct TALE repeat assembly (Timing: 3 d (4 h hands-on time))

29. Transformation. Transform the ligation products from Step 27 into a competent E. coli strain; e.g., Stbl3 for routine transformation. Transformation may be done according to the protocol supplied with the cells. Briefly, add 5 μl of the ligation product to 50 μl of ice-cold chemically competent Stb13 cells, incubate on ice for 5 min, incubate at 42° C. for 45 s, return immediately to ice for 5 min, add 250 µl of SOC medium, incubate at 37° C. for 1 h on a shaking incubator (250 r.p.m.), plate 100 µl of the transformation on an LB plate containing 100 µg ml−1 ampicillin and incubate overnight at 37° C.

30. Inspect all plates from Step 29 for bacterial colony growth. Typically, few colonies on the negative control plates are seen (only backbone in the Golden Gate digestion-ligation) and tens to hundreds of colonies on the complete TALE ligation plates.

31. For each TALE plate, pick eight colonies to check the assembly fidelity. Use a sterile 20-µl pipette tip to touch a single colony, streak onto a single square on a prewarmed, new, gridded LB-ampicillin plate to save the colony, and then swirl the tip in 100 µl of distilled water to dissolve the colony for colony PCR. Repeat this procedure for all colonies to be checked, streaking each new colony into a separate square on the gridded LB-ampicillin plate. After finishing, incubate the gridded plate at 37° C. for at least 4 h to grow the colony streaks.

32. Colony PCR. By using the colonies selected in Step 31 as templates, set up colony PCR to verify that the correctly assembled tandem 18-mer repeat has been ligated into the TALE backbone. The colony PCR is found to be sensitive to excessive template concentration, and therefore typically 1 µl of the 100-µl colony suspension from Step 31 is used. For colony PCR, use primers TALE-Seq-F1 and TALE-Seq-R1 for amplification (FIG. 15). Set up the following colony PCR:

| Component | Amount (µl) | Final concentration |
|---|---|---|
| Colony suspension from Step 31 | 1 | |
| dNTP, 100 mM (25 mM each) | 0.25 | 1 mM |
| Taq-B polymerase buffer, 10× | 2.5 | 1× |
| TALE-Seq-F1 and TALE-Seq-R1 primers, 10 µM each | 0.25 | 100 nM |
| Taq-B polymerase (5 U µl$^{-1}$) | 0.1 | 0.02 U µl$^{-1}$ |
| Distilled water | 20.9 | |
| Total | 25 | |

33. Perform colony PCR on the reactions in Step 32 using the following cycling conditions:

| Cycle number | Denature | Anneal | Extend |
|---|---|---|---|
| 1 | 94° C., 3 min | | |
| 2-31 | 94° C., 30 s | 60° C., 30 s | 68° C., 2 min |
| 32 | | | 68° C., 5 min |

34. To check the colony PCR result, cast a 1% (wt/vol) agarose gel in 1×TBE electrophoresis buffer with 1×SYBR Safe dye. The gel should have enough lanes to run out 10 µl of each PCR product from Step 33. Include 1 µg of the 1-kb Plus DNA ladder in one lane. Run the gel at 15 V cm−1 until there is clear separation of the 1,650- and 2,000-bp ladder bands.

35. Image the gel and identify which colonies have the correct insert size. For an insert of 18 monomers (three hexamers ligated into the TALE backbone vector), the product should be a single band of size 2,175 bp (FIG. 16b, lane 1). Incorrect ligation products show bands of different sizes. In place of colony PCR, plasmid DNA from prepared clones may be digested with AfeI. In both backbones (TALE-TF and TALEN), AfeI cuts four times. For both backbones, one fragment contains the entire tandem repeat region and should be 2,118 bp in size for a correctly assembled 18-mer. For the TALE-TF backbone, the correct clone produces four bands with sizes 165, 2,118, 3,435 and 3,544 bp (FIG. 16b, lane 2). The 3,435- and 3,544-bp bands are difficult to separate on a 1% (wt/vol) agarose gel, and therefore a correct clone shows three bands with the middle 2,118-bp band indicating an intact tandem 18-mer repeat (FIG. 16b, lane 2). For the TALEN backbone, the correct clone produces four bands with sizes 165, 2,118, 2,803 and 3,236 bp.

36. Miniprep and sequencing. For each clone with the correct band size, inoculate a colony from the gridded plate into 3 ml of LB medium with 100 µg ml−1 ampicillin and incubate it at 37° C. in a shaking incubator overnight.

37. Isolate plasmid DNA from overnight cultures using a QIAprep Spin miniprep kit according to the manufacturer's instructions.

38. Verify the sequence of each clone by sequencing the tandem repeat region using sequencing primers (Table 2) TALE-Seq-F1 (forward primer annealing just before the first monomer), TALE-Seq-F2 (forward primer annealing at the beginning of the seventh monomer) and TALE-Seq-R1 (reverse primer annealing after the final 0.5 monomer). For most TALEs, reads from all three primers are necessary to unambiguously verify the entire sequence. Reference sequences for each custom TALE may be generated using the Applicants' free online software (available at the website of taleffectors under the section "tools"). After entering the target site sequence, the Applicants' software generates a TALE-TF or TALEN reference sequence in either FASTA format or as an annotated GenBank vector map (*.gb file) that may be viewed using standard plasmid editor software (e.g., everyVECTOR, Vector NTI or LaserGene SeqBuilder). Detailed instructions may be found on the website mentioned above.

Steps 39-45: Transfection of TALE-TF and TALEN into HEK293FT cells (Timing: 2 d (1 h hands-on time))

39. Plate HEK293FT cells onto six-well plates in D10 culture medium without antibiotics ~24 h before transfection at a seeding density of around 1×10$^6$ cells per well and a seeding volume of 2 ml. Scale up and down the culture according to the manufacturer's manual provided with the 293FT cells, if needed.

40. Prepare DNA for transfection. Quantify the DNA concentration of the TALE plasmids used for transfection using reliable methods (such as UV spectrophotometry or gel quantification).

Critical step: The DNA concentration of the TALE plasmids are quantified to guarantee that an accurate amount of TALE DNA is used during the transfection.

41. Prepare the DNA-Opti-MEM mix as follows using option A if you are testing transcriptional modulation, or option B if you are testing nuclease activity.

A. DNA-Opti-MEM mix for testing transcriptional modulation.

i. Mix 4 µg of TALE-TF plasmid DNA with 250 µl of Opti-MEM medium. Include controls (e.g., RFP plasmid or mock transfection) to monitor transfection efficiency and cell health, respectively.

B. DNA-Opti-MEM mix for testing nuclease activity.

i. Mix 2 µg of the left and 2 µg of the right TALEN (FIG. 17) plasmid DNA with 250 µl of Opti-MEM medium. Control transfections should be done by omitting one or both of the TALENs. Also include controls (e.g., an RFP plasmid or mock transfection) to monitor transfection efficiency and cell health, respectively. For all transfections, make sure the total amount of DNA transfected is the same across conditions— when omitting one or both TALENs, supplement with empty vector DNA to maintain the same total DNA amount.

42. Prepare the Lipofectamine—Opti-MEM solution by diluting 10 µl of Lipofectamine 2000 with 250 µl of Opti-MEM. Mix the solution thoroughly by tapping the tube and incubating for 5 min at room temperature.

43. Add the Lipofectamine—Opti-MEM solution to the DNA—Opti-MEM solution to form the DNA-Lipofectamine complex. Mix well by gently pipetting up and down. Incubate for 20 min at room temperature.

Critical step: Make sure the complex is thoroughly mixed. Insufficient mixing results in lower transfection efficiency.

Pause point: The transfection complex remains stable for 6 h at room temperature.

44. Add 500 µl of the DNA-Lipofectamine complex to each well of the six-well plates from Step 39 directly. Mix gently by rocking the plates back and forth.

45. Incubate cells at 37° C. with 5% $CO_2$ for 24 h. At this point, determine the transfection efficiency by estimating the fraction of fluorescent cells in the positive control transfection (e.g., RFP plasmid) using a fluorescence microscope.

Critical step: If incubation beyond 48 h is needed, change the culture medium with fresh D10 supplemented with antibiotics on a daily basis. This will not affect the transfection efficiency.

Step 46: TALE functional characterization.

46. To measure TALEN cutting efficiency using Surveyor nuclease follow option A, or to measure TALE-TF transcriptional activation using qRT-PCR, follow option B.

A. Measuring TALEN cutting efficiency using Surveyor nuclease (Timing: 6 h (3 h hands-on time)).

i. Remove culture medium from each well from Step 45 and add 100 µl of QuickExtract DNA extraction solution to each well and pipette thoroughly to lyse cells. Transfer the lysate to a PCR tube.

ii. Extract DNA from the lysate from Step 46A(i) using the following cycling conditions:

| Cycle number | Condition |
| --- | --- |
| 1 | 68° C., 15 min |
| 2 | 95° C., 8 min | iii. PCR amplification of the region surrounding TALEN target site. Prepare the following PCR using the genomic DNA from Step 46A(ii):

| Component | Amount (µl) | Final concentration |
| --- | --- | --- |
| gDNA from Step 46A(ii) | 0.5 | |
| dNTP, 100 mM (25 mM each) | 0.5 | 1 mM |
| Herculase II reaction buffer, 5× | 10 | 1× |
| Target-specific Surveyor forward and reverse primers, 10 µM each (see EXPERIMENTAL DESIGN) | 1 | 200 nM |
| Herculase II Fusion DNA polymerase | 0.5 | 1× |
| Distilled water | 37.5 | |
| Total | 50 | |

Critical step: The Surveyor procedure (Steps 46A(iii-xv)) is carried out according to the manufacturer's protocol and is described in greater detail in the Surveyor manual. Brief details are provided here, as mutation detection by mismatch endonuclease is not a very common procedure.

Critical step: When performing the Surveyor assay for the first time, carrying out the positive control reaction included with the Surveyor nuclease kit is suggested.

iv. Perform PCR using the following cycling conditions:

| Cycle number | Denature | Anneal | Extend |
| --- | --- | --- | --- |
| 1 | 95° C., 3 min | | |
| 2-36 | 95° C., 30 s | 55° C., 15 s | 72° C., 30 s |
| 37 | | | 72° C., 5 min | v. Check the PCR result by running 5 µl of PCR product on a 2% (wt/vol) agarose gel in 1×TBE electrophoresis buffer with 1×SYBR Safe dye. Include 10 µl of the quantitative DNA ladder in one lane. Run the gel at 15 V cm−1 until all bands are clearly separated. For all templates, it is important to make sure that there is only a single band corresponding to the intended product for the primer pair. The size of this band should be the same as calculated from the distance between the two primer annealing sites in the genome.

Critical step: If multiple amplicons are generated from the PCR, redesign primers and reoptimize the PCR conditions to avoid off-target amplification.

vi. Image the gel using a quantitative gel imaging system. Make sure the exposure is short enough so that none of the bands are saturated. Quantify the integrated intensity of each PCR product using ImageJ or other gel quantification software. Use the quantitative ladder with known DNA mass (5, 10, 20, 40, 100 ng) to generate a linear fit. Adjust the DNA concentration of the PCR product by diluting it with 1× Herculase II reaction buffer so that it is in the range of 25-80 ng µl-1.

vii. DNA heteroduplex formation. At this point, the amplified PCR product includes a mixture of both modified and unmodified genomic DNA (TALEN-modified DNA has a few bases of sequence deletion near the TALEN cut site because of NHEJ exonuclease activity). For Surveyor mismatch detection, this mixture of products must first be melted and reannealed such that heteroduplexes are formed. DNA heteroduplexes contain strands of DNA that are slightly different but annealed (imperfectly) together. Given the presence of both unmodified and modified DNA in a sample, a heteroduplex may include one strand of unmodified DNA and one strand of TALEN-modified DNA. Heteroduplexes may also be formed from reannealing of two different TALEN-modified products, as NHEJ exonuclease activity may produce different mutations. To cross-hybridize wild type and TALEN-modified PCR products into hetero- and homoduplexes, all strands are melted and then slowly reannealed (FIG. 17b). Place 300 ng of the PCR product from Step 46A(vi) in a thermocycler tube and bring it to a total volume of 20 µl with 1× Herculase II reaction buffer.

viii. Perform cross-hybridization on the diluted PCR amplicon from Step 46A(vii) using the following cycling conditions:

| Cycle number | Condition |
| --- | --- |
| 1 | 95° C., 10 min |
| 2 | 95-85° C., −2° C. $s^{-1}$ |
| 3 | 85° C., 1 min |

-continued

| Cycle number | Condition |
|---|---|
| 4 | 85-75° C. −0.3° C. s$^{-1}$ |
| 5 | 75° C., 1 min |
| 6 | 75-65° C. −0.3° C. s$^{-1}$ |
| 7 | 65° C., 1 min |
| 8 | 65-55° C. −0.3° C. s$^{-1}$ |
| 9 | 55° C., 1 min |
| 10 | 55-45° C. −0.3° C. s$^{-1}$ |
| 11 | 45° C., 1 min |
| 12 | 45-35° C. −0.3° C. s$^{-1}$ |
| 13 | 35° C., 1 min |
| 14 | 35-25° C. −0.3° C. s$^{-1}$ |
| 15 | 25° C., 1 min | ix. Surveyor Nuclease S digestion. To treat the cross-hybridized homo- and heteroduplexes using Surveyor Nuclease S to determine TALEN cleavage efficiency (FIG. 17b), add the following components together on ice and mix by pipetting gently:

| Component | Amount (μl) | Final concentration |
|---|---|---|
| MgCl$_2$ solution, 0.15M | 2 | 15 mM |
| Surveyor nuclease S | 1 | 1× |
| Surveyor enhancer S | 1 | 1× |
|  | 4 |  |
| Reannealed duplexes from Step 46A(viii) | 16 |  |
| Total | 20 |  | x. Incubate the reaction from Step 46A(ix) at 42° C. for 1 h.

xi. Add 2 μl of the Stop Solution from the Surveyor kit.

Pause point: The digestion product may be stored at −20° C. for analysis at a later time.

xii. Cast a 2% (wt/vol) agarose gel in 1×TBE electrophoresis buffer with 1×SYBR Safe dye. When casting the gel, it is preferable to use a thin comb size (<1 mm) for the sharpest possible bands. The gel should have enough lanes to run out 20 μl of each digestion product band from Step 46A(xi). Include 1 μg of the 1-kb Plus DNA ladder in one lane. Run the gel at 5 V cm−1 until the Orange G loading dye has migrated two-thirds of the way down the gel.

xiii. Image the gel using a quantitative gel imaging system. Make sure the exposure is short enough so that none of the bands are saturated. Each lane from samples transfected with both left and right TALENs should have a larger band corresponding to the uncut genomic amplicon (the same size as in Step 46A(v)) and smaller bands corresponding to the DNA fragments resulting from the cleavage of the genomic amplicon by Surveyor nuclease. Controls (no transfection, control plasmid transfection or transfection omitting one of the TALENs) should only have the larger band corresponding to the uncut genomic amplicon.

xiv. Quantify the integrated intensity of each band using ImageJ or other gel quantification software. For each lane, calculate the fraction of the PCR product cleaved (fcut) using the following formula: fcut=a/(a+b), where a=the integrated intensity of both of the cleavage product bands and b=the integrated intensity of uncleaved PCR product band. A sample Surveyor gel for TALENs targeting human AAVS1 is shown in FIG. 17c.

xv. Estimate the percentage of TALEN-mediated gene modification using the following formula (47):

$$100 \times (1-(1-f_{cut})^{1/2})$$

This calculation may be derived from the binomial probability distribution given a few conditions: that strand reassortment during the duplex formation is random, that there is a negligible probability of the identical mutations reannealing during duplex formation and that the Surveyor nuclease digestion is complete.

B. Measuring TALE-TF transcriptional activation using qRT-PCR (Timing: 5 h (3 h hands-on time))

i. RNA extraction. Aspirate the medium in each well of the six-well plates from Step 45 at 72 h after transfection.

Critical step: Use proper RNA handling techniques to prevent RNA degradation, including cleaning bench surfaces and pipettes with RNaseZAP. Use RNase-free consumables and reagents.

ii. Wash the cells in each well twice with 1 ml of DPBS.

iii. Harvest approximately 1×10$^6$ cells for subsequent total RNA extraction by trypsinizing the cells with 500 μl trypsin with EDTA. Incubate for 1-2 min to let the cells detach from the bottom of the wells.

Critical step: Do not leave the cells in trypsin for longer than a few minutes.

iv. Neutralize the trypsin by adding 2 ml of D10 medium.

v. In a 15-ml centrifuge tube, centrifuge the cell suspension at 300 g for 5 min at 4° C. Carefully aspirate all of the supernatant.

Critical step: Incomplete removal of the supernatant may result in inhibition of cell lysis.

Pause point: Cells may be frozen at −80° C. for 24 h.

vi. Extract and purify RNA from the cells in Step 46B(v) using the RNeasy mini kit and QIAshredder following the manufacturer's directions. Elute the RNA from each column using 30 μl of nuclease-free water.

vii. Measure the RNA concentration using a UV spectrophotometer.

viii. cDNA reverse transcription. Generate cDNA using the iScript cDNA synthesis kit according to the manufacturer's directions. For matched negative controls, perform the reverse transcription without the reverse-transcriptase enzyme.

ix. Quantitative PCR. Thaw on ice the appropriate TaqMan probe for the target gene and for an endogenous control gene.

Critical step: Protect the probes from light and do not allow the thawed probes to stay on ice for an extended time.

x. By following the TaqMan Universal PCR Master Mix manufacturer's directions, prepare four technical replicate qPCRs for each sample in optical thermocycler strip tubes or 96-well plates. Set up negative controls for nonspecific amplification as indicated in the directions: namely, RNA template processed without reverse transcriptase ('no RT') and a no-template control.

xi. Briefly centrifuge the samples to remove any bubbles and amplify them in a TaqMan-compatible qRT-PCR machine with the following cycling parameters.

| Cycle number | Denature | Anneal and extend |
|---|---|---|
| 1 | 95° C., 10 min |  |
| 2-41 | 92° C., 15 s | 60° C., 1 min | xii. Analyze data and calculate the level of gene activation using the ΔΔCt method46, 55. TALE-TF results from qRT-PCR assay of SOX2 activation in HEK293 cells are shown in FIG. 17d, e.

Critical step: The ΔΔC$_t$ method assumes that amplification efficiency is 100% (i.e., the number of amplicons doubles after each cycle). For new probes (such as custom TaqMan probes), amplification from a template dilution series (spanning at least five orders of magnitude) should be performed to characterize amplification efficiency. For standard TaqMan gene expression assay probes, this is not necessary, as they are designed to have 100±10% amplification efficiency.

Troubleshooting Table:

11, 12, 13, 14, 15) (FIG. 9). TALENs may be readily designed to introduce double-stranded breaks at specific genomic loci with high efficiency. In Applicants' experience, a pair of TALENs designed to target the human AAVS1 locus is able to achieve up to 3.6% cutting efficiency in 293FT cells, as determined by Surveyor nuclease assay (FIG. 17a-d). TALE-TFs may also robustly increase the mRNA levels of endogenous

| Step | Problem | Possible reason | Solution |
|---|---|---|---|
| 4 | Uneven amplification across monomers | Not using Herculase II Fusion polymerase | Optimize annealing temperature and $Mg^{2+}$ and DMSO concentrations |
| 8 | Low DNA concentration after elution | Residual ethanol on purification column | Air-dry columns before elution at 37° C. for a longer period of time |
| | | Incorrect vacuum pressure during DNA binding | Adjust vacuum pressure according to the manufacturer's suggestions |
| 15 | No visible hexamer band (~700 bp) | Equimolar amounts of monomers were not added | Gel-normalize the monomer concentration |
| | | Degraded DTT or ATP | Use fresh stocks of DTT and ATP, which degrade easily |
| | No visible hexamer band (~700 bp) but smaller bands present | Wrong monomer(s) added during pipetting | Re-select monomers |
| | | Monomer concentration is too low | Increase the number of Golden Gate digestion-ligation cycles and/or increase the concentration of monomers to >20 ng $\mu l^{-1}$; there is no detrimental effect to using more monomers in an equimolar ratio |
| 20 | No visible hexamer band (~700 bp) | Unsuccessful Golden Gate digestion-ligation | Verify on a gel that the Golden Gate digestion-ligation product from Step 15 is visible; increase the monomer concentration |
| 24 | Low concentration for purified hexamers | Unsuccessful gel extraction | Ensure that there is no residual ethanol during elution or increase PCR reaction volume |
| 28 | No visible 18-mer band (~1.8 kbp) | Unsuccessful Golden Gate digestion-ligation | Increase hexamer concentration in Golden Gate digestion-ligation in Step 26 or proceed directly to transformation in Step 29 |
| 30 | More than a few colonies on negative control plate | Compromised TALE backbone | Perform a restriction digest of the backbone to verify integrity |
| 35 | Colony PCR bands are smeared | Too much template | Dilute colony suspension 10× to 100× |
| 38 | Monomers assembled in incorrect order | Misligation | Misligation occurs at a very low frequency; analyze two additional clones |
| 45 | Low transfection efficiency | Low DNA quality | Prepare DNA using high-quality plasmid preparation |
| | | Suboptimal ratio of DNA to Lipofectamine 2000 | Titrate the ratio of DNA to Lipofectamine 2000 to determine optimal transfection conditions |
| 46A(v) | Multiple amplicons | Nonspecific primers | Design new primers and verify specificity using PrimerBLAST; use touchdown PCR |
| | No amplification | Suboptimal PCR condition | Optimize annealing temperature and $Mg^{2+}$ and DMSO concentrations |
| 46A(xiii) | No cleavage bands visible | TALEN is unable to cleave the target site | Design new TALEN pairs targeting nearby sequences |
| 46B(xii) | No increase in transcription in target mRNA | TALE-TF is unable to access the target site | Design new TALE-TFs targeting nearby sequences |

Timing:
Steps 1-9, Monomer library amplification and normalization: 6 h
Steps 10-28, TALE hierarchical ligation assembly: 1.5 d (5 h hands-on time)
Steps 29-38, TALE transformation and sequence verification: 3 d (4 h hands-on time)
Steps 39-45, Transfection of TALE-TF and TALEN into HEK293FT cells: 2 d (1 h hands-on time)
Steps 46A and 46B, TALE functional characterization with qRT-PCR or Surveyor: 5-6 h (3 h hands-on time)

TALE-TFs and TALENs may facilitate site-specific transcriptional modulation (3, 4, 5, 8) and genome editing (4, 7, 9, genes. For example, a TALE-TF designed to target the proximal promoter region of SOX2 in human cells is able to elevate the level of endogenous SOX2 gene expression by up to fivefold (FIG. 17d, e). The ability for TALE-TFs and TALENs to act at endogenous genomic loci is dependent on the chromatin state, as well as yet-to-be-determined mechanisms regulating TALE DNA binding (56, 57). For these reasons, several TALE-TFs or TALEN pairs for each genomic locus targeted are typically built. These TALE-TFs and TALENs are designed to bind to neighboring regions around a specific target site, as some binding sites might be more accessible than others. The reason why some TALEs exhibit significantly lower levels of activity remains unknown, although it is likely to be due to position- or cell-state-specific epigenetic modifications preventing access to the binding site. Because of differences in epigenetic states between different cells, it is possible that TALEs that fail to work in a particular cell type might work in a different cell type.

REFERENCES

1. Boch, J. et al. Breaking the code of DNA binding specificity of TAL-type III effectors. *Science* 326, 1509-1512 (2009).
2. Moscou, M. J. & Bogdanove, A. J. A simple cipher governs DNA recognition by TAL effectors. *Science* 326, 1501 (2009).
3. Zhang, F. et al. Efficient construction of sequence-specific TAL effectors for modulating mammalian transcription. *Nat. Biotechnol.* 29, 149-153 (2011).
4. Miller, J. C. et al. A TALE nuclease architecture for efficient genome editing. *Nat. Biotechnol.* 29, 143-148 (2011).
5. Morbitzer, R., Romer, P., Boch, J. & Lahaye, T. Regulation of selected genome loci using de novo-engineered transcription activator-like effector (TALE)-type transcription factors. *Proc. Natl. Acad. Sci. USA* 107, 21617-21622 (2010).
6. Weber, E., Gruetzner, R., Werner, S., Engler, C. & Marillonnet, S. Assembly of designer TAL effectors by golden gate cloning. *PLoS ONE* 6, e19722 (2011).
7. Cermak, T. et al. Efficient design and assembly of custom TALEN and other TAL effector-based constructs for DNA targeting. *Nucleic Acids Res.* 39, e82 (2011).
8. Geissler, R. et al. Transcriptional activators of human genes with programmable DNA-specificity. *PLoS ONE* 6, e19509 (2011).
9. Li, T. et al. Modularly assembled designer TAL effector nucleases for targeted gene knockout and gene replacement in eukaryotes. *Nucleic Acids Res.* 39, 6315-6325 (2011).
10. Morbitzer, R., Elsaesser, J., Hausner, J. & Lahaye, T. Assembly of custom TALE-type DNA binding domains by modular cloning. *Nucleic Acids Res.* 39, 5790-5799 (2011).
11. Wood, A. J. et al. Targeted genome editing across species using ZFNs and TALENs. *Science* 333, 307 (2011).
12. Christian, M. et al. Targeting DNA double-strand breaks with TAL effector nucleases. *Genetics* 186, 757-761 (2010).
13. Hockemeyer, D. et al. Genetic engineering of human pluripotent cells using TALE nucleases. *Nat. Biotechnol.* 29, 731-734 (2011).
14. Li, T. et al. TAL nucleases (TALNs): hybrid proteins composed of TAL effectors and FokI DNA-cleavage domain. *Nucleic Acids Res.* 39, 359-372 (2011).
15. Mahfouz, M. M. et al. De novo-engineered transcription activator-like effector (TALE) hybrid nuclease with novel DNA binding specificity creates double-strand breaks. *Proc. Natl. Acad. Sci. USA* 108, 2623-2628 (2011).
16. Boch, J. & Bonas, U. *Xanthomonas* AvrBs3 family-type III effectors: discovery and function. *Annu. Rev. Phytopathol.* 48, 419-436 (2010).
17. Bogdanove, A. J., Schornack, S. & Lahaye, T. TAL effectors: finding plant genes for disease and defense. *Curr. Opin. Plant Biol.* 13, 394-401 (2010).
18. Romer, P. et al. Plant pathogen recognition mediated by promoter activation of the pepper Bs3 resistance gene. *Science* 318, 645-648 (2007).
19. Kay, S., Hahn, S., Marois, E., Hause, G. & Bonas, U. A bacterial effector acts as a plant transcription factor and induces a cell size regulator. *Science* 318, 648-651 (2007).
20. Kay, S., Hahn, S., Marois, E., Wieduwild, R. & Bonas, U. Detailed analysis of the DNA recognition motifs of the *Xanthomonas* type III effectors AvrBs3 and AvrBs3Deltarep16. *Plant J.* 59, 859-871 (2009).
21. Romer, P. et al. Recognition of AvrBs3-like proteins is mediated by specific binding to promoters of matching pepper Bs3 alleles. *Plant Physiol.* 150, 1697-1712 (2009).
22. Hinnen, A., Hicks, J. B. & Fink, G. R. Transformation of yeast. *Proc. Natl. Acad. Sci. USA* 75, 1929-1933 (1978).
23. Szostak, J. W., Orr-Weaver, T. L., Rothstein, R. J. & Stahl, F. W. The double-strand-break repair model for recombination. *Cell* 33, 25-35 (1983).
24. Thomas, K. R., Folger, K. R. & Capecchi, M. R. High frequency targeting of genes to specific sites in the mammalian genome. *Cell* 44, 419-428 (1986).
25. Ivies, Z., Hackett, P. B., Plasterk, R. H. & Izsvak, Z. Molecular reconstruction of Sleeping Beauty, a Tc1-like transposon from fish, and its transposition in human cells. *Cell* 91, 501-510 (1997).
26. Kawakami, K., Shima, A. & Kawakami, N. Identification of a functional transposase of the Tol2 element, an Ac-like element from the Japanese medaka fish, and its transposition in the zebrafish germ lineage. *Proc. Natl. Acad. Sci. USA* 97, 11403-11408 (2000).
27. Akagi, K. et al. Cre-mediated somatic site-specific recombination in mice. *Nucleic Acids Res.* 25, 1766-1773 (1997).
28. Epinat, J. C. et al. A novel engineered meganuclease induces homologous recombination in yeast and mammalian cells. *Nucleic Acids Res.* 31, 2952-2962 (2003).
29. Lois, C., Hong, E. J., Pease, S., Brown, E. J. & Baltimore, D. Germline transmission and tissue-specific expression of transgenes delivered by lentiviral vectors. *Science* 295, 868-872 (2002).
30. Khan, I. F., Hirata, R. K. & Russell, D. W. AAV-mediated gene targeting methods for human cells. *Nat. Protoc.* 6, 482-501 (2011).
31. Pavletich, N. P. & Pabo, C. O. Zinc finger-DNA recognition: crystal structure of a Zif268-DNA complex at 2.1 A. *Science* 252, 809-817 (1991).
32. Klug, A. The discovery of zinc fingers and their development for practical applications in gene regulation and genome manipulation. *Q. Rev. Biophys.* 43, 1-21 (2010).
33. Maeder, M. L., Thibodeau-Beganny, S., Sander, J. D., Voytas, D. F. & Joung, J. K. Oligomerized pool engineering (OPEN): an 'open-source' protocol for making customized zinc-finger arrays. *Nat. Protoc.* 4, 1471-1501 (2009).
34. Kim, J. S., Lee, H. J. & Carroll, D. Genome editing with modularly assembled zinc-finger nucleases. *Nat. Methods* 7, 91; author reply 91-92 (2010).
35. Sander, J. D. et al. Selection-free zinc-finger-nuclease engineering by context-dependent assembly (CoDA). *Nat. Methods* 8, 67-69 (2011).
36. Perez, E. E. et al. Establishment of HIV-1 resistance in CD4+ T cells by genome editing using zinc-finger nucleases. *Nat. Biotechnol.* 26, 808-816 (2008).
37. Keenholtz, R. A., Rowland, S. J., Boocock, M. R., Stark, W. M. & Rice, P. A. Structural basis for catalytic activation of a serine recombinase. *Structure* 19, 799-809 (2011).
38. Gersbach, C. A., Gaj, T., Gordley, R. M., Mercer, A. C. & Barbas, C. F. III. Targeted plasmid integration into the human genome by an engineered zinc-finger recombinase. *Nucleic Acids Res.* 39, 7868-7878 (2011).
39. Gaj, T., Mercer, A. C., Gersbach, C. A., Gordley, R. M. & Barbas, C. F. III. Structure-guided reprogramming of serine recombinase DNA sequence specificity. *Proc. Natl. Acad. Sci. USA* 108, 498-503 (2011).

40. Urnov, F. D. et al. Highly efficient endogenous human gene correction using designed zinc-finger nucleases. *Nature* 435, 646-651 (2005).
41. Wilson, M. H., Kaminski, J. M. & George, A. L. Jr. Functional zinc finger/sleeping beauty transposase chimeras exhibit attenuated overproduction inhibition. FEBS Lett. 579, 6205-6209 (2005).
42. Engler, C., Kandzia, R. & Marillonnet, S. A one pot, one step, precision cloning method with high throughput capability. PLoS ONE 3, e3647 (2008).
43. Engler, C., Gruetzner, R., Kandzia, R. & Marillonnet, S. Golden gate shuffling: a one-pot DNA shuffling method based on type IIs restriction enzymes. PLoS ONE 4, e5553 (2009).
44. Weber, E., Engler, C., Gruetzner, R., Werner, S. & Marillonnet, S. A modular cloning system for standardized assembly of multigene constructs. PLoS ONE 6, e16765 (2011).
45. Huertas, P. DNA resection in eukaryotes: deciding how to fix the break. *Nat. Struct. Mol. Biol.* 17, 11-16 (2010).
46. Nolan, T., Hands, R. E. & Bustin, S. A. Quantification of mRNA using real-time RT-PCR. *Nat. Protoc.* 1, 1559-1582 (2006).
47. Guschin, D. Y. et al. A rapid and general assay for monitoring endogenous gene modification. *Methods Mol. Biol.* 649, 247-256 (2010).
48. Zhang, F. et al. High frequency targeted mutagenesis in *Arabidopsis thaliana* using zinc finger nucleases. *Proc. Natl. Acad. Sci. USA* 107, 12028-12033 (2010).
49. Buzdin, A. A. in Nucleic Acids Hybridization (eds. Buzdin, A., Lukyanov, S.) 211-239 (Springer, 2007).
50. Till, B. J., Burtner, C., Comai, L. & Henikoff, S. Mismatch cleavage by single-strand specific nucleases. *Nucleic Acids Res.* 32, 2632-2641 (2004).
51. Babon, J. J., McKenzie, M. & Cotton, R. G. The use of resolvases T4 endonuclease VII and T7 endonuclease I in mutation detection. *Mol. Biotechnol.* 23, 73-81 (2003).
52. Yang, B. et al. Purification, cloning, and characterization of the CEL I nuclease. Biochemistry 39, 3533-3541 (2000).
53. Kulinski, J., Besack, D., Oleykowski, C. A., Godwin, A. K. & Yeung, A. T. CEL I enzymatic mutation detection assay. Biotechniques 29, 44-46, 48 (2000).
54. Oleykowski, C. A., Bronson Mullins, C. R., Godwin, A. K. & Yeung, A. T. Mutation detection using a novel plant endonuclease. *Nucleic Acids Res.* 26, 4597-4602 (1998).
55. Pfaffl, M. W. A new mathematical model for relative quantification in real-time RT-PCR. *Nucleic Acids Res.* 29, e45 (2001).
56. Murakami, M. T. et al. The repeat domain of the type III effector protein PthA shows a TPR-like structure and undergoes conformational changes upon DNA interaction. *Proteins* 78, 3386-3395 (2010).
57. Scholze, H. & Boch, J. TAL effectors are remote controls for gene activation. *Curr. Opin. Microbiol.* 14, 47-53 (2011).
58. Huang, P. et al. Heritable gene targeting in zebrafish using customized TALENs. *Nat. Biotechnol.* 29, 699-700 (2011).
59. Sander, J. D. et al. Targeted gene disruption in somatic zebrafish cells using engineered TALENs. *Nat. Biotechnol.* 29, 697-698 (2011).
60. Tesson, L. et al. Knockout rats generated by embryo microinjection of TALENs. *Nat. Biotechnol.* 29, 695-696 (2011).

Example 3

Comprehensive Interrogation of Natural TALE DNA Binding Modules and Transcriptional Repressor Domains A family of sequence-specific DNA binding protein, transcription activator-like effector (TALE), harbors modular repetitive DNA binding domains that have enabled customizable designer transcriptional factors and nucleases for genome engineering. Presented here are two improvements to the TALE toolbox for achieving efficient activation and repression of endogenous gene expression in mammalian cells. First, the naturally occurring repeat variable diresidue (RVD) Asn-His (NH) has high biological activity and specificity for guanine, a highly prevalent base in mammalian genomes. Second, an effective TALE transcriptional repressor architecture for targeted inhibition of transcription in mammalian cells is reported. These results further improve the TALE toolbox for achieving precise and effective genome engineering. Transcription activator-like effectors (TALEs) are bacterial effector proteins found in *Xanthamonas* sp. and *Ralstonia* sp. Each TALE contains a DNA binding domain consisting of 34 amino acid tandem repeat modules, where the 12th and 13th residues of each module, referred to as repeat variable diresidues (RVDs), specify the target DNA base (1, 2). Four of the most abundant RVDs from naturally occurring TALEs have established a simple code for DNA recognition (e.g., NI for adenine, HD for cytosine, NG for thymine, and NN for guanine or adenine) (1, 2). Using this simple code, TALEs were developed into a versatile platform for achieving precise genomic and transcriptomic perturbations across a diverse range of biological systems (3, 8). However, two limitations remain: first, there lacks a RVD capable of robustly and specifically recognizing the DNA base guanine, a highly prevalent base in mammalian genomes (9); and second, a viable TALE transcriptional repressor for mammalian applications has remained elusive, which repressor is highly desirable for a variety of synthetic biology and disease-modeling applications (9). To address these two limitations, series of screens were conducted and it was found that: first, of all naturally occurring TALE RVDs, the previously unidentified RVD Asn-His (NH) may be used to achieve guanine-specific recognition; and second, the mSin Interaction Domain (SID) (10) may be fused to TALEs to facilitate targeted transcriptional repression of endogenous mammalian gene expression. These advances further improve the power and precision of TALE-based genome engineering technologies, enabling efficient bimodal control of mammalian transcriptional processes.

Screening of novel TALE RVDs: Previously, the RVD NK was reported to have more specificity for guanine than NN (4). However, recent studies have shown that substitution of NK with NN leads to substantially lower levels of activity (11). To identify a more specific guanine-binding RVD with higher biological activity, a total of 23 naturally occurring RVDs were identified and evaluated (FIG. 18a) from the set of known *Xanthomonas* TALE sequences in Genbank. In order to directly compare the DNA binding specificity and activity of all RVDs in an unbiased manner, a set of 2312.5-repeat TALEs were designed where RVDs 5 and 6 were systematically substituted with the 23 naturally occurring RVDs (RVD-TALEs; FIG. 18a). This design allowed the maintenance of a consistent RVD context surrounding the two varied RVD positions. Additionally, a *Gaussia* luciferase gene (Gluc) with a 2A peptide linker was fused to the RVD-TALEs to control for the differences in TALE protein expression levels (FIG. 18a). Each RVD-TALE (e.g. NI-TALE, HD-TALE, etc.) was used to assess the base-preference and activity strength of its corresponding RVD—this is measured by comparing each RVD-TALE's ability to activate transcription from each of the four base-specific *Cypridina* luciferase reporter (Cluc) plasmids with A, G, T, and C substituted in the 6th and 7th positions of the TALE binding site (A-, G-, T-, or C-reporters; FIG. 18a).

The 23 RVD-TALEs exhibited a wide range of DNA base preferences and biological activities in the reporter assay (FIG. 18b). In particular, NH— and HN-TALEs activated the guanine-reporter preferentially and at similar levels as the NN-TALE. Interestingly, the NH-TALE also exhibited significantly higher specificity for the G-reporter than the NN-TALE (ratio of G- to A-reporter activations: 16.9 for NH-TALE and 2.7 for NN-TALE; FIG. 18b), suggesting that NH might be a more optimal RVD for targeting guanines Computational analysis of TALE-RVD specificity using a recently published crystal structure of TALE-dsDNA complex (12) also suggests that NH has a significantly higher affinity for guanine than NN (FIG. 20). It was found that substitution of NN with NH in one repeat within the TALE DNA binding domain resulted in a gain of 0.86±0.67 kcal/mol in free energy ($\Delta\Delta G$) in the DNA bound state (FIG. 20). This result could be explained by the observation that the imidazole ring on the histidine residue (NH RVD) has a more compact base-stacking interaction with the target guanine base (FIG. 20b), indicating that NH would be able to bind guanine more tightly than NN, thus suggesting a possible mechanism for the increased specificity of NH for guanine Additionally, the RVD NA exhibited similar levels of reporter activation for all four bases and may be a promising candidate for high efficiency targeting of degenerate DNA sequences in scenarios where non-specific binding is desired (13).

Figure 19A:
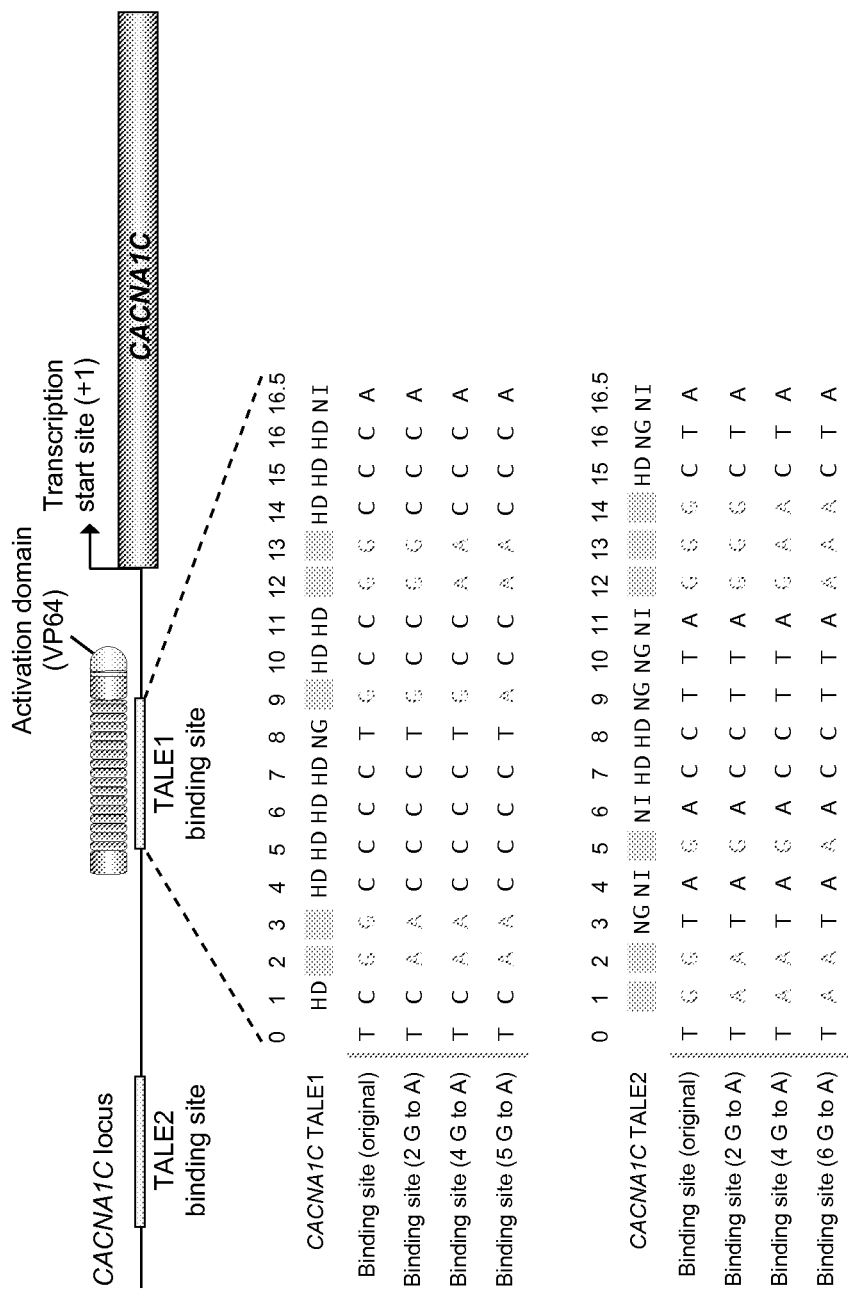

Relative activity and specificity of guanine-binding RVDs: To determine whether NH and HN are suitable replacements for NN as the G-specific RVD, specificity and activity strength of NN, NK, NH, and HN were directly compared. Two 18 bp targets within the CACNA1C locus in the human genome were chosen and four TALEs for each target were constructed, using NN, NK, NH, or HN as the G-targeting RVD (FIG. 19a). Since the screening result (FIG. 18b) suggested that HN might be less discriminatory than NH when the targeted base is A instead of G, a luciferase assay was first designed to further characterize the G-specificity of each RVD. For each CACNA1C target site, four luciferase reporters were constructed: wild type genomic target, and wild type target with 2, 4, or all guanines mutated into adenines (FIG. 19a, G-to-A reporters), and compared the activity of each TALE using these reporters (FIG. 19a). For both CACNA1C target sites, it was found that the TALE with NH as the G-targeting RVD exhibited significantly higher specificity for guanine over adenine than the corresponding NK-, HN-, and NN-containing TALEs. For target site 1, introduction of 2 G to A mutations led to 35.4% (TALE1-NN), 40.3% (TALE1-NK), 71.4% (TALE1-NH), and 30.8% (TALE1-HN) of reduction in luciferase activity. For target site 2, two G-to-A mutations led to 21.8% (TALE2-NN), 36.3% (TALE2-NK), 66.1% (TALE2-NH), and 13.9% (TALE2-HN) reduction in reporter activity. Additional G-to-A mutations resulted in further reduction of reporter activity, with NH exhibiting the highest level of discrimination (FIG. 19a). Additionally, NH TALEs exhibited significantly higher levels of reporter induction than NK TALEs (1.9 times for site 1 and 2.7 times for site 2), and comparable to NN and NH TALEs (FIG. 19a). Thus, focus was placed on the RVDs NN, NK, and NH in subsequent experiments to assess their usefulness in modulating transcription at endogenous human genome targets.

Figure 19B:
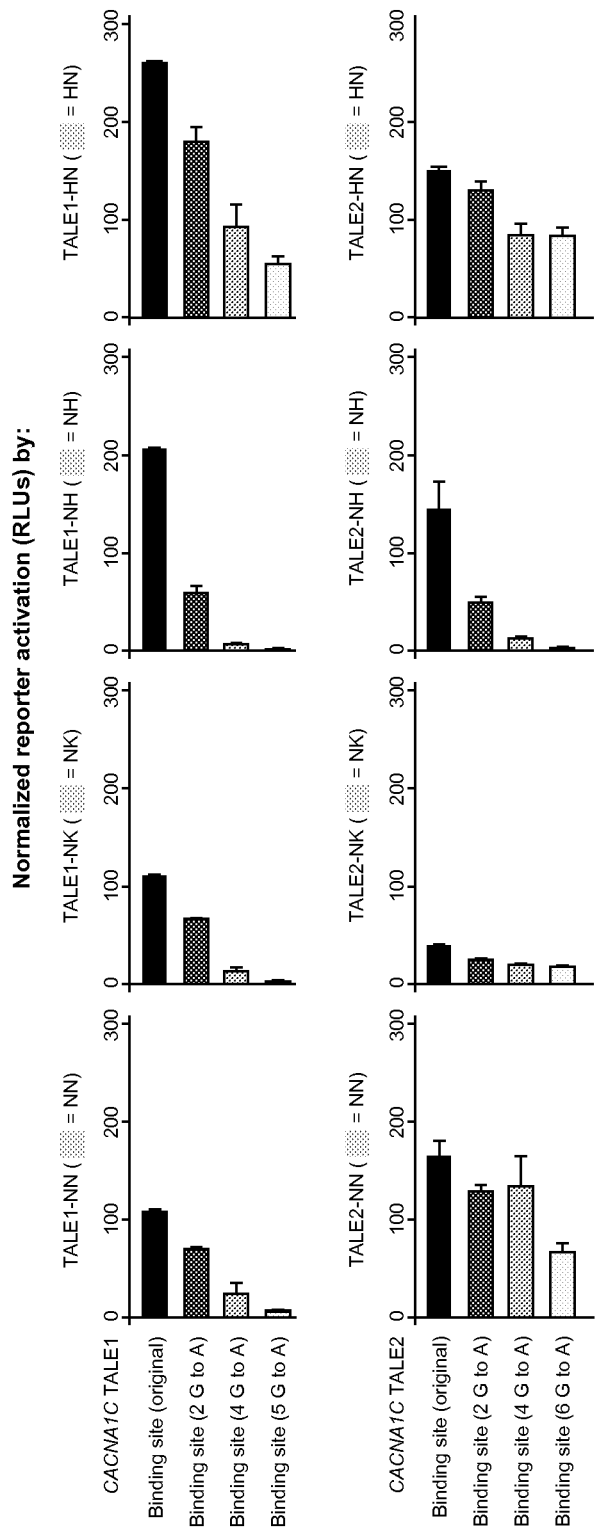

Evaluation of guanine-binding RVDs at endogenous genome loci: Using qRT-PCR, the performance of NN, NK, NH, and HN for targeting endogenous genomic sequences was further compared. The ability of NN-, NK-, NH-, and HN-TALEs to activate CACNA1C transcription by targeting the two endogenous target sites was tested (FIG. 19b). To control for differences in TALE expression levels, all TALEs were fused to 2A-GFP and exhibited similar levels of GFP fluorescence (3). Using qRT-PCR, it was found that the endogenous activity of each TALE corresponded to the reporter assay. Both TALE1-NH and TALE2-NH were able to achieve similar levels of transcriptional activation as TALE 1-NN and TALE2-NN (~5 and ~3 folds of activation for targets 1 and 2, respectively) and twice more than TALE 1-NK and TALE2-NK (FIG. 19b). Although TALE1-HN and TALE2-HN exhibited comparable activity with TALEs bearing RVDs NN and NH, the lack of specificity in distinguishing guanine and adenosine bases as shown in previous test (FIG. 19a) does not warrant the superiority of HN over existing guanine-binding RVDs. On the other hand, based on all the results from specificity and endogenous activity tests, the RVD NH seems to be a more suitable substitute for NN than NK when higher targeting specificity is desired, as it also provides higher levels of biological activity. Further testing using additional endogenous genomic targets helps validate the broad utility of NH as a highly specific G-targeting RVD.

Development of mammalian TALE transcriptional repressors: Having identified NH as a more specific G-recognizing RVD, a mammalian TALE repressor architecture to enable researchers to suppress transcription of endogenous genes was developed. TALE repressors have the potential to suppress the expression of genes as well as non-coding transcripts such as microRNAs, rendering them a highly desirable tool for testing the causal role of specific genetic elements. In order to identify a suitable repression domain for use with TALEs in mammalian cells, a TALE targeting the promoter of the human SOX2 gene was used to evaluate the transcriptional repression activity of a collection of candidate repression domains (FIG. 21a). Repression domains across a range of eukaryotic host species were selected to increase the chance of finding a potent synthetic repressor, including the PIE-1 repression domain (PIE-1)(14) from *Caenorhabditis elegans*, the QA domain within the Ubx gene (Ubx-QA)(15) from *Drosophila melanogaster*, the IAA28 repression domain (IAA28-RD)(16) from *Arabidopsis thaliana*, the mSin interaction domain (SID) (10), Tbx3 repression domain (Tbx3-RD), and the Krüppel-associated box (KRAB) (17) repression domain from *Homo Sapiens* (FIG. 20b). Since different truncations of KRAB were known to exhibit varying levels of transcriptional repression (17), three different truncations of KRAB were tested (FIG. 21c). These candidate TALE repressors were expressed in HEK 293FT cells and it was found that TALEs carrying two widely used mammalian transcriptional repression domains, the SID (10) and KRAB (17) domains, were able to repress endogenous SOX2 expression, while the other domains had little effect on transcriptional activity (FIG. 21c). To control for potential perturbation of SOX2 transcription due to TALE binding, expression of the SOX2-targeting TALE DNA binding domain alone without any effector domain had no effect (similar to mock or expression of GFP) on the transcriptional activity of SOX2 (FIG. 21c, Null condition). Since the SID domain was able to achieve 26% more transcriptional repression of the endogenous SOX2 locus than the KRAB domain (FIG. 21c), it was decided to use the SID domain for subsequent studies.

To further test the effectiveness of the SID repressor domain for down regulating endogenous transcription, SID was combined with CACNA1C-target TALEs from the previous experiment (FIG. 19, FIG. 21d). Using qRT-PCR, it was found that replacement of the VP64 domain on CACNA1C-targeting TALEs with SID was able to repress CACNA1C transcription. Additionally, similar to the transcriptional activation study (FIG. 19b, left), the NH-containing TALE repressor was able to achieve a similar level of transcriptional repression as the NN-containing TALE (~4 fold repression), while the TALE repressor using NK was significantly less active (~2 fold repression) (FIG. 21d). These data demonstrate that SID is indeed a suitable repression domain, while also further supporting NH as a more suitable G-targeting RVD than NK.

Discussion

TALEs may be easily customized to recognize specific sequences on the endogenous genome. Here, a series of screens were conducted to address two important limitations of the TALE toolbox. Together, the identification of a more stringent G-specific RVD with uncompromised activity strength as well as a robust TALE repressor architecture further expands the utility of TALEs for probing mammalian transcription and genome function.

Methods

Construction of TALE activators, repressors and reporters: All TALE activators and repressors were constructed as previously described using a hierarchical ligation strategy (3). The sequences for all constructs used in this study may be found in the table below:

| TALE repressor screening constructs amino acid sequences | |
|---|---|
| >SOX2 TALE repressor (KRAB 1-97) | MSRTRLPSPPAPSPAFSADSFSDLLRQFDPSLFNTSLFDS LPPFGAHHTEAATGEWDEVQSGLRAADAPPPTMRVAVTAA RPPRAKPAPRRRAAQPSDASPAAQVDLRTLGYSQQQQEKI KPKVRSTVAQHHEALVGHGFTHAHIVALSQHPAALGTVAV KYQDMIAALPEATHEAIVGVGKQWSGARALEALLTVAGEL RGPPLQLDTGQLLKIAKRGGVTAVEAVHAWRNALTGAPLN LTPEQVVAIASNGGGKQALETVQRLLPVLCQAHGLTPEQV VAIASNGGGKQALETVQRLLPVLCQAHGLTPEQVVAIASN IGGKQALETVQRLLPVLCQAHGLTPEQVVAIASNGGGKQA LETVQRLLPVLCQAHGLTPEQVVAIASNGGGKQALETVQR LLPVLCQAHGLTPEQVVAIASHDGGKQALETVQRLLPVLC QAHGLTPEQVVAIASHDGGKQALETVQRLLPVLCQAHGLT PEQVVAIASHDGGKQALETVQRLLPVLCQAHGLTPEQVVA IASNGGGKQALETVQRLLPVLCQAHGLTPEQVVAIASNNG GKQALETVQRLLPVLCQAHGLTPEQVVAIASNIGGKQALE TVQRLLPVLCQAHGLTPEQVVAIASHDGGKQALETVQRLL PVLCQAHGLTPEQVVAIASNIGGRPALESIVAQLSRPDPA LAALTNDHLVALACLGGRPALDAVKKGLPHAPALIKRTNR RIPERTSHRVADHAQVVRVLGFFQCHSHPAQAFDDAMTQF GMSRHGLLQLFRRVGVTELEARSGTLPPASQRWDRILQAS GMKRAKPSPTSTQTPDQASLHAFADSLERDLDAPSPMHEG DQTRASASPKKKRKVEASMDAKSLTAWSRTLVTFKDVFVD FTREEWKLLDTAQQIVYRNVMLENYKNLVSLGYQLTKPDV ILRLEKGEEPWLVEREIHQETHPDSETAFEIKSSV (SEQ ID NO: 29) |
| >SOX2 TALE repressor (KRAB 1-75) | MSRTRLPSPPAPSPAFSADSFSDLLRQFDPSLFNTSLFDS LPPFGAHHTEAATGEWDEVQSGLRAADAPPPTMRVAVTAA RPPRAKPAPRRRAAQPSDASPAAQVDLRTLGYSQQQQEKI KPKVRSTVAQHHEALVGHGFTHAHIVALSQHPAALGTVAV KYQDMIAALPEATHEAIVGVGKQWSGARALEALLTVAGEL RGPPLQLDTGQLLKIAKRGGVTAVEAVHAWRNALTGAPLN LTPEQVVAIASNGGGKQALETVQRLLPVLCQAHGLTPEQV VAIASNGGGKQALETVQRLLPVLCQAHGLTPEQVVAIASN IGGKQALETVQRLLPVLCQAHGLTPEQVVAIASNGGGKQA LETVQRLLPVLCQAHGLTPEQVVAIASNGGGKQALETVQR LLPVLCQAHGLTPEQVVAIASHDGGKQALETVQRLLPVLC QAHGLTPEQVVAIASHDGGKQALETVQRLLPVLCQAHGLT PEQVVAIASHDGGKQALETVQRLLPVLCQAHGLTPEQVVA IASNGGGKQALETVQRLLPVLCQAHGLTPEQVVAIASNNG GKQALETVQRLLPVLCQAHGLTPEQVVAIASNIGGKQALE TVQRLLPVLCQAHGLTPEQVVAIASHDGGKQALETVQRLL PVLCQAHGLTPEQVVAIASNIGGRPALESIVAQLSRPDPA LAALTNDHLVALACLGGRPALDAVKKGLPHAPALIKRTNR RIPERTSHRVADHAQVVRVLGFFQCHSHPAQAFDDAMTQF GMSRHGLLQLFRRVGVTELEARSGTLPPASQRWDRILQAS GMKRAKPSPTSTQTPDQASLHAFADSLERDLDAPSPMHEG DQTRASASPKKKRKVEASMDAKSLTAWSRTLVTFKDVFVD FTREEWKLLDTAQQIVYRNVMLENYKNLVSLGYQLTKPDV ILRLEKGEEPWLV (SEQ ID NO: 30) |
| >SOX2 TALE repressor (KRAB 11-75) | MSRTRLPSPPAPSPAFSADSFSDLLRQFDPSLFNTSLFDS LPPFGAHHTEAATGEWDEVQSGLRAADAPPPTMRVAVTAA RPPRAKPAPRRRAAQPSDASPAAQVDLRTLGYSQQQQEKI KPKVRSTVAQHHEALVGHGFTHAHIVALSQHPAALGTVAV KYQDMIAALPEATHEAIVGVGKQWSGARALEALLTVAGEL RGPPLQLDTGQLLKIAKRGGVTAVEAVHAWRNALTGAPLN |

| | |
|---|---|
| | LTPEQVVAIASNGGGKQALETVQRLLPVLCQAHGLTPEQV<br>VAIASNGGGKQALETVQRLLPVLCQAHGLTPEQVVAIASN<br>IGGKQALETVQRLLPVLCQAHGLTPEQVVAIASNGGGKQA<br>LETVQRLLPVLCQAHGLTPEQVVAIASNGGGKQALETVQR<br>LLPVLCQAHGLTPEQVVAIASHDGGKQALETVQRLLPVLC<br>QAHGLTPEQVVAIASHDGGKQALETVQRLLPVLCQAHGLT<br>PEQVVAIASHDGGKQALETVQRLLPVLCQAHGLTPEQVVA<br>IASNGGGKQALETVQRLLPVLCQAHGLTPEQVVAIASNNG<br>GKQALETVQRLLPVLCQAHGLTPEQVVAIASNIGGKQALE<br>TVQRLLPVLCQAHGLTPEQVVAIASHDGGKQALETVQRLL<br>PVLCQAHGLTPEQVVAIASNIGGRPALESIVAQLSRPDPA<br>LAALTNDHLVALACLGGRPALDAVKKGLPHAPALIKRTNR<br>RIPERTSHRVADHAQVVRVLGFFQCHSHPAQAFDDAMTQF<br>GMSRHGLLQLFRRVGVTELEARSGTLPPASQRWDRILQAS<br>GMKRAKPSPTSTQTPDQASLHAFADSLERDLDAPSPMHEG<br>DQTRASASPKKKRKVEASRTLVTFKDVFVDFTREEWKLLD<br>TAQQIVYRNVMLENYKNLVSLGYQLTKPDVILRLEKGEEP<br>WLV<br>(SEQ ID NO: 31) |
| >SOX2 TALE repressor (mSin<br>Interaction Domain, SID) | MSRTRLPSPPAPSPAFSADSFSDLLRQFDPSLFNTSLFDS<br>LPPFGAHHTEAATGEWDEVQSGLRAADAPPPTMRVAVTAA<br>RPPRAKPAPRRRAAQPSDASPAAQVDLRTLGYSQQQQEKI<br>KPKVRSTVAQHHEALVGHGFTHAHIVALSQHPAALGTVAV<br>KYQDMIAALPEATHEAIVGVGKQWSGARALEALLTVAGEL<br>RGPPLQLDTGQLLKIAKRGGVTAVEAVHAWRNALTGAPLN<br>LTPEQVVAIASNGGGKQALETVQRLLPVLCQAHGLTPEQV<br>VAIASNGGGKQALETVQRLLPVLCQAHGLTPEQVVAIASN<br>IGGKQALETVQRLLPVLCQAHGLTPEQVVAIASNGGGKQA<br>LETVQRLLPVLCQAHGLTPEQVVAIASNGGGKQALETVQR<br>LLPVLCQAHGLTPEQVVAIASHDGGKQALETVQRLLPVLC<br>QAHGLTPEQVVAIASHDGGKQALETVQRLLPVLCQAHGLT<br>PEQVVAIASHDGGKQALETVQRLLPVLCQAHGLTPEQVVA<br>IASNGGGKQALETVQRLLPVLCQAHGLTPEQVVAIASNNG<br>GKQALETVQRLLPVLCQAHGLTPEQVVAIASNIGGKQALE<br>TVQRLLPVLCQAHGLTPEQVVAIASHDGGKQALETVQRLL<br>PVLCQAHGLTPEQVVAIASNIGGRPALESIVAQLSRPDPA<br>LAALTNDHLVALACLGGRPALDAVKKGLPHAPALIKRTNR<br>RIPERTSHRVADHAQVVRVLGFFQCHSHPAQAFDDAMTQF<br>GMSRHGLLQLFRRVGVTELEARSGTLPPASQRWDRILQAS<br>GMKRAKPSPTSTQTPDQASLHAFADSLERDLDAPSPMHEG<br>DQTRASASPKKKRKVEASMNIQMLLEAADYLERREREAEH<br>GYASMLP<br>(SEQ ID NO: 32) |
| >SOX2 TALE repressor candidate<br>(PIE-1) | MSRTRLPSPPAPSPAFSADSFSDLLRQFDPSLFNTSLFDS<br>LPPFGAHHTEAATGEWDEVQSGLRAADAPPPTMRVAVTAA<br>RPPRAKPAPRRRAAQPSDASPAAQVDLRTLGYSQQQQEKI<br>KPKVRSTVAQHHEALVGHGFTHAHIVALSQHPAALGTVAV<br>KYQDMIAALPEATHEAIVGVGKQWSGARALEALLTVAGEL<br>RGPPLQLDTGQLLKIAKRGGVTAVEAVHAWRNALTGAPLN<br>LTPEQVVAIASNGGGKQALETVQRLLPVLCQAHGLTPEQV<br>VAIASNGGGKQALETVQRLLPVLCQAHGLTPEQVVAIASN<br>IGGKQALETVQRLLPVLCQAHGLTPEQVVAIASNGGGKQA<br>LETVQRLLPVLCQAHGLTPEQVVAIASNGGGKQALETVQR<br>LLPVLCQAHGLTPEQVVAIASHDGGKQALETVQRLLPVLC<br>QAHGLTPEQVVAIASHDGGKQALETVQRLLPVLCQAHGLT<br>PEQVVAIASHDGGKQALETVQRLLPVLCQAHGLTPEQVVA<br>IASNGGGKQALETVQRLLPVLCQAHGLTPEQVVAIASNNG<br>GKQALETVQRLLPVLCQAHGLTPEQVVAIASNIGGKQALE<br>TVQRLLPVLCQAHGLTPEQVVAIASHDGGKQALETVQRLL<br>PVLCQAHGLTPEQVVAIASNIGGRPALESIVAQLSRPDPA<br>LAALTNDHLVALACLGGRPALDAVKKGLPHAPALIKRTNR<br>RIPERTSHRVADHAQVVRVLGFFQCHSHPAQAFDDAMTQF<br>GMSRHGLLQLFRRVGVTELEARSGTLPPASQRWDRILQAS<br>GMKRAKPSPTSTQTPDQASLHAFADSLERDLDAPSPMHEG<br>DQTRASASPKKKRKVEASCRFIHVEQMQHFNANATVYAPP<br>SSDCPPPIAYYHHHPQHQQQFLPFPMPYFLAPPPQAQQGA<br>PFPVQYIPQQHDLMNSQPMYAPMAPTYYYQPINSNGMPMM<br>DVTIDPNATGGAFEVFPDGFFSQPPPTIIS<br>(SEQ ID NO: 33) |
| >SOX2 TALE repressor candidate<br>(IAA28-RD) | MSRTRLPSPPAPSPAFSADSFSDLLRQFDPSLFNTSLFDS<br>LPPFGAHHTEAATGEWDEVQSGLRAADAPPPTMRVAVTAA<br>RPPRAKPAPRRRAAQPSDASPAAQVDLRTLGYSQQQQEKI<br>KPKVRSTVAQHHEALVGHGFTHAHIVALSQHPAALGTVAV<br>KYQDMIAALPEATHEAIVGVGKQWSGARALEALLTVAGEL<br>RGPPLQLDTGQLLKIAKRGGVTAVEAVHAWRNALTGAPLN<br>LTPEQVVAIASNGGGKQALETVQRLLPVLCQAHGLTPEQV<br>VAIASNGGGKQALETVQRLLPVLCQAHGLTPEQVVAIASN |

```
                                IGGKQALETVQRLLPVLCQAHGLTPEQVVAIASNGGGKQA
                                LETVQRLLPVLCQAHGLTPEQVVAIASNGGGKQALETVQR
                                LLPVLCQAHGLTPEQVVAIASHDGGKQALETVQRLLPVLC
                                QAHGLTPEQVVAIASHDGGKQALETVQRLLPVLCQAHGLT
                                PEQVVAIASHDGGKQALETVQRLLPVLCQAHGLTPEQVVA
                                IASNGGGKQALETVQRLLPVLCQAHGLTPEQVVAIASNNG
                                GKQALETVQRLLPVLCQAHGLTPEQVVAIASNIGGKQALE
                                TVQRLLPVLCQAHGLTPEQVVAIASHDGGKQALETVQRLL
                                PVLCQAHGLTPEQVVAIASNIGGRPALESIVAQLSRPDPA
                                LAALTNDHLVALACLGGRPALDAVKKGLPHAPALIKRTNR
                                RIPERTSHRVADHAQVVRVLGFFQCHSHPAQAFDDAMTQF
                                GMSRHGLLQLFRRVGVTELEARSGTLPPASQRWDRILQAS
                                GMKRAKPSPTSTQTPDQASLHAFADSLERDLDAPSPMHEG
                                DQTRASASPKKKRKVEASMEEEKRLELRLAPPCHQFTSNN
                                NI
                                (SEQ ID NO: 34)

>SOX2 TALE repressor candidate  MSRTRLPSPPAPSPAFSADSFSDLLRQFDPSLFNTSLFDS
(Tbx3-RD)                       LPPFGAHHTEAATGEWDEVQSGLRAADAPPPTMRVAVTAA
                                RPPRAKPAPRRRAAQPSDASPAAQVDLRTLGYSQQQQEKI
                                KPKVRSTVAQHHEALVGHGFTHAHIVALSQHPAALGTVAV
                                KYQDMIAALPEATHEAIVGVGKQWSGARALEALLTVAGEL
                                RGPPLQLDTGQLLKIAKRGGVTAVEAVHAWRNALTGAPLN
                                LTPEQVVAIASNGGGKQALETVQRLLPVLCQAHGLTPEQV
                                VAIASNGGGKQALETVQRLLPVLCQAHGLTPEQVVAIASN
                                IGGKQALETVQRLLPVLCQAHGLTPEQVVAIASNGGGKQA
                                LETVQRLLPVLCQAHGLTPEQVVAIASNGGGKQALETVQR
                                LLPVLCQAHGLTPEQVVAIASHDGGKQALETVQRLLPVLC
                                QAHGLTPEQVVAIASHDGGKQALETVQRLLPVLCQAHGLT
                                PEQVVAIASHDGGKQALETVQRLLPVLCQAHGLTPEQVVA
                                IASNGGGKQALETVQRLLPVLCQAHGLTPEQVVAIASNNG
                                GKQALETVQRLLPVLCQAHGLTPEQVVAIASNIGGKQALE
                                TVQRLLPVLCQAHGLTPEQVVAIASHDGGKQALETVQRLL
                                PVLCQAHGLTPEQVVAIASNIGGRPALESIVAQLSRPDPA
                                LAALTNDHLVALACLGGRPALDAVKKGLPHAPALIKRTNR
                                RIPERTSHRVADHAQVVRVLGFFQCHSHPAQAFDDAMTQF
                                GMSRHGLLQLFRRVGVTELEARSGTLPPASQRWDRILQAS
                                GMKRAKPSPTSTQTPDQASLHAFADSLERDLDAPSPMHEG
                                DQTRASASPKKKRKVEASLASQGLAMSPFGSLFPYPYTYM
                                AAAAAASSAAASSSVHRHPFLNLNTMRPRLRYSPY
                                (SEQ ID NO: 35)

>SOX2 TALE repressor candidate  MSRTRLPSPPAPSPAFSADSFSDLLRQFDPSLFNTSLFDS
(Ubx-QA)                        LPPFGAHHTEAATGEWDEVQSGLRAADAPPPTMRVAVTAA
                                RPPRAKPAPRRRAAQPSDASPAAQVDLRTLGYSQQQQEKI
                                KPKVRSTVAQHHEALVGHGFTHAHIVALSQHPAALGTVAV
                                KYQDMIAALPEATHEAIVGVGKQWSGARALEALLTVAGEL
                                RGPPLQLDTGQLLKIAKRGGVTAVEAVHAWRNALTGAPLN
                                LTPEQVVAIASNGGGKQALETVQRLLPVLCQAHGLTPEQV
                                VAIASNGGGKQALETVQRLLPVLCQAHGLTPEQVVAIASN
                                IGGKQALETVQRLLPVLCQAHGLTPEQVVAIASNGGGKQA
                                LETVQRLLPVLCQAHGLTPEQVVAIASNGGGKQALETVQR
                                LLPVLCQAHGLTPEQVVAIASHDGGKQALETVQRLLPVLC
                                QAHGLTPEQVVAIASHDGGKQALETVQRLLPVLCQAHGLT
                                PEQVVAIASHDGGKQALETVQRLLPVLCQAHGLTPEQVVA
                                IASNGGGKQALETVQRLLPVLCQAHGLTPEQVVAIASNNG
                                GKQALETVQRLLPVLCQAHGLTPEQVVAIASNIGGKQALE
                                TVQRLLPVLCQAHGLTPEQVVAIASHDGGKQALETVQRLL
                                PVLCQAHGLTPEQVVAIASNIGGRPALESIVAQLSRPDPA
                                LAALTNDHLVALACLGGRPALDAVKKGLPHAPALIKRTNR
                                RIPERTSHRVADHAQVVRVLGFFQCHSHPAQAFDDAMTQF
                                GMSRHGLLQLFRRVGVTELEARSGTLPPASQRWDRILQAS
                                GMKRAKPSPTSTQTPDQASLHAFADSLERDLDAPSPMHEG
                                DQTRAS
                                (SEQ ID NO: 36)

>SOX2 TALE negative control    MSRTRLPSPPAPSPAFSADSFSDLLRQFDPSLFNTSLFDS
(Null)                          LPPFGAHHTEAATGEWDEVQSGLRAADAPPPTMRVAVTAA
                                RPPRAKPAPRRRAAQPSDASPAAQVDLRTLGYSQQQQEKI
                                KPKVRSTVAQHHEALVGHGFTHAHIVALSQHPAALGTVAV
                                KYQDMIAALPEATHEAIVGVGKQWSGARALEALLTVAGEL
                                RGPPLQLDTGQLLKIAKRGGVTAVEAVHAWRNALTGAPLN
                                LTPEQVVAIASNGGGKQALETVQRLLPVLCQAHGLTPEQV
                                VAIASNGGGKQALETVQRLLPVLCQAHGLTPEQVVAIASN
                                IGGKQALETVQRLLPVLCQAHGLTPEQVVAIASNGGGKQA
                                LETVQRLLPVLCQAHGLTPEQVVAIASNGGGKQALETVQR
                                LLPVLCQAHGLTPEQVVAIASHDGGKQALETVQRLLPVLC
                                QAHGLTPEQVVAIASHDGGKQALETVQRLLPVLCQAHGLT
                                PEQVVAIASHDGGKQALETVQRLLPVLCQAHGLTPEQVVA
                                IASNGGGKQALETVQRLLPVLCQAHGLTPEQVVAIASNNG
```

```
                    GKQALETVQRLLPVLCQAHGLTPEQVVAIASNIGGKQALE
                    TVQRLLPVLCQAHGLTPEQVVAIASHDGGKQALETVQRLL
                    PVLCQAHGLTPEQVVAIASNIGGRPALESIVAQLSRPDPA
                    LAALTNDHLVALACLGGRPALDAVKKGLPHAPALIKRTNR
                    RIPERTSHRVADHAQVVRVLGFFQCHSHPAQAFDDAMTQF
                    GMSRHGLLQLFRRVGVTELEARSGTLPPASQRWDRILQAS
                    GMKRAKPSPTSTQTPDQASLHAFADSLERDLDAPSPMHEG
                    DQTRASASPKKKRKVEAS
                    (SEQ ID NO: 37)

CACNA1C TALEs amino acid sequences

>CACNA1C Site 1 NN        MSRTRLPSPPAPSPAFSADSFSDLLRQFDPSLFNTSLFDS
activator (TALE1-NN)      LPPFGAHHTEAATGEWDEVQSGLRAADAPPPTMRVAVTAA
                          RPPRAKPAPRRRAAQPSDASPAAQVDLRTLGYSQQQQEKI
                          KPKVRSTVAQHHEALVGHGFTHAHIVALSQHPAALGTVAV
                          KYQDMIAALPEATHEAIVGVGKQWSGARALEALLTVAGEL
                          RGPPLQLDTGQLLKIAKRGGVTAVEAVHAWRNALTGAPLN
                          LTPEQVVAIASHDGGKQALETVQRLLPVLCQAHGLTPEQV
                          VAIASNNGGKQALETVQRLLPVLCQAHGLTPEQVVAIASN
                          NGGKQALETVQRLLPVLCQAHGLTPEQVVAIASHDGGKQA
                          LETVQRLLPVLCQAHGLTPEQVVAIASHDGGKQALETVQR
                          LLPVLCQAHGLTPEQVVAIASHDGGKQALETVQRLLPVLC
                          QAHGLTPEQVVAIASHDGGKQALETVQRLLPVLCQAHGLT
                          PEQVVAIASNGGGKQALETVQRLLPVLCQAHGLTPEQVVA
                          IASNNGGKQALETVQRLLPVLCQAHGLTPEQVVAIASHDG
                          GKQALETVQRLLPVLCQAHGLTPEQVVAIASHDGGKQALE
                          TVQRLLPVLCQAHGLTPEQVVAIASNNGGKQALETVQRLL
                          PVLCQAHGLTPEQVVAIASNNGGKQALETVQRLLPVLCQA
                          HGLTPEQVVAIASHDGGKQALETVQRLLPVLCQAHGLTPE
                          QVVAIASHDGGKQALETVQRLLPVLCQAHGLTPEQVVAIA
                          SHDGGKQALETVQRLLPVLCQAHGLTPEQVVAIASNIGGR
                          PALESIVAQLSRPDPALAALTNDHLVALACLGGRPALDAV
                          KKGLPHAPALIKRTNRRIPERTSHRVADHAQVVRVLGFFQ
                          CHSHPAQAFDDAMTQFGMSRHGLLQLFRRVGVTELEARSG
                          TLPPASQRWDRILQASGMKRAKPSPTSTQTPDQASLHAFA
                          DSLERDLDAPSPMHEGDQTRASASPKKKRKVEASGSGRAD
                          ALDDFDLDMLGSDALDDFDLDMLGSDALDDFDLDMLGSDA
                          LDDFDLDMLIN
                          (SEQ ID NO: 38)

>CACNA1C Site 1 NK        MSRTRLPSPPAPSPAFSADSFSDLLRQFDPSLFNTSLFDS
activator (TALE1-NK)      LPPFGAHHTEAATGEWDEVQSGLRAADAPPPTMRVAVTAA
                          RPPRAKPAPRRRAAQPSDASPAAQVDLRTLGYSQQQQEKI
                          KPKVRSTVAQHHEALVGHGFTHAHIVALSQHPAALGTVAV
                          KYQDMIAALPEATHEAIVGVGKQWSGARALEALLTVAGEL
                          RGPPLQLDTGQLLKIAKRGGVTAVEAVHAWRNALTGAPLN
                          LTPEQVVAIASHDGGKQALETVQRLLPVLCQAHGLTPEQV
                          VAIASNKGGKQALETVQRLLPVLCQAHGLTPEQVVAIASN
                          KGGKQALETVQRLLPVLCQAHGLTPEQVVAIASHDGGKQA
                          LETVQRLLPVLCQAHGLTPEQVVAIASHDGGKQALETVQR
                          LLPVLCQAHGLTPEQVVAIASHDGGKQALETVQRLLPVLC
                          QAHGLTPEQVVAIASHDGGKQALETVQRLLPVLCQAHGLT
                          PEQVVAIASNGGGKQALETVQRLLPVLCQAHGLTPEQVVA
                          IASNKGGKQALETVQRLLPVLCQAHGLTPEQVVAIASHDG
                          GKQALETVQRLLPVLCQAHGLTPEQVVAIASHDGGKQALE
                          TVQRLLPVLCQAHGLTPEQVVAIASNKGGKQALETVQRLL
                          PVLCQAHGLTPEQVVAIASNKGGKQALETVQRLLPVLCQA
                          HGLTPEQVVAIASHDGGKQALETVQRLLPVLCQAHGLTPE
                          QVVAIASHDGGKQALETVQRLLPVLCQAHGLTPEQVVAIA
                          SHDGGKQALETVQRLLPVLCQAHGLTPEQVVAIASNIGGR
                          PALESIVAQLSRPDPALAALTNDHLVALACLGGRPALDAV
                          KKGLPHAPALIKRTNRRIPERTSHRVADHAQVVRVLGFFQ
                          CHSHPAQAFDDAMTQFGMSRHGLLQLFRRVGVTELEARSG
                          TLPPASQRWDRILQASGMKRAKPSPTSTQTPDQASLHAFA
                          DSLERDLDAPSPMHEGDQTRASASPKKKRKVEASGSGRAD
                          ALDDFDLDMLGSDALDDFDLDMLGSDALDDFDLDMLGSDA
                          LDDFDLDMLIN
                          (SEQ ID NO: 39)

>CACNA1C Site 1 NH        MSRTRLPSPPAPSPAFSADSFSDLLRQFDPSLFNTSLFDS
activator (TALE1-NH)      LPPFGAHHTEAATGEWDEVQSGLRAADAPPPTMRVAVTAA
                          RPPRAKPAPRRRAAQPSDASPAAQVDLRTLGYSQQQQEKI
                          KPKVRSTVAQHHEALVGHGFTHAHIVALSQHPAALGTVAV
                          KYQDMIAALPEATHEAIVGVGKQWSGARALEALLTVAGEL
                          RGPPLQLDTGQLLKIAKRGGVTAVEAVHAWRNALTGAPLN
                          LTPEQVVAIASHDGGKQALETVQRLLPVLCQAHGLTPEQV
                          VAIASNHGGKQALETVQRLLPVLCQAHGLTPEQVVAIASN
                          HGGKQALETVQRLLPVLCQAHGLTPEQVVAIASHDGGKQA
                          LETVQRLLPVLCQAHGLTPEQVVAIASHDGGKQALETVQR
```

```
                           LLPVLCQAHGLTPEQVVAIASHDGGKQALETVQRLLPVLC
                           QAHGLTPEQVVAIASHDGGKQALTRVQRLLPVLCQAHGLT
                           PEQVVAIASNGGGKQALETVQRLLPVLCQAHGLTPEQVVA
                           IASNHGGKQALETVQRLLPVLCQAHGLTPEQVVAIASHDG
                           GKQALETVQRLLPVLCQAHGLTPEQVVAIASHDGGKQALE
                           TVQRLLPVLCQAHGLTPEQVVAIASNHGGKQALETVQRLL
                           PVLCQAHGLTPEQVVAIASNHGGKQALETVQRLLPVLCQA
                           HGLTPEQVVAIASHDGGKQALETVQRLLPVLCQAHGLTPE
                           QVVAIASHDGGKQALETVQRLLPVLCQAHGLTPEQVVAIA
                           SHDGGKQALETVQRLLPVLCQAHGLTPEQVVAIASNIGGR
                           PALESIVAQLSRPDPALAALTNDHLVALACLGGRPALDAV
                           KKGLPHAPALIKRTNRRIPERTSHRVADHAQVVRVLGRRQ
                           CHSHPAQAFDDAMTQFGMSRHGLLQLFRRVGVTELEARSG
                           TLPPASQRWDRILQASGMKRAKPSPTSTQTPDQASLHAFA
                           DSLERDLDAPSPMHEGDQTRASASPKKKRKVEASGSGRAD
                           ALDDFDLDMLGSDALDDFDLDMLGSDALDDFDLDMLGSDA
                           LDDFDLDMLIN
                           (SEQ ID NO: 40)

>CACNA1C Site 1 HN         MSRTRLPSPPAPSPAFSADSFSDLLRQFDPSLFNTSLFDS
activator (TALE1-HN)       LPPFGAHHTEAATGEWDEVQSGLRAADAPPPTMRVAVTAA
                           RPPRAKPAPRRRAAQPSDASPAAQVDLRTLGYSQQQQEKI
                           KPKVRSTVAQHHEALVGHGFTHAHIVALSQHPAALGTVAV
                           KYQDMIAALPEATHEAIVGVGKQWSGARALEALLTVAGEL
                           RGPPLQLDTGQLLKIAKRGGVTAVEAVHAWRNALTGAPLN
                           LTPEQVVAIASHDGGKQALETVQRLLPVLCQAHGLTPEQV
                           VAIASHNGGKQALETVQRLLPVLCQAHGLTPEQVVAIASH
                           NGGKQALETVQRLLPVLCQAHGLTPEQVVAIASHDGGKQA
                           LETVQRLLPVLCQAHGLTPEQVVAIASHDGGKQALETVQR
                           LLPVLCQAHGLTPEQVVAIASHDGGKQALETVQRLLPVLC
                           QAHGLTPEQVVAIASHDGGKQALETVQRLLPVLCQAHGLT
                           PEQVVAIASNGGGKQALETVQRLLPVLCQAHGLTPEQVVA
                           IASNHGGKQALETVQRLLPVLCQAHGLTPEQVVAIASHDG
                           GKQALETVQRLLPVLCQAHGLTPEQVVAIASHDGGKQALE
                           TVQRLLPVLCQAHGLTPEQVVAIASNHGGKQALETVQRLL
                           PVLCQAHGLTPEQVVAIASNHGGKQALETVQRLLPVLCQA
                           HGLTPEQVVAIASHDGGKQALETVQRLLPVLCQAHGLTPE
                           QVVAIASHDGGKQALETVQRLLPVLCQAHGLTPEQVVAIA
                           SHDGGKQALETVQRLLPVLCQAHGLTPEQVVAIASNIGGR
                           PALESIVAQLSRPDPALAALTNDHLVALACLGGRPALDAV
                           KKGLPHAPALIKRTNRRIPERTSHRVADHAQVVRVLGFFQ
                           CHSHPAQAFDDAMTQFGMSRHGLLQLFRRVGVTELEARSG
                           TLPPASQRWDRILQASGMKRAKPSPTSTQTPDQASLHAFA
                           DSLERDLDAPSPMHEGDQTRASASPKKKRKVEASGSGRAD
                           ALDDFDLDMLGSDALDDFDLDMLGSDALDDFDLDMLGSDA
                           LDDFDLDMLIN
                           (SEQ ID NO: 41)

>CACNA1C Site 2 NN         MSRTRLPSPPAPSPAFSADSFSDLLRQFDPSLFNTSLFDS
activator (TALE2-NN)       LPPFGAHHTEAATGEWDEVQSGLRAADAPPPTMRVAVTAA
                           RPPRAKPAPRRRAAQPSDASPAAQVDLRTLGYSQQQQEKI
                           KPKVRSTVAQHHEALVGHGFTHAHIVALSQHPAALGTVAV
                           KYQDMIAALPEATHEAIVGVGKQWSGARALEALLTVAGEL
                           RGPPLQLDTGQLLKIAKRGGVTAVEAVHAWRNALTGAPLN
                           LTPEQVVAIASNNGGKQALETVQRLLPVLCQAHGLTPEQV
                           VAIASNNGGKQALETVQRLLPVLCQAHGLTPEQVVAIASN
                           GGGKQALETVQRLLPVLCQAHGLTPEQVVAIASNIGGKQA
                           LETVQRLLPVLCQAHGLTPEQVVAIASNNGGKQALETVRR
                           LLPVLCQAHGLTPEQVVAIASNIGGKQALETVQRLLPVLC
                           QAHGLTPEQVVAIASHDGGKQALETVQRLLPVLCQAHGLT
                           PEQVVAIASHDGGKQALETVQRLLPVLCQAHGLTPEQVVA
                           IASNGGGKQALETVQRLLPVLCQAHGLTPEQVVAIASNGG
                           GKQALETVQRLLPVLCQAHGLTPEQVVAIASNIGGKQALE
                           TVQRLLPVLCQAHGLTPEQVVAIASNNGGKQALETVQRLL
                           PVLCQAHGLTPEQVVAIASNNGGKQALETVQRLLPVLCQA
                           HGLTPEQVVAIASNGGGKQALETVQRLLPVLCQAHGLTPE
                           QVVAIASHDGGKQALETVQRLLPVLCQAHGLTPEQVVAIA
                           SNGGGKQALETVQRLLPVLCQAHGLTPEQVVAIASNIGGR
                           PALESIVAQLSRPDPALAALTNDHLVALACLGGRPALDAV
                           KKGLPHAPALIKRTNRRIPERTSHRVADHAQVVRVLGFFQ
                           CHSHPAQAFDDAMTQFGMSRHGLLQLFRRVGVTELEARSG
                           TLPPASQRWDRILQASGMKRAKPSPTSTQTPDQASLHAFA
                           DSLERDLDAPSPMHEGDQTRASASPKKKRKVEASGSGRAD
                           ALDDFDLDMLGSDALDDFDLDMLGSDALDDFDLDMLGSDA
                           LDDFDLDMLIN
                           (SEQ ID NO: 42)
```

| | |
|---|---|
| >CACNA1C Site 2 NK activator (TALE2-NK) | MSRTRLPSPPAPSPAFSADSFSDLLRQFDPSLFNTSLFDS LPPFGAHHTEAATGEWDEVQSGLRAADAPPPTMRVAVTAA RPPRAKPAPRRRAAQPSDASPAAQVDLRTLGYSQQQQEKI KPKVRSTVAQHHEALVGHGFTHAHIVALSQHPAALGTVAV KYQDMIAALPEATHEAIVGVGKQWSGARALEALLTVAGEL RGPPLQLDTGQLLKIAKRGGVTAVEAVHAWRNALTGAPLN LTPEQVVAIASNKGGKQALETVQRLLPVLCQAHGLTPEQV VAISNKGGKQALETVQRLLPVLCQAHGLTPEQVVAIASNG GGKQALETVQRLLPVLCQAHGLTPEQVVAIASNIGGKQAL ETVQRLLPVLCQAHGLTPEQVVAIASNKGGKQALETVQRL LPVLCQAHGLTPEQVVAIASNIGGKQALETVQRLLPVLCQ AHGLTPEQVVAIASHDGGKQALETVQRLLPVLCQAHGLTP EQVVAIASHDGGKQALETVQRLLPVLCQAHGLTPEQVVAI ASNGGGKQALETVQRLLPVLCQAHGLTPEQVVAIASNGGG KQALETVQRLLPVLCQAHGLTPEQVVAIASNIGGKQALET VQRLLPVLCQAHGLTPEQVVAIASNKGGKQALETVQRLLP VLCQAHGLTPEQVVAIASNKGGKQALETVQRLLPVLCQAH GLTPEQVVAIASNKGGKQALETVQRLLPVLCQAHGLTPEQ VVAIASHDGGKQALETVQRLLPVLCQAHGLTPEQVVAIAS NGGGKQALETVQRLLPVLCQAHGLTPEQVVAIASNIGGRP ALESIVAQLSRPDPALAALTNDHLVALACLGGRPALDAVK KGLPHAPALIKRTNRRIPERTSHRVADHAQVVRVLGFFQC HSHPAQAFDDAMTQFGMSRHGLLQLFRRVGVTELEARSGT LPPASQRWDRILQASGMKRAKPSPTSTQTPDQASLHAFAD SLERDLDAPSPMHEGDQTRASASPKKKRKVEASGSGRADA LDDFDLDMLGSDALDDFDLDMLGSDALDDFDLDMLGSDAL DDFDLDMLIN (SEQ ID NO: 43) |
| >CACNA1C Site 2 NH activator (TALE2-NH) | MSRTRLPSPPAPSPAFSADSFSDLLRQFDPSLFNTSLFDS LPPFGAHHTEAATGEWDEVQSGLRAADAPPPTMRVAVTAA RPPRAKPAPRRRAAQPSDASPAAQVDLRTLGYSQQQQEKI KPKVRSTVAQHHEALVGHGFTHAHIVALSQHPAALGTVAV KYQDMIAALPEATHEAIVGVGKQWSGARALEALLTVAGEL RGPPLQLDTGQLLKIAKRGGVTAVEAVHAWRNALTGAPLN LTPEQVVAISNHGGKQALETVQRLLPVLCQAHGLTPEQVV AIASNHGGKQALETVQRLLPVLCQAHGLTPEQVVAIASNG GGKQALETVQRLLPVLCQAHGLTPEQVVAIASNIGGKQAL ETVQRLLPVLCQAHGLTPEQVVAIASNHGGKQALETVQRL LPVLCQAHGLTPEQVVAIASNIGGKQALETVQRLLPVLCQ AHGLTPEQVVAIASHDGGKQALETVQRLLPVLCQAHGLTP EQVVAIASHDGGKQALETVQRLLPVLCQAHGLTPEQVVAI ASNGGGKQALETVQRLLPVLCQAHGLTPEQVVAIASNGGG KQALETVQRLLPVLCQAHGLTPEQVVAIASNIGGKQALET VQRLLPVLCQAHGLTPEQVVAIASNHGGKQALETVQRLLP VLCQAHGLTPEQVVAIASNHGGKQALETVQRLLPVLCQAH GLTPEQVVAIASNHGGKQALETVQRLLPVLCQAHGLTPEQ VVAIASHDGGKQALETVQRLLPVLCQAHGLTPEQVVAIAS NGGGKQALETVQRLLPVLCQAHGLTPEQVVAIASNIGGRP ALESIVAQLSRPDPALAALTNDHLVALACLGGRPALDAVK KGLPHAPALIKRTNRRIPERTSHRVADHAQVVRVLGFFQC HSHPAQAFDDAMTQFGMSRHGLLQLFRRVGVTELEARSGT LPPASQRWDRILQASGMKRAKPSPTSTQTPDQASLHAFAD SLERDLDAPSPMHEGDQTRASASPKKKRKVEASGSGRADA LDDFDLDMLGSDALDDFDLDMLGSDALDDFDLDMLGSDAL DDFDLDMLIN (SEQ ID NO: 44) |
| >CACNA1C Site 2 HN activator (TALE2-HN) | MSRTRLPSPPAPSPAFSADSFSDLLRQFDPSLFNTSLFDS LPPFGAHHTEAATGEWDEVQSGLRAADAPPPTMRVAVTAA RPPRAKPAPRRRAAQPSDASPAAQVDLRTLGYSQQQQEKI KPKVRSTVAQHHEALVGHGFTHAHIVALSQHPAALGTVAV KYQDMIAALPEATHEAIVGVGKQWSGARALEALLTVAGEL RGPPLQLDTGQLLKIAKRGGVTAVEAVHAWRNALTGAPL NLTPEQVVAIASHNGGKQALETVQRLLPVLCQAHGLTPEQ VVAIASHNGGKQALETVQRLLPVLCQAHGLTEPQVVAIS NGGGKQALETVQRLLPVLCQAHGLTPEQVVAIASNIGGKQ ALETVTRLLPVLCQAHGLTPEVQQAIASHNGGKQALETVQ RLLPVLCQAHGLTPEQVVAIASNIGGKQALETVQRLLPVL CQAHGLTPEQVVAIASHDGGKQALETVQRLLPVLCQAHGL TPEQVVAIASHDGGKQALETVQRLLPVLCQAHGLTPEQVV AIASNGGGKQALETVQRLLPVLCQAHGLTPEQVVAIASNG GGKQALETVQRLLPVLCQAHGLTPEQVVAIASNIGGKQAL ETVQRLLPVLCQAHGLTPEQVVAIASHNGGKQALETVQRL LPVLCQAHGLTPEQVVAIASHNGGKQALETVQRLLPVLCQ AHGLTPEQVVAIASHNGGKQALETVQRLLPVLCQAHGLTP EQVVAIASHDGGKQALETVQRLLPVLCQAHGLTPEQVVAI ASNGGGKQALETVQRLLPVLCQAHGLTPEQVVAIASNHIG GRPALESIVAQLSRPDPALAALTNDHLVALACLGGRPALD |

|   |   |
|---|---|
|   | AVKKGLPHAPALIKRTNRRIPERTSHRVADHAQVVRVLGF<br>FQCHSHPAQAFDDAMTQFGMSRHGLLQLFRRVGVTELEAR<br>SGTLPPASQRWDRILQASGMKRAKPSPTSTQTPDQASLHA<br>FADSLERDLDAPSPMHEGDQTRASASPKKKRKVEASGSGR<br>ADALDDFDLDMLGSDALDDFDLDMLGSDALDDFDLDMLGS<br>DALDDFDLDMLIN<br>(SEQ ID NO: 45) |
| >CACNA1C Site 1 NN<br>repressor (TALE1-NN) | MSRTRLPSPPAPSPAFSADSFSDLLRQFDPSLFNTSLFDS<br>LPPFGAHHTEAATGEWDEVQSGLRAADAPPPTMRVAVTAA<br>RPPRAKPAPRRRAAQPSDASPAAQVDLRTLGYSQQQQEKI<br>KPKVRSTVAQHHEALVGHGFTHAHIVALSQHPAALGTVAV<br>KYQDMIAALPEATHEAIVGVGKQWSGARALEALLTVAGEL<br>RGPPLQLDTGQLLKIAKRGGVTAVEAVHAWRNALTGAPLN<br>LTPEQVVAIASHDGGKQALETVQRLLPVLCQAHGLTPEQV<br>VAIASNNGGKQALETVQRLLPVLCQAHGLTPEQVVAIASN<br>NGGKQALETVQRLLPVLCQAHGLTPEQVVAIASHDGGKQA<br>LETVQRLLPVLCQAHGLTPEQVVAIASHDGGKQALETVQR<br>LLPVLCQAHGLTPEQVVAIASHDGGKQALETVQRLLPVLC<br>QAHGLTPEQVVAIASHDGGKQALETVQRLLPVLCQAHGLT<br>PEQVVAIASNGGGKQALETVQRLLPVLCQAHGLTPEQVVA<br>IASNNGGKQALETVQRLLPVLCQAHGLTPEQVVAIASHDG<br>GKQALETVQRLLPVLCQAHGLTPEQVVAIASHDGGKQALE<br>TVQRLLPVLCQAHGLTPEQVVAIASNNGGKQALETVQRLL<br>PVLCQAHGLTPEQVVAIASNNGGKQALETVQRLLPVLCQA<br>HGLTPEQVVAIASHDGGKQALETVQRLLPVLCQAHGLTPE<br>QVVAIASHDGGKQALETVQRLLPVLCQAHGLTPEQVVAIA<br>SHDGGKQALETVQRLLPVLCQAHGLTPEQVVAIASNIGGR<br>PALESIVAQLSRPDPALAALTNDHLVALACLGGRPALDAV<br>KKGLPHAPALIKRTNRRIPERTSHRVADHAQVVRVLGFFQ<br>CHSHPAQAFDDAMTQFGMSRHGLLQLFRRVGVTELEARSG<br>TLPPASQRWDRILQASGMKRAKPSPTSTQTPDQASLHAFA<br>DSLERDLDAPSPMHEGDQTRASASPKKKRKVEASMNIQML<br>LEAADYLERREREAEHGYASMLP<br>(SEQ ID NO: 46) |
| >CACNA1C Site 1 NK<br>repressor (TALE1-NK) | MSRTRLPSPPAPSPAFSADSFSDLLRQFDPSLFNTSLFDS<br>LPPFGAHHTEAATGEWDEVQSGLRAADAPPPTMRVAVTAA<br>RPPRAKPAPRRRAAQPSDASPAAQVDLRTLGYSQQQQEKI<br>KPKVRSTVAQHHEALVGHGFTHAHIVALSQHPAALGTVAV<br>KYQDMIAALPEATHEAIVGVGKQWSGARALEALLTVAGEL<br>RGPPLQLDTGQLLKIAKRGGVTAVEAVHAWRNALTGAPLN<br>LTPEQVVAIASHDGGKQALETVQRLLPVLCQAHGLTPEQV<br>VAIASNKGGKQALETVQRLLPVLCQAHGLTPEQVVAIASN<br>KGGKQALETVQRLLPVLCQAHGLTPEQVVAIASHDGGKQA<br>LETVQRLLPVLCQAHGLTPEQVVAIASHDGGKQALETVQR<br>LLPVLCQAHGLTPEQVVAIASHDGGKQALETVQRLLPVLC<br>QAHGLTPEQVVAIASHDGGKQALETVQRLLPVLCQAHGLT<br>PEQVVAISASNGGGKQALETVQRLLPVLCQAHGLTPEQVV<br>AIASNKGGKQALETVQRLLPVLCQAHGLTPEQVVAIASHD<br>GGKQALETVQRLLPVLCQAHGLTPEQVVAIASHDGGKQAL<br>ETVQRLLPVLCQAHGLTPEQVVAIASNKGGKQALETVQRL<br>LPVLCQAHGLTPEQVVAIASNKGGKQALETVQRLLPVLCQ<br>AHGLTPEQVVAIASHDGGKQALETVQRLLPVLCQAHGLTP<br>EQVVAIASHDGGKQALETVQRLLPVLCQAHGLTPEQVVAI<br>ASHDGGKQALETVQRLLPVLCQAHGLTPEQVVAIASNIGG<br>RPALESIVAQLSRPDPALAALTNDHLVALACLGGRPALDA<br>VKKGLPHAPALIKRTNRRIPERTSHRVADHAQVVRVLGFF<br>QCHSHPAQAFDDAMTQFGMSRHGLLQLFRRVGVTELEARS<br>GTLPPASQRWDRILQASGMKRAKPSPTSTQTPDQASLHAF<br>ADSLERDLDAPSPMHEGDQTRASASPKKKRKVEASMNIQ<br>MLLEAADYLERREREAEHGYASMLP<br>(SEQ ID NO: 47) |
| >CACNA1C Site 1 NH<br>repressor (TALE1-NH) | MSRTRLPSPPAPSPAFSADSFSDLLRQFDPSLFNTSLFDS<br>LPPFGAHHTEAATGEWDEVQSGLRAADAPPPTMRVAVTAA<br>RPPRAKPAPRRRAAQPSDASPAAQVDLRTLGYSQQQQEKI<br>KPKVRSTVAQHHEALVGHGFTHAHIVALSQHPAALGTVAV<br>KYQDMIAALPEATHEAIVGVGKQWSGARALEALLTVAGEL<br>RGPPLQLDTGQLLKIAKRGGVTAVEAVHAWRNALTGAPLN<br>LTPEQVVAIASHDGGKQALETVQRLLPVLCQAHGLTPEQV<br>VAIASNHGGKQALETVQRLLPVLCQAHGLTPEQVVAIASN<br>HGGKQALETVQRLLPVLCQAHGLTPEQVVAIASHDGGKQA<br>LETVQRLLPVLCQAHGLTPEQVVAIASHDGGKQALETVQR<br>LLPVLCQAHGLTPEQVVAIASHDGGKQALETVQRLLPVLC<br>QAHGLTPEQVVAIASHDGGKQALETVQRLLPVLCQAHGLT<br>PEQVVAIASNGGGKQALETVQRLLPVLCQAHGLTPEQVVA<br>IASNHGGKQALETVQRLLPVLCQAHGLTPEQVVAIASHDG<br>GKQALETVQRLLPVLCQAHGLTPEQVVAIASHDGGKQALE<br>TVQRLLPVLCQAHGLTPEQVVAIASNHGGKQALETVQRLL |

```
PVLCQAHGLTPEQVVAIASNHGGKQALETVQRLLPVLCQA
HGLTPEQVVAIASHDGGKQALETVQRLLPVLCQAHGLTPE
QVVAIASHDGGKQALETVQRLLPVLCQAHGLTPEQVVAIA
SHDGGKQALETVQRLLPVLCQAHGLTPEQVVAIASNIGGR
PALESIVAQLSRPDPALAALTNDHLVALACLGGRPALDAV
KKGLPHAPALIKRTNRRIPERTSHRVADHAQVVRVLGFFQ
CHSHPAQAFDDAMTQFGMSRHGLLQLFRRVGVTELEARSG
TLPPASQRWDRILQASGMKRAKPSPTSTQTPDQASLHAFA
DSLERDLDAPSPMHEGDQTRASASPKKKRKVEASMNIQML
LEAADYLERREREAEHGYASMLP
(SEQ ID NO: 48)
```

The KRAB fragments utilized in this application are as follows:

```
KRAB(1-97)
                                      (SEQ ID NO: 344)
MDAKSLTAWSRTLVTFKDVFVDFTREEWKLLDTAQQIVYRNVMLENY
KNLVSLGYQLTKPDVILRLEKGEEPWLVEREIHQETHPDSETAFEIK
SSV

KRAB(1-75)
                                      (SEQ ID NO: 345)
MDAKSLTAWSRTLVTFKDVFVDFTREEWKLLDTAQQIVYRNVMLENY
KNLVSLGYQLTKPDVILRLEKGEEPWLV

KRAB(11-75)
                                      (SEQ ID NO: 346)
RTLVTFKDVFVDFTREEWKLLDTAQQIVYRNVMLENYKNLVSLGYQL
TKPDVILRLEKGEEPWLV
```

To control for differences in the expression of each TALE, all TALEs are in-frame fused with the *Gaussia* luciferase (Gluc) gene via a 2A linker. The Gluc gene is translated in an equimolar amount as TALEs. Truncation variants of the Krüppel-associated box (KRAB) domain, the PIE-1 repression domain (PIE-1), the QA domain within the Ubx gene (Ubx-QA), the IAA28 repression domain (IAA28-RD), Tbx3 repression domain (Tbx3-RD), and the mSin interaction domain (SID) were codon optimized for mammalian expression and synthesized with flanking NheI and XbaI restriction sites (Genscript). All repressor domains were cloned into the TALE backbone by replacing the VP64 activation domain using NheI and Xba l restriction sites. To control for any effect on transcription resulting from TALE binding, expression vectors carrying the TALE DNA binding domain alone were constructed using PCR cloning. The coding regions of all constructs were completely verified using Sanger sequencing.

All luciferase reporter plasmids were designed and synthesized by inserting the TALE binding site upstream of the minimal CMV promoter driving the expression of a *Cypridina* luciferase (Cluc) gene (FIG. 18), similar to minCMV-mCherry reporter used in previous studies (3).

Cell culture and luciferase reporter activation assay: Maintenance of human embryonic kidney cell line HEK 293FT (Invitrogen) were carried out with Dulbecco's modified Eagle's Medium (DMEM) supplemented with 10% fetal bovine serum (HyClone), 2 mM GlutaMAX (Invitrogen), 100 U/mL Penicillin, and 100 m/mL Streptomycin, under 37° C., 5% $CO_2$ incubation condition.

Luciferase reporter assays were performed by co-transfecting HEK 293FT cells with TALE-2A-luciferase expression and luciferase reporter plasmids. In the case of the reporter-only control, cells were co-transfected with a control *Gaussia* luciferase plasmid (pCMV-Gluc, New England BioLabs). HEK 293FT cells were seeded into 24-well plates the day prior to transfection at densities of $2 \times 10^5$ cells/well. Approximately 24 h after initial seeding, cells were transfected using Lipofectamine-2000 (Invitrogen) following the manufacturer's protocol. For each well of the 24-well plates 700 ng of dTALE and 50 ng of each reporter plasmids were used to transfect HEK 293FT cells.

Dual luciferase reporter assays were carried out with the BioLux *Gaussia* luciferase flex assay kit and BioLux *Cypridina* luciferase assay kit (New England Biolabs) following the manufacturer's recommended protocol. Briefly, media from each well of transfected cells were collected 48 hours after transfection. For each sample, 20 uL of the media were added into a 96-well assay plate, mixed with each one of the dual luciferase assay mixes. After brief incubation, as indicated in the manufacturer's protocol, luminescence levels of each sample were measured using the Varioskan flash multimode reader (Thermo Scientific).

The activity of each TALE is determined by measuring the level of luciferase reporter induction, calculated as the level of Cluc induction in the presence of TALE activator minus the level of Cluc induction without TALE activator. The activity of each TALE is normalized to the level of TALE expression as determined by the Gluc activity level (each TALE is in-frame fused to 2A-Gluc), to control for differences in cell number, sample preparation, transfection efficiency, and protein expression level. The concentrations of all DNA used in transfection experiments were determined using gel analysis.

The base preference of each RVD was determined according to the induction of each base-specific reporters by the corresponding RVD screening TALE (RVD-TALE, FIG. 18a). Statistical analysis was performed using one-way analysis of variance (ANOVA) tests. Each RVD was tested by taking the reporter with the highest luciferase activity as the putative preferred base and comparing it with the remaining three bases as a group. For a given RVD, if the putative preferred base gave statistically significant test results ($p<0.05$, one-way ANOVA), that RVD was classified as having a single preferred base, otherwise that RVD was tagged as not having a single preferred base.

Endogenous gene transcriptional activation assay: For the endogenous gene transcriptional level assay to test the biological activities of TALE activators and TALE repressors, HEK 293FT cells were seeded into 24-well plates. 1 ug of TALE plasmid was transfected using Lipofectamine-2000 (Invitrogen) according to manufacturer's protocol. Transfected cells were cultured at 37° C. for 72 hours before RNA extraction. At least 100,000 cells were harvested and subsequently processed for total RNA extraction using the RNAeasyPlus Mini Kit (Qiagen). cDNA was generated using the High Capacity RNA-to-cDNA Master Mix (Applied Biosystems) according to the manufacturer's recommended protocol. After cDNA synthesis, cDNA from each sample was added to the qRT-PCR assay with the Taqman Advanced PCR Master Mix (Applied Biosystems) using a StepOne Plus qRT-PCR machine. The fold activation in the transcriptional levels of SOX2 and CACNA1C mRNA were detected using standard TaqMan Gene Expression Assays with probes having the best coverage (Applied Biosystems; SOX2, Hs01053049_1; CACNA1C, Hs00167681_1).

Computational analysis of RVD specificity: To assess the guanine-specificity of NH, extensive computational simulations were performed to compare the relative binding affinities between guanine and NN or NH using free energy perturbation (FEP)(18, 19), a widely used approach for calculating binding affinities for a variety of biological interactions, such as ligand-receptor binding, protein-protein interaction, and protein-nucleic acid binding (20, 21). Molecular dynamics simulations were carried out as previously described (20, 21). Calculations were based on the recently released crystal structure of the TALE PthXo1 bound to DNA (PDB ID: 3UGM)(12). A fragment of the crystal structure containing repeats 11-18 of PthXo1 (RVD sequence was used: HD[11]-NG[12]-NI[13]-HD[14]-NG[15]-NN[16]-NG[17]-NI[18], repeat number specified in square brackets) and the corresponding double-stranded DNA molecule containing the TALE binding sequence (5'-CTACTGTA-3') to compare the binding affinities of RVDs NN, NK, and NH for guanine Since the 16th repeat in the structure is NN, NN was computationally mutated into NH or NK and the binding affinity of each configuration (NN:G, NH:G) was calculated. The affinity was calculated as the gain of free energy (AAG) in the DNA bound state taking NN:G as reference (AAG=0).

REFERENCES

1. Boch, J. et al. Breaking the code of DNA binding specificity of TAL-type III effectors. *Science* 326, 1509-1512 (2009).
2. Moscou, M. J. & Bogdanove, A. J. A simple cipher governs DNA recognition by TAL effectors. *Science* 326, 1501 (2009).
3. Zhang, F. et al. Efficient construction of sequence-specific TAL effectors for modulating mammalian transcription. *Nat. Biotechnol.* 29, 149-153 (2011).
4. Morbitzer, R., Romer, P., Boch, J. & Lahaye, T. Regulation of selected genome loci using de novo-engineered transcription activator-like effector (TALE)-type transcription factors. *Proc. Natl. Acad. Sci. USA* 107, 21617-21622 (2010).
5. Miller, J. C. et al. A TALE nuclease architecture for efficient genome editing. *Nat. Biotechnol.* 29, 143-148 (2011).
6. Geißler, R. et al. Transcriptional Activators of Human Genes with Programmable DNA-Specificity. *PLoS One* 6, e19509 (2011).
7. Sanjana, N. E. et al. A transcription activator-like effector toolbox for genome engineering. *Nat. Protoc.* 7, 171-192 (2012).
8. Mahfouz, M. M. et al. Targeted transcriptional repression using a chimeric TALE-SRDX repressor protein. *Plant. Mol. Biol.* 78, 311-321 (2012).
9. Bogdanove, A. J. & Voytas, D. F. TAL effectors: customizable proteins for DNA targeting. *Science* 333, 1843-1846 (2011).
10. Ayer, D. E., Laherty, C. D., Lawrence, Q. A., Armstrong, A. P. & Eisenman, R. N. Mad proteins contain a dominant transcription repression domain. *Mol. Cell. Biol.* 16, 5772-5781 (1996).
11. Huang, P. et al. Heritable gene targeting in zebrafish using customized TALENs. *Nat. Biotechnol.* 29, 699-700 (2011).
12. Mak, A. N., Bradley, P., Cernadas, R. A., Bogdanove, A. J. & Stoddard, B. L. The crystal structure of TAL effector PthXo1 bound to its DNA target. *Science* 335, 716-719 (2012).
13. Scholze, H. & Boch, J. TAL effectors are remote controls for gene activation. *Curr. Opin. Microbiol.* 14, 47-53 (2011).
14. Batchelder, C. et al. Transcriptional repression by the *Caenorhabditis elegans* germ-line protein PIE-1. *Genes Dev.* 13, 202-212 (1999).
15. Tour, E., Hittinger, C. T. & McGinnis, W. Evolutionarily conserved domains required for activation and repression functions of the *Drosophila* Hox protein Ultrabithorax. *Development* 132, 5271-5281 (2005).
16. Tiwari, S. B., Hagen, G. & Guilfoyle, T. J. Aux/IAA proteins contain a potent transcriptional repression domain. *Plant Cell* 16, 533-543 (2004).
17. Margolin, J. F. et al. Kruppel-associated boxes are potent transcriptional repression domains. *Proc. Natl. Acad. Sci. USA* 91, 4509-4513 (1994).
18. Almlof, M., Aqvist, J., Smalas, A. O. & Brandsdal, B. O. Probing the effect of point mutations at protein-protein interfaces with free energy calculations. *Biophys. J.* 90, 433-442 (2006).
19. Wang, J., Deng, Y. & Roux, B. Absolute binding free energy calculations using molecular dynamics simulations with restraining potentials. *Biophys. J.* 91, 2798-2814 (2006).
20. Zhou, R., Das, P. & Royyuru, A. K. Single mutation induced H3N2 hemagglutinin antibody neutralization: a free energy perturbation study. *J. Phys. Chem. B* 112, 15813-15820 (2008).
21. Chodera, J. D. et al. Alchemical free energy methods for drug discovery: progress and challenges. *Curr. Opin. Struct. Biol.* 21, 150-160 (2011).

Example 4

Development of Mammalian TALE Transcriptional Repressors with SID4X Domain

TALE repressors have the potential to suppress the expression of genes as well as non-coding transcripts such as microRNAs, rendering them a highly desirable tool for testing the causal role of specific genetic elements.

After identifying SID (mSin interaction domain) as a robust novel repressor domain to be used with TALEs, more active repression domain architecture based on SID domain for use with TALEs in mammalian cells were further designed and verified. This domain is called SID4X, which is a tandem repeat of four SID domains linked by short peptide linkers. For testing different TALE repressor architectures, a TALE targeting the promoter of the mouse (*Mus musculus*) p11 (s100a10) gene was used to evaluate the transcriptional repression activity of a series of candidate TALE repressor architectures (FIG. 22a). Since different truncations of TALE are known to exhibit varying levels of transcriptional activation activity, two different truncations of TALE fused to SID or SID4X domain were tested, one version with 136 and 183 amino acids at N- and C-termini flanking the DNA binding tandem repeats, with another one retaining 240 and 183 amino acids at N- and C-termini (FIG. 22b, c). The candidate TALE repressors were expressed in mouse Neuro2A cells and it was found that TALEs carrying both SID and SID4X domains were able to repress endogenous p11 expression up to 4.8 folds, while the GFP-encoding negative control construct had no effect on transcriptional of target gene (FIG.

22b, c). To control for potential perturbation of p11 transcription due to TALE binding, expression of the p11-targeting TALE DNA binding domain (with the same N- and C-termini truncations as the tested constructs) without any effector domain had no effect on the transcriptional activity of endogenous p11 (FIG. 22b, c, null constructs).

Because the constructs harboring SID4X domain were able to achieve 167% and 66% more transcriptional repression of the endogenous p11 locus than the SID domain depending on the truncations of TALE DNA binding domain (FIG. 22c), it was concluded that a truncated TALE DNA binding domain, bearing 136 and 183 amino acids at N- and C-termini respectively, fused to the SID4X domain is a potent TALE repressor architecture that enables down-regulation of target gene expression and is more active than the previous design employing SID domain.

Methods

Construction of TALE activators and repressors: All TALE activators or repressors were constructed as previously described using a hierarchical ligation strategy. The following sequences for all constructs were used:

| Repressor domain and TALE repressor constructs amino acid sequences | |
|---|---|
| >SID | MNIQMLLEAADYLERREREAEHGYASLMP (SEQ ID NO: 49) |
| >SID4X | MNIQMLLEAADYLERREREAEHGYASMLPGSGMNIQMLLEAADYLERREREAEHGYQAMLPGSGMNIQMLLEAADYLERREREAEHGYQAMLPGSGMNIQMLLEAADYLERREREAEHGYASMLPSR (SEQ ID NO: 50) |
| >p11 TALE(+240/+183)-VP64 | MSRTRLPSPPAPSPAFSADSFSDLLRQFDPSLFNTSLFDSLPPFGAHHTEAATGEWDEVQSGLRAADAPPPTMRVAVTAARPPRAKPAPRRRAAQPSDASPAAQVDLRTLGYSQQQQEKIKPKVRSTVAQHHEALVGHGFTHAHIVALSQHPAALGTVAVKYQDMIAALPEATHEAIVGVGKQWSGARALEALLTVAGELRGPPLQLDTGQLLKIAKRGGVTAVEAVHAWRNALTGAPLNLTPEQVVAIASNNGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASNGGGKQALETVQRLLPVLCQAHGLTPEQVVAIASNNGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASNGGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASNIGGKQALETVQRLLPVLCQAHGLTPEQVVAIASNNGGKQALETVQRLLPVLCQAHGLTPEQVVAIASNNGGKQALETVQRLLPVLCQAHGLTPEQVVAIASHDGGKQALETVQRLLPVLCQAHGLTPEQVVAIASNGGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASNGGGRPALESIVAQLSRPDPALAALTNDHLVALACLGGRPALDAVKKGLPHAPALIKRTNRRIPERTSHRVADHAQVVRVLGFFQCHSHPAQAFDDAMTQFGMSRHGLLQLFRRVGVTELEARSGTLPPASQRWDRILQASGMKRAKPSPTSTQTPDQASLHAFADSLERDLDAPSPMHEGDQTRASASPKKKRKVEASGSGRADALDDFDLDMLGSDALDDFDLDMLGSDALDDFDLDMLGSDALDDFDLDMLIN (SEQ ID NO: 51) |
| >p11 TALE(+136/+183)-SID | MVDLRTLGYSQQQQEKIKPKVRSTVAQHHEALVGHGFTHAHIVALSQHPAALGTVAVKYQDMIAALPEATHEAIVGVGKQWSGARALEALLTVAGELRGPPLQLDTGQLLKIAKRGGVTAVEAVHAWRNALTGAPLNLTPEQVVAIASNNGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASNGGGKQALETVQRLLPVLCQAHGLTPEQVVAIASNNGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASNGGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASNIGGKQALETVQRLLPVLCQAHGLTPEQVVAIASNNGGKQALETVQRLLPVLCQAHGLTPEQVVAIASNNGGKQALETVQRLLPVLCQAHGLTPEQVVAIASHDGGKQALETVQRLLPVLCQAHGLTPEQVVAIASNGGGKQALETVQRLLPVLCQAHGLTPEQVVAIASHDGGKQALETVQRLLPVLCQAHGLTPEQVVAIASHDGGKQALETVQRLLPVLCQAHGLTPEQVVAIASHDGGRPALESIVAQLSRPDPALAALTNDHLVALACLGGRPALDAVKKGLPHAPALIKRTNRRIPERTSHRVADHAQVVRVLGFFQCHSHPAQAFDDAMTQFGMSRHGLLQLFRR |

Repressor domain and TALE repressor constructs amino acid sequences

>p11 TALE(+136/+183)-SID4X

VGVTELEARSGTLPPASQRWDRILQASGMKRAKPSPTS
TQTPDQASLHAFADSLERDLDAPSPMHEGDQTRASASP
KKKRKVEASGSGMNIQMLLEAADYLERREREAEHGYAS
MLP
(SEQ ID NO: 52)

MVDLRTLGYSQQQQEKIKPKVRSTVAQHHEALVGHGFT
HAHIVALSQHPAALGTVAVKYQDMIAALPEATHEAIVG
VGKQWSGARALEALLTVAGELRGPPLQLDTGQLLKIAK
RGGVTAVEAVHAWRNALTGAPLNLTPEQVVAIASNNGG
KQALETVQRLLPVLCQAHGLTPEQVVAIASHDGGKQAL
ETVQRLLPVLCQAHGLTPEQVVAIASHDGGKQALETVQ
RLLPVLCQAHGLTPEQVVAIASNGGGKQALETVQRLLP
VLCQAHGLTPEQVVAIASNNGGKQALETVQRLLPVLCQ
AHGLTPEQVVAIASHDGGKQALETVQRLLPVLCQAHGL
TPEQVVAIASHDGGKQALETVQRLLPVLCQAHGLTPEQ
VVAIASHDGGKQALETVQRLLPVLCQAHGLTPEQVVAI
ASNGGGKQALETVQRLLPVLCQAHGLTPEQVVAIASHD
GGKQALETVQRLLPVLCQAHGLTPEQVVAIASHDGGKQ
ALETVQRLLPVLCQAHGLTPEQVVAIASNIGGKQALET
VQRLLPVLCQAHGLTPEQVVAIASNNGGKQALETVQRL
LPVLCQAHGLTPEQVVAIASNNGGKQALETVQRLLPVL
CQAHGLTPEQVVAIASHDGGKQALETVQRLLPVLCQAH
GLTPEQVVAIASNGGGKQALETVQRLLPVLCQAHGLTP
EQVVAIASHDGGKQALETVQRLLPVLCQAHGLTPEQVV
AIASHDGGKQALETVQRLLPVLCQAHGLTPEQVVAIAS
HDGGRPALESIVAQLSRPDPALAALTNDHLVALACLGG
RPALDAVKKGLPHAPALIKRTNRRIPERTSHRVADHAQ
VVRVLGFFQCHSHPAQAFDDAMTQFGMSRHGLLQLFRR
VGVTELEARSGTLPPASQRWDRILQASGMKRAKPSPTS
TQTPDQASLHAFADSLERDLDAPSPMHEGDQTRASASP
KKKRKVEASGSGMNIQMLLEAADYLERREREAEHGYAS
MLPGSGMNIQMLLEAADYLERREREAEHGYASMLPGSG
MNIQMLLEAADYLERREREAEHGYASMLPGSGMNIQML
LEAADYLERREREAEHGYASMLPSR
(SEQ ID NO: 53)

>p11 TALE(+240/+183)-SID

MSRTRLPSPPAPSPAFSADSFSDLLRQFDPSLFNTSLF
DSLPPFGAHHTEAATGEWDEVQSGLRAADAPPPTMRVA
VTAARPPRAKPAPRRRAAQPSDASPAAQVDLRTLGYSQ
QQQEKIKPKVRSTVAQHHEALVGHGFTHAHIVALSQHP
AALGTVAVKYQDMIAALPEATHEAIVGVGKQWSGARAL
EALLTVAGELRGPPLQLDTGQLLKIAKRGGVTAVEAVH
AWRNALTGAPLNLTPEQVVAIASNNGGKQALETVQRLL
PVLCQAHGLTPEQVVAIASHDGGKQALETVQRLLPVLC
QAHGLTPEQVVAIASHDGGKQALETVQRLLPVLCQAHG
LTPEQVVAIASNGGGKQALETVQRLLPVLCQAHGLTPE
QVVAIASNNGGKQALETVQRLLPVLCQAHGLTPEQVVA
IASHDGGKQALETVQRLLPVLCQAHGLTPEQVVAIASH
DGGKQALETVQRLLPVLCQAHGLTPEQVVAIASHDGGK
QALETVQRLLPVLCQAHGLTPEQVVAIASNGGGKQALE
TVQRLLPVLCQAHGLTPEQVVAIASHDGGKQALETVQR
LLPVLCQAHGLTPEQVVAIASHDGGKQALETVQRLLPV
LCQAHGLTPEQVVAIASNIGGKQALETVQRLLPVLCQA
HGLTPEQVVAIASNNGGKQALETVQRLLPVLCQAHGLT
PEQVVAIASNNGGKQALETVQRLLPVLCQAHGLTPEQV
VAIASHDGGKQALETVQRLLPVLCQAHGLTPEQVVAIA
SNGGGKQALETVQRLLPVLCQAHGLTPEQVVAIASHDG
GKQALETVQRLLPVLCQAHGLTPEQVVAIASHDGGKQA
LETVQRLLPVLCQAHGLTPEQVVAIASHDGGRPALESI
VAQLSRPDPALAALTNDHLVALACLGGRPALDAVKKGL
PHAPALIKRTNRRPERRTSHRVADHAQVVRVLGRRQCH
SHPAQAFDDAMTQFGMSRHGLLQLFRRVGVTELEARSG
TLPPASQRWDRILQASGMKRAKPSPTSTQTPDQASLHA
FADSLERDLDAPSPMHEGDQTRASASPKKKRKVEASGS
GMNIQMLLEAADYLERREREAEHGYASMLP
(SEQ ID NO: 54)

>p11 TALE(+240/+183)-SID4X

MSRTRLPSPPAPSPAFSADSFSDLLRQFDPSLFNTSLF
DSLPPFGAHHTEAATGEWDEVQSGLRAADAPPPTMRVA
VTAARPPRAKPAPRRRAAQPSDASPAAQVDLRTLGYSQ
QQQEKIKPKVRSTVAQHHEALVGHGFTHAHIVALSQHP
AALGTVAVKYQDMIAALPEATHEAIVGVGKQWSGARAL
EALLTVAGELRGPPLQLDTGQLLKIAKRGGVTAVEAVH
AWRNALTGAPLNLTPEQVVAIASNNGGKQALETVQRLL
PVLCQAHGLTPEQVVAIASHDGGKQALETVQRLLPVLC
QAHGLTPEQVVAIASHDGGKQALETVQRLLPVLCQAHG
LTPEQVVAIASNGGGKQALETVQRLLPVLCQAHGLTPE

| Repressor domain and TALE repressor constructs amino acid sequences |
|---|
| QVVAIASNNGGKQALETVQRLLPVLCQAHGLTPEQVVA
IASHDGGKQALETVQRLLPVLCQAHGLTPEQVVAIASH
DGGKQALETVQRLLPVLCQAHGLTPEQVVAIASHDGGK
QALETVQRLLPVLCQAHGLTPEQVVAIASNGGGKQALE
TVQRLLPVLCQAHGLTPEQVVAIASHDGGKQALETVQR
LLPVLCQAHGLTPEQVVAIASHDGGKQALETVQRLLPV
LCQAHGLTPEQVVAIASNIGGKQALETVQRLLPVLCQA
HGLTPEQVVAIASNNGGKQALETVQRLLPVLCQAHGLT
PEQVVAIASNNGGKQALETVQRLLPVLCQAHGLTPEQV
VAIASHDGGKQALETVQRLLPVLCQAHGLTPEQVVAIA
SNGGGKQALETVQRLLPVLCQAHGLTPEQVVAIASHDG
GKQALETVQRLLPVLCQAHGLTPEQVVAIASHDGGKQA
LETVQRLLPVLCQAHGLTPEQVVAIASHDGGRPALESI
VAQLSRPDPALAALTNDHLVALACLGGRPALDAVKKGL
PHAPALIKRTNRRIPERTSHRVADHAQVVRVLGFFQCH
SHPAQAFDDAMTQFGMSRHGLLQLFRRVGVTELEARSG
TLPPASQRWDRILQASGMKRAKPSPTSTQTPDQASLHA
FADSLERDLDAPSPMHEGDQTRASASPKKKRKVEASGS
GMNIQMLLEAADYLERREREAEHGYASMLPGSGMNIQM
LLEAADYLERREREAEHGYASMLPGSGMNIQMLLEAAD
YLERREREAEHGYASMLPGSGMNIQMLLEAADYLERRE
REAEHGYASMLPSR
(SEQ ID NO: 55) |

The mSin interaction domain (SID) and SID4X domain were codon optimized for mammalian expression and synthesized with flanking NheI and XbaI restriction sites (Genscript). Truncation variants of the TALE DNA binding domains are PCR amplified and fused to the SID or the SID4X domain using NheI and XbaI restriction sites. To control for any effect on transcription resulting from TALE binding, expression vectors carrying the TALE DNA binding domain alone using PCR cloning were constructed. The coding regions of all constructs were completely verified using Sanger sequencing.

Cell culture and endogenous gene transcriptional activation assay: Maintenance of mouse neuroblastoma cell line Neuro2A (ATCC) were carried out with Dulbecco's modified Eagle's Medium (DMEM) supplemented with 5% fetal bovine serum (HyClone), 2 mM GlutaMAX (Invitrogen), 100 U/mL Penicillin, and 100 µg/mL Streptomycin, under 37° C., 5% $CO_2$ incubation condition.

For the endogenous gene transcriptional level assay to test the biological activities of TALE activators and TALE repressors, Neuro2A cells were seeded into 24-well plates. 1 µg of TALE plasmid was transfected using Lipofectamine-2000 (Invitrogen) according to manufacturer's protocol. Transfected cells were cultured at 37° C. for 72 hours before RNA extraction. At least 100,000 cells were harvested and subsequently processed for total RNA extraction using the Fastlane cell-to-cDNA kit (Qiagen) according to the manufacturer's recommended protocol. After cDNA synthesis, cDNA from each samples were added to the qRT-PCR assay with the Taqman Advanced PCR Master Mix (Applied Biosystems) using a StepOne Plus qRT-PCR machine. The fold activation in the transcriptional levels of SOX2 and CACNA1C mRNA were detected using standard TaqMan Gene Expression Assays with probes having the best coverage (Applied Biosystems; p11: Mm00501457_1).

A comparison of two different types of TALE architecture is seen in FIG. 23.

Example 5

The TALE Recombinase System

Neurological and psychiatric diseases arise from a combination of genetic and environmental factors that influence the molecular, morphological, and physiological properties of neurons and glia in the brain (1). Elucidation and treatment of these diseases benefit from understanding how specific brain cell types connect and signal in neural circuits, and how genetic factors affect their cellular function. Traditional transgenic techniques were widely used to test the role of genes and mutations in diseases, as well as for targeting genetically encoded reporter and modulator expression in specific cell populations. However these conventional genome manipulation technologies have low efficiency and are largely limited to the mouse, whereas other animal models that are commonly used for neuroscience and disease studies (e.g. rats and primates) are still mostly inaccessible. Additionally, since many non-rodent animal models have long reproductive cycles, fundamentally new genome modification technologies that precisely manipulate the genomes of cells in the brain have enormous impact.

Applicants have recently pioneered a novel mammalian DNA recognition technology based on the transcriptional activator like effectors (TALE) from the microbial pathogen *Xanthamonas oryze* (2). TALEs are naturally occurring DNA binding proteins consisting of tandem repeats of 34 amino acid peptides (FIG. 27a)(3). The repeat units within each TALE protein are identical except at the 12th and 13th positions, and the two variable amino acids in each repeat specify the DNA base being targeted (HD=C, NI=A, NG=T, NK=G, NS=A/G/T/C) (4-6). Compared to the zinc finger (ZF) technology (7), another programmable DNA binding protein, the TALE DNA recognition code is much more modular and novel TALEs with customized DNA binding sequence may be synthesized much more quickly and with much more predictable binding activity.

TALEs and ZFs may be used to generate site-specific nucleases (zinc finger nuclease and TALENs) by fusing each DNA binding domain to the catalytic domain of the FokI endonuclease (7, 8). While these site-specific nucleases have enabled precise modification of genomes in a wide range of experimental animal models, the overall efficiency of genome modification depends on the host cell's DNA damage and repair pathway (7, 8) and is too low for direct in vivo applications in the brain. Leveraging the TALE technology, Applicants developed a TALE-based site-specific recombinase (TALER) platform, consisting of recombinases and a viral delivery system, to facilitate precise insertion, deletion, or replacement of DNA sequences in the genome. Since TALEs may be programmed to recognize any DNA sequence of interest, TALER achieves precise genome modification at any location in the mammalian genome. The major benefit of TALER over site-specific nucleases is that, similar to natural site-specific DNA recombinases (e.g. Cre, Flp, Dre, and phiC31), TALERs are completely self-sufficient and do not depend on any host machinery. Therefore the efficiency of TALERs is much higher and more suitable for direct genome modification in the brain in vivo.

The TALER technology has broad impacts both within neuroscience and across many fields of biology, including but not limited to: 1. enabling functional genomic studies (knockin, knockout, mutations) in traditionally inaccessible organisms and cell types; 2. enabling targeting of optogenetic tools (Chlamydomonas channelrhodopsin-2 (ChR5), halorhodopsins (HRs), synthetic rhodopsin/GPCR chimeras, XFPs (XFP is the generic term for fluorescent proteins of different colors), genetically-encoded neural activity indicators) to specific cell types in mice as well as higher animal models such as nonhuman primates; and 3. establishing a potential therapeutic system for repairing genomic defects in genetically based neuropsychiatric diseases.

Applicants aim to gain better understanding of the genetic and environmental mechanisms underlying neuropsychiatric disease, and foster technologies that enable nervous system repair. The TALE recombinase toolkit for precise genome engineering is an indispensible piece of the technological repertoire necessary to achieving this ultimate objective.

The goal of enabling high efficiency and precise genome modification is a long sought after goal for the past decade. However, the ideal technology for achieving precise and scarless (without introduction of any exogenous sequence) genome engineering has remained challenging. While several naturally occurring recombinases, integrases, or artificial nucleases were widely used for genome engineering applications, they all suffer from one or more limitations including: difficulty in changing the DNA substrate specificity of the recombination site (9, 10), random integration into the host genome (11), and low efficiency of genome modification (11, 12). To overcome these challenges, Applicants developed a novel DNA targeting technology based on the TALE proteins from the plant pathogenic bacteria *Xanthamonas oryze*. TALEs are programmed to target DNA sequences of interest and are used to target DNA sequences on the mammalian genome in vivo. Using this novel DNA binding protein, Applicants developed a programmable DNA recombinase platform for achieving precise genome modification in the mammalian brain in vivo.

Programmable DNA targeting using designer TALEs: TALEs are naturally occurring microbial pathogen effectors. However due to the repetitive nature of TALEs, it is extremely difficult to construct designer TALEs with novel DNA binding properties.

Applicants have pioneered a novel hierarchical ligation-based strategy for assembling individual TALE repeat monomers into a specific order and found that designer TALEs do bind to DNA sequences that are predicted based on the variable diresidue sequence in the tandem repeat region (FIGS. 12 and 28*a*) (2). Compared with other DNA binding protein technologies such as artificial zinc finger proteins, TALEs are much more designable and do not require sophisticated screening processes. Applicants have designed their method as a high-throughput TALE synthesis platform for constructing artificial TALEs for targeting any arbitrary DNA sequences. The system may be easily scaled up so that hundreds of designer TALEs may be constructed within a few days. This unprecedented ability to construct designer DNA binding proteins capable of targeting any desired DNA sequence is a fundamental requisite for enabling the TALE recombinase technology.

TALEs may directly interact with the mammalian genome. Since natural TALEs are used by microbial pathogens to modulate gene expression from the genome of their host plants (3, 13), it is not clear whether designer TALEs may readily bind to DNA in the mammalian genome. Due to differences in chromatin structures and methylation patterns between mammalian and plant genomes, it is necessary to verify that TALEs may directly interact with the genome in mammalian cells. Applicants have demonstrated that 1.) Designer TALEs may indeed interact with the target sequence on the endogenous genome of the host cell (2, 8), and 2.) Transcription modulators or nuclease domains may be anchored to specific sites on the endogenous genome when fused to designer TALEs (2, 8) (FIG. 28 *b, c*).

Designer TALE transcription factors may be functionally expressed in the brain in vivo to alter the fate of neurons. Applicants' previous studies focused on characterizing TALE activities in mammalian cells were conducted in cell lines that are actively dividing. However, whether TALEs may function properly in mitotically arrested, terminally differentiated cells such as neurons remains unknown. Applicants have designed TALE transcription factors to target the transcription factor FezF2 in post mitotic neurons. FezF2 is a master fate regulator of cortical spinal motor neuron (CSMN) development and heterologous expression of FezF2 in non-CSMN cortical progenitors may switch those cells to adopt the molecular phenotype of a CSMN neuron. When the FezF2-targeting TALE transcription activator is introduced Applicants were able achieve a similar fate switch, suggesting that the designer TALE was indeed able to bind to the FezF2 promoter in the endogenous genome and drive the expression of FezF2. These results indicate that TALE recombinases also bind to the endogenous genome in post-mitotic neurons and facilitate site-specific recombination at target sites.

Applicants have developed a complete toolkit for precise genome engineering consisting of both the TALER as well as the delivery system. This toolkit may be used both in vitro and in vivo. In addition to applications in the mammalian brain to facilitate the study of neural circuits as well as genetic factors underlying psychiatric diseases, the TALER technology has wide utility for many fields of biology to facilitate genetic and genomic perturbations The TALER technology is developed using the following objectives:

1. Design and optimization of a TALER architecture with high catalytic activity and specificity for mammalian genome manipulation: Applicants used protein engineering, directed evolution, and ecological prospecting approaches to identify recombinases with robust activity but lacking sequencing specificity. These recombinases are fused to TALEs that were programmed to target specific genome sequences to generate site-specific TALERs (FIG. 29*a*).

Currently, site specific recombinases such as Cre and Flp were widely used to facilitate genome modification. However Cre and Flp have strict sequence requirements for the recombination site. Many attempts were made to alter the site-specificity of Cre and Flp but were only able to shift the site-specificity by a few bases. This is largely due to the tight integration between DNA binding domain and catalytic domain of tyrosine recombinases.

Developing a TALER architecture: Natural recombinases may be roughly classified into two categories based on their catalytic residues: serine and tyrosine recombinases. Taking inspiration from the development of zinc finger nucleases and recombinase, where zinc finger was fused to sequence agnostic catalytic nuclease or recombinase domains, Applicants developed TALERs using the modular catalytic domain from serine recombinases. Most serine recombinases such as Gin, Hin, Tn3, and gamma-delta recombinases have catalytic domains that are separate from the DNA binding domain (FIGS. 30, 31). Applicants have generated a number of TALE recombinase fusion proteins. In a celline based assay where the TALER is used to recombine out a transcriptional stop cassette (3× poly adenylation signal plus a neomycin gene) inserted between the promoter and the mCherry or luciferase reporter, co-transfection of cells with both the TALER (fusion between TALE and the catalytic domain from the Gin serine recombinase) and the reporter construct is able to activate the expression of the reporter gene (FIGS. 32, 33). Using this reporter system, Applicants have optimized the design of TALE-recombinase fusion. Applicants know that a fragment of the N-terminus of TALE may be truncated while maintaining similar levels of DNA binding activity. By fusing the recombinase catalytic domain to different Nterm truncation mutants of TALE, as well as changing the protein sequence used as the linker between TALE and the recombinase domain, Applicants are able to identify the most active TALER architecture (FIGS. 34, 35, 36). TALER activity for all the TALE recombinase fusion proteins was determined using Luciferase reporter assays. The assays were performed by co-transfecting HEK 293FT cells with TALE Recombinase-2A-*Gaussia* Luciferase expression plasmid and luciferase reporter plasmids. In the case of the reporter-only control, cells were co-transfected with a control *Gaussia* luciferase plasmid (pCMV-Gluc, New England BioLabs). HEK 293FT cells were seeded into 24-well plates the day before transfection at densities of $2\times10^5$ cells per well. Approximately 24 h after initial seeding, cells were transfected using Lipofectamine-2000 (Invitrogen) following the manufacturer's protocol. For each well of the 24-well plates 400 ng of TALE Recombinase and 50 ng of each reporter plasmids were used to transfect HEK 293FT cells. For the mCherry reporter assay, the protocol is similar to above, except the 293FT cells are co-transfected with TALE Recombinase-2A-GFP expression plasmid and mCherry reporter plasmids. The DNA amount is 200 ng of TALE recombinase and 200 ng of each reporter plasmid. All images in FIGS. 28b and 33 were taken 72 h after transfection.

Dual luciferase reporter assays were carried out with the BioLux *Gaussia* luciferase flex assay kit and BioLux *Cypridina* luciferase assay kit (New England Biolabs) following the manufacturer's recommended protocol. Briefly, media from each well of transfected cells were collected 48 h or 72 h after transfection. For each sample, 20 µl of the media were added into a 96-well assay plate and mixed with each one of the dual luciferase assay mixes. After brief incubation, as indicated in the manufacturer's protocol, luminescence levels of each sample were measured using the Varioskan flash multimode reader (Thermo Scientific).

Evolving Gin recombinase to relax substrate specificity: Although the wild type Gin recombinase consists of separate catalytic and DNA binding domains, the catalytic domain still maintains some preference for specific DNA sequences (14, 15). Therefore TALERs based on the wild type Gin has some bias for the recombination sites that are similar to the natural Gin target sequence. To generate a modified version of Gin catalytic domain that does not have any inherent sequence preferences, Applicants used directed evolution and saturation mutagenesis to evolve the Gin catalytic domain to become sequence agnostic (2, 8). It has already been shown that the Gin catalytic domain may be evolved to recognize a single but completely different recombination site (9, 10). Therefore Applicants believe that Gin has the ability to operate on the entire sequence space. Applicants have also quantified TALER activity of the Gin catalytic domain for the LoxP site. (FIG. 37)

Multiplexing recombination: The development of a single TALER architecture based on the Gin recombinase domain enables precise integration or deletion of DNA from a single site in the genome. This is useful for knock-in or knockout experiments where a reporter gene needs to be knocked into a specific locus or a specific gene need to be removed from the genome. However, some experiments need to modify multiple sites simultaneously. To achieve this Applicants have developed orthogonal sets of TALER architectures based on catalytic domains from other serine recombinases (16, 17) which include but are not limited to Hin, Tn3, and gamma-delta resolvase). These other recombinase domains utlize the same strategy utilized for developing the TALE-Gin fusion architecture.

2. Improvement of TALE DNA targeting and specificity: the current TALE DNA binding code targets different DNA sequences with variable efficiency. Applicants optimized the amino acid repeats in TALEs through directed evolution and screening of naturally occurring repeats to improve the DNA binding property. The DNA recognition property of each TALE is specified by the variable diresidues on the repeat domains. Previous studies based on bioinformatics analysis of natural TALEs and their binding sites on the host plant genome have identified four canonical diresidues that have strong preferences for each of the four nucleic acid bases (HD=C, NI=A, NG=T, and NK=G) (4-6). However, based on biochemical and cellular transcription assays, these four diresidues may still recognize non-preferred bases. In addition, for reasons yet to be discovered, these four canonical diresidues may have completely altered DNA base preference depending on the nearby DNA sequence. As a result Applicants' success rate at generating designer TALEs with predicted binding specificity is only around 80%. Applicants have screened all naturally occurring TALE sequences to identify more specific and tighter binding diresidue sequences and have computationally identified all 24 naturally occurring diresidues from known TALEs in NCBI and environmental sequencing databases. Using their high throughput TALE assembly process, Applicants may build sets of designer TALEs with these natural diresidues inserted as specific positions while keeping all of the other positions identical. A combination of biochemical SELEX and cellular transcription assays is used to test the binding preference as well activity of all 24 naturally occurring diresidues. A functional and quantitative understanding of the binding preference of each diresidue is elucidated. The most specific and highest functioning diresidues are used in constructing TALE-recombinases and other TALE-effector domain fusion proteins.

3. Development of optimal in vivo delivery system: by harnessing the packaging machineries of lentiviruses, Applicants developed a novel packaging system capable of delivering the recombinase protein as well as the DNA sequence used for genome modification within a single viral particle (FIG. 29b). This system provides a self-sufficient delivery system without requiring multiple viruses or raising concerns about viral-mediated random integration.

For in vitro applications in cultured cell lines and neurons, TALERs may be delivered either as DNA or RNA. However, for in vivo application this requires the delivery of at least three viral vectors: two vectors for the pair of recombinases and one for the DNA fragment to be inserted into the genome. It is important to minimize the viral vectors that need to be simultaneously delivered, particularly since the probability of achieving triple co-infection is substantially lower than achieving a single infection. Additionally, for most viral vectors used to deliver genes into the brain, the transgene expresses for a prolonged period of time. As prolonged expression of recombinases, even the commonly used Cre and Flp, may lead to genome rearrangements and toxicity (18), it is important to devise a new delivery system that minimizes recombinase expression as well as unifies all of the recombinase-associated material within a single package.

Lentiviral vectors are typically packaged using a three-plasmid system (20): the first vector encodes the viral genome and is transcribed into RNA and packaged into the virus particle, the second vector encodes the viral glycoprotein, and the third vector encodes the viral structural proteins (GAG) and viral enzymes (POL: consisting of reverse transcriptase, protease, and integrase). To enable the virus to package TALER proteins into the viral genome, Applicants replace the integrase gene with TALER genes. During viral packaging, the viral enzymes are made a single polyprotein in the form of GAG-POL. By inserting TALER in place of integrase, TALER is also synthesized as a part of the viral GAG-POL polyprotein, which is packaged into the viral particle.

Applicants have reengineered the commonly used lentiviral vector system to facilitate the delivery of (TALERs as well as the target DNA construct. Rather than delivering TALERs as DNA or RNAs, the TALER proteins are directly packaged into each lentivirus particle. Lentivirus typically packages its own integrase enzyme into the viral particles to facilitate integration of the viral DNA into the host genome (19). The integrase enzyme is replaced with TALERs so that DNA encoded in the packaged viral genome is integrated into the target position in the host genome.

The in vitro and in vivo data presented herein demonstrate that TALEs may be customized to recognize specific DNA sequences on the endogenous genome of post-mitotic and terminally differentiated neurons. By constructing TALEs with novel DNA binding sequences and TALEs coupled with distinct effector domains to facilitate transcriptional modulation or double strand break at specific sites in the genome, Applicants have developed a fundamentally new class of site-specific genome engineering tools for neural circuits as well as genetic analysis.

Methods

Construction of TALE recombinases: All TALERs were constructed as previously described using a hierarchical ligation strategy.

Names of constructs generated follow this format:

| Part of construct name | Example |
| --- | --- |
| Recombinase domain name | Gin |
| truncation position of recombinase domain | 134 or 143 |
| TALE name | TALE1 (TALE recognizing designated sequence) |
| Start position of truncated TALE | Nterm |
| Exact amino acids at which truncation was made | V124 |

The following sequences were used for the constructs generated:

| | |
| --- | --- |
| Gin (EE3 mutant) | MLIGYARVSTNGQSTDLQRDALVCAGCEQIFEDKLSGTRTDRPGLKRALERLQ EGDTLVVWKLDRLGRSVKHLISLVGELRERGINFRSLTDCVNTSSPMGRFFFH VMGALAEVERELIVERTMAGLAAARSKGRIGGRPPKSGSGEMPY (SEQ ID NO: 347) |
| Gin134-TALE1-NtermA187 (TALREN 4) | MLIGYARVSTNGQSTDLQRDALVCAGCEQIFEDKLSGTRTDRPGLKRALERLQ EGDTLVVWKLDRLGRSVKHLISLVGELRERGINFRSLTDCVNTSSPMGRFFFH VMGALAEVERELIVERTMAGLAAARSKGGSGGSGGSGGSGTSARALEALLTVA GELRGPPLQLDTGQLLKIAKRGGVTAVEAVHAWRNALTGAPLNLTPEQVVAIA SNIGGKQALETVQRLLPVLCQAHGLTPEQVVAIASHDGGKQALETVQRLLPVL CQAHGLTPEQVVAIASNNGGKQALETVQRLLPVLCQAHGLTPEQVVAIASNIG GKQALETVQRLLPVLCQAHGLTPEQVVAIASHDGGKQALETVQRLLPVLCQAH GLTPEQVVAIASNGGGKQALETVQRLLPVLCQAHGLTPEQVVAIASHDGGKQA LETVQRLLPVLCQAHGLTPEQVVAIASNIGGKQALETVQRLLPVLCQAHGLTP EQVVAIASHDGGKQALETVQRLLPVLCQAHGLTPEQVVAIASNGGGKQALETV QRLLPVLCQAHGLTPEQVVAIASNIGGKQALETVQRLLPVLCQAHGLTPEQVV AIASNGGGKQALETVQRLLPVLCQAHGLTPEQVVAIASNIGGRPALESIVAQL SRPDPALAALTNDHLVALACLGGRPALDAVKKGLPHAPALIKRTNRRIPERTS HRVADKAELIPEPPKKKRKVELGTA (SEQ ID NO: 348) |
| Gin134-TALE1-NtermV124 (TALREN 5) | MLIGYARVSTNGQSTDLQRDALVCAGCEQIFEDKLSGTRTDRPGLKRALERLQ EGDTLVVWKLDRLGRSVKHLISLVGELRERGINFRSLTDCVNTSSPMGRFFFH VMGALAEVERELIVERTMAGLAAARSKGGSGGSGGSGGSGTSVRSTVAQHHEA LVGHGFTHAHIVALSQHPAALGTVAVKYQDMIAALPEATHEAIVGVGKQWSGA RALEALLTVAGELRGPPLQLDTGQLLKIAKRGGVTAVEAVHAWRNALTGAPLN LTPEQVVAIASNIGGKQALETVQRLLPVLCQAHGLTPEQVVAIASHDGGKQAL ETVQRLLPVLCQAHGLTPEQVVAIASNNGGKQALETVQRLLPVLCQAHGLTPE QVVAIASNIGGKQALETVQRLLPVLCQAHGLTPEQVVAIASHDGGKQALETVQ RLLPVLCQAHGLTPEQVVAIASNGGGKQALETVQRLLPVLCQAHGLTPEVQQA IASHDGGKQALETVQRLLPVLCQAHGLTPEQVVAIASNIGGKQALETVQRLLP VLCQAHGLTPEQVVAIASHDGGKQALETVQRLLPVLCQAHGLTPEQVVAIASN GGGKQALETVQRLLPVLCQAHGLTPEQVVAIASNIGGKQALETVQRLLPVLCQ AHGLTPEQVVAIASNGGGKQALETVQRLLPVLCQAHGLTPEQVVAIASNIGGR PALESIVAQLSRPDPALAALTNDHLVALACLGGRPALDAVKKGLPHAPALIKR TNRRIPERTSHRVADKAELIPEPPKKKRKVELGTA (SEQ ID NO: 349) |

| | |
|---|---|
| Gin134-<br>TALE1-<br>Repeat 0th<br>(TALREN 6) | MLIGYARVSTNGQSTDLQRDALVCAGCEQIFEDKLSGTRTDRPGLKRALERLQ<br>EGDTLVVWKLDRLGRSVKHLISLVGELRERGINFRSLTDCVNTSSPMGRFFFH<br>VMGALAEVERELIVERTMAGLAAARSKGGSGGSGGSGGSGTSLQLDTGQLLKI<br>AKRGGVTAVEAVHAWRNALTGAPLNLTPEQVVAIASNIGGKQALETVQRLLPV<br>LCQAHGLTPEQVVAIASHDGGKQALETVQRLLPVLCQAHGLTPEQVVAIASNN<br>GGKQALETVQRLLPVLCQAHGLTPEQVVAIASNIGGKQALETVQRLLPVLCQA<br>HGLTPEQVVAIASHDGGKQALETVQRLLPVLCQAHGLTPEQVVAIASNGGGKQ<br>ALETVQRLLPVLCQAHGLTPEQVVAIASHDGGKQALETVQRLLPVLCQAHGLT<br>PEQVVAIASNIGGKQALETVQRLLPVLCQAHGLTPEQVVAIASHDGGKQALET<br>VQRLLPVLCQAHGLTPEQVVAIASNGGGKQALETVQRLLPVLCQAHGLTPEQV<br>VAIASNIGGKQALETVQRLLPVLCQAHGLTPEQVVAIASNGGGKQALETVQRL<br>LPVLCQAHGLTPEQVVAIASNIGGRPALESIVQALSRPDPALAALTNDHLVAL<br>ACLGGRPALDAVKKGLPHAPALIKRTNRRIPERTSHRVADKAELIPEPPKKKR<br>KVELGTA<br>(SEQ ID NO: 350) |
| Gin134-<br>TALE1-<br>Repeat 0th-<br>No. 12 AA | MLIGYARVSTNGQSTDLQRDALVCAGCEQIFEDKLSGTRTDRPGLKRALERLQ<br>EGDTLVVWKLDRLGRSVKHLISLVGELRERGINFRSLTDCVNTSSPMGRFFFH<br>VMGALAEVERELIVERTMAGLAAARSKGGSGGSGGSGGSGTSKRGGVTAVEAV<br>HAWRNALTGAPLNLTPEQVVAIASNIGGKQALETVQRLLPVLCQAHGLTPEQV<br>VAIASHDGGKQALETVQRLLPVLCQAHGLTPEQVVAIASNNGGKQALETVQRL<br>LPVLCQAHGLTPEQVVAIASNIGGKQALETVQRLLPVLCQAHGLTPEQVVAIA<br>SHDGGKQALETVQRLLPVLCQAHGLTPEQVVAIASNGGGKQALETVQRLLPVL<br>CQAHGLTPEQVVAIASHDGGKQALETVQRLLPVLCQAHGLTPEQVVAIASNIG<br>GKQALETVQRLLPVLCQAHGLTPEQVVAIASHDGGKQALETVQRLLPVLCQAH<br>GLTPEQVVAIASNGGGKQALETVQRLLPVLCQAHGLTPEQVVAIASNIGGKQA<br>LETQRLLPVLCQAHGLTPEQVVAIASNGGGKQALETVQRLLPVLCQAHGLTPE<br>QVVAIASNIGGRPALESIVAQLSRPDPALAALTNDHLVALACLGGRPALDAVK<br>KGLPHAPALIKRTNRRIPERTSHRVADKAELIPEPPKKKRKVELGTA<br>(SEQ ID NO: 351) |
| Gin134-<br>TALE1-<br>Repeat 1st | MLIGYARVSTNGQSTDLQRDALVCAGCEQIFEDKLSGTRTDRPGLKRALERLQ<br>EGDTLVVWKLDRLGRSVKHLISLVGELRERGINFRSLTDCVNTSSPMGRFFFH<br>VMGALAEVERELIVERTMAGLAAARSKGGSGGSGGSGGSGTSLTPEQVVAIAS<br>NIGGKQALETVQRLLPVLCQAHGLTPEQVVAIASHDGGKQALETVQRLLPVLC<br>QAHGLTPEQVVAIASNNGGKQALETVQRLLPVLCQAHGLTPEQVVAIASNIGG<br>KQALETVQRLLPVLCQAHGLTPEQVVAIASHDGGKQALETVQRLLPVLCQAHG<br>LTPEQVVAIASNGGGKQALETVQRLLPVLCQAHGLTPEQVVAIASHDGGKQAL<br>ETVQRLLPVLCQAHGLTPEQVVAIASNIGGKQALETVQRLLPVLCQAHGLTPE<br>QVVAIASHDGGKQALETVQRLLPVLCQAHGLTPEQVVAIASNGGGKQALETVQ<br>RLLPVLCQAHGLTPEQVVAIASNIGGKQALETVQRLLPVLCQAHGLTPEQVVA<br>IASNGGGKQALETVQRLLPVLCQAHGLTPEQVVAIASNIGGRPALESIVAQLS<br>RPDPALAALTNDHLVALACLGGRPALDAVKKGLPHAPALIKRTNRRIPERTSH<br>RVADKAELIPEPPKKKRKVELGTA<br>(SEQ ID NO: 352) |
| Gin134-<br>TALE1-<br>Repeat 1st-<br>12th AA<br>position | MLIGYARVSTNGQSTDLQRDALVCAGCEQIFEDKLSGTRTDRPGLKRALERLQ<br>EGDTLVVWKLDRLGRSVKHLISLVGELRERGINFRSLTDCVNTSSPMGRFFFH<br>VMGALAEVERELIVERTMAGLAAARSKGGSGGSGGSGGSGTSLTPEQVVAIAS<br>NIGGKQALETVQRLLPVLCQAHGLTPEQVVAIASHDGGKQALETVQRLLPVLC<br>QAHGLTPEQVVAIASNNGGKQALETVQRLLPVLCQAHGLTPEQVVAIASNIGG<br>KQALETVQRLLPVLCQAHGLTPEQVVAIASHDGGKQALETVQRLLPVLCQAHG<br>LTPEQVVAIASNGGGKQALETVQRLLPVLCQAHGLTPEQVVAIASHDGGKQAL<br>ETVQRLLPVLCQAHGLTPEQVVAIASNIGGKQALETVQRLLPVLCQAHGLTPE<br>QVVAIASHDGGKQALETVQRLLPVLCQAHGLTPEQVVAIASNGGGKQALETVQ<br>RLLPVLCQAHGLTPEQVVAIASNIGGKQALETVQRLLPVLCQAHGLTPEQVVA<br>IASNGGGKQALETVQRLLPVLCQAHGLTPEQVVAIASNIGGRPALESIVAQLS<br>RPDPALAALTNDHLVALACLGGRPALDAVKKGLPHAPALIKRTNRRIPERTSH<br>RVADKAELIPEPPKKKRKVELGTA<br>(SEQ ID NO: 353) |
| Gin134-<br>TALE1-<br>1st Repeat,<br>14th AA<br>position | MLIGYARVSTNGQSTDLQRDALVCAGCEQIFEDKLSGTRTDRPGLKRALERLQ<br>EGDTLVVWKLDRLGRSVHKLISLVGELRERGINFRSLTDCVNTSSPMGRFFFH<br>VMGALAEVERELIVERTMAGLAAARSKGGSGGSGGSGGSGTSGGKQALETVQR<br>LLPVLCQAHGLTPEQVVAIASHDGGKQALETVQRLLPVLCQAHGLTPEQVVAI<br>ASNNGGKQALETVQRLLPVLCQAHGLTPEQVVAIASNIGGKQALETVQRLLPV<br>LCQAHGLTPEQVVAIASHDGGKQALETVQRLLPVLCQAHGLTPEQVVAIASNG<br>GGKQALETVQRLLPVLCQAHGLTPEQVVAIASHDGGKQALETVQRLLPVLCQA<br>HGLTPEQVVAIASNIGGKQALETVQRLLPVLCQAHGLTPEQVVAIASHDGGKQ<br>ALETVQRLLPVLCQAHGLTPEQVVAIASNGGGKQALETVQRLLPVLCQAHGLT<br>PEQVVAIASNIGGKQALETVQRLLPVLCQAHGLTPEQVVAIASNGGGKQALET<br>VQRLLPVLCQAHGLTPEQVVAIASNIGGRPALESIVAQLSRPDPALAALTNDH<br>LVALACLGGRPALDAVKKGLPHAPALIKRTNRRIPERTSHRVADKAELIPEPP<br>KKKRKVELGTA<br>(SEQ ID NO: 354) |
| Gin143<br>constructs | All Gin143 constructs are identical to the Gin134<br>except that instead of having the 134 amino acid<br>recombinase domain, all of them have the 143 amino |

-continued

```
acid recombinase domain:
MLIGYARVSTNGQSTDLQRDLAVCAGCEQIFEDKLSGTRTDRPGLKRALERLQ
EGDTLVVWKLDRLGRSVKHLISLVGELRERGINFRSLTDCVNTSSPMGRFFFH
VMGALAEVERELIVERTMAGLAAARSKGRIGGRPPKS
(SEQ ID NO: 355)
```

Significance

The development of customizable recombinase system has enormous benefits for neuroscience as well as many other fields of biological research. Some of the specific impacts for neuroscience include:

Systems Neuroscience: Many systems neuroscience studies are limited by the ability to genetically restrict reporter or optogenetic proteins in non-transgenic animals (e.g. rats and nonhuman primates), and the TALER system enables researchers not working on mice to enjoy the same benefits of genetically targetable probes and activity modulators.

Molecular Neuroscience: For functional study of genes and RNAs involved in neural functions, the TALER system allows researchers to easily knockin or knockout the gene of interest in vivo, without waiting a long period of time to generate a transgenic animal.

Neuropsychiatric Diseases: Data from genome sequencing of neuropsychiatric patient population have highlighted many genetic mutations (SNPs or copy number variations) that might have a causal role in the disease manifestation. The TALER system enables researchers to introduce these disease mutations into an otherwise normal genomic background and compare the resulting phenotype. This type of comparison between different genetic mutations within an isogenic genomic background enables researchers to confidently link specific mutations with disease, and to identify novel drug targets.

REFERENCES

1. Insel, T. R. & Wang, P. S. Rethinking mental illness. *Jama* 303, 1970-1971 (2010).
2. Zhang, F. et al. Efficient construction of sequence-specific TAL effectors for modulating mammalian transcription. *Nature biotechnology* 29, 149-153 (2011).
3. Boch, J. & Bonas, U. *Xanthomonas* AvrBs3 family-type III effectors: discovery and function. *Annual review of phytopathology* 48, 419-436 (2010).
4. Boch, J. et al. Breaking the code of DNA binding specificity of TAL-type III effectors. *Science* 326, 1509-1512 (2009).
5. Moscou, M. J. & Bogdanove, A. J. A simple cipher governs DNA recognition by TAL effectors. *Science* 326, 1501 (2009).
6. Morbitzer, R., Romer, P., Boch, J. & Lahaye, T. Regulation of selected genome loci using de novo-engineered transcription activator-like effector (TALE)-type transcription factors. *Proceedings of the National Academy of Sciences of the United States of America* 107, 21617-21622 (2010).
7. Urnov, F. D., Rebar, E. J., Holmes, M. C., Zhang, H. S. & Gregory, P. D. Genome editing with engineered zinc finger nucleases. *Nat Rev Genet.* 11, 636-646 (2010).
8. Miller, J. C. et al. A TALE nuclease architecture for efficient genome editing. *Nature biotechnology* 29, 143-148 (2011).
9. Gaj, T., Mercer, A. C., Gersbach, C. A., Gordley, R. M. & Barbas, C. F., 3rd Structure-guided reprogramming of serine recombinase DNA sequence specificity. *Proceedings of the National Academy of Sciences of the United States of America* 108, 498-503 (2011).
10. Gersbach, C. A., Gaj, T., Gordley, R. M. & Barbas, C. F., 3rd Directed evolution of recombinase specificity by split gene reassembly. *Nucleic acids research* 38, 4198-4206 (2010).
11. Feng, X., Bednarz, A. L. & Colloms, S. D. Precise targeted integration by a chimaeric transposase zinc-finger fusion protein. *Nucleic acids research* 38, 1204-1216 (2010).
12. Matrai, J., Chuah, M. K. & VandenDriessche, T. Recent advances in lentiviral vector development and applications. *Molecular therapy: the journal of the American Society of Gene Therapy* 18, 477-490 (2010).
13. Romer, P., Recht, S. & Lahaye, T. A single plant resistance gene promoter engineered to recognize multiple TAL effectors from disparate pathogens. *Proceedings of the National Academy of Sciences of the United States of America* 106, 20526-20531 (2009).
14. Klippel, A., Kanaar, R., Kahmann, R. & Cozzarelli, N. R. Analysis of strand exchange and DNA binding of enhancer-independent Gin recombinase mutants. *The EMBO journal* 12, 1047-1057 (1993).
15. Maeser, S. & Kahmann, R. The Gin recombinase of phage Mu can catalyse site-specific recombination in plant protoplasts. *Mol Gen Genet.* 230, 170-176 (1991).
16. Rice, P. A. et al. Orchestrating serine resolvases. *Biochemical Society transactions* 38, 384-387 (2010).
17. Grindley, N. D., Whiteson, K. L. & Rice, P. A. Mechanisms of site-specific recombination. *Annu Rev Biochem* 75, 567-605 (2006).
18. Loonstra, A. et al. Growth inhibition and DNA damage induced by Cre recombinase in mammalian cells. *Proceedings of the National Academy of Sciences of the United States of America* 98, 9209-9214 (2001).
19. Federico, M. From lentiviruses to lentivirus vectors. *Methods in molecular biology* 229, 3-15 (2003).
20. Tiscornia, G., Singer, O. & Verma, I. M. Production and purification of lentiviral vectors. *Nature protocols* 1, 241-245 (2006).

Equivalents

Those skilled in the art recognize, or be able to ascertain using no more than routine experimentation, many equivalents of the specific embodiments of the subject matter described herein. Such equivalents are intended to be encompassed by the following claims.

Incorporation By Reference

All publications, patents, and patent applications cited in this specification are herein incorporated by reference to the same extent as if each individual publication or patent application was specifically and individually indicated to be incorporated by reference.

The invention is further described by the following numbered paragraphs:

1. A method of repressing expression of a genomic locus of interest in a mammalian cell, comprising contacting the genomic locus with a non-naturally occurring or engineered composition comprising a deoxyribonucleic acid (DNA) binding polypeptide comprising:
- (a) a N-terminal capping region
- (b) a DNA binding domain comprising at least five or more Transcription activator-like effector (TALE) monomers and at least one or more half-monomers specifically ordered to target the genomic locus of interest, and
- (c) a C-terminal capping region wherein (a), (b) and (c) are arranged in a predetermined N-terminus to C-terminus orientation, wherein the polypeptide includes at least one or more repressor domains, and wherein the polypeptide is encoded by and translated from a codon optimized nucleic acid molecule so that the polypeptide preferentially binds to DNA of the genomic locus.

2. The method according to paragraph 1, wherein the polypeptide includes at least one mSin interaction domain (SID) repressor domain.

3. The method according to paragraph 2, wherein the polypeptide includes at least four SID repressor domains.

4. The method according to paragraph 1, wherein the polypeptide includes a Krüppel-associated box (KRAB) repressor domain or a fragment thereof.

5. The method according to paragraph 1, wherein the DNA binding domain comprises $(X_{1-11}\text{-}X_{12}X_{13}\text{-}X_{14\text{-}33\ or\ 34\ or\ 35})_z$,
wherein $X_{1-11}$ is a chain of 11 contiguous amino acids,
wherein $X_{12}X_{13}$ is a repeat variable diresidue (RVD),
wherein $X_{14\text{-}33\ or\ 34\ or\ 35}$ is a chain of 21, 22 or 23 contiguous amino acids,
wherein z is at least 5 to 40, and
wherein at least one RVD is selected from the group consisting of NI, HD, NG, NN, KN, RN, NH, NQ, SS, SN, NK, KH, RH, HH, HI, KI, RI, SI, KG, HG, RG, SD, ND, KD, RD, YG, HN, NV, NS, HA, S*, N*, KA, H*, RA, NA, and NC, wherein (*) means that the amino acid at $X_{13}$ is absent.

6. The method according to paragraph 5, wherein z is at least 10 to 26.

7. The method according to paragraph 5, wherein
at least one of $X_{1-11}$ is a sequence of 11 contiguous amino acids set forth as amino acids 1-11 in a sequence $(X_{1-11}\text{-}X_{14\text{-}34}$ or $X_{1-11}\text{-}X_{14\text{-}35})$ of FIG. 24 or
at least one of $X_{14\text{-}34}$ or $X_{14\text{-}35}$ is a sequence of 21 or 22 contiguous amino acids set forth as amino acids 12-32 or 12-33 in a sequence $(X_{1-11}\text{-}X_{14\text{-}34}$ or $X_{1-11}\text{-}X_{14\text{-}35})$ of FIG. 24.

8. The method according to paragraph 1, wherein
the N-terminal capping region or fragment thereof comprises 147 contiguous amino acids of a wild type N-terminal capping region, or
the C-terminal capping region or fragment thereof comprises 68 contiguous amino acids of a wild type C-terminal capping region, or
the N-terminal capping region or fragment thereof comprises 136 contiguous amino acids of a wild type N-terminal capping region and the C-terminal capping region or fragment thereof comprises 183 contiguous amino acids of a wild type C-terminal capping region.

9. A method of selectively targeting a genomic locus of interest in an animal cell, comprising contacting the genomic locus with a non-naturally occurring or engineered composition comprising a DNA binding polypeptide comprising:
- (a) a N-terminal capping region
- (b) a DNA binding domain comprising at least five or more Transcription activator-like effector (TALE) monomers and at least one or more half-monomers specifically ordered to target the genomic locus of interest, and
- (c) a C-terminal capping region wherein (a), (b) and (c) are arranged in a predetermined N-terminus to C-terminus orientation, wherein the polypeptide includes at least one or more effector domains, wherein the polypeptide is encoded by and translated from a codon optimized nucleic acid molecule so that the polypeptide preferentially binds to DNA of the genomic locus, wherein the DNA binding domain comprises $(X_{1-11}\text{-}X_{12}X_{13}\text{-}X_{14\text{-}33\ or\ 34\ or\ 35})_z$,
wherein $X_{1-11}$ is a chain of 11 contiguous amino acids,
wherein $X_{12}X_{13}$ is a repeat variable diresidue (RVD),
wherein $X_{14\text{-}33\ or\ 34\ or\ 35}$ is a chain of 21, 22 or 23 contiguous amino acids, wherein z is at least 5 to 40, and
wherein at least one RVD is selected from the group consisting of HH, KH, NH, NK, NQ, RH, RN, SS, SI, HG, KG, RG, RD, SD, NV, H*, HA, KA, N*, NA, NC, NS, RA, and S* wherein (*) means that the amino acid at $X_{13}$ is absent.

10. The method according to paragraph 9, wherein the at least one RVD is selected from the group consisting of (a) HH, KH, NH, NK, NQ, RH, RN, SS for recognition of guanine (G); (b) SI for recognition of adenine (A); (c) HG, KG, RG for recognition of thymine (T); (d) RD, SD for recognition of cytosine (C); (e) NV for recognition of A or G; and (f) H*, HA, KA, N*, NA, NC, NS, RA, S* for recognition of A or T or G or C, wherein (*) means that the amino acid at $X_{13}$ is absent.

11. The method according to paragraph 10, wherein
the RVD for the recognition of G is RN, NH, RH or KH; or
the RVD for the recognition of A is SI; or
the RVD for the recognition of T is KG or RG; and
the RVD for the recognition of C is SD or RD.

12. The method according to paragraph 9, wherein the animal is a mammal.

13. The method according to paragraph 9, wherein the effector domain is an activator domain, a repressor domain, a DNA methyltransferase domain, a recombinase domain or a nuclease domain.

14. The method according to paragraph 9, wherein at least one $(X_{1-11}\text{-}X_{14\text{-}34})$ or $(X_{1-11}\text{-}X_{14\text{-}35})$ is selected from FIG. 24.

15. The method according to paragraph 9, wherein
the N-terminal capping region or fragment thereof comprises 147 contiguous amino acids of a wild type N-terminal capping region, or
the C-terminal capping region or fragment thereof comprises 68 contiguous amino acids of a wild type C-terminal capping region, or
the N-terminal capping region or fragment thereof comprises 136 contiguous amino acids of a wild type N-terminal capping region and the C-terminal capping region or fragment thereof comprises 183 contiguous amino acids of a wild type C-terminal capping region.

16. A method of selectively targeting a genomic locus of interest in an animal cell, comprising contacting the genomic locus with a non-naturally occurring or engineered composition comprising a DNA binding polypeptide comprising:
- (a) a N-terminal capping region
- (b) a DNA binding domain comprising at least five or more Transcription activator-like effector (TALE) monomers and at least one or more half-monomers specifically ordered to target the genomic locus of interest, and
- (c) a C-terminal capping region wherein (a), (b) and (c) are arranged in a predetermined N-terminus to C-terminus orientation, wherein the polypeptide includes at least one or more effector domains, wherein the polypeptide is encoded by and translated from a codon optimized nucleic acid molecule so that the polypeptide preferentially binds to DNA of the genomic locus, wherein the DNA binding domain comprises $(X_{1-11}\text{-}X_{12}X_{13}\text{-}X_{14\text{-}33\ or\ 34\ or\ 35})_z$, wherein $X_{1-11}$ is a chain of 11 contiguous amino acids, wherein $X_{12}X_{13}$ is a repeat variable diresidue (RVD), wherein $X_{14\text{-}33\ or\ 34\ or\ 35}$ is a chain of 21, 22 or 23 contiguous amino acids, wherein z is at least 5 to 40, and wherein at least one of the following is present

[LTLD] (SEQ ID NO: 1) or [LTLA] (SEQ ID NO: 2) or [LTQV] (SEQ ID NO: 3) at $X_{1-4}$, or

[EQHG] (SEQ ID NO: 4) or [RDHG] (SEQ ID NO: 5) at positions $X_{30\text{-}33}$ or $X_{31\text{-}34}$ or $X_{32\text{-}35}$.

17. The method according to paragraph 16, wherein the animal is a mammal.

18. The method according to paragraph 16, wherein the effector domain is an activator domain, a repressor domain, a DNA methyltransferase domain, a recombinase domain or a nuclease domain.

19. The method according to paragraph 16, wherein at least one RVD is selected from the group consisting of NI, HD, NG, NN, KN, RN, NH, NQ, SS, SN, NK, KH, RH, HH, HI, KI, RI, HI, SI, KG, HG, RG, SD, ND, KD, RD, YG, HN, NV, NS, HA, S*, N*, KA, H*, RA, NA, and NC, wherein (*) means that the amino acid at $X_{13}$ is absent.

20. The method according to paragraph 16, wherein the N-terminal capping region or fragment thereof comprises 147 contiguous amino acids of a wild type N-terminal capping region, or the C-terminal capping region or fragment thereof comprises 68 contiguous amino acids of a wild type C-terminal capping region, or the N-terminal capping region or fragment thereof comprises 136 contiguous amino acids of a wild type N-terminal capping region and the C-terminal capping region or fragment thereof comprises 183 contiguous amino acids of a wild type C-terminal capping region.

21. A method of alteringing expression of a genomic locus of interest in a mammalian cell, comprising contacting the genomic locus with a non-naturally occurring or engineered composition comprising a deoxyribonucleic acid (DNA) binding polypeptide comprising:

(a) a N-terminal capping region (b) a DNA binding domain comprising at least five or more Transcription activator-like effector (TALE) monomers and at least one or more half-monomers specifically ordered to target the genomic locus of interest, and (c) a C-terminal capping region wherein (a), (b) and (c) are arranged in a predetermined N-terminus to C-terminus orientation, wherein the polypeptide includes at least one or more recombinase domains, and wherein the polypeptide is encoded by and translated from a codon optimized nucleic acid molecule so that the polypeptide preferentially binds to DNA of the genomic locus.

22. The method according to paragraph 21, wherein the polypeptide includes at least one Gin recombinase domain or a fragment thereof 23. The method according to paragraph 22, wherein the fragment of the Gin recombinase domain comprises 134 contiguous aminio acids of the Gin recombinase domain.

24. The method according to paragraph 22, wherein the fragment of the Gin recombinase domain comprises 143 contiguous aminio acids of the Gin recombinase domain.

25. The method according to paragraph 21, wherein the DNA binding domain comprises $(X_{1-11}\text{-}X_{12}X_{13}\text{-}X_{14\text{-}33\ or\ 34\ or\ 35})_z$;

wherein $X_{1-11}$ is a chain of 11 contiguous amino acids, wherein $X_{12}X_{13}$ is a repeat variable diresidue (RVD), wherein $X_{14\text{-}33\ or\ 34\ or\ 35}$ is a chain of 21, 22 or 23 contiguous amino acids, wherein z is at least 5 to 40, and wherein at least one RVD is selected from the group consisting of NI, HD, NG, NN, KN, RN, NH, NQ, SS, SN, NK, KH, RH, HH, HI, KI, RI, SI, KG, HG, RG, SD, ND, KD, RD, YG, HN, NV, NS, HA, S*, N*, KA, H*, RA, NA, and NC, wherein (*) means that the amino acid at $X_{13}$ is absent.

26. The method according to paragraph 25, wherein z is at least 10 to 26.

27. The method according to paragraph 25, wherein at least one of $X_{1-11}$ is a sequence of 11 contiguous amino acids set forth as amino acids 1-11 in a sequence $(X_{1-11}\text{-}X_{14\text{-}34}$ or $X_{1-11}\text{-}X_{14\text{-}35})$ of FIG. 24 or at least one of $X_{14\text{-}34}$ or $X_{14\text{-}35}$ is a sequence of 21 or 22 contiguous amino acids set forth as amino acids 12-32 or 12-33 in a sequence $(X_{1-11}\text{-}X_{14\text{-}34}$ or $X_{1-11}\text{-}X_{14\text{-}35})$ of FIG. 24.

28. The method according to paragraph 21, wherein the N-terminal capping region or fragment thereof comprises 147 contiguous amino acids of a wild type N-terminal capping region, or the C-terminal capping region or fragment thereof comprises 68 contiguous amino acids of a wild type C-terminal capping region, or the N-terminal capping region or fragment thereof comprises 136 contiguous amino acids of a wild type N-terminal capping region and the C-terminal capping region or fragment thereof comprises 183 contiguous amino acids of a wild type C-terminal capping region.

\* \* \*

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

We claim:

1. A method of repressing expression of a genomic locus of interest comprising a coding or regulatory sequence susceptible to repression by a repressor domain or a fragment thereof having activity of a repressor in a cell, comprising contacting the genomic locus with a non-naturally occurring or engineered composition comprising a deoxyribonucleic acid (DNA) binding polypeptide comprising:
   (a) a N-terminal capping region
   (b) a DNA binding domain comprising at least 5 to 40 Transcription activator-like effector (TALE) monomers and at least one or more half-monomers specifically ordered to target the genomic locus of interest, and
   (c) a C-terminal capping region
   wherein (a), (b) and (c) are arranged in a predetermined N-terminus to C-terminus orientation,
   wherein the genomic locus comprises a target DNA sequence 5'-$T_0 N_1 N_2 \ldots N_z N_{z+1}$ -3', where $T_0$ and N=A, G, T or C,
   wherein the target DNA sequence binds to the DNA binding domain, and the DNA binding domain comprises $(X_{1-11}\text{-}X_{12}X_{13}\text{-}X_{14-33 \text{ or } 34 \text{ or } 35})_z$,
   wherein $X_{1-11}$ is a chain of 11 contiguous amino acids,
   wherein $X_{12}X_{13}$ is a repeat variable diresidue (RVD),
   wherein $X_{14}\text{-}X_{33 \text{ or } 34 \text{ or } 35}$ is a chain of 21, 22 or 23 contiguous amino acids,
   wherein z is at least 5 to 40,
   wherein at least one RVD is selected from the group consisting of (a) HH, KH, NH, NK, NQ, RH, RN, SS, NN, SN, KN for recognition of guanine (G); (b) NI, KI, RI, HI, SI for recognition of adenine (A); (c) NG, HG, KG, RG for recognition of thymine (T); (d) RD, SD, HD, ND, KD, YG for recognition of cytosine (C); (e) NV, HN for recognition of A or G; and (f) H*, HA, KA, N*, NA, NC, NS, RA, S*for recognition of A or T or G or C, wherein (*) means that the amino acid at $X_{13}$ is absent,
   wherein the polypeptide is encoded by and translated from a codon optimized nucleic acid molecule so that the polypeptide preferentially binds to DNA of the genomic locus, and
   wherein repressing expression of the genomic locus comprises a decrease in transcript level corresponding to the genomic locus of interest in the cell contacted with the polypeptide as compared to a control cell in which the genomic locus of interest is contacted with a control polypeptide that does not have at least one or more repressor domains or a fragment thereof.

2. The method according to claim 1, wherein the cell is a mammalian cell.

3. The method of claim 1, wherein the N-terminal capping region or fragment thereof comprises 147 contiguous amino acids of a wild type N-terminal capping region, or
   the C-terminal capping region or fragment thereof comprises 68 contiguous amino acids of a wild type C-terminal capping region, or
   the N-terminal capping region or fragment thereof comprises 136 contiguous amino acids of a wild type N-terminal capping region and the C-terminal capping region or fragment thereof comprises 183 contiguous amino acids of a wild type C-terminal capping region.

4. The method of claim 2, wherein the N-terminal capping region or fragment thereof comprises 147 contiguous amino acids of a wild type N-terminal capping region, or
   the C-terminal capping region or fragment thereof comprises 68 contiguous amino acids of a wild type C-terminal capping region, or
   the N-terminal capping region or fragment thereof comprises 136 contiguous amino acids of a wild type N-terminal capping region and the C-terminal capping region or fragment thereof comprises 183 contiguous amino acids of a wild type C-terminal capping region.

5. The method according to claim 1, wherein at least one RVD is selected from the group consisting of (a) HH, KH, NH, NK, NQ, RH, RN, SS for recognition of guanine (G); (b) SI for recognition of adenine (A); (c) HG, KG, RG for recognition of thymine (T); (d) RD, SD for recognition of cytosine (C); (e) NV, HN for recognition of A or G and (f) H*, HA, KA, N*, NA, NC, NS, RA, S*for recognition of A or T or G or C, wherein (*) means that the amino acid at $X_{13}$ is absent.

6. The method according to claim 5, wherein
   the RVD for the recognition of G is RN, NH, RH or KH; or
   the RVD for the recognition of A is SI; or
   the RVD for the recognition of T is KG or RG; and
   the RVD for the recognition of C is SD or RD.

7. The method according to any one of claim 1-4 or 5 or 6, wherein at least one of the following is present
   [LTLD] (SEQ ID NO: 1) or [LTLA] (SEQ ID NO: 2) or [LTQV] (SEQ ID NO: 3) at $X_{1-4}$, or
   [EQHG] (SEQ ID NO: 4) or [RDHG] (SEQ ID NO: 5) at positions $X_{30-33}$ or $X_{31-34}$ or $X_{32-35}$,
   wherein the sequence $X_{1-11}\text{-}X_{12}X_{13}\text{-}X_{14-33 \text{ or } 34 \text{ or } 35}$ is selected from the group consisting of: LTLDQVVAIAS $X_{12}X_{13}$ GGKQALETVQRLLPVLCQDHG (SEQ ID NO: 356), LTLDQVVAIAS $X_{12}X_{13}$ GGKQALETVQRLLPVLCQAHG (SEQ ID NO: 357), LTLDQVVAIAS $X_{12}X_{13}$ GSKQALETVQRLLPVLCQDHG (SEQ ID NO: 358), LTLDQVVAIAS $X_{12}X_{13}$ GGKKALETVQRLLPVLCQDHG (SEQ ID NO: 359), LTLDKVVAIAS $X_{12}X_{13}$ GGKQALETVQRLLPVLCQDHG (SEQ ID NO: 360), LTLDQVVAIAS $X_{12}X_{13}$ GSKQALETVQRLLPVLCQAHG (SEQ ID NO: 361), LTLDQVVAIAS $X_{12}X_{13}$ GGKQALETVQRLLPVLCQARG (SEQ ID NO: 362), LTLDQVVAIAS $X_{12}X_{13}$ GGKQALETVQRLLPVLCEQHG (SEQ ID NO: 363), LTLDQVVAIAS $X_{12}X_{13}$ GGKQALETVQRLLPVLCQTHG (SEQ ID NO: 364), LTLDQVAAIAS $X_{12}X_{13}$ GGKQALETVQRLLPVLCQAHG (SEQ ID NO: 365), LTLDQVVAIAS $X_{12}X_{13}$ GSKQALETVQRLLPVLCQTHG (SEQ ID NO: 366), LTLDQVVAIAS $X_{12}X_{13}$ GGKQALETVQRLLPVLCQEHG (SEQ ID NO: 367), LTLDQVVSIAS $X_{12}X_{13}$ GGKQALETVQRLLPVLCQDHG (SEQ ID NO: 368), LTLAQVVAIAS $X_{12}X_{13}$ GGKQALETVQRLLPVLCQAHG (SEQ ID NO: 369), LTLAQVVAIAS $X_{12}X_{13}$ GGKQALETVQRLLPVLCQDHG (SEQ ID NO: 370), LTLAQVVAIAN $X_{12}X_{13}$ GGKQALETVQRLLPVLCQAHG (SEQ ID NO: 371), LTLAQVVAIAN $X_{12}X_{13}$ GGKQALETVQRLLPVLCQDHG (SEQ ID NO: 372), LTLAQVVAIAS $X_{12}X_{13}$ GGKQALETVQRLLPVLCQTHG (SEQ ID NO: 373), LTQVQVVAIAS $X_{12}X_{13}$ GGKQALETVQRLLPVLCQAHG (SEQ ID NO: 374), LTPDQVVAIAS $X_{12}X_{13}$ GGKQALETVQRLLPVLCEQHG (SEQ ID NO: 376), LTPAQVVAIAS $X_{12}X_{13}$ GGKQALETVQQLLPVLCEQHG (SEQ ID NO: 377), LTPAQVVAIAS $X_{12}X_{13}$ GGKQALETVQRLLPVLCEQHG (SEQ ID NO: 378), LTPDQVVAIAS $X_{12}X_{13}$ GGRPALETVQRLLPVLCEQHG (SEQ ID NO: 379), LTPAQVVAIAS $X_{12}X_{13}$ GGKQALKTVQQLLPVLCEQHG (SEQ ID NO: 380), LTPDQVVAIAS $X_{12}X_{13}$ GGKQALERVQRLLPVLCEQHG (SEQ ID NO: 381), LTRAQVVAIAS $X_{12}X_{13}$ GGKQALETVQRLLPVLCEQHG (SEQ ID NO: 382), LTLDQVVAIAS $X_{12}X_{13}$ GGKQALETVQRLLPVL- CEQHG (SEQ ID NO: 383), LTPAQVVTIAS $X_{12}X_{13}$ GGKQALETVQRLLPVLCEQHG (SEQ ID NO: 384), LTPQQVVAIAS $X_{12}X_{13}$ GGKQALETVQRLLPVL-CEQHG (SEQ ID NO: 385), LTPAQVVAIAS $X_{12}X_{13}$ GGKPALETVQRLLPVLCEQHG (SEQ ID NO: 386), LTPDQVVAIAS $X_{12}X_{13}$ GGRQALETVQRLLPVL-CEQHG (SEQ ID NO: 387), LTPDQVVAIAS $X_{12}X_{13}$ GGKPALETVQRLLPVLCEQHG (SEQ ID NO: 388), LTPDQVVAIAS $X_{12}X_{13}$ GGKQALETVQRLLPVL-CRDHG (SEQ ID NO: 389), and LTPAQVVAIAS $X_{12}X_{13}$ GGKQALETVQRLLPVLCRDHG (SEQ ID NO: 390).

8. The method according to any one of claims 1-4, wherein the sequence $X_{1-11}$-$X_{12}X_{13}$-$X_{14\text{-}33 \text{ or } 34 \text{ or } 35}$ is LTLTQVVA-IAS $X_{12}X_{13}$ GGKQALETVQRLLPVLCQAHG (SEQ ID NO: 375).

9. The method according to claim 5, wherein the sequence $X_{1-11}$-$X_{12}X_{13}$-$X_{14\text{-}33 \text{ or } 34 \text{ or } 35}$ is LTLTQVVAIAS $X_{12}X_{13}$ GGKQALETVQRLLPVLCQAHG (SEQ ID NO: 375).

10. The method according to claim 6, wherein the sequence $X_{1-11}$-$X_{12}X_{13}$-$X_{14\text{-}33 \text{ or } 34 \text{ or } 35}$ is LTLTQVVAIAS $X_{12}X_{13}$ GGKQALETVQRLLPVLCQAHG (SEQ ID NO: 375).

11. A non-naturally occurring or engineered composition comprising a deoxyribonucleic acid (DNA) binding polypeptide comprising:
   (a) a N-terminal capping region
   (b) a DNA binding domain comprising at least 5 to 40 Transcription activator-like effector (TALE) monomers and at least one or more half-monomers specifically ordered to target the genomic locus of interest, and
   (c) a C-terminal capping region
   wherein (a), (b) and (c) are arranged in a predetermined N-terminus to C-terminus orientation,
   wherein the genomic locus comprises a target DNA sequence 5'-$T_0N_1N_2...N_zN_{z+1}$-3', where $T_0$ and N=A, G, T or C,
   wherein the target DNA sequence binds to the DNA binding domain, and the DNA binding domain comprises $(X_{1-11}$-$X_{12}X_{13}$-$X_{14\text{-}33 \text{ or } 34 \text{ or } 35})_z$,
   wherein $X_{1-11}$ is a chain of 11 contiguous amino acids,
   wherein $X_{12}X_{13}$ is a repeat variable diresidue (RVD),
   wherein $X_{14\text{-}33 \text{ or } 34 \text{ or } 35}$ is a chain of 21, 22 or 23 contiguous amino acids,
   wherein z is at least 5 to 40,
   wherein at least one RVD is selected from the group consisting of (a) HH, KH, NH, NK, NQ, RH, RN, SS, NN, SN, KN for recognition of guanine (G); (b) NI, KI, RI, HI, SI for recognition of adenine (A); (c) NG, HG, KG, RG for recognition of thymine (T); (d) RD, SD, HD, ND, KD, YG for recognition of cytosine (C); (e) NV, HN for recognition of A or G; and (f) H*, HA, KA, N*, NA, NC, NS, RA, S* for recognition of A or T or G or C, wherein (*) means that the amino acid at $X_{13}$ is absent,
   wherein the polypeptide is encoded by and translated from a codon optimized nucleic acid molecule so that the polypeptide preferentially binds to DNA of a genomic locus of interest comprising a coding or regulatory sequence susceptible to repression by a repressor domain or a fragment thereof having activity of a repressor in a cell, and
   wherein repressing expression of the genomic locus comprises a decrease in transcript level corresponding to the genomic locus of interest in the cell contacted with the polypeptide as compared to a control cell in which the genomic locus of interest is contacted with a control polypeptide that does not have at least one or more repressor domains or a fragment thereof.

12. The composition of claim 11, wherein the cell is a mammalian cell.

13. The composition according to claim 11, wherein
   the N-terminal capping region or fragment thereof comprises 147 contiguous amino acids of a wild type N-terminal capping region, or
   the C-terminal capping region or fragment thereof comprises 68 contiguous amino acids of a wild type C-terminal capping region, or
   the N-terminal capping region or fragment thereof comprises 136 contiguous amino acids of a wild type N-terminal capping region and the C-terminal capping region or fragment thereof comprises 183 contiguous amino acids of a wild type C-terminal capping region.

14. The composition according to claim 12, wherein
   the N-terminal capping region or fragment thereof comprises 147 contiguous amino acids of a wild type N-terminal capping region, or
   the C-terminal capping region or fragment thereof comprises 68 contiguous amino acids of a wild type C-terminal capping region, or
   the N-terminal capping region or fragment thereof comprises 136 contiguous amino acids of a wild type N-terminal capping region and the C-terminal capping region or fragment thereof comprises 183 contiguous amino acids of a wild type C-terminal capping region.

15. The composition according to claim 11, wherein at least one RVD is selected from the group consisting of (a) HH, KH, NH, NK, NQ, RH, RN, SS for recognition of guanine (G); (b) SI for recognition of adenine (A); (c) HG, KG, RG for recognition of thymine (T); (d) RD, SD for recognition of cytosine (C); (e) NV, HN for recognition of A or G and (f) H*, HA, KA, N*, NA, NC, NS, RA, S* for recognition of A or T or G or C, wherein (*) means that the amino acid at $X_{13}$ is absent.

16. The composition according to claim 15, wherein
   the RVD for the recognition of G is RN, NH, RH or KH; or
   the RVD for the recognition of A is SI; or
   the RVD for the recognition of T is KG or RG; and
   the RVD for the recognition of C is SD or RD.

17. The composition according to any one of claim 11-14 or 15 or 16, wherein at least one of the following is present [LTLD] (SEQ ID NO: 1) or [LTLA] (SEQ ID NO: 2) or [LTQV] (SEQ ID NO: 3) at $X_{1-4}$, or [EQHG] (SEQ ID NO: 4) or [RDHG] (SEQ ID NO: 5) at positions $X_{30-33}$ or $X_{31-34}$ or $X_{32-35}$,
   wherein the sequence $X_{1-11}$-$X_{12}X_{13}$-$X_{14\text{-}33 \text{ or } 34 \text{ or } 35}$ is selected from the group consisting of: LTLDQVVAIAS $X_{12}X_{13}$ GGKQALETVQRLLPVLCQDHG (SEQ ID NO: 356), LTLDQVVAIAS $X_{12}X_{13}$ GGKQALETVQRLLPVLCQAHG (SEQ ID NO: 357), LTLDQVVAIAS $X_{12}X_{13}$ GSKQALETVQRLLPVL-CQDHG (SEQ ID NO: 358), LTLDQVVAIAS $X_{12}X_{13}$ GGKKALETVQRLLPVLCQDHG (SEQ ID NO: 359), LTLDKVVAIAS $X_{12}X_{13}$ GGKQALETVQRLLPVL-CQDHG (SEQ ID NO: 360), LTLDQVVAIAS $X_{12}X_{13}$ GSKQALETVQRLLPVLCQAHG (SEQ ID NO: 361), LTLDQVVAIAS $X_{12}X_{13}$ GGKQALETVQRLLPVL-CQARG (SEQ ID NO: 362), LTLDQVVAIAS $X_{12}X_{13}$ GGKQALETVQRLLPVLCEQHG (SEQ ID NO: 363), LTLDQVVAIAS $X_{12}X_{13}$ GGKQALETVQRLLPVL-CQTHG (SEQ ID NO: 364), LTLDQVAAIAS $X_{12}X_{13}$ GGKQALETVQRLLPVLCQAHG (SEQ ID NO: 365), LTLDQVVAIAS $X_{12}X_{13}$ GSKQALETVQRLLPVL-CQTHG (SEQ ID NO: 366), LTLDQVVAIAS $X_{12}X_{13}$ GGKQALETVQRLLPVLCQEHG (SEQ ID NO: 367), LTLDQVVSIAS $X_{12}X_{13}$ GGKQALETVQRLLPVL- CQDHG (SEQ ID NO: 368), LTLAQVVAIAS $X_{12}X_{13}$ GGKQALETVQRLLPVLCQAHG (SEQ ID NO: 369), LTLAQVVAIAS $X_{12}X_{13}$ GGKQALETVQRLLPVLCQDHG (SEQ ID NO: 370), LTLAQVVAIAN $X_{12}X_{13}$ GGKQALETVQRLLPVLCQAHG (SEQ ID NO: 371), LTLAQVVAIAN $X_{12}X_{13}$ GGKQALETVQRLLPVLCQDHG (SEQ ID NO: 372), LTLAQVVAIAS $X_{12}X_{13}$ GGKQALETVQRLLPVLCQTHG (SEQ ID NO: 373), LTQVQVVAIAS $X_{12}X_{13}$ GGKQALETVQRLLPVLCQAHG (SEQ ID NO: 374), LTPDQVVAIAS $X_{12}X_{13}$ GGKQALETVQRLLPVLCEQHG (SEQ ID NO: 376), LTPAQVVAIAS $X_{12}X_{13}$ GGKQALETVQQLLPVLCEQHG (SEQ ID NO: 377), LTPAQVVAIAS $X_{12}X_{13}$ GGKQALETVQRLLPVLCEQHG (SEQ ID NO: 378), LTPDQVVAIAS $X_{12}X_{13}$ GGRPALETVQRLLPVLCEQHG (SEQ ID NO: 379), LTPAQVVAIAS $X_{12}X_{13}$ GGKQALKTVQQLLPVLCEQHG (SEQ ID NO: 380), LTPDQVVAIAS $X_{12}X_{13}$ GGKQALERVQRLLPVLCEQHG (SEQ ID NO: 381), LTRAQVVAIAS $X_{12}X_{13}$ GGKQALETVQRLLPVLCEQHG (SEQ ID NO: 382), LTLDQVVAIAS $X_{12}X_{13}$ GGKQALETVQRLLPVLCEQHG (SEQ ID NO: 383), LTPAQVVTIAS $X_{12}X_{13}$ GGKQALETVQRLLPVLCEQHG (SEQ ID NO: 384), LTPQQVVAIAS $X_{12}X_{13}$ GGKQALETVQRLLPVLCEQHG (SEQ ID NO: 385), LTPAQVVAIAS $X_{12}X_{13}$ GGKPALETVQRLLPVLCEQHG (SEQ ID NO: 386), LTPDQVVAIAS $X_{12}X_{13}$ GGRQALETVQRLLPVLCEQHG (SEQ ID NO: 387), LTPDQVVAIAS $X_{12}X_{13}$ GGKPALETVQRLLPVLCEQHG (SEQ ID NO: 388), LTPDQVVAIAS $X_{12}X_{13}$ GGKQALETVQRLLPVLCRDHG (SEQ ID NO: 389), and LTPAQVVAIAS $X_{12}X_{13}$ GGKQALETVQRLLPVLCRDHG (SEQ ID NO: 390).

18. The composition according to any one of claims 11-14 wherein the sequence $X_{1-11}$-$X_{12}X_{13}$-$X_{14-33 \text{ or } 34 \text{ or } 35}$ is LTLTQVVAIAS $X_{12}X_{13}$ GGKQALETVQRLLPVLCQAHG (SEQ ID NO: 375).

19. The composition according to claim 15, wherein the sequence $X_{1-11}$-$X_{12}X_{13}$-$X_{14-33 \text{ or } 34 \text{ or } 35}$ is LTLTQVVAIAS $X_{12}X_{13}$ GGKQALETVQRLLPVLCQAHG (SEQ ID NO: 375).

20. The composition according to claim 16, wherein the sequence $X_{1-11}$-$X_{12}X_{13}$-$X_{14-33 \text{ or } 34 \text{ or } 35}$ is LTLTQVVAIAS $X_{12}X_{13}$ GGKQALETVQRLLPVLCQAHG (SEQ ID NO: 375).

* * * * *

SEQUENCE LISTING

```
<160> NUMBER OF SEQ ID NOS: 392

<210> SEQ ID NO 1
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 1

Leu Thr Leu Asp
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Thr Leu Ala
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Thr Gln Val
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Gln His Gly
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Asp His Gly
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Thr Pro Asp
1

<210> SEQ ID NO 7
```

-continued

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Gln Ala Leu Glu
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Arg Ala Leu Glu
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Thr Pro Glu
1

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Gly Lys Gln Ala Leu Glu
1               5

<210> SEQ ID NO 11
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid

<400> SEQUENCE: 11

Leu Thr Pro Ala Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 12
<211> LENGTH: 33
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Any amino acid

<400> SEQUENCE: 12

Leu Thr Pro Ala Gln Val Val Ala Ile Ala Ser Xaa Gly Gly Lys Gln
1               5                   10                  15

Ala Leu Glu Thr Val Gln Arg Leu Leu Pro Val Leu Cys Gln Asp His
            20                  25                  30

Gly

<210> SEQ ID NO 13
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid

<400> SEQUENCE: 13

Leu Thr Pro Asp Gln Val Val Ala Ile Ala Asn Xaa Xaa Gly Gly Lys
1               5                   10                  15

Gln Ala Leu Ala Thr Val Gln Arg Leu Leu Pro Val Leu Cys Gln Asp
            20                  25                  30

His Gly

<210> SEQ ID NO 14
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid

<400> SEQUENCE: 14

Leu Thr Pro Asp Gln Val Val Ala Ile Ala Asn Xaa Xaa Gly Gly Lys
1               5                   10                  15

Gln Ala Leu Glu Thr Leu Gln Arg Leu Leu Pro Val Leu Cys Gln Asp
            20                  25                  30

His Gly

<210> SEQ ID NO 15
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid

<400> SEQUENCE: 15
```

Leu Thr Pro Asp Gln Val Val Ala Ile Ala Asn Xaa Xaa Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid

<400> SEQUENCE: 16

Leu Thr Pro Asp Gln Val Val Ala Ile Ala Ser Xaa Xaa Gly Gly Lys
1               5                   10                  15

Gln Ala Leu Ala Thr Val Gln Arg Leu Leu Pro Val Leu Cys Gln Asp
            20                  25                  30

His Gly

<210> SEQ ID NO 17
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid

<400> SEQUENCE: 17

Leu Thr Pro Asp Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 18
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid

<400> SEQUENCE: 18

Leu Thr Pro Asp Gln Val Val Ala Ile Ala Ser Xaa Xaa Gly Gly Lys
1               5                   10                  15

Gln Ala Leu Glu Thr Val Gln Arg Val Leu Pro Val Leu Cys Gln Asp
            20                  25                  30

His Gly

<210> SEQ ID NO 19

```
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid

<400> SEQUENCE: 19

Leu Thr Pro Glu Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 20
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid

<400> SEQUENCE: 20

Leu Thr Pro Tyr Gln Val Val Ala Ile Ala Ser Xaa Xaa Gly Ser Lys
1               5                   10                  15

Gln Ala Leu Glu Thr Val Gln Arg Leu Leu Pro Val Leu Cys Gln Asp
            20                  25                  30

His Gly

<210> SEQ ID NO 21
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid

<400> SEQUENCE: 21

Leu Thr Arg Glu Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 22
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid
```

```
<400> SEQUENCE: 22

Leu Ser Thr Ala Gln Val Val Ala Ile Ala Ser Xaa Xaa Gly Gly Lys
1               5                   10                  15

Gln Ala Leu Glu Gly Ile Gly Glu Gln Leu Leu Lys Leu Arg Thr Ala
                20                  25                  30

Pro Tyr Gly
        35

<210> SEQ ID NO 23
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: Any amino acid

<400> SEQUENCE: 23

Leu Ser Thr Ala Gln Val Val Ala Val Ala Ser Xaa Xaa Gly Gly Lys
1               5                   10                  15

Pro Ala Leu Glu Ala Val Arg Ala Gln Leu Leu Ala Leu Arg Ala Ala
                20                  25                  30

Pro Tyr Gly
        35

<210> SEQ ID NO 24
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
                20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
                100                 105                 110

Ala Ala Asp Ala Pro Pro Pro Thr Met Arg Val Ala Val Thr Ala Ala
                115                 120                 125

Arg Pro Pro Arg Ala Lys Pro Ala Pro Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
```

```
                   180                 185                 190
Ile Val Ala Leu Ser Gln His Pro Ala Leu Gly Thr Val Ala Val
            195                 200                 205
Lys Tyr Gln Asp Met Ile Ala Ala Leu Pro Glu Ala Thr His Glu Ala
            210                 215                 220
Ile Val Gly Val Gly Lys Gln Trp Ser Gly Ala Arg Ala Leu Glu Ala
225                 230                 235                 240
Leu Leu Thr Val Ala Gly Glu Leu Arg Gly Pro Pro Leu Gln Leu Asp
                245                 250                 255
Thr Gly Gln Leu Leu Lys Ile Ala Lys Arg Gly Gly Val Thr Ala Val
            260                 265                 270
Glu Ala Val His Ala Trp Arg Asn Ala Leu Thr Gly Ala Pro Leu Asn
            275                 280                 285

<210> SEQ ID NO 25
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Arg Pro Ala Leu Glu Ser Ile Val Ala Gln Leu Ser Arg Pro Asp Pro
1               5                   10                  15
Ala Leu Ala Ala Leu Thr Asn Asp His Leu Val Ala Leu Ala Cys Leu
            20                  25                  30
Gly Gly Arg Pro Ala Leu Asp Ala Val Lys Lys Gly Leu Pro His Ala
        35                  40                  45
Pro Ala Leu Ile Lys Arg Thr Asn Arg Arg Ile Pro Glu Arg Thr Ser
    50                  55                  60
His Arg Val Ala Asp His Ala Gln Val Val Arg Val Leu Gly Phe Phe
65                  70                  75                  80
Gln Cys His Ser His Pro Ala Gln Ala Phe Asp Asp Ala Met Thr Gln
                85                  90                  95
Phe Gly Met Ser Arg His Gly Leu Leu Gln Leu Phe Arg Arg Val Gly
            100                 105                 110
Val Thr Glu Leu Glu Ala Arg Ser Gly Thr Leu Pro Pro Ala Ser Gln
        115                 120                 125
Arg Trp Asp Arg Ile Leu Gln Ala Ser Gly Met Lys Arg Ala Lys Pro
    130                 135                 140
Ser Pro Thr Ser Thr Gln Thr Pro Asp Gln Ala Ser Leu His Ala Phe
145                 150                 155                 160
Ala Asp Ser Leu Glu Arg Asp Leu Asp Ala Pro Ser Pro Met His Glu
                165                 170                 175
Gly Asp Gln Thr Arg Ala Ser
            180

<210> SEQ ID NO 26
<211> LENGTH: 11
<212> TYPE: PRT
<213> ORGANISM: Human immunodeficiency virus

<400> SEQUENCE: 26

Tyr Gly Arg Lys Lys Arg Arg Gln Arg Arg Arg
1               5                   10

<210> SEQ ID NO 27
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 27

His His His His His His
1               5

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tgaagcactt actttagaaa                                                    20

<210> SEQ ID NO 29
<211> LENGTH: 955
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Gln Glu Lys Ile Lys Pro Lys Val Arg Ser Thr Val
        115                 120                 125

Ala Gln His His Glu Ala Leu Val Gly His Gly Phe Thr His Ala His
    130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
        195                 200                 205

Thr Gly Gln Leu Leu Lys Ile Ala Lys Arg Gly Gly Val Thr Ala Val
    210                 215                 220

Glu Ala Val His Ala Trp Arg Asn Ala Leu Thr Gly Ala Pro Leu Asn
225                 230                 235                 240
```

```
Leu Thr Pro Glu Gln Val Val Ala Ile Ala Ser Asn Gly Gly Lys
            245                 250                 255

Gln Ala Leu Glu Thr Val Gln Arg Leu Leu Pro Val Leu Cys Gln Ala
        260                 265                 270

His Gly Leu Thr Pro Glu Gln Val Val Ala Ile Ala Ser Asn Gly Gly
            275                 280                 285

Gly Lys Gln Ala Leu Glu Thr Val Gln Arg Leu Leu Pro Val Leu Cys
290                 295                 300

Gln Ala His Gly Leu Thr Pro Glu Gln Val Val Ala Ile Ala Ser Asn
305                 310                 315                 320

Ile Gly Gly Lys Gln Ala Leu Glu Thr Val Gln Arg Leu Leu Pro Val
            325                 330                 335

Leu Cys Gln Ala His Gly Leu Thr Pro Glu Gln Val Val Ala Ile Ala
            340                 345                 350

Ser Asn Gly Gly Lys Gln Ala Leu Glu Thr Val Gln Arg Leu Leu
            355                 360                 365

Pro Val Leu Cys Gln Ala His Gly Leu Thr Pro Glu Gln Val Val Ala
        370                 375                 380

Ile Ala Ser Asn Gly Gly Lys Gln Ala Leu Glu Thr Val Gln Arg
385                 390                 395                 400

Leu Leu Pro Val Leu Cys Gln Ala His Gly Leu Thr Pro Glu Gln Val
            405                 410                 415

Val Ala Ile Ala Ser His Asp Gly Gly Lys Gln Ala Leu Glu Thr Val
            420                 425                 430

Gln Arg Leu Leu Pro Val Leu Cys Gln Ala His Gly Leu Thr Pro Glu
        435                 440                 445

Gln Val Val Ala Ile Ala Ser His Asp Gly Gly Lys Gln Ala Leu Glu
        450                 455                 460

Thr Val Gln Arg Leu Leu Pro Val Leu Cys Gln Ala His Gly Leu Thr
465                 470                 475                 480

Pro Glu Gln Val Val Ala Ile Ala Ser His Asp Gly Gly Lys Gln Ala
            485                 490                 495

Leu Glu Thr Val Gln Arg Leu Leu Pro Val Leu Cys Gln Ala His Gly
            500                 505                 510

Leu Thr Pro Glu Gln Val Val Ala Ile Ala Ser Asn Gly Gly Lys
            515                 520                 525

Gln Ala Leu Glu Thr Val Gln Arg Leu Leu Pro Val Leu Cys Gln Ala
        530                 535                 540

His Gly Leu Thr Pro Glu Gln Val Val Ala Ile Ala Ser Asn Asn Gly
545                 550                 555                 560

Gly Lys Gln Ala Leu Glu Thr Val Gln Arg Leu Leu Pro Val Leu Cys
            565                 570                 575

Gln Ala His Gly Leu Thr Pro Glu Gln Val Val Ala Ile Ala Ser Asn
            580                 585                 590

Ile Gly Gly Lys Gln Ala Leu Glu Thr Val Gln Arg Leu Leu Pro Val
            595                 600                 605

Leu Cys Gln Ala His Gly Leu Thr Pro Glu Gln Val Val Ala Ile Ala
            610                 615                 620

Ser His Asp Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
            645                 650                 655

Ile Ala Ser Asn Ile Gly Gly Arg Pro Ala Leu Glu Ser Ile Val Ala
```

```
                        660                 665                 670
Gln Leu Ser Arg Pro Asp Pro Ala Leu Ala Ala Leu Thr Asn Asp His
            675                 680                 685

Leu Val Ala Leu Ala Cys Leu Gly Gly Arg Pro Ala Leu Asp Ala Val
        690                 695                 700

Lys Lys Gly Leu Pro His Ala Pro Ala Leu Ile Lys Arg Thr Asn Arg
705                 710                 715                 720

Arg Ile Pro Glu Arg Thr Ser His Arg Val Ala Asp His Ala Gln Val
                725                 730                 735

Val Arg Val Leu Gly Phe Phe Gln Cys His Ser His Pro Ala Gln Ala
            740                 745                 750

Phe Asp Asp Ala Met Thr Gln Phe Gly Met Ser Arg His Gly Leu Leu
        755                 760                 765

Gln Leu Phe Arg Arg Val Gly Val Thr Glu Leu Glu Ala Arg Ser Gly
    770                 775                 780

Thr Leu Pro Pro Ala Ser Gln Arg Trp Asp Arg Ile Leu Gln Ala Ser
785                 790                 795                 800

Gly Met Lys Arg Ala Lys Pro Ser Pro Thr Ser Thr Gln Thr Pro Asp
                805                 810                 815

Gln Ala Ser Leu His Ala Phe Ala Asp Ser Leu Glu Arg Asp Leu Asp
            820                 825                 830

Ala Pro Ser Pro Met His Glu Gly Asp Gln Thr Arg Ala Ser Ala Ser
        835                 840                 845

Pro Lys Lys Lys Arg Lys Val Glu Ala Ser Met Asp Ala Lys Ser Leu
    850                 855                 860

Thr Ala Trp Ser Arg Thr Leu Val Thr Phe Lys Asp Val Phe Val Asp
865                 870                 875                 880

Phe Thr Arg Glu Glu Trp Lys Leu Leu Asp Thr Ala Gln Gln Ile Val
                885                 890                 895

Tyr Arg Asn Val Met Leu Glu Asn Tyr Lys Asn Leu Val Ser Leu Gly
            900                 905                 910

Tyr Gln Leu Thr Lys Pro Asp Val Ile Leu Arg Leu Glu Lys Gly Glu
        915                 920                 925

Glu Pro Trp Leu Val Glu Arg Glu Ile His Gln Glu Thr His Pro Asp
    930                 935                 940

Ser Glu Thr Ala Phe Glu Ile Lys Ser Ser Val
945                 950                 955

<210> SEQ ID NO 30
<211> LENGTH: 933
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Pro Thr Met Arg Val Ala Val Thr Ala Ala
```

-continued

```
                65                  70                  75                  80
Arg Pro Pro Arg Ala Lys Pro Ala Pro Arg Arg Ala Ala Gln Pro
                    85                  90                  95

Ser Asp Ala Ser Pro Ala Ala Gln Val Asp Leu Arg Thr Leu Gly Tyr
                    100                 105                 110

Ser Gln Gln Gln Glu Lys Ile Lys Pro Lys Val Arg Ser Thr Val
                115                 120                 125

Ala Gln His His Glu Ala Leu Val Gly His Gly Phe Thr His Ala His
            130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
                180                 185                 190

Leu Leu Thr Val Ala Gly Glu Leu Arg Gly Pro Pro Leu Gln Leu Asp
                195                 200                 205

Thr Gly Gln Leu Leu Lys Ile Ala Lys Arg Gly Gly Val Thr Ala Val
210                 215                 220

Glu Ala Val His Ala Trp Arg Asn Ala Leu Thr Gly Ala Pro Leu Asn
225                 230                 235                 240

Leu Thr Pro Glu Gln Val Val Ala Ile Ala Ser Asn Gly Gly Gly Lys
                245                 250                 255

Gln Ala Leu Glu Thr Val Gln Arg Leu Leu Pro Val Leu Cys Gln Ala
                260                 265                 270

His Gly Leu Thr Pro Glu Gln Val Val Ala Ile Ala Ser Asn Gly Gly
            275                 280                 285

Gly Lys Gln Ala Leu Glu Thr Val Gln Arg Leu Leu Pro Val Leu Cys
        290                 295                 300

Gln Ala His Gly Leu Thr Pro Glu Gln Val Val Ala Ile Ala Ser Asn
305                 310                 315                 320

Ile Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
                340                 345                 350

Ser Asn Gly Gly Gly Lys Gln Ala Leu Glu Thr Val Gln Arg Leu Leu
                355                 360                 365

Pro Val Leu Cys Gln Ala His Gly Leu Thr Pro Glu Gln Val Val Ala
            370                 375                 380

Ile Ala Ser Asn Gly Gly Gly Lys Gln Ala Leu Glu Thr Val Gln Arg
385                 390                 395                 400

Leu Leu Pro Val Leu Cys Gln Ala His Gly Leu Thr Pro Glu Gln Val
                405                 410                 415

Val Ala Ile Ala Ser His Asp Gly Gly Lys Gln Ala Leu Glu Thr Val
                420                 425                 430

Gln Arg Leu Leu Pro Val Leu Cys Gln Ala His Gly Leu Thr Pro Glu
                435                 440                 445

Gln Val Val Ala Ile Ala Ser His Asp Gly Gly Lys Gln Ala Leu Glu
            450                 455                 460

Thr Val Gln Arg Leu Leu Pro Val Leu Cys Gln Ala His Gly Leu Thr
465                 470                 475                 480

Pro Glu Gln Val Val Ala Ile Ala Ser His Asp Gly Gly Lys Gln Ala
                485                 490                 495
```

```
Leu Glu Thr Val Gln Arg Leu Leu Pro Val Leu Cys Gln Ala His Gly
            500                 505                 510

Leu Thr Pro Glu Gln Val Val Ala Ile Ala Ser Asn Gly Gly Lys
        515                 520                 525

Gln Ala Leu Glu Thr Val Gln Arg Leu Leu Pro Val Leu Cys Gln Ala
530                 535                 540

His Gly Leu Thr Pro Glu Gln Val Val Ala Ile Ala Ser Asn Asn Gly
545                 550                 555                 560

Gly Lys Gln Ala Leu Glu Thr Val Gln Arg Leu Leu Pro Val Leu Cys
                565                 570                 575

Gln Ala His Gly Leu Thr Pro Glu Gln Val Val Ala Ile Ala Ser Asn
            580                 585                 590

Ile Gly Gly Lys Gln Ala Leu Glu Thr Val Gln Arg Leu Leu Pro Val
        595                 600                 605

Leu Cys Gln Ala His Gly Leu Thr Pro Glu Gln Val Val Ala Ile Ala
    610                 615                 620

Ser His Asp Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
                645                 650                 655

Ile Ala Ser Asn Ile Gly Gly Arg Pro Ala Leu Glu Ser Ile Val Ala
            660                 665                 670

Gln Leu Ser Arg Pro Asp Pro Ala Leu Ala Ala Leu Thr Asn Asp His
        675                 680                 685

Leu Val Ala Leu Ala Cys Leu Gly Gly Arg Pro Ala Leu Asp Ala Val
    690                 695                 700

Lys Lys Gly Leu Pro His Ala Pro Ala Leu Ile Lys Arg Thr Asn Arg
705                 710                 715                 720

Arg Ile Pro Glu Arg Thr Ser His Arg Val Ala Asp His Ala Gln Val
                725                 730                 735

Val Arg Val Leu Gly Phe Phe Gln Cys His Ser His Pro Ala Gln Ala
            740                 745                 750

Phe Asp Asp Ala Met Thr Gln Phe Gly Met Ser Arg His Gly Leu Leu
        755                 760                 765

Gln Leu Phe Arg Arg Val Gly Val Thr Glu Leu Glu Ala Arg Ser Gly
    770                 775                 780

Thr Leu Pro Pro Ala Ser Gln Arg Trp Asp Arg Ile Leu Gln Ala Ser
785                 790                 795                 800

Gly Met Lys Arg Ala Lys Pro Ser Pro Thr Ser Thr Gln Thr Pro Asp
                805                 810                 815

Gln Ala Ser Leu His Ala Phe Ala Asp Ser Leu Glu Arg Asp Leu Asp
            820                 825                 830

Ala Pro Ser Pro Met His Glu Gly Asp Gln Thr Arg Ala Ser Ala Ser
        835                 840                 845

Pro Lys Lys Lys Arg Lys Val Glu Ala Ser Met Asp Ala Lys Ser Leu
    850                 855                 860

Thr Ala Trp Ser Arg Thr Leu Val Thr Phe Lys Asp Val Phe Val Asp
865                 870                 875                 880

Phe Thr Arg Glu Glu Trp Lys Leu Leu Asp Thr Ala Gln Gln Ile Val
                885                 890                 895

Tyr Arg Asn Val Met Leu Glu Asn Tyr Lys Asn Leu Val Ser Leu Gly
            900                 905                 910

Tyr Gln Leu Thr Lys Pro Asp Val Ile Leu Arg Leu Glu Lys Gly Glu
        915                 920                 925
```

```
Glu Pro Trp Leu Val
    930

<210> SEQ ID NO 31
<211> LENGTH: 923
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Gln Glu Lys Ile Lys Pro Lys Val Arg Ser Thr Val
            115                 120                 125

Ala Gln His His Glu Ala Leu Val Gly His Gly Phe Thr His Ala His
    130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
        195                 200                 205

Thr Gly Gln Leu Leu Lys Ile Ala Lys Arg Gly Gly Val Thr Ala Val
    210                 215                 220

Glu Ala Val His Ala Trp Arg Asn Ala Leu Thr Gly Ala Pro Leu Asn
225                 230                 235                 240

Leu Thr Pro Glu Gln Val Val Ala Ile Ala Ser Asn Gly Gly Gly Lys
                245                 250                 255

Gln Ala Leu Glu Thr Val Gln Arg Leu Leu Pro Val Leu Cys Gln Ala
            260                 265                 270

His Gly Leu Thr Pro Glu Gln Val Val Ala Ile Ala Ser Asn Gly Gly
        275                 280                 285

Gly Lys Gln Ala Leu Glu Thr Val Gln Arg Leu Leu Pro Val Leu Cys
    290                 295                 300

Gln Ala His Gly Leu Thr Pro Glu Gln Val Val Ala Ile Ala Ser Asn
305                 310                 315                 320

Ile Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
            340                 345                 350
```

```
Ser Asn Gly Gly Gly Lys Gln Ala Leu Glu Thr Val Gln Arg Leu Leu
        355                 360                 365

Pro Val Leu Cys Gln Ala His Gly Leu Thr Pro Glu Gln Val Val Ala
    370                 375                 380

Ile Ala Ser Asn Gly Gly Lys Gln Ala Leu Glu Thr Val Gln Arg
385                 390                 395                 400

Leu Leu Pro Val Leu Cys Gln Ala His Gly Leu Thr Pro Glu Gln Val
                405                 410                 415

Val Ala Ile Ala Ser His Asp Gly Gly Lys Gln Ala Leu Glu Thr Val
            420                 425                 430

Gln Arg Leu Leu Pro Val Leu Cys Gln Ala His Gly Leu Thr Pro Glu
        435                 440                 445

Gln Val Val Ala Ile Ala Ser His Asp Gly Gly Lys Gln Ala Leu Glu
    450                 455                 460

Thr Val Gln Arg Leu Leu Pro Val Leu Cys Gln Ala His Gly Leu Thr
465                 470                 475                 480

Pro Glu Gln Val Val Ala Ile Ala Ser His Asp Gly Gly Lys Gln Ala
                485                 490                 495

Leu Glu Thr Val Gln Arg Leu Leu Pro Val Leu Cys Gln Ala His Gly
            500                 505                 510

Leu Thr Pro Glu Gln Val Val Ala Ile Ala Ser Asn Gly Gly Gly Lys
        515                 520                 525

Gln Ala Leu Glu Thr Val Gln Arg Leu Leu Pro Val Leu Cys Gln Ala
    530                 535                 540

His Gly Leu Thr Pro Glu Gln Val Val Ala Ile Ala Ser Asn Asn Gly
545                 550                 555                 560

Gly Lys Gln Ala Leu Glu Thr Val Gln Arg Leu Leu Pro Val Leu Cys
                565                 570                 575

Gln Ala His Gly Leu Thr Pro Glu Gln Val Val Ala Ile Ala Ser Asn
            580                 585                 590

Ile Gly Gly Lys Gln Ala Leu Glu Thr Val Gln Arg Leu Leu Pro Val
        595                 600                 605

Leu Cys Gln Ala His Gly Leu Thr Pro Glu Gln Val Val Ala Ile Ala
    610                 615                 620

Ser His Asp Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
                645                 650                 655

Ile Ala Ser Asn Ile Gly Gly Arg Pro Ala Leu Glu Ser Ile Val Ala
            660                 665                 670

Gln Leu Ser Arg Pro Asp Pro Ala Leu Ala Ala Leu Thr Asn Asp His
        675                 680                 685

Leu Val Ala Leu Ala Cys Leu Gly Gly Arg Pro Ala Leu Asp Ala Val
    690                 695                 700

Lys Lys Gly Leu Pro His Ala Pro Ala Leu Ile Lys Arg Thr Asn Arg
705                 710                 715                 720

Arg Ile Pro Glu Arg Thr Ser His Arg Val Ala Asp His Ala Gln Val
                725                 730                 735

Val Arg Val Leu Gly Phe Phe Gln Cys His Ser His Pro Ala Gln Ala
            740                 745                 750

Phe Asp Asp Ala Met Thr Gln Phe Gly Met Ser Arg His Gly Leu Leu
        755                 760                 765

Gln Leu Phe Arg Arg Val Gly Val Thr Glu Leu Glu Ala Arg Ser Gly
```

```
            770                 775                 780
Thr Leu Pro Pro Ala Ser Gln Arg Trp Asp Arg Ile Leu Gln Ala Ser
785                 790                 795                 800

Gly Met Lys Arg Ala Lys Pro Ser Pro Thr Ser Thr Gln Thr Pro Asp
                805                 810                 815

Gln Ala Ser Leu His Ala Phe Ala Asp Ser Leu Glu Arg Asp Leu Asp
                820                 825                 830

Ala Pro Ser Pro Met His Glu Gly Asp Gln Thr Arg Ala Ser Ala Ser
                835                 840                 845

Pro Lys Lys Lys Arg Lys Val Glu Ala Ser Arg Thr Leu Val Thr Phe
            850                 855                 860

Lys Asp Val Phe Val Asp Phe Thr Arg Glu Glu Trp Lys Leu Leu Asp
865                 870                 875                 880

Thr Ala Gln Gln Ile Val Tyr Arg Asn Val Met Leu Glu Asn Tyr Lys
                885                 890                 895

Asn Leu Val Ser Leu Gly Tyr Gln Leu Thr Lys Pro Asp Val Ile Leu
                900                 905                 910

Arg Leu Glu Lys Gly Glu Glu Pro Trp Leu Val
            915                 920

<210> SEQ ID NO 32
<211> LENGTH: 887
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
                20                  25                  30

Phe Asn Thr Ser Leu Phe Asp Ser Leu Pro Pro Phe Gly Ala His His
            35                  40                  45

Thr Glu Ala Ala Thr Gly Glu Trp Asp Glu Val Gln Ser Gly Leu Arg
        50                  55                  60

Ala Ala Asp Ala Pro Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
                100                 105                 110

Ser Gln Gln Gln Gln Glu Lys Ile Lys Pro Lys Val Arg Ser Thr Val
            115                 120                 125

Ala Gln His His Glu Ala Leu Val Gly His Gly Phe Thr His Ala His
        130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
        195                 200                 205

Thr Gly Gln Leu Leu Lys Ile Ala Lys Arg Gly Gly Val Thr Ala Val
```

```
                210                 215                 220
Glu Ala Val His Ala Trp Arg Asn Ala Leu Thr Gly Ala Pro Leu Asn
225                 230                 235                 240

Leu Thr Pro Glu Gln Val Val Ala Ile Ala Ser Asn Gly Gly Gly Lys
                245                 250                 255

Gln Ala Leu Glu Thr Val Gln Arg Leu Leu Pro Val Leu Cys Gln Ala
                260                 265                 270

His Gly Leu Thr Pro Glu Gln Val Val Ala Ile Ala Ser Asn Gly Gly
                275                 280                 285

Gly Lys Gln Ala Leu Glu Thr Val Gln Arg Leu Leu Pro Val Leu Cys
290                 295                 300

Gln Ala His Gly Leu Thr Pro Glu Gln Val Val Ala Ile Ala Ser Asn
305                 310                 315                 320

Ile Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
                340                 345                 350

Ser Asn Gly Gly Gly Lys Gln Ala Leu Glu Thr Val Gln Arg Leu Leu
                355                 360                 365

Pro Val Leu Cys Gln Ala His Gly Leu Thr Pro Glu Gln Val Val Ala
370                 375                 380

Ile Ala Ser Asn Gly Gly Gly Lys Gln Ala Leu Glu Thr Val Gln Arg
385                 390                 395                 400

Leu Leu Pro Val Leu Cys Gln Ala His Gly Leu Thr Pro Glu Gln Val
                405                 410                 415

Val Ala Ile Ala Ser His Asp Gly Gly Lys Gln Ala Leu Glu Thr Val
                420                 425                 430

Gln Arg Leu Leu Pro Val Leu Cys Gln Ala His Gly Leu Thr Pro Glu
                435                 440                 445

Gln Val Val Ala Ile Ala Ser His Asp Gly Gly Lys Gln Ala Leu Glu
                450                 455                 460

Thr Val Gln Arg Leu Leu Pro Val Leu Cys Gln Ala His Gly Leu Thr
465                 470                 475                 480

Pro Glu Gln Val Val Ala Ile Ala Ser His Asp Gly Gly Lys Gln Ala
                485                 490                 495

Leu Glu Thr Val Gln Arg Leu Leu Pro Val Leu Cys Gln Ala His Gly
                500                 505                 510

Leu Thr Pro Glu Gln Val Val Ala Ile Ala Ser Asn Gly Gly Gly Lys
                515                 520                 525

Gln Ala Leu Glu Thr Val Gln Arg Leu Leu Pro Val Leu Cys Gln Ala
530                 535                 540

His Gly Leu Thr Pro Glu Gln Val Val Ala Ile Ala Ser Asn Asn Gly
545                 550                 555                 560

Gly Lys Gln Ala Leu Glu Thr Val Gln Arg Leu Leu Pro Val Leu Cys
                565                 570                 575

Gln Ala His Gly Leu Thr Pro Glu Gln Val Val Ala Ile Ala Ser Asn
                580                 585                 590

Ile Gly Gly Lys Gln Ala Leu Glu Thr Val Gln Arg Leu Leu Pro Val
                595                 600                 605

Leu Cys Gln Ala His Gly Leu Thr Pro Glu Gln Val Val Ala Ile Ala
                610                 615                 620

Ser His Asp Gly Gly Lys Gln Ala Leu Glu Thr Val Gln Arg Leu Leu
625                 630                 635                 640
```

```
Pro Val Leu Cys Gln Ala His Gly Leu Thr Pro Glu Gln Val Val Ala
            645                 650                 655

Ile Ala Ser Asn Ile Gly Gly Arg Pro Ala Leu Glu Ser Ile Val Ala
        660                 665                 670

Gln Leu Ser Arg Pro Asp Pro Ala Leu Ala Ala Leu Thr Asn Asp His
    675                 680                 685

Leu Val Ala Leu Ala Cys Leu Gly Gly Arg Pro Ala Leu Asp Ala Val
690                 695                 700

Lys Lys Gly Leu Pro His Ala Pro Ala Leu Ile Lys Arg Thr Asn Arg
705                 710                 715                 720

Arg Ile Pro Glu Arg Thr Ser His Arg Val Ala Asp His Ala Gln Val
                725                 730                 735

Val Arg Val Leu Gly Phe Phe Gln Cys His Ser His Pro Ala Gln Ala
            740                 745                 750

Phe Asp Asp Ala Met Thr Gln Phe Gly Met Ser Arg His Gly Leu Leu
        755                 760                 765

Gln Leu Phe Arg Arg Val Gly Val Thr Glu Leu Glu Ala Arg Ser Gly
    770                 775                 780

Thr Leu Pro Pro Ala Ser Gln Arg Trp Asp Arg Ile Leu Gln Ala Ser
785                 790                 795                 800

Gly Met Lys Arg Ala Lys Pro Ser Pro Thr Ser Thr Gln Thr Pro Asp
                805                 810                 815

Gln Ala Ser Leu His Ala Phe Ala Asp Ser Leu Glu Arg Asp Leu Asp
            820                 825                 830

Ala Pro Ser Pro Met His Glu Gly Asp Gln Thr Arg Ala Ser Ala Ser
        835                 840                 845

Pro Lys Lys Lys Arg Lys Val Glu Ala Ser Met Asn Ile Gln Met Leu
    850                 855                 860

Leu Glu Ala Ala Asp Tyr Leu Glu Arg Glu Arg Glu Ala Glu His
865                 870                 875                 880

Gly Tyr Ala Ser Met Leu Pro
                885

<210> SEQ ID NO 33
<211> LENGTH: 990
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Ser Arg Thr Arg Leu Pro Ser Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
            100                 105                 110
```

```
Ser Gln Gln Gln Gln Glu Lys Ile Lys Pro Lys Val Arg Ser Thr Val
        115                 120                 125
Ala Gln His His Glu Ala Leu Val Gly His Gly Phe Thr His Ala His
    130                 135                 140
Ile Val Ala Leu Ser Gln His Pro Ala Ala Leu Gly Thr Val Ala Val
145                 150                 155                 160
Lys Tyr Gln Asp Met Ile Ala Ala Leu Pro Glu Ala Thr His Glu Ala
                165                 170                 175
Ile Val Gly Val Gly Lys Gln Trp Ser Gly Ala Arg Ala Leu Glu Ala
                180                 185                 190
Leu Leu Thr Val Ala Gly Glu Leu Arg Gly Pro Leu Gln Leu Asp
        195                 200                 205
Thr Gly Gln Leu Leu Lys Ile Ala Lys Arg Gly Gly Val Thr Ala Val
    210                 215                 220
Glu Ala Val His Ala Trp Arg Asn Ala Leu Thr Gly Ala Pro Leu Asn
225                 230                 235                 240
Leu Thr Pro Glu Gln Val Val Ala Ile Ala Ser Asn Gly Gly Gly Lys
                245                 250                 255
Gln Ala Leu Glu Thr Val Gln Arg Leu Leu Pro Val Leu Cys Gln Ala
        260                 265                 270
His Gly Leu Thr Pro Glu Gln Val Val Ala Ile Ala Ser Asn Gly Gly
    275                 280                 285
Gly Lys Gln Ala Leu Glu Thr Val Gln Arg Leu Leu Pro Val Leu Cys
290                 295                 300
Gln Ala His Gly Leu Thr Pro Glu Gln Val Val Ala Ile Ala Ser Asn
305                 310                 315                 320
Ile Gly Gly Lys Gln Ala Leu Glu Thr Val Gln Arg Leu Leu Pro Val
                325                 330                 335
Leu Cys Gln Ala His Gly Leu Thr Pro Glu Gln Val Val Ala Ile Ala
        340                 345                 350
Ser Asn Gly Gly Gly Lys Gln Ala Leu Glu Thr Val Gln Arg Leu Leu
    355                 360                 365
Pro Val Leu Cys Gln Ala His Gly Leu Thr Pro Glu Gln Val Val Ala
370                 375                 380
Ile Ala Ser Asn Gly Gly Gly Lys Gln Ala Leu Glu Thr Val Gln Arg
385                 390                 395                 400
Leu Leu Pro Val Leu Cys Gln Ala His Gly Leu Thr Pro Glu Gln Val
                405                 410                 415
Val Ala Ile Ala Ser His Asp Gly Gly Lys Gln Ala Leu Glu Thr Val
        420                 425                 430
Gln Arg Leu Leu Pro Val Leu Cys Gln Ala His Gly Leu Thr Pro Glu
    435                 440                 445
Gln Val Val Ala Ile Ala Ser His Asp Gly Gly Lys Gln Ala Leu Glu
450                 455                 460
Thr Val Gln Arg Leu Leu Pro Val Leu Cys Gln Ala His Gly Leu Thr
465                 470                 475                 480
Pro Glu Gln Val Val Ala Ile Ala Ser His Asp Gly Gly Lys Gln Ala
                485                 490                 495
Leu Glu Thr Val Gln Arg Leu Leu Pro Val Leu Cys Gln Ala His Gly
        500                 505                 510
Leu Thr Pro Glu Gln Val Val Ala Ile Ala Ser Asn Gly Gly Gly Lys
    515                 520                 525
Gln Ala Leu Glu Thr Val Gln Arg Leu Leu Pro Val Leu Cys Gln Ala
530                 535                 540
```

-continued

```
His Gly Leu Thr Pro Glu Gln Val Val Ala Ile Ala Ser Asn Asn Gly
545                 550                 555                 560

Gly Lys Gln Ala Leu Glu Thr Val Gln Arg Leu Leu Pro Val Leu Cys
                565                 570                 575

Gln Ala His Gly Leu Thr Pro Glu Gln Val Val Ala Ile Ala Ser Asn
            580                 585                 590

Ile Gly Gly Lys Gln Ala Leu Glu Thr Val Gln Arg Leu Leu Pro Val
        595                 600                 605

Leu Cys Gln Ala His Gly Leu Thr Pro Glu Gln Val Val Ala Ile Ala
    610                 615                 620

Ser His Asp Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
                645                 650                 655

Ile Ala Ser Asn Ile Gly Gly Arg Pro Ala Leu Glu Ser Ile Val Ala
            660                 665                 670

Gln Leu Ser Arg Pro Asp Pro Ala Leu Ala Ala Leu Thr Asn Asp His
        675                 680                 685

Leu Val Ala Leu Ala Cys Leu Gly Gly Arg Pro Ala Leu Asp Ala Val
    690                 695                 700

Lys Lys Gly Leu Pro His Ala Pro Ala Leu Ile Lys Arg Thr Asn Arg
705                 710                 715                 720

Arg Ile Pro Glu Arg Thr Ser His Arg Val Ala Asp His Ala Gln Val
                725                 730                 735

Val Arg Val Leu Gly Phe Phe Gln Cys His Ser His Pro Ala Gln Ala
            740                 745                 750

Phe Asp Asp Ala Met Thr Gln Phe Gly Met Ser Arg His Gly Leu Leu
        755                 760                 765

Gln Leu Phe Arg Arg Val Gly Val Thr Glu Leu Glu Ala Arg Ser Gly
    770                 775                 780

Thr Leu Pro Pro Ala Ser Gln Arg Trp Asp Arg Ile Leu Gln Ala Ser
785                 790                 795                 800

Gly Met Lys Arg Ala Lys Pro Ser Pro Thr Ser Thr Gln Thr Pro Asp
                805                 810                 815

Gln Ala Ser Leu His Ala Phe Ala Asp Ser Leu Glu Arg Asp Leu Asp
            820                 825                 830

Ala Pro Ser Pro Met His Glu Gly Asp Gln Thr Arg Ala Ser Ala Ser
        835                 840                 845

Pro Lys Lys Lys Arg Lys Val Glu Ala Ser Cys Arg Phe Ile His Val
    850                 855                 860

Glu Gln Met Gln His Phe Asn Ala Asn Ala Thr Val Tyr Ala Pro Pro
865                 870                 875                 880

Ser Ser Asp Cys Pro Pro Pro Ile Ala Tyr Tyr His His Pro Gln
                885                 890                 895

His Gln Gln Gln Phe Leu Pro Phe Pro Met Pro Tyr Phe Leu Ala Pro
            900                 905                 910

Pro Pro Gln Ala Gln Gln Gly Ala Pro Phe Pro Val Gln Tyr Ile Pro
        915                 920                 925

Gln Gln His Asp Leu Met Asn Ser Gln Pro Met Tyr Ala Pro Met Ala
    930                 935                 940

Pro Thr Tyr Tyr Tyr Gln Pro Ile Asn Ser Asn Gly Met Pro Met Met
945                 950                 955                 960

Asp Val Thr Ile Asp Pro Asn Ala Thr Gly Gly Ala Phe Glu Val Phe
```

```
                    965                 970                 975
Pro Asp Gly Phe Phe Ser Gln Pro Pro Thr Ile Ile Ser
                980                 985                 990

<210> SEQ ID NO 34
<211> LENGTH: 882
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
                20                  25                  30

Phe Asn Thr Ser Leu Phe Asp Ser Leu Pro Pro Phe Gly Ala His His
            35                  40                  45

Thr Glu Ala Ala Thr Gly Glu Trp Asp Glu Val Gln Ser Gly Leu Arg
    50                  55                  60

Ala Ala Asp Ala Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
                100                 105                 110

Ser Gln Gln Gln Gln Glu Lys Ile Lys Pro Lys Val Arg Ser Thr Val
            115                 120                 125

Ala Gln His His Glu Ala Leu Val Gly His Gly Phe Thr His Ala His
        130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
        195                 200                 205

Thr Gly Gln Leu Leu Lys Ile Ala Lys Arg Gly Gly Val Thr Ala Val
    210                 215                 220

Glu Ala Val His Ala Trp Arg Asn Ala Leu Thr Gly Ala Pro Leu Asn
225                 230                 235                 240

Leu Thr Pro Glu Gln Val Val Ala Ile Ala Ser Asn Gly Gly Gly Lys
                245                 250                 255

Gln Ala Leu Glu Thr Val Gln Arg Leu Leu Pro Val Leu Cys Gln Ala
            260                 265                 270

His Gly Leu Thr Pro Glu Gln Val Val Ala Ile Ala Ser Asn Gly Gly
        275                 280                 285

Gly Lys Gln Ala Leu Glu Thr Val Gln Arg Leu Leu Pro Val Leu Cys
    290                 295                 300

Gln Ala His Gly Leu Thr Pro Glu Gln Val Val Ala Ile Ala Ser Asn
305                 310                 315                 320

Ile Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
```

```
                    340             345              350
Ser Asn Gly Gly Gly Lys Gln Ala Leu Glu Thr Val Gln Arg Leu Leu
            355                 360                 365

Pro Val Leu Cys Gln Ala His Gly Leu Thr Pro Glu Gln Val Val Ala
        370                 375                 380

Ile Ala Ser Asn Gly Gly Lys Gln Ala Leu Glu Thr Val Gln Arg
385                 390                 395                 400

Leu Leu Pro Val Leu Cys Gln Ala His Gly Leu Thr Pro Glu Gln Val
                405                 410                 415

Val Ala Ile Ala Ser His Asp Gly Gly Lys Gln Ala Leu Glu Thr Val
            420                 425                 430

Gln Arg Leu Leu Pro Val Leu Cys Gln Ala His Gly Leu Thr Pro Glu
        435                 440                 445

Gln Val Val Ala Ile Ala Ser His Asp Gly Gly Lys Gln Ala Leu Glu
    450                 455                 460

Thr Val Gln Arg Leu Leu Pro Val Leu Cys Gln Ala His Gly Leu Thr
465                 470                 475                 480

Pro Glu Gln Val Val Ala Ile Ala Ser His Asp Gly Gly Lys Gln Ala
                485                 490                 495

Leu Glu Thr Val Gln Arg Leu Leu Pro Val Leu Cys Gln Ala His Gly
            500                 505                 510

Leu Thr Pro Glu Gln Val Val Ala Ile Ala Ser Asn Gly Gly Lys
        515                 520                 525

Gln Ala Leu Glu Thr Val Gln Arg Leu Leu Pro Val Leu Cys Gln Ala
    530                 535                 540

His Gly Leu Thr Pro Glu Gln Val Val Ala Ile Ala Ser Asn Asn Gly
545                 550                 555                 560

Gly Lys Gln Ala Leu Glu Thr Val Gln Arg Leu Leu Pro Val Leu Cys
                565                 570                 575

Gln Ala His Gly Leu Thr Pro Glu Gln Val Val Ala Ile Ala Ser Asn
            580                 585                 590

Ile Gly Gly Lys Gln Ala Leu Glu Thr Val Gln Arg Leu Leu Pro Val
        595                 600                 605

Leu Cys Gln Ala His Gly Leu Thr Pro Glu Gln Val Val Ala Ile Ala
    610                 615                 620

Ser His Asp Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
                645                 650                 655

Ile Ala Ser Asn Ile Gly Gly Arg Pro Ala Leu Glu Ser Ile Val Ala
            660                 665                 670

Gln Leu Ser Arg Pro Asp Pro Ala Leu Ala Ala Leu Thr Asn Asp His
        675                 680                 685

Leu Val Ala Leu Ala Cys Leu Gly Gly Arg Pro Ala Leu Asp Ala Val
    690                 695                 700

Lys Lys Gly Leu Pro His Ala Pro Ala Leu Ile Lys Arg Thr Asn Arg
705                 710                 715                 720

Arg Ile Pro Glu Arg Thr Ser His Arg Val Ala Asp His Ala Gln Val
                725                 730                 735

Val Arg Val Leu Gly Phe Phe Gln Cys His Ser His Pro Ala Gln Ala
            740                 745                 750

Phe Asp Asp Ala Met Thr Gln Phe Gly Met Ser Arg His Gly Leu Leu
        755                 760                 765
```

```
Gln Leu Phe Arg Arg Val Gly Val Thr Glu Leu Glu Ala Arg Ser Gly
        770                 775                 780

Thr Leu Pro Pro Ala Ser Gln Arg Trp Asp Arg Ile Leu Gln Ala Ser
785                 790                 795                 800

Gly Met Lys Arg Ala Lys Pro Ser Pro Thr Ser Thr Gln Thr Pro Asp
            805                 810                 815

Gln Ala Ser Leu His Ala Phe Ala Asp Ser Leu Glu Arg Asp Leu Asp
            820                 825                 830

Ala Pro Ser Pro Met His Glu Gly Asp Gln Thr Arg Ala Ser Ala Ser
            835                 840                 845

Pro Lys Lys Lys Arg Lys Val Glu Ala Ser Met Glu Glu Glu Lys Arg
        850                 855                 860

Leu Glu Leu Arg Leu Ala Pro Pro Cys His Gln Phe Thr Ser Asn Asn
865                 870                 875                 880

Asn Ile

<210> SEQ ID NO 35
<211> LENGTH: 915
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Gln Glu Lys Ile Lys Pro Lys Val Arg Ser Thr Val
        115                 120                 125

Ala Gln His His Glu Ala Leu Val Gly His Gly Phe Thr His Ala His
    130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
        195                 200                 205

Thr Gly Gln Leu Leu Lys Ile Ala Lys Arg Gly Gly Val Thr Ala Val
    210                 215                 220

Glu Ala Val His Ala Trp Arg Asn Ala Leu Thr Gly Ala Pro Leu Asn
225                 230                 235                 240

Leu Thr Pro Glu Gln Val Val Ala Ile Ala Ser Asn Gly Gly Gly Lys
```

-continued

```
                245                 250                 255
Gln Ala Leu Glu Thr Val Gln Arg Leu Leu Pro Val Leu Cys Gln Ala
                260                 265                 270
His Gly Leu Thr Pro Glu Gln Val Val Ala Ile Ala Ser Asn Gly Gly
                275                 280                 285
Gly Lys Gln Ala Leu Glu Thr Val Gln Arg Leu Leu Pro Val Leu Cys
            290                 295                 300
Gln Ala His Gly Leu Thr Pro Glu Gln Val Val Ala Ile Ala Ser Asn
305                 310                 315                 320
Ile Gly Gly Lys Gln Ala Leu Glu Thr Val Gln Arg Leu Leu Pro Val
                325                 330                 335
Leu Cys Gln Ala His Gly Leu Thr Pro Glu Gln Val Val Ala Ile Ala
                340                 345                 350
Ser Asn Gly Gly Gly Lys Gln Ala Leu Glu Thr Val Gln Arg Leu Leu
                355                 360                 365
Pro Val Leu Cys Gln Ala His Gly Leu Thr Pro Glu Gln Val Val Ala
            370                 375                 380
Ile Ala Ser Asn Gly Gly Gly Lys Gln Ala Leu Glu Thr Val Gln Arg
385                 390                 395                 400
Leu Leu Pro Val Leu Cys Gln Ala His Gly Leu Thr Pro Glu Gln Val
                405                 410                 415
Val Ala Ile Ala Ser His Asp Gly Gly Lys Gln Ala Leu Glu Thr Val
            420                 425                 430
Gln Arg Leu Leu Pro Val Leu Cys Gln Ala His Gly Leu Thr Pro Glu
            435                 440                 445
Gln Val Val Ala Ile Ala Ser His Asp Gly Gly Lys Gln Ala Leu Glu
        450                 455                 460
Thr Val Gln Arg Leu Leu Pro Val Leu Cys Gln Ala His Gly Leu Thr
465                 470                 475                 480
Pro Glu Gln Val Val Ala Ile Ala Ser His Asp Gly Gly Lys Gln Ala
                485                 490                 495
Leu Glu Thr Val Gln Arg Leu Leu Pro Val Leu Cys Gln Ala His Gly
            500                 505                 510
Leu Thr Pro Glu Gln Val Val Ala Ile Ala Ser Asn Gly Gly Gly Lys
        515                 520                 525
Gln Ala Leu Glu Thr Val Gln Arg Leu Leu Pro Val Leu Cys Gln Ala
            530                 535                 540
His Gly Leu Thr Pro Glu Gln Val Val Ala Ile Ala Ser Asn Asn Gly
545                 550                 555                 560
Gly Lys Gln Ala Leu Glu Thr Val Gln Arg Leu Leu Pro Val Leu Cys
                565                 570                 575
Gln Ala His Gly Leu Thr Pro Glu Gln Val Val Ala Ile Ala Ser Asn
            580                 585                 590
Ile Gly Gly Lys Gln Ala Leu Glu Thr Val Gln Arg Leu Leu Pro Val
        595                 600                 605
Leu Cys Gln Ala His Gly Leu Thr Pro Glu Gln Val Val Ala Ile Ala
        610                 615                 620
Ser His Asp Gly Gly Lys Gln Ala Leu Glu Thr Val Gln Arg Leu Leu
625                 630                 635                 640
Pro Val Leu Cys Gln Ala His Gly Leu Thr Pro Glu Gln Val Val Ala
            645                 650                 655
Ile Ala Ser Asn Ile Gly Gly Arg Pro Ala Leu Glu Ser Ile Val Ala
            660                 665                 670
```

Gln Leu Ser Arg Pro Asp Pro Ala Leu Ala Ala Leu Thr Asn Asp His
        675                 680                 685

Leu Val Ala Leu Ala Cys Leu Gly Gly Arg Pro Ala Leu Asp Ala Val
690                 695                 700

Lys Lys Gly Leu Pro His Ala Pro Ala Leu Ile Lys Arg Thr Asn Arg
705                 710                 715                 720

Arg Ile Pro Glu Arg Thr Ser His Arg Val Ala Asp His Ala Gln Val
                725                 730                 735

Val Arg Val Leu Gly Phe Phe Gln Cys His Ser His Pro Ala Gln Ala
            740                 745                 750

Phe Asp Asp Ala Met Thr Gln Phe Gly Met Ser Arg His Gly Leu Leu
        755                 760                 765

Gln Leu Phe Arg Arg Val Gly Val Thr Glu Leu Glu Ala Arg Ser Gly
    770                 775                 780

Thr Leu Pro Pro Ala Ser Gln Arg Trp Asp Arg Ile Leu Gln Ala Ser
785                 790                 795                 800

Gly Met Lys Arg Ala Lys Pro Ser Pro Thr Ser Gln Thr Pro Asp
                805                 810                 815

Gln Ala Ser Leu His Ala Phe Ala Asp Ser Leu Glu Arg Asp Leu Asp
                820                 825                 830

Ala Pro Ser Pro Met His Glu Gly Asp Gln Thr Arg Ala Ser Ala Ser
            835                 840                 845

Pro Lys Lys Lys Arg Lys Val Glu Ala Ser Leu Ala Ser Gln Gly Leu
    850                 855                 860

Ala Met Ser Pro Phe Gly Ser Leu Phe Pro Tyr Pro Tyr Thr Tyr Met
865                 870                 875                 880

Ala Ala Ala Ala Ala Ser Ser Ala Ala Ala Ser Ser Ser Val His
                885                 890                 895

Arg His Pro Phe Leu Asn Leu Asn Thr Met Arg Pro Arg Leu Arg Tyr
            900                 905                 910

Ser Pro Tyr
        915

<210> SEQ ID NO 36
<211> LENGTH: 846
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
            100                 105                 110

-continued

```
Ser Gln Gln Gln Gln Glu Lys Ile Lys Pro Lys Val Arg Ser Thr Val
    115                 120                 125
Ala Gln His His Glu Ala Leu Val Gly His Gly Phe Thr His Ala His
    130                 135                 140
Ile Val Ala Leu Ser Gln His Pro Ala Ala Leu Gly Thr Val Ala Val
145                 150                 155                 160
Lys Tyr Gln Asp Met Ile Ala Ala Leu Pro Glu Ala Thr His Glu Ala
                165                 170                 175
Ile Val Gly Val Gly Lys Gln Trp Ser Gly Ala Arg Ala Leu Glu Ala
                180                 185                 190
Leu Leu Thr Val Ala Gly Glu Leu Arg Gly Pro Leu Gln Leu Asp
    195                 200                 205
Thr Gly Gln Leu Leu Lys Ile Ala Lys Arg Gly Gly Val Thr Ala Val
    210                 215                 220
Glu Ala Val His Ala Trp Arg Asn Ala Leu Thr Gly Ala Pro Leu Asn
225                 230                 235                 240
Leu Thr Pro Glu Gln Val Val Ala Ile Ala Ser Asn Gly Gly Gly Lys
                245                 250                 255
Gln Ala Leu Glu Thr Val Gln Arg Leu Leu Pro Val Leu Cys Gln Ala
                260                 265                 270
His Gly Leu Thr Pro Glu Gln Val Val Ala Ile Ala Ser Asn Gly Gly
                275                 280                 285
Gly Lys Gln Ala Leu Glu Thr Val Gln Arg Leu Leu Pro Val Leu Cys
        290                 295                 300
Gln Ala His Gly Leu Thr Pro Glu Gln Val Val Ala Ile Ala Ser Asn
305                 310                 315                 320
Ile Gly Gly Lys Gln Ala Leu Glu Thr Val Gln Arg Leu Leu Pro Val
                325                 330                 335
Leu Cys Gln Ala His Gly Leu Thr Pro Glu Gln Val Val Ala Ile Ala
                340                 345                 350
Ser Asn Gly Gly Gly Lys Gln Ala Leu Glu Thr Val Gln Arg Leu Leu
        355                 360                 365
Pro Val Leu Cys Gln Ala His Gly Leu Thr Pro Glu Gln Val Val Ala
    370                 375                 380
Ile Ala Ser Asn Gly Gly Gly Lys Gln Ala Leu Glu Thr Val Gln Arg
385                 390                 395                 400
Leu Leu Pro Val Leu Cys Gln Ala His Gly Leu Thr Pro Glu Gln Val
                405                 410                 415
Val Ala Ile Ala Ser His Asp Gly Gly Lys Gln Ala Leu Glu Thr Val
                420                 425                 430
Gln Arg Leu Leu Pro Val Leu Cys Gln Ala His Gly Leu Thr Pro Glu
        435                 440                 445
Gln Val Val Ala Ile Ala Ser His Asp Gly Gly Lys Gln Ala Leu Glu
    450                 455                 460
Thr Val Gln Arg Leu Leu Pro Val Leu Cys Gln Ala His Gly Leu Thr
465                 470                 475                 480
Pro Glu Gln Val Val Ala Ile Ala Ser His Asp Gly Gly Lys Gln Ala
                485                 490                 495
Leu Glu Thr Val Gln Arg Leu Leu Pro Val Leu Cys Gln Ala His Gly
                500                 505                 510
Leu Thr Pro Glu Gln Val Val Ala Ile Ala Ser Asn Gly Gly Gly Lys
        515                 520                 525
Gln Ala Leu Glu Thr Val Gln Arg Leu Leu Pro Val Leu Cys Gln Ala
    530                 535                 540
```

His Gly Leu Thr Pro Glu Gln Val Val Ala Ile Ala Ser Asn Asn Gly
545                 550                 555                 560

Gly Lys Gln Ala Leu Glu Thr Val Gln Arg Leu Leu Pro Val Leu Cys
            565                 570                 575

Gln Ala His Gly Leu Thr Pro Glu Gln Val Val Ala Ile Ala Ser Asn
        580                 585                 590

Ile Gly Gly Lys Gln Ala Leu Glu Thr Val Gln Arg Leu Leu Pro Val
    595                 600                 605

Leu Cys Gln Ala His Gly Leu Thr Pro Glu Gln Val Val Ala Ile Ala
610                 615                 620

Ser His Asp Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
            645                 650                 655

Ile Ala Ser Asn Ile Gly Gly Arg Pro Ala Leu Glu Ser Ile Val Ala
        660                 665                 670

Gln Leu Ser Arg Pro Asp Pro Ala Leu Ala Ala Leu Thr Asn Asp His
    675                 680                 685

Leu Val Ala Leu Ala Cys Leu Gly Gly Arg Pro Ala Leu Asp Ala Val
690                 695                 700

Lys Lys Gly Leu Pro His Ala Pro Ala Leu Ile Lys Arg Thr Asn Arg
705                 710                 715                 720

Arg Ile Pro Glu Arg Thr Ser His Arg Val Ala Asp His Ala Gln Val
            725                 730                 735

Val Arg Val Leu Gly Phe Phe Gln Cys His Ser His Pro Ala Gln Ala
        740                 745                 750

Phe Asp Asp Ala Met Thr Gln Phe Gly Met Ser Arg His Gly Leu Leu
    755                 760                 765

Gln Leu Phe Arg Arg Val Gly Val Thr Glu Leu Glu Ala Arg Ser Gly
770                 775                 780

Thr Leu Pro Pro Ala Ser Gln Arg Trp Asp Arg Ile Leu Gln Ala Ser
785                 790                 795                 800

Gly Met Lys Arg Ala Lys Pro Ser Pro Thr Ser Thr Gln Thr Pro Asp
            805                 810                 815

Gln Ala Ser Leu His Ala Phe Ala Asp Ser Leu Glu Arg Asp Leu Asp
        820                 825                 830

Ala Pro Ser Pro Met His Glu Gly Asp Gln Thr Arg Ala Ser
    835                 840                 845

<210> SEQ ID NO 37
<211> LENGTH: 858
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

-continued

```
Ala Ala Asp Ala Pro Pro Thr Met Arg Val Ala Val Thr Ala Ala
 65                  70                  75                  80

Arg Pro Pro Arg Ala Lys Pro Ala Pro Arg Arg Ala Ala Gln Pro
                 85                  90                  95

Ser Asp Ala Ser Pro Ala Ala Gln Val Asp Leu Arg Thr Leu Gly Tyr
                100                 105                 110

Ser Gln Gln Gln Gln Glu Lys Ile Lys Pro Lys Val Arg Ser Thr Val
                115                 120                 125

Ala Gln His His Glu Ala Leu Val Gly His Gly Phe Thr His Ala His
            130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
                180                 185                 190

Leu Leu Thr Val Ala Gly Glu Leu Arg Gly Pro Pro Leu Gln Leu Asp
            195                 200                 205

Thr Gly Gln Leu Leu Lys Ile Ala Lys Arg Gly Gly Val Thr Ala Val
            210                 215                 220

Glu Ala Val His Ala Trp Arg Asn Ala Leu Thr Gly Ala Pro Leu Asn
225                 230                 235                 240

Leu Thr Pro Glu Gln Val Val Ala Ile Ala Ser Asn Gly Gly Gly Lys
                245                 250                 255

Gln Ala Leu Glu Thr Val Gln Arg Leu Leu Pro Val Leu Cys Gln Ala
                260                 265                 270

His Gly Leu Thr Pro Glu Gln Val Val Ala Ile Ala Ser Asn Gly Gly
            275                 280                 285

Gly Lys Gln Ala Leu Glu Thr Val Gln Arg Leu Leu Pro Val Leu Cys
290                 295                 300

Gln Ala His Gly Leu Thr Pro Glu Gln Val Val Ala Ile Ala Ser Asn
305                 310                 315                 320

Ile Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
            340                 345                 350

Ser Asn Gly Gly Gly Lys Gln Ala Leu Glu Thr Val Gln Arg Leu Leu
            355                 360                 365

Pro Val Leu Cys Gln Ala His Gly Leu Thr Pro Glu Gln Val Val Ala
370                 375                 380

Ile Ala Ser Asn Gly Gly Gly Lys Gln Ala Leu Glu Thr Val Gln Arg
385                 390                 395                 400

Leu Leu Pro Val Leu Cys Gln Ala His Gly Leu Thr Pro Glu Gln Val
                405                 410                 415

Val Ala Ile Ala Ser His Asp Gly Gly Lys Gln Ala Leu Glu Thr Val
            420                 425                 430

Gln Arg Leu Leu Pro Val Leu Cys Gln Ala His Gly Leu Thr Pro Glu
            435                 440                 445

Gln Val Val Ala Ile Ala Ser His Asp Gly Gly Lys Gln Ala Leu Glu
            450                 455                 460

Thr Val Gln Arg Leu Leu Pro Val Leu Cys Gln Ala His Gly Leu Thr
465                 470                 475                 480

Pro Glu Gln Val Val Ala Ile Ala Ser His Asp Gly Gly Lys Gln Ala
```

```
                    485                 490                 495
Leu Glu Thr Val Gln Arg Leu Leu Pro Val Leu Cys Gln Ala His Gly
                500                 505                 510

Leu Thr Pro Glu Gln Val Val Ala Ile Ala Ser Asn Gly Gly Gly Lys
            515                 520                 525

Gln Ala Leu Glu Thr Val Gln Arg Leu Leu Pro Val Leu Cys Gln Ala
        530                 535                 540

His Gly Leu Thr Pro Glu Gln Val Val Ala Ile Ala Ser Asn Asn Gly
545                 550                 555                 560

Gly Lys Gln Ala Leu Glu Thr Val Gln Arg Leu Leu Pro Val Leu Cys
                565                 570                 575

Gln Ala His Gly Leu Thr Pro Glu Gln Val Val Ala Ile Ala Ser Asn
            580                 585                 590

Ile Gly Gly Lys Gln Ala Leu Glu Thr Val Gln Arg Leu Leu Pro Val
        595                 600                 605

Leu Cys Gln Ala His Gly Leu Thr Pro Glu Gln Val Val Ala Ile Ala
    610                 615                 620

Ser His Asp Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
                645                 650                 655

Ile Ala Ser Asn Ile Gly Gly Arg Pro Ala Leu Glu Ser Ile Val Ala
            660                 665                 670

Gln Leu Ser Arg Pro Asp Pro Ala Leu Ala Ala Leu Thr Asn Asp His
        675                 680                 685

Leu Val Ala Leu Ala Cys Leu Gly Gly Arg Pro Ala Leu Asp Ala Val
    690                 695                 700

Lys Lys Gly Leu Pro His Ala Pro Ala Leu Ile Lys Arg Thr Asn Arg
705                 710                 715                 720

Arg Ile Pro Glu Arg Thr Ser His Arg Val Ala Asp His Ala Gln Val
                725                 730                 735

Val Arg Val Leu Gly Phe Phe Gln Cys His Ser His Pro Ala Gln Ala
            740                 745                 750

Phe Asp Asp Ala Met Thr Gln Phe Gly Met Ser Arg His Gly Leu Leu
        755                 760                 765

Gln Leu Phe Arg Arg Val Gly Val Thr Glu Leu Glu Ala Arg Ser Gly
        770                 775                 780

Thr Leu Pro Pro Ala Ser Gln Arg Trp Asp Arg Ile Leu Gln Ala Ser
785                 790                 795                 800

Gly Met Lys Arg Ala Lys Pro Ser Pro Thr Ser Thr Gln Thr Pro Asp
                805                 810                 815

Gln Ala Ser Leu His Ala Phe Ala Asp Ser Leu Glu Arg Asp Leu Asp
            820                 825                 830

Ala Pro Ser Pro Met His Glu Gly Asp Gln Thr Arg Ala Ser Ala Ser
        835                 840                 845

Pro Lys Lys Lys Arg Lys Val Glu Ala Ser
    850                 855

<210> SEQ ID NO 38
<211> LENGTH: 1051
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 38

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Gln Glu Lys Ile Lys Pro Lys Val Arg Ser Thr Val
        115                 120                 125

Ala Gln His His Glu Ala Leu Val Gly His Gly Phe Thr His Ala His
        130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
        195                 200                 205

Thr Gly Gln Leu Leu Lys Ile Ala Lys Arg Gly Gly Val Thr Ala Val
    210                 215                 220

Glu Ala Val His Ala Trp Arg Asn Ala Leu Thr Gly Ala Pro Leu Asn
225                 230                 235                 240

Leu Thr Pro Glu Gln Val Val Ala Ile Ala Ser His Asp Gly Gly Lys
                245                 250                 255

Gln Ala Leu Glu Thr Val Gln Arg Leu Leu Pro Val Leu Cys Gln Ala
            260                 265                 270

His Gly Leu Thr Pro Glu Gln Val Val Ala Ile Ala Ser Asn Asn Gly
        275                 280                 285

Gly Lys Gln Ala Leu Glu Thr Val Gln Arg Leu Leu Pro Val Leu Cys
    290                 295                 300

Gln Ala His Gly Leu Thr Pro Glu Gln Val Val Ala Ile Ala Ser Asn
305                 310                 315                 320

Asn Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
            340                 345                 350

Ser His Asp Gly Gly Lys Gln Ala Leu Glu Thr Val Gln Arg Leu Leu
        355                 360                 365

Pro Val Leu Cys Gln Ala His Gly Leu Thr Pro Glu Gln Val Val Ala
    370                 375                 380

Ile Ala Ser His Asp Gly Gly Lys Gln Ala Leu Glu Thr Val Gln Arg
385                 390                 395                 400

Leu Leu Pro Val Leu Cys Gln Ala His Gly Leu Thr Pro Glu Gln Val
                405                 410                 415
```

```
Val Ala Ile Ala Ser His Asp Gly Gly Lys Gln Ala Leu Glu Thr Val
            420                 425                 430

Gln Arg Leu Leu Pro Val Leu Cys Gln Ala His Gly Leu Thr Pro Glu
        435                 440                 445

Gln Val Val Ala Ile Ala Ser His Asp Gly Gly Lys Gln Ala Leu Glu
450                 455                 460

Thr Val Gln Arg Leu Leu Pro Val Leu Cys Gln Ala His Gly Leu Thr
465                 470                 475                 480

Pro Glu Gln Val Val Ala Ile Ala Ser Asn Gly Gly Lys Gln Ala
                485                 490                 495

Leu Glu Thr Val Gln Arg Leu Leu Pro Val Leu Cys Gln Ala His Gly
            500                 505                 510

Leu Thr Pro Glu Gln Val Val Ala Ile Ala Ser Asn Asn Gly Gly Lys
        515                 520                 525

Gln Ala Leu Glu Thr Val Gln Arg Leu Leu Pro Val Leu Cys Gln Ala
530                 535                 540

His Gly Leu Thr Pro Glu Gln Val Val Ala Ile Ala Ser His Asp Gly
545                 550                 555                 560

Gly Lys Gln Ala Leu Glu Thr Val Gln Arg Leu Leu Pro Val Leu Cys
                565                 570                 575

Gln Ala His Gly Leu Thr Pro Glu Gln Val Val Ala Ile Ala Ser His
            580                 585                 590

Asp Gly Gly Lys Gln Ala Leu Glu Thr Val Gln Arg Leu Leu Pro Val
        595                 600                 605

Leu Cys Gln Ala His Gly Leu Thr Pro Glu Gln Val Val Ala Ile Ala
610                 615                 620

Ser Asn Asn Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
                645                 650                 655

Ile Ala Ser Asn Asn Gly Gly Lys Gln Ala Leu Glu Thr Val Gln Arg
            660                 665                 670

Leu Leu Pro Val Leu Cys Gln Ala His Gly Leu Thr Pro Glu Gln Val
        675                 680                 685

Val Ala Ile Ala Ser His Asp Gly Gly Lys Gln Ala Leu Glu Thr Val
690                 695                 700

Gln Arg Leu Leu Pro Val Leu Cys Gln Ala His Gly Leu Thr Pro Glu
705                 710                 715                 720

Gln Val Val Ala Ile Ala Ser His Asp Gly Gly Lys Gln Ala Leu Glu
                725                 730                 735

Thr Val Gln Arg Leu Leu Pro Val Leu Cys Gln Ala His Gly Leu Thr
            740                 745                 750

Pro Glu Gln Val Val Ala Ile Ala Ser His Asp Gly Gly Lys Gln Ala
        755                 760                 765

Leu Glu Thr Val Gln Arg Leu Leu Pro Val Leu Cys Gln Ala His Gly
770                 775                 780

Leu Thr Pro Glu Gln Val Val Ala Ile Ala Ser Asn Ile Gly Gly Arg
785                 790                 795                 800

Pro Ala Leu Glu Ser Ile Val Ala Gln Leu Ser Arg Pro Asp Pro Ala
                805                 810                 815

Leu Ala Ala Leu Thr Asn Asp His Leu Val Ala Leu Ala Cys Leu Gly
            820                 825                 830

Gly Arg Pro Ala Leu Asp Ala Val Lys Lys Gly Leu Pro His Ala Pro
        835                 840                 845
```

```
Ala Leu Ile Lys Arg Thr Asn Arg Arg Ile Pro Glu Arg Thr Ser His
    850                 855                 860
Arg Val Ala Asp His Ala Gln Val Val Arg Val Leu Gly Phe Phe Gln
865                 870                 875                 880
Cys His Ser His Pro Ala Gln Ala Phe Asp Asp Ala Met Thr Gln Phe
                885                 890                 895
Gly Met Ser Arg His Gly Leu Leu Gln Leu Phe Arg Arg Val Gly Val
            900                 905                 910
Thr Glu Leu Glu Ala Arg Ser Gly Thr Leu Pro Pro Ala Ser Gln Arg
            915                 920                 925
Trp Asp Arg Ile Leu Gln Ala Ser Gly Met Lys Arg Ala Lys Pro Ser
            930                 935                 940
Pro Thr Ser Thr Gln Thr Pro Asp Gln Ala Ser Leu His Ala Phe Ala
945                 950                 955                 960
Asp Ser Leu Glu Arg Asp Leu Asp Ala Pro Ser Pro Met His Glu Gly
                965                 970                 975
Asp Gln Thr Arg Ala Ser Ala Ser Pro Lys Lys Arg Lys Val Glu
            980                 985                 990
Ala Ser Gly Ser Gly Arg Ala Asp  Ala Leu Asp Asp Phe  Asp Leu Asp
            995                 1000                1005
Met Leu Gly Ser Asp Ala Leu  Asp Asp Phe Asp Leu  Asp Met Leu
    1010                1015                1020
Gly Ser  Asp Ala Leu Asp Asp  Phe Asp Leu Asp Met  Leu Gly Ser
    1025                1030                1035
Asp Ala  Leu Asp Asp Phe Asp  Leu Asp Met Leu Ile  Asn
    1040                1045                1050

<210> SEQ ID NO 39
<211> LENGTH: 1051
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Ser Arg Thr Arg Leu Pro Ser Pro Ala Pro Ser Pro Ala Phe
1               5                   10                  15
Ser Ala Asp Ser Phe Ser Asp Leu Leu Arg Gln Phe Asp Pro Ser Leu
                20                  25                  30
Phe Asn Thr Ser Leu Phe Asp Ser Leu Pro Pro Phe Gly Ala His His
            35                  40                  45
Thr Glu Ala Ala Thr Gly Glu Trp Asp Glu Val Gln Ser Gly Leu Arg
    50                  55                  60
Ala Ala Asp Ala Pro Pro Pro Thr Met Arg Val Ala Val Thr Ala Ala
65                  70                  75                  80
Arg Pro Pro Arg Ala Lys Pro Ala Pro Arg Arg Ala Ala Gln Pro
                85                  90                  95
Ser Asp Ala Ser Pro Ala Ala Gln Val Asp Leu Arg Thr Leu Gly Tyr
            100                 105                 110
Ser Gln Gln Gln Gln Glu Lys Ile Lys Pro Lys Val Arg Ser Thr Val
        115                 120                 125
Ala Gln His His Glu Ala Leu Val Gly His Gly Phe Thr His Ala His
    130                 135                 140
Ile Val Ala Leu Ser Gln His Pro Ala Ala Leu Gly Thr Val Ala Val
145                 150                 155                 160
```

-continued

```
Lys Tyr Gln Asp Met Ile Ala Ala Leu Pro Glu Ala Thr His Glu Ala
                165                 170                 175
Ile Val Gly Val Gly Lys Gln Trp Ser Gly Arg Ala Leu Glu Ala
            180                 185                 190
Leu Leu Thr Val Ala Gly Glu Leu Arg Gly Pro Pro Leu Gln Leu Asp
            195                 200                 205
Thr Gly Gln Leu Leu Lys Ile Ala Lys Arg Gly Gly Val Thr Ala Val
210                 215                 220
Glu Ala Val His Ala Trp Arg Asn Ala Leu Thr Gly Ala Pro Leu Asn
225                 230                 235                 240
Leu Thr Pro Glu Gln Val Ala Ile Ala Ser His Asp Gly Gly Lys
            245                 250                 255
Gln Ala Leu Glu Thr Val Gln Arg Leu Leu Pro Val Leu Cys Gln Ala
            260                 265                 270
His Gly Leu Thr Pro Glu Gln Val Val Ala Ile Ala Ser Asn Lys Gly
            275                 280                 285
Gly Lys Gln Ala Leu Glu Thr Val Gln Arg Leu Leu Pro Val Leu Cys
            290                 295                 300
Gln Ala His Gly Leu Thr Pro Glu Gln Val Val Ala Ile Ala Ser Asn
305                 310                 315                 320
Lys Gly Gly Lys Gln Ala Leu Glu Thr Val Gln Arg Leu Leu Pro Val
            325                 330                 335
Leu Cys Gln Ala His Gly Leu Thr Pro Glu Gln Val Val Ala Ile Ala
            340                 345                 350
Ser His Asp Gly Gly Lys Gln Ala Leu Glu Thr Val Gln Arg Leu Leu
            355                 360                 365
Pro Val Leu Cys Gln Ala His Gly Leu Thr Pro Glu Gln Val Val Ala
            370                 375                 380
Ile Ala Ser His Asp Gly Gly Lys Gln Ala Leu Glu Thr Val Gln Arg
385                 390                 395                 400
Leu Leu Pro Val Leu Cys Gln Ala His Gly Leu Thr Pro Glu Gln Val
            405                 410                 415
Val Ala Ile Ala Ser His Asp Gly Gly Lys Gln Ala Leu Glu Thr Val
            420                 425                 430
Gln Arg Leu Leu Pro Val Leu Cys Gln Ala His Gly Leu Thr Pro Glu
            435                 440                 445
Gln Val Val Ala Ile Ala Ser His Asp Gly Gly Lys Gln Ala Leu Glu
            450                 455                 460
Thr Val Gln Arg Leu Leu Pro Val Leu Cys Gln Ala His Gly Leu Thr
465                 470                 475                 480
Pro Glu Gln Val Val Ala Ile Ala Ser Asn Gly Gly Lys Gln Ala
            485                 490                 495
Leu Glu Thr Val Gln Arg Leu Leu Pro Val Leu Cys Gln Ala His Gly
            500                 505                 510
Leu Thr Pro Glu Gln Val Val Ala Ile Ala Ser Asn Lys Gly Gly Lys
            515                 520                 525
Gln Ala Leu Glu Thr Val Gln Arg Leu Leu Pro Val Leu Cys Gln Ala
            530                 535                 540
His Gly Leu Thr Pro Glu Gln Val Val Ala Ile Ala Ser His Asp Gly
545                 550                 555                 560
Gly Lys Gln Ala Leu Glu Thr Val Gln Arg Leu Leu Pro Val Leu Cys
            565                 570                 575
Gln Ala His Gly Leu Thr Pro Glu Gln Val Val Ala Ile Ala Ser His
```

-continued

```
              580                 585                 590
Asp Gly Gly Lys Gln Ala Leu Glu Thr Val Gln Arg Leu Leu Pro Val
            595                 600                 605

Leu Cys Gln Ala His Gly Leu Thr Pro Glu Gln Val Val Ala Ile Ala
            610                 615                 620

Ser Asn Lys Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
            645                 650                 655

Ile Ala Ser Asn Lys Gly Gly Lys Gln Ala Leu Glu Thr Val Gln Arg
            660                 665                 670

Leu Leu Pro Val Leu Cys Gln Ala His Gly Leu Thr Pro Glu Gln Val
            675                 680                 685

Val Ala Ile Ala Ser His Asp Gly Gly Lys Gln Ala Leu Glu Thr Val
            690                 695                 700

Gln Arg Leu Leu Pro Val Leu Cys Gln Ala His Gly Leu Thr Pro Glu
705                 710                 715                 720

Gln Val Val Ala Ile Ala Ser His Asp Gly Gly Lys Gln Ala Leu Glu
                    725                 730                 735

Thr Val Gln Arg Leu Leu Pro Val Leu Cys Gln Ala His Gly Leu Thr
                    740                 745                 750

Pro Glu Gln Val Val Ala Ile Ala Ser His Asp Gly Gly Lys Gln Ala
            755                 760                 765

Leu Glu Thr Val Gln Arg Leu Leu Pro Val Leu Cys Gln Ala His Gly
            770                 775                 780

Leu Thr Pro Glu Gln Val Val Ala Ile Ala Ser Asn Ile Gly Gly Arg
785                 790                 795                 800

Pro Ala Leu Glu Ser Ile Val Ala Gln Leu Ser Arg Pro Asp Pro Ala
                    805                 810                 815

Leu Ala Ala Leu Thr Asn Asp His Leu Val Ala Leu Ala Cys Leu Gly
                    820                 825                 830

Gly Arg Pro Ala Leu Asp Ala Val Lys Lys Gly Leu Pro His Ala Pro
            835                 840                 845

Ala Leu Ile Lys Arg Thr Asn Arg Arg Ile Pro Glu Arg Thr Ser His
850                 855                 860

Arg Val Ala Asp His Ala Gln Val Val Arg Val Leu Gly Phe Phe Gln
865                 870                 875                 880

Cys His Ser His Pro Ala Gln Ala Phe Asp Asp Ala Met Thr Gln Phe
                    885                 890                 895

Gly Met Ser Arg His Gly Leu Leu Gln Leu Phe Arg Arg Val Gly Val
                    900                 905                 910

Thr Glu Leu Glu Ala Arg Ser Gly Thr Leu Pro Pro Ala Ser Gln Arg
            915                 920                 925

Trp Asp Arg Ile Leu Gln Ala Ser Gly Met Lys Arg Ala Lys Pro Ser
            930                 935                 940

Pro Thr Ser Thr Gln Thr Pro Asp Gln Ala Ser Leu His Ala Phe Ala
945                 950                 955                 960

Asp Ser Leu Glu Arg Asp Leu Asp Ala Pro Ser Pro Met His Glu Gly
                    965                 970                 975

Asp Gln Thr Arg Ala Ser Ala Ser Pro Lys Lys Lys Arg Lys Val Glu
                    980                 985                 990

Ala Ser Gly Ser Gly Arg Ala Asp  Ala Leu Asp Asp Phe  Asp Leu Asp
            995                 1000                1005
```

-continued

```
Met Leu Gly Ser Asp Ala Leu Asp Asp Phe Asp Leu Asp Met Leu
    1010                1015                1020

Gly Ser Asp Ala Leu Asp Asp Phe Asp Leu Asp Met Leu Gly Ser
    1025                1030                1035

Asp Ala Leu Asp Asp Phe Asp Leu Asp Met Leu Ile Asn
    1040                1045                1050

<210> SEQ ID NO 40
<211> LENGTH: 1051
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Gln Glu Lys Ile Lys Pro Lys Val Arg Ser Thr Val
        115                 120                 125

Ala Gln His His Glu Ala Leu Val Gly His Gly Phe Thr His Ala His
    130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
        195                 200                 205

Thr Gly Gln Leu Leu Lys Ile Ala Lys Arg Gly Gly Val Thr Ala Val
    210                 215                 220

Glu Ala Val His Ala Trp Arg Asn Ala Leu Thr Gly Ala Pro Leu Asn
225                 230                 235                 240

Leu Thr Pro Glu Gln Val Val Ala Ile Ala Ser His Asp Gly Gly Lys
                245                 250                 255

Gln Ala Leu Glu Thr Val Gln Arg Leu Leu Pro Val Leu Cys Gln Ala
            260                 265                 270

His Gly Leu Thr Pro Glu Gln Val Val Ala Ile Ala Ser Asn His Gly
        275                 280                 285

Gly Lys Gln Ala Leu Glu Thr Val Gln Arg Leu Leu Pro Val Leu Cys
    290                 295                 300

Gln Ala His Gly Leu Thr Pro Glu Gln Val Val Ala Ile Ala Ser Asn
305                 310                 315                 320
```

-continued

```
His Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
            340                 345                 350

Ser His Asp Gly Gly Lys Gln Ala Leu Glu Thr Val Gln Arg Leu Leu
        355                 360                 365

Pro Val Leu Cys Gln Ala His Gly Leu Thr Pro Glu Gln Val Val Ala
    370                 375                 380

Ile Ala Ser His Asp Gly Gly Lys Gln Ala Leu Glu Thr Val Gln Arg
385                 390                 395                 400

Leu Leu Pro Val Leu Cys Gln Ala His Gly Leu Thr Pro Glu Gln Val
                405                 410                 415

Val Ala Ile Ala Ser His Asp Gly Gly Lys Gln Ala Leu Glu Thr Val
            420                 425                 430

Gln Arg Leu Leu Pro Val Leu Cys Gln Ala His Gly Leu Thr Pro Glu
        435                 440                 445

Gln Val Val Ala Ile Ala Ser His Asp Gly Gly Lys Gln Ala Leu Glu
    450                 455                 460

Thr Val Gln Arg Leu Leu Pro Val Leu Cys Gln Ala His Gly Leu Thr
465                 470                 475                 480

Pro Glu Gln Val Val Ala Ile Ala Ser Asn Gly Gly Lys Gln Ala
                485                 490                 495

Leu Glu Thr Val Gln Arg Leu Leu Pro Val Leu Cys Gln Ala His Gly
            500                 505                 510

Leu Thr Pro Glu Gln Val Val Ala Ile Ala Ser Asn His Gly Gly Lys
        515                 520                 525

Gln Ala Leu Glu Thr Val Gln Arg Leu Leu Pro Val Leu Cys Gln Ala
    530                 535                 540

His Gly Leu Thr Pro Glu Gln Val Val Ala Ile Ala Ser His Asp Gly
545                 550                 555                 560

Gly Lys Gln Ala Leu Glu Thr Val Gln Arg Leu Leu Pro Val Leu Cys
                565                 570                 575

Gln Ala His Gly Leu Thr Pro Glu Gln Val Val Ala Ile Ala Ser His
            580                 585                 590

Asp Gly Gly Lys Gln Ala Leu Glu Thr Val Gln Arg Leu Leu Pro Val
        595                 600                 605

Leu Cys Gln Ala His Gly Leu Thr Pro Glu Gln Val Val Ala Ile Ala
    610                 615                 620

Ser Asn His Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
                645                 650                 655

Ile Ala Ser Asn His Gly Gly Lys Gln Ala Leu Glu Thr Val Gln Arg
            660                 665                 670

Leu Leu Pro Val Leu Cys Gln Ala His Gly Leu Thr Pro Glu Gln Val
        675                 680                 685

Val Ala Ile Ala Ser His Asp Gly Gly Lys Gln Ala Leu Glu Thr Val
    690                 695                 700

Gln Arg Leu Leu Pro Val Leu Cys Gln Ala His Gly Leu Thr Pro Glu
705                 710                 715                 720

Gln Val Val Ala Ile Ala Ser His Asp Gly Gly Lys Gln Ala Leu Glu
                725                 730                 735

Thr Val Gln Arg Leu Leu Pro Val Leu Cys Gln Ala His Gly Leu Thr
            740                 745                 750
```

```
Pro Glu Gln Val Val Ala Ile Ala Ser His Asp Gly Gly Lys Gln Ala
            755                 760                 765

Leu Glu Thr Val Gln Arg Leu Leu Pro Val Leu Cys Gln Ala His Gly
    770                 775                 780

Leu Thr Pro Glu Gln Val Ala Ile Ala Ser Asn Ile Gly Gly Arg
785                 790                 795                 800

Pro Ala Leu Glu Ser Ile Val Ala Gln Leu Ser Arg Pro Asp Pro Ala
                805                 810                 815

Leu Ala Ala Leu Thr Asn Asp His Leu Val Ala Leu Ala Cys Leu Gly
            820                 825                 830

Gly Arg Pro Ala Leu Asp Ala Val Lys Lys Gly Leu Pro His Ala Pro
            835                 840                 845

Ala Leu Ile Lys Arg Thr Asn Arg Arg Ile Pro Glu Arg Thr Ser His
            850                 855                 860

Arg Val Ala Asp His Ala Gln Val Val Arg Val Leu Gly Phe Phe Gln
865                 870                 875                 880

Cys His Ser His Pro Ala Gln Ala Phe Asp Asp Ala Met Thr Gln Phe
                885                 890                 895

Gly Met Ser Arg His Gly Leu Leu Gln Leu Phe Arg Arg Val Gly Val
            900                 905                 910

Thr Glu Leu Glu Ala Arg Ser Gly Thr Leu Pro Pro Ala Ser Gln Arg
            915                 920                 925

Trp Asp Arg Ile Leu Gln Ala Ser Gly Met Lys Arg Ala Lys Pro Ser
            930                 935                 940

Pro Thr Ser Thr Gln Thr Pro Asp Gln Ala Ser Leu His Ala Phe Ala
945                 950                 955                 960

Asp Ser Leu Glu Arg Asp Leu Asp Ala Pro Ser Pro Met His Glu Gly
                965                 970                 975

Asp Gln Thr Arg Ala Ser Ala Ser Pro Lys Lys Arg Lys Val Glu
            980                 985                 990

Ala Ser Gly Ser Gly Arg Ala Asp  Ala Leu Asp Asp Phe  Asp Leu Asp
            995                 1000                 1005

Met Leu  Gly Ser Asp Ala Leu  Asp Asp Phe Asp Leu  Asp Met Leu
    1010                 1015                 1020

Gly Ser Asp Ala Leu Asp Asp  Phe Asp Leu Asp Met  Leu Gly Ser
    1025                 1030                 1035

Asp Ala  Leu Asp Asp Phe Asp  Leu Asp Met Leu Ile  Asn
    1040                 1045                 1050

<210> SEQ ID NO 41
<211> LENGTH: 1051
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Ser Arg Thr Arg Leu Pro Ser Pro Ala Pro Ser Pro Ala Phe
1               5                   10                  15

Ser Ala Asp Ser Phe Ser Asp Leu Leu Arg Gln Phe Asp Pro Ser Leu
                20                  25                  30

Phe Asn Thr Ser Leu Phe Asp Ser Leu Pro Pro Phe Gly Ala His His
            35                  40                  45

Thr Glu Ala Ala Thr Gly Glu Trp Asp Glu Val Gln Ser Gly Leu Arg
    50                  55                  60
```

```
Ala Ala Asp Ala Pro Pro Thr Met Arg Val Ala Val Thr Ala Ala
 65                  70                  75                  80

Arg Pro Pro Arg Ala Lys Pro Ala Pro Arg Arg Ala Ala Gln Pro
                 85                  90                  95

Ser Asp Ala Ser Pro Ala Ala Gln Val Asp Leu Arg Thr Leu Gly Tyr
                100                 105                 110

Ser Gln Gln Gln Gln Glu Lys Ile Lys Pro Lys Val Arg Ser Thr Val
                115                 120                 125

Ala Gln His His Glu Ala Leu Val Gly His Gly Phe Thr His Ala His
                130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
                180                 185                 190

Leu Leu Thr Val Ala Gly Glu Leu Arg Gly Pro Pro Leu Gln Leu Asp
                195                 200                 205

Thr Gly Gln Leu Leu Lys Ile Ala Lys Arg Gly Gly Val Thr Ala Val
                210                 215                 220

Glu Ala Val His Ala Trp Arg Asn Ala Leu Thr Gly Ala Pro Leu Asn
225                 230                 235                 240

Leu Thr Pro Glu Gln Val Val Ala Ile Ala Ser His Asp Gly Gly Lys
                245                 250                 255

Gln Ala Leu Glu Thr Val Gln Arg Leu Leu Pro Val Leu Cys Gln Ala
                260                 265                 270

His Gly Leu Thr Pro Glu Gln Val Val Ala Ile Ala Ser His Asn Gly
                275                 280                 285

Gly Lys Gln Ala Leu Glu Thr Val Gln Arg Leu Leu Pro Val Leu Cys
                290                 295                 300

Gln Ala His Gly Leu Thr Pro Glu Gln Val Val Ala Ile Ala Ser His
305                 310                 315                 320

Asn Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
                340                 345                 350

Ser His Asp Gly Gly Lys Gln Ala Leu Glu Thr Val Gln Arg Leu Leu
                355                 360                 365

Pro Val Leu Cys Gln Ala His Gly Leu Thr Pro Glu Gln Val Val Ala
                370                 375                 380

Ile Ala Ser His Asp Gly Gly Lys Gln Ala Leu Glu Thr Val Gln Arg
385                 390                 395                 400

Leu Leu Pro Val Leu Cys Gln Ala His Gly Leu Thr Pro Glu Gln Val
                405                 410                 415

Val Ala Ile Ala Ser His Asp Gly Gly Lys Gln Ala Leu Glu Thr Val
                420                 425                 430

Gln Arg Leu Leu Pro Val Leu Cys Gln Ala His Gly Leu Thr Pro Glu
                435                 440                 445

Gln Val Val Ala Ile Ala Ser His Asp Gly Gly Lys Gln Ala Leu Glu
                450                 455                 460

Thr Val Gln Arg Leu Leu Pro Val Leu Cys Gln Ala His Gly Leu Thr
465                 470                 475                 480

Pro Glu Gln Val Val Ala Ile Ala Ser Asn Gly Gly Gly Lys Gln Ala
```

```
                485                 490                 495
Leu Glu Thr Val Gln Arg Leu Leu Pro Val Leu Cys Gln Ala His Gly
                500                 505                 510
Leu Thr Pro Glu Gln Val Val Ala Ile Ala Ser His Asn Gly Gly Lys
                515                 520                 525
Gln Ala Leu Glu Thr Val Gln Arg Leu Leu Pro Val Leu Cys Gln Ala
                530                 535                 540
His Gly Leu Thr Pro Glu Gln Val Val Ala Ile Ala Ser His Asp Gly
545                 550                 555                 560
Gly Lys Gln Ala Leu Glu Thr Val Gln Arg Leu Leu Pro Val Leu Cys
                565                 570                 575
Gln Ala His Gly Leu Thr Pro Glu Gln Val Val Ala Ile Ala Ser His
                580                 585                 590
Asp Gly Gly Lys Gln Ala Leu Glu Thr Val Gln Arg Leu Leu Pro Val
                595                 600                 605
Leu Cys Gln Ala His Gly Leu Thr Pro Glu Gln Val Val Ala Ile Ala
                610                 615                 620
Ser His Asn Gly Gly Lys Gln Ala Leu Glu Thr Val Gln Arg Leu Leu
625                 630                 635                 640
Pro Val Leu Cys Gln Ala His Gly Leu Thr Pro Glu Gln Val Val Ala
                645                 650                 655
Ile Ala Ser His Asn Gly Gly Lys Gln Ala Leu Glu Thr Val Gln Arg
                660                 665                 670
Leu Leu Pro Val Leu Cys Gln Ala His Gly Leu Thr Pro Glu Gln Val
                675                 680                 685
Val Ala Ile Ala Ser His Asp Gly Gly Lys Gln Ala Leu Glu Thr Val
                690                 695                 700
Gln Arg Leu Leu Pro Val Leu Cys Gln Ala His Gly Leu Thr Pro Glu
705                 710                 715                 720
Gln Val Val Ala Ile Ala Ser His Asp Gly Gly Lys Gln Ala Leu Glu
                725                 730                 735
Thr Val Gln Arg Leu Leu Pro Val Leu Cys Gln Ala His Gly Leu Thr
                740                 745                 750
Pro Glu Gln Val Val Ala Ile Ala Ser His Asp Gly Gly Lys Gln Ala
                755                 760                 765
Leu Glu Thr Val Gln Arg Leu Leu Pro Val Leu Cys Gln Ala His Gly
                770                 775                 780
Leu Thr Pro Glu Gln Val Val Ala Ile Ala Ser Asn Ile Gly Gly Arg
785                 790                 795                 800
Pro Ala Leu Glu Ser Ile Val Ala Gln Leu Ser Arg Pro Asp Pro Ala
                805                 810                 815
Leu Ala Ala Leu Thr Asn Asp His Leu Val Ala Leu Ala Cys Leu Gly
                820                 825                 830
Gly Arg Pro Ala Leu Asp Ala Val Lys Lys Gly Leu Pro His Ala Pro
                835                 840                 845
Ala Leu Ile Lys Arg Thr Asn Arg Arg Ile Pro Glu Arg Thr Ser His
850                 855                 860
Arg Val Ala Asp His Ala Gln Val Val Arg Val Leu Gly Phe Phe Gln
865                 870                 875                 880
Cys His Ser His Pro Ala Gln Ala Phe Asp Asp Ala Met Thr Gln Phe
                885                 890                 895
Gly Met Ser Arg His Gly Leu Leu Gln Leu Phe Arg Arg Val Gly Val
                900                 905                 910
```

```
Thr Glu Leu Glu Ala Arg Ser Gly Thr Leu Pro Pro Ala Ser Gln Arg
        915                 920                 925

Trp Asp Arg Ile Leu Gln Ala Ser Gly Met Lys Arg Ala Lys Pro Ser
    930                 935                 940

Pro Thr Ser Thr Gln Thr Pro Asp Gln Ala Ser Leu His Ala Phe Ala
945                 950                 955                 960

Asp Ser Leu Glu Arg Asp Leu Asp Ala Pro Ser Pro Met His Glu Gly
            965                 970                 975

Asp Gln Thr Arg Ala Ser Ala Ser Pro Lys Lys Lys Arg Lys Val Glu
            980                 985                 990

Ala Ser Gly Ser Gly Arg Ala Asp Ala Leu Asp Asp Phe Asp Leu Asp
            995                 1000                1005

Met Leu Gly Ser Asp Ala Leu Asp Asp Phe Asp Leu Asp Met Leu
    1010                1015                1020

Gly Ser Asp Ala Leu Asp Asp Phe Asp Leu Asp Met Leu Gly Ser
    1025                1030                1035

Asp Ala Leu Asp Asp Phe Asp Leu Asp Met Leu Ile Asn
    1040                1045                1050
```

<210> SEQ ID NO 42
<211> LENGTH: 1051
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Pro Thr Met Arg Val Ala Val Thr Ala Ala
65                  70                  75                  80

Arg Pro Pro Arg Ala Lys Pro Ala Pro Arg Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Gln Glu Lys Ile Lys Pro Lys Val Arg Ser Thr Val
        115                 120                 125

Ala Gln His His Glu Ala Leu Val Gly His Gly Phe Thr His Ala His
    130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
        195                 200                 205

Thr Gly Gln Leu Leu Lys Ile Ala Lys Arg Gly Gly Val Thr Ala Val
    210                 215                 220
```

```
Glu Ala Val His Ala Trp Arg Asn Ala Leu Thr Gly Ala Pro Leu Asn
225                 230                 235                 240

Leu Thr Pro Glu Gln Val Val Ala Ile Ala Ser Asn Asn Gly Gly Lys
            245                 250                 255

Gln Ala Leu Glu Thr Val Gln Arg Leu Leu Pro Val Leu Cys Gln Ala
        260                 265                 270

His Gly Leu Thr Pro Glu Gln Val Val Ala Ile Ala Ser Asn Asn Gly
    275                 280                 285

Gly Lys Gln Ala Leu Glu Thr Val Gln Arg Leu Leu Pro Val Leu Cys
290                 295                 300

Gln Ala His Gly Leu Thr Pro Glu Gln Val Val Ala Ile Ala Ser Asn
305                 310                 315                 320

Gly Gly Gly Lys Gln Ala Leu Glu Thr Val Gln Arg Leu Leu Pro Val
            325                 330                 335

Leu Cys Gln Ala His Gly Leu Thr Pro Glu Gln Val Val Ala Ile Ala
        340                 345                 350

Ser Asn Ile Gly Gly Lys Gln Ala Leu Glu Thr Val Gln Arg Leu Leu
    355                 360                 365

Pro Val Leu Cys Gln Ala His Gly Leu Thr Pro Glu Gln Val Val Ala
370                 375                 380

Ile Ala Ser Asn Asn Gly Gly Lys Gln Ala Leu Glu Thr Val Gln Arg
385                 390                 395                 400

Leu Leu Pro Val Leu Cys Gln Ala His Gly Leu Thr Pro Glu Gln Val
            405                 410                 415

Val Ala Ile Ala Ser Asn Ile Gly Gly Lys Gln Ala Leu Glu Thr Val
        420                 425                 430

Gln Arg Leu Leu Pro Val Leu Cys Gln Ala His Gly Leu Thr Pro Glu
    435                 440                 445

Gln Val Val Ala Ile Ala Ser His Asp Gly Gly Lys Gln Ala Leu Glu
450                 455                 460

Thr Val Gln Arg Leu Leu Pro Val Leu Cys Gln Ala His Gly Leu Thr
465                 470                 475                 480

Pro Glu Gln Val Val Ala Ile Ala Ser His Asp Gly Gly Lys Gln Ala
            485                 490                 495

Leu Glu Thr Val Gln Arg Leu Leu Pro Val Leu Cys Gln Ala His Gly
        500                 505                 510

Leu Thr Pro Glu Gln Val Val Ala Ile Ala Ser Asn Gly Gly Gly Lys
    515                 520                 525

Gln Ala Leu Glu Thr Val Gln Arg Leu Leu Pro Val Leu Cys Gln Ala
530                 535                 540

His Gly Leu Thr Pro Glu Gln Val Val Ala Ile Ala Ser Asn Gly Gly
545                 550                 555                 560

Gly Lys Gln Ala Leu Glu Thr Val Gln Arg Leu Leu Pro Val Leu Cys
            565                 570                 575

Gln Ala His Gly Leu Thr Pro Glu Gln Val Val Ala Ile Ala Ser Asn
        580                 585                 590

Ile Gly Gly Lys Gln Ala Leu Glu Thr Val Gln Arg Leu Leu Pro Val
    595                 600                 605

Leu Cys Gln Ala His Gly Leu Thr Pro Glu Gln Val Val Ala Ile Ala
610                 615                 620

Ser Asn Asn Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
            645                 650                 655
```

```
Ile Ala Ser Asn Asn Gly Gly Lys Gln Ala Leu Glu Thr Val Gln Arg
            660                 665                 670

Leu Leu Pro Val Leu Cys Gln Ala His Gly Leu Thr Pro Glu Gln Val
        675                 680                 685

Val Ala Ile Ala Ser Asn Asn Gly Gly Lys Gln Ala Leu Glu Thr Val
    690                 695                 700

Gln Arg Leu Leu Pro Val Leu Cys Gln Ala His Gly Leu Thr Pro Glu
705                 710                 715                 720

Gln Val Val Ala Ile Ala Ser His Asp Gly Gly Lys Gln Ala Leu Glu
                725                 730                 735

Thr Val Gln Arg Leu Leu Pro Val Leu Cys Gln Ala His Gly Leu Thr
            740                 745                 750

Pro Glu Gln Val Val Ala Ile Ala Ser Asn Gly Gly Lys Gln Ala
        755                 760                 765

Leu Glu Thr Val Gln Arg Leu Leu Pro Val Leu Cys Gln Ala His Gly
    770                 775                 780

Leu Thr Pro Glu Gln Val Val Ala Ile Ala Ser Asn Ile Gly Gly Arg
785                 790                 795                 800

Pro Ala Leu Glu Ser Ile Val Ala Gln Leu Ser Arg Pro Asp Pro Ala
                805                 810                 815

Leu Ala Ala Leu Thr Asn Asp His Leu Val Ala Leu Ala Cys Leu Gly
            820                 825                 830

Gly Arg Pro Ala Leu Asp Ala Val Lys Lys Gly Leu Pro His Ala Pro
        835                 840                 845

Ala Leu Ile Lys Arg Thr Asn Arg Arg Ile Pro Glu Arg Thr Ser His
    850                 855                 860

Arg Val Ala Asp His Ala Gln Val Val Arg Val Leu Gly Phe Phe Gln
865                 870                 875                 880

Cys His Ser His Pro Ala Gln Ala Phe Asp Asp Ala Met Thr Gln Phe
                885                 890                 895

Gly Met Ser Arg His Gly Leu Leu Gln Leu Phe Arg Arg Val Gly Val
            900                 905                 910

Thr Glu Leu Glu Ala Arg Ser Gly Thr Leu Pro Pro Ala Ser Gln Arg
        915                 920                 925

Trp Asp Arg Ile Leu Gln Ala Ser Gly Met Lys Arg Ala Lys Pro Ser
    930                 935                 940

Pro Thr Ser Thr Gln Thr Pro Asp Gln Ala Ser Leu His Ala Phe Ala
945                 950                 955                 960

Asp Ser Leu Glu Arg Asp Leu Asp Ala Pro Ser Pro Met His Glu Gly
                965                 970                 975

Asp Gln Thr Arg Ala Ser Ala Ser Pro Lys Lys Lys Arg Lys Val Glu
            980                 985                 990

Ala Ser Gly Ser Gly Arg Ala Asp  Ala Leu Asp Asp Phe  Asp Leu Asp
        995                 1000                1005

Met Leu  Gly Ser Asp Ala Leu  Asp Asp Phe Asp Leu  Asp Met Leu
    1010                1015                1020

Gly Ser  Asp Ala Leu Asp Asp  Phe Asp Leu Asp Met  Leu Gly Ser
    1025                1030                1035

Asp Ala  Leu Asp Asp Phe Asp  Leu Asp Met Leu Ile  Asn
    1040                1045                1050

<210> SEQ ID NO 43
<211> LENGTH: 1051
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 43

```
Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
            35                  40                  45

Thr Glu Ala Ala Thr Gly Glu Trp Asp Glu Val Gln Ser Gly Leu Arg
        50                  55                  60

Ala Ala Asp Ala Pro Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
                100                 105                 110

Ser Gln Gln Gln Glu Lys Ile Lys Pro Lys Val Arg Ser Thr Val
        115                 120                 125

Ala Gln His His Glu Ala Leu Val Gly His Gly Phe Thr His Ala His
        130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
                180                 185                 190

Leu Leu Thr Val Ala Gly Glu Leu Arg Gly Pro Pro Leu Gln Leu Asp
            195                 200                 205

Thr Gly Gln Leu Leu Lys Ile Ala Lys Arg Gly Gly Val Thr Ala Val
        210                 215                 220

Glu Ala Val His Ala Trp Arg Asn Ala Leu Thr Gly Ala Pro Leu Asn
225                 230                 235                 240

Leu Thr Pro Glu Gln Val Val Ala Ile Ala Ser Asn Lys Gly Gly Lys
                245                 250                 255

Gln Ala Leu Glu Thr Val Gln Arg Leu Leu Pro Val Leu Cys Gln Ala
            260                 265                 270

His Gly Leu Thr Pro Glu Gln Val Val Ala Ile Ala Ser Asn Lys Gly
        275                 280                 285

Gly Lys Gln Ala Leu Glu Thr Val Gln Arg Leu Leu Pro Val Leu Cys
        290                 295                 300

Gln Ala His Gly Leu Thr Pro Glu Gln Val Val Ala Ile Ala Ser Asn
305                 310                 315                 320

Gly Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
            340                 345                 350

Ser Asn Ile Gly Gly Lys Gln Ala Leu Glu Thr Val Gln Arg Leu Leu
            355                 360                 365

Pro Val Leu Cys Gln Ala His Gly Leu Thr Pro Glu Gln Val Val Ala
        370                 375                 380

Ile Ala Ser Asn Lys Gly Gly Lys Gln Ala Leu Glu Thr Val Gln Arg
```

```
                385                 390                 395                 400
Leu Leu Pro Val Leu Cys Gln Ala His Gly Leu Thr Pro Glu Gln Val
                405                 410                 415

Val Ala Ile Ala Ser Asn Ile Gly Gly Lys Gln Ala Leu Glu Thr Val
                420                 425                 430

Gln Arg Leu Leu Pro Val Leu Cys Gln Ala His Gly Leu Thr Pro Glu
                435                 440                 445

Gln Val Val Ala Ile Ala Ser His Asp Gly Gly Lys Gln Ala Leu Glu
                450                 455                 460

Thr Val Gln Arg Leu Leu Pro Val Leu Cys Gln Ala His Gly Leu Thr
465                 470                 475                 480

Pro Glu Gln Val Val Ala Ile Ala Ser His Asp Gly Gly Lys Gln Ala
                485                 490                 495

Leu Glu Thr Val Gln Arg Leu Leu Pro Val Leu Cys Gln Ala His Gly
                500                 505                 510

Leu Thr Pro Glu Gln Val Val Ala Ile Ala Ser Asn Gly Gly Gly Lys
                515                 520                 525

Gln Ala Leu Glu Thr Val Gln Arg Leu Leu Pro Val Leu Cys Gln Ala
                530                 535                 540

His Gly Leu Thr Pro Glu Gln Val Val Ala Ile Ala Ser Asn Gly Gly
545                 550                 555                 560

Gly Lys Gln Ala Leu Glu Thr Val Gln Arg Leu Leu Pro Val Leu Cys
                565                 570                 575

Gln Ala His Gly Leu Thr Pro Glu Gln Val Val Ala Ile Ala Ser Asn
                580                 585                 590

Ile Gly Gly Lys Gln Ala Leu Glu Thr Val Gln Arg Leu Leu Pro Val
                595                 600                 605

Leu Cys Gln Ala His Gly Leu Thr Pro Glu Gln Val Val Ala Ile Ala
                610                 615                 620

Ser Asn Lys Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
                645                 650                 655

Ile Ala Ser Asn Lys Gly Gly Lys Gln Ala Leu Glu Thr Val Gln Arg
                660                 665                 670

Leu Leu Pro Val Leu Cys Gln Ala His Gly Leu Thr Pro Glu Gln Val
                675                 680                 685

Val Ala Ile Ala Ser Asn Lys Gly Gly Lys Gln Ala Leu Glu Thr Val
                690                 695                 700

Gln Arg Leu Leu Pro Val Leu Cys Gln Ala His Gly Leu Thr Pro Glu
705                 710                 715                 720

Gln Val Val Ala Ile Ala Ser His Asp Gly Gly Lys Gln Ala Leu Glu
                725                 730                 735

Thr Val Gln Arg Leu Leu Pro Val Leu Cys Gln Ala His Gly Leu Thr
                740                 745                 750

Pro Glu Gln Val Val Ala Ile Ala Ser Asn Gly Gly Gly Lys Gln Ala
                755                 760                 765

Leu Glu Thr Val Gln Arg Leu Leu Pro Val Leu Cys Gln Ala His Gly
                770                 775                 780

Leu Thr Pro Glu Gln Val Val Ala Ile Ala Ser Asn Ile Gly Gly Arg
785                 790                 795                 800

Pro Ala Leu Glu Ser Ile Val Ala Gln Leu Ser Arg Pro Asp Pro Ala
                805                 810                 815
```

Leu Ala Ala Leu Thr Asn Asp His Leu Val Ala Leu Ala Cys Leu Gly
          820                 825                 830

Gly Arg Pro Ala Leu Asp Ala Val Lys Lys Gly Leu Pro His Ala Pro
          835                 840                 845

Ala Leu Ile Lys Arg Thr Asn Arg Arg Ile Pro Glu Arg Thr Ser His
          850                 855                 860

Arg Val Ala Asp His Ala Gln Val Val Arg Val Leu Gly Phe Phe Gln
865                 870                 875                 880

Cys His Ser His Pro Ala Gln Ala Phe Asp Asp Ala Met Thr Gln Phe
                  885                 890                 895

Gly Met Ser Arg His Gly Leu Leu Gln Leu Phe Arg Arg Val Gly Val
          900                 905                 910

Thr Glu Leu Glu Ala Arg Ser Gly Thr Leu Pro Pro Ala Ser Gln Arg
          915                 920                 925

Trp Asp Arg Ile Leu Gln Ala Ser Gly Met Lys Arg Ala Lys Pro Ser
          930                 935                 940

Pro Thr Ser Thr Gln Thr Pro Asp Gln Ala Ser Leu His Ala Phe Ala
945                 950                 955                 960

Asp Ser Leu Glu Arg Asp Leu Ser Ala Pro Ser Pro Met His Glu Gly
                  965                 970                 975

Asp Gln Thr Arg Ala Ser Ala Ser Pro Lys Lys Lys Arg Lys Val Glu
          980                 985                 990

Ala Ser Gly Ser Gly Arg Ala Asp Ala Leu Asp Asp Phe Asp Leu Asp
          995                 1000                1005

Met Leu Gly Ser Asp Ala Leu Asp Asp Phe Asp Leu Asp Met Leu
    1010                1015                1020

Gly Ser Asp Ala Leu Asp Asp Phe Asp Leu Asp Met Leu Gly Ser
    1025                1030                1035

Asp Ala Leu Asp Asp Phe Asp Leu Asp Met Leu Ile Asn
    1040                1045                1050

<210> SEQ ID NO 44
<211> LENGTH: 1051
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Pro Thr Met Arg Val Ala Val Thr Ala Ala
65                  70                  75                  80

Arg Pro Pro Arg Ala Lys Pro Ala Pro Arg Arg Ala Ala Gln Pro
            85                  90                  95

Ser Asp Ala Ser Pro Ala Ala Gln Val Asp Leu Arg Thr Leu Gly Tyr
            100                 105                 110

Ser Gln Gln Gln Gln Glu Lys Ile Lys Pro Lys Val Arg Ser Thr Val
        115                 120                 125

-continued

```
Ala Gln His His Glu Ala Leu Val Gly His Gly Phe Thr His Ala His
    130                 135                 140
Ile Val Ala Leu Ser Gln His Pro Ala Ala Leu Gly Thr Val Ala Val
145                 150                 155                 160
Lys Tyr Gln Asp Met Ile Ala Ala Leu Pro Glu Ala Thr His Glu Ala
                165                 170                 175
Ile Val Gly Val Gly Lys Gln Trp Ser Gly Ala Arg Ala Leu Glu Ala
                180                 185                 190
Leu Leu Thr Val Ala Gly Glu Leu Arg Gly Pro Leu Gln Leu Asp
        195                 200                 205
Thr Gly Gln Leu Leu Lys Ile Ala Lys Arg Gly Gly Val Thr Ala Val
    210                 215                 220
Glu Ala Val His Ala Trp Arg Asn Ala Leu Thr Gly Ala Pro Leu Asn
225                 230                 235                 240
Leu Thr Pro Glu Gln Val Val Ala Ile Ala Ser Asn His Gly Gly Lys
                245                 250                 255
Gln Ala Leu Glu Thr Val Gln Arg Leu Leu Pro Val Leu Cys Gln Ala
                260                 265                 270
His Gly Leu Thr Pro Glu Gln Val Val Ala Ile Ala Ser Asn His Gly
        275                 280                 285
Gly Lys Gln Ala Leu Glu Thr Val Gln Arg Leu Leu Pro Val Leu Cys
    290                 295                 300
Gln Ala His Gly Leu Thr Pro Glu Gln Val Val Ala Ile Ala Ser Asn
305                 310                 315                 320
Gly Gly Gly Lys Gln Ala Leu Glu Thr Val Gln Arg Leu Leu Pro Val
                325                 330                 335
Leu Cys Gln Ala His Gly Leu Thr Pro Glu Gln Val Val Ala Ile Ala
                340                 345                 350
Ser Asn Ile Gly Gly Lys Gln Ala Leu Glu Thr Val Gln Arg Leu Leu
        355                 360                 365
Pro Val Leu Cys Gln Ala His Gly Leu Thr Pro Glu Gln Val Val Ala
    370                 375                 380
Ile Ala Ser Asn His Gly Gly Lys Gln Ala Leu Glu Thr Val Gln Arg
385                 390                 395                 400
Leu Leu Pro Val Leu Cys Gln Ala His Gly Leu Thr Pro Glu Gln Val
                405                 410                 415
Val Ala Ile Ala Ser Asn Ile Gly Gly Lys Gln Ala Leu Glu Thr Val
                420                 425                 430
Gln Arg Leu Leu Pro Val Leu Cys Gln Ala His Gly Leu Thr Pro Glu
        435                 440                 445
Gln Val Val Ala Ile Ala Ser His Asp Gly Gly Lys Gln Ala Leu Glu
    450                 455                 460
Thr Val Gln Arg Leu Leu Pro Val Leu Cys Gln Ala His Gly Leu Thr
465                 470                 475                 480
Pro Glu Gln Val Val Ala Ile Ala Ser His Asp Gly Gly Lys Gln Ala
                485                 490                 495
Leu Glu Thr Val Gln Arg Leu Leu Pro Val Leu Cys Gln Ala His Gly
                500                 505                 510
Leu Thr Pro Glu Gln Val Val Ala Ile Ala Ser Asn Gly Gly Gly Lys
        515                 520                 525
Gln Ala Leu Glu Thr Val Gln Arg Leu Leu Pro Val Leu Cys Gln Ala
    530                 535                 540
His Gly Leu Thr Pro Glu Gln Val Val Ala Ile Ala Ser Asn Gly Gly
545                 550                 555                 560
```

```
Gly Lys Gln Ala Leu Glu Thr Val Gln Arg Leu Leu Pro Val Leu Cys
            565                 570                 575

Gln Ala His Gly Leu Thr Pro Glu Gln Val Val Ala Ile Ala Ser Asn
            580                 585                 590

Ile Gly Gly Lys Gln Ala Leu Glu Thr Val Gln Arg Leu Leu Pro Val
            595                 600                 605

Leu Cys Gln Ala His Gly Leu Thr Pro Glu Gln Val Val Ala Ile Ala
            610                 615                 620

Ser Asn His Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
            645                 650                 655

Ile Ala Ser Asn His Gly Gly Lys Gln Ala Leu Glu Thr Val Gln Arg
            660                 665                 670

Leu Leu Pro Val Leu Cys Gln Ala His Gly Leu Thr Pro Glu Gln Val
            675                 680                 685

Val Ala Ile Ala Ser Asn His Gly Gly Lys Gln Ala Leu Glu Thr Val
            690                 695                 700

Gln Arg Leu Leu Pro Val Leu Cys Gln Ala His Gly Leu Thr Pro Glu
705                 710                 715                 720

Gln Val Val Ala Ile Ala Ser His Asp Gly Gly Lys Gln Ala Leu Glu
            725                 730                 735

Thr Val Gln Arg Leu Leu Pro Val Leu Cys Gln Ala His Gly Leu Thr
            740                 745                 750

Pro Glu Gln Val Val Ala Ile Ala Ser Asn Gly Gly Gly Lys Gln Ala
            755                 760                 765

Leu Glu Thr Val Gln Arg Leu Leu Pro Val Leu Cys Gln Ala His Gly
            770                 775                 780

Leu Thr Pro Glu Gln Val Val Ala Ile Ala Ser Asn Ile Gly Gly Arg
785                 790                 795                 800

Pro Ala Leu Glu Ser Ile Val Ala Gln Leu Ser Arg Pro Asp Pro Ala
            805                 810                 815

Leu Ala Ala Leu Thr Asn Asp His Leu Val Ala Leu Ala Cys Leu Gly
            820                 825                 830

Gly Arg Pro Ala Leu Asp Ala Val Lys Lys Gly Leu Pro His Ala Pro
            835                 840                 845

Ala Leu Ile Lys Arg Thr Asn Arg Arg Ile Pro Glu Arg Thr Ser His
850                 855                 860

Arg Val Ala Asp His Ala Gln Val Val Arg Val Leu Gly Phe Phe Gln
865                 870                 875                 880

Cys His Ser His Pro Ala Gln Ala Phe Asp Asp Ala Met Thr Gln Phe
            885                 890                 895

Gly Met Ser Arg His Gly Leu Leu Gln Leu Phe Arg Arg Val Gly Val
            900                 905                 910

Thr Glu Leu Glu Ala Arg Ser Gly Thr Leu Pro Pro Ala Ser Gln Arg
            915                 920                 925

Trp Asp Arg Ile Leu Gln Ala Ser Gly Met Lys Arg Ala Lys Pro Ser
930                 935                 940

Pro Thr Ser Thr Gln Thr Pro Asp Gln Ala Ser Leu His Ala Phe Ala
945                 950                 955                 960

Asp Ser Leu Glu Arg Asp Leu Asp Ala Pro Ser Pro Met His Glu Gly
            965                 970                 975

Asp Gln Thr Arg Ala Ser Ala Ser Pro Lys Lys Lys Arg Lys Val Glu
```

-continued

```
                       980                 985                 990
Ala Ser Gly Ser Gly Arg Ala Asp  Ala Leu Asp Asp Phe  Asp Leu Asp
                995                 1000                1005

Met Leu  Gly Ser Asp Ala Leu  Asp Asp Phe Asp Leu   Asp Met Leu
    1010                1015                1020

Gly Ser  Asp Ala Leu Asp Asp  Phe Asp Leu Asp Met   Leu Gly Ser
    1025                1030                1035

Asp Ala  Leu Asp Asp Phe Asp  Leu Asp Met Leu Ile   Asn
    1040                1045                1050
```

<210> SEQ ID NO 45
<211> LENGTH: 1051
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
                20                  25                  30

Phe Asn Thr Ser Leu Phe Asp Ser Leu Pro Pro Phe Gly Ala His His
            35                  40                  45

Thr Glu Ala Ala Thr Gly Glu Trp Asp Glu Val Gln Ser Gly Leu Arg
        50                  55                  60

Ala Ala Asp Ala Pro Pro Thr Met Arg Val Ala Val Thr Ala Ala
65                  70                  75                  80

Arg Pro Pro Arg Ala Lys Pro Ala Pro Arg Arg Arg Ala Ala Gln Pro
                85                  90                  95

Ser Asp Ala Ser Pro Ala Ala Gln Val Asp Leu Arg Thr Leu Gly Tyr
                100                 105                 110

Ser Gln Gln Gln Gln Glu Lys Ile Lys Pro Lys Val Arg Ser Thr Val
            115                 120                 125

Ala Gln His His Glu Ala Leu Val Gly His Gly Phe Thr His Ala His
        130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
                180                 185                 190

Leu Leu Thr Val Ala Gly Glu Leu Arg Gly Pro Pro Leu Gln Leu Asp
            195                 200                 205

Thr Gly Gln Leu Leu Lys Ile Ala Lys Arg Gly Gly Val Thr Ala Val
        210                 215                 220

Glu Ala Val His Ala Trp Arg Asn Ala Leu Thr Gly Ala Pro Leu Asn
225                 230                 235                 240

Leu Thr Pro Glu Gln Val Val Ala Ile Ala Ser His Asn Gly Gly Lys
                245                 250                 255

Gln Ala Leu Glu Thr Val Gln Arg Leu Leu Pro Val Leu Cys Gln Ala
                260                 265                 270

His Gly Leu Thr Pro Glu Gln Val Val Ala Ile Ala Ser His Asn Gly
            275                 280                 285

Gly Lys Gln Ala Leu Glu Thr Val Gln Arg Leu Leu Pro Val Leu Cys
```

```
                290                 295                 300
Gln Ala His Gly Leu Thr Pro Glu Gln Val Val Ala Ile Ala Ser Asn
305                 310                 315                 320
Gly Gly Gly Lys Gln Ala Leu Glu Thr Val Gln Arg Leu Leu Pro Val
                325                 330                 335
Leu Cys Gln Ala His Gly Leu Thr Pro Glu Gln Val Val Ala Ile Ala
                340                 345                 350
Ser Asn Ile Gly Gly Lys Gln Ala Leu Glu Thr Val Gln Arg Leu Leu
                355                 360                 365
Pro Val Leu Cys Gln Ala His Gly Leu Thr Pro Glu Gln Val Val Ala
370                 375                 380
Ile Ala Ser His Asn Gly Gly Lys Gln Ala Leu Glu Thr Val Gln Arg
385                 390                 395                 400
Leu Leu Pro Val Leu Cys Gln Ala His Gly Leu Thr Pro Glu Gln Val
                405                 410                 415
Val Ala Ile Ala Ser Asn Ile Gly Gly Lys Gln Ala Leu Glu Thr Val
                420                 425                 430
Gln Arg Leu Leu Pro Val Leu Cys Gln Ala His Gly Leu Thr Pro Glu
                435                 440                 445
Gln Val Val Ala Ile Ala Ser His Asp Gly Gly Lys Gln Ala Leu Glu
                450                 455                 460
Thr Val Gln Arg Leu Leu Pro Val Leu Cys Gln Ala His Gly Leu Thr
465                 470                 475                 480
Pro Glu Gln Val Val Ala Ile Ala Ser His Asp Gly Gly Lys Gln Ala
                485                 490                 495
Leu Glu Thr Val Gln Arg Leu Leu Pro Val Leu Cys Gln Ala His Gly
                500                 505                 510
Leu Thr Pro Glu Gln Val Val Ala Ile Ala Ser Asn Gly Gly Gly Lys
                515                 520                 525
Gln Ala Leu Glu Thr Val Gln Arg Leu Leu Pro Val Leu Cys Gln Ala
                530                 535                 540
His Gly Leu Thr Pro Glu Gln Val Val Ala Ile Ala Ser Asn Gly Gly
545                 550                 555                 560
Gly Lys Gln Ala Leu Glu Thr Val Gln Arg Leu Leu Pro Val Leu Cys
                565                 570                 575
Gln Ala His Gly Leu Thr Pro Glu Gln Val Val Ala Ile Ala Ser Asn
                580                 585                 590
Ile Gly Gly Lys Gln Ala Leu Glu Thr Val Gln Arg Leu Leu Pro Val
                595                 600                 605
Leu Cys Gln Ala His Gly Leu Thr Pro Glu Gln Val Val Ala Ile Ala
610                 615                 620
Ser His Asn Gly Gly Lys Gln Ala Leu Glu Thr Val Gln Arg Leu Leu
625                 630                 635                 640
Pro Val Leu Cys Gln Ala His Gly Leu Thr Pro Glu Gln Val Val Ala
                645                 650                 655
Ile Ala Ser His Asn Gly Gly Lys Gln Ala Leu Glu Thr Val Gln Arg
                660                 665                 670
Leu Leu Pro Val Leu Cys Gln Ala His Gly Leu Thr Pro Glu Gln Val
                675                 680                 685
Val Ala Ile Ala Ser His Asn Gly Gly Lys Gln Ala Leu Glu Thr Val
                690                 695                 700
Gln Arg Leu Leu Pro Val Leu Cys Gln Ala His Gly Leu Thr Pro Glu
705                 710                 715                 720
```

```
Gln Val Val Ala Ile Ala Ser His Asp Gly Lys Gln Ala Leu Glu
            725                 730                 735

Thr Val Gln Arg Leu Leu Pro Val Leu Cys Gln Ala His Gly Leu Thr
        740                 745                 750

Pro Glu Gln Val Val Ala Ile Ala Ser Asn Gly Gly Lys Gln Ala
            755                 760                 765

Leu Glu Thr Val Gln Arg Leu Leu Pro Val Leu Cys Gln Ala His Gly
770                 775                 780

Leu Thr Pro Glu Gln Val Val Ala Ile Ala Ser Asn Ile Gly Gly Arg
785                 790                 795                 800

Pro Ala Leu Glu Ser Ile Val Ala Gln Leu Ser Arg Pro Asp Pro Ala
                805                 810                 815

Leu Ala Ala Leu Thr Asn Asp His Leu Val Ala Leu Ala Cys Leu Gly
                820                 825                 830

Gly Arg Pro Ala Leu Asp Ala Val Lys Lys Gly Leu Pro His Ala Pro
            835                 840                 845

Ala Leu Ile Lys Arg Thr Asn Arg Arg Ile Pro Glu Arg Thr Ser His
850                 855                 860

Arg Val Ala Asp His Ala Gln Val Val Arg Val Leu Gly Phe Phe Gln
865                 870                 875                 880

Cys His Ser His Pro Ala Gln Ala Phe Asp Asp Ala Met Thr Gln Phe
                885                 890                 895

Gly Met Ser Arg His Gly Leu Leu Gln Leu Phe Arg Arg Val Gly Val
            900                 905                 910

Thr Glu Leu Glu Ala Arg Ser Gly Thr Leu Pro Pro Ala Ser Gln Arg
        915                 920                 925

Trp Asp Arg Ile Leu Gln Ala Ser Gly Met Lys Arg Ala Lys Pro Ser
930                 935                 940

Pro Thr Ser Thr Gln Thr Pro Asp Gln Ala Ser Leu His Ala Phe Ala
945                 950                 955                 960

Asp Ser Leu Glu Arg Asp Leu Asp Ala Pro Ser Pro Met His Glu Gly
                965                 970                 975

Asp Gln Thr Arg Ala Ser Ala Ser Pro Lys Lys Lys Arg Lys Val Glu
            980                 985                 990

Ala Ser Gly Ser Gly Arg Ala Asp  Ala Leu Asp Asp Phe  Asp Leu Asp
            995                 1000                1005

Met Leu  Gly Ser Asp Ala Leu  Asp Asp Phe Asp Leu  Asp Met Leu
    1010                1015                1020

Gly Ser  Asp Ala Leu Asp Asp  Phe Asp Leu Asp Met  Leu Gly Ser
    1025                1030                1035

Asp Ala  Leu Asp Asp Phe Asp  Leu Asp Met Leu Ile  Asn
    1040                1045                1050

<210> SEQ ID NO 46
<211> LENGTH: 1023
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30
```

-continued

```
Phe Asn Thr Ser Leu Phe Asp Ser Leu Pro Pro Phe Gly Ala His His
         35                  40                  45
Thr Glu Ala Ala Thr Gly Glu Trp Asp Glu Val Gln Ser Gly Leu Arg
 50                  55                  60
Ala Ala Asp Ala Pro Pro Thr Met Arg Val Ala Val Thr Ala Ala
 65                  70                  75                  80
Arg Pro Pro Arg Ala Lys Pro Ala Pro Arg Arg Ala Ala Gln Pro
                 85                  90                  95
Ser Asp Ala Ser Pro Ala Ala Gln Val Asp Leu Arg Thr Leu Gly Tyr
                100                 105                 110
Ser Gln Gln Gln Glu Lys Ile Lys Pro Lys Val Arg Ser Thr Val
                115                 120                 125
Ala Gln His His Glu Ala Leu Val Gly His Gly Phe Thr His Ala His
 130                 135                 140
Ile Val Ala Leu Ser Gln His Pro Ala Ala Leu Gly Thr Val Ala Val
 145                 150                 155                 160
Lys Tyr Gln Asp Met Ile Ala Ala Leu Pro Glu Ala Thr His Glu Ala
                165                 170                 175
Ile Val Gly Val Gly Lys Gln Trp Ser Gly Ala Arg Ala Leu Glu Ala
                180                 185                 190
Leu Leu Thr Val Ala Gly Glu Leu Arg Gly Pro Pro Leu Gln Leu Asp
                195                 200                 205
Thr Gly Gln Leu Leu Lys Ile Ala Lys Arg Gly Gly Val Thr Ala Val
 210                 215                 220
Glu Ala Val His Ala Trp Arg Asn Ala Leu Thr Gly Ala Pro Leu Asn
 225                 230                 235                 240
Leu Thr Pro Glu Gln Val Val Ala Ile Ala Ser His Asp Gly Gly Lys
                245                 250                 255
Gln Ala Leu Glu Thr Val Gln Arg Leu Leu Pro Val Leu Cys Gln Ala
                260                 265                 270
His Gly Leu Thr Pro Glu Gln Val Val Ala Ile Ala Ser Asn Asn Gly
                275                 280                 285
Gly Lys Gln Ala Leu Glu Thr Val Gln Arg Leu Leu Pro Val Leu Cys
 290                 295                 300
Gln Ala His Gly Leu Thr Pro Glu Gln Val Val Ala Ile Ala Ser Asn
 305                 310                 315                 320
Asn Gly Gly Lys Gln Ala Leu Glu Thr Val Gln Arg Leu Leu Pro Val
                325                 330                 335
Leu Cys Gln Ala His Gly Leu Thr Pro Glu Gln Val Val Ala Ile Ala
                340                 345                 350
Ser His Asp Gly Gly Lys Gln Ala Leu Glu Thr Val Gln Arg Leu Leu
                355                 360                 365
Pro Val Leu Cys Gln Ala His Gly Leu Thr Pro Glu Gln Val Val Ala
 370                 375                 380
Ile Ala Ser His Asp Gly Gly Lys Gln Ala Leu Glu Thr Val Gln Arg
 385                 390                 395                 400
Leu Leu Pro Val Leu Cys Gln Ala His Gly Leu Thr Pro Glu Gln Val
                405                 410                 415
Val Ala Ile Ala Ser His Asp Gly Gly Lys Gln Ala Leu Glu Thr Val
                420                 425                 430
Gln Arg Leu Leu Pro Val Leu Cys Gln Ala His Gly Leu Thr Pro Glu
                435                 440                 445
Gln Val Val Ala Ile Ala Ser His Asp Gly Gly Lys Gln Ala Leu Glu
                450                 455                 460
```

-continued

```
Thr Val Gln Arg Leu Leu Pro Val Leu Cys Gln Ala His Gly Leu Thr
465                 470                 475                 480

Pro Glu Gln Val Val Ala Ile Ala Ser Asn Gly Gly Lys Gln Ala
                485                 490                 495

Leu Glu Thr Val Gln Arg Leu Leu Pro Val Leu Cys Gln Ala His Gly
            500                 505                 510

Leu Thr Pro Glu Gln Val Val Ala Ile Ala Ser Asn Asn Gly Gly Lys
        515                 520                 525

Gln Ala Leu Glu Thr Val Gln Arg Leu Leu Pro Val Leu Cys Gln Ala
    530                 535                 540

His Gly Leu Thr Pro Glu Gln Val Val Ala Ile Ala Ser His Asp Gly
545                 550                 555                 560

Gly Lys Gln Ala Leu Glu Thr Val Gln Arg Leu Leu Pro Val Leu Cys
                565                 570                 575

Gln Ala His Gly Leu Thr Pro Glu Gln Val Val Ala Ile Ala Ser His
            580                 585                 590

Asp Gly Gly Lys Gln Ala Leu Glu Thr Val Gln Arg Leu Leu Pro Val
        595                 600                 605

Leu Cys Gln Ala His Gly Leu Thr Pro Glu Gln Val Val Ala Ile Ala
    610                 615                 620

Ser Asn Asn Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
                645                 650                 655

Ile Ala Ser Asn Asn Gly Gly Lys Gln Ala Leu Glu Thr Val Gln Arg
            660                 665                 670

Leu Leu Pro Val Leu Cys Gln Ala His Gly Leu Thr Pro Glu Gln Val
        675                 680                 685

Val Ala Ile Ala Ser His Asp Gly Gly Lys Gln Ala Leu Glu Thr Val
    690                 695                 700

Gln Arg Leu Leu Pro Val Leu Cys Gln Ala His Gly Leu Thr Pro Glu
705                 710                 715                 720

Gln Val Val Ala Ile Ala Ser His Asp Gly Gly Lys Gln Ala Leu Glu
                725                 730                 735

Thr Val Gln Arg Leu Leu Pro Val Leu Cys Gln Ala His Gly Leu Thr
            740                 745                 750

Pro Glu Gln Val Val Ala Ile Ala Ser His Asp Gly Gly Lys Gln Ala
        755                 760                 765

Leu Glu Thr Val Gln Arg Leu Leu Pro Val Leu Cys Gln Ala His Gly
    770                 775                 780

Leu Thr Pro Glu Gln Val Val Ala Ile Ala Ser Asn Ile Gly Gly Arg
785                 790                 795                 800

Pro Ala Leu Glu Ser Ile Val Ala Gln Leu Ser Arg Pro Asp Pro Ala
                805                 810                 815

Leu Ala Ala Leu Thr Asn Asp His Leu Val Ala Leu Ala Cys Leu Gly
            820                 825                 830

Gly Arg Pro Ala Leu Asp Ala Val Lys Lys Gly Leu Pro His Ala Pro
        835                 840                 845

Ala Leu Ile Lys Arg Thr Asn Arg Arg Ile Pro Glu Arg Thr Ser His
    850                 855                 860

Arg Val Ala Asp His Ala Gln Val Val Arg Val Leu Gly Phe Phe Gln
865                 870                 875                 880

Cys His Ser His Pro Ala Gln Ala Phe Asp Asp Ala Met Thr Gln Phe
```

885                 890                 895
Gly Met Ser Arg His Gly Leu Leu Gln Leu Phe Arg Arg Val Gly Val
            900                 905                 910
Thr Glu Leu Glu Ala Arg Ser Gly Thr Leu Pro Pro Ala Ser Gln Arg
            915                 920                 925
Trp Asp Arg Ile Leu Gln Ala Ser Gly Met Lys Arg Ala Lys Pro Ser
            930                 935                 940
Pro Thr Ser Thr Gln Thr Pro Asp Gln Ala Ser Leu His Ala Phe Ala
945                 950                 955                 960
Asp Ser Leu Glu Arg Asp Leu Asp Ala Pro Ser Pro Met His Glu Gly
            965                 970                 975
Asp Gln Thr Arg Ala Ser Ala Ser Pro Lys Lys Lys Arg Lys Val Glu
            980                 985                 990
Ala Ser Met Asn Ile Gln Met Leu  Leu Glu Ala Ala Asp Tyr Leu Glu
            995                 1000                1005
Arg  Arg  Glu Arg Glu Ala Glu  His Gly Tyr Ala Ser  Met Leu Pro
        1010                1015                1020

<210> SEQ ID NO 47
<211> LENGTH: 1023
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Ser Arg Thr Arg Leu Pro Ser Pro Pro Ala Pro Ser Pro Ala Phe
1               5                   10                  15
Ser Ala Asp Ser Phe Ser Asp Leu Leu Arg Gln Phe Asp Pro Ser Leu
            20                  25                  30
Phe Asn Thr Ser Leu Phe Asp Ser Leu Pro Pro Phe Gly Ala His His
            35                  40                  45
Thr Glu Ala Ala Thr Gly Glu Trp Asp Glu Val Gln Ser Gly Leu Arg
        50                  55                  60
Ala Ala Asp Ala Pro Pro Thr Met Arg Val Ala Val Thr Ala Ala
65                  70                  75                  80
Arg Pro Pro Arg Ala Lys Pro Ala Pro Arg Arg Ala Ala Gln Pro
            85                  90                  95
Ser Asp Ala Ser Pro Ala Ala Gln Val Asp Leu Arg Thr Leu Gly Tyr
            100                 105                 110
Ser Gln Gln Gln Gln Glu Lys Ile Lys Pro Lys Val Arg Ser Thr Val
            115                 120                 125
Ala Gln His His Glu Ala Leu Val Gly His Gly Phe Thr His Ala His
            130                 135                 140
Ile Val Ala Leu Ser Gln His Pro Ala Ala Leu Gly Thr Val Ala Val
145                 150                 155                 160
Lys Tyr Gln Asp Met Ile Ala Ala Leu Pro Glu Ala Thr His Glu Ala
            165                 170                 175
Ile Val Gly Val Gly Lys Gln Trp Ser Gly Ala Arg Ala Leu Glu Ala
            180                 185                 190
Leu Leu Thr Val Ala Gly Glu Leu Arg Gly Pro Pro Leu Gln Leu Asp
            195                 200                 205
Thr Gly Gln Leu Leu Lys Ile Ala Lys Arg Gly Gly Val Thr Ala Val
            210                 215                 220
Glu Ala Val His Ala Trp Arg Asn Ala Leu Thr Gly Ala Pro Leu Asn

```
                225                 230                 235                 240
Leu Thr Pro Glu Gln Val Val Ala Ile Ala Ser His Asp Gly Gly Lys
                245                 250                 255

Gln Ala Leu Glu Thr Val Gln Arg Leu Leu Pro Val Leu Cys Gln Ala
                260                 265                 270

His Gly Leu Thr Pro Glu Gln Val Val Ala Ile Ala Ser Asn Lys Gly
                275                 280                 285

Gly Lys Gln Ala Leu Glu Thr Val Gln Arg Leu Leu Pro Val Leu Cys
                290                 295                 300

Gln Ala His Gly Leu Thr Pro Glu Gln Val Val Ala Ile Ala Ser Asn
305                 310                 315                 320

Lys Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
                340                 345                 350

Ser His Asp Gly Gly Lys Gln Ala Leu Glu Thr Val Gln Arg Leu Leu
                355                 360                 365

Pro Val Leu Cys Gln Ala His Gly Leu Thr Pro Glu Gln Val Val Ala
                370                 375                 380

Ile Ala Ser His Asp Gly Gly Lys Gln Ala Leu Glu Thr Val Gln Arg
385                 390                 395                 400

Leu Leu Pro Val Leu Cys Gln Ala His Gly Leu Thr Pro Glu Gln Val
                405                 410                 415

Val Ala Ile Ala Ser His Asp Gly Gly Lys Gln Ala Leu Glu Thr Val
                420                 425                 430

Gln Arg Leu Leu Pro Val Leu Cys Gln Ala His Gly Leu Thr Pro Glu
                435                 440                 445

Gln Val Val Ala Ile Ala Ser His Asp Gly Gly Lys Gln Ala Leu Glu
                450                 455                 460

Thr Val Gln Arg Leu Leu Pro Val Leu Cys Gln Ala His Gly Leu Thr
465                 470                 475                 480

Pro Glu Gln Val Val Ala Ile Ala Ser Asn Gly Gly Gly Lys Gln Ala
                485                 490                 495

Leu Glu Thr Val Gln Arg Leu Leu Pro Val Leu Cys Gln Ala His Gly
                500                 505                 510

Leu Thr Pro Glu Gln Val Val Ala Ile Ala Ser Asn Lys Gly Gly Lys
                515                 520                 525

Gln Ala Leu Glu Thr Val Gln Arg Leu Leu Pro Val Leu Cys Gln Ala
                530                 535                 540

His Gly Leu Thr Pro Glu Gln Val Val Ala Ile Ala Ser His Asp Gly
545                 550                 555                 560

Gly Lys Gln Ala Leu Glu Thr Val Gln Arg Leu Leu Pro Val Leu Cys
                565                 570                 575

Gln Ala His Gly Leu Thr Pro Glu Gln Val Val Ala Ile Ala Ser His
                580                 585                 590

Asp Gly Gly Lys Gln Ala Leu Glu Thr Val Gln Arg Leu Leu Pro Val
                595                 600                 605

Leu Cys Gln Ala His Gly Leu Thr Pro Glu Gln Val Val Ala Ile Ala
                610                 615                 620

Ser Asn Lys Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
                645                 650                 655
```

```
Ile Ala Ser Asn Lys Gly Gly Lys Gln Ala Leu Glu Thr Val Gln Arg
            660                 665                 670

Leu Leu Pro Val Leu Cys Gln Ala His Gly Leu Thr Pro Glu Gln Val
        675                 680                 685

Val Ala Ile Ala Ser His Asp Gly Gly Lys Gln Ala Leu Glu Thr Val
    690                 695                 700

Gln Arg Leu Leu Pro Val Leu Cys Gln Ala His Gly Leu Thr Pro Glu
705                 710                 715                 720

Gln Val Val Ala Ile Ala Ser His Asp Gly Gly Lys Gln Ala Leu Glu
                725                 730                 735

Thr Val Gln Arg Leu Leu Pro Val Leu Cys Gln Ala His Gly Leu Thr
            740                 745                 750

Pro Glu Gln Val Val Ala Ile Ala Ser His Asp Gly Gly Lys Gln Ala
        755                 760                 765

Leu Glu Thr Val Gln Arg Leu Leu Pro Val Leu Cys Gln Ala His Gly
    770                 775                 780

Leu Thr Pro Glu Gln Val Val Ala Ile Ala Ser Asn Ile Gly Gly Arg
785                 790                 795                 800

Pro Ala Leu Glu Ser Ile Val Ala Gln Leu Ser Arg Pro Asp Pro Ala
                805                 810                 815

Leu Ala Ala Leu Thr Asn Asp His Leu Val Ala Leu Ala Cys Leu Gly
            820                 825                 830

Gly Arg Pro Ala Leu Asp Ala Val Lys Lys Gly Leu Pro His Ala Pro
        835                 840                 845

Ala Leu Ile Lys Arg Thr Asn Arg Arg Ile Pro Glu Arg Thr Ser His
    850                 855                 860

Arg Val Ala Asp His Ala Gln Val Val Arg Val Leu Gly Phe Phe Gln
865                 870                 875                 880

Cys His Ser His Pro Ala Gln Ala Phe Asp Asp Ala Met Thr Gln Phe
                885                 890                 895

Gly Met Ser Arg His Gly Leu Leu Gln Leu Phe Arg Arg Val Gly Val
            900                 905                 910

Thr Glu Leu Glu Ala Arg Ser Gly Thr Leu Pro Pro Ala Ser Gln Arg
        915                 920                 925

Trp Asp Arg Ile Leu Gln Ala Ser Gly Met Lys Arg Ala Lys Pro Ser
    930                 935                 940

Pro Thr Ser Thr Gln Thr Pro Asp Gln Ala Ser Leu His Ala Phe Ala
945                 950                 955                 960

Asp Ser Leu Glu Arg Asp Leu Asp Ala Pro Ser Pro Met His Glu Gly
                965                 970                 975

Asp Gln Thr Arg Ala Ser Ala Ser Pro Lys Lys Lys Arg Lys Val Glu
            980                 985                 990

Ala Ser Met Asn Ile Gln Met Leu  Leu Glu Ala Ala Asp  Tyr Leu Glu
        995                 1000                1005

Arg Arg  Glu Arg Glu Ala Glu  His Gly Tyr Ala Ser   Met Leu Pro
    1010                1015                1020

<210> SEQ ID NO 48
<211> LENGTH: 1023
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48
```

-continued

```
Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
        35                  40                  45

Thr Glu Ala Ala Thr Gly Glu Trp Asp Glu Val Gln Ser Gly Leu Arg
    50                  55                  60

Ala Ala Asp Ala Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
                100                 105                 110

Ser Gln Gln Gln Glu Lys Ile Lys Pro Lys Val Arg Ser Thr Val
        115                 120                 125

Ala Gln His His Glu Ala Leu Val Gly His Gly Phe Thr His Ala His
        130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
                180                 185                 190

Leu Leu Thr Val Ala Gly Glu Leu Arg Gly Pro Pro Leu Gln Leu Asp
        195                 200                 205

Thr Gly Gln Leu Leu Lys Ile Ala Lys Arg Gly Gly Val Thr Ala Val
    210                 215                 220

Glu Ala Val His Ala Trp Arg Asn Ala Leu Thr Gly Ala Pro Leu Asn
225                 230                 235                 240

Leu Thr Pro Glu Gln Val Ala Ile Ala Ser His Asp Gly Gly Lys
            245                 250                 255

Gln Ala Leu Glu Thr Val Gln Arg Leu Leu Pro Val Leu Cys Gln Ala
        260                 265                 270

His Gly Leu Thr Pro Glu Gln Val Val Ala Ile Ala Ser Asn His Gly
        275                 280                 285

Gly Lys Gln Ala Leu Glu Thr Val Gln Arg Leu Leu Pro Val Leu Cys
        290                 295                 300

Gln Ala His Gly Leu Thr Pro Glu Gln Val Val Ala Ile Ala Ser Asn
305                 310                 315                 320

His Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
        340                 345                 350

Ser His Asp Gly Gly Lys Gln Ala Leu Glu Thr Val Gln Arg Leu Leu
        355                 360                 365

Pro Val Leu Cys Gln Ala His Gly Leu Thr Pro Glu Gln Val Val Ala
        370                 375                 380

Ile Ala Ser His Asp Gly Gly Lys Gln Ala Leu Glu Thr Val Gln Arg
385                 390                 395                 400

Leu Leu Pro Val Leu Cys Gln Ala His Gly Leu Thr Pro Glu Gln Val
                405                 410                 415

Val Ala Ile Ala Ser His Asp Gly Gly Lys Gln Ala Leu Glu Thr Val
        420                 425                 430
```

```
Gln Arg Leu Leu Pro Val Leu Cys Gln Ala His Gly Leu Thr Pro Glu
        435                 440                 445

Gln Val Val Ala Ile Ala Ser His Asp Gly Gly Lys Gln Ala Leu Glu
        450                 455                 460

Thr Val Gln Arg Leu Leu Pro Val Leu Cys Gln Ala His Gly Leu Thr
465                 470                 475                 480

Pro Glu Gln Val Val Ala Ile Ala Ser Asn Gly Gly Lys Gln Ala
                    485                 490                 495

Leu Glu Thr Val Gln Arg Leu Leu Pro Val Leu Cys Gln Ala His Gly
                500                 505                 510

Leu Thr Pro Glu Gln Val Val Ala Ile Ala Ser Asn His Gly Gly Lys
            515                 520                 525

Gln Ala Leu Glu Thr Val Gln Arg Leu Leu Pro Val Leu Cys Gln Ala
        530                 535                 540

His Gly Leu Thr Pro Glu Gln Val Val Ala Ile Ala Ser His Asp Gly
545                 550                 555                 560

Gly Lys Gln Ala Leu Glu Thr Val Gln Arg Leu Leu Pro Val Leu Cys
                    565                 570                 575

Gln Ala His Gly Leu Thr Pro Glu Gln Val Val Ala Ile Ala Ser His
                580                 585                 590

Asp Gly Gly Lys Gln Ala Leu Glu Thr Val Gln Arg Leu Leu Pro Val
            595                 600                 605

Leu Cys Gln Ala His Gly Leu Thr Pro Glu Gln Val Val Ala Ile Ala
        610                 615                 620

Ser Asn His Gly Gly Lys Gln Ala Leu Glu Thr Val Gln Arg Leu Leu
625                 630                 635                 640

Pro Val Leu Cys Gln Ala His Gly Leu Thr Pro Glu Gln Val Val Ala
                    645                 650                 655

Ile Ala Ser Asn His Gly Gly Lys Gln Ala Leu Glu Thr Val Gln Arg
                660                 665                 670

Leu Leu Pro Val Leu Cys Gln Ala His Gly Leu Thr Pro Glu Gln Val
            675                 680                 685

Val Ala Ile Ala Ser His Asp Gly Gly Lys Gln Ala Leu Glu Thr Val
        690                 695                 700

Gln Arg Leu Leu Pro Val Leu Cys Gln Ala His Gly Leu Thr Pro Glu
705                 710                 715                 720

Gln Val Val Ala Ile Ala Ser His Asp Gly Gly Lys Gln Ala Leu Glu
                    725                 730                 735

Thr Val Gln Arg Leu Leu Pro Val Leu Cys Gln Ala His Gly Leu Thr
                740                 745                 750

Pro Glu Gln Val Val Ala Ile Ala Ser His Asp Gly Gly Lys Gln Ala
            755                 760                 765

Leu Glu Thr Val Gln Arg Leu Leu Pro Val Leu Cys Gln Ala His Gly
        770                 775                 780

Leu Thr Pro Glu Gln Val Val Ala Ile Ala Ser Asn Ile Gly Gly Arg
785                 790                 795                 800

Pro Ala Leu Glu Ser Ile Val Ala Gln Leu Ser Arg Pro Asp Pro Ala
                    805                 810                 815

Leu Ala Ala Leu Thr Asn Asp His Leu Val Ala Leu Ala Cys Leu Gly
                820                 825                 830

Gly Arg Pro Ala Leu Asp Ala Val Lys Lys Gly Leu Pro His Ala Pro
            835                 840                 845

Ala Leu Ile Lys Arg Thr Asn Arg Arg Ile Pro Glu Arg Thr Ser His
```

```
                   850                 855                 860
Arg Val Ala Asp His Ala Gln Val Val Arg Val Leu Gly Phe Phe Gln
865                 870                 875                 880

Cys His Ser His Pro Ala Gln Ala Phe Asp Asp Ala Met Thr Gln Phe
                885                 890                 895

Gly Met Ser Arg His Gly Leu Leu Gln Leu Phe Arg Arg Val Gly Val
            900                 905                 910

Thr Glu Leu Glu Ala Arg Ser Gly Thr Leu Pro Pro Ala Ser Gln Arg
        915                 920                 925

Trp Asp Arg Ile Leu Gln Ala Ser Gly Met Lys Arg Ala Lys Pro Ser
    930                 935                 940

Pro Thr Ser Thr Gln Thr Pro Asp Gln Ala Ser Leu His Ala Phe Ala
945                 950                 955                 960

Asp Ser Leu Glu Arg Asp Leu Asp Ala Pro Ser Pro Met His Glu Gly
                965                 970                 975

Asp Gln Thr Arg Ala Ser Ala Ser Pro Lys Lys Lys Arg Lys Val Glu
            980                 985                 990

Ala Ser Met Asn Ile Gln Met Leu  Leu Glu Ala Ala Asp  Tyr Leu Glu
        995                 1000                1005

Arg Arg  Glu Arg Glu Ala Glu  His Gly Tyr Ala Ser  Met Leu Pro
    1010                1015                1020

<210> SEQ ID NO 49
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Met Asn Ile Gln Met Leu Leu Glu Ala Ala Asp Tyr Leu Glu Arg Arg
1               5                   10                  15

Glu Arg Glu Ala Glu His Gly Tyr Ala Ser Met Leu Pro
            20                  25

<210> SEQ ID NO 50
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Asn Ile Gln Met Leu Leu Glu Ala Ala Asp Tyr Leu Glu Arg Arg
1               5                   10                  15

Glu Arg Glu Ala Glu His Gly Tyr Ala Ser Met Leu Pro Gly Ser Gly
            20                  25                  30

Met Asn Ile Gln Met Leu Leu Glu Ala Ala Asp Tyr Leu Glu Arg Arg
        35                  40                  45

Glu Arg Glu Ala Glu His Gly Tyr Ala Ser Met Leu Pro Gly Ser Gly
    50                  55                  60

Met Asn Ile Gln Met Leu Leu Glu Ala Ala Asp Tyr Leu Glu Arg Arg
65                  70                  75                  80

Glu Arg Glu Ala Glu His Gly Tyr Ala Ser Met Leu Pro Gly Ser Gly
                85                  90                  95

Met Asn Ile Gln Met Leu Leu Glu Ala Ala Asp Tyr Leu Glu Arg Arg
            100                 105                 110
```

```
Glu Arg Glu Ala Glu His Gly Tyr Ala Ser Met Leu Pro Ser Arg
        115                 120                 125

<210> SEQ ID NO 51
<211> LENGTH: 1119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Ser Arg Thr Arg Leu Pro Ser Pro Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
            35                  40                  45

Thr Glu Ala Ala Thr Gly Glu Trp Asp Glu Val Gln Ser Gly Leu Arg
        50                  55                  60

Ala Ala Asp Ala Pro Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Gln Glu Lys Ile Lys Pro Lys Val Arg Ser Thr Val
            115                 120                 125

Ala Gln His His Glu Ala Leu Val Gly His Gly Phe Thr His Ala His
130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
            195                 200                 205

Thr Gly Gln Leu Leu Lys Ile Ala Lys Arg Gly Gly Val Thr Ala Val
        210                 215                 220

Glu Ala Val His Ala Trp Arg Asn Ala Leu Thr Gly Ala Pro Leu Asn
225                 230                 235                 240

Leu Thr Pro Glu Gln Val Val Ala Ile Ala Ser Asn Asn Gly Gly Lys
                245                 250                 255

Gln Ala Leu Glu Thr Val Gln Arg Leu Leu Pro Val Leu Cys Gln Ala
            260                 265                 270

His Gly Leu Thr Pro Glu Gln Val Val Ala Ile Ala Ser His Asp Gly
            275                 280                 285

Gly Lys Gln Ala Leu Glu Thr Val Gln Arg Leu Leu Pro Val Leu Cys
        290                 295                 300

Gln Ala His Gly Leu Thr Pro Glu Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
            340                 345                 350
```

-continued

```
Ser Asn Gly Gly Gly Lys Gln Ala Leu Glu Thr Val Gln Arg Leu Leu
        355                 360                 365
Pro Val Leu Cys Gln Ala His Gly Leu Thr Pro Glu Gln Val Val Ala
    370                 375                 380
Ile Ala Ser Asn Asn Gly Gly Lys Gln Ala Leu Glu Thr Val Gln Arg
385                 390                 395                 400
Leu Leu Pro Val Leu Cys Gln Ala His Gly Leu Thr Pro Glu Gln Val
                405                 410                 415
Val Ala Ile Ala Ser His Asp Gly Gly Lys Gln Ala Leu Glu Thr Val
            420                 425                 430
Gln Arg Leu Leu Pro Val Leu Cys Gln Ala His Gly Leu Thr Pro Glu
        435                 440                 445
Gln Val Val Ala Ile Ala Ser His Asp Gly Gly Lys Gln Ala Leu Glu
    450                 455                 460
Thr Val Gln Arg Leu Leu Pro Val Leu Cys Gln Ala His Gly Leu Thr
465                 470                 475                 480
Pro Glu Gln Val Val Ala Ile Ala Ser His Asp Gly Gly Lys Gln Ala
                485                 490                 495
Leu Glu Thr Val Gln Arg Leu Leu Pro Val Leu Cys Gln Ala His Gly
            500                 505                 510
Leu Thr Pro Glu Gln Val Val Ala Ile Ala Ser Asn Gly Gly Gly Lys
        515                 520                 525
Gln Ala Leu Glu Thr Val Gln Arg Leu Leu Pro Val Leu Cys Gln Ala
    530                 535                 540
His Gly Leu Thr Pro Glu Gln Val Val Ala Ile Ala Ser His Asp Gly
545                 550                 555                 560
Gly Lys Gln Ala Leu Glu Thr Val Gln Arg Leu Leu Pro Val Leu Cys
                565                 570                 575
Gln Ala His Gly Leu Thr Pro Glu Gln Val Val Ala Ile Ala Ser His
            580                 585                 590
Asp Gly Gly Lys Gln Ala Leu Glu Thr Val Gln Arg Leu Leu Pro Val
        595                 600                 605
Leu Cys Gln Ala His Gly Leu Thr Pro Glu Gln Val Val Ala Ile Ala
    610                 615                 620
Ser Asn Ile Gly Gly Lys Gln Ala Leu Glu Thr Val Gln Arg Leu Leu
625                 630                 635                 640
Pro Val Leu Cys Gln Ala His Gly Leu Thr Pro Glu Gln Val Val Ala
                645                 650                 655
Ile Ala Ser Asn Asn Gly Gly Lys Gln Ala Leu Glu Thr Val Gln Arg
            660                 665                 670
Leu Leu Pro Val Leu Cys Gln Ala His Gly Leu Thr Pro Glu Gln Val
        675                 680                 685
Val Ala Ile Ala Ser Asn Asn Gly Gly Lys Gln Ala Leu Glu Thr Val
    690                 695                 700
Gln Arg Leu Leu Pro Val Leu Cys Gln Ala His Gly Leu Thr Pro Glu
705                 710                 715                 720
Gln Val Val Ala Ile Ala Ser His Asp Gly Gly Lys Gln Ala Leu Glu
                725                 730                 735
Thr Val Gln Arg Leu Leu Pro Val Leu Cys Gln Ala His Gly Leu Thr
            740                 745                 750
Pro Glu Gln Val Val Ala Ile Ala Ser Asn Gly Gly Gly Lys Gln Ala
        755                 760                 765
Leu Glu Thr Val Gln Arg Leu Leu Pro Val Leu Cys Gln Ala His Gly
```

```
            770                 775                 780
Leu Thr Pro Glu Gln Val Val Ala Ile Ala Ser His Asp Gly Gly Lys
785                 790                 795                 800

Gln Ala Leu Glu Thr Val Gln Arg Leu Leu Pro Val Leu Cys Gln Ala
                805                 810                 815

His Gly Leu Thr Pro Glu Gln Val Val Ala Ile Ala Ser His Asp Gly
            820                 825                 830

Gly Lys Gln Ala Leu Glu Thr Val Gln Arg Leu Leu Pro Val Leu Cys
        835                 840                 845

Gln Ala His Gly Leu Thr Pro Glu Gln Val Val Ala Ile Ala Ser Asn
850                 855                 860

Gly Gly Gly Arg Pro Ala Leu Glu Ser Ile Val Ala Gln Leu Ser Arg
865                 870                 875                 880

Pro Asp Pro Ala Leu Ala Ala Leu Thr Asn Asp His Leu Val Ala Leu
                885                 890                 895

Ala Cys Leu Gly Gly Arg Pro Ala Leu Asp Ala Val Lys Lys Gly Leu
            900                 905                 910

Pro His Ala Pro Ala Leu Ile Lys Arg Thr Asn Arg Arg Ile Pro Glu
        915                 920                 925

Arg Thr Ser His Arg Val Ala Asp His Ala Gln Val Val Arg Val Leu
    930                 935                 940

Gly Phe Phe Gln Cys His Ser His Pro Ala Gln Ala Phe Asp Asp Ala
945                 950                 955                 960

Met Thr Gln Phe Gly Met Ser Arg His Gly Leu Leu Gln Leu Phe Arg
                965                 970                 975

Arg Val Gly Val Thr Glu Leu Glu Ala Arg Ser Gly Thr Leu Pro Pro
            980                 985                 990

Ala Ser Gln Arg Trp Asp Arg Ile Leu Gln Ala Ser Gly Met Lys Arg
        995                 1000                1005

Ala Lys  Pro Ser Pro Thr Ser  Thr Gln Thr Pro Asp  Gln Ala Ser
    1010                1015                1020

Leu His  Ala Phe Ala Asp Ser  Leu Glu Arg Asp Leu  Asp Ala Pro
    1025                1030                1035

Ser Pro  Met His Glu Gly Asp  Gln Thr Arg Ala Ser  Ala Ser Pro
    1040                1045                1050

Lys Lys  Lys Arg Lys Val Glu  Ala Ser Gly Ser Gly  Arg Ala Asp
    1055                1060                1065

Ala Leu  Asp Asp Phe Asp Leu  Asp Met Leu Gly Ser  Asp Ala Leu
    1070                1075                1080

Asp Asp  Phe Asp Leu Asp Met  Leu Gly Ser Asp Ala  Leu Asp Asp
    1085                1090                1095

Phe Asp  Leu Asp Met Leu Gly  Ser Asp Ala Leu Asp  Asp Phe Asp
    1100                1105                1110

Leu Asp  Met Leu Ile Asn
    1115

<210> SEQ ID NO 52
<211> LENGTH: 991
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Val Asp Leu Arg Thr Leu Gly Tyr Ser Gln Gln Gln Gln Glu Lys
```

-continued

```
1               5                   10                  15
Ile Lys Pro Lys Val Arg Ser Thr Val Ala Gln His His Glu Ala Leu
                20                  25                  30

Val Gly His Gly Phe Thr His Ala His Ile Val Ala Leu Ser Gln His
                35                  40                  45

Pro Ala Ala Leu Gly Thr Val Ala Val Lys Tyr Gln Asp Met Ile Ala
 50                  55                  60

Ala Leu Pro Glu Ala Thr His Glu Ala Ile Val Gly Val Gly Lys Gln
 65                  70                  75                  80

Trp Ser Gly Ala Arg Ala Leu Glu Ala Leu Leu Thr Val Ala Gly Glu
                85                  90                  95

Leu Arg Gly Pro Pro Leu Gln Leu Asp Thr Gly Gln Leu Leu Lys Ile
                100                 105                 110

Ala Lys Arg Gly Gly Val Thr Ala Val Glu Ala Val His Ala Trp Arg
                115                 120                 125

Asn Ala Leu Thr Gly Ala Pro Leu Asn Leu Thr Pro Glu Gln Val Val
                130                 135                 140

Ala Ile Ala Ser Asn Asn Gly Gly Lys Gln Ala Leu Glu Thr Val Gln
145                 150                 155                 160

Arg Leu Leu Pro Val Leu Cys Gln Ala His Gly Leu Thr Pro Glu Gln
                165                 170                 175

Val Val Ala Ile Ala Ser His Asp Gly Gly Lys Gln Ala Leu Glu Thr
                180                 185                 190

Val Gln Arg Leu Leu Pro Val Leu Cys Gln Ala His Gly Leu Thr Pro
                195                 200                 205

Glu Gln Val Val Ala Ile Ala Ser His Asp Gly Gly Lys Gln Ala Leu
                210                 215                 220

Glu Thr Val Gln Arg Leu Leu Pro Val Leu Cys Gln Ala His Gly Leu
225                 230                 235                 240

Thr Pro Glu Gln Val Val Ala Ile Ala Ser Asn Gly Gly Gly Lys Gln
                245                 250                 255

Ala Leu Glu Thr Val Gln Arg Leu Leu Pro Val Leu Cys Gln Ala His
                260                 265                 270

Gly Leu Thr Pro Glu Gln Val Val Ala Ile Ala Ser Asn Asn Gly Gly
                275                 280                 285

Lys Gln Ala Leu Glu Thr Val Gln Arg Leu Leu Pro Val Leu Cys Gln
                290                 295                 300

Ala His Gly Leu Thr Pro Glu Gln Val Val Ala Ile Ala Ser His Asp
305                 310                 315                 320

Gly Gly Lys Gln Ala Leu Glu Thr Val Gln Arg Leu Leu Pro Val Leu
                325                 330                 335

Cys Gln Ala His Gly Leu Thr Pro Glu Gln Val Val Ala Ile Ala Ser
                340                 345                 350

His Asp Gly Gly Lys Gln Ala Leu Glu Thr Val Gln Arg Leu Leu Pro
                355                 360                 365

Val Leu Cys Gln Ala His Gly Leu Thr Pro Glu Gln Val Val Ala Ile
                370                 375                 380

Ala Ser His Asp Gly Gly Lys Gln Ala Leu Glu Thr Val Gln Arg Leu
385                 390                 395                 400

Leu Pro Val Leu Cys Gln Ala His Gly Leu Thr Pro Glu Gln Val Val
                405                 410                 415

Ala Ile Ala Ser Asn Gly Gly Gly Lys Gln Ala Leu Glu Thr Val Gln
                420                 425                 430
```

```
Arg Leu Leu Pro Val Leu Cys Gln Ala His Gly Leu Thr Pro Glu Gln
            435                 440                 445

Val Val Ala Ile Ala Ser His Asp Gly Gly Lys Gln Ala Leu Glu Thr
450                 455                 460

Val Gln Arg Leu Leu Pro Val Leu Cys Gln Ala His Gly Leu Thr Pro
465                 470                 475                 480

Glu Gln Val Val Ala Ile Ala Ser His Asp Gly Gly Lys Gln Ala Leu
                485                 490                 495

Glu Thr Val Gln Arg Leu Leu Pro Val Leu Cys Gln Ala His Gly Leu
            500                 505                 510

Thr Pro Glu Gln Val Val Ala Ile Ala Ser Asn Ile Gly Gly Lys Gln
        515                 520                 525

Ala Leu Glu Thr Val Gln Arg Leu Leu Pro Val Leu Cys Gln Ala His
530                 535                 540

Gly Leu Thr Pro Glu Gln Val Val Ala Ile Ala Ser Asn Asn Gly Gly
545                 550                 555                 560

Lys Gln Ala Leu Glu Thr Val Gln Arg Leu Leu Pro Val Leu Cys Gln
                565                 570                 575

Ala His Gly Leu Thr Pro Glu Gln Val Val Ala Ile Ala Ser Asn Asn
            580                 585                 590

Gly Gly Lys Gln Ala Leu Glu Thr Val Gln Arg Leu Leu Pro Val Leu
        595                 600                 605

Cys Gln Ala His Gly Leu Thr Pro Glu Gln Val Val Ala Ile Ala Ser
610                 615                 620

His Asp Gly Gly Lys Gln Ala Leu Glu Thr Val Gln Arg Leu Leu Pro
625                 630                 635                 640

Val Leu Cys Gln Ala His Gly Leu Thr Pro Glu Gln Val Val Ala Ile
                645                 650                 655

Ala Ser Asn Gly Gly Gly Lys Gln Ala Leu Glu Thr Val Gln Arg Leu
            660                 665                 670

Leu Pro Val Leu Cys Gln Ala His Gly Leu Thr Pro Glu Gln Val Val
        675                 680                 685

Ala Ile Ala Ser His Asp Gly Gly Lys Gln Ala Leu Glu Thr Val Gln
690                 695                 700

Arg Leu Leu Pro Val Leu Cys Gln Ala His Gly Leu Thr Pro Glu Gln
705                 710                 715                 720

Val Val Ala Ile Ala Ser His Asp Gly Gly Lys Gln Ala Leu Glu Thr
                725                 730                 735

Val Gln Arg Leu Leu Pro Val Leu Cys Gln Ala His Gly Leu Thr Pro
            740                 745                 750

Glu Gln Val Val Ala Ile Ala Ser His Asp Gly Gly Arg Pro Ala Leu
        755                 760                 765

Glu Ser Ile Val Ala Gln Leu Ser Arg Pro Asp Pro Ala Leu Ala Ala
770                 775                 780

Leu Thr Asn Asp His Leu Val Ala Leu Ala Cys Leu Gly Gly Arg Pro
785                 790                 795                 800

Ala Leu Asp Ala Val Lys Lys Gly Leu Pro His Ala Pro Ala Leu Ile
                805                 810                 815

Lys Arg Thr Asn Arg Arg Ile Pro Glu Arg Thr Ser His Arg Val Ala
            820                 825                 830

Asp His Ala Gln Val Val Arg Val Leu Gly Phe Phe Gln Cys His Ser
        835                 840                 845

His Pro Ala Gln Ala Phe Asp Asp Ala Met Thr Gln Phe Gly Met Ser
850                 855                 860
```

```
Arg His Gly Leu Leu Gln Leu Phe Arg Arg Val Gly Thr Glu Leu
865                 870                 875                 880

Glu Ala Arg Ser Gly Thr Leu Pro Pro Ala Ser Gln Arg Trp Asp Arg
            885                 890                 895

Ile Leu Gln Ala Ser Gly Met Lys Arg Ala Lys Pro Ser Pro Thr Ser
                900                 905                 910

Thr Gln Thr Pro Asp Gln Ala Ser Leu His Ala Phe Ala Asp Ser Leu
            915                 920                 925

Glu Arg Asp Leu Asp Ala Pro Ser Pro Met His Glu Gly Asp Gln Thr
        930                 935                 940

Arg Ala Ser Ala Ser Pro Lys Lys Lys Arg Lys Val Glu Ala Ser Gly
945                 950                 955                 960

Ser Gly Met Asn Ile Gln Met Leu Leu Glu Ala Ala Asp Tyr Leu Glu
                965                 970                 975

Arg Arg Glu Arg Glu Ala Glu His Gly Tyr Ala Ser Met Leu Pro
            980                 985                 990

<210> SEQ ID NO 53
<211> LENGTH: 1089
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Val Asp Leu Arg Thr Leu Gly Tyr Ser Gln Gln Gln Gln Glu Lys
1               5                   10                  15

Ile Lys Pro Lys Val Arg Ser Thr Val Ala Gln His His Glu Ala Leu
            20                  25                  30

Val Gly His Gly Phe Thr His Ala His Ile Val Ala Leu Ser Gln His
        35                  40                  45

Pro Ala Ala Leu Gly Thr Val Ala Val Lys Tyr Gln Asp Met Ile Ala
    50                  55                  60

Ala Leu Pro Glu Ala Thr His Glu Ala Ile Val Gly Val Gly Lys Gln
65                  70                  75                  80

Trp Ser Gly Ala Arg Ala Leu Glu Ala Leu Leu Thr Val Ala Gly Glu
                85                  90                  95

Leu Arg Gly Pro Pro Leu Gln Leu Asp Thr Gly Gln Leu Leu Lys Ile
            100                 105                 110

Ala Lys Arg Gly Gly Val Thr Ala Val Glu Ala Val His Ala Trp Arg
        115                 120                 125

Asn Ala Leu Thr Gly Ala Pro Leu Asn Leu Thr Pro Glu Gln Val Val
    130                 135                 140

Ala Ile Ala Ser Asn Asn Gly Gly Lys Gln Ala Leu Glu Thr Val Gln
145                 150                 155                 160

Arg Leu Leu Pro Val Leu Cys Gln Ala His Gly Leu Thr Pro Glu Gln
                165                 170                 175

Val Val Ala Ile Ala Ser His Asp Gly Gly Lys Gln Ala Leu Glu Thr
            180                 185                 190

Val Gln Arg Leu Leu Pro Val Leu Cys Gln Ala His Gly Leu Thr Pro
        195                 200                 205

Glu Gln Val Val Ala Ile Ala Ser His Asp Gly Gly Lys Gln Ala Leu
    210                 215                 220

Glu Thr Val Gln Arg Leu Leu Pro Val Leu Cys Gln Ala His Gly Leu
225                 230                 235                 240
```

```
Thr Pro Glu Gln Val Val Ala Ile Ala Ser Asn Gly Gly Lys Gln
            245                 250                 255

Ala Leu Glu Thr Val Gln Arg Leu Leu Pro Val Leu Cys Gln Ala His
            260                 265                 270

Gly Leu Thr Pro Glu Gln Val Val Ala Ile Ala Ser Asn Asn Gly Gly
            275                 280                 285

Lys Gln Ala Leu Glu Thr Val Gln Arg Leu Leu Pro Val Leu Cys Gln
290                 295                 300

Ala His Gly Leu Thr Pro Glu Gln Val Val Ala Ile Ala Ser His Asp
305                 310                 315                 320

Gly Gly Lys Gln Ala Leu Glu Thr Val Gln Arg Leu Leu Pro Val Leu
                325                 330                 335

Cys Gln Ala His Gly Leu Thr Pro Glu Gln Val Val Ala Ile Ala Ser
                340                 345                 350

His Asp Gly Gly Lys Gln Ala Leu Glu Thr Val Gln Arg Leu Leu Pro
                355                 360                 365

Val Leu Cys Gln Ala His Gly Leu Thr Pro Glu Gln Val Val Ala Ile
            370                 375                 380

Ala Ser His Asp Gly Gly Lys Gln Ala Leu Glu Thr Val Gln Arg Leu
385                 390                 395                 400

Leu Pro Val Leu Cys Gln Ala His Gly Leu Thr Pro Glu Gln Val Val
                405                 410                 415

Ala Ile Ala Ser Asn Gly Gly Gly Lys Gln Ala Leu Glu Thr Val Gln
                420                 425                 430

Arg Leu Leu Pro Val Leu Cys Gln Ala His Gly Leu Thr Pro Glu Gln
            435                 440                 445

Val Val Ala Ile Ala Ser His Asp Gly Gly Lys Gln Ala Leu Glu Thr
450                 455                 460

Val Gln Arg Leu Leu Pro Val Leu Cys Gln Ala His Gly Leu Thr Pro
465                 470                 475                 480

Glu Gln Val Val Ala Ile Ala Ser His Asp Gly Gly Lys Gln Ala Leu
                485                 490                 495

Glu Thr Val Gln Arg Leu Leu Pro Val Leu Cys Gln Ala His Gly Leu
                500                 505                 510

Thr Pro Glu Gln Val Val Ala Ile Ala Ser Asn Ile Gly Gly Lys Gln
            515                 520                 525

Ala Leu Glu Thr Val Gln Arg Leu Leu Pro Val Leu Cys Gln Ala His
            530                 535                 540

Gly Leu Thr Pro Glu Gln Val Val Ala Ile Ala Ser Asn Asn Gly Gly
545                 550                 555                 560

Lys Gln Ala Leu Glu Thr Val Gln Arg Leu Leu Pro Val Leu Cys Gln
                565                 570                 575

Ala His Gly Leu Thr Pro Glu Gln Val Val Ala Ile Ala Ser Asn Asn
                580                 585                 590

Gly Gly Lys Gln Ala Leu Glu Thr Val Gln Arg Leu Leu Pro Val Leu
            595                 600                 605

Cys Gln Ala His Gly Leu Thr Pro Glu Gln Val Val Ala Ile Ala Ser
            610                 615                 620

His Asp Gly Gly Lys Gln Ala Leu Glu Thr Val Gln Arg Leu Leu Pro
625                 630                 635                 640

Val Leu Cys Gln Ala His Gly Leu Thr Pro Glu Gln Val Val Ala Ile
                645                 650                 655

Ala Ser Asn Gly Gly Gly Lys Gln Ala Leu Glu Thr Val Gln Arg Leu
```

-continued

```
              660                 665                 670
Leu Pro Val Leu Cys Gln Ala His Gly Leu Thr Pro Glu Gln Val Val
            675                 680                 685

Ala Ile Ala Ser His Asp Gly Lys Gln Ala Leu Glu Thr Val Gln
        690                 695                 700

Arg Leu Leu Pro Val Leu Cys Gln Ala His Gly Leu Thr Pro Glu Gln
705                 710                 715                 720

Val Val Ala Ile Ala Ser His Asp Gly Gly Lys Gln Ala Leu Glu Thr
                725                 730                 735

Val Gln Arg Leu Leu Pro Val Leu Cys Gln Ala His Gly Leu Thr Pro
            740                 745                 750

Glu Gln Val Val Ala Ile Ala Ser His Asp Gly Gly Arg Pro Ala Leu
        755                 760                 765

Glu Ser Ile Val Ala Gln Leu Ser Arg Pro Asp Pro Ala Leu Ala Ala
        770                 775                 780

Leu Thr Asn Asp His Leu Val Ala Leu Ala Cys Leu Gly Gly Arg Pro
785                 790                 795                 800

Ala Leu Asp Ala Val Lys Lys Gly Leu Pro His Ala Pro Ala Leu Ile
                805                 810                 815

Lys Arg Thr Asn Arg Arg Ile Pro Glu Arg Thr Ser His Arg Val Ala
                820                 825                 830

Asp His Ala Gln Val Val Arg Val Leu Gly Phe Phe Gln Cys His Ser
                835                 840                 845

His Pro Ala Gln Ala Phe Asp Asp Ala Met Thr Gln Phe Gly Met Ser
            850                 855                 860

Arg His Gly Leu Leu Gln Leu Phe Arg Arg Val Gly Val Thr Glu Leu
865                 870                 875                 880

Glu Ala Arg Ser Gly Thr Leu Pro Pro Ala Ser Gln Arg Trp Asp Arg
                885                 890                 895

Ile Leu Gln Ala Ser Gly Met Lys Arg Ala Lys Pro Ser Pro Thr Ser
                900                 905                 910

Thr Gln Thr Pro Asp Gln Ala Ser Leu His Ala Phe Ala Asp Ser Leu
            915                 920                 925

Glu Arg Asp Leu Asp Ala Pro Ser Pro Met His Glu Gly Asp Gln Thr
930                 935                 940

Arg Ala Ser Ala Ser Pro Lys Lys Lys Arg Lys Val Glu Ala Ser Gly
945                 950                 955                 960

Ser Gly Met Asn Ile Gln Met Leu Leu Glu Ala Ala Asp Tyr Leu Glu
                965                 970                 975

Arg Arg Glu Arg Glu Ala Glu His Gly Tyr Ala Ser Met Leu Pro Gly
                980                 985                 990

Ser Gly Met Asn Ile Gln Met Leu  Leu Glu Ala Ala Asp Tyr Leu Glu
            995                 1000                1005

Arg Arg  Glu Arg Glu Ala Glu  His Gly Tyr Ala Ser  Met Leu Pro
        1010                1015                1020

Gly Ser  Gly Met Asn Ile Gln  Met Leu Leu Glu Ala  Ala Asp Tyr
        1025                1030                1035

Leu Glu  Arg Arg Glu Arg Glu  Ala Glu His Gly Tyr  Ala Ser Met
        1040                1045                1050

Leu Pro  Gly Ser Gly Met Asn  Ile Gln Met Leu Leu  Glu Ala Ala
        1055                1060                1065

Asp Tyr  Leu Glu Arg Arg Glu  Arg Glu Ala Glu His  Gly Tyr Ala
        1070                1075                1080
```

-continued

Ser Met Leu Pro Ser Arg
     1085

<210> SEQ ID NO 54
<211> LENGTH: 1094
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Ser Arg Thr Arg Leu Pro Ser Pro Ala Pro Ser Pro Ala Phe
1               5                   10                  15

Ser Ala Asp Ser Phe Ser Asp Leu Leu Arg Gln Phe Asp Pro Ser Leu
            20                  25                  30

Phe Asn Thr Ser Leu Phe Asp Ser Leu Pro Pro Phe Gly Ala His His
            35                  40                  45

Thr Glu Ala Ala Thr Gly Glu Trp Asp Glu Val Gln Ser Gly Leu Arg
    50                  55                  60

Ala Ala Asp Ala Pro Pro Pro Thr Met Arg Val Ala Val Thr Ala Ala
65                  70                  75                  80

Arg Pro Pro Arg Ala Lys Pro Ala Pro Arg Arg Ala Ala Gln Pro
                85                  90                  95

Ser Asp Ala Ser Pro Ala Ala Gln Val Asp Leu Arg Thr Leu Gly Tyr
            100                 105                 110

Ser Gln Gln Gln Gln Glu Lys Ile Lys Pro Lys Val Arg Ser Thr Val
            115                 120                 125

Ala Gln His His Glu Ala Leu Val Gly His Gly Phe Thr His Ala His
            130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
            195                 200                 205

Thr Gly Gln Leu Leu Lys Ile Ala Lys Arg Gly Gly Val Thr Ala Val
    210                 215                 220

Glu Ala Val His Ala Trp Arg Asn Ala Leu Thr Gly Ala Pro Leu Asn
225                 230                 235                 240

Leu Thr Pro Glu Gln Val Val Ala Ile Ala Ser Asn Asn Gly Gly Lys
                245                 250                 255

Gln Ala Leu Glu Thr Val Gln Arg Leu Leu Pro Val Leu Cys Gln Ala
            260                 265                 270

His Gly Leu Thr Pro Glu Gln Val Val Ala Ile Ala Ser His Asp Gly
            275                 280                 285

Gly Lys Gln Ala Leu Glu Thr Val Gln Arg Leu Leu Pro Val Leu Cys
    290                 295                 300

Gln Ala His Gly Leu Thr Pro Glu Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
            340                 345                 350

-continued

```
Ser Asn Gly Gly Gly Lys Gln Ala Leu Glu Thr Val Gln Arg Leu Leu
    355                 360                 365
Pro Val Leu Cys Gln Ala His Gly Leu Thr Pro Glu Gln Val Val Ala
370                 375                 380
Ile Ala Ser Asn Asn Gly Gly Lys Gln Ala Leu Glu Thr Val Gln Arg
385                 390                 395                 400
Leu Leu Pro Val Leu Cys Gln Ala His Gly Leu Thr Pro Glu Gln Val
                405                 410                 415
Val Ala Ile Ala Ser His Asp Gly Gly Lys Gln Ala Leu Glu Thr Val
            420                 425                 430
Gln Arg Leu Leu Pro Val Leu Cys Gln Ala His Gly Leu Thr Pro Glu
        435                 440                 445
Gln Val Val Ala Ile Ala Ser His Asp Gly Gly Lys Gln Ala Leu Glu
    450                 455                 460
Thr Val Gln Arg Leu Leu Pro Val Leu Cys Gln Ala His Gly Leu Thr
465                 470                 475                 480
Pro Glu Gln Val Val Ala Ile Ala Ser His Asp Gly Gly Lys Gln Ala
                485                 490                 495
Leu Glu Thr Val Gln Arg Leu Leu Pro Val Leu Cys Gln Ala His Gly
            500                 505                 510
Leu Thr Pro Glu Gln Val Val Ala Ile Ala Ser Asn Gly Gly Gly Lys
        515                 520                 525
Gln Ala Leu Glu Thr Val Gln Arg Leu Leu Pro Val Leu Cys Gln Ala
    530                 535                 540
His Gly Leu Thr Pro Glu Gln Val Val Ala Ile Ala Ser His Asp Gly
545                 550                 555                 560
Gly Lys Gln Ala Leu Glu Thr Val Gln Arg Leu Leu Pro Val Leu Cys
                565                 570                 575
Gln Ala His Gly Leu Thr Pro Glu Gln Val Val Ala Ile Ala Ser His
            580                 585                 590
Asp Gly Gly Lys Gln Ala Leu Glu Thr Val Gln Arg Leu Leu Pro Val
        595                 600                 605
Leu Cys Gln Ala His Gly Leu Thr Pro Glu Gln Val Val Ala Ile Ala
    610                 615                 620
Ser Asn Ile Gly Gly Lys Gln Ala Leu Glu Thr Val Gln Arg Leu Leu
625                 630                 635                 640
Pro Val Leu Cys Gln Ala His Gly Leu Thr Pro Glu Gln Val Val Ala
                645                 650                 655
Ile Ala Ser Asn Asn Gly Gly Lys Gln Ala Leu Glu Thr Val Gln Arg
            660                 665                 670
Leu Leu Pro Val Leu Cys Gln Ala His Gly Leu Thr Pro Glu Gln Val
        675                 680                 685
Val Ala Ile Ala Ser Asn Asn Gly Gly Lys Gln Ala Leu Glu Thr Val
    690                 695                 700
Gln Arg Leu Leu Pro Val Leu Cys Gln Ala His Gly Leu Thr Pro Glu
705                 710                 715                 720
Gln Val Val Ala Ile Ala Ser His Asp Gly Gly Lys Gln Ala Leu Glu
                725                 730                 735
Thr Val Gln Arg Leu Leu Pro Val Leu Cys Gln Ala His Gly Leu Thr
            740                 745                 750
Pro Glu Gln Val Val Ala Ile Ala Ser Asn Gly Gly Gly Lys Gln Ala
        755                 760                 765
Leu Glu Thr Val Gln Arg Leu Leu Pro Val Leu Cys Gln Ala His Gly
    770                 775                 780
```

```
Leu Thr Pro Glu Gln Val Val Ala Ile Ala Ser His Asp Gly Gly Lys
785                 790                 795                 800

Gln Ala Leu Glu Thr Val Gln Arg Leu Leu Pro Val Leu Cys Gln Ala
                805                 810                 815

His Gly Leu Thr Pro Glu Gln Val Val Ala Ile Ala Ser His Asp Gly
            820                 825                 830

Gly Lys Gln Ala Leu Glu Thr Val Gln Arg Leu Leu Pro Val Leu Cys
        835                 840                 845

Gln Ala His Gly Leu Thr Pro Glu Gln Val Val Ala Ile Ala Ser His
    850                 855                 860

Asp Gly Gly Arg Pro Ala Leu Glu Ser Ile Val Ala Gln Leu Ser Arg
865                 870                 875                 880

Pro Asp Pro Ala Leu Ala Ala Leu Thr Asn Asp His Leu Val Ala Leu
                885                 890                 895

Ala Cys Leu Gly Gly Arg Pro Ala Leu Asp Ala Val Lys Lys Gly Leu
            900                 905                 910

Pro His Ala Pro Ala Leu Ile Lys Arg Thr Asn Arg Arg Ile Pro Glu
        915                 920                 925

Arg Thr Ser His Arg Val Ala Asp His Ala Gln Val Val Arg Val Leu
    930                 935                 940

Gly Phe Phe Gln Cys His Ser His Pro Ala Gln Ala Phe Asp Asp Ala
945                 950                 955                 960

Met Thr Gln Phe Gly Met Ser Arg His Gly Leu Leu Gln Leu Phe Arg
                965                 970                 975

Arg Val Gly Val Thr Glu Leu Glu Ala Arg Ser Gly Thr Leu Pro Pro
            980                 985                 990

Ala Ser Gln Arg Trp Asp Arg Ile Leu Gln Ala Ser Gly Met Lys Arg
        995                 1000                1005

Ala Lys Pro Ser Pro Thr Ser Thr Gln Thr Pro Asp Gln Ala Ser
    1010                1015                1020

Leu His Ala Phe Ala Asp Ser Leu Glu Arg Asp Leu Asp Ala Pro
    1025                1030                1035

Ser Pro Met His Glu Gly Asp Gln Thr Arg Ala Ser Ala Ser Pro
    1040                1045                1050

Lys Lys Lys Arg Lys Val Glu Ala Ser Gly Ser Gly Met Asn Ile
    1055                1060                1065

Gln Met Leu Leu Glu Ala Ala Asp Tyr Leu Glu Arg Arg Glu Arg
    1070                1075                1080

Glu Ala Glu His Gly Tyr Ala Ser Met Leu Pro
    1085                1090

<210> SEQ ID NO 55
<211> LENGTH: 1192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Ser Arg Thr Arg Leu Pro Ser Pro Ala Pro Ser Pro Ala Phe
1               5                   10                  15

Ser Ala Asp Ser Phe Ser Asp Leu Leu Arg Gln Phe Asp Pro Ser Leu
                20                  25                  30

Phe Asn Thr Ser Leu Phe Asp Ser Leu Pro Pro Phe Gly Ala His His
            35                  40                  45
```

```
Thr Glu Ala Ala Thr Gly Glu Trp Asp Glu Val Gln Ser Gly Leu Arg
     50                  55                  60

Ala Ala Asp Ala Pro Pro Thr Met Arg Val Ala Val Thr Ala Ala
65                  70                  75                  80

Arg Pro Pro Arg Ala Lys Pro Ala Pro Arg Arg Ala Ala Gln Pro
                 85                  90                  95

Ser Asp Ala Ser Pro Ala Ala Gln Val Asp Leu Arg Thr Leu Gly Tyr
                100                 105                 110

Ser Gln Gln Gln Glu Lys Ile Lys Pro Lys Val Arg Ser Thr Val
            115                 120                 125

Ala Gln His His Glu Ala Leu Val Gly His Gly Phe Thr His Ala His
            130                 135                 140

Ile Val Ala Leu Ser Gln His Pro Ala Ala Leu Gly Thr Val Ala Val
145                 150                 155                 160

Lys Tyr Gln Asp Met Ile Ala Ala Leu Pro Glu Ala Thr His Glu Ala
                165                 170                 175

Ile Val Gly Val Gly Lys Gln Trp Ser Gly Ala Arg Ala Leu Glu Ala
            180                 185                 190

Leu Leu Thr Val Ala Gly Glu Leu Arg Gly Pro Pro Leu Gln Leu Asp
            195                 200                 205

Thr Gly Gln Leu Leu Lys Ile Ala Lys Arg Gly Gly Val Thr Ala Val
210                 215                 220

Glu Ala Val His Ala Trp Arg Asn Ala Leu Thr Gly Ala Pro Leu Asn
225                 230                 235                 240

Leu Thr Pro Glu Gln Val Val Ala Ile Ala Ser Asn Asn Gly Gly Lys
                245                 250                 255

Gln Ala Leu Glu Thr Val Gln Arg Leu Leu Pro Val Leu Cys Gln Ala
            260                 265                 270

His Gly Leu Thr Pro Glu Gln Val Val Ala Ile Ala Ser His Asp Gly
            275                 280                 285

Gly Lys Gln Ala Leu Glu Thr Val Gln Arg Leu Leu Pro Val Leu Cys
290                 295                 300

Gln Ala His Gly Leu Thr Pro Glu Gln Val Val Ala Ile Ala Ser His
305                 310                 315                 320

Asp Gly Gly Lys Gln Ala Leu Glu Thr Val Gln Arg Leu Leu Pro Val
                325                 330                 335

Leu Cys Gln Ala His Gly Leu Thr Pro Glu Gln Val Val Ala Ile Ala
            340                 345                 350

Ser Asn Gly Gly Gly Lys Gln Ala Leu Glu Thr Val Gln Arg Leu Leu
            355                 360                 365

Pro Val Leu Cys Gln Ala His Gly Leu Thr Pro Glu Gln Val Val Ala
370                 375                 380

Ile Ala Ser Asn Asn Gly Gly Lys Gln Ala Leu Glu Thr Val Gln Arg
385                 390                 395                 400

Leu Leu Pro Val Leu Cys Gln Ala His Gly Leu Thr Pro Glu Gln Val
                405                 410                 415

Val Ala Ile Ala Ser His Asp Gly Gly Lys Gln Ala Leu Glu Thr Val
            420                 425                 430

Gln Arg Leu Leu Pro Val Leu Cys Gln Ala His Gly Leu Thr Pro Glu
            435                 440                 445

Gln Val Val Ala Ile Ala Ser His Asp Gly Gly Lys Gln Ala Leu Glu
450                 455                 460

Thr Val Gln Arg Leu Leu Pro Val Leu Cys Gln Ala His Gly Leu Thr
```

-continued

```
            465                 470                 475                 480
        Pro Glu Gln Val Val Ala Ile Ala Ser His Asp Gly Gly Lys Gln Ala
                            485                 490                 495
        Leu Glu Thr Val Gln Arg Leu Leu Pro Val Leu Cys Gln Ala His Gly
                            500                 505                 510
        Leu Thr Pro Glu Gln Val Val Ala Ile Ala Ser Asn Gly Gly Gly Lys
                            515                 520                 525
        Gln Ala Leu Glu Thr Val Gln Arg Leu Leu Pro Val Leu Cys Gln Ala
                            530                 535                 540
        His Gly Leu Thr Pro Glu Gln Val Val Ala Ile Ala Ser His Asp Gly
        545                 550                 555                 560
        Gly Lys Gln Ala Leu Glu Thr Val Gln Arg Leu Leu Pro Val Leu Cys
                            565                 570                 575
        Gln Ala His Gly Leu Thr Pro Glu Gln Val Val Ala Ile Ala Ser His
                            580                 585                 590
        Asp Gly Gly Lys Gln Ala Leu Glu Thr Val Gln Arg Leu Leu Pro Val
                            595                 600                 605
        Leu Cys Gln Ala His Gly Leu Thr Pro Glu Gln Val Val Ala Ile Ala
                            610                 615                 620
        Ser Asn Ile Gly Gly Lys Gln Ala Leu Glu Thr Val Gln Arg Leu Leu
        625                 630                 635                 640
        Pro Val Leu Cys Gln Ala His Gly Leu Thr Pro Glu Gln Val Val Ala
                            645                 650                 655
        Ile Ala Ser Asn Asn Gly Gly Lys Gln Ala Leu Glu Thr Val Gln Arg
                            660                 665                 670
        Leu Leu Pro Val Leu Cys Gln Ala His Gly Leu Thr Pro Glu Gln Val
                            675                 680                 685
        Val Ala Ile Ala Ser Asn Asn Gly Gly Lys Gln Ala Leu Glu Thr Val
                            690                 695                 700
        Gln Arg Leu Leu Pro Val Leu Cys Gln Ala His Gly Leu Thr Pro Glu
        705                 710                 715                 720
        Gln Val Val Ala Ile Ala Ser His Asp Gly Gly Lys Gln Ala Leu Glu
                            725                 730                 735
        Thr Val Gln Arg Leu Leu Pro Val Leu Cys Gln Ala His Gly Leu Thr
                            740                 745                 750
        Pro Glu Gln Val Val Ala Ile Ala Ser Asn Gly Gly Gly Lys Gln Ala
                            755                 760                 765
        Leu Glu Thr Val Gln Arg Leu Leu Pro Val Leu Cys Gln Ala His Gly
                            770                 775                 780
        Leu Thr Pro Glu Gln Val Val Ala Ile Ala Ser His Asp Gly Gly Lys
        785                 790                 795                 800
        Gln Ala Leu Glu Thr Val Gln Arg Leu Leu Pro Val Leu Cys Gln Ala
                            805                 810                 815
        His Gly Leu Thr Pro Glu Gln Val Val Ala Ile Ala Ser His Asp Gly
                            820                 825                 830
        Gly Lys Gln Ala Leu Glu Thr Val Gln Arg Leu Leu Pro Val Leu Cys
                            835                 840                 845
        Gln Ala His Gly Leu Thr Pro Glu Gln Val Val Ala Ile Ala Ser His
                            850                 855                 860
        Asp Gly Gly Arg Pro Ala Leu Glu Ser Ile Val Ala Gln Leu Ser Arg
        865                 870                 875                 880
        Pro Asp Pro Ala Leu Ala Ala Leu Thr Asn Asp His Leu Val Ala Leu
                            885                 890                 895
```

```
Ala Cys Leu Gly Gly Arg Pro Ala Leu Asp Ala Val Lys Lys Gly Leu
                900                 905                 910

Pro His Ala Pro Ala Leu Ile Lys Arg Thr Asn Arg Ile Pro Glu
    915                 920                 925

Arg Thr Ser His Arg Val Ala Asp His Ala Gln Val Val Arg Val Leu
    930                 935                 940

Gly Phe Phe Gln Cys His Ser His Pro Ala Gln Ala Phe Asp Asp Ala
945                 950                 955                 960

Met Thr Gln Phe Gly Met Ser Arg His Gly Leu Leu Gln Leu Phe Arg
                965                 970                 975

Arg Val Gly Val Thr Glu Leu Glu Ala Arg Ser Gly Leu Pro Pro
    980                 985                 990

Ala Ser Gln Arg Trp Asp Arg Ile Leu Gln Ala Ser Gly Met Lys Arg
    995                 1000                1005

Ala Lys Pro Ser Pro Thr Ser Thr Gln Thr Pro Asp Gln Ala Ser
    1010                1015                1020

Leu His Ala Phe Ala Asp Ser Leu Glu Arg Asp Leu Asp Ala Pro
    1025                1030                1035

Ser Pro Met His Glu Gly Asp Gln Thr Arg Ala Ser Ala Ser Pro
    1040                1045                1050

Lys Lys Lys Arg Lys Val Glu Ala Ser Gly Ser Gly Met Asn Ile
    1055                1060                1065

Gln Met Leu Leu Glu Ala Ala Asp Tyr Leu Glu Arg Arg Glu Arg
    1070                1075                1080

Glu Ala Glu His Gly Tyr Ala Ser Met Leu Pro Gly Ser Gly Met
    1085                1090                1095

Asn Ile Gln Met Leu Leu Glu Ala Ala Asp Tyr Leu Glu Arg Arg
    1100                1105                1110

Glu Arg Glu Ala Glu His Gly Tyr Ala Ser Met Leu Pro Gly Ser
    1115                1120                1125

Gly Met Asn Ile Gln Met Leu Leu Glu Ala Ala Asp Tyr Leu Glu
    1130                1135                1140

Arg Arg Glu Arg Glu Ala Glu His Gly Tyr Ala Ser Met Leu Pro
    1145                1150                1155

Gly Ser Gly Met Asn Ile Gln Met Leu Leu Glu Ala Ala Asp Tyr
    1160                1165                1170

Leu Glu Arg Arg Glu Arg Glu Ala Glu His Gly Tyr Ala Ser Met
    1175                1180                1185

Leu Pro Ser Arg
    1190

<210> SEQ ID NO 56
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ttcttaatta taac                                                       14

<210> SEQ ID NO 57
<211> LENGTH: 14
<212> TYPE: DNA
<213> ORGANISM: Artificial Sequence
<220> FEATURE:
<223> OTHER INFORMATION: Description of Artificial Sequence: Synthetic
```

```
                                oligonucleotide

<400> SEQUENCE: 57 ttcttttta taac                                                          14

<210> SEQ ID NO 58
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ttcttggtta taac                                                         14

<210> SEQ ID NO 59
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ttcttcctta taac                                                         14

<210> SEQ ID NO 60
<211> LENGTH: 18
<212> TYPE: DNA
<213> ORGANISM: Homo sapiens

<400> SEQUENCE: 60 tcaacccta ccaaccca                                                      18

<210> SEQ ID NO 61
<211> LENGTH: 18
<212> TYPE: DNA
<213> ORGANISM: Homo sapiens

<400> SEQUENCE: 61
taataaacct taaaacta                                                     18

<210> SEQ ID NO 62
<211> LENGTH: 18
<212> TYPE: DNA
<213> ORGANISM: Homo sapiens

<400> SEQUENCE: 62
tggtagacct tagggcta                                                     18

<210> SEQ ID NO 63
<211> LENGTH: 18
<212> TYPE: DNA
<213> ORGANISM: Homo sapiens

<400> SEQUENCE: 63
tcggcccctg ccggccca                                                     18

<210> SEQ ID NO 64
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 64
tttattccct gacc                                                       14

<210> SEQ ID NO 65
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Leu Thr Pro Glu Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 66
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
ctcaccccag agcaggtcgt ggcaattgcg agcaacatcg ggggaaagca ggcactcgaa     60
accgtccaga ggttgctgcc tgtgctgtgc caagcgcacg ga                       102

<210> SEQ ID NO 67
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
ctcaccccag agcaggtcgt ggcaattgcg agcaacggag ggggaaagca ggcactcgaa     60
accgtccaga ggttgctgcc tgtgctgtgc caagcgcacg ga                       102

<210> SEQ ID NO 68
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
ctcaccccag agcaggtcgt ggcaattgcg agcaacaacg ggggaaagca ggcactcgaa     60
accgtccaga ggttgctgcc tgtgctgtgc caagcgcacg ga                       102

<210> SEQ ID NO 69
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
```

```
ctcacccag agcaggtcgt ggcaattgcg agccatgacg ggggaaagca ggcactcgaa      60
accgtccaga ggttgctgcc tgtgctgtgc caagcgcacg ga                        102

<210> SEQ ID NO 70
<211> LENGTH: 3782
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
atgtcgcgga cccggctccc ttccccaccc gcacccagcc cagcgttttc ggccgactcg      60
ttctcagacc tgcttaggca gttcgacccc tcactgttta acacatcgtt gttcgactcc     120
cttcctccgt ttggggcgca ccatacggag gcggccaccg gggagtggga tgaggtgcag     180
tcgggattga gagctgcgga tgcaccaccc ccaaccatgc gggtggccgt caccgctgcc     240
cgaccgccga gggcgaagcc cgcaccaagg cggagggcag cgcaaccgtc cgacgcaagc     300
cccgcagcgc aagtagattt gagaactttg ggatattcac agcagcagca ggaaaagatc     360
aagcccaaag tgaggtcgac agtcgcgcag catcacgaag cgctggtggg tcatgggttt     420
acacatgccc acatcgtagc cttgtcgcag caccctgcag cccttggcac ggtcgccgtc     480
aagtaccagg acatgattgc ggcgttgccg gaagccacac atgaggcgat cgtcggtgtg     540
gggaaacagt ggagcggagc ccgagcgctt gaggccctgt tgacggtcgc gggagagctg     600
agagggcctc cccttcagct ggacacgggc cagttgctga agatcgcgaa gcggggagga     660
gtcacggcgg tcgaggcggt gcacgcgtgg cgcaatgcgc tcacgggagc acccctcaac     720
ctgacagaga ccgcggccgc attaggcacc ccaggcttta cactttatgc ttccggctcg     780
tataatgtgt ggattttgag ttaggatccg tcgagatttt caggagctaa ggaagctaaa     840
atggagaaaa aaatcactgg atataccacc gttgatatat cccaatggca tcgtaaagaa     900
cattttgagg catttcagtc agttgctcaa tgtacctata accagaccgt tcagctggat     960
attacggcct ttttaaagac cgtaaagaaa aataagcaca gttttatcc ggcctttatt     1020 cacattcttg cccgcctgat gaatgctcat ccggaattcc gtatggcaat gaaagacggt     1080
gagctggtga tatgggatag tgttcaccct tgttacaccg ttttccatga gcaaactgaa     1140
acgttttcat cgctctggag tgaataccac gacgatttcc ggcagtttct acacatatat     1200
tcgcaagatg tggcgtgtta cggtgaaaac ctggcctatt tccctaaagg gtttattgag     1260
aatatgtttt tcgtctcagc caatccctgg gtgagtttca ccagttttga tttaaacgtg     1320
gccaatatgg acaacttctt cgcccccgtt ttcaccatgg gcaaatatta tacgcaaggc     1380
gacaaggtgc tgatgccgct ggcgattcag gttcatcatg ccgtttgtga tggcttccat     1440
gtcggcagaa tgcttaatga attacaacag tactgcgatg agtggcaggg cggggcgtaa     1500
agatctggat ccgcttact aaaagccaga taacagtatg cgtatttgcg cgctgatttt     1560
tgcggtataa gaatatatac tgatatgtat acccgaagta tgtcaaaaag aggtatgcta     1620
tgaagcagcg tattacagtg acagttgaca gcgacagcta tcagttgctc aaggcatata     1680
tgatgtcaat atctccggtc tggtaagcac aaccatgcag aatgaagccc gtcgtctgcg     1740
tgccgaacgc tggaaagcgg aaaatcagga agggatggct gaggtcgccc ggtttattga     1800
aatgaacggc tcttttgctg acgagaacag gggctggtga atgcagtttt aaggtttaca     1860
cctataaaag agagagccgt tatcgtctgt ttgtggatgt acagagtgat attattgaca     1920
cgcccgggcg acggatggtg atccccctgg ccagtgcacg tctgctgtca gataaagtct     1980
```

```
cccgtgaact ttacccggtg gtgcatatcg gggatgaaag ctggcgcatg atgaccaccg    2040
atatggccag tgtgccggtc tccgttatcg gggaagaagt ggctgatctc agccaccgcg    2100
aaaatgacat caaaaacgcc attaacctga tgttctgggg aatataaatg tcaggctccc    2160
ttatacacag ccagtctgca ggtcgacggt ctcgactcac gcctgagcag gtagtggcta    2220
ttgcatccaa tatcggggc agacccgcac tggagtcaat cgtggcccag ctttcgaggc     2280
cggaccccgc gctggccgca ctcactaatg atcatcttgt agcgctggcc tgcctcggcg    2340
gacgacccgc cttggatgcg gtgaagaagg ggctcccgca cgcgcctgca ttgattaagc    2400
ggaccaacag aaggattccc gagaggacat cacatcgagt ggcagatcac gcgcaagtgg    2460
tccgcgtgct cggattcttc cagtgtcact cccacccccgc acaagcgttc gatgacgcca   2520
tgactcaatt tggtatgtcg agacacggac tgctgcagct ctttcgtaga gtcggtgtca    2580
cagaactcga ggcccgctcg ggcacactgc ctcccgcctc ccagcggtgg gacaggattc    2640
tccaagcgag cggtatgaaa cgcgcgaagc cttcacctac gtcaactcag acacctgacc    2700
aggcgagcct tcatgcgttc gcagactcgc tggagaggga tttggacgcg ccctcgccca    2760
tgcatgaagg ggaccaaaact cgcgcgtcag ctagccccaa gaagaagaga aggtggagg    2820 ccagcggttc cggacgggct gacgcattgg acgattttga tctggatatg ctgggaagtg    2880
acgccctcga tgattttgac cttgacatgc ttggttcgga tgcccttgat gactttgacc    2940
tcgacatgct cggcagtgac gcccttgatg atttcgacct ggacatgctg attaactcta    3000
gaggcagtgg agagggcaga ggaagtctgc taacatgcgg tgacgtcgag gagaatcctg    3060
gcccagtgag caagggcgag gagctgttca ccggggtggt gcccatcctg gtcgagctgg    3120
acggcgacgt aaacggccac aagttcagcg tgtccggcga gggcgagggc gatgccacct    3180
acggcaagct gaccctgaag ttcatctgca ccaccggcaa gctgcccgtg ccctggccca    3240
ccctcgtgac caccctgacc tacggcgtgc agtgcttcag ccgctacccc gaccacatga    3300
agcagcacga cttcttcaag tccgccatgc ccgaaggcta cgtccaggag cgcaccatct    3360
tcttcaagga cgacggcaac tacaagaccc gcgccgaggt gaagttcgag ggcgacaccc    3420
tggtgaaccg catcgagctg aagggcatcg acttcaagga ggacggcaac atcctggggc    3480
acaagctgga gtacaactac aacagccaca cgtctatat catggccgac aagcagaaga    3540
acggcatcaa ggtgaacttc aagatccgcc acaacatcga ggacggcagc gtgcagctcg    3600
ccgaccacta ccagcagaac ccccccatcg gcgacggccc cgtgctgctg cccgacaacc    3660
actacctgag cacccagtcc gccctgagca agacccccaa cgagaagcgc gatcacatgg    3720
tcctgctgga gttcgtgacc gccgccggga tcactctcgg catggacgag ctgtacaagt    3780
aa                                                                   3782
```

<210> SEQ ID NO 71
<211> LENGTH: 3782
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
atgtcgcgga cccggctccc ttccccaccc gcacccagcc cagcgttttc ggccgactcg      60
ttctcagacc tgcttaggca gttcgacccc tcactgttta acacatcgtt gttcgactcc     120
cttcctccgt ttggggcgca ccatacggag gcggccaccg gggagtggga tgaggtgcag     180
```

```
tcgggattga gagctgcgga tgcaccaccc ccaaccatgc gggtggccgt caccgctgcc    240
cgaccgccga gggcgaagcc cgcaccaagg cggagggcag cgcaaccgtc cgacgcaagc    300
cccgcagcgc aagtagattt gagaactttg ggatattcac agcagcagca ggaaaagatc    360
aagcccaaag tgaggtcgac agtcgcgcag catcacgaag cgctggtggg tcatgggttt    420
acacatgccc acatcgtagc cttgtcgcag caccctgcag cccttggcac ggtcgccgtc    480
aagtaccagg acatgattgc ggcgttgccg gaagccacac atgaggcgat cgtcggtgtg    540
gggaaacagt ggagcggagc ccgagcgctt gaggccctgt tgacggtcgc gggagagctg    600
agagggcctc cccttcagct ggacacgggc cagttgctga gatcgcgaa gcggggagga    660 gtcacggcgg tcgaggcggt gcacgcgtgg cgcaatgcgc tcacgggagc acccctcaac    720
ctgacagaga ccgcggccgc attaggcacc ccaggcttta cactttatgc ttccggctcg    780
tataatgtgt ggattttgag ttaggatccg tcgagatttt caggagctaa ggaagctaaa    840
atggagaaaa aaatcactgg atataccacc gttgatatat cccaatggca tcgtaaagaa    900
cattttgagg catttcagtc agttgctcaa tgtacctata accagaccgt tcagctggat    960
attacggcct ttttaaagac cgtaaagaaa aataagcaca agttttatcc ggcctttatt   1020
cacattcttg cccgcctgat gaatgctcat ccggaattcc gtatggcaat gaaagacggt   1080
gagctggtga tatgggatag tgttcaccct tgttacaccg ttttccatga gcaaactgaa   1140
acgttttcat cgctctggag tgaataccac gacgatttcc ggcagtttct acacatatat   1200
tcgcaagatg tggcgtgtta cggtgaaaac ctggcctatt tccctaaagg gtttattgag   1260
aatatgtttt tcgtctcagc caatccctgg gtgagtttca ccagttttga tttaaacgtg   1320
gccaatatgg acaacttctt cgcccccgtt ttcaccatgg gcaaatatta tacgcaaggc   1380
gacaaggtgc tgatgccgct ggcgattcag gttcatcatg ccgtttgtga tggcttccat   1440
gtcggcagaa tgcttaatga attacaacag tactgcgatg agtggcaggg cggggcgtaa   1500
agatctggat ccggcttact aaaagccaga taacagtatg cgtatttgcg cgctgatttt   1560
tgcggtataa gaatatatac tgatatgtat acccgaagta tgtcaaaaag aggtatgcta   1620
tgaagcagcg tattacagtg acagttgaca gcgacgcta tcagttgctc aaggcatata   1680
tgatgtcaat atctccggtc tggtaagcac aaccatgcag aatgaagccc gtcgtctgcg   1740
tgccgaacgc tggaaagcgg aaaatcagga agggatggct gaggtcgccc ggtttattga   1800
aatgaacggc tcttttgctg acgagaacag gggctggtga atgcagtttt aaggtttaca   1860
cctataaaag agagagccgt tatcgtctgt ttgtggatgt acagagtgat attattgaca   1920
cgcccgggcg acggatggtg atcccccctgg ccagtgcacg tctgctgtca gataaagtct   1980
cccgtgaact ttacccggtg gtgcatatcg gggatgaaag ctggcgcatg atgaccaccg   2040
atatggccag tgtgccggtc tccgttatcg gggaagaagt ggctgatctc agccaccgcg   2100
aaaatgacat caaaaacgcc attaacctga tgttctgggg aatataaatg tcaggctccc   2160
ttatacacag ccagtctgca ggtcgacggt ctcgactcac gcctgagcag gtagtggcta   2220
ttgcatccaa tggcggggc agacccgcac tggagtcaat cgtggcccag ctttcgaggc   2280
cggaccccgc gctggccgca ctcactaatg atcatcttgt agcgctggcc tgcctcggcg   2340
gacgacccgc cttggatgcg gtgaagaagg ggctcccgca cgcgcctgca ttgattaagc   2400
ggaccaacag aaggattccc gagaggacat cacatcgagt ggcagatcac gcgcaagtgg   2460
tccgcgtgct cggattcttc cagtgtcact cccaccccgc acaagcgttc gatgacgcca   2520
tgactcaatt tggtatgtcg agacacggac tgctgcagct ctttcgtaga gtcggtgtca   2580
```

| | |
|---|---:|
| cagaactcga ggcccgctcg ggcacactgc ctcccgcctc ccagcggtgg gacaggattc | 2640 |
| tccaagcgag cggtatgaaa cgcgcgaagc cttcacctac gtcaactcag acacctgacc | 2700 |
| aggcgagcct tcatgcgttc gcagactcgc tggagaggga tttggacgcg ccctcgccca | 2760 |
| tgcatgaagg ggaccaaact cgcgcgtcag ctagccccaa gaagaagaga aaggtggagg | 2820 |
| ccagcggttc cggacgggct gacgcattgg acgattttga tctggatatg ctgggaagtg | 2880 |
| acgccctcga tgattttgac cttgacatgc ttggttcgaa tgcccttgat gactttgacc | 2940 |
| tcgacatgct cggcagtgac gcccttgatg atttcgacct ggacatgctg attaactcta | 3000 |
| gaggcagtgg agagggcaga ggaagtctgc taacatgcgg tgacgtcgag gagaatcctg | 3060 |
| gcccagtgag caagggcgag gagctgttca ccggggtggt gcccatcctg gtcgagctgg | 3120 |
| acggcgacgt aaacggccac aagttcagcg tgtccggcga gggcgagggc gatgccacct | 3180 |
| acggcaagct gaccctgaag ttcatctgca ccaccggcaa gctgcccgtg ccctggccca | 3240 |
| ccctcgtgac caccctgacc tacggcgtgc agtgcttcag ccgctacccc gaccacatga | 3300 |
| agcagcacga cttcttcaag tccgccatgc ccgaaggcta cgtccaggag cgcaccatct | 3360 |
| tcttcaagga cgacggcaac tacaagaccc gcgccgaggt gaagttcgag ggcgacaccc | 3420 |
| tggtgaaccg catcgagctg aagggcatcg acttcaagga ggacggcaac atcctggggc | 3480 |
| acaagctgga gtacaactac aacagccaca acgtctatat catggccgac aagcagaaga | 3540 |
| acggcatcaa ggtgaacttc aagatccgcc acaacatcga ggacggcagc gtgcagctcg | 3600 |
| ccgaccacta ccagcagaac acccccatcg gcgacggccc cgtgctgctg cccgacaacc | 3660 |
| actacctgag cacccagtcc gccctgagca agacccccaa cgagaagcgc gatcacatgg | 3720 |
| tcctgctgga gttcgtgacc gccgccggga tcactctcgg catggacgag ctgtacaagt | 3780 |
| aa | 3782 |

<210> SEQ ID NO 72
<211> LENGTH: 3782
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

| | |
|---|---:|
| atgtcgcgga cccggctccc ttccccaccc gcacccagcc cagcgttttc ggccgactcg | 60 |
| ttctcagacc tgcttaggca gttcgacccc tcactgttta acacatcgtt gttcgactcc | 120 |
| cttcctccgt ttggggcgca ccatacggag gcggccaccg gggagtggga tgaggtgcag | 180 |
| tcgggattga gagctgcgga tgcaccaccc ccaaccatgc gggtggccgt caccgctgcc | 240 |
| cgaccgccga gggcgaagcc cgcaccaagg cggagggcag cgcaaccgtc cgacgcaagc | 300 |
| cccgcagcgc aagtagattt gagaactttg ggatattcac agcagcagca ggaaaagatc | 360 |
| aagcccaaag tgaggtcgac agtcgcgcag catcacgaag cgctggtggg tcatgggttt | 420 |
| acacatgccc acatcgtagc cttgtcgcag caccctgcag cccttggcac ggtcgccgtc | 480 |
| aagtaccagg acatgattgc ggcgttgccg gaagccacac atgaggcgat cgtcggtgtg | 540 |
| gggaaacagt ggagcggagc ccgagcgctt gaggccctgt tgacggtcgc gggagagctg | 600 |
| agagggcctc cccttcagct ggacacgggc cagttgctga gatcgcgaa gcggggagga | 660 |
| gtcacggcgg tcgaggcggt gcacgcgtgg cgcaatgcgc tcacgggagc acccctcaac | 720 |
| ctgacagaga ccgcggccgc attaggcacc ccaggcttta cactttatgc ttccggctcg | 780 |
| tataatgtgt ggattttgag ttaggatccg tcgagatttt caggagctaa ggaagctaaa | 840 |

```
atggagaaaa aaatcactgg atataccacc gttgatatat cccaatggca tcgtaaagaa    900
cattttgagg catttcagtc agttgctcaa tgtacctata accagaccgt tcagctggat    960
attacggcct ttttaaagac cgtaaagaaa aataagcaca agttttatcc ggcctttatt   1020
cacattcttg cccgcctgat gaatgctcat ccggaattcc gtatggcaat gaaagacggt   1080
gagctggtga tatgggatag tgttcaccct tgttacaccg ttttccatga gcaaactgaa   1140
acgttttcat cgctctggag tgaataccac gacgatttcc ggcagtttct acacatatat   1200
tcgcaagatg tggcgtgtta cggtgaaaac ctggcctatt ccctaaagg gtttattgag    1260
aatatgtttt tcgtctcagc caatccctgg gtgagtttca ccagttttga tttaaacgtg   1320
gccaatatgg acaacttctt cgccccgtt ttcaccatgg gcaaatatta tacgcaaggc    1380
gacaaggtgc tgatgccgct ggcgattcag gttcatcatg ccgtttgtga tggcttccat   1440
gtcggcagaa tgcttaatga attacaacag tactgcgatg agtggcaggg cggggcgtaa   1500
agatctggat ccggcttact aaaagccaga taacagtatg cgtatttgcg cgctgatttt   1560
tgcggtataa gaatatatac tgatatgtat acccgaagta tgtcaaaaag aggtatgcta   1620
tgaagcagcg tattacagtg acagttgaca gcgacagcta tcagttgctc aaggcatata   1680
tgatgtcaat atctccggtc tggtaagcac aaccatgcag aatgaagccc gtcgtctgcg   1740
tgccgaacgc tggaaagcgg aaaatcagga agggatggct gaggtcgccc ggtttattga   1800
aatgaacggc tcttttgctg acgagaacag gggctggtga aatgcagttt aaggtttaca   1860
cctataaaag agagagccgt tatcgtctgt ttgtggatgt acagagtgat attattgaca   1920
cgcccgggcg acggatggtg atcccccctgg ccagtgcacg tctgctgtca gataaagtct   1980
cccgtgaact ttaccggtg gtgcatatcg gggatgaaag ctggcgcatg atgaccaccg    2040
atatggccag tgtgccggtc tccgttatcg gggaagaagt ggctgatctc agccaccgcg   2100
aaaatgacat caaaaacgcc attaacctga tgttctgggg aatataaatg tcaggctccc   2160
ttatacacag ccagtctgca ggtcgacggt ctcgactcac gcctgagcag gtagtggcta   2220
ttgcatccaa taacggggc agacccgcac tggagtcaat cgtggcccag ctttcgaggc    2280
cggaccccgc gctggccgca ctcactaatg atcatcttgt agcgctggcc tgcctcggcg   2340
gacgacccgc cttggatgcg gtgaagaagg ggctcccgca cgcgcctgca ttgattaagc   2400
ggaccaacag aaggattccc gagaggacat cacatcgagt ggcagatcac gcgcaagtgg   2460
tccgcgtgct cggattcttc cagtgtcact cccacccccgc acaagcgttc gatgacgcca   2520
tgactcaatt tggtatgtcg agacacggac tgctgcagct cttcgtaga gtcggtgtca    2580
cagaactcga ggcccgctcg ggcacactgc ctcccgcctc ccagcggtgg acaggattc    2640
tccaagcgag cggtatgaaa cgcgcgaagc cttcacctac gtcaactcag acacctgacc   2700
aggcgagcct tcatgcgttc gcagactcgc tggagaggga tttggacgcg ccctcgccca   2760
tgcatgaagg ggaccaaact cgcgcgtcag ctagccccaa gaagaagaga aggtggagg    2820
ccagcggttc cggacgggct gacgcattgg acgattttga tctggatatg ctgggaagtg   2880
acgccctcga tgattttgac cttgacatgc ttggttcgga tgcccttgat gactttgacc   2940
tcgacatgct cggcagtgac gcccttgatg atttcgacct ggacatgctg attaactcta   3000
gaggcagtgg agagggcaga ggaagtctgc taacatgcgg tgacgtcgag gagaatcctg   3060
gcccagtgag caagggcgag gagctgttca ccggggtggt gcccatcctg gtcgagctgg   3120
acggcgacgt aaacgccac aagttcagcg tgtccggcga gggcgagggc gatgccacct   3180
acggcaagct gaccctgaag ttcatctgca ccaccggcaa gctgcccgtg ccctggccca   3240
```

-continued

| | |
|---|---|
| ccctcgtgac cacccctgacc tacggcgtgc agtgcttcag ccgctacccc gaccacatga | 3300 |
| agcagcacga cttcttcaag tccgccatgc ccgaaggcta cgtccaggag cgcaccatct | 3360 |
| tcttcaagga cgacggcaac tacaagaccc gcgccgaggt gaagttcgag ggcgacaccc | 3420 |
| tggtgaaccg catcgagctg aagggcatcg acttcaagga ggacggcaac atcctggggc | 3480 |
| acaagctgga gtacaactac aacagccaca cgtctatat catggccgac aagcagaaga | 3540 |
| acggcatcaa ggtgaacttc aagatccgcc acaacatcga ggacggcagc gtgcagctcg | 3600 |
| ccgaccacta ccagcagaac acccccatcg gcgacggccc cgtgctgctg cccgacaacc | 3660 |
| actacctgag cacccagtcc gccctgagca agacccccaa cgagaagcgc gatcacatgg | 3720 |
| tcctgctgga gttcgtgacc gccgccggga tcactctcgg catggacgag ctgtacaagt | 3780 |
| aa | 3782 |

<210> SEQ ID NO 73
<211> LENGTH: 3782
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

| | |
|---|---|
| atgtcgcgga cccggctccc ttccccaccc gcacccagcc cagcgttttc ggccgactcg | 60 |
| ttctcagacc tgcttaggca gttcgacccc tcactgttta acacatcgtt gttcgactcc | 120 |
| cttcctccgt ttggggcgca ccatacggag gcggccaccg gggagtggga tgaggtgcag | 180 |
| tcgggattga gagctgcgga tgcaccaccc ccaaccatgc gggtggccgt caccgctgcc | 240 |
| cgaccgccga gggcgaagcc cgcaccaagg cggagggcag cgcaaccgtc cgacgcaagc | 300 |
| cccgcagcgc aagtagattt gagaactttg ggatattcac agcagcagca ggaaaagatc | 360 |
| aagcccaaag tgaggtcgac agtcgcgcag catcacgaag cgctggtggg tcatgggttt | 420 |
| acacatgccc acatcgtagc cttgtcgcag caccctgcag cccttggcac ggtcgccgtc | 480 |
| aagtaccagg acatgattgc ggcgttgccg gaagccacac atgaggcgat cgtcggtgtg | 540 |
| gggaaacagt ggagcggagc ccgagcgctt gaggccctgt tgacggtcgc gggagagctg | 600 |
| agagggcctc cccttcagct ggacacgggc cagttgctga agatcgcgaa gcggggagga | 660 |
| gtcacggcgg tcgaggcggt gcacgcgtgg cgcaatgcgc tcacgggagc acccctcaac | 720 |
| ctgacagaga ccgcggccgc attaggcacc ccaggcttta cactttatgc ttccggctcg | 780 |
| tataatgtgt ggattttgag ttaggatccg tcgagatttt caggagctaa ggaagctaaa | 840 |
| atggagaaaa aaatcactgg atataccacc gttgatatat cccaatggca tcgtaaagaa | 900 |
| cattttgagg catttcagtc agttgctcaa tgtacctata accagaccgt tcagctggat | 960 |
| attacggcct ttttaaagac cgtaaagaaa aataagcaca agttttatcc ggcctttatt | 1020 |
| cacattcttg cccgcctgat gaatgctcat ccggaattcc gtatggcaat gaaagacggt | 1080 |
| gagctggtga tatgggatag tgttcaccct tgttacaccg ttttccatga gcaaactgaa | 1140 |
| acgttttcat cgctctggag tgaataccac gacgatttcc ggcagtttct acacatatat | 1200 |
| tcgcaagatg tggcgtgtta cggtgaaaac ctggcctatt tccctaaagg gtttattgag | 1260 |
| aatatgtttt tcgtctcagc caatccctgg gtgagtttca ccagttttga tttaaacgtg | 1320 |
| gccaatatgg acaacttctt cgcccccgtt ttcaccatgg caaatatta tacgcaaggc | 1380 |
| gacaaggtgc tgatgccgct ggcgattcag gttcatcatg ccgtttgtga tggcttccat | 1440 |

-continued

| | |
|---|---|
| gtcggcagaa tgcttaatga attacaacag tactgcgatg agtggcaggg cggggcgtaa | 1500 |
| agatctggat ccggcttact aaaagccaga taacagtatg cgtatttgcg cgctgatttt | 1560 |
| tgcggtataa gaatatatac tgatatgtat acccgaagta tgtcaaaaag aggtatgcta | 1620 |
| tgaagcagcg tattacagtg acagttgaca gcgacagcta tcagttgctc aaggcatata | 1680 |
| tgatgtcaat atctccggtc tggtaagcac aaccatgcag aatgaagccc gtcgtctgcg | 1740 |
| tgccgaacgc tggaaagcgg aaaatcagga agggatggct gaggtcgccc ggtttattga | 1800 |
| aatgaacggc tcttttgctg acgagaacag gggctggtga aatgcagttt aaggtttaca | 1860 |
| cctataaaag agagagccgt tatcgtctgt ttgtggatgt acagagtgat attattgaca | 1920 |
| cgcccgggcg acggatggtg atcccctgg ccagtgcacg tctgctgtca gataaagtct | 1980 |
| cccgtgaact ttaccggtg gtgcatatcg gggatgaaag ctggcgcatg atgaccaccg | 2040 |
| atatggccag tgtgccggtc tccgttatcg gggaagaagt ggctgatctc agccaccgcg | 2100 |
| aaaatgacat caaaaacgcc attaacctga tgttctgggg aatataaatg tcaggctccc | 2160 |
| ttatacacag ccagtctgca ggtcgacggt ctcgactcac gcctgagcag gtagtggcta | 2220 |
| ttgcatccca tgacggggc agacccgcac tggagtcaat cgtggcccag ctttcgaggc | 2280 |
| cggaccccgc gctggccgca ctcactaatg atcatcttgt agcgctggcc tgcctcggcg | 2340 |
| gacgacccgc cttggatgcg gtgaagaagg ggctcccgca cgcgcctgca ttgattaagc | 2400 |
| ggaccaacag aaggattccc gagaggacat cacatcgagt ggcagatcac gcgcaagtgg | 2460 |
| tccgcgtgct cggattcttc cagtgtcact cccaccccgc acaagcgttc gatgacgcca | 2520 |
| tgactcaatt tggtatgtcg agacacggac tgctgcagct ctttcgtaga gtcggtgtca | 2580 |
| cagaactcga ggcccgctcg ggcacactgc ctcccgcctc ccagcggtgg gacaggattc | 2640 |
| tccaagcgag cggtatgaaa cgcgcgaagc cttcacctac gtcaactcag acacctgacc | 2700 |
| aggcgagcct tcatgcgttc gcagactcgc tggagaggga tttggacgcg ccctcgccca | 2760 |
| tgcatgaagg ggaccaaact cgcgcgtcag ctagccccaa gaagaagaga aaggtggagg | 2820 |
| ccagcggttc cggacgggct gacgcattgg acgattttga tctggatatg ctgggaagtg | 2880 |
| acgccctcga tgattttgac cttgacatgc ttggttcgga tgcccttgat gactttgacc | 2940 |
| tcgacatgct cggcagtgac gcccttgatg atttcgacct ggacatgctg attaactcta | 3000 |
| gaggcagtgg agagggcaga ggaagtctgc taacatgcgg tgacgtcgag gagaatcctg | 3060 |
| gcccagtgag caagggcgag gagctgttca ccggggtggt gcccatcctg gtcgagctgg | 3120 |
| acggcgacgt aaacggccac aagttcagcg tgtccggcga gggcgagggc gatgccacct | 3180 |
| acggcaagct gaccctgaag ttcatctgca ccaccggcaa gctgcccgtg ccctggccca | 3240 |
| ccctcgtgac caccctgacc tacggcgtgc agtgcttcag ccgctacccc gaccacatga | 3300 |
| agcagcacga cttcttcaag tccgccatgc ccgaaggcta cgtccaggag cgcaccatct | 3360 |
| tcttcaagga cgacggcaac tacaagaccc gcgccgaggt gaagttcgag ggcgacaccc | 3420 |
| tggtgaaccg catcgagctg aagggcatcg acttcaagga ggacggcaac atcctggggc | 3480 |
| acaagctgga gtacaactac aacagccaca acgtctatat catggccgac aagcagaaga | 3540 |
| acggcatcaa ggtgaacttc aagatccgcc acaacatcga ggacggcagc gtgcagctcg | 3600 |
| ccgaccacta ccagcagaac ccccatcg gcgacggccc cgtgctgctg cccgacaacc | 3660 |
| actacctgag cacccagtcc gccctgagca agacccccaa cgagaagcgc gatcacatgg | 3720 |
| tcctgctgga gttcgtgacc gccgccggga tcactctcgg catggacgag ctgtacaagt | 3780 |
| aa | 3782 |

<210> SEQ ID NO 74
<211> LENGTH: 2855
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 74

| | | | | | |
|---|---|---|---|---|---|
| atggactata | aggaccacga | cggagactac | aaggatcatg | atattgatta | caaagacgat | 60 |
| gacgataaga | tggccccaaa | gaagaagcgg | aaggtcggta | tccacggagt | cccagcagcc | 120 |
| gtagatttga | gaactttggg | atattcacag | cagcagcagg | aaaagatcaa | gcccaaagtg | 180 |
| aggtcgacag | tcgcgcagca | tcacgaagcg | ctggtgggtc | atgggtttac | acatgcccac | 240 |
| atcgtagcct | tgtcgcagca | ccctgcagcc | cttggcacgg | tcgccgtcaa | gtaccaggac | 300 |
| atgattgcgg | cgttgccgga | agccacacat | gaggcgatcg | tcggtgtggg | gaaacagtgg | 360 |
| agcggagccc | gagcgcttga | ggccctgttg | acggtcgcgg | gagagctgag | agggcctccc | 420 |
| cttcagctgg | acacgggcca | gttgctgaag | atcgcgaagc | ggggaggagt | cacggcggtc | 480 |
| gaggcggtgc | acgcgtggcg | caatgcgctc | acgggagcac | ccctcaacct | gacagagacc | 540 |
| gcggccgcat | taggcacccc | aggctttaca | ctttatgctt | ccggctcgta | taatgtgtgg | 600 |
| attttgagtt | aggatccgtc | gagattttca | ggagctaagg | aagctaaaat | ggagaaaaaa | 660 |
| atcactggat | ataccaccgt | tgatatatcc | caatggcatc | gtaaagaaca | ttttgaggca | 720 |
| tttcagtcag | ttgctcaatg | tacctataac | cagaccgttc | agctggatat | tacggccttt | 780 |
| ttaaagaccg | taaagaaaaa | taagcacaag | ttttatccgg | cctttattca | cattcttgcc | 840 |
| cgcctgatga | atgctcatcc | ggaattccgt | atggcaatga | agacggtga | gctggtgata | 900 |
| tgggatagtg | ttcacccttg | ttacaccgtt | ttccatgagc | aaactgaaac | gttttcatcg | 960 |
| ctctggagtg | aataccacga | cgatttccgg | cagtttctac | acatatattc | gcaagatgtg | 1020 |
| gcgtgttacg | gtgaaaacct | ggcctatttc | cctaaagggt | ttattgagaa | tatgttttc | 1080 |
| gtctcagcca | atccctgggt | gagtttcacc | agttttgatt | taaacgtggc | caatatggac | 1140 |
| aacttcttcg | cccccgtttt | caccatgggc | aaatattata | cgcaaggcga | caaggtgctg | 1200 |
| atgccgctgg | cgattcaggt | tcatcatgcc | gtttgtgatg | gcttccatgt | cggcagaatg | 1260 |
| cttaatgaat | tacaacagta | ctgcgatgag | tggcagggcg | gggcgtaaag | atctggatcc | 1320 |
| ggcttactaa | aagccagata | acagtatgcg | tatttgcgcg | ctgatttttg | cggtataaga | 1380 |
| atatatactg | atatgtatac | ccgaagtatg | tcaaaaagag | gtatgctatg | aagcagcgta | 1440 |
| ttacagtgac | agttgacagc | gacagctatc | agttgctcaa | ggcatatatg | atgtcaatat | 1500 |
| ctccggtctg | gtaagcacaa | ccatgcagaa | tgaagcccgt | cgtctgcgtg | ccgaacgctg | 1560 |
| gaaagcggaa | aatcaggaag | ggatggctga | ggtcgcccgg | tttattgaaa | tgaacggctc | 1620 |
| ttttgctgac | gagaacaggg | gctggtgaaa | tgcagtttaa | ggtttacacc | tataaaagag | 1680 |
| agagccgtta | tcgtctgttt | gtggatgtac | agagtgatat | tattgacacg | cccgggcgac | 1740 |
| ggatggtgat | ccccctggcc | agtgcacgtc | tgctgtcaga | taaagtctcc | cgtgaacttt | 1800 |
| acccggtggt | gcatatcggg | gatgaaagct | ggcgcatgat | gaccaccgat | atggccagtg | 1860 |
| tgccggtctc | cgttatcggg | gaagaagtgg | ctgatctcag | ccaccgcgaa | aatgacatca | 1920 |
| aaaacgccat | taacctgatg | ttctggggaa | tataaatgtc | aggctccctt | atacacagcc | 1980 |
| agtctgcagg | tcgaccggtct | cgactcacgc | tgagcaggt | agtggctatt | gcatccaaca | 2040 |
| tcggggggcag | acccgcactg | gagtcaatcg | tggcccagct | ttcgaggccg | gaccccgcgc | 2100 |

```
tggccgcact cactaatgat catcttgtag cgctggcctg cctcggcgga cgacccgcct    2160
tggatgcggt gaagaagggg ctcccgcacg cgcctgcatt gattaagcgg accaacagaa    2220
ggattcccga gaggacatca catcgagtgg caggttccca actcgtgaag agtgaacttg    2280
aggagaaaaa gtcggagctg cggcacaaat tgaaatacgt accgcatgaa tacatcgaac    2340
ttatcgaaat tgctaggaac tcgactcaag acagaatcct tgagatgaag gtaatggagt    2400
tctttatgaa ggtttatgga taccgaggga agcatctcgg tggatcacga aaacccgacg    2460
gagcaatcta tacggtgggg agcccgattg attacggagt gatcgtcgac acgaaagcct    2520
acagcggtgg gtacaatctt cccatcgggc aggcagatga gatgcaacgt tatgtcgaag    2580
aaaatcagac caggaacaaa cacatcaatc caaatgagtg gtggaaagtg tatccttcat    2640
cagtgaccga gtttaagttt ttgtttgtct ctgggcattt caaaggcaac tataaggccc    2700
agctcacacg gttgaatcac attacgaact gcaatggtgc ggttttgtcc gtagaggaac    2760
tgctcattgg tggagaaatg atcaaagcgg gaactctgac actggaagaa gtcagacgca    2820
agtttaacaa tggcgagatc aatttccgct cataa                              2855

<210> SEQ ID NO 75
<211> LENGTH: 2855
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
atggactata aggaccacga cggagactac aaggatcatg atattgatta caaagacgat      60
gacgataaga tggccccaaa gaagaagcgg aaggtcggta tccacggagt cccagcagcc     120
gtagatttga gaactttggg atattcacag cagcagcagg aaaagatcaa gcccaaagtg     180
aggtcgacag tcgcgcagca tcacgaagcg ctggtgggtc atgggtttac acatgcccac     240
atcgtagcct tgtcgcagca ccctgcagcc cttggcacgg tcgccgtcaa gtaccaggac     300
atgattgcgc gttgccgga agccacacat gaggcgatcg tcggtgtggg gaaacagtgg      360
agcggagccc gagcgcttga ggccctgttg acggtcgcgg gagagctgag agggcctccc     420
cttcagctgg acacgggcca gttgctgaag atcgcgaagc ggggaggagt cacggcggtc     480
gaggcggtgc acgcgtggcg caatgcgctc acgggagcac ccctcaacct gacagagacc     540
gcggccgcat taggcacccc aggctttaca ctttatgctt ccggctcgta taatgtgtgg     600
attttgagtt aggatccgtc gagatttttca ggagctaagg aagctaaaat ggagaaaaaa     660
atcactggat ataccaccgt tgatatatcc caatggcatc gtaaagaaca ttttgaggca     720
tttcagtcag ttgctcaatg tacctataac cagaccgttc agctggatat acggccttt      780 ttaaagaccg taaagaaaaa taagcacaag ttttatccgg cctttattca cattcttgcc     840
cgcctgatga atgctcatcc ggaattccgt atggcaatga agacggtga gctggtgata      900 tgggatagtg ttcacccttg ttacaccgtt ttccatgagc aaactgaaac gttttcatcg     960
ctctggagtg aataccacga cgatttccgg cagtttctac acatatattc gcaagatgtg    1020
gcgtgttacg gtgaaaacct ggcctatttc cctaaagggt ttattgagaa tatgtttttc    1080
gtctcagcca atccctgggt gagtttcacc agttttgatt taaacgtggc caatatggac    1140
aacttcttcg cccccgtttt caccatgggc aaatattata cgcaaggcga caaggtgctg    1200
atgccgctgg cgattcaggt tcatcatgcc gtttgtgatg gcttccatgt cggcagaatg    1260
```

```
cttaatgaat tacaacagta ctgcgatgag tggcagggcg gggcgtaaag atctggatcc    1320
ggcttactaa aagccagata acagtatgcg tatttgcgcg ctgattttg cggtataaga     1380 atatatactg atatgtatac ccgaagtatg tcaaaaagag gtatgctatg aagcagcgta    1440
ttacagtgac agttgacagc gacagctatc agttgctcaa ggcatatatg atgtcaatat    1500
ctccggtctg gtaagcacaa ccatgcagaa tgaagcccgt cgtctgcgtg ccgaacgctg    1560
gaaagcggaa aatcaggaag ggatggctga ggtcgcccgg tttattgaaa tgaacggctc    1620
ttttgctgac gagaacaggg gctggtgaaa tgcagtttaa ggtttacacc tataaaagag    1680
agagccgtta tcgtctgttt gtggatgtac agagtgatat tattgacacg cccgggcgac    1740
ggatggtgat ccccctggcc agtgcacgtc tgctgtcaga taaagtctcc cgtgaacttt    1800
acccggtggt gcatatcggg gatgaaagct ggcgcatgat gaccaccgat atggccagtg    1860
tgccggtctc cgttatcggg gaagaagtgg ctgatctcag ccaccgcgaa aatgacatca    1920
aaaacgccat taacctgatg ttctggggaa tataaatgtc aggctccctt atacacagcc    1980
agtctgcagg tcgacggtct cgactcacgc ctgagcaggt agtggctatt gcatccaacg    2040 gaggggggcag acccgcactg gagtcaatcg tggcccagct ttcgaggccg accccgcgc    2100 tggccgcact cactaatgat catcttgtag cgctggcctg cctcggcgga cgacccgcct    2160
tggatgcggt gaagaagggg ctcccgcacg cgcctgcatt gattaagcgg accaacagaa    2220
ggattcccga gaggacatca catcgagtgg caggttccca actcgtgaag agtgaacttg    2280
aggagaaaaa gtcggagctg cggcacaaat tgaaatacgt accgcatgaa tacatcgaac    2340
ttatcgaaat tgctaggaac tcgactcaag acagaatcct tgagatgaag gtaatggagt    2400
tctttatgaa ggtttatgga taccgaggga agcatctcgg tggatcacga aaacccgacg    2460
gagcaatcta tacggtgggg agcccgattg attacgagt gatcgtcgac acgaaagcct    2520
acagcggtgg gtacaatctt cccatcgggc aggcagatga gatgcaacgt tatgtcgaag    2580
aaaatcagac caggaacaaa cacatcaatc caaatgagtg gtggaaagtg tatccttcat    2640
cagtgaccga gtttaagttt ttgtttgtct ctgggcattt caaaggcaac tataaggccc    2700
agctcacacg gttgaatcac attacgaact gcaatggtgc ggttttgtcc gtagaggaac    2760
tgctcattgg tggagaaatg atcaaagcgg gaactctgac actggaagaa gtcagacgca    2820
agtttaacaa tggcgagatc aatttccgct cataa                              2855
```

<210> SEQ ID NO 76
<211> LENGTH: 2855
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
atggactata aggaccacga cggagactac aaggatcatg atattgatta caaagacgat      60
gacgataaga tggcccccaaa gaagaagcgg aaggtcggta tccacggagt cccagcagcc    120
gtagatttga gaactttggg atattcacag cagcagcagg aaaagatcaa gcccaaagtg    180
aggtcgacag tcgcgcagca tcacgaagcg ctggtgggtc atgggtttac acatgcccac    240
atcgtagcct tgtcgcagca ccctgcagcc cttggcacgg tcgccgtcaa gtaccaggac    300
atgattgcgg cgttgccgga agccacacat gaggcgatcg tcggtgtggg gaaacagtgg    360
agcggagccc gagcgcttga ggccctgttg acgtcgcgcg gagagctgag agggcctccc    420
cttcagctgg acacgggcca gttgctgaag atcgcgaagc ggggaggagt cacggcggtc    480
```

```
gaggcggtgc acgcgtggcg caatgcgctc acgggagcac ccctcaacct gacagagacc    540
gcggccgcat taggcacccc aggctttaca ctttatgctt ccggctcgta taatgtgtgg    600
attttgagtt aggatccgtc gagattttca ggagctaagg aagctaaaat ggagaaaaaa    660
atcactggat ataccaccgt tgatatatcc caatggcatc gtaaagaaca ttttgaggca    720
tttcagtcag ttgctcaatg tacctataac cagaccgttc agctggatat tacggccttt    780
ttaaagaccg taaagaaaaa taagcacaag ttttatccgg cctttattca cattcttgcc    840
cgcctgatga atgctcatcc ggaattccgt atggcaatga agacggtga gctggtgata    900
tgggatagtg ttcacccttg ttacaccgtt ttccatgagc aaactgaaac gttttcatcg    960
ctctggagtg aataccacga cgatttccgg cagtttctac acatatattc gcaagatgtg   1020
gcgtgttacg gtgaaaacct ggcctatttc cctaaagggt ttattgagaa tatgtttttc   1080
gtctcagcca atccctgggt gagttttcacc agttttgatt taaacgtggc caatatggac   1140
aacttcttcg cccccgtttt caccatgggc aaatattata cgcaaggcga caaggtgctg   1200
atgccgctgg cgattcaggt tcatcatgcc gtttgtgatg cttccatgt cggcagaatg   1260
cttaatgaat tacaacagta ctgcgatgag tggcagggcg gggcgtaaag atctggatcc   1320
ggcttactaa aagccagata acagtatgcg tatttgcgcg ctgattttg cggtataaga   1380
atatatactg atatgtatac ccgaagtatg tcaaaagag gtatgctatg aagcagcgta   1440
ttacagtgac agttgacagc gacagctatc agttgctcaa ggcatatatg atgtcaatat   1500
ctccggtctg gtaagcacaa ccatgcagaa tgaagcccgt cgtctgcgtg ccgaacgctg   1560
gaaagcggaa aatcaggaag ggatggctga ggtcgcccgg tttattgaaa tgaacggctc   1620
ttttgctgac gagaacaggg gctggtgaaa tgcagtttaa ggtttacacc tataaaagag   1680
agagccgtta tcgtctgttt gtggatgtac agagtgatat tattgacacg cccgggcgac   1740
ggatggtgat cccctggcc agtgcacgtc tgctgtcaga taaagtctcc cgtgaactt   1800
acccggtggt gcatatcggg gatgaaagct ggcgcatgat gaccaccgat atggccagtg   1860
tgccggtctc cgttatcggg gaagaagtgg ctgatctcag ccaccgcgaa aatgacatca   1920
aaaacgccat taacctgatg ttctggggaa tataaatgtc aggctcccctt atacacagcc   1980
agtctgcagg tcgacggtct cgactcacgc ctgagcaggt agtggctatt gcatccaaca   2040
acggggggcag acccgcactg gagtcaatcg tggcccagct ttcgaggccg acccccgcgc   2100
tggccgcact cactaatgat catcttgtag cgctggcctg cctcggcgga cgacccgcct   2160
tggatgcggt gaagaagggg ctcccgcacg cgcctgcatt gattaagcgg accaacagaa   2220
ggattcccga gaggacatca catcgagtgg caggttccca actcgtgaag agtgaacttg   2280
aggagaaaaa gtcggagctg cggcacaaat tgaaatacgt accgcatgaa tacatcgaac   2340
ttatcgaaat tgctaggaac tcgactcaag acagaatcct tgagatgaag gtaatggagt   2400
tctttatgaa ggtttatgga taccgaggga agcatctcgg tggatcacga aaacccgacg   2460
gagcaatcta tacggtgggg agcccgattg attacggagt gatcgtcgac acgaaagcct   2520
acagcggtgg gtacaatctt cccatcgggc aggcagatga gatgcaacgt tatgtcgaag   2580
aaaatcagac caggaacaaa cacatcaatc caaatgagtg gtggaaagtg tatccttcat   2640
cagtgaccga gtttaagttt ttgtttgtct ctggcatttt caaaggcaac tataaggccc   2700
agctcacacg gttgaatcac attacgaact gcaatggtgc ggttttgtcc gtagaggaac   2760
tgctcattgg tggagaaatg atcaaagcgg gaactctgac actggaagaa gtcagacgca   2820
agtttaacaa tggcgagatc aatttccgct cataa                              2855
```

<210> SEQ ID NO 77
<211> LENGTH: 2855
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 77

| | | | | | |
|---|---|---|---|---|---|
| atggactata | aggaccacga | cggagactac | aaggatcatg | atattgatta caaagacgat | 60 |
| gacgataaga | tggccccaaa | gaagaagcgg | aaggtcggta | tccacggagt cccagcagcc | 120 |
| gtagatttga | aactttggg | atattcacag | cagcagcagg | aaaagatcaa gcccaaagtg | 180 |
| aggtcgacag | tcgcgcagca | tcacgaagcg | ctggtgggtc | atgggtttac acatgcccac | 240 |
| atcgtagcct | tgtcgcagca | ccctgcagcc | cttggcacgg | tcgccgtcaa gtaccaggac | 300 |
| atgattgcgg | cgttgccgga | agccacacat | gaggcgatcg | tcggtgtggg gaaacagtgg | 360 |
| agcggagccc | gagcgcttga | ggccctgttg | acggtcgcgg | gagagctgag agggcctccc | 420 |
| cttcagctgg | acacgggcca | gttgctgaag | atcgcgaagc | ggggaggagt cacggcggtc | 480 |
| gaggcggtgc | acgcgtggcg | caatgcgctc | acgggagcac | ccctcaacct gacagagacc | 540 |
| gcggccgcat | taggcacccc | aggctttaca | ctttatgctt | ccggctcgta taatgtgtgg | 600 |
| attttgagtt | aggatccgtc | gagattttca | ggagctaagg | aagctaaaat ggagaaaaaa | 660 |
| atcactggat | ataccaccgt | tgatatatcc | caatggcatc | gtaaagaaca ttttgaggca | 720 |
| tttcagtcag | ttgctcaatg | tacctataac | cagaccgttc | agctggatat acggcctttt | 780 |
| ttaaagaccg | taaagaaaaa | taagcacaag | ttttatccgg | cctttattca cattcttgcc | 840 |
| cgcctgatga | atgctcatcc | ggaattccgt | atggcaatga | agacggtga gctggtgata | 900 |
| tgggatagtg | ttcacccttg | ttacaccgtt | ttccatgagc | aaactgaaac gttttcatcg | 960 |
| ctctggagtg | aataccacga | cgatttccgg | cagtttctac | acatatattc gcaagatgtg | 1020 |
| gcgtgttacg | gtgaaaacct | ggcctatttc | cctaaagggt | ttattgagaa tatgtttttc | 1080 |
| gtctcagcca | atccctgggt | gagtttcacc | agttttgatt | taaacgtggc caatatggac | 1140 |
| aacttcttcg | cccccgtttt | caccatgggc | aaatattata | cgcaaggcga caaggtgctg | 1200 |
| atgccgctgg | cgattcaggt | tcatcatgcc | gtttgtgatg | gcttccatgt cggcagaatg | 1260 |
| cttaatgaat | tacaacagta | ctgcgatgag | tggcagggcg | ggcgtaaag atctggatcc | 1320 |
| ggcttactaa | aagccagata | acagtatgcg | tatttgcgcg | ctgatttttg cggtataaga | 1380 |
| atatatactg | atatgtatac | ccgaagtatg | tcaaaaagag | gtatgctatg aagcagcgta | 1440 |
| ttacagtgac | agttgacagc | gacagctatc | agttgctcaa | gcatatatg atgtcaatat | 1500 |
| ctccggtctg | gtaagcacaa | ccatgcagaa | tgaagcccgt | cgtctgcgtg ccgaacgctg | 1560 |
| gaaagcggaa | aatcaggaag | ggatggctga | ggtcgcccgg | tttattgaaa tgaacggctc | 1620 |
| ttttgctgac | gagaacaggg | gctggtgaaa | tgcagtttaa | ggtttacacc tataaaagag | 1680 |
| agagccgtta | tcgtctgttt | gtggatgtac | agagtgatat | tattgacacg cccgggcgac | 1740 |
| ggatggtgat | ccccctggcc | agtgcacgtc | tgctgtcaga | taaagtctcc cgtgaacttt | 1800 |
| acccggtggt | gcatatcggg | gatgaaagct | ggcgcatgat | gaccaccgat atggccagtg | 1860 |
| tgccggtctc | cgttatcggg | gaagaagtgg | ctgatctcag | ccaccgcgaa atgacatca | 1920 |
| aaaacgccat | taacctgatg | ttctggggaa | tataaatgtc | aggctccctt atacacagcc | 1980 |
| agtctgcagg | tcgacggtct | cgactcacgc | ctgagcaggt | agtggctatt gcatcccatg | 2040 |

```
acgggggcag acccgcactg gagtcaatcg tggcccagct ttcgaggccg gaccccgcgc    2100
tggccgcact cactaatgat catcttgtag cgctggcctg cctcggcgga cgacccgcct    2160
tggatgcggt gaagaagggg ctcccgcacg cgcctgcatt gattaagcgg accaacagaa    2220
ggattcccga gaggacatca catcgagtgg caggttccca actcgtgaag agtgaacttg    2280
aggagaaaaa gtcggagctg cggcacaaat tgaaatacgt accgcatgaa tacatcgaac    2340
ttatcgaaat tgctaggaac tcgactcaag acagaatcct tgagatgaag gtaatggagt    2400
tctttatgaa ggtttatgga taccgaggga agcatctcgg tggatcacga aaacccgacg    2460
gagcaatcta tacggtgggg agcccgattg attacggagt gatcgtcgac acgaaagcct    2520
acagcggtgg gtacaatctt cccatcgggc aggcagatga gatgcaacgt tatgtcgaag    2580
aaaatcagac caggaacaaa cacatcaatc caaatgagtg gtggaaagtg tatccttcat    2640
cagtgaccga gtttaagttt ttgtttgtct ctgggcattt caaaggcaac tataaggccc    2700
agctcacacg gttgaatcac attacgaact gcaatggtgc ggttttgtcc gtagaggaac    2760
tgctcattgg tggagaaatg atcaaagcgg gaactctgac actggaagaa gtcagacgca    2820
agtttaacaa tggcgagatc aatttccgct cataa                              2855

<210> SEQ ID NO 78
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tgcgtccgtc tccgaacctt aaaccggcca acataccggt ctcctgaccc cagagcaggt    60
cgtg                                                                64

<210> SEQ ID NO 79
<211> LENGTH: 78
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tgcgtccgtc tccgaacctt aaaccggcca acataccggt ctcgacttac acccgaacaa    60
gtcgtggcaa ttgcgagc                                                 78

<210> SEQ ID NO 80
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tgcgtccgtc tccgaacctt aaaccggcca acataccggt ctcgcggcct caccccagag    60
caggtcg                                                             67

<210> SEQ ID NO 81
<211> LENGTH: 67
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 81
tgcgtccgtc tccgaacctt aaaccggcca acataccggt ctcgtgggct caccccagag    60
caggtcg                                                              67

<210> SEQ ID NO 82
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gctgaccgtc tccgttcagt ctgtctttcc cctttccggt ctctaagtcc gtgcgcttgg    60
cac                                                                  63

<210> SEQ ID NO 83
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gctgaccgtc tccgttcagt ctgtctttcc cctttccggt ctcagccgtg cgcttggcac    60
ag                                                                   62

<210> SEQ ID NO 84
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gctgaccgtc tccgttcagt ctgtctttcc cctttccggt ctctcccatg ggcctgacat    60
aacacaggca gcaacctctg                                                80

<210> SEQ ID NO 85
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gctgaccgtc tccgttcagt ctgtctttcc cctttccggt ctctgagtcc gtgcgcttgg    60
cac                                                                  63

<210> SEQ ID NO 86
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cttgttatgg acgagttgcc cgtctcgtac gccagagcag gtcgtggc                 48

<210> SEQ ID NO 87
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ccaaagattc aaccgtcctg cgtctcgaac cccagagcag gtcgtg                    46

<210> SEQ ID NO 88
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tattcatgct tggacggact cgtctcggtt gaccccagag caggtcgtg                 49

<210> SEQ ID NO 89
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gtcctagtga ggaataccgg cgtctcgcct gaccccagag caggtcgtg                 49

<210> SEQ ID NO 90
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ttccttgata ccgtagctcg cgtctcggac accagagcag gtcgtggc                  48

<210> SEQ ID NO 91
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
tcttatcggt gcttcgttct cgtctcccgt aagtccgtgc gcttggcac                 49

<210> SEQ ID NO 92
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
cgtttctttc cggtcgttag cgtctctggt tagtccgtgc gcttggcac                 49

-continued

```
<210> SEQ ID NO 93
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tgagccttat gatttcccgt cgtctctcaa cccgtgcgct tggcacag                48

<210> SEQ ID NO 94
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
agtctgtctt tcccctttcc cgtctctcag gccgtgcgct tggcacag                48

<210> SEQ ID NO 95
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ccgaagaatc gcagatccta cgtctcttgt cagtccgtgc gcttggcac               49

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
cttaaaccgg ccaacatacc                                               20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
agtctgtctt tcccctttcc                                               20

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ccagttgctg aagatcgcga agc                                           23

<210> SEQ ID NO 99
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
acttacaccc gaacaagtcg                                              20

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
tgccactcga tgtgatgtcc tc                                           22

<210> SEQ ID NO 101
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cccatgggcc tgacataa                                                18

<210> SEQ ID NO 102
<211> LENGTH: 18
<212> TYPE: DNA
<213> ORGANISM: Homo sapiens

<400> SEQUENCE: 102
tgtcccctcc accccaca                                                18

<210> SEQ ID NO 103
<211> LENGTH: 18
<212> TYPE: DNA
<213> ORGANISM: Homo sapiens

<400> SEQUENCE: 103
gtcctaacca ctgtcttt                                                18

<210> SEQ ID NO 104
<211> LENGTH: 14
<212> TYPE: DNA
<213> ORGANISM: Homo sapiens

<400> SEQUENCE: 104
tttattccct gaca                                                    14

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tcaacccctg ccggccca                                                18
```

```
<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tcaacccctg ccaaccca                                                  18

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
taatagacct tagggcta                                                  18

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
taatagacct tagaacta                                                  18

<210> SEQ ID NO 109
<211> LENGTH: 20
<212> TYPE: DNA
<213> ORGANISM: Mus musculus

<400> SEQUENCE: 109
tgcctgccct ccaggctcct                                                20

<210> SEQ ID NO 110
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 111
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Leu Thr Pro Glu Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
```

20                  25                  30

<210> SEQ ID NO 112
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
                20                  25                  30

<210> SEQ ID NO 113
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
                20                  25                  30

<210> SEQ ID NO 114
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
                20                  25                  30

<210> SEQ ID NO 115
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Glu Gln His Gly
                20                  25                  30

<210> SEQ ID NO 116
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Leu Thr Pro Asp Gln Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 117
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 118
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Leu Thr Pro Gln Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 119
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Leu Thr Pro Asp Gln Val Val Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 120
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Leu Thr Pro Asn Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 121
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 121

Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Leu Thr Pro Ala Gln Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 123
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Leu Thr Pro Glu Gln Val Val Ala Ile Ala Ser Gly Gly Lys Gln Ala
1               5                   10                  15

Leu Glu Thr Val Gln Ala Leu Leu Pro Val Leu Cys Gln Ala His Gly
            20                  25                  30

<210> SEQ ID NO 124
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Leu Thr Leu Asp Gln Val Val Ala Ile Ala Ser Gly Ser Lys Gln Ala
1               5                   10                  15

Leu Glu Thr Val Gln Arg Leu Leu Pro Val Leu Cys Gln Asp His Gly
            20                  25                  30

<210> SEQ ID NO 125
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Leu Thr Gln Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

```
<210> SEQ ID NO 126
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Leu Ser Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 127
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Leu Thr Pro Asp Gln Val Val Ala Ile Ala Asn Gly Gly Lys Gln Ala
1               5                   10                  15

Leu Glu Thr Leu Gln Arg Leu Leu Pro Val Leu Cys Gln Asp His Gly
            20                  25                  30

<210> SEQ ID NO 128
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Leu Thr Pro Asp Gln Val Val Ala Ile Ala Ser Gly Gly Lys Gln Ala
1               5                   10                  15

Leu Glu Thr Leu Gln Arg Leu Leu Pro Val Leu Cys Gln Asp His Gly
            20                  25                  30

<210> SEQ ID NO 129
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Arg Gln Ala His Gly
            20                  25                  30

<210> SEQ ID NO 130
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Leu Thr Pro Asp Gln Val Val Ala Ile Ala Ser Gly Gly Asn Gln Ala
```

```
                1               5                  10                  15
Leu Glu Thr Val Gln Arg Leu Leu Pro Val Leu Cys Gln Ala His Gly
            20                  25                  30

<210> SEQ ID NO 131
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Leu Thr Pro Asp Gln Val Val Ala Ile Ala Ser Gly Gly Lys Gln Ala
1               5                   10                  15

Leu Ala Thr Val Gln Arg Leu Leu Pro Val Leu Cys Gln Ala His Gly
            20                  25                  30

<210> SEQ ID NO 132
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Leu Thr Pro Ala Gln Val Val Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 133
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Leu Thr Leu Ala Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 134
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Leu Thr Pro Glu Gln Val Val Ala Ile Ala Cys Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 135
<211> LENGTH: 32
<212> TYPE: PRT
<213> ORGANISM: Artificial Sequence
<220> FEATURE:
<223> OTHER INFORMATION: Description of Artificial Sequence: Synthetic
```

```
                                polypeptide

<400> SEQUENCE: 135

Leu Thr Pro Ala Gln Val Val Ala Ile Ala Ser Gly Gly Lys Gln Ala
1               5                   10                  15

Leu Glu Thr Val Gln Gln Leu Leu Pro Val Leu Cys Glu Gln His Gly
                20                  25                  30

<210> SEQ ID NO 136
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Leu Thr Pro Gln Gln Val Val Ala Ile Ala Ser Gly Gly Arg Pro Ala
1               5                   10                  15

Leu Glu Thr Val Gln Arg Leu Leu Pro Val Leu Cys Gln Ala His Gly
                20                  25                  30

<210> SEQ ID NO 137
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Leu Thr Pro Asp Gln Val Val Ala Ile Ala Ser Gly Ser Lys Gln Ala
1               5                   10                  15

Leu Glu Thr Val Gln Arg Leu Leu Pro Val Leu Cys Gln Asp His Gly
                20                  25                  30

<210> SEQ ID NO 138
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Leu Thr Pro Asn Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
                20                  25                  30

<210> SEQ ID NO 139
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Leu Thr Pro Asp Gln Val Val Ala Ile Ala Ser Gly Gly Lys Gln Ala
1               5                   10                  15

Leu Gly Thr Val Gln Arg Leu Leu Pro Val Leu Cys Gln Asp His Gly
                20                  25                  30

<210> SEQ ID NO 140
```

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Leu Thr Leu Ala Gln Val Val Ala Ile Ala Ser Gly Gly Lys Gln Ala
 1               5                  10                  15

Leu Glu Thr Val Gln Arg Leu Leu Pro Val Leu Cys Gln Asp His Gly
                20                  25                  30

<210> SEQ ID NO 141
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Leu Thr Pro Ala Gln Ala Val Ala Ile Ala Ser Gly Gly Lys Gln Ala
 1               5                  10                  15

Leu Glu Thr Val Gln Arg Leu Leu Pro Val Leu Cys Gln Asp His Gly
                20                  25                  30

<210> SEQ ID NO 142
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Leu Thr Pro Ala Gln Val Val Ala Ile Ala Ser Gly Gly Asn Gln Ala
 1               5                  10                  15

Leu Glu Thr Val Gln Arg Leu Leu Pro Val Leu Cys Gln Asp His Gly
                20                  25                  30

<210> SEQ ID NO 143
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Leu Thr Pro Asp Gln Val Val Ala Ile Ala Ser Gly Gly Lys Gln Ala
 1               5                  10                  15

Leu Glu Thr Leu Gln Arg Leu Leu Pro Val Leu Cys Gln Ala His Gly
                20                  25                  30

<210> SEQ ID NO 144
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Leu Thr Pro Asp Gln Val Val Ala Ile Ala Asn Gly Gly Lys Gln Ala
 1               5                  10                  15
```

Leu Glu Thr Leu Gln Arg Leu Leu Pro Val Leu Cys Gln Ala His Gly
            20                  25                  30

<210> SEQ ID NO 145
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Leu Thr Pro Asp Gln Val Val Thr Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 146
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Leu Thr Pro Ala Gln Val Val Ala Ile Ala Asn Gly Gly Lys Gln Ala
1               5                   10                  15

Leu Glu Thr Val Arg Arg Leu Leu Pro Val Leu Cys Gln Asp His Gly
            20                  25                  30

<210> SEQ ID NO 147
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Leu Thr Pro Asp Gln Val Val Ala Ile Ala Ser Gly Gly Asn Gln Ala
1               5                   10                  15

Leu Glu Thr Val Gln Arg Leu Leu Pro Val Leu Cys Gln Asp His Gly
            20                  25                  30

<210> SEQ ID NO 148
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Thr His Gly
            20                  25                  30

<210> SEQ ID NO 149
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 149

Leu Pro Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 150
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Leu Thr Ser Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 151
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Glu Gln His Gly
            20                  25                  30

<210> SEQ ID NO 152
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Leu Ile Pro Ala Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 153
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Leu Thr Pro Ala Gln Val Val Ala Ile Ala Ser Gly Gly Lys Gln Ala
1               5                   10                  15

Leu Glu Thr Met Gln Arg Leu Leu Pro Val Leu Cys Gln Ala His Gly
            20                  25                  30

<210> SEQ ID NO 154
<211> LENGTH: 32
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 154

Leu Thr Arg Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 155
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Leu Thr Pro Asp Gln Val Val Ala Thr Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 156
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Leu Ile Pro Asp Gln Val Val Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 157
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asn His Gly
            20                  25                  30

<210> SEQ ID NO 158
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Leu Thr Leu Asp Gln Val Val Ala Ile Ala Ser Gly Gly Lys Lys Ala
1               5                   10                  15

Leu Glu Thr Val Gln Arg Leu Leu Pro Val Leu Cys Gln Asp His Gly
            20                  25                  30
```

<210> SEQ ID NO 159
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Leu Thr Pro Asp Gln Leu Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 160
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Gly His Gly
            20                  25                  30

<210> SEQ ID NO 161
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Glu His Gly
            20                  25                  30

<210> SEQ ID NO 162
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Leu Thr Leu Asp Lys Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 163
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

```
Leu Thr Pro Ala Gln Val Val Ala Ile Ala Ser Gly Ser Lys Gln Ala
1               5                   10                  15

Leu Glu Thr Val Gln Arg Leu Leu Pro Val Leu Cys Gln Ala His Gly
            20                  25                  30
```

<210> SEQ ID NO 164
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

```
Leu Thr Pro Asp Lys Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30
```

<210> SEQ ID NO 165
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

```
Leu Thr Gln Asp Gln Val Val Ala Ile Ala Ser Gly Gly Lys Gln Ala
1               5                   10                  15

Leu Glu Thr Val Gln Arg Leu Leu Pro Val Leu Tyr Gln Asp His Gly
            20                  25                  30
```

<210> SEQ ID NO 166
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

```
Leu Thr Pro Ala Gln Val Val Ala Ile Val Ser Gly Gly Lys Gln Ala
1               5                   10                  15

Leu Glu Thr Val Gln Arg Leu Leu Pro Val Leu Cys Gln Ala His Gly
            20                  25                  30
```

<210> SEQ ID NO 167
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

```
Leu Thr Pro Asp Lys Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 168
<211> LENGTH: 32
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 168

Leu Thr Gln Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 169
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Leu Thr Pro Asp Gln Val Met Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 170
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Leu Thr Thr Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 171
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Leu Thr Pro Asp Gln Val Val Ala Ile Ala Ser Gly Ser Lys Gln Ala
1               5                   10                  15

Leu Glu Thr Val Gln Arg Leu Leu Pro Val Leu Cys Gln Ala His Gly
            20                  25                  30

<210> SEQ ID NO 172
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Leu Thr Pro Asp Gln Val Val Ala Ile Ala Asn Gly Gly Lys Gln Ala
1               5                   10                  15

Leu Glu Thr Val Gln Arg Leu Leu Leu Val Leu Cys Gln Ala His Gly
            20                  25                  30

```
<210> SEQ ID NO 173
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Leu Thr Gln Glu Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 174
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Leu Thr Pro Asp Gln Val Val Thr Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 175
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Leu Ser Pro Ala Gln Val Val Ala Ile Ala Ser Gly Gly Lys Gln Ala
1               5                   10                  15

Leu Glu Thr Val Gln Arg Leu Leu Pro Val Leu Cys His Asp His Gly
            20                  25                  30

<210> SEQ ID NO 176
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Leu Thr Pro Asp Gln Val Val Ala Ile Ala Ser Gly Gly Lys Gln Ala
1               5                   10                  15

Leu Glu Met Val Gln Arg Leu Leu Pro Val Leu Cys Gln Ala His Gly
            20                  25                  30

<210> SEQ ID NO 177
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Leu Ile Pro Asp Gln Val Val Ala Ile Ala Ser Gly Gly Lys Gln Ala
1               5                   10                  15
```

Leu Glu Thr Val Gln Arg Leu Leu Pro Val Leu Cys Gln Asp His Gly
            20                  25                  30

<210> SEQ ID NO 178
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Leu Thr Pro Val Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 179
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Leu Thr Pro Asp Gln Val Val Ala Ile Ala Ser Gly Gly Lys Gln Ala
1               5                   10                  15

Leu Lys Thr Val Gln Arg Leu Leu Pro Val Leu Cys Gln Asp His Gly
            20                  25                  30

<210> SEQ ID NO 180
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Leu Thr Pro Asp Gln Val Val Ala Ile Ala Ser Gly Gly Lys Gln Ala
1               5                   10                  15

Leu Glu Thr Met Gln Arg Leu Leu Pro Val Leu Cys Gln Ala His Gly
            20                  25                  30

<210> SEQ ID NO 181
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Leu Thr Pro Ala Gln Val Val Ala Ile Ala Ser Gly Gly Lys Gln Ala
1               5                   10                  15

Leu Glu Thr Val Gln Arg Leu Phe Pro Val Leu Cys Gln Asp His Gly
            20                  25                  30

<210> SEQ ID NO 182
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Leu Thr Pro Ala Gln Val Val Ala Ile Ala Ser Gly Gly Lys Gln Ala
1               5                   10                  15

Leu Glu Thr Val Gln Gln Leu Leu Pro Val Leu Cys Gln Ala His Gly
            20                  25                  30

<210> SEQ ID NO 183
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Leu Thr Pro Ala Gln Val Val Ala Leu Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 184
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Leu Thr Pro Asp Gln Val Val Ala Ile Ala Ser Gly Gly Arg Pro Ala
1               5                   10                  15

Leu Glu Thr Val Gln Arg Leu Leu Pro Val Leu Cys Glu Gln His Gly
            20                  25                  30

<210> SEQ ID NO 185
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Leu Thr Pro Asp Gln Val Val Ala Ile Ala Ser Gly Gly Lys Gln Ala
1               5                   10                  15

Leu Ala Thr Val Gln Arg Leu Leu Pro Val Leu Cys Gln Asp His Gly
            20                  25                  30

<210> SEQ ID NO 186
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Leu Thr Gln Val Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 187
<211> LENGTH: 32

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Leu Thr Pro Asp Gln Val Val Ala Ile Ala Arg Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 188
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Leu Pro Pro Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 189
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Leu Thr Leu Asp Gln Val Val Ala Ile Ala Ser Gly Ser Lys Gln Ala
1               5                   10                  15

Leu Glu Thr Val Gln Arg Leu Leu Pro Val Leu Cys Gln Ala His Gly
            20                  25                  30

<210> SEQ ID NO 190
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Leu Ser Pro Asp Gln Val Val Ala Ile Ala Asn Gly Gly Lys Gln Ala
1               5                   10                  15

Leu Glu Thr Leu Gln Arg Leu Leu Pro Val Leu Cys Gln Thr His Ala
            20                  25                  30

<210> SEQ ID NO 191
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Leu Asn Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
```

```
                    20                  25                  30

<210> SEQ ID NO 192
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Leu Thr Pro Asp Gln Val Met Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 193
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Leu Thr Pro Ala Gln Val Val Ala Ile Ala Ser Gly Gly Lys Gln Ala
1               5                   10                  15

Leu Glu Thr Val Arg Arg Leu Leu Pro Val Leu Cys Gln Ala His Gly
            20                  25                  30

<210> SEQ ID NO 194
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Leu Thr Pro Asp Gln Val Val Ala Ile Ala Ser Gly Gly Lys Gln Thr
1               5                   10                  15

Leu Glu Thr Val Gln Arg Leu Leu Pro Val Leu Cys Gln Asp His Gly
            20                  25                  30

<210> SEQ ID NO 195
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Leu Thr Pro Asp Gln Val Met Thr Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 196
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196
```

Leu Thr Pro Ala Gln Val Val Thr Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 197
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Arg Ala His Gly
            20                  25                  30

<210> SEQ ID NO 198
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Leu Ser Pro Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 199
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Leu Thr Pro Asp Gln Val Val Gly Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 200
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Ala Asn Gly
            20                  25                  30

<210> SEQ ID NO 201
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 201

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Gln Thr His Gly
            20                  25                  30

<210> SEQ ID NO 202
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Leu Thr Pro Asp Gln Val Val Ala Ile Ala Ser Gly Gly Lys Gln Ala
1               5                   10                  15

Leu Glu Met Val Gln Arg Leu Leu Pro Val Leu Cys Gln Asp His Gly
            20                  25                  30

<210> SEQ ID NO 203
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Leu Thr Pro Asp Gln Val Val Ala Ile Ala Ser Gly Gly Lys Gln Ala
1               5                   10                  15

Leu Glu Thr Met Gln Arg Leu Leu Pro Val Leu Cys Gln Asp His Gly
            20                  25                  30

<210> SEQ ID NO 204
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Leu Thr Pro Asp Gln Val Val Ala Ile Ala Asn Gly Gly Lys Gln Ala
1               5                   10                  15

Leu Ala Thr Val Gln Arg Leu Leu Pro Val Leu Cys Gln Asp His Gly
            20                  25                  30

<210> SEQ ID NO 205
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Leu Thr Pro Asp Gln Val Val Thr Ile Ala Ser Gly Gly Lys Gln Ala
1               5                   10                  15

Leu Glu Thr Val Gln Arg Leu Leu Pro Val Leu Cys Gln Ala His Gly
            20                  25                  30
```

```
<210> SEQ ID NO 206
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Leu Thr Pro Asp Gln Val Val Ala Ile Ala Ser Gly Gly Lys Gln Ala
1               5                   10                  15

Leu Glu Thr Val Gln Arg Leu Leu Thr Val Leu Cys Gln Asp His Gly
            20                  25                  30

<210> SEQ ID NO 207
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Met Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 208
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Leu Ala Pro Asp Gln Val Val Ala Val Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 209
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Leu Thr Pro Ala Gln Val Val Ala Ile Ala Ser Gly Gly Lys Gln Ala
1               5                   10                  15

Leu Lys Thr Val Gln Gln Leu Leu Pro Val Leu Cys Glu Gln His Gly
            20                  25                  30

<210> SEQ ID NO 210
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Leu Thr Pro Asp Gln Val Val Ala Ile Ala Arg Gly Gly Lys Gln Ala
```

```
                1               5                  10                  15
Leu Glu Thr Val Gln Arg Leu Leu Pro Val Leu Cys Gln Asp His Gly
            20                  25                  30

<210> SEQ ID NO 211
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Leu Thr Pro Asp Gln Val Val Ala Ile Ala Ser Gly Gly Lys Gln Ala
1               5                   10                  15

Leu Glu Thr Val Gln Gln Leu Leu Pro Val Leu Cys Gln Ala His Gly
            20                  25                  30

<210> SEQ ID NO 212
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Leu Thr Pro Asp Gln Val Leu Ala Ile Ala Ser Gly Gly Lys Gln Ala
1               5                   10                  15

Leu Glu Thr Leu Gln Arg Leu Leu Pro Val Leu Cys Gln Asp His Gly
            20                  25                  30

<210> SEQ ID NO 213
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Leu Thr Pro Glu Gln Val Val Ala Ile Ala Arg Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 214
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Leu Thr Pro Ala Gln Val Val Ala Ile Ala Ser Gly Gly Lys Gln Ala
1               5                   10                  15

Leu Glu Thr Met Gln Arg Leu Leu Pro Val Leu Cys Arg Ala His Gly
            20                  25                  30

<210> SEQ ID NO 215
<211> LENGTH: 32
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 215

Leu Thr Pro Asp Gln Val Val Ala Ile Ala Asn Gly Gly Lys Gln Ala
1               5                   10                  15

Leu Glu Met Val Gln Arg Leu Leu Pro Val Leu Cys Gln Asp His Gly
            20                  25                  30

<210> SEQ ID NO 216
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Leu Thr Thr Asp Gln Val Val Thr Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 217
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Leu Thr Pro Thr Gln Val Met Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 218
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Leu Thr Pro Gln Gln Val Val Ala Ile Ala Ser Gly Gly Lys Gln Ala
1               5                   10                  15

Leu Glu Thr Val Gln Ala Leu Leu Pro Val Leu Cys Gln Ala His Gly
            20                  25                  30

<210> SEQ ID NO 219
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Leu Thr Pro Asp Gln Val Val Ala Ile Ala Ser Gly Gly Lys Gln Ala
1               5                   10                  15

Leu Glu Thr Val Gln Arg Leu Leu Pro Met Leu Cys Gln Asp His Gly
            20                  25                  30

<210> SEQ ID NO 220

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Leu Thr Ser Ala Gln Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 221
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Leu Thr Pro Asp Gln Val Val Ala Ile Ala Ser Gly Gly Lys Gln Ala
1               5                   10                  15

Leu Glu Thr Val Gln Gln Leu Leu Pro Val Leu Cys Gln Asp His Gly
            20                  25                  30

<210> SEQ ID NO 222
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Leu Thr Pro Asp Gln Val Val Ala Ile Ala Asn Gly Gly Lys Gln Ala
1               5                   10                  15

Leu Ala Thr Val Gln Arg Leu Leu Pro Val Leu Cys Gln Ala His Gly
            20                  25                  30

<210> SEQ ID NO 223
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Leu Thr Pro Ala Gln Val Val Ala Ile Ala Ser Gly Gly Lys Gln Ala
1               5                   10                  15

Leu Glu Thr Val Gln Arg Leu Leu Pro Met Leu Cys Gln Ala His Gly
            20                  25                  30

<210> SEQ ID NO 224
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Leu Thr Leu Asp Gln Val Val Ala Ile Ala Ser Gly Gly Lys Gln Ala
1               5                   10                  15
```

```
Leu Glu Thr Val Gln Arg Leu Leu Pro Val Leu Cys Gln Ala Arg Gly
            20                  25                  30

<210> SEQ ID NO 225
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Leu Thr Pro Ala Gln Val Val Ala Ile Ala Ser Gly Gly Lys Gln Ala
1               5                   10                  15

Leu Glu Thr Leu Gln Arg Leu Leu Pro Val Leu Cys Gln Asp His Gly
            20                  25                  30

<210> SEQ ID NO 226
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Leu Thr Pro Asp Gln Val Val Ala Ile Ala Asn Gly Gly Lys Gln Ala
1               5                   10                  15

Leu Glu Thr Val Gln Arg Leu Leu Pro Val Leu Cys Gln Asn His Gly
            20                  25                  30

<210> SEQ ID NO 227
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Leu Thr Pro Asp Gln Val Val Thr Ile Ala Ser Gly Gly Lys Gln Ala
1               5                   10                  15

Leu Glu Met Val Gln Arg Leu Leu Pro Val Leu Cys Gln Asp His Gly
            20                  25                  30

<210> SEQ ID NO 228
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Leu Thr Pro Asp Gln Val Val Ala Ile Ala Ser Gly Gly Lys Gln Ala
1               5                   10                  15

Leu Glu Arg Val Gln Arg Leu Leu Pro Val Leu Cys Glu Gln His Gly
            20                  25                  30

<210> SEQ ID NO 229
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 229

Leu Thr Pro Glu Gln Val Val Ala Ile Ala Cys Gly Gly Lys Gln Ala
1               5                   10                  15

Leu Glu Thr Val Gln Ala Leu Leu Pro Val Leu Arg Gln Ala His Gly
            20                  25                  30

<210> SEQ ID NO 230
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Arg Asp His Gly
            20                  25                  30

<210> SEQ ID NO 231
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Leu Thr Pro Glu Gln Val Val Ala Ile Ala Ser Gly Gly Lys Gln Ala
1               5                   10                  15

Leu Glu Thr Val Gln Arg Leu Leu Pro Met Leu Cys Gln Ala His Gly
            20                  25                  30

<210> SEQ ID NO 232
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Leu Thr Pro Glu Gln Val Val Ala Ile Ala Cys Gly Gly Lys Gln Ala
1               5                   10                  15

Leu Glu Thr Val Gln Arg Leu Leu Pro Val Leu Arg His Ala His Gly
            20                  25                  30

<210> SEQ ID NO 233
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln His His Gly
            20                  25                  30

<210> SEQ ID NO 234
<211> LENGTH: 32
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 234

Leu Ile Pro Asp Gln Val Val Ala Ile Ala Ser Gly Gly Lys Gln Ala
1               5                   10                  15

Leu Glu Thr Val Gln Arg Leu Leu Pro Val Leu Cys Gln His His Gly
            20                  25                  30

<210> SEQ ID NO 235
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Leu Thr Arg Ala Gln Val Val Ala Ile Ala Ser Gly Gly Lys Gln Ala
1               5                   10                  15

Leu Glu Thr Val Gln Arg Leu Leu Pro Val Leu Cys Glu Gln His Gly
            20                  25                  30

<210> SEQ ID NO 236
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Leu Thr Pro Asp Gln Val Val Ala Ile Ala Asn Gly Gly Lys Gln Ala
1               5                   10                  15

Val Gly Thr Val Gln Arg Leu Leu Pro Val Leu Cys Gln Ala His Gly
            20                  25                  30

<210> SEQ ID NO 237
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Glu Gln His Gly
            20                  25                  30

<210> SEQ ID NO 238
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Leu Thr Pro Ala Gln Val Val Ala Ile Ala Ser Gly Gly Lys Gln Ala
1               5                   10                  15

Leu Glu Thr Val Gln Arg Leu Leu Pro Met Leu Cys Gln Asp His Gly
            20                  25                  30
```

<210> SEQ ID NO 239
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Leu Thr Pro Asp Gln Val Val Ala Ile Ala Ser Gly Ser Lys Gln Ala
1               5                   10                  15

Leu Glu Thr Met Gln Arg Leu Leu Pro Val Leu Cys Gln Asp His Gly
            20                  25                  30

<210> SEQ ID NO 240
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Lys Gln His Gly
            20                  25                  30

<210> SEQ ID NO 241
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Gln Thr His Gly
            20                  25                  30

<210> SEQ ID NO 242
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Leu Thr Pro Asp Gln Val Val Ala Ile Ala Ser Gly Gly Lys Gln Ala
1               5                   10                  15

Leu Glu Ala Val Gln Arg Leu Leu Pro Val Leu Cys Gln Asp His Gly
            20                  25                  30

<210> SEQ ID NO 243
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

```
Leu Thr Pro Ala Gln Val Val Thr Ile Ala Ser Gly Gly Lys Gln Ala
1               5                   10                  15

Leu Glu Thr Val Gln Arg Leu Leu Pro Val Leu Cys Glu Gln His Gly
            20                  25                  30
```

<210> SEQ ID NO 244
<211> LENGTH: 32
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 244

```
Leu Thr Pro Ala Gln Val Met Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 245
<211> LENGTH: 32
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 245

```
Leu Thr Arg Glu Gln Val Val Ala Ile Ala Ser Gly Gly Lys Gln Ala
1               5                   10                  15

Leu Glu Thr Val Gln Arg Leu Leu Pro Val Leu Arg Gln Ala His Gly
            20                  25                  30
```

<210> SEQ ID NO 246
<211> LENGTH: 32
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 246

```
Leu Thr Leu Ala Gln Val Val Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30
```

<210> SEQ ID NO 247
<211> LENGTH: 32
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 247

```
Leu Thr Leu Glu Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30
```

<210> SEQ ID NO 248
<211> LENGTH: 32
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 248

Leu Thr Pro Gln Gln Val Val Ala Ile Ala Ser Gly Gly Lys Gln Ala
1               5                   10                  15

Leu Glu Thr Val Gln Arg Leu Leu Pro Val Leu Cys Glu Gln His Gly
            20                  25                  30

<210> SEQ ID NO 249
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Leu Ser Pro Asp Gln Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 250
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Leu Thr Pro Asp Gln Val Val Ala Ile Ala Asn Gly Gly Lys Gln Ala
1               5                   10                  15

Leu Glu Thr Val Gln Arg Leu Leu Pro Val Leu Cys Gln His His Gly
            20                  25                  30

<210> SEQ ID NO 251
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Leu Thr Pro Glu Gln Val Val Ala Ile Ala Ser Gly Gly Lys Gln Ala
1               5                   10                  15

Leu Glu Thr Val Gln Ala Leu Leu Pro Val Leu Arg Gln Ala His Gly
            20                  25                  30

<210> SEQ ID NO 252
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Leu Ser Gln Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

-continued

```
<210> SEQ ID NO 253
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Leu Pro Pro Glu Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 254
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Leu Thr Pro Asp Gln Val Val Ala Ile Ala Ser Gly Gly Lys Gln Ala
1               5                   10                  15

Leu Glu Ala Val Gln Arg Leu Leu Pro Val Leu Cys Gln Ala His Gly
            20                  25                  30

<210> SEQ ID NO 255
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Leu Thr Pro Asp Gln Val Val Ala Ile Ala Asn Gly Gly Lys Gln Ala
1               5                   10                  15

Leu Glu Thr Val Gln Arg Leu Leu Pro Val Leu Cys Gln Glu His Gly
            20                  25                  30

<210> SEQ ID NO 256
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Leu Thr Leu Asp Gln Val Ala Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 257
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Leu Thr Pro Asp Gln Val Val Ala Ile Ala Ser Gly Gly Lys Gln Ala
1               5                   10                  15
```

```
Leu Glu Thr Val Gln Arg Val Leu Pro Val Leu Cys Gln Asp His Gly
            20                  25                  30

<210> SEQ ID NO 258
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Leu Ile Pro Ala Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 259
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Arg Gln Ala His Gly
            20                  25                  30

<210> SEQ ID NO 260
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Leu Thr Pro Ala Gln Val Val Ala Ile Ala Ser Gly Ser Lys Gln Ala
1               5                   10                  15

Leu Glu Thr Val Gln Arg Leu Leu Pro Val Leu Cys Gln Thr His Gly
            20                  25                  30

<210> SEQ ID NO 261
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Leu Thr Pro Gln Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 262
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 262

Leu Thr Pro Asp Gln Val Val Ala Ile Ala Asn Gly Gly Lys Gln Ala
1               5                   10                  15

Val Glu Thr Val Gln Arg Leu Leu Pro Val Leu Cys Gln Ala His Gly
            20                  25                  30

<210> SEQ ID NO 263
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Leu Ser Pro Asp Gln Val Val Thr Ile Ala Ser Gly Gly Lys Gln Ala
1               5                   10                  15

Leu Glu Thr Leu Gln Arg Leu Leu Pro Val Leu Cys Gln Asp His Gly
            20                  25                  30

<210> SEQ ID NO 264
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Leu Thr Pro Val Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 265
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Leu Thr Leu Asp Gln Val Val Ala Ile Ala Ser Gly Ser Lys Gln Ala
1               5                   10                  15

Leu Glu Thr Val Gln Arg Leu Leu Pro Val Leu Cys Gln Thr His Gly
            20                  25                  30

<210> SEQ ID NO 266
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Leu Thr Pro Ala Gln Val Val Ala Ile Ala Cys Gly Gly Lys Gln Ala
1               5                   10                  15

Leu Glu Thr Val Arg Arg Leu Leu Pro Val Leu Cys Gln Ala His Gly
            20                  25                  30

<210> SEQ ID NO 267
<211> LENGTH: 32
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Leu Thr Pro Ala Gln Val Val Ala Ile Ala Ser Gly Ser Lys Gln Ala
1               5                   10                  15

Leu Glu Thr Val Gln Arg Leu Phe Pro Val Leu Cys Gln Ala His Gly
            20                  25                  30

<210> SEQ ID NO 268
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Leu Pro Pro Ala Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 269
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Phe Gln Glu His Gly
            20                  25                  30

<210> SEQ ID NO 270
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Leu Thr Pro Ala Lys Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 271
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Leu Thr Pro Val Gln Val Val Ala Ile Ala Ser Gly Gly Lys Gln Ala
1               5                   10                  15

Leu Ala Thr Val Gln Arg Leu Leu Pro Val Leu Cys Gln Asp His Gly
```

20                  25                  30

<210> SEQ ID NO 272
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Leu Thr Pro Asp Gln Val Val Ala Ile Ala Ser Gly Gly Lys Gln Ala
1               5                   10                  15

Leu Glu Thr Val Gln Arg Leu Leu Pro Gly Leu Cys Gln Asp His Gly
            20                  25                  30

<210> SEQ ID NO 273
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Leu Thr Leu Ala Gln Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 274
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Leu Thr Pro Ala Gln Val Val Ala Ile Ala Ser Gly Gly Lys Gln Ala
1               5                   10                  15

Leu Glu Thr Val Gln Arg Leu Leu Thr Val Leu Cys Gln Asp His Gly
            20                  25                  30

<210> SEQ ID NO 275
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Leu Pro Pro Ala Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 276
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

```
Leu Thr Pro Ala Gln Ala Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30
```

<210> SEQ ID NO 277
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

```
Leu Thr Pro Ala Gln Val Val Ala Ile Val Ser Gly Gly Lys Gln Ala
1               5                   10                  15

Leu Glu Thr Val Gln Arg Leu Leu Pro Val Leu Cys Gln Thr His Gly
            20                  25                  30
```

<210> SEQ ID NO 278
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

```
Leu Thr Pro Asp Gln Val Val Ala Val Ala Gly Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 279
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

```
Leu Thr Pro Asp Gln Val Val Ala Ile Ala Ser Gly Gly Lys Gln Ala
1               5                   10                  15

Leu Gly Thr Val Gln Arg Leu Leu Pro Val Leu Cys Gln Ala His Gly
            20                  25                  30
```

<210> SEQ ID NO 280
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

```
Leu Pro Pro Ala Gln Val Val Ala Ile Ala Ser Gly Gly Lys Gln Ala
1               5                   10                  15

Leu Glu Thr Val Gln Arg Leu Leu Pro Val Leu Cys Glu Ala His Gly
            20                  25                  30
```

<210> SEQ ID NO 281
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 281

Leu Thr Thr Asp Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
                20                  25                  30

<210> SEQ ID NO 282
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Leu Thr Pro Asp Gln Val Val Ala Ile Ala Asn Gly Gly Lys Gln Ala
1               5                   10                  15

Leu Glu Thr Val Gln Arg Leu Val Pro Val Leu Cys Gln Asp His Gly
                20                  25                  30

<210> SEQ ID NO 283
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Cys Gln Thr His Ala
                20                  25                  30

<210> SEQ ID NO 284
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Leu Thr Leu Ala Gln Val Val Ala Ile Ala Ser Gly Gly Lys Gln Ala
1               5                   10                  15

Leu Glu Thr Val Gln Arg Leu Leu Pro Val Leu Cys Gln Thr His Gly
                20                  25                  30

<210> SEQ ID NO 285
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Leu Thr Pro Asn Gln Leu Val Ala Ile Ala Asn Gly Gly Lys Gln Ala
1               5                   10                  15

Leu Glu Thr Val Gln Arg Leu Leu Pro Val Leu Cys Gln Asp His Gly
                20                  25                  30
```

```
<210> SEQ ID NO 286
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Leu Ser Pro Ala Gln Val Val Ala Ile Ala Ser Gly Ser Lys Gln Ala
1               5                   10                  15

Leu Glu Thr Val Gln Arg Leu Leu Pro Val Leu Cys Gln Asp His Gly
            20                  25                  30

<210> SEQ ID NO 287
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Leu Thr Pro Asp Gln Val Val Ala Ile Ala Ser Gly Gly Lys Gln Ala
1               5                   10                  15

Leu Glu Thr Val Gln Arg Val Leu Pro Val Leu Cys Gln Ala His Gly
            20                  25                  30

<210> SEQ ID NO 288
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Leu Thr Pro Asp Gln Val Met Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 289
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Leu Thr Pro Glu Gln Val Val Ala Ile Ala Ser Gly Gly Arg Gln Ala
1               5                   10                  15

Leu Glu Thr Val Gln Arg Leu Leu Pro Val Leu Cys Gln Ala His Gly
            20                  25                  30

<210> SEQ ID NO 290
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Leu Thr Pro Ala Gln Val Val Ala Ile Ala Ser Gly Gly Lys Gln Ala
```

```
1               5                   10                  15
Leu Glu Thr Val Gln Trp Leu Leu Pro Val Leu Cys Gln Ala His Gly
            20                  25                  30

<210> SEQ ID NO 291
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Leu Thr Pro Asp Lys Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 292
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Leu Thr Pro Ala Gln Val Met Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 293
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Leu Thr Gln Asp Gln Val Val Ala Ile Ala Ser Gly Gly Lys Gln Ala
1               5                   10                  15

Leu Glu Thr Val Gln Arg Leu Leu Pro Val Leu Cys Gln Ala Asn Gly
            20                  25                  30

<210> SEQ ID NO 294
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Leu Thr Pro Ala Gln Val Val Ala Ile Ala Ser Gly Gly Lys Pro Ala
1               5                   10                  15

Leu Glu Thr Val Gln Arg Leu Leu Pro Val Leu Cys Glu Gln His Gly
            20                  25                  30

<210> SEQ ID NO 295
<211> LENGTH: 32
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 295

Leu Thr Pro Asp Gln Val Val Ala Ile Ala Ser Ser Gly Lys Gln Ala
1               5                   10                  15

Leu Glu Thr Met Gln Arg Leu Leu Pro Val Leu Cys Gln Asp His Gly
            20                  25                  30

<210> SEQ ID NO 296
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Leu Thr Pro Asp Gln Val Val Ala Ile Ala Ser Gly Ser Lys Gln Ala
1               5                   10                  15

Leu Glu Thr Val Gln Arg Leu Leu Pro Val Leu Arg Gln Asp His Gly
            20                  25                  30

<210> SEQ ID NO 297
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Leu Thr Pro Tyr Gln Val Val Ala Ile Ala Ser Gly Ser Lys Gln Ala
1               5                   10                  15

Leu Glu Thr Val Gln Arg Leu Leu Pro Val Leu Cys Gln Asp His Gly
            20                  25                  30

<210> SEQ ID NO 298
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Leu Thr Pro Tyr Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 299
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Leu Thr Leu Asp Gln Val Val Ala Ile Ala Ser Gly Gly Lys Gln Ala
1               5                   10                  15

Leu Glu Thr Val Gln Arg Leu Leu Pro Val Leu Cys Gln Glu His Gly
            20                  25                  30

<210> SEQ ID NO 300

```
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Leu Thr Leu Glu Gln Val Val Ala Ile Ala Ser Gly Gly Lys Gln Ala
1               5                   10                  15

Leu Glu Thr Val Gln Arg Leu Leu Leu Val Leu Cys Gln Ala His Gly
            20                  25                  30

<210> SEQ ID NO 301
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Leu Thr Pro Asp Gln Val Val Ala Ile Ala Ser Gly Gly Lys Gln Ala
1               5                   10                  15

Leu Glu Thr Val Arg Arg Leu Leu Gln Val Leu Cys Gln Asp His Gly
            20                  25                  30

<210> SEQ ID NO 302
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Leu Thr Pro Asp Gln Val Val Ala Ile Ala Ser Gly Gly Lys Gln Ala
1               5                   10                  15

Leu Glu Thr Val Gln Arg Leu Leu Pro Val Leu Arg Gln Asp His Gly
            20                  25                  30

<210> SEQ ID NO 303
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Leu Thr Pro Asp Gln Val Val Ser Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 304
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Leu Thr Pro Asp Gln Val Val Ala Ile Ala Asn Gly Gly Lys Gln Ala
1               5                   10                  15
```

```
Leu Glu Thr Val Gln Arg Leu Leu Pro Val Leu Cys Gln Thr His Gly
            20                  25                  30

<210> SEQ ID NO 305
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Leu Thr Pro Asp Gln Val Val Ala Ile Ala Ser Gly Gly Lys Gln Ala
1               5                   10                  15

Leu Glu Thr Val Lys Arg Leu Leu Pro Val Leu Cys Gln Ala His Gly
            20                  25                  30

<210> SEQ ID NO 306
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Leu Thr Thr Asp Gln Val Val Ala Ile Ala Asn Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 307
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Leu Ile Pro Gln Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 308
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Leu Thr Leu Thr Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 309
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 309

Leu Thr Pro Thr Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 310
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Leu Thr Pro Thr Gln Val Met Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 311
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Leu Thr Pro Asp Gln Val Val Ala Val Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 312
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Leu Thr Pro Ala Gln Val Ala Ile Ala Ser Gly Ser Lys Gln Ala
1               5                   10                  15

Leu Glu Thr Val Gln Arg Leu Leu Pro Val Leu Cys Gln Asp His Gly
            20                  25                  30

<210> SEQ ID NO 313
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Leu Thr Pro Gly Gln Val Val Ala Ile Ala Ser Gly Gly Lys Arg Ala
1               5                   10                  15

Leu Glu Thr Val Gln Arg Leu Leu Pro Val Leu Cys Gln Asp His Gly
            20                  25                  30

<210> SEQ ID NO 314
<211> LENGTH: 32
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 314

Leu Thr Pro Asp Gln Val Val Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 315
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Leu Pro Pro Asp Gln Val Val Ala Ile Ala Ser Gly Ser Lys Gln Ala
1               5                   10                  15

Leu Glu Thr Val Gln Arg Leu Leu Pro Val Leu Cys Gln Asp His Gly
            20                  25                  30

<210> SEQ ID NO 316
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Leu Thr Pro Asp Gln Val Val Thr Ile Ala Asn Gly Ser Lys Gln Ala
1               5                   10                  15

Leu Glu Thr Val Gln Arg Leu Leu Pro Val Leu Cys Gln Ala His Gly
            20                  25                  30

<210> SEQ ID NO 317
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Leu Thr Pro Ala Gln Val Val Ala Ile Ala Ser Gly Gly Lys Gln Ala
1               5                   10                  15

Leu Glu Thr Val Gln Arg Leu Leu Gln Val Leu Cys Gln Asp His Gly
            20                  25                  30

<210> SEQ ID NO 318
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Leu Thr Pro Asp His Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30
```

<210> SEQ ID NO 319
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Leu Thr Pro Asp Gln Val Val Ala Ile Ala Ser Gly Gly Lys Gln Ala
1               5                   10                  15

Leu Glu Thr Val Gln Arg Leu Leu Gln Val Leu Cys Gln Asp His Gly
            20                  25                  30

<210> SEQ ID NO 320
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Leu Thr Pro Asp Gln Val Val Ala Ile Ala Ser Gly Gly Arg Gln Ala
1               5                   10                  15

Leu Glu Thr Val Gln Arg Leu Leu Pro Val Leu Cys Glu Gln His Gly
            20                  25                  30

<210> SEQ ID NO 321
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Leu His Pro Gly Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 322
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Leu Thr Leu Asp Gln Val Val Ser Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 323
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

```
Leu Thr Pro Asp Gln Val Val Ala Ile Ala Ser Gly Gly Lys Gln Ala
1               5                   10                  15

Leu Glu Thr Val Gln Arg Leu Leu Pro Ala Leu Cys Gln Asp His Gly
            20                  25                  30

<210> SEQ ID NO 324
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Leu Thr Pro Asp Gln Val Val Ala Ile Ala Ser Gly Gly Lys Pro Ala
1               5                   10                  15

Leu Glu Thr Val Gln Arg Leu Leu Pro Val Leu Cys Glu Gln His Gly
            20                  25                  30

<210> SEQ ID NO 325
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Leu Thr Pro Ala Gln Val Val Ala Ile Ala Ser Gly Gly Lys Gln Ala
1               5                   10                  15

Leu Lys Thr Val Gln Arg Leu Leu Pro Val Leu Cys Gln Ala His Gly
            20                  25                  30

<210> SEQ ID NO 326
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Leu Thr Pro Asp Gln Val Val Ala Ile Ala Ser Gly Gly Lys Arg Ala
1               5                   10                  15

Leu Glu Thr Val Gln Arg Leu Leu Pro Val Leu Cys Gln Ala His Gly
            20                  25                  30

<210> SEQ ID NO 327
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Leu Asn Pro Asp Gln Val Val Ala Ile Ala Ser Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 328
<211> LENGTH: 32
<212> TYPE: PRT
<213> ORGANISM: Artificial Sequence
<220> FEATURE:
```

-continued

<223> OTHER INFORMATION: Description of Artificial Sequence: Synthetic
      polypeptide

<400> SEQUENCE: 328

Leu Thr Pro Asp Gln Val Val Ala Ile Ala Ser Gly Gly Lys Gln Ala
1               5                   10                  15

Leu Glu Thr Val Lys Arg Leu Leu Pro Val Leu Cys Gln Asp His Gly
            20                  25                  30

<210> SEQ ID NO 329
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Leu Thr Leu Asp Gln Val Val Ala Ile Ala Asn Gly Gly Lys Gln Ala
1               5                   10                  15

Leu Glu Thr Val Gln Arg Leu Leu Pro Val Leu Cys Gln Ala His Gly
            20                  25                  30

<210> SEQ ID NO 330
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Arg Asp His Gly
            20                  25                  30

<210> SEQ ID NO 331
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Leu Thr Pro Ala Gln Val Leu Ala Ile Ala Ser Gly Gly Lys Gln Ala
1               5                   10                  15

Leu Glu Thr Val Gln Arg Leu Leu Thr Val Leu Cys Gln Asp His Gly
            20                  25                  30

<210> SEQ ID NO 332
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Leu Thr Pro Ala Gln Val Val Ala Ile Ala Ser Gly Gly Lys Gln Ala
1               5                   10                  15

Leu Glu Thr Met Gln Arg Leu Leu Pro Val Leu Cys Gln Asp His Gly
            20                  25                  30

```
<210> SEQ ID NO 333
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Leu Thr Pro Asp Gln Val Val Ala Ile Ala Ser Gly Gly Lys Gln Ala
1               5                   10                  15

Leu Glu Thr Val Gln Arg Leu Leu Pro Gly Leu Cys Gln Ala His Gly
            20                  25                  30

<210> SEQ ID NO 334
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Leu Thr Arg Glu Gln Val Val Ala Ile Ala Ser Gly Gly Lys Gln Ala
1               5                   10                  15

Leu Glu Thr Val Gln Ala Leu Leu Pro Val Leu Arg Gln Ala His Gly
            20                  25                  30

<210> SEQ ID NO 335
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Leu Thr Pro Ala Gln Val Val Ala Ile Ala Ser Gly Gly Lys Gln Ala
1               5                   10                  15

Leu Glu Thr Val Gln Arg Leu Leu Pro Val Leu Cys Gln Val His Gly
            20                  25                  30

<210> SEQ ID NO 336
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Leu Thr Pro Asn Gln Val Val Ala Ile Ala Ser Gly Gly Lys Gln Ala
1               5                   10                  15

Leu Glu Thr Val Gln Arg Leu Leu Leu Val Leu Cys Gln Asp His Gly
            20                  25                  30

<210> SEQ ID NO 337
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Leu Thr Pro Asp Gln Val Met Ala Ile Ala Ser Gly Gly Lys Gln Ala
1               5                   10                  15
```

```
Leu Glu Thr Val Gln Arg Leu Leu Pro Val Leu Cys Gln Ala His Gly
            20                  25                  30

<210> SEQ ID NO 338
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Leu Thr Arg Glu Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 339
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Leu Ser Thr Ala Gln Val Val Ala Ile Ala Ser Gly Gly Lys Gln Ala
1               5                   10                  15

Leu Glu Gly Ile Gly Glu Gln Leu Leu Lys Leu Arg Thr Ala Pro Tyr
            20                  25                  30

Gly

<210> SEQ ID NO 340
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Leu Ser Thr Ala Gln Val Val Ala Val Ala Ser Gly Gly Lys Pro Ala
1               5                   10                  15

Leu Glu Ala Val Arg Ala Gln Leu Leu Ala Leu Arg Ala Ala Pro Tyr
            20                  25                  30

Gly

<210> SEQ ID NO 341
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Leu Thr Gln Val Gln Val Val Ala Ile Ala Ser Gly Gly Lys Gln Ala
1               5                   10                  15

Leu Glu Thr Val Gln Arg Leu Leu Pro Val Leu Cys Gln Asp His Gly
            20                  25                  30

<210> SEQ ID NO 342
<211> LENGTH: 32
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 342

Leu Thr Pro Asp Gln Val Val Ala Ile Ala Ser Asn Gly Lys Gln Ala
1               5                   10                  15

Leu Glu Thr Val Gln Arg Leu Leu Pro Val Leu Cys Gln Asp His Gly
            20                  25                  30

<210> SEQ ID NO 343
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Leu Thr Pro Asp Gln Val Val Ala Ile Ala Ser Gly Gly Lys Arg Ala
1               5                   10                  15

Leu Glu Thr Val Gln Arg Leu Leu Pro Val Leu Cys Gln Asp His Gly
            20                  25                  30

<210> SEQ ID NO 344
<211> LENGTH: 97
<212> TYPE: PRT
<213> ORGANISM: Homo sapiens

<400> SEQUENCE: 344

Met Asp Ala Lys Ser Leu Thr Ala Trp Ser Arg Thr Leu Val Thr Phe
1               5                   10                  15

Lys Asp Val Phe Val Asp Phe Thr Arg Glu Glu Trp Lys Leu Leu Asp
            20                  25                  30

Thr Ala Gln Gln Ile Val Tyr Arg Asn Val Met Leu Glu Asn Tyr Lys
        35                  40                  45

Asn Leu Val Ser Leu Gly Tyr Gln Leu Thr Lys Pro Asp Val Ile Leu
    50                  55                  60

Arg Leu Glu Lys Gly Glu Glu Pro Trp Leu Val Glu Arg Glu Ile His
65                  70                  75                  80

Gln Glu Thr His Pro Asp Ser Glu Thr Ala Phe Glu Ile Lys Ser Ser
                85                  90                  95

Val

<210> SEQ ID NO 345
<211> LENGTH: 75
<212> TYPE: PRT
<213> ORGANISM: Homo sapiens

<400> SEQUENCE: 345

Met Asp Ala Lys Ser Leu Thr Ala Trp Ser Arg Thr Leu Val Thr Phe
1               5                   10                  15

Lys Asp Val Phe Val Asp Phe Thr Arg Glu Glu Trp Lys Leu Leu Asp
            20                  25                  30

Thr Ala Gln Gln Ile Val Tyr Arg Asn Val Met Leu Glu Asn Tyr Lys
        35                  40                  45

Asn Leu Val Ser Leu Gly Tyr Gln Leu Thr Lys Pro Asp Val Ile Leu
    50                  55                  60

Arg Leu Glu Lys Gly Glu Glu Pro Trp Leu Val
65                  70                  75
```

<210> SEQ ID NO 346
<211> LENGTH: 65
<212> TYPE: PRT
<213> ORGANISM: Homo sapiens

<400> SEQUENCE: 346

Arg Thr Leu Val Thr Phe Lys Asp Val Phe Val Asp Phe Thr Arg Glu
1               5                   10                  15

Glu Trp Lys Leu Leu Asp Thr Ala Gln Gln Ile Val Tyr Arg Asn Val
            20                  25                  30

Met Leu Glu Asn Tyr Lys Asn Leu Val Ser Leu Gly Tyr Gln Leu Thr
        35                  40                  45

Lys Pro Asp Val Ile Leu Arg Leu Glu Lys Gly Glu Glu Pro Trp Leu
    50                  55                  60

Val
65

<210> SEQ ID NO 347
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Met Leu Ile Gly Tyr Ala Arg Val Ser Thr Asn Gly Gln Ser Thr Asp
1               5                   10                  15

Leu Gln Arg Asp Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Glu Arg Leu Gln Gly Asp Thr Leu Val Val Trp Lys Leu Asp
    50                  55                  60

Arg Leu Gly Arg Ser Val Lys His Leu Ile Ser Leu Val Gly Glu Leu
65                  70                  75                  80

Arg Glu Arg Gly Ile Asn Phe Arg Ser Leu Thr Asp Cys Val Asn Thr
            85                  90                  95

Ser Ser Pro Met Gly Arg Phe Phe Phe His Val Met Gly Ala Leu Ala
        100                 105                 110

Glu Val Glu Arg Glu Leu Ile Val Glu Arg Thr Met Ala Gly Leu Ala
    115                 120                 125

Ala Ala Arg Ser Lys Gly Arg Ile Gly Gly Arg Pro Pro Lys Ser Gly
130                 135                 140

Ser Gly Glu Met Pro Tyr
145                 150

<210> SEQ ID NO 348
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Met Leu Ile Gly Tyr Ala Arg Val Ser Thr Asn Gly Gln Ser Thr Asp
1               5                   10                  15

Leu Gln Arg Asp Ala Leu Val Cys Ala Gly Cys Glu Gln Ile Phe Glu

```
            20                  25                  30
Asp Lys Leu Ser Gly Thr Arg Thr Asp Arg Pro Gly Leu Lys Arg Ala
         35                  40                  45

Leu Glu Arg Leu Gln Glu Gly Asp Thr Leu Val Val Trp Lys Leu Asp
 50                  55                  60

Arg Leu Gly Arg Ser Val Lys His Leu Ile Ser Leu Val Gly Glu Leu
 65                  70                  75                  80

Arg Glu Arg Gly Ile Asn Phe Arg Ser Leu Thr Asp Cys Val Asn Thr
                 85                  90                  95

Ser Ser Pro Met Gly Arg Phe Phe Phe His Val Met Gly Ala Leu Ala
                100                 105                 110

Glu Val Glu Arg Glu Leu Ile Val Glu Arg Thr Met Ala Gly Leu Ala
            115                 120                 125

Ala Ala Arg Ser Lys Gly Gly Ser Gly Gly Ser Gly Gly Ser Gly Gly
        130                 135                 140

Ser Gly Thr Ser Ala Arg Ala Leu Glu Ala Leu Leu Thr Val Ala Gly
145                 150                 155                 160

Glu Leu Arg Gly Pro Pro Leu Gln Leu Asp Thr Gly Gln Leu Leu Lys
                165                 170                 175

Ile Ala Lys Arg Gly Gly Val Thr Ala Val Glu Ala Val His Ala Trp
                180                 185                 190

Arg Asn Ala Leu Thr Gly Ala Pro Leu Asn Leu Thr Pro Glu Gln Val
            195                 200                 205

Val Ala Ile Ala Ser Asn Ile Gly Gly Lys Gln Ala Leu Glu Thr Val
        210                 215                 220

Gln Arg Leu Leu Pro Val Leu Cys Gln Ala His Gly Leu Thr Pro Glu
225                 230                 235                 240

Gln Val Val Ala Ile Ala Ser His Asp Gly Gly Lys Gln Ala Leu Glu
                245                 250                 255

Thr Val Gln Arg Leu Leu Pro Val Leu Cys Gln Ala His Gly Leu Thr
                260                 265                 270

Pro Glu Gln Val Val Ala Ile Ala Ser Asn Asn Gly Gly Lys Gln Ala
            275                 280                 285

Leu Glu Thr Val Gln Arg Leu Leu Pro Val Leu Cys Gln Ala His Gly
        290                 295                 300

Leu Thr Pro Glu Gln Val Val Ala Ile Ala Ser Asn Ile Gly Gly Lys
305                 310                 315                 320

Gln Ala Leu Glu Thr Val Gln Arg Leu Leu Pro Val Leu Cys Gln Ala
                325                 330                 335

His Gly Leu Thr Pro Glu Gln Val Val Ala Ile Ala Ser His Asp Gly
                340                 345                 350

Gly Lys Gln Ala Leu Glu Thr Val Gln Arg Leu Leu Pro Val Leu Cys
            355                 360                 365

Gln Ala His Gly Leu Thr Pro Glu Gln Val Val Ala Ile Ala Ser Asn
        370                 375                 380

Gly Gly Gly Lys Gln Ala Leu Glu Thr Val Gln Arg Leu Leu Pro Val
385                 390                 395                 400

Leu Cys Gln Ala His Gly Leu Thr Pro Glu Gln Val Val Ala Ile Ala
                405                 410                 415

Ser His Asp Gly Gly Lys Gln Ala Leu Glu Thr Val Gln Arg Leu Leu
                420                 425                 430

Pro Val Leu Cys Gln Ala His Gly Leu Thr Pro Glu Gln Val Val Ala
            435                 440                 445
```

```
Ile Ala Ser Asn Ile Gly Gly Lys Gln Ala Leu Glu Thr Val Gln Arg
            450                 455                 460

Leu Leu Pro Val Leu Cys Gln Ala His Gly Leu Thr Pro Glu Gln Val
465                 470                 475                 480

Val Ala Ile Ala Ser His Asp Gly Gly Lys Gln Ala Leu Glu Thr Val
                485                 490                 495

Gln Arg Leu Leu Pro Val Leu Cys Gln Ala His Gly Leu Thr Pro Glu
            500                 505                 510

Gln Val Val Ala Ile Ala Ser Asn Gly Gly Lys Gln Ala Leu Glu
        515                 520                 525

Thr Val Gln Arg Leu Leu Pro Val Leu Cys Gln Ala His Gly Leu Thr
530                 535                 540

Pro Glu Gln Val Val Ala Ile Ala Ser Asn Ile Gly Gly Lys Gln Ala
545                 550                 555                 560

Leu Glu Thr Val Gln Arg Leu Leu Pro Val Leu Cys Gln Ala His Gly
                565                 570                 575

Leu Thr Pro Glu Gln Val Val Ala Ile Ala Ser Asn Gly Gly Lys
            580                 585                 590

Gln Ala Leu Glu Thr Val Gln Arg Leu Leu Pro Val Leu Cys Gln Ala
        595                 600                 605

His Gly Leu Thr Pro Glu Gln Val Val Ala Ile Ala Ser Asn Ile Gly
            610                 615                 620

Gly Arg Pro Ala Leu Glu Ser Ile Val Ala Gln Leu Ser Arg Pro Asp
625                 630                 635                 640

Pro Ala Leu Ala Ala Leu Thr Asn Asp His Leu Val Ala Leu Ala Cys
                645                 650                 655

Leu Gly Gly Arg Pro Ala Leu Asp Ala Val Lys Lys Gly Leu Pro His
            660                 665                 670

Ala Pro Ala Leu Ile Lys Arg Thr Asn Arg Arg Ile Pro Glu Arg Thr
        675                 680                 685

Ser His Arg Val Ala Asp Lys Ala Glu Leu Ile Pro Glu Pro Pro Lys
    690                 695                 700

Lys Lys Arg Lys Val Glu Leu Gly Thr Ala
705                 710

<210> SEQ ID NO 349
<211> LENGTH: 777
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Met Leu Ile Gly Tyr Ala Arg Val Ser Thr Asn Gly Gln Ser Thr Asp
1               5                   10                  15

Leu Gln Arg Asp Ala Leu Val Cys Ala Gly Cys Glu Gln Ile Phe Glu
                20                  25                  30

Asp Lys Leu Ser Gly Thr Arg Thr Asp Arg Pro Gly Leu Lys Arg Ala
            35                  40                  45

Leu Glu Arg Leu Gln Glu Gly Asp Thr Leu Val Val Trp Lys Leu Asp
        50                  55                  60

Arg Leu Gly Arg Ser Val Lys His Leu Ile Ser Leu Val Gly Glu Leu
65                  70                  75                  80

Arg Glu Arg Gly Ile Asn Phe Arg Ser Leu Thr Asp Cys Val Asn Thr
                85                  90                  95
```

```
Ser Ser Pro Met Gly Arg Phe Phe His Val Met Gly Ala Leu Ala
            100                 105                 110

Glu Val Glu Arg Glu Leu Ile Val Glu Arg Thr Met Ala Gly Leu Ala
        115                 120                 125

Ala Ala Arg Ser Lys Gly Gly Ser Gly Gly Ser Gly Gly Ser Gly Gly
130                 135                 140

Ser Gly Thr Ser Val Arg Ser Thr Val Ala Gln His His Glu Ala Leu
145                 150                 155                 160

Val Gly His Gly Phe Thr His Ala His Ile Val Ala Leu Ser Gln His
                165                 170                 175

Pro Ala Ala Leu Gly Thr Val Ala Val Lys Tyr Gln Asp Met Ile Ala
            180                 185                 190

Ala Leu Pro Glu Ala Thr His Glu Ala Ile Val Gly Val Gly Lys Gln
        195                 200                 205

Trp Ser Gly Ala Arg Ala Leu Glu Ala Leu Leu Thr Val Ala Gly Glu
210                 215                 220

Leu Arg Gly Pro Pro Leu Gln Leu Asp Thr Gly Gln Leu Leu Lys Ile
225                 230                 235                 240

Ala Lys Arg Gly Gly Val Thr Ala Val Glu Ala Val His Ala Trp Arg
                245                 250                 255

Asn Ala Leu Thr Gly Ala Pro Leu Asn Leu Thr Pro Glu Gln Val Val
            260                 265                 270

Ala Ile Ala Ser Asn Ile Gly Gly Lys Gln Ala Leu Glu Thr Val Gln
        275                 280                 285

Arg Leu Leu Pro Val Leu Cys Gln Ala His Gly Leu Thr Pro Glu Gln
290                 295                 300

Val Val Ala Ile Ala Ser His Asp Gly Gly Lys Gln Ala Leu Glu Thr
305                 310                 315                 320

Val Gln Arg Leu Leu Pro Val Leu Cys Gln Ala His Gly Leu Thr Pro
                325                 330                 335

Glu Gln Val Val Ala Ile Ala Ser Asn Asn Gly Gly Lys Gln Ala Leu
            340                 345                 350

Glu Thr Val Gln Arg Leu Leu Pro Val Leu Cys Gln Ala His Gly Leu
        355                 360                 365

Thr Pro Glu Gln Val Val Ala Ile Ala Ser Asn Ile Gly Gly Lys Gln
370                 375                 380

Ala Leu Glu Thr Val Gln Arg Leu Leu Pro Val Leu Cys Gln Ala His
385                 390                 395                 400

Gly Leu Thr Pro Glu Gln Val Val Ala Ile Ala Ser His Asp Gly Gly
                405                 410                 415

Lys Gln Ala Leu Glu Thr Val Gln Arg Leu Leu Pro Val Leu Cys Gln
            420                 425                 430

Ala His Gly Leu Thr Pro Glu Gln Val Val Ala Ile Ala Ser Asn Gly
        435                 440                 445

Gly Gly Lys Gln Ala Leu Glu Thr Val Gln Arg Leu Leu Pro Val Leu
450                 455                 460

Cys Gln Ala His Gly Leu Thr Pro Glu Gln Val Val Ala Ile Ala Ser
465                 470                 475                 480

His Asp Gly Gly Lys Gln Ala Leu Glu Thr Val Gln Arg Leu Leu Pro
                485                 490                 495

Val Leu Cys Gln Ala His Gly Leu Thr Pro Glu Gln Val Val Ala Ile
            500                 505                 510

Ala Ser Asn Ile Gly Gly Lys Gln Ala Leu Glu Thr Val Gln Arg Leu
        515                 520                 525
```

Leu Pro Val Leu Cys Gln Ala His Gly Leu Thr Pro Glu Gln Val Val
    530                 535                 540

Ala Ile Ala Ser His Asp Gly Gly Lys Gln Ala Leu Glu Thr Val Gln
545                 550                 555                 560

Arg Leu Leu Pro Val Leu Cys Gln Ala His Gly Leu Thr Pro Glu Gln
                565                 570                 575

Val Val Ala Ile Ala Ser Asn Gly Gly Gly Lys Gln Ala Leu Glu Thr
            580                 585                 590

Val Gln Arg Leu Leu Pro Val Leu Cys Gln Ala His Gly Leu Thr Pro
        595                 600                 605

Glu Gln Val Val Ala Ile Ala Ser Asn Ile Gly Gly Lys Gln Ala Leu
    610                 615                 620

Glu Thr Val Gln Arg Leu Leu Pro Val Leu Cys Gln Ala His Gly Leu
625                 630                 635                 640

Thr Pro Glu Gln Val Val Ala Ile Ala Ser Asn Gly Gly Gly Lys Gln
                645                 650                 655

Ala Leu Glu Thr Val Gln Arg Leu Leu Pro Val Leu Cys Gln Ala His
            660                 665                 670

Gly Leu Thr Pro Glu Gln Val Val Ala Ile Ala Ser Asn Ile Gly Gly
        675                 680                 685

Arg Pro Ala Leu Glu Ser Ile Val Ala Gln Leu Ser Arg Pro Asp Pro
690                 695                 700

Ala Leu Ala Ala Leu Thr Asn Asp His Leu Val Ala Leu Ala Cys Leu
705                 710                 715                 720

Gly Gly Arg Pro Ala Leu Asp Ala Val Lys Lys Gly Leu Pro His Ala
                725                 730                 735

Pro Ala Leu Ile Lys Arg Thr Asn Arg Arg Ile Pro Glu Arg Thr Ser
            740                 745                 750

His Arg Val Ala Asp Lys Ala Glu Leu Ile Pro Glu Pro Pro Lys Lys
        755                 760                 765

Lys Arg Lys Val Glu Leu Gly Thr Ala
770                 775

<210> SEQ ID NO 350
<211> LENGTH: 696
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Met Leu Ile Gly Tyr Ala Arg Val Ser Thr Asn Gly Gln Ser Thr Asp
1               5                   10                  15

Leu Gln Arg Asp Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Glu Arg Leu Gln Glu Gly Asp Thr Leu Val Val Trp Lys Leu Asp
    50                  55                  60

Arg Leu Gly Arg Ser Val Lys His Leu Ile Ser Leu Val Gly Glu Leu
65                  70                  75                  80

Arg Glu Arg Gly Ile Asn Phe Arg Ser Leu Thr Asp Cys Val Asn Thr
                85                  90                  95

Ser Ser Pro Met Gly Arg Phe Phe Phe His Val Met Gly Ala Leu Ala
            100                 105                 110

-continued

```
Glu Val Glu Arg Glu Leu Ile Val Glu Arg Thr Met Ala Gly Leu Ala
            115                 120                 125
Ala Ala Arg Ser Lys Gly Gly Ser Gly Gly Ser Gly Gly
        130                 135                 140
Ser Gly Thr Ser Leu Gln Leu Asp Thr Gly Gln Leu Leu Lys Ile Ala
145                 150                 155                 160
Lys Arg Gly Gly Val Thr Ala Val Glu Ala Val His Ala Trp Arg Asn
                    165                 170                 175
Ala Leu Thr Gly Ala Pro Leu Asn Leu Thr Pro Glu Gln Val Val Ala
                180                 185                 190
Ile Ala Ser Asn Ile Gly Gly Lys Gln Ala Leu Glu Thr Val Gln Arg
            195                 200                 205
Leu Leu Pro Val Leu Cys Gln Ala His Gly Leu Thr Pro Glu Gln Val
        210                 215                 220
Val Ala Ile Ala Ser His Asp Gly Gly Lys Gln Ala Leu Glu Thr Val
225                 230                 235                 240
Gln Arg Leu Leu Pro Val Leu Cys Gln Ala His Gly Leu Thr Pro Glu
                245                 250                 255
Gln Val Val Ala Ile Ala Ser Asn Gly Gly Lys Gln Ala Leu Glu
                260                 265                 270
Thr Val Gln Arg Leu Leu Pro Val Leu Cys Gln Ala His Gly Leu Thr
            275                 280                 285
Pro Glu Gln Val Val Ala Ile Ala Ser Asn Ile Gly Gly Lys Gln Ala
        290                 295                 300
Leu Glu Thr Val Gln Arg Leu Leu Pro Val Leu Cys Gln Ala His Gly
305                 310                 315                 320
Leu Thr Pro Glu Gln Val Val Ala Ile Ala Ser His Asp Gly Gly Lys
                325                 330                 335
Gln Ala Leu Glu Thr Val Gln Arg Leu Leu Pro Val Leu Cys Gln Ala
                340                 345                 350
His Gly Leu Thr Pro Glu Gln Val Val Ala Ile Ala Ser Asn Gly Gly
            355                 360                 365
Gly Lys Gln Ala Leu Glu Thr Val Gln Arg Leu Leu Pro Val Leu Cys
        370                 375                 380
Gln Ala His Gly Leu Thr Pro Glu Gln Val Val Ala Ile Ala Ser His
385                 390                 395                 400
Asp Gly Gly Lys Gln Ala Leu Glu Thr Val Gln Arg Leu Leu Pro Val
                405                 410                 415
Leu Cys Gln Ala His Gly Leu Thr Pro Glu Gln Val Val Ala Ile Ala
                420                 425                 430
Ser Asn Ile Gly Gly Lys Gln Ala Leu Glu Thr Val Gln Arg Leu Leu
            435                 440                 445
Pro Val Leu Cys Gln Ala His Gly Leu Thr Pro Glu Gln Val Val Ala
        450                 455                 460
Ile Ala Ser His Asp Gly Gly Lys Gln Ala Leu Glu Thr Val Gln Arg
465                 470                 475                 480
Leu Leu Pro Val Leu Cys Gln Ala His Gly Leu Thr Pro Glu Gln Val
                485                 490                 495
Val Ala Ile Ala Ser Asn Gly Gly Gly Lys Gln Ala Leu Glu Thr Val
                500                 505                 510
Gln Arg Leu Leu Pro Val Leu Cys Gln Ala His Gly Leu Thr Pro Glu
            515                 520                 525
Gln Val Val Ala Ile Ala Ser Asn Ile Gly Gly Lys Gln Ala Leu Glu
```

```
                530             535             540
Thr Val Gln Arg Leu Leu Pro Val Leu Cys Gln Ala His Gly Leu Thr
545             550             555             560

Pro Glu Gln Val Val Ala Ile Ala Ser Asn Gly Gly Lys Gln Ala
            565             570             575

Leu Glu Thr Val Gln Arg Leu Leu Pro Val Leu Cys Gln Ala His Gly
            580             585             590

Leu Thr Pro Glu Gln Val Val Ala Ile Ala Ser Asn Ile Gly Gly Arg
            595             600             605

Pro Ala Leu Glu Ser Ile Val Ala Gln Leu Ser Arg Pro Asp Pro Ala
            610             615             620

Leu Ala Ala Leu Thr Asn Asp His Leu Val Ala Leu Ala Cys Leu Gly
625             630             635             640

Gly Arg Pro Ala Leu Asp Ala Val Lys Lys Gly Leu Pro His Ala Pro
            645             650             655

Ala Leu Ile Lys Arg Thr Asn Arg Arg Ile Pro Glu Arg Thr Ser His
            660             665             670

Arg Val Ala Asp Lys Ala Glu Leu Ile Pro Glu Pro Pro Lys Lys Lys
            675             680             685

Arg Lys Val Glu Leu Gly Thr Ala
            690             695

<210> SEQ ID NO 351
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

Met Leu Ile Gly Tyr Ala Arg Val Ser Thr Asn Gly Gln Ser Thr Asp
1               5               10              15

Leu Gln Arg Asp Ala Leu Val Cys Ala Gly Cys Glu Gln Ile Phe Glu
            20              25              30

Asp Lys Leu Ser Gly Thr Arg Thr Asp Arg Pro Gly Leu Lys Arg Ala
        35              40              45

Leu Glu Arg Leu Gln Glu Gly Asp Thr Leu Val Val Trp Lys Leu Asp
    50              55              60

Arg Leu Gly Arg Ser Val Lys His Leu Ile Ser Leu Val Gly Glu Leu
65              70              75              80

Arg Glu Arg Gly Ile Asn Phe Arg Ser Leu Thr Asp Cys Val Asn Thr
            85              90              95

Ser Ser Pro Met Gly Arg Phe Phe His Val Met Gly Ala Leu Ala
            100             105             110

Glu Val Glu Arg Glu Leu Ile Val Glu Arg Thr Met Ala Gly Leu Ala
            115             120             125

Ala Ala Arg Ser Lys Gly Gly Ser Gly Gly Ser Gly Gly Ser Gly Gly
        130             135             140

Ser Gly Thr Ser Lys Arg Gly Gly Val Thr Ala Val Glu Ala Val His
145             150             155             160

Ala Trp Arg Asn Ala Leu Thr Gly Ala Pro Leu Asn Leu Thr Pro Glu
            165             170             175

Gln Val Val Ala Ile Ala Ser Asn Ile Gly Gly Lys Gln Ala Leu Glu
            180             185             190

Thr Val Gln Arg Leu Leu Pro Val Leu Cys Gln Ala His Gly Leu Thr
```

-continued

```
              195                 200                 205
Pro Glu Gln Val Val Ala Ile Ala Ser His Asp Gly Gly Lys Gln Ala
210                 215                 220
Leu Glu Thr Val Gln Arg Leu Leu Pro Val Leu Cys Gln Ala His Gly
225                 230                 235                 240
Leu Thr Pro Glu Gln Val Val Ala Ile Ala Ser Asn Asn Gly Gly Lys
            245                 250                 255
Gln Ala Leu Glu Thr Val Gln Arg Leu Leu Pro Val Leu Cys Gln Ala
                260                 265                 270
His Gly Leu Thr Pro Glu Gln Val Val Ala Ile Ala Ser Asn Ile Gly
        275                 280                 285
Gly Lys Gln Ala Leu Glu Thr Val Gln Arg Leu Leu Pro Val Leu Cys
290                 295                 300
Gln Ala His Gly Leu Thr Pro Glu Gln Val Val Ala Ile Ala Ser His
305                 310                 315                 320
Asp Gly Gly Lys Gln Ala Leu Glu Thr Val Gln Arg Leu Leu Pro Val
            325                 330                 335
Leu Cys Gln Ala His Gly Leu Thr Pro Glu Gln Val Val Ala Ile Ala
                340                 345                 350
Ser Asn Gly Gly Gly Lys Gln Ala Leu Glu Thr Val Gln Arg Leu Leu
        355                 360                 365
Pro Val Leu Cys Gln Ala His Gly Leu Thr Pro Glu Gln Val Val Ala
370                 375                 380
Ile Ala Ser His Asp Gly Gly Lys Gln Ala Leu Glu Thr Val Gln Arg
385                 390                 395                 400
Leu Leu Pro Val Leu Cys Gln Ala His Gly Leu Thr Pro Glu Gln Val
            405                 410                 415
Val Ala Ile Ala Ser Asn Ile Gly Gly Lys Gln Ala Leu Glu Thr Val
                420                 425                 430
Gln Arg Leu Leu Pro Val Leu Cys Gln Ala His Gly Leu Thr Pro Glu
        435                 440                 445
Gln Val Val Ala Ile Ala Ser His Asp Gly Gly Lys Gln Ala Leu Glu
450                 455                 460
Thr Val Gln Arg Leu Leu Pro Val Leu Cys Gln Ala His Gly Leu Thr
465                 470                 475                 480
Pro Glu Gln Val Val Ala Ile Ala Ser Asn Gly Gly Lys Gln Ala
            485                 490                 495
Leu Glu Thr Val Gln Arg Leu Leu Pro Val Leu Cys Gln Ala His Gly
                500                 505                 510
Leu Thr Pro Glu Gln Val Val Ala Ile Ala Ser Asn Ile Gly Gly Lys
        515                 520                 525
Gln Ala Leu Glu Thr Val Gln Arg Leu Leu Pro Val Leu Cys Gln Ala
530                 535                 540
His Gly Leu Thr Pro Glu Gln Val Val Ala Ile Ala Ser Asn Gly Gly
545                 550                 555                 560
Gly Lys Gln Ala Leu Glu Thr Val Gln Arg Leu Leu Pro Val Leu Cys
            565                 570                 575
Gln Ala His Gly Leu Thr Pro Glu Gln Val Val Ala Ile Ala Ser Asn
                580                 585                 590
Ile Gly Gly Arg Pro Ala Leu Glu Ser Ile Val Ala Gln Leu Ser Arg
        595                 600                 605
Pro Asp Pro Ala Leu Ala Ala Leu Thr Asn Asp His Leu Val Ala Leu
610                 615                 620
```

```
Ala Cys Leu Gly Gly Arg Pro Ala Leu Asp Ala Val Lys Lys Gly Leu
625                 630                 635                 640

Pro His Ala Pro Ala Leu Ile Lys Arg Thr Asn Arg Arg Ile Pro Glu
            645                 650                 655

Arg Thr Ser His Arg Val Ala Asp Lys Ala Glu Leu Ile Pro Glu Pro
        660                 665                 670

Pro Lys Lys Lys Arg Lys Val Glu Leu Gly Thr Ala
    675                 680

<210> SEQ ID NO 352
<211> LENGTH: 660
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Met Leu Ile Gly Tyr Ala Arg Val Ser Thr Asn Gly Gln Ser Thr Asp
1               5                   10                  15

Leu Gln Arg Asp Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Glu Arg Leu Gln Glu Gly Asp Thr Leu Val Val Trp Lys Leu Asp
50                  55                  60

Arg Leu Gly Arg Ser Val Lys His Leu Ile Ser Leu Val Gly Glu Leu
65                  70                  75                  80

Arg Glu Arg Gly Ile Asn Phe Arg Ser Leu Thr Asp Cys Val Asn Thr
                85                  90                  95

Ser Ser Pro Met Gly Arg Phe Phe Phe His Val Met Gly Ala Leu Ala
            100                 105                 110

Glu Val Glu Arg Glu Leu Ile Val Glu Arg Thr Met Ala Gly Leu Ala
        115                 120                 125

Ala Ala Arg Ser Lys Gly Gly Ser Gly Gly Ser Gly Gly Ser Gly Gly
    130                 135                 140

Ser Gly Thr Ser Leu Thr Pro Glu Gln Val Val Ala Ile Ala Ser Asn
145                 150                 155                 160

Ile Gly Gly Lys Gln Ala Leu Glu Thr Val Gln Arg Leu Leu Pro Val
                165                 170                 175

Leu Cys Gln Ala His Gly Leu Thr Pro Glu Gln Val Val Ala Ile Ala
            180                 185                 190

Ser His Asp Gly Gly Lys Gln Ala Leu Glu Thr Val Gln Arg Leu Leu
        195                 200                 205

Pro Val Leu Cys Gln Ala His Gly Leu Thr Pro Glu Gln Val Val Ala
    210                 215                 220

Ile Ala Ser Asn Asn Gly Gly Lys Gln Ala Leu Glu Thr Val Gln Arg
225                 230                 235                 240

Leu Leu Pro Val Leu Cys Gln Ala His Gly Leu Thr Pro Glu Gln Val
                245                 250                 255

Val Ala Ile Ala Ser Asn Ile Gly Gly Lys Gln Ala Leu Glu Thr Val
            260                 265                 270

Gln Arg Leu Leu Pro Val Leu Cys Gln Ala His Gly Leu Thr Pro Glu
        275                 280                 285

Gln Val Val Ala Ile Ala Ser His Asp Gly Gly Lys Gln Ala Leu Glu
    290                 295                 300
```

```
Thr Val Gln Arg Leu Leu Pro Val Leu Cys Gln Ala His Gly Leu Thr
305                 310                 315                 320

Pro Glu Gln Val Val Ala Ile Ala Ser Asn Gly Gly Lys Gln Ala
            325                 330                 335

Leu Glu Thr Val Gln Arg Leu Leu Pro Val Leu Cys Gln Ala His Gly
        340                 345                 350

Leu Thr Pro Glu Gln Val Val Ala Ile Ala Ser His Asp Gly Gly Lys
    355                 360                 365

Gln Ala Leu Glu Thr Val Gln Arg Leu Leu Pro Val Leu Cys Gln Ala
370                 375                 380

His Gly Leu Thr Pro Glu Gln Val Val Ala Ile Ala Ser Asn Ile Gly
385                 390                 395                 400

Gly Lys Gln Ala Leu Glu Thr Val Gln Arg Leu Leu Pro Val Leu Cys
            405                 410                 415

Gln Ala His Gly Leu Thr Pro Glu Gln Val Val Ala Ile Ala Ser His
        420                 425                 430

Asp Gly Gly Lys Gln Ala Leu Glu Thr Val Gln Arg Leu Leu Pro Val
    435                 440                 445

Leu Cys Gln Ala His Gly Leu Thr Pro Glu Gln Val Val Ala Ile Ala
450                 455                 460

Ser Asn Gly Gly Gly Lys Gln Ala Leu Glu Thr Val Gln Arg Leu Leu
465                 470                 475                 480

Pro Val Leu Cys Gln Ala His Gly Leu Thr Pro Glu Gln Val Val Ala
            485                 490                 495

Ile Ala Ser Asn Ile Gly Gly Lys Gln Ala Leu Glu Thr Val Gln Arg
        500                 505                 510

Leu Leu Pro Val Leu Cys Gln Ala His Gly Leu Thr Pro Glu Gln Val
    515                 520                 525

Val Ala Ile Ala Ser Asn Gly Gly Gly Lys Gln Ala Leu Glu Thr Val
530                 535                 540

Gln Arg Leu Leu Pro Val Leu Cys Gln Ala His Gly Leu Thr Pro Glu
545                 550                 555                 560

Gln Val Val Ala Ile Ala Ser Asn Ile Gly Gly Arg Pro Ala Leu Glu
            565                 570                 575

Ser Ile Val Ala Gln Leu Ser Arg Pro Asp Pro Ala Leu Ala Ala Leu
        580                 585                 590

Thr Asn Asp His Leu Val Ala Leu Ala Cys Leu Gly Gly Arg Pro Ala
    595                 600                 605

Leu Asp Ala Val Lys Lys Gly Leu Pro His Ala Pro Ala Leu Ile Lys
610                 615                 620

Arg Thr Asn Arg Arg Ile Pro Glu Arg Thr Ser His Arg Val Ala Asp
625                 630                 635                 640

Lys Ala Glu Leu Ile Pro Glu Pro Pro Lys Lys Arg Lys Val Glu
            645                 650                 655

Leu Gly Thr Ala
            660

<210> SEQ ID NO 353
<211> LENGTH: 649
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353
```

```
Met Leu Ile Gly Tyr Ala Arg Val Ser Thr Asn Gly Gln Ser Thr Asp
1               5                   10                  15

Leu Gln Arg Asp Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Glu Arg Leu Gln Glu Gly Asp Thr Leu Val Val Trp Lys Leu Asp
    50                  55                  60

Arg Leu Gly Arg Ser Val Lys His Leu Ile Ser Leu Val Gly Glu Leu
65                  70                  75                  80

Arg Glu Arg Gly Ile Asn Phe Arg Ser Leu Thr Asp Cys Val Asn Thr
                85                  90                  95

Ser Ser Pro Met Gly Arg Phe Phe Phe His Val Met Gly Ala Leu Ala
            100                 105                 110

Glu Val Glu Arg Glu Leu Ile Val Glu Arg Thr Met Ala Gly Leu Ala
        115                 120                 125

Ala Ala Arg Ser Lys Gly Gly Ser Gly Gly Ser Gly Ser Gly Gly
    130                 135                 140

Ser Gly Thr Ser Asn Ile Gly Gly Lys Gln Ala Leu Glu Thr Val Gln
145                 150                 155                 160

Arg Leu Leu Pro Val Leu Cys Gln Ala His Gly Leu Thr Pro Glu Gln
                165                 170                 175

Val Val Ala Ile Ala Ser His Asp Gly Gly Lys Gln Ala Leu Glu Thr
            180                 185                 190

Val Gln Arg Leu Leu Pro Val Leu Cys Gln Ala His Gly Leu Thr Pro
        195                 200                 205

Glu Gln Val Val Ala Ile Ala Ser Asn Asn Gly Gly Lys Gln Ala Leu
210                 215                 220

Glu Thr Val Gln Arg Leu Leu Pro Val Leu Cys Gln Ala His Gly Leu
225                 230                 235                 240

Thr Pro Glu Gln Val Val Ala Ile Ala Ser Asn Ile Gly Gly Lys Gln
                245                 250                 255

Ala Leu Glu Thr Val Gln Arg Leu Leu Pro Val Leu Cys Gln Ala His
            260                 265                 270

Gly Leu Thr Pro Glu Gln Val Val Ala Ile Ala Ser His Asp Gly Gly
        275                 280                 285

Lys Gln Ala Leu Glu Thr Val Gln Arg Leu Leu Pro Val Leu Cys Gln
290                 295                 300

Ala His Gly Leu Thr Pro Glu Gln Val Val Ala Ile Ala Ser Asn Gly
305                 310                 315                 320

Gly Gly Lys Gln Ala Leu Glu Thr Val Gln Arg Leu Leu Pro Val Leu
                325                 330                 335

Cys Gln Ala His Gly Leu Thr Pro Glu Gln Val Val Ala Ile Ala Ser
            340                 345                 350

His Asp Gly Gly Lys Gln Ala Leu Glu Thr Val Gln Arg Leu Leu Pro
        355                 360                 365

Val Leu Cys Gln Ala His Gly Leu Thr Pro Glu Gln Val Val Ala Ile
    370                 375                 380

Ala Ser Asn Ile Gly Gly Lys Gln Ala Leu Glu Thr Val Gln Arg Leu
385                 390                 395                 400

Leu Pro Val Leu Cys Gln Ala His Gly Leu Thr Pro Glu Gln Val Val
                405                 410                 415

Ala Ile Ala Ser His Asp Gly Gly Lys Gln Ala Leu Glu Thr Val Gln
            420                 425                 430
```

```
Arg Leu Leu Pro Val Leu Cys Gln Ala His Gly Leu Thr Pro Glu Gln
            435                 440                 445

Val Val Ala Ile Ala Ser Asn Gly Gly Gly Lys Gln Ala Leu Glu Thr
    450                 455                 460

Val Gln Arg Leu Leu Pro Val Leu Cys Gln Ala His Gly Leu Thr Pro
465                 470                 475                 480

Glu Gln Val Val Ala Ile Ala Ser Asn Ile Gly Gly Lys Gln Ala Leu
                485                 490                 495

Glu Thr Val Gln Arg Leu Leu Pro Val Leu Cys Gln Ala His Gly Leu
            500                 505                 510

Thr Pro Glu Gln Val Val Ala Ile Ala Ser Asn Gly Gly Gly Lys Gln
    515                 520                 525

Ala Leu Glu Thr Val Gln Arg Leu Leu Pro Val Leu Cys Gln Ala His
530                 535                 540

Gly Leu Thr Pro Glu Gln Val Val Ala Ile Ala Ser Asn Ile Gly Gly
545                 550                 555                 560

Arg Pro Ala Leu Glu Ser Ile Val Ala Gln Leu Ser Arg Pro Asp Pro
                565                 570                 575

Ala Leu Ala Ala Leu Thr Asn Asp His Leu Val Ala Leu Ala Cys Leu
            580                 585                 590

Gly Gly Arg Pro Ala Leu Asp Ala Val Lys Lys Gly Leu Pro His Ala
    595                 600                 605

Pro Ala Leu Ile Lys Arg Thr Asn Arg Arg Ile Pro Glu Arg Thr Ser
610                 615                 620

His Arg Val Ala Asp Lys Ala Glu Leu Ile Pro Glu Pro Pro Lys Lys
625                 630                 635                 640

Lys Arg Lys Val Glu Leu Gly Thr Ala
                645

<210> SEQ ID NO 354
<211> LENGTH: 647
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Met Leu Ile Gly Tyr Ala Arg Val Ser Thr Asn Gly Gln Ser Thr Asp
1               5                   10                  15

Leu Gln Arg Asp Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Glu Arg Leu Gln Glu Gly Asp Thr Leu Val Val Trp Lys Leu Asp
    50                  55                  60

Arg Leu Gly Arg Ser Val Lys His Leu Ile Ser Leu Val Gly Glu Leu
65                  70                  75                  80

Arg Glu Arg Gly Ile Asn Phe Arg Ser Leu Thr Asp Cys Val Asn Thr
                85                  90                  95

Ser Ser Pro Met Gly Arg Phe Phe His Val Met Gly Ala Leu Ala
            100                 105                 110

Glu Val Glu Arg Glu Leu Ile Val Glu Arg Thr Met Ala Gly Leu Ala
        115                 120                 125

Ala Ala Arg Ser Lys Gly Gly Ser Gly Gly Ser Gly Gly Ser Gly Gly
    130                 135                 140
```

```
Ser Gly Thr Ser Gly Gly Lys Gln Ala Leu Glu Thr Val Gln Arg Leu
145                 150                 155                 160

Leu Pro Val Leu Cys Gln Ala His Gly Leu Thr Pro Glu Gln Val Val
                165                 170                 175

Ala Ile Ala Ser His Asp Gly Gly Lys Gln Ala Leu Glu Thr Val Gln
            180                 185                 190

Arg Leu Leu Pro Val Leu Cys Gln Ala His Gly Leu Thr Pro Glu Gln
        195                 200                 205

Val Val Ala Ile Ala Ser Asn Asn Gly Gly Lys Gln Ala Leu Glu Thr
    210                 215                 220

Val Gln Arg Leu Leu Pro Val Leu Cys Gln Ala His Gly Leu Thr Pro
225                 230                 235                 240

Glu Gln Val Val Ala Ile Ala Ser Asn Ile Gly Gly Lys Gln Ala Leu
                245                 250                 255

Glu Thr Val Gln Arg Leu Leu Pro Val Leu Cys Gln Ala His Gly Leu
            260                 265                 270

Thr Pro Glu Gln Val Val Ala Ile Ala Ser His Asp Gly Gly Lys Gln
        275                 280                 285

Ala Leu Glu Thr Val Gln Arg Leu Leu Pro Val Leu Cys Gln Ala His
    290                 295                 300

Gly Leu Thr Pro Glu Gln Val Val Ala Ile Ala Ser Asn Gly Gly Gly
305                 310                 315                 320

Lys Gln Ala Leu Glu Thr Val Gln Arg Leu Leu Pro Val Leu Cys Gln
                325                 330                 335

Ala His Gly Leu Thr Pro Glu Gln Val Val Ala Ile Ala Ser His Asp
            340                 345                 350

Gly Gly Lys Gln Ala Leu Glu Thr Val Gln Arg Leu Leu Pro Val Leu
        355                 360                 365

Cys Gln Ala His Gly Leu Thr Pro Glu Gln Val Val Ala Ile Ala Ser
370                 375                 380

Asn Ile Gly Gly Lys Gln Ala Leu Glu Thr Val Gln Arg Leu Leu Pro
385                 390                 395                 400

Val Leu Cys Gln Ala His Gly Leu Thr Pro Glu Gln Val Val Ala Ile
                405                 410                 415

Ala Ser His Asp Gly Gly Lys Gln Ala Leu Glu Thr Val Gln Arg Leu
            420                 425                 430

Leu Pro Val Leu Cys Gln Ala His Gly Leu Thr Pro Glu Gln Val Val
        435                 440                 445

Ala Ile Ala Ser Asn Gly Gly Gly Lys Gln Ala Leu Glu Thr Val Gln
    450                 455                 460

Arg Leu Leu Pro Val Leu Cys Gln Ala His Gly Leu Thr Pro Glu Gln
465                 470                 475                 480

Val Val Ala Ile Ala Ser Asn Ile Gly Gly Lys Gln Ala Leu Glu Thr
                485                 490                 495

Val Gln Arg Leu Leu Pro Val Leu Cys Gln Ala His Gly Leu Thr Pro
            500                 505                 510

Glu Gln Val Val Ala Ile Ala Ser Asn Gly Gly Gly Lys Gln Ala Leu
        515                 520                 525

Glu Thr Val Gln Arg Leu Leu Pro Val Leu Cys Gln Ala His Gly Leu
    530                 535                 540

Thr Pro Glu Gln Val Val Ala Ile Ala Ser Asn Ile Gly Gly Arg Pro
545                 550                 555                 560

Ala Leu Glu Ser Ile Val Ala Gln Leu Ser Arg Pro Asp Pro Ala Leu
```

```
                        565                 570                 575
Ala Ala Leu Thr Asn Asp His Leu Val Ala Leu Ala Cys Leu Gly Gly
                580                 585                 590

Arg Pro Ala Leu Asp Ala Val Lys Lys Gly Leu Pro His Ala Pro Ala
            595                 600                 605

Leu Ile Lys Arg Thr Asn Arg Arg Ile Pro Glu Arg Thr Ser His Arg
    610                 615                 620

Val Ala Asp Lys Ala Glu Leu Ile Pro Glu Pro Pro Lys Lys Arg
625                 630                 635                 640

Lys Val Glu Leu Gly Thr Ala
                645

<210> SEQ ID NO 355
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Met Leu Ile Gly Tyr Ala Arg Val Ser Thr Asn Gly Gln Ser Thr Asp
1               5                   10                  15

Leu Gln Arg Asp Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Glu Arg Leu Gln Glu Gly Asp Thr Leu Val Val Trp Lys Leu Asp
    50                  55                  60

Arg Leu Gly Arg Ser Val Lys His Leu Ile Ser Leu Val Gly Glu Leu
65                  70                  75                  80

Arg Glu Arg Gly Ile Asn Phe Arg Ser Leu Thr Asp Cys Val Asn Thr
                85                  90                  95

Ser Ser Pro Met Gly Arg Phe Phe Phe His Val Met Gly Ala Leu Ala
            100                 105                 110

Glu Val Glu Arg Glu Leu Ile Val Glu Arg Thr Met Ala Gly Leu Ala
        115                 120                 125

Ala Ala Arg Ser Lys Gly Arg Ile Gly Gly Arg Pro Pro Lys Ser
    130                 135                 140

<210> SEQ ID NO 356
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 356
```

```
Leu Thr Leu Asp Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Asp
                20                  25                  30

His Gly

<210> SEQ ID NO 357
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 357

Leu Thr Leu Asp Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
                20                  25                  30

His Gly

<210> SEQ ID NO 358
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 358

Leu Thr Leu Asp Gln Val Val Ala Ile Ala Ser Xaa Xaa Gly Ser Lys
1               5                   10                  15

Gln Ala Leu Glu Thr Val Gln Arg Leu Leu Pro Val Leu Cys Gln Asp
                20                  25                  30

His Gly

<210> SEQ ID NO 359
<211> LENGTH: 34
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 359

Leu Thr Leu Asp Gln Val Val Ala Ile Ala Ser Xaa Xaa Gly Gly Lys
 1               5                  10                  15

Lys Ala Leu Glu Thr Val Gln Arg Leu Leu Pro Val Leu Cys Gln Asp
             20                  25                  30

His Gly

<210> SEQ ID NO 360
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 360

Leu Thr Leu Asp Lys Val Val Ala Ile Ala Ser Xaa Xaa Gly Gly Lys
 1               5                  10                  15

Gln Ala Leu Glu Thr Val Gln Arg Leu Leu Pro Val Leu Cys Gln Asp
             20                  25                  30

His Gly

<210> SEQ ID NO 361
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
```

```
        Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 361

Leu Thr Leu Asp Gln Val Val Ala Ile Ala Ser Xaa Xaa Gly Ser Lys
1               5                   10                  15

Gln Ala Leu Glu Thr Val Gln Arg Leu Leu Pro Val Leu Cys Gln Ala
            20                  25                  30

His Gly

<210> SEQ ID NO 362
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 362

Leu Thr Leu Asp Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

Arg Gly

<210> SEQ ID NO 363
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 363

Leu Thr Leu Asp Gln Val Val Ala Ile Ala Ser Xaa Xaa Gly Gly Lys
```

```
1               5                  10                  15
Gln Ala Leu Glu Thr Val Gln Arg Leu Leu Pro Val Leu Cys Glu Gln
            20                  25                  30

His Gly

<210> SEQ ID NO 364
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 364

Leu Thr Leu Asp Gln Val Val Ala Ile Ala Ser Xaa Xaa Gly Gly Lys
1               5                  10                  15

Gln Ala Leu Glu Thr Val Gln Arg Leu Leu Pro Val Leu Cys Gln Thr
            20                  25                  30

His Gly

<210> SEQ ID NO 365
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 365

Leu Thr Leu Asp Gln Val Ala Ala Ile Ala Ser Xaa Xaa Gly Gly Lys
1               5                  10                  15

Gln Ala Leu Glu Thr Val Gln Arg Leu Leu Pro Val Leu Cys Gln Ala
            20                  25                  30

His Gly

<210> SEQ ID NO 366
<211> LENGTH: 34
<212> TYPE: PRT
<213> ORGANISM: Artificial Sequence
```

-continued

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 366

Leu Thr Leu Asp Gln Val Val Ala Ile Ala Ser Xaa Xaa Gly Ser Lys
1               5                   10                  15

Gln Ala Leu Glu Thr Val Gln Arg Leu Leu Pro Val Leu Cys Gln Thr
            20                  25                  30

His Gly

<210> SEQ ID NO 367
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 367

Leu Thr Leu Asp Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Glu
            20                  25                  30

His Gly

<210> SEQ ID NO 368
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
```

```
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 368

Leu Thr Leu Asp Gln Val Val Ser Ile Ala Ser Xaa Xaa Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 369
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 369

Leu Thr Leu Ala Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 370
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 370

Leu Thr Leu Ala Gln Val Val Ala Ile Ala Ser Xaa Xaa Gly Gly Lys
1               5                   10                  15
```

```
Gln Ala Leu Glu Thr Val Gln Arg Leu Leu Pro Val Leu Cys Gln Asp
            20                  25                  30

His Gly

<210> SEQ ID NO 371
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 371

Leu Thr Leu Ala Gln Val Val Ala Ile Ala Asn Xaa Xaa Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 372
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 372

Leu Thr Leu Ala Gln Val Val Ala Ile Ala Asn Xaa Xaa Gly Gly Lys
1               5                   10                  15

Gln Ala Leu Glu Thr Val Gln Arg Leu Leu Pro Val Leu Cys Gln Asp
            20                  25                  30

His Gly

<210> SEQ ID NO 373
<211> LENGTH: 34
<212> TYPE: PRT
<213> ORGANISM: Artificial Sequence
<220> FEATURE:
<223> OTHER INFORMATION: Description of Artificial Sequence: Synthetic
```

-continued

```
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 373

Leu Thr Leu Ala Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Thr
            20                  25                  30

His Gly

<210> SEQ ID NO 374
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 374

Leu Thr Gln Val Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 375
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
```

-continued

```
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 375

Leu Thr Leu Thr Gln Val Val Ala Ile Ala Ser Xaa Xaa Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 376
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 376

Leu Thr Pro Asp Gln Val Val Ala Ile Ala Ser Xaa Xaa Gly Gly Lys
1               5                   10                  15

Gln Ala Leu Glu Thr Val Gln Arg Leu Leu Pro Val Leu Cys Glu Gln
            20                  25                  30

His Gly

<210> SEQ ID NO 377
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 377

Leu Thr Pro Ala Gln Val Val Ala Ile Ala Ser Xaa Xaa Gly Gly Lys
1               5                   10                  15

Gln Ala Leu Glu Thr Val Gln Gln Leu Leu Pro Val Leu Cys Glu Gln
            20                  25                  30
```

His Gly

```
<210> SEQ ID NO 378
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 378

Leu Thr Pro Ala Gln Val Val Ala Ile Ala Ser Xaa Xaa Gly Gly Lys
1               5                   10                  15
Gln Ala Leu Glu Thr Val Gln Arg Leu Leu Pro Val Leu Cys Glu Gln
            20                  25                  30
His Gly

<210> SEQ ID NO 379
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 379

Leu Thr Pro Asp Gln Val Val Ala Ile Ala Ser Xaa Xaa Gly Gly Arg
1               5                   10                  15
Pro Ala Leu Glu Thr Val Gln Arg Leu Leu Pro Val Leu Cys Glu Gln
            20                  25                  30
His Gly

<210> SEQ ID NO 380
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 380

Leu Thr Pro Ala Gln Val Val Ala Ile Ala Ser Xaa Xaa Gly Gly Lys
1               5                   10                  15

Gln Ala Leu Lys Thr Val Gln Gln Leu Leu Pro Val Leu Cys Glu Gln
            20                  25                  30

His Gly

<210> SEQ ID NO 381
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 381

Leu Thr Pro Asp Gln Val Val Ala Ile Ala Ser Xaa Xaa Gly Gly Lys
1               5                   10                  15

Gln Ala Leu Glu Arg Val Gln Arg Leu Leu Pro Val Leu Cys Glu Gln
            20                  25                  30

His Gly

<210> SEQ ID NO 382
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
```

```
          Gly," "His Asn," "Asn Val," "Asn Ser," "His Ala," "Ser," "Asn,"
          "Lys Ala," "His," "Arg Ala," "Asn Ala," or "Asn Cys"

<400> SEQUENCE: 382

Leu Thr Arg Ala Gln Val Val Ala Ile Ala Ser Xaa Xaa Gly Gly Lys
1               5                   10                  15

Gln Ala Leu Glu Thr Val Gln Arg Leu Leu Pro Val Leu Cys Glu Gln
            20                  25                  30

His Gly

<210> SEQ ID NO 383
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 383

Leu Thr Leu Asp Gln Val Val Ala Ile Ala Ser Xaa Xaa Gly Gly Lys
1               5                   10                  15

Gln Ala Leu Glu Thr Val Gln Arg Leu Leu Pro Val Leu Cys Glu Gln
            20                  25                  30

His Gly

<210> SEQ ID NO 384
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 384

Leu Thr Pro Ala Gln Val Val Thr Ile Ala Ser Xaa Xaa Gly Gly Lys
1               5                   10                  15

Gln Ala Leu Glu Thr Val Gln Arg Leu Leu Pro Val Leu Cys Glu Gln
            20                  25                  30

His Gly
```

```
<210> SEQ ID NO 385
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 385

Leu Thr Pro Gln Gln Val Val Ala Ile Ala Ser Xaa Xaa Gly Gly Lys
1               5                   10                  15

Gln Ala Leu Glu Thr Val Gln Arg Leu Leu Pro Val Leu Cys Glu Gln
            20                  25                  30

His Gly

<210> SEQ ID NO 386
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 386

Leu Thr Pro Ala Gln Val Val Ala Ile Ala Ser Xaa Xaa Gly Gly Lys
1               5                   10                  15

Pro Ala Leu Glu Thr Val Gln Arg Leu Leu Pro Val Leu Cys Glu Gln
            20                  25                  30

His Gly

<210> SEQ ID NO 387
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
```

```
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 387

Leu Thr Pro Asp Gln Val Val Ala Ile Ala Ser Xaa Xaa Gly Gly Arg
1               5                   10                  15

Gln Ala Leu Glu Thr Val Gln Arg Leu Leu Pro Val Leu Cys Glu Gln
            20                  25                  30

His Gly

<210> SEQ ID NO 388
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 388

Leu Thr Pro Asp Gln Val Val Ala Ile Ala Ser Xaa Xaa Gly Gly Lys
1               5                   10                  15

Pro Ala Leu Glu Thr Val Gln Arg Leu Leu Pro Val Leu Cys Glu Gln
            20                  25                  30

His Gly

<210> SEQ ID NO 389
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"
```

```
<400> SEQUENCE: 389

Leu Thr Pro Asp Gln Val Val Ala Ile Ala Ser Xaa Xaa Gly Gly Lys
1               5                   10                  15

Gln Ala Leu Glu Thr Val Gln Arg Leu Leu Pro Val Leu Cys Arg Asp
            20                  25                  30

His Gly

<210> SEQ ID NO 390
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(13)
<223> OTHER INFORMATION: This region may encompass 1 to 2 residues
      selected from "Asn Ile," "His Asp," "Asn Gly," "Asn Asn," "Lys
      Asn," "Arg Asn," "Asn His," "Asn Gln," "Ser Ser," "Ser Asn," "Asn
      Lys," "Lys His," "Arg His," "His His," "Lys Ile," "Arg Ile," "His
      Ile,";
<220> FEATURE:
<221> NAME/KEY: MOD_RES
<222> LOCATION: (12)..(13)
<223> OTHER INFORMATION: cont'd from above; "Ser Ile," "Lys Gly," "His
      Gly," "Arg Gly," "Ser Asp," "Asn Asp," "Lys Asp," "Arg Asp," "Tyr
      Gly," "His Asn," "Asn Val," "Asn Ser," "His Ala," "Ser," "Asn,"
      "Lys Ala," "His," "Arg Ala," "Asn Ala," or "Asn Cys"

<400> SEQUENCE: 390

Leu Thr Pro Ala Gln Val Val Ala Ile Ala Ser Xaa Xaa Gly Gly Lys
1               5                   10                  15

Gln Ala Leu Glu Thr Val Gln Arg Leu Leu Pro Val Leu Cys Arg Asp
            20                  25                  30

His Gly

<210> SEQ ID NO 391
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
tacgactcac tata                                                         14

<210> SEQ ID NO 392
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other
<220> FEATURE:
<221> NAME/KEY: modified_base
<222> LOCATION: (26)..(30)
<223> OTHER INFORMATION: a, c, t, g, unknown or other

<400> SEQUENCE: 392
nnnnntccaa aaccatggtt tacagnnnnn                                        30
```